US012433994B2

(12) United States Patent
Gibson et al.

(10) Patent No.: US 12,433,994 B2
(45) Date of Patent: Oct. 7, 2025

(54) DRUG DELIVERY DEVICE, METHOD OF MANUFACTURE, AND METHOD OF USE

(71) Applicant: AMGEN INC., Thousand Oaks, CA (US)

(72) Inventors: Scott R. Gibson, Granada Hills, CA (US); Sheldon B. Moberg, Thousand Oaks, CA (US); Basel Hasan Taha, Westlake Village, CA (US); Margaux Frances Boyaval, Newbury Park, CA (US); Mark A. Destefano, Collegeville, PA (US); John C. Love, San Diego, CA (US); Ian B. Hanson, Wayne, PA (US); Paul F. Bente, IV, Wayne, PA (US); Matthew J. Clemente, Carmel, IN (US); Rajan Ramaswamy, San Diego, CA (US); Daniel S. Codd, Escondido, CA (US); Scott Beaver, San Marcos, CA (US); Kevin L. Bokelman, San Diego, CA (US); Sean M. O'connor, West Chester, PA (US); Robert Decker, Dillsburg, PA (US); Gautam N. Shetty, Hanover, MD (US); Ryan M. Agard, Royersford, PA (US); Nicholas J. Ciccarelli, Philadelphia, PA (US); Daniel Davenport, Collegeville, PA (US)

(73) Assignee: AMGEN INC., Thousand Oaks, CA (US)

(*) Notice: Subject to any disclaimer, the term of this patent is extended or adjusted under 35 U.S.C. 154(b) by 667 days.

(21) Appl. No.: 17/688,578

(22) Filed: Mar. 7, 2022

(65) Prior Publication Data

US 2022/0218900 A1 Jul. 14, 2022

Related U.S. Application Data

(63) Continuation of application No. 16/071,873, filed as application No. PCT/US2017/017627 on Feb. 13, 2017, now Pat. No. 11,266,777.

(Continued)

(51) Int. Cl.
*A61M 5/142* (2006.01)
*A61M 5/145* (2006.01)
(Continued)

(52) U.S. Cl.
CPC ........ *A61M 5/14248* (2013.01); *A61M 5/142* (2013.01); *A61M 5/14566* (2013.01);
(Continued)

(58) Field of Classification Search
CPC .............. A61M 5/142; A61M 5/14248; A61M 5/14566; A61M 5/2033; A61M 2005/14252; A61M 2005/14268
See application file for complete search history.

(56) References Cited

U.S. PATENT DOCUMENTS 4,894,054 A 1/1990 Miskinyar
5,380,315 A * 1/1995 Isono .................... A61J 1/2089 604/82

(Continued)

FOREIGN PATENT DOCUMENTS

EP 1965449 A2 9/2008
EP 3260146 A1 12/2017

(Continued)

OTHER PUBLICATIONS

Uruguay Patent Application No. 37122, Examination Report, dated Jul. 7, 2023.

(Continued)

*Primary Examiner* — Laura A Bouchelle
(74) *Attorney, Agent, or Firm* — MARSHALL, GERSTEIN & BORUN LLP

(57) ABSTRACT

Disclosed herein is a wearable drug delivery device including a container filled at least partially with a drug including at least one of a PCSK9 (Proprotein Convertase Subtilisin/Kexin Type 9) specific antibody, a granulocyte colony-stimulating factor (G-CSF), a sclerostin antibody, or a calcitonin gene-related peptide (CGRP) antibody. The wear- (Continued)

able drug delivery device may include a needle and an insertion mechanism configured to insert the needle into a patient. A fluid pathway connector may define a sterile fluid flowpath between the container and the insertion mechanism. Optionally, a cannula initially disposed about the needle may be included. The cannula may be retained in the patient at an injection site created by the needle after the needle is withdrawn from the patient. Methods of assembly and operation are also provided.

19 Claims, 166 Drawing Sheets

Related U.S. Application Data

(60) Provisional application No. 62/320,438, filed on Apr. 8, 2016, provisional application No. 62/297,718, filed on Feb. 19, 2016, provisional application No. 62/294,842, filed on Feb. 12, 2016.

(51) Int. Cl.
*A61M 5/315* (2006.01)
*A61M 5/24* (2006.01)

(52) U.S. Cl.
CPC ... *A61M 5/315* (2013.01); *A61M 2005/14252* (2013.01); *A61M 2005/14268* (2013.01); *A61M 2005/2481* (2013.01); *A61M 2205/3368* (2013.01); *A61M 2205/35* (2013.01)

(56) References Cited

U.S. PATENT DOCUMENTS

| | | | |
|---|---|---|---|
| 7,455,663 B2 | 11/2008 | Bikovsky | |
| 7,708,717 B2 | 5/2010 | Estes et al. | |
| 7,981,085 B2 | 7/2011 | Ethelfeld | |
| 8,226,610 B2 | 7/2012 | Edwards et al. | |
| 8,282,601 B2 | 10/2012 | Mernoe et al. | |
| 8,668,675 B2 | 3/2014 | Chase et al. | |
| 8,939,935 B2 | 1/2015 | O'Connor et al. | |
| 9,061,097 B2 | 6/2015 | Holt et al. | |
| 9,987,419 B2 | 6/2018 | Hanson et al. | |
| 10,342,918 B2 | 7/2019 | Politis et al. | |
| 2005/0197625 A1 | 9/2005 | Haueter et al. | |
| 2011/0066012 A1 | 3/2011 | Hanson et al. | |
| 2012/0004640 A1 | 1/2012 | Rosen et al. | |
| 2012/0302844 A1* | 11/2012 | Schnidrig | C09J 7/20 600/309 |
| 2012/0323183 A1* | 12/2012 | Peterson | A61M 37/0015 604/195 |
| 2013/0006196 A1 | 1/2013 | Sonderegger et al. | |
| 2013/0060196 A1 | 3/2013 | O'Connor et al. | |
| 2013/0060233 A1 | 3/2013 | O'Connor et al. | |
| 2013/0066274 A1* | 3/2013 | O'Connor | A61M 5/16877 604/151 |
| 2013/0237916 A1 | 9/2013 | Hanson et al. | |
| 2013/0331791 A1 | 12/2013 | Gross et al. | |
| 2014/0200510 A1 | 7/2014 | Agard et al. | |
| 2014/0213975 A1 | 7/2014 | Clemente et al. | |
| 2014/0288511 A1 | 9/2014 | Tan-Malecki et al. | |
| 2014/0296787 A1 | 10/2014 | Agard et al. | |
| 2014/0316337 A1 | 10/2014 | Kadamus et al. | |
| 2015/0057613 A1 | 2/2015 | Clemente et al. | |
| 2015/0190588 A1 | 7/2015 | Hanson et al. | |
| 2015/0209505 A1 | 7/2015 | Hanson et al. | |
| 2015/0217045 A1 | 8/2015 | Bente, IV et al. | |
| 2015/0290390 A1 | 10/2015 | Ring et al. | |
| 2015/0297827 A1 | 10/2015 | Hanson et al. | |
| 2015/0359965 A1 | 12/2015 | O'Connor et al. | |
| 2015/0374919 A1 | 12/2015 | Gibson | |
| 2016/0082189 A1 | 3/2016 | Anderson et al. | |
| 2016/0175515 A1 | 6/2016 | McCullough | |
| 2016/0175527 A1 | 6/2016 | McCullough | |
| 2017/0361015 A1 | 12/2017 | McCullough | |
| 2018/0021508 A1 | 1/2018 | Destefano et al. | |
| 2018/0028747 A1 | 2/2018 | Hanson et al. | |
| 2018/0036476 A1 | 2/2018 | McCullough et al. | |
| 2018/0085517 A1 | 3/2018 | Laurence et al. | |
| 2018/0353682 A1 | 12/2018 | Laurence et al. | |

FOREIGN PATENT DOCUMENTS

| | | | |
|---|---|---|---|
| JP | S4828863 | A | 4/1973 |
| JP | S53146489 | A | 12/1978 |
| JP | 2008245505 | A | 10/2008 |
| JP | 2010533525 | A | 10/2010 |
| JP | 2014510571 | A | 5/2014 |
| WO | WO-2009010399 | A1 | 1/2009 |
| WO | WO-2011/075100 | A1 | 6/2011 |
| WO | WO-2011/133823 | A1 | 10/2011 |
| WO | WO-2013/040032 | A1 | 3/2013 |
| WO | WO-2013/033467 | A3 | 4/2013 |
| WO | WO-2013/033421 | A3 | 6/2013 |
| WO | WO-2014/036308 | A2 | 3/2014 |
| WO | WO-2014/116274 | A1 | 7/2014 |
| WO | WO-2015/027174 | A4 | 4/2015 |
| WO | WO-2015/061386 | A1 | 4/2015 |
| WO | WO-2015061389 | A1 | 4/2015 |
| WO | WO-2015/091761 | A1 | 6/2015 |
| WO | WO-2015/171777 | A1 | 11/2015 |
| WO | WO-2015187793 | A1 | 12/2015 |
| WO | WO-2015187797 | A1 | 12/2015 |
| WO | WO-2015187799 | A1 | 12/2015 |
| WO | WO-2015187802 | A1 | 12/2015 |
| WO | WO-2016/003813 | A1 | 1/2016 |
| WO | WO-2016/033496 | A1 | 3/2016 |
| WO | WO-2016/049501 | A1 | 3/2016 |
| WO | WO-2016/049532 | A1 | 3/2016 |
| WO | WO-2015/187805 | A3 | 4/2016 |
| WO | WO-2016/033507 | A3 | 4/2016 |
| WO | WO-2016/053954 | A8 | 6/2016 |
| WO | WO-2016/100781 | A1 | 6/2016 |
| WO | WO-2016/130679 | A2 | 8/2016 |
| WO | WO-2016/133947 | A1 | 8/2016 |
| WO | WO-2016/141082 | A1 | 9/2016 |
| WO | WO-2016/145094 | A3 | 11/2016 |
| WO | WO-2016/186706 | A1 | 11/2016 |
| WO | WO-2017/093803 | A1 | 6/2017 |
| WO | WO-2017/106247 | A1 | 6/2017 |
| WO | WO-2017/139003 | A1 | 8/2017 |
| WO | WO-2017/139573 | A1 | 8/2017 |

OTHER PUBLICATIONS

European Patent Application No. 21154819, Communication Pursuant to Article 94(3) EPC, dated Oct. 17, 2023.
Taiwan Patent Application No. 110109360, Office Action and Search Report, dated Dec. 7, 2021.
Japanese Patent Application No. 2022-078231, Decision of Rejection, mailed Dec. 19, 2023.
Australian Patent Application No. 2022203334, Office Action, dated Jun. 15, 2023.
U.S. Appl. No. 17/386,659, Nonfinal Office Action, dated May 10, 2023.
U.S. Appl. No. 17/386,659, Nonfinal Office Action, dated Jan. 25, 2024.
Japanese Patent Application No. 2022-010712, Office Action, dated Jan. 10, 2023.
International Search Report and Written Opinion for International Application No. PCT/US2017/026524, mailed Sep. 22, 2017.
International Search Report and Written Opinion for International Application No. PCT/US2017/017627, mailed Jul. 27, 2017.
Taiwan Patent Application No. 106104660, Office Action and Search Report, dated May 4, 2020.
European Patent Application No. 21154819, Extended European Search Report, dated Apr. 29, 2021.

(56) References Cited

OTHER PUBLICATIONS

U.S. Appl. No. 16/089,685, Nonfinal Office Action, dated Dec. 18, 2020.

U.S. Appl. No. 16/071,873, Nonfinal Office Action, dated Jul. 6, 2021.

* cited by examiner

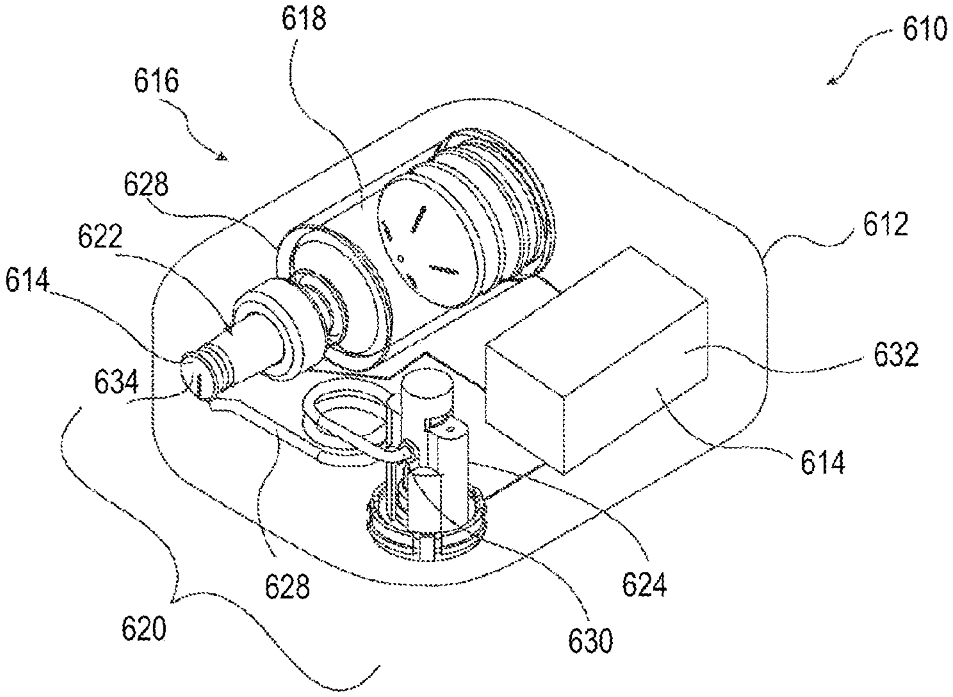

FIG. 25

| Fluid Pathway Connection with Drug Container | Fluid Pathway Connection Attachment to Needle Insertion Mechanism | Fill-Finish Cartridge Alignment | Carrier |
|---|---|---|---|
| Mounted | Snap | Axial fill and use | None |
| Integrated | Threaded | Axial fill and non-axial use | Integrated |
| Other | Interference | Non-axial fill and axial use | Fully Disposable |
| | Tongue and groove | Non-axial fill and use | Partially Disposable |
| | External support | | |
| | Other | | |

FIG. 26B

| | | | | | | |
|---|---|---|---|---|---|---|
| Total Variation from Model | 354 | s | 5 m 54 s | Viscosity Inputs | | |
| Total Variation from Linearized Contribution | 261 | s | 4 m 21 s | Min | Nom | Max |
| % Variation Captured in Linearized Form | 74% | | | 6.89 | 12.12 | 22.7 |

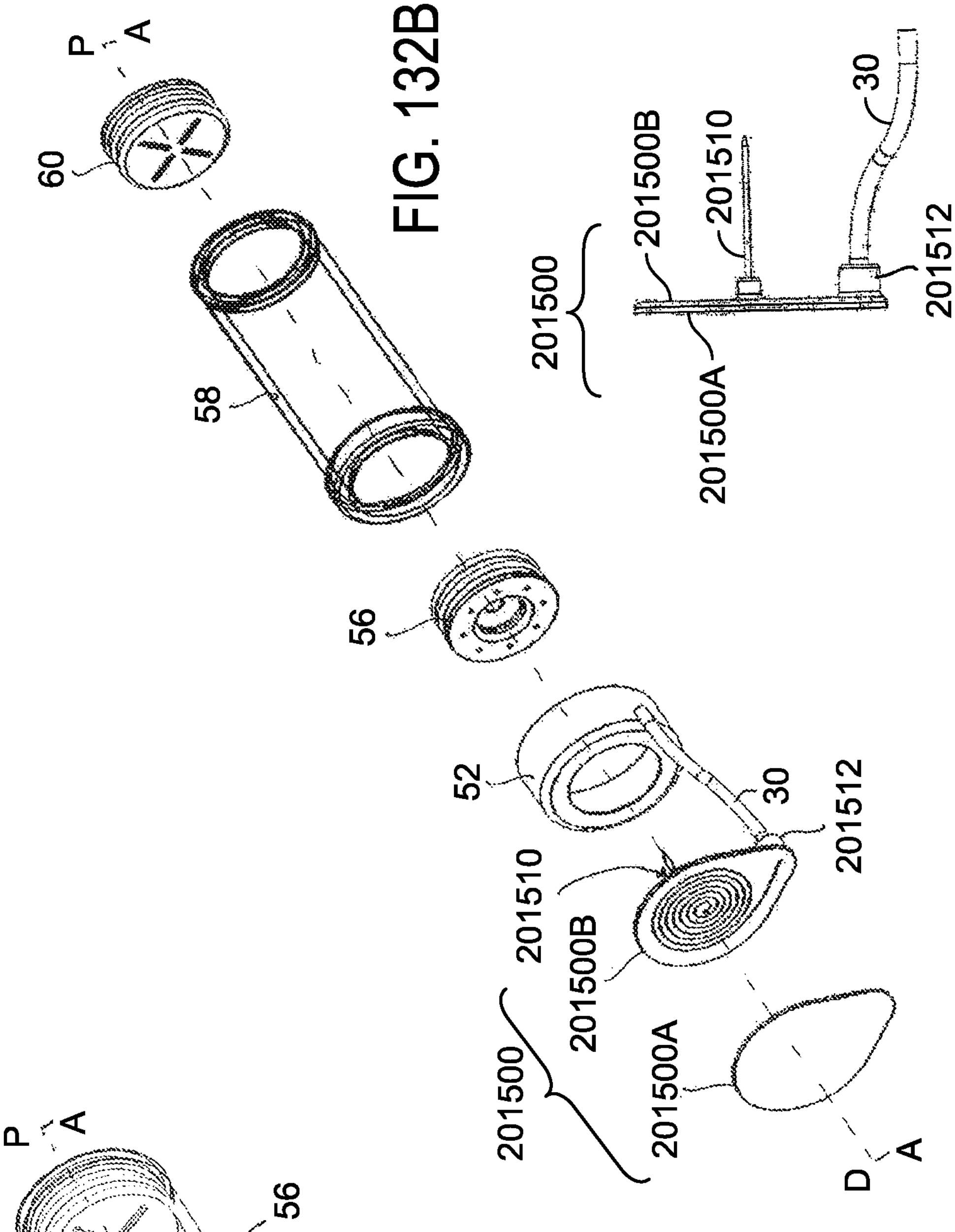
FIG. 132B
FIG. 132C
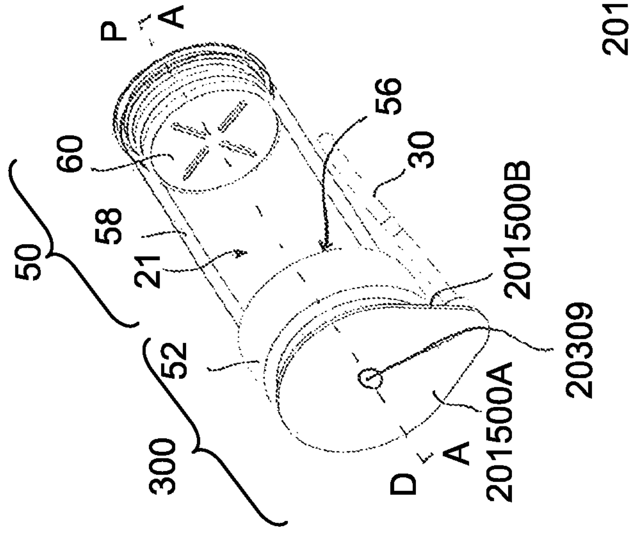
FIG. 132A

22200

DRUG DELIVERY DEVICE, METHOD OF MANUFACTURE, AND METHOD OF USE

CROSS-REFERENCE TO RELATED APPLICATIONS

This application is a continuation of U.S. patent application Ser. No. 16/071,873, filed Jul. 20, 2018, which is the U.S. national phase of International Patent Application No. PCT/US2017/017627, having an international filing date of Feb. 13, 2017, which claims the priority benefit of each of U.S. Provisional Patent Application No. 62/294,842, filed Feb. 12, 2016, U.S. Provisional Patent Application No. 62/297,718, filed Feb. 19, 2016, and U.S. Provisional Patent Application No. 62/320,438, filed Apr. 8, 2016. The entire contents of each of the foregoing are expressly incorporated by reference herein for all purposes.

FIELD OF THE DISCLOSURE

The present disclosure generally relates to drug delivery devices and, more particularly, a drug delivery device capable of being worn by a patient while the drug delivery device delivers a drug to the patient.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

There is a strong market demand for drug delivery devices which are easy-to-use, cost-efficient, and which include integrated safety features. However, manufacturing of such devices can be cost intensive, which results in higher costs to patients. Much of the manufacturing costs can be attributed to the need to maintain a sterile fluid pathway from the drug container to the needle, prior to introduction of the drug to the patient. Some commercial products seek to maintain the sterility of the device by manufacturing the components in a non-sterile environment and then sterilizing the entire device. A recognized downside of such processes is the need to separately fill the drug container after device sterilization but prior to drug injection, as most pharmaceutical compounds are not capable of withstanding the device sterilization process. Alternatively, the drug delivery device may be manufactured as a pre-filled device, wherein the device is filled with the drug aseptically during assembly. Such manufacturing processes may be costly since the entire process must be kept sterile and because the fill and assembly lines need to be specially-tailored for the device. Accordingly, this adds substantial operating costs to pharmaceutical companies and contract drug-fillers.

Drug delivery devices are generally prepared by molding or shaping the various components and then assembling the components. The assembling steps and other processing operations typically produce a device that subsequently must be cleaned to remove particulates adhering to the surfaces to satisfy cleanliness standards for drug delivery devices. After cleaning, conventional drug delivery devices are packaged and sterilized. Such delivery devices have been classified into several general types. The first type is assembled and placed in sterile packaging which can be shipped with a vial or ampoule of a drug or other injectable solution. The delivery device is filled with the drug or other solution at the point of use and injected into the patient. These devices have the disadvantage of increasing the time and difficulty of filling the device at the point of use, increasing the risk of contamination of the delivery device and/or drug solution, and increasing the likelihood of accidental spills of the drug. There is a further risk of glass particles from the ampoules contaminating the drug solution when the ampoules are opened. Furthermore, the healthcare provider and/or patient may be require training to ensure that they fill the device properly Several of these disadvantages are overcome by providing prefilled delivery devices which can be filled with a suitable drug solution prior to use. Prefilled delivery devices, as the term is known in the art, are devices that are filled by the drug manufacturer and shipped to the health care provider or self-administering patient in a condition that is ready for use. The vial or ampoule is generally made of glass or other clear material that does not interfere with the stability of the drug during prolonged storage. Prefilled delivery devices have the advantage of convenience and ease of application with reduced risk of contamination of the drug solution. Prefilled drug delivery devices are generally assembled and packaged in clean rooms to maintain proper cleanliness levels. The clean rooms are equipped with extensive filter assemblies and air control systems to remove particulates and pyrogens from the air in the room and to prevent particulates and pyrogens from entering the room. The operators and other personnel in the clean room are required to wear appropriate protective garments to reduce contamination of the air and the drug delivery devices being manufactured or assembled. As people and equipment enter and leave the clean room, the risk of contamination and introduction of foreign particulates and pyrogens increases. Various operations are able to form clean and sterile drug delivery devices. However, subsequent handling, filling and printing of the drug delivery device can contaminate the device. It is then necessary to clean and sterilize such conventional drug delivery devices before use. Accordingly, there is a continuing need in the industry for an improved system for manufacturing and assembling clean and sterile medical devices and filling such devices.

SUMMARY

One aspect of the present disclosure provides a wearable drug delivery device including a housing, a container disposed in the housing, a drug disposed in the container, an insertion mechanism disposed in the housing, a fluid pathway connector defining a sterile fluid flowpath between the container and the insertion mechanism, a needle, and a cannula initially disposed around the needle. The drug may include at least one of: a PCSK9 (Proprotein Convertase Subtilisin/Kexin Type 9) specific antibody, a granulocyte colony-stimulating factor (G-CSF), a sclerostin antibody, or a calcitonin gene-related peptide (CGRP) antibody. The fluid pathway connector may include a flexible fluid conduit. The insertion mechanism may include a wall stationarily fixed relative to the housing, a manifold guide movable relative to the wall, an insertion biasing member initially held in an energized state between the wall and the manifold, a hub connected to the needle, a retraction biasing member initially held in an energized state between the hub and the manifold, a flexible clip initially holding the retraction biasing member in the energized state, and a manifold connected to the manifold guide and movable between a first position and a second position. The manifold may have an internal chamber and a septum. The cannula and the flexible fluid conduit may each be in fluid communication with the internal chamber of the manifold. The cannula and the flexible fluid conduit may each be connected to the manifold such that the cannula and the flexible fluid conduit each moves relative to the wall of the insertion mechanism when the manifold moves between the first position and the second position.

Another aspect of the present disclosure provides a wearable drug delivery device including a housing, a container disposed in the housing, a drug, a needle, an insertion mechanism, and a fluid pathway connector defining a sterile fluid flowpath between the container and the insertion mechanism. The container may include a barrel, a plunger seal moveable through the barrel, and a pierceable seal. The drug may be disposed in the barrel of the container. The drug may include at least one of: a PCSK9 specific antibody, a G-CSF, a sclerostin antibody, or a CGRP antibody. The insertion mechanism may be configured to move the needle from a retracted position to an inserted position. The fluid pathway connector may include a connection hub, a piercing member connected to the connection hub, and a sterile sleeve having a first end connected to the connection hub and a second end connected to the container. The piercing member may be initially retained within the sterile sleeve between the connection hub and the pierceable seal of the container.

Yet another aspect of the present disclosure provides a cartridge to be assembled in a drug delivery device. The cartridge may include a container having a longitudinal axis, a drug disposed in the container, a needle, an insertion mechanism, and a fluid pathway connector defining a sterile fluid flowpath between the container and the insertion mechanism. The drug may include at least one of: a PCSK9 specific antibody, a G-CSF, a sclerostin antibody, or a CGRP antibody. The insertion mechanism may be configured to move the needle from a retracted position to an inserted position. The fluid pathway connector may have: (i) a first configuration, prior to assembly of the cartridge in the drug delivery device, where the insertion mechanism is aligned with the longitudinal axis, and (ii) a second configuration, after assembly of the cartridge in the drug delivery device, where the insertion mechanism is not aligned with the longitudinal axis.

An additional aspect of the present disclosure provides a method of manufacturing a drug delivery device. The method may include: (a) fluidly coupling a container and a needle insertion mechanism with a fluid pathway connector; (b) sterilizing the fluid pathway connector, the container, and the needle insertion mechanism, separately or together, to create a sterile fluid flow path between the container and the needle insertion mechanism; (c) disposing a drug in the container after fluidly coupling the container and the needle insertion mechanism with the fluid pathway connector; and (d) disposing the container, the needle insertion mechanism, and the fluid pathway in a housing of the drug delivery device. The drug may include at least one of: a PCSK9 specific antibody, a G-CSF, a sclerostin antibody, or a CGRP antibody.

Another aspect of the present disclosure provides a method of manufacturing a cartridge for a drug delivery device. The method may include: (a) fluidly coupling a container and a needle insertion mechanism with a fluid pathway connector; (b) sterilizing the fluid pathway connector, the container, and the needle insertion mechanism, separately or together, to create a sterile fluid flow path between the container and the needle insertion mechanism; and (c) disposing a drug in the container after fluidly coupling the container and the needle insertion mechanism with the fluid pathway connector. The drug may include at least one of: a PCSK9 specific antibody, a G-CSF, a sclerostin antibody, or a CGRP antibody.

Another aspect of the present disclosure provides a method of drug administration. The method may include: (a) providing a wearable drug delivery device including a container, a needle and a drug disposed in the container; (b) removably attaching the wearable drug delivery device to a patient's skin; and (c) activating the wearable drug delivery device to insert a pointed end of the needle into the patient to define an injection site and discharging the drug from the container into the patient at the injection site. The drug may include at least one of: a PCSK9 specific antibody, a G-CSF, a sclerostin antibody, or a CGRP antibody.

An additional aspect of the present disclosure provides a method of operating a wearable drug delivery device. The method may include: (a) displacing an activation mechanism to disengage one or more lockout pins from corresponding lockout windows of an insertion mechanism housing, wherein such disengagement permits an insertion biasing member to expand in a distal direction substantially along a longitudinal axis of the insertion mechanism housing, wherein such expansion drives insertion of a needle and a cannula into the body of a patient; (b) disengaging one or more release surfaces of a clip from engagement with a hub retained within a manifold guide within the insertion mechanism housing, wherein such disengagement permits a retraction biasing member to expand in a proximal direction substantially along the longitudinal axis of the insertion mechanism housing, wherein such expansion drives retraction of the needle while retaining the cannula in the body of the patient; (c) establishing fluid communication between a fluid pathway connector having a piercing member and a container having a pierceable seal, wherein a drug is disposed in the container; and (d) activating a drive mechanism to force the drug through the fluid pathway connector, the cannula, and into the body of the patient. The drug may include at least one of: a PCSK9 specific antibody, a G-CSF, a sclerostin antibody, or a CGRP antibody.

Another aspect of the present disclosure provides a wearable drug delivery device including a container, a drug disposed in the container, and a drive mechanism. The drug may include at least one of: a PCSK9 specific antibody, a G-CSF, a sclerostin antibody, or a CGRP antibody. The drive mechanism may include: a drive housing having an axial aperture, a contact sleeve slidably mounted to the drive housing through the axial aperture of the drive housing, a status switch interconnect, a drive biasing member, and a piston. The contact sleeve may have a contact sleeve proximal end, a contact sleeve distal end, and sleeve hooks at the contact sleeve distal end. The piston may have a piston proximal end, a piston distal end, an interface surface, and a contact protrusion near the piston proximal end. The sleeve hooks may be caused to contact the piston between the interface surface and the contact protrusion during operation of the wearable drug delivery device. The drive biasing member may be configured to bear upon the interface surface of the piston.

Another aspect of the present disclosure provides a wearable drug delivery device including a container, a drug, a needle, an insertion mechanism configured to move the needle from a retracted position to an inserted position; and a fluid pathway connector defining a sterile fluid flowpath between the container and the insertion mechanism. The container may include a barrel, a plunger seal moveable through the barrel, and a pierceable seal. The pierceable seal may include a first internal chamber accessible through a first aperture formed in the pierceable seal. The drug may be disposed in the barrel of the container. The drug may include at least one of: a PCSK9 specific antibody, a G-CSF, a sclerostin antibody, or a CGRP antibody. The fluid pathway connector may include: a connection hub having a second internal chamber accessible through a second aperture formed in the connection hub; a first film attached to the connection hub to cover the second aperture and maintain sterility of the second internal chamber; a second film attached to the container to cover the first aperture and maintain sterility of the first internal chamber; and a piercing member at least partially disposed in the second internal chamber and configured to pierce the first film and the second film in response to activation of the wearable drug delivery device.

Yet another aspect of the present disclosure provides a wearable drug delivery device including a container, a drug disposed in the container, a needle, an insertion mechanism configured to move the needle from a retracted position to an inserted position, and a fluid pathway connector defining a sterile fluid flowpath between the container and the insertion mechanism. The drug may include at least one of: a PCSK9 specific antibody, a G-CSF, a sclerostin antibody, or a CGRP antibody. The insertion mechanism includes: a housing having an internal chamber, a shell disposed in the internal chamber, a rotational biasing member initially held in an energized state with at least a portion of the rotational biasing member engaged with the housing, a hub connected to a proximal end of the needle, and a retraction biasing member initially held in an energized state between the hub and the shell.

An additional aspect of the present disclosure provides a wearable drug delivery device including a container, a drug, and a drive mechanism. The container may include a barrel, a plunger seal configured to move axially within the barrel, and a pierceable seal. The drug may be disposed in the barrel of the container. The drug may include at least one of: a PCSK9 specific antibody, a G-CSF, a sclerostin antibody, or a CGRP antibody. The drive mechanism may include: an actuator; a gear assembly; a piston connected to the plunger seal and configured to move axially within the barrel, a biasing member initially retained in an energized state; and a tether. The biasing member may be configured to expand to impart axial movement to the piston when released from the energized state. The tether may have a first end and a second end connected to, respectively, the piston and the gear assembly. The tether may be configured to restrain expansion of the biasing member when the biasing member is released from the energized state, such that the tether restrains axial movement of the piston within the barrel.

An additional aspect of the present disclosure provides a drug delivery device including an insertion mechanism, a drive mechanism, a sterile fluid pathway, and a drug container comprising a drug. The device may be configured to delivery to a human patient about 2 mL of the drug at a flow rate of up to about 12 mL per minute. The drug may include at least one of a sclerostin antibody or a calcitonin gene-related peptide (CGRP) antibody.

Another aspect of the present disclosure provides a drug delivery device including a means for delivering a drug to a patient of about 2 mL at a flow rate of up to about 12 mL per minute. The drug includes at least one of a sclerostin antibody or a calcitonin gene-related peptide (CGRP) antibody.

Yet another aspect of the present disclosure provides a method of administering a drug including: (a) contacting a human patient with a drug delivery device configured to deliver about 2 mL of a drug at a flow rate of up to about 12 mL per minute, wherein the drug comprises at least one of a sclerostin antibody or a calcitonin gene-related peptide (CGRP) antibody; and (b) actuating the drug delivery device to deliver the drug to the patient.

Another aspect of the present disclosure provides a wearable drug delivery device including a container, a drug, a needle, an activation member manually operable by a patient, an insertion mechanism, a fluid pathway connector, a locking assembly, and a selector. The drug may be disposed in the container. The drug may include at least one of: a PCSK9 specific antibody, a G-CSF, a sclerostin antibody, or a CGRP antibody. The insertion mechanism may be configured to move the needle between a retracted position and an inserted position. The insertion mechanism may a rotatable housing and a rotational biasing member initially held in an energized state. The fluid pathway connector may define a sterile fluid flowpath between the container and the insertion mechanism. The locking assembly may have a lock configuration, where the locking assembly engages the rotatable housing to inhibit rotation of the rotatable housing, and an unlock configuration, where the locking assembly disengages the rotatable housing to permit rotation of the rotatable housing. The selector may have a first configuration, where the selector operatively decouples the activation member and the locking assembly, and a second configuration, where the selector operatively couples the activation member and the locking assembly to allow the activation member to change the locking assembly from the lock configuration to the unlock configuration.

An additional aspect of the present disclosure provides a wearable drug delivery device including a main housing, a container, a drug, a window, an introducer needle, a cannula, a drive mechanism, an insertion mechanism, a fluid pathway connector, a button, and a trigger assembly. The container may be disposed in the main housing. The container may include a barrel, a plunger seal moveable through the barrel, and a first pierceable seal controlling access to an interior of the barrel. The drug may be disposed in the barrel. The drug may include at least one of: a PCSK9 specific antibody, a G-CSF, a sclerostin antibody, or a CGRP antibody. The window may cover an opening in the main housing. At least a portion of the container may be visible through the window. The introduce needle may have a proximal end and a distal end. The cannula may be initially disposed around the distal end of the introducer needle. The drive mechanism may be disposed in the main housing. The drive mechanism may include: a drive housing, a piston moveable relative to the drive housing and configured to impart movement to the plunger seal, a piston biasing member disposed between the drive housing and the piston, and a first retainer. The piston biasing member may be initially retained in a piston biasing member energized state. The piston biasing member may be configured to move the piston as the piston biasing member de-energizes. The first retainer may be moveable between: (i) a first retainer retaining position, where the first retainer retains the piston biasing member in the piston biasing member energized state, and (ii) a first retainer releasing position, where the first retainer allows the piston biasing member to de-energize. The fluid pathway connector may define a sterile fluid flowpath between the container and the insertion mechanism. The fluid pathway connector may include a tubular conduit, a container access needle, and a connection hub. The tubular conduit may have a first end and a second end. The container access needle may be configured to pierce the first pierceable seal to establish fluid communication between the between the barrel and the tubular conduit during drug delivery. The connection hub may be connected to the container access needle and the first end of the tubular conduit. The connection hub may have a connection hub interior chamber providing fluid communication between the container access needle and the tubular conduit during drug delivery. The insertion mechanism may be disposed in the main housing. The insertion mechanism may include an insertion mechanism a manifold, a second pierceable seal, an insertion biasing member, a second retainer, a hub, a retraction biasing member, and a third retainer. The manifold may be moveable relative to the insertion mechanism housing. The manifold may be connected to the cannula and the second end of the tubular conduit, the manifold having a manifold internal chamber providing fluid communication between the tubular conduit and the cannula during drug delivery. The second pierceable seal may be connected to the manifold and control access to the manifold internal chamber. The distal end of the introducer needle may be disposed through the second pierceable seal. The insertion biasing member may be disposed between the insertion mechanism housing and the manifold. The insertion biasing member may be initially retained in an insertion biasing member energized state. The insertion biasing member may be configured to move the manifold in a distal direction as the insertion biasing member de-energizes. The second retainer may be moveable between: (i) a second retainer retaining position, where the second retainer retains the insertion biasing member in the insertion biasing member energized state, and (ii) a second retainer releasing position, where the second retainer allows the insertion biasing member to de-energize. The hub may be connected to the proximal end of the introducer needle. The retraction biasing member may be disposed between the hub and the manifold. The retraction biasing member may be initially retained in a retraction biasing member energized state. The retraction biasing member may be configured to move the hub in a proximal direction as the retraction biasing member de-energizes. The third retainer may be moveable between: (i) a third retainer retaining position, where the third retainer retains the retraction biasing member in the retraction biasing member energized state, and (ii) a third retainer releasing position, where the third retainer allows the retraction biasing member to de-energized. The button may protrude from the main housing and may be manually displaceable by a user. The trigger assembly may be configured to, in response to displacement of the button by the user, move: (i) the first retainer from the first retainer retaining position to the first retainer releasing position, and (ii) the second retainer from the second retainer retaining position to the second retainer releasing position.

Another aspect of the present disclosure provides a wearable drug delivery device including a main housing, a container, a drug, a window, an introducer needle, a cannula, a drive mechanism, an insertion mechanism, a fluid pathway connector, a button, and a trigger assembly. The container may be disposed in the main housing. The container may include a barrel, a plunger seal moveable through the barrel, and a first pierceable seal controlling access to an interior of the barrel. The drug may be disposed in the barrel. The drug may include at least one of: a PCSK9 specific antibody, a G-CSF, a sclerostin antibody, or a CGRP antibody. The window may cover an opening in the main housing, and at least a portion of the container may be visible through the window. The introducer needle may have a hollow interior, a proximal end, and a distal end. The drive mechanism may be disposed in the main housing. The drive mechanism may include a drive housing, a piston moveable relative to the drive housing and configured to impart movement to the plunger seal, a gear assembly, an electrical actuator, a gear interface, a piston biasing member, and a tether. The gear interface may be rotatable by the electrical actuator. Rotation of the gear interface may cause the gear interface to selectively engage the gear assembly to prevent or allow rotation of the gear assembly. The piston biasing member may be disposed between the drive housing and the piston. The piston biasing member may be initially retained in a piston biasing member energized state. The piston biasing member may be configured to move the piston as the piston biasing member de-energizes. The tether may be connected at opposite ends to the gear assembly and the piston. The tether may initially retain the piston biasing member in the piston biasing member energized state. Rotation of the gear assembly may create slack in the tether which allows the piston biasing member to de-energize. The a fluid pathway connector may define a sterile fluid flowpath between the container and the insertion mechanism. The fluid pathway connector may include a tubular conduit having a first end and a second end. The second end of the tubular conduit may be in fluid communication with the hollow interior of the introducer needle during drug delivery. The container access needle may be configured to pierce the first pierceable seal to establish fluid communication between the between the barrel and the tubular conduit during drug delivery. The connection hub may be connected to the container access needle and the first end of the tubular conduit. The connection hub may provide fluid communication between the container access needle and the tubular conduit during drug delivery. The insertion biasing mechanism may be disposed in the main housing. The insertion biasing mechanism may include a base, an insertion mechanism housing rotatable relative to the base, a rotational biasing member connected to the insertion mechanism housing, a first retainer, a hub, a retraction biasing member, and a second retainer. The rotational biasing member may be initially retained in a rotational biasing member energized state, the rotational biasing member being configured to rotate the insertion mechanism housing as the rotational biasing member de-energizes. The first retainer may be moveable between: (i) a first retainer retaining position, where the first retainer retains the rotational biasing member in the rotational biasing member energized state, and (ii) a first retainer releasing position, where the first retainer allows the rotational biasing member to de-energize. The hub may be connected to the proximal end of the introducer needle. The hub may be configured to translate relative to the insertion mechanism housing. The retraction biasing member may be disposed between the hub and the base. The retraction biasing member may have a retraction biasing member energized state. The retraction biasing member may be configured to translate the hub in a proximal direction as the retraction biasing member de-energizes. The second retainer may be moveable between: (i) a second retainer retaining position, where the second retainer retains the retraction biasing member in the retraction biasing member energized state, and (ii) a second retainer releasing position, where the second retainer allows the retraction biasing member to de-energize. The button may protrude from the main housing and may be manually displaceable by a user. The trigger assembly may be configured to move the first retainer from the first retainer retaining position to the first retainer releasing position in response to displacement of the button by the user.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. Also, none of the drawings is necessarily to scale.

FIG. 25 is an isometric view of a drug delivery device incorporating an embodiment of a fill-finish cartridge according to aspects of the disclosure;

FIG. 26B is a chart of exemplary combinations of components of a fill-finish cartridge according to aspects of the disclosure;

FIG. 69C shows an isometric view of the interior components of the drug delivery device shown in FIG. 69A (shown without the adhesive patch) from yet another viewpoint;

FIG. 69D shows a top view, along an axis "A," of the interior components of the drug delivery device shown in FIG. 69A;

FIG. 70A shows an isometric view of a multi-function drive mechanism, according to at least one embodiment of the present disclosure prior to activation;

FIG. 70B shows an isometric view of a multi-function drive mechanism, according to at least one embodiment of the present disclosure during activation;

FIG. 70C shows an isometric view of a multi-function drive mechanism, according to at least one embodiment of the present disclosure at a later stage during activation;

FIG. 70D shows an isometric view of a multi-function drive mechanism, according to at least one embodiment of the present disclosure near or at completion of drug delivery;

FIGS. 71A-71D show top views which correspond with the stages of operation shown in FIGS. 70A-70D, respectively;

FIG. 72 shows the multi-function drive mechanism, according to at least one embodiment of the present disclosure, in isolation from the drug delivery device;

FIGS. 73A-73B show top and bottom views, respectively, of the multi-function drive mechanism shown in FIG. 72;

FIGS. 73C-73D show front and back perspective views, respectively, of the multi-function drive mechanism shown in FIG. 72;

FIG. 74 illustrates a top view of an embodiment of an activation mechanism arranged in a lower housing of a drug delivery device;

FIG. 75 depicts an exploded assembly view of the activation mechanism shown in FIG. 74;

Figure 76A:
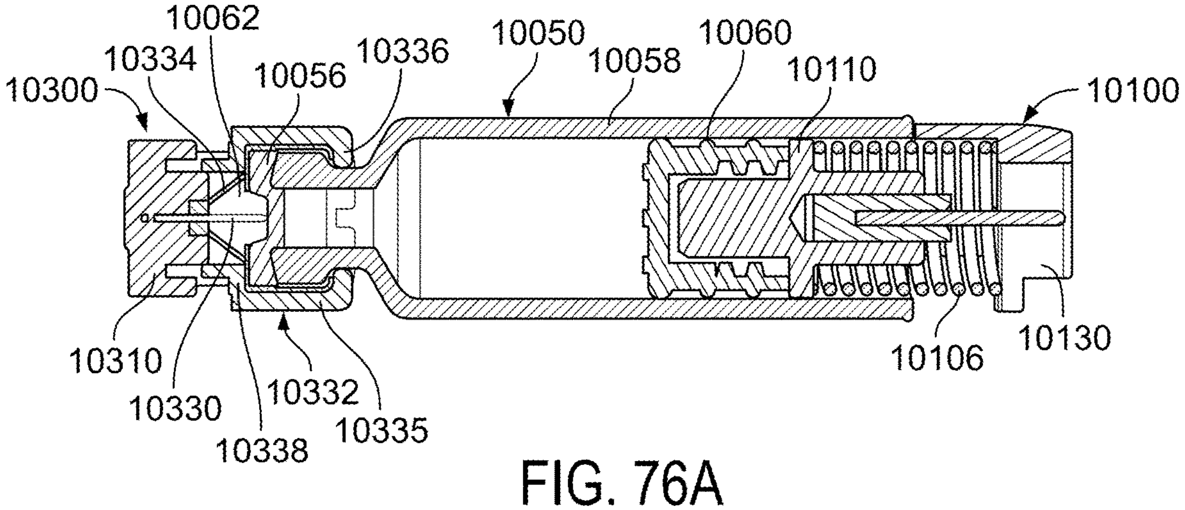
Figure 76B:
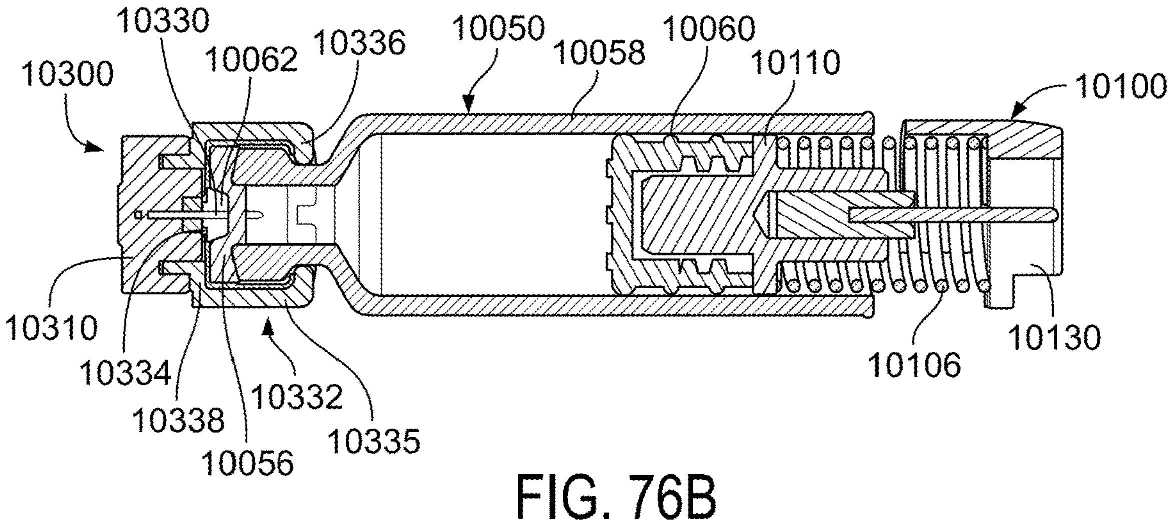
Figure 76C:
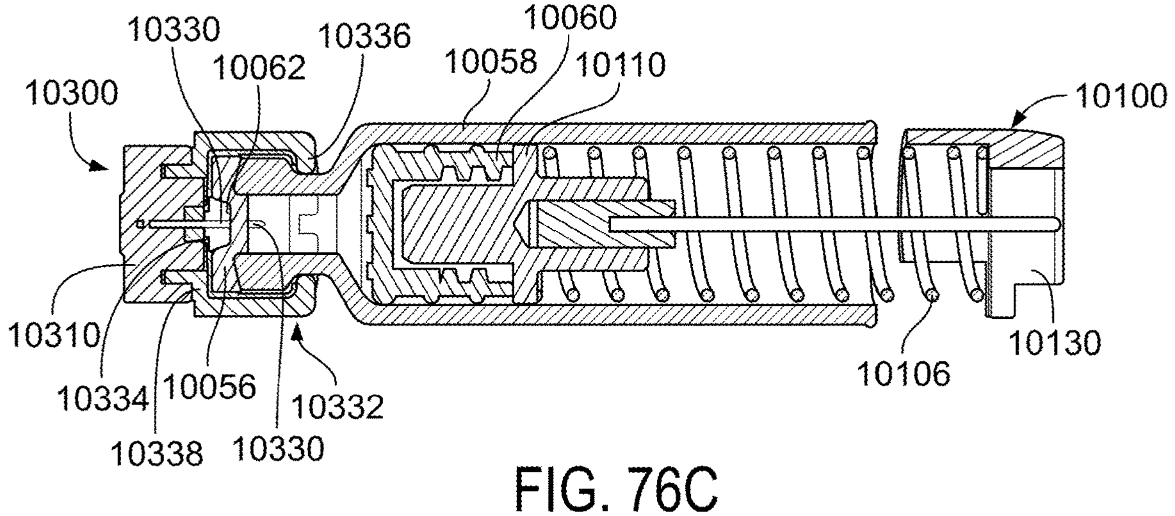
Figure 77:
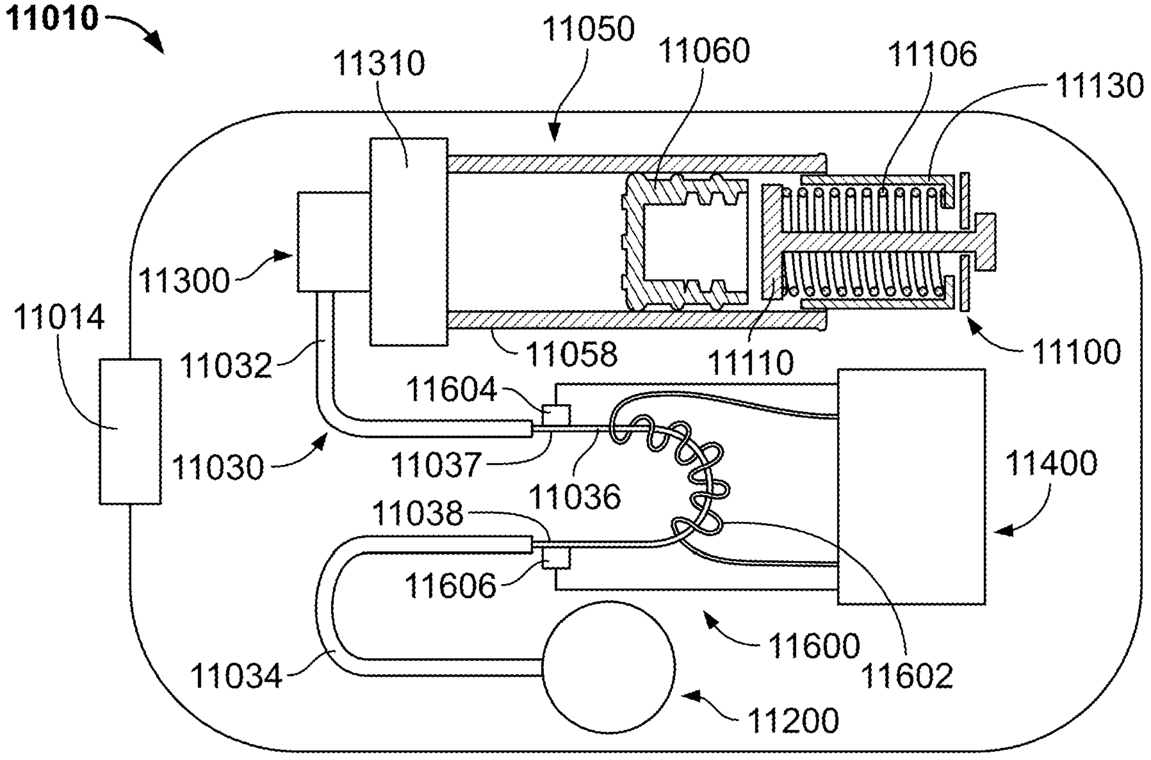
Figure 78A:
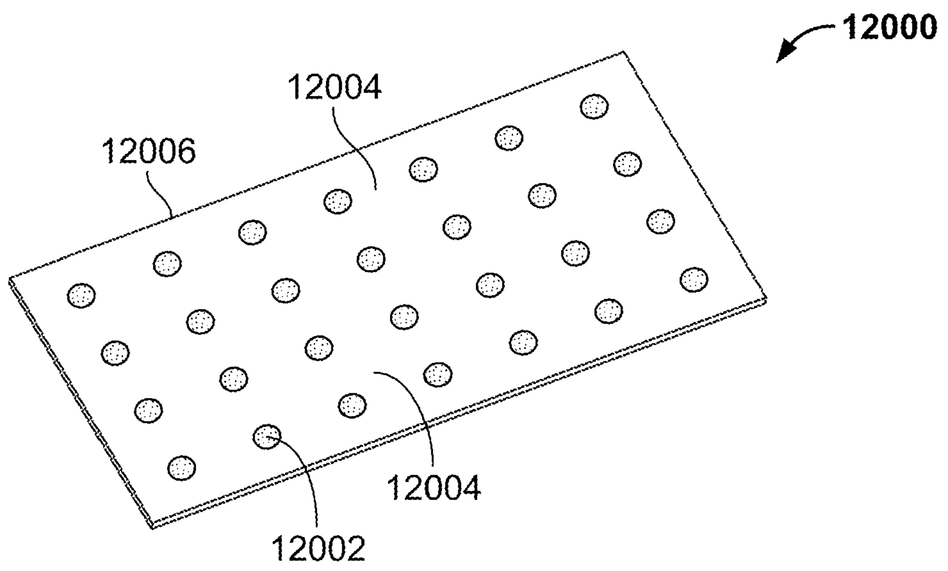
Figure 78B:
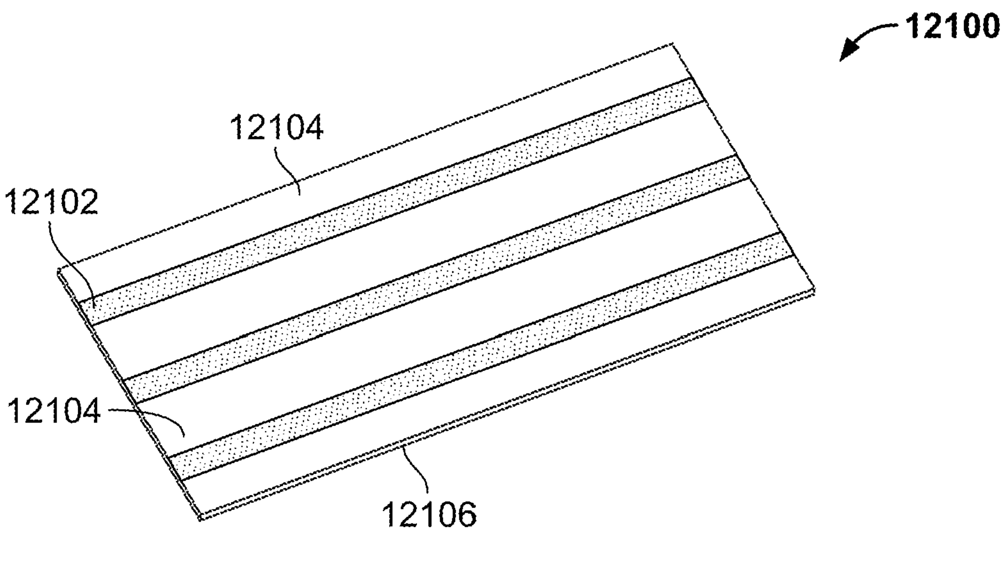
Figure 79:
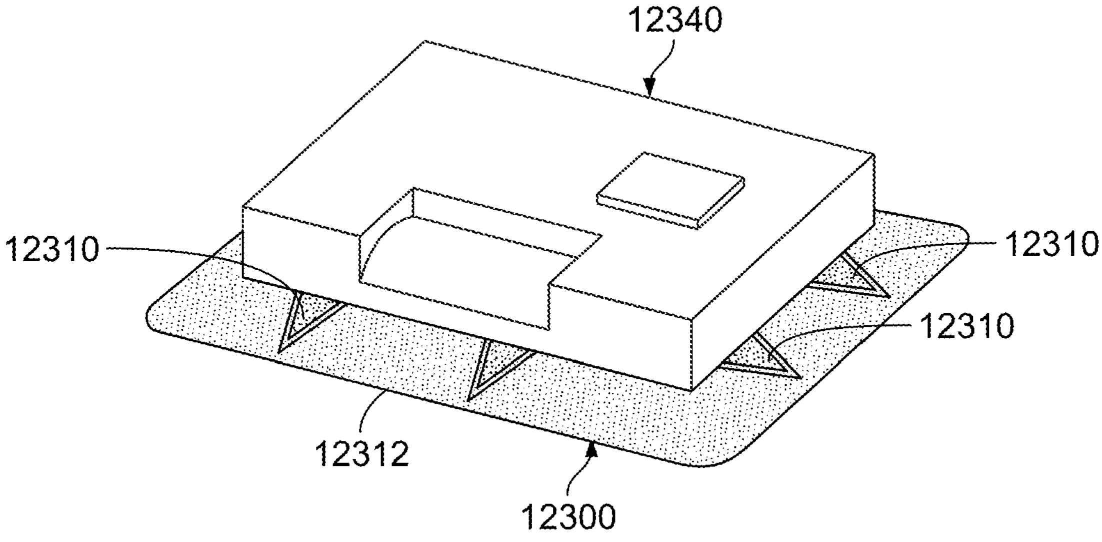
Figure 80A:
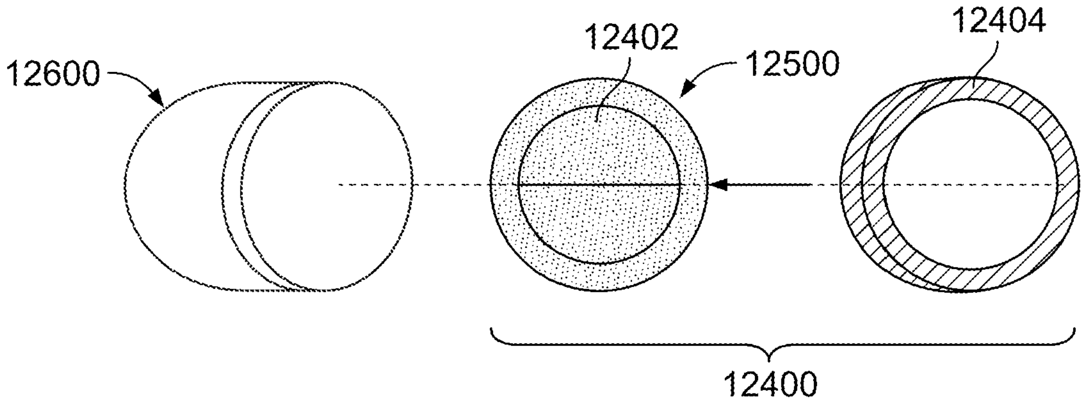
Figure 80B:
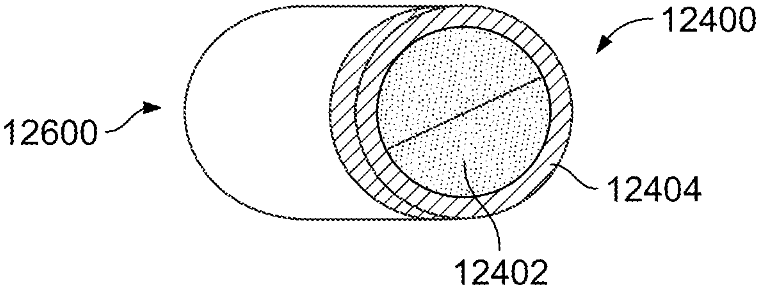
Figure 81:
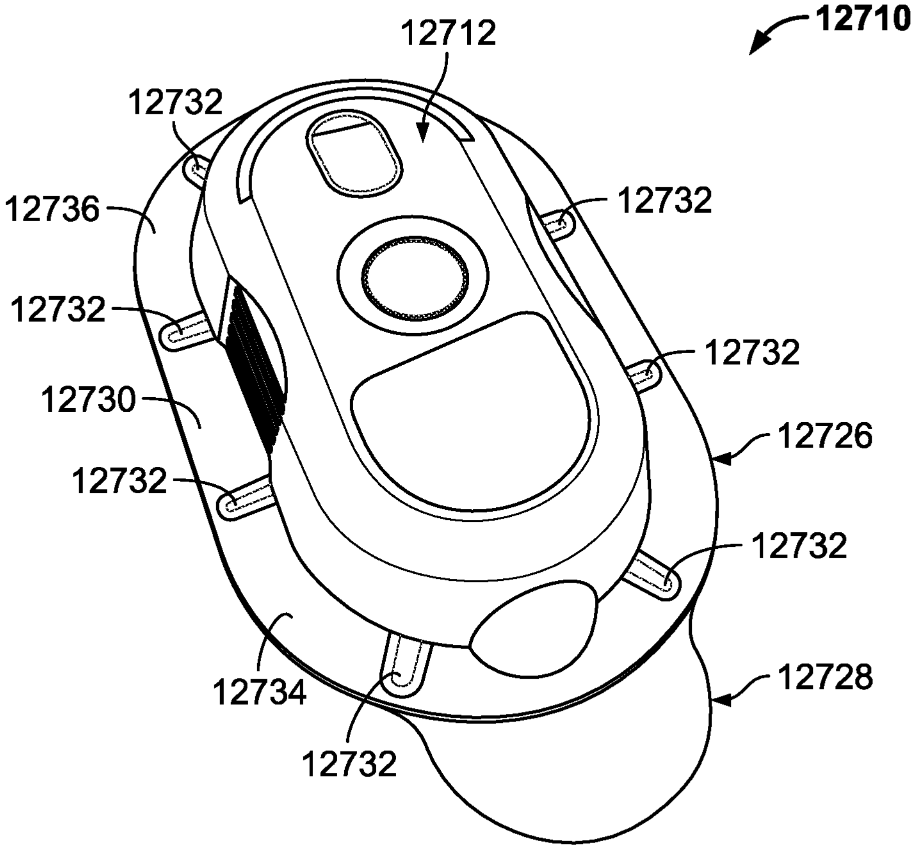
Figure 82:
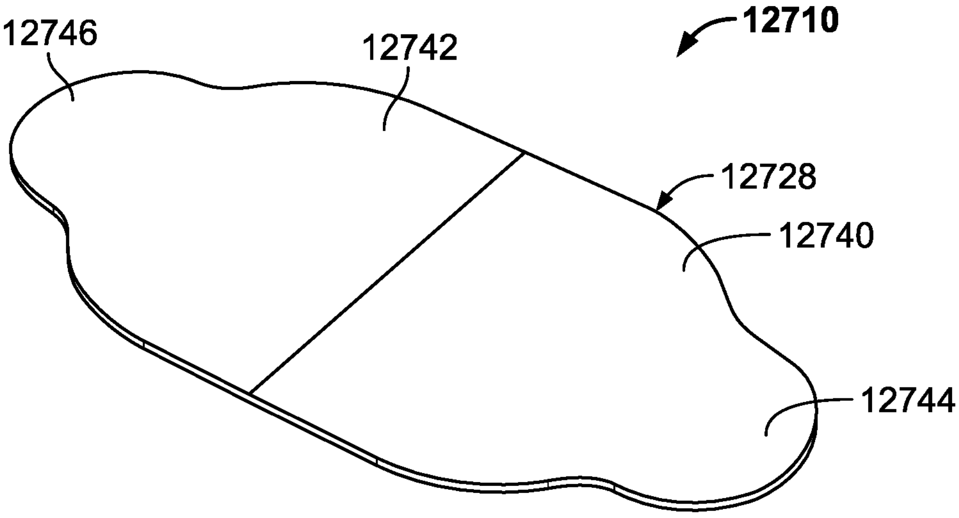
Figure 83A:
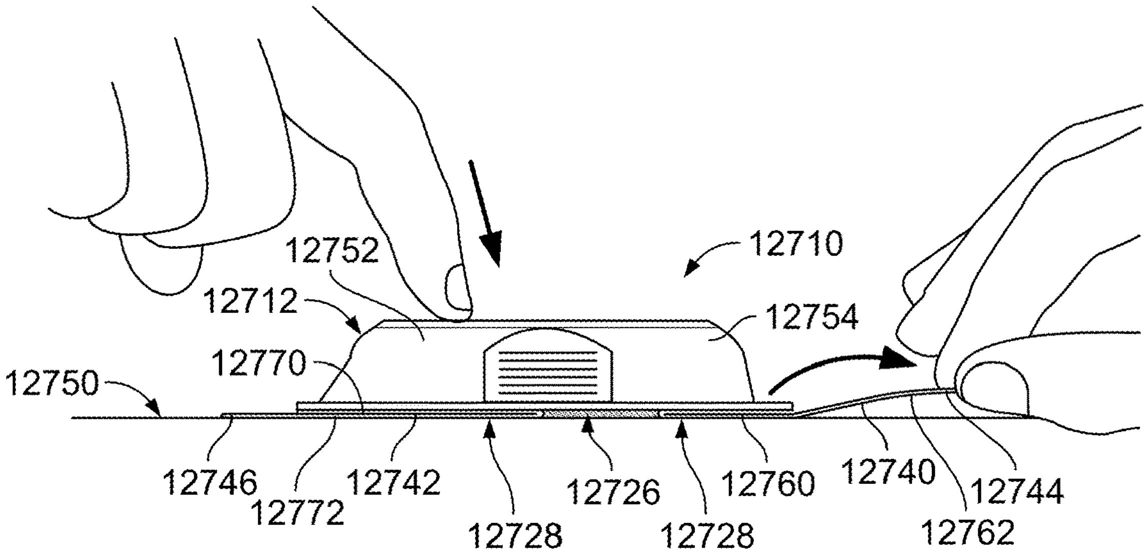
Figure 83B:
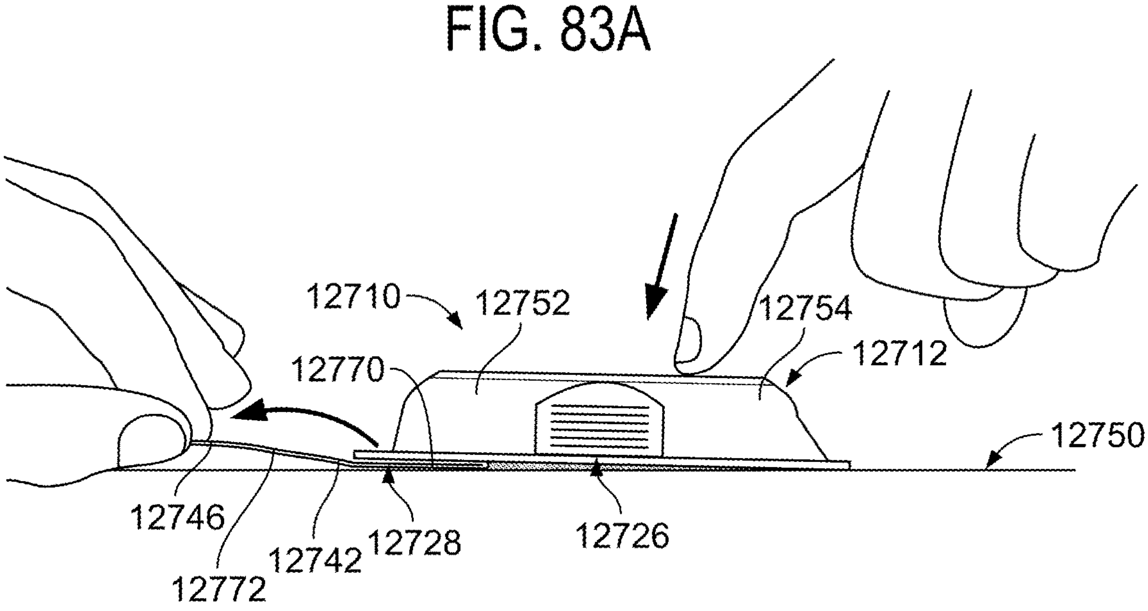
Figure 83C:
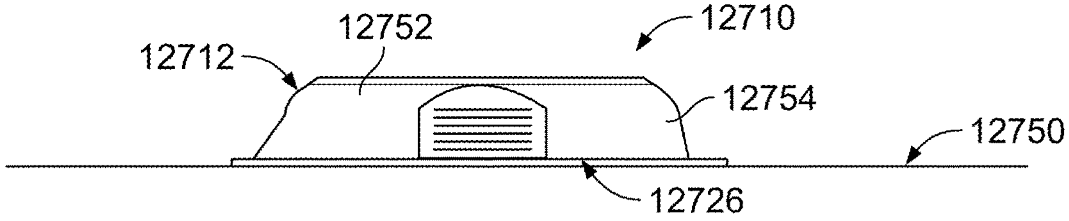
Figure 84:
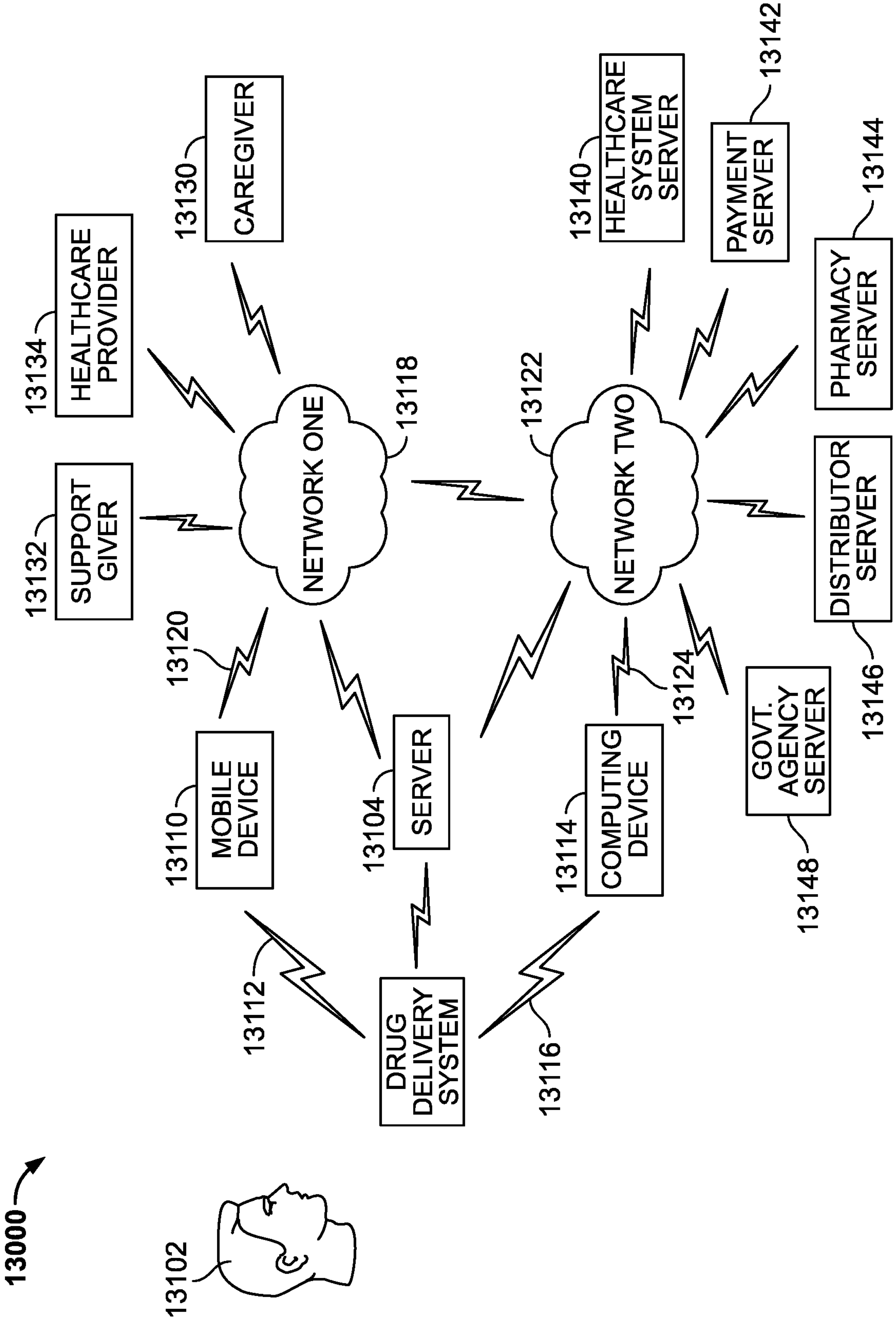
Figure 85A:
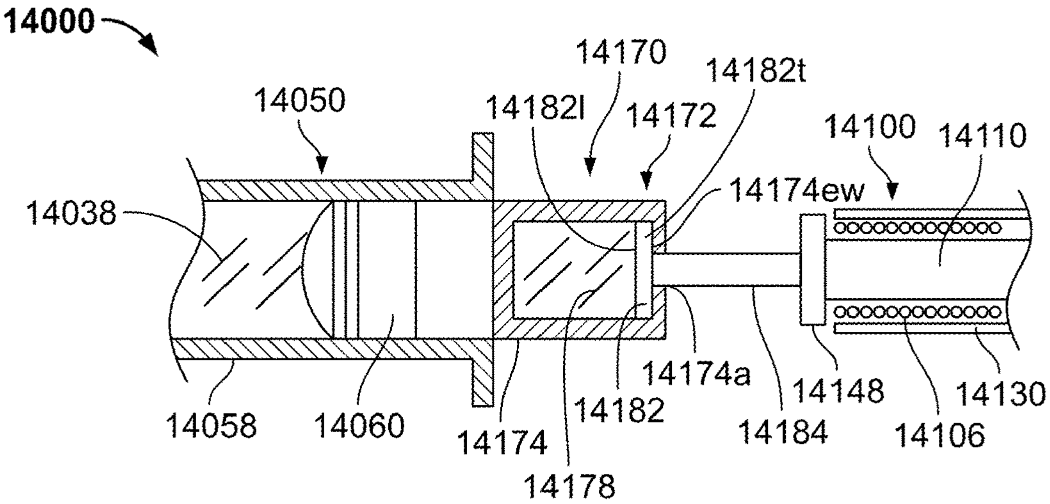
Figure 85B:
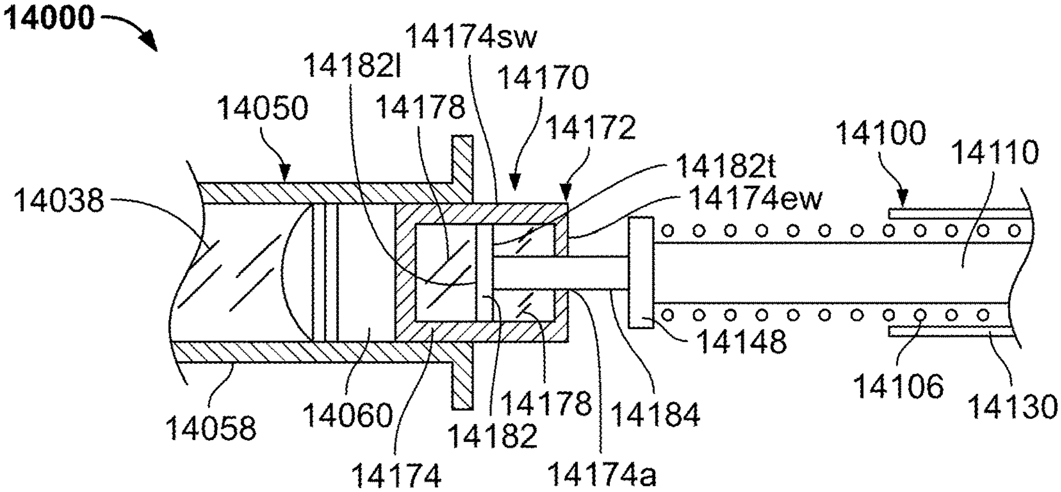
Figure 85C:
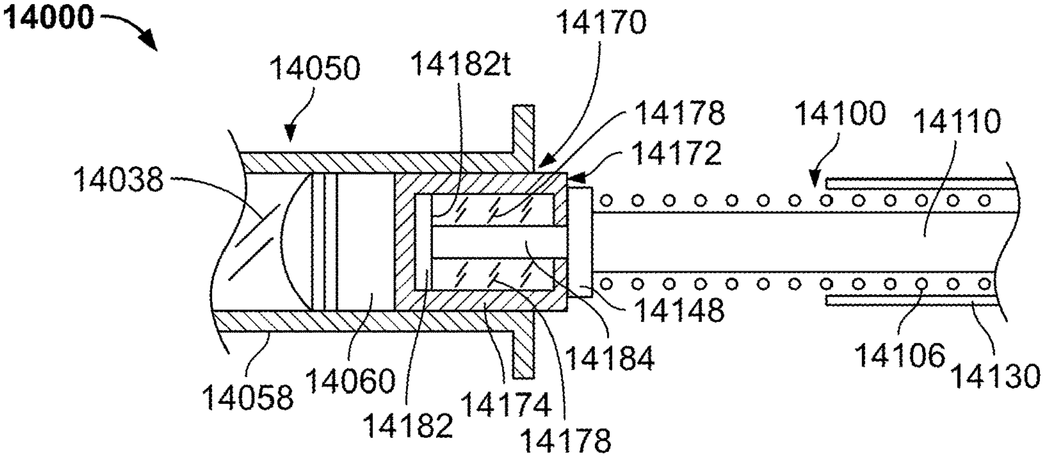
Figures 86A, 86B, 86C:
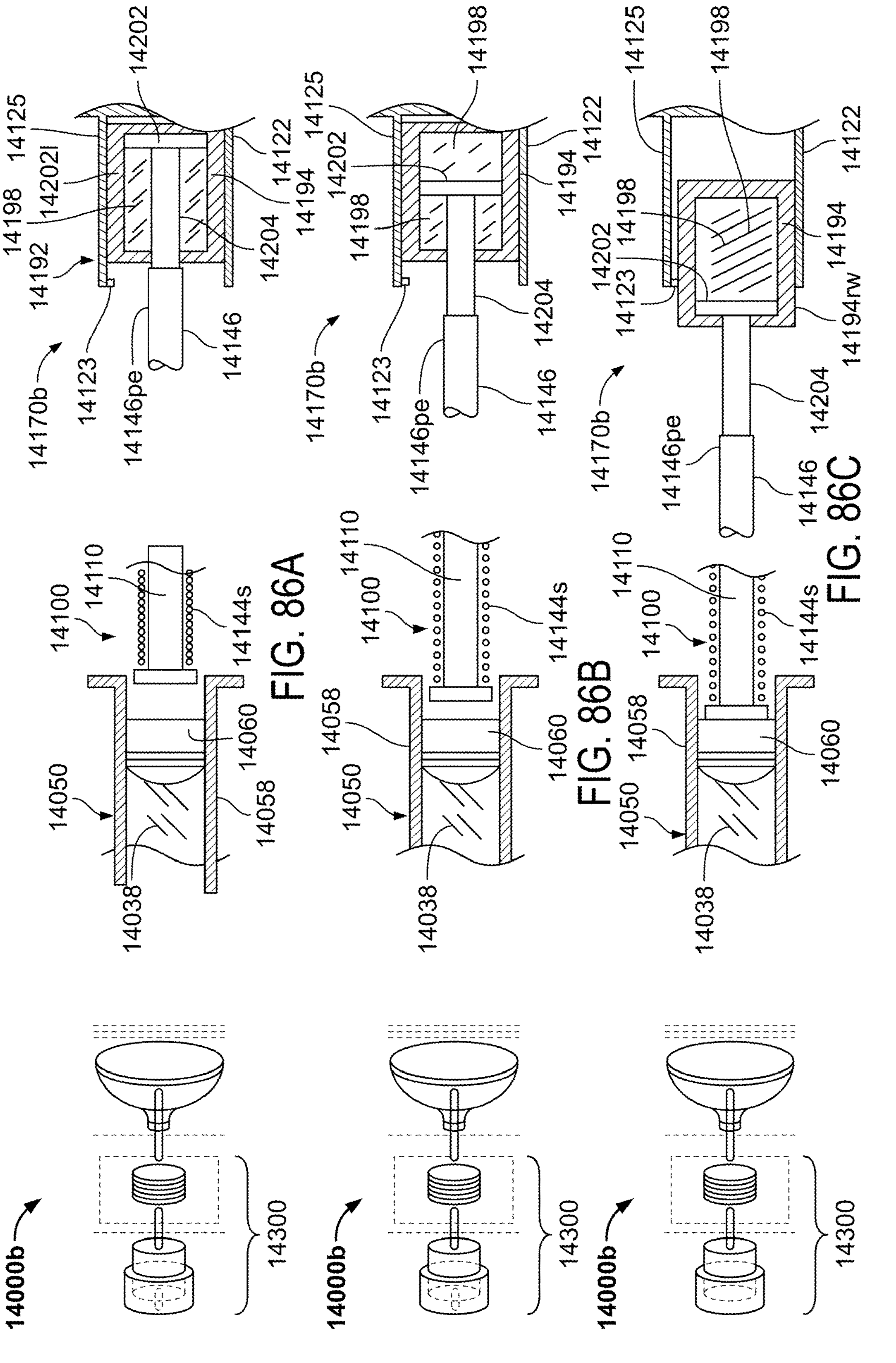
Figure 87A:
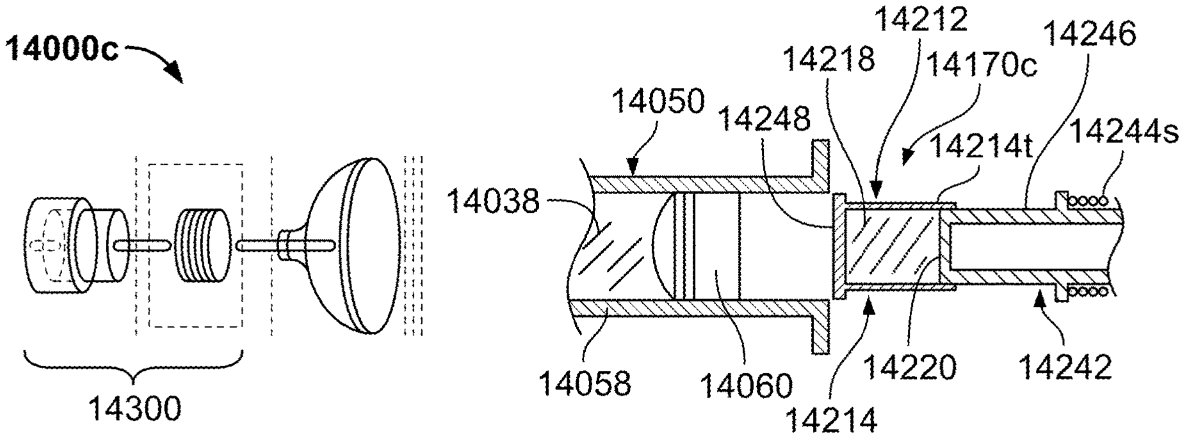
Figure 87B:
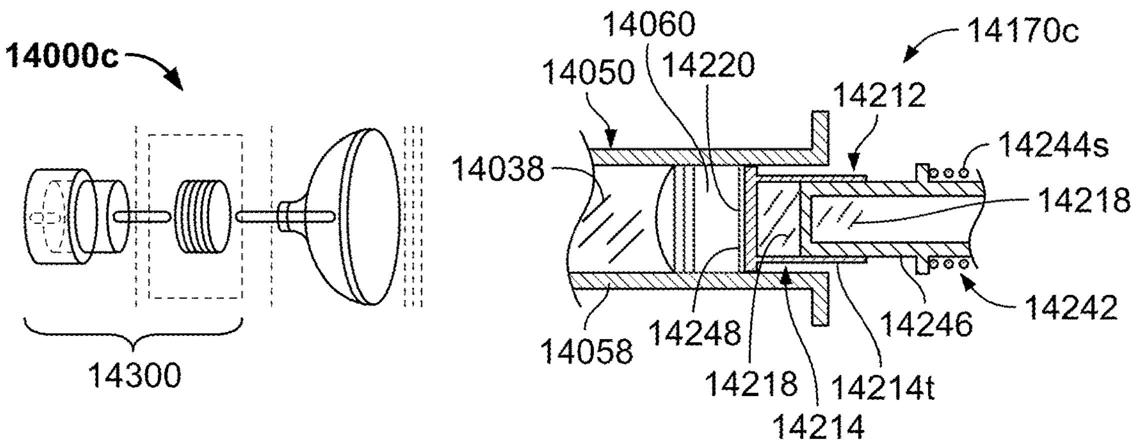
Figure 87C:
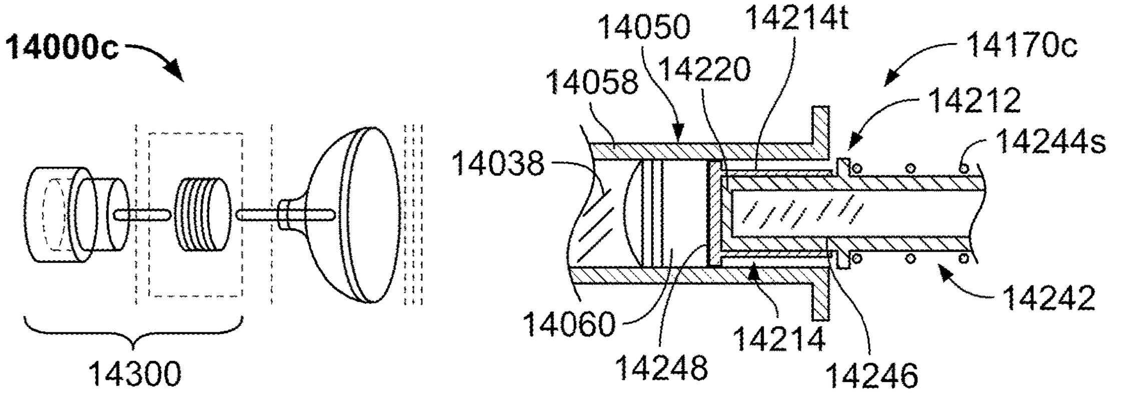
Figure 88:
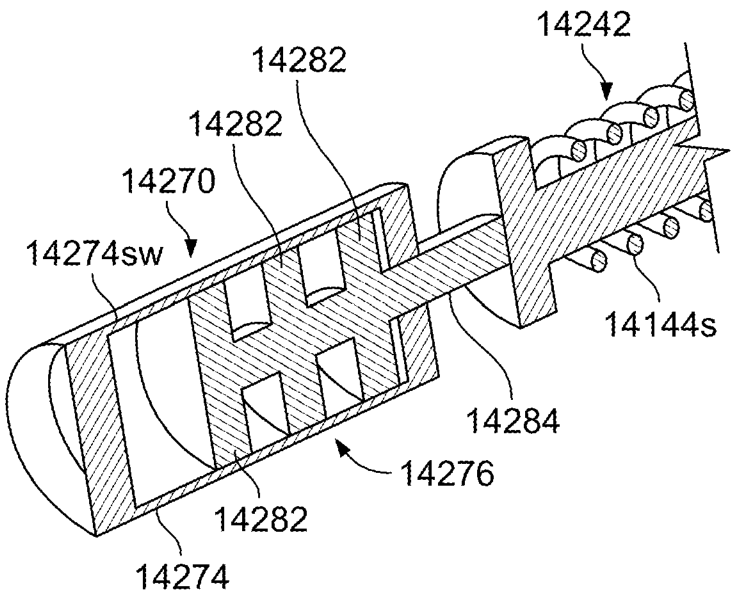
Figure 89:
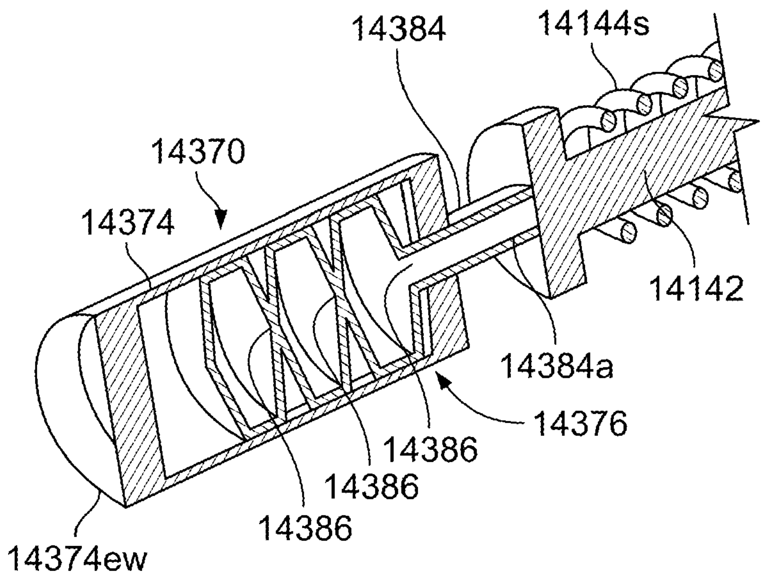
Figure 90:
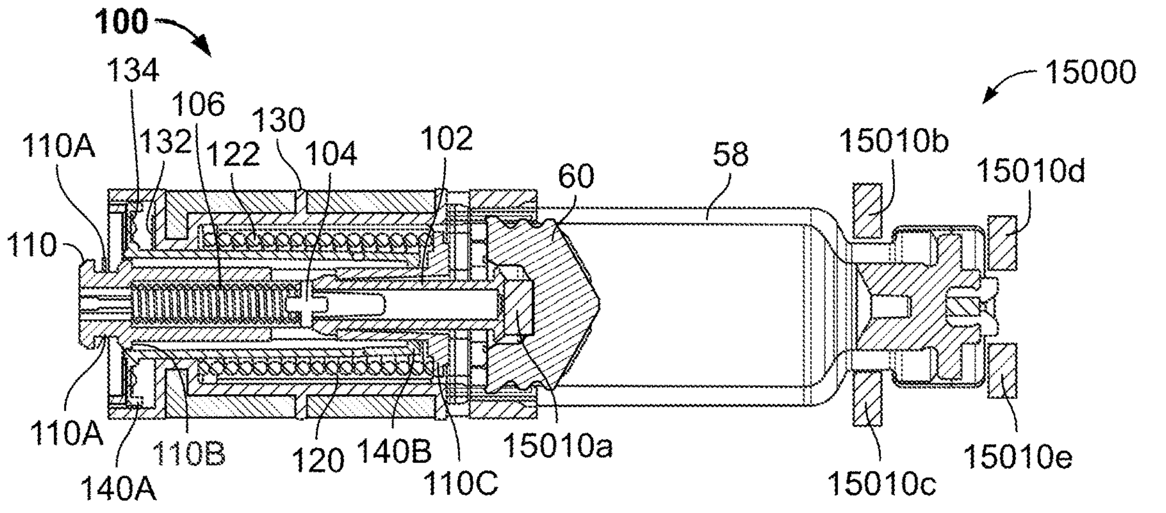
Figure 91A:
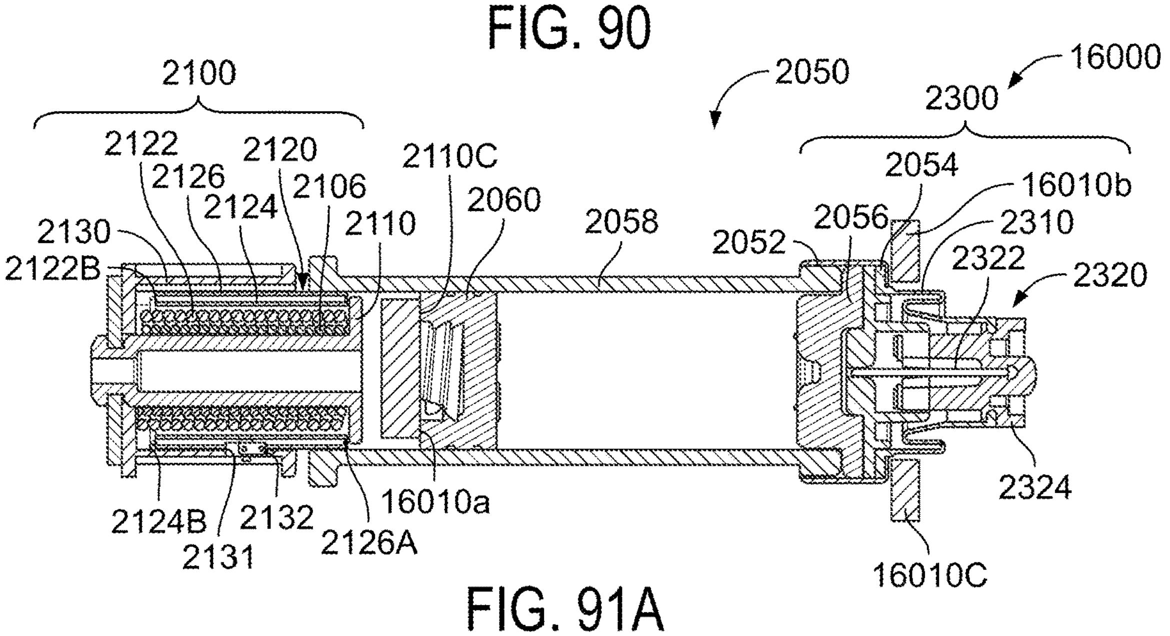
Figure 91B:
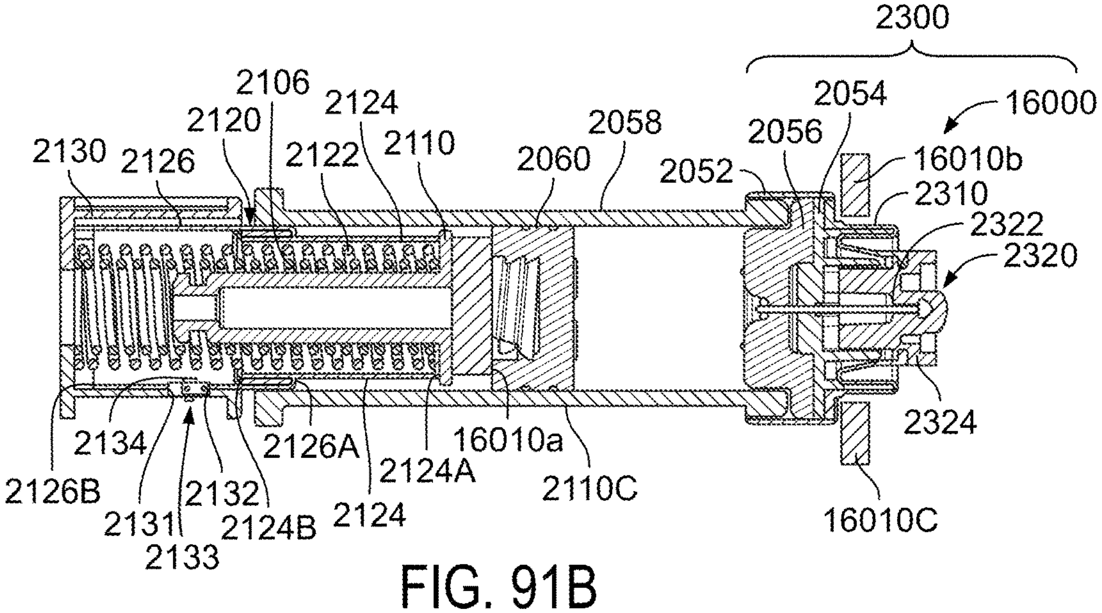
Figure 92:
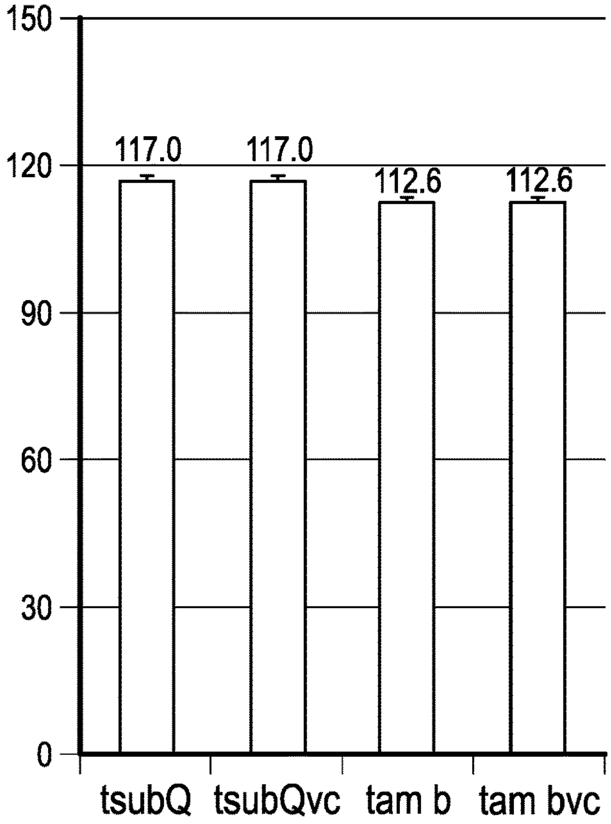
Figure 93:
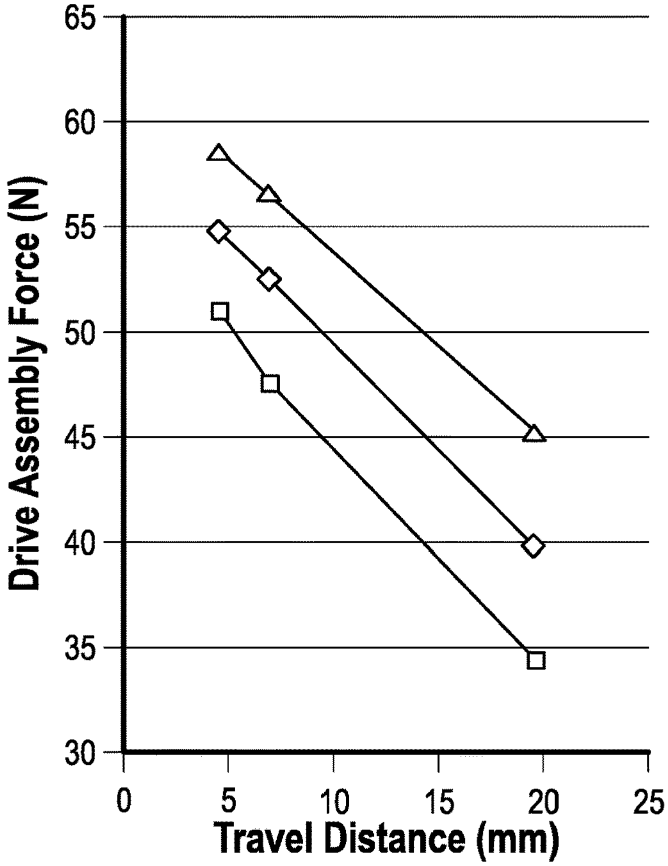
Figure 94:
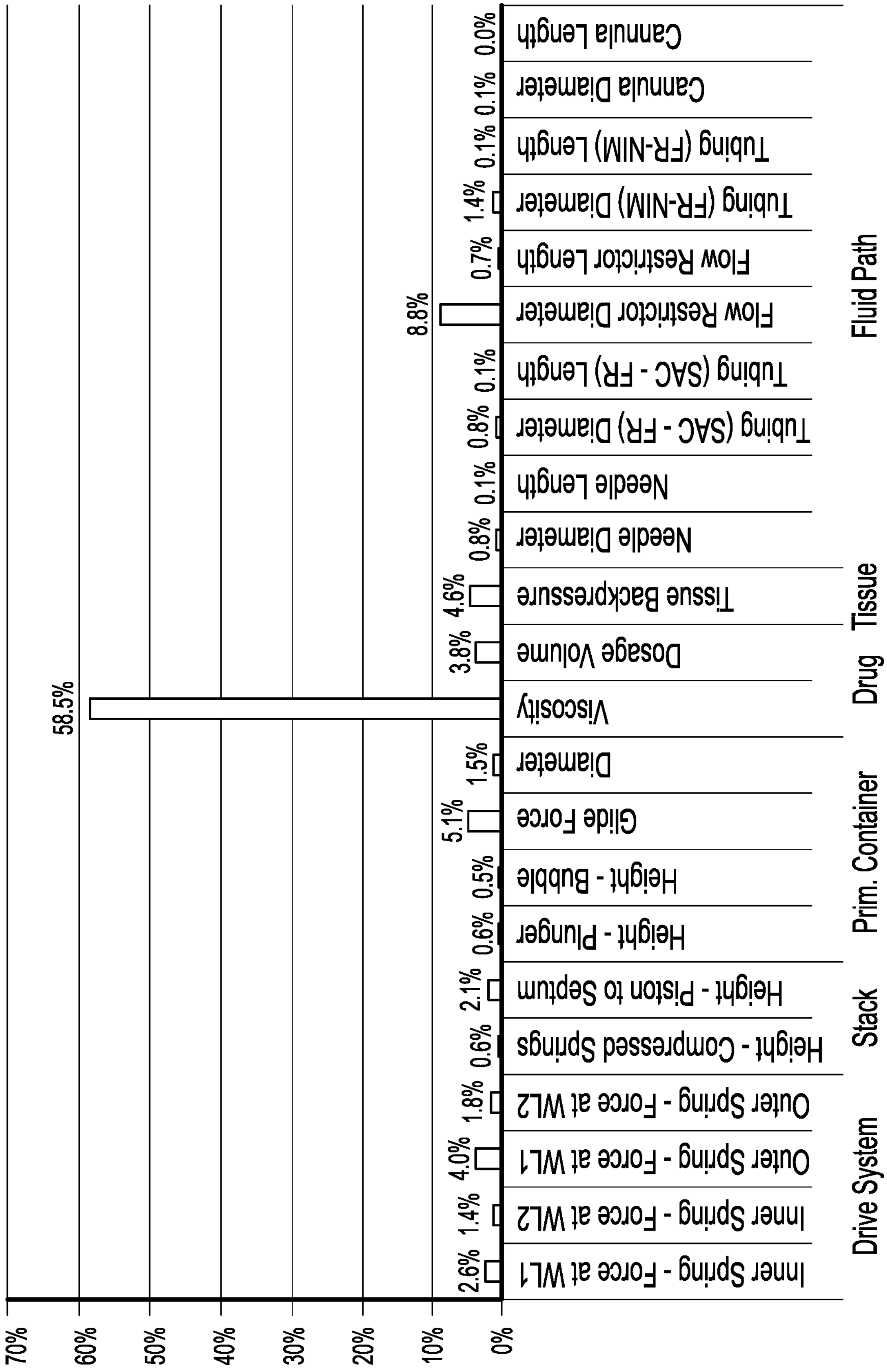
Figure 95:
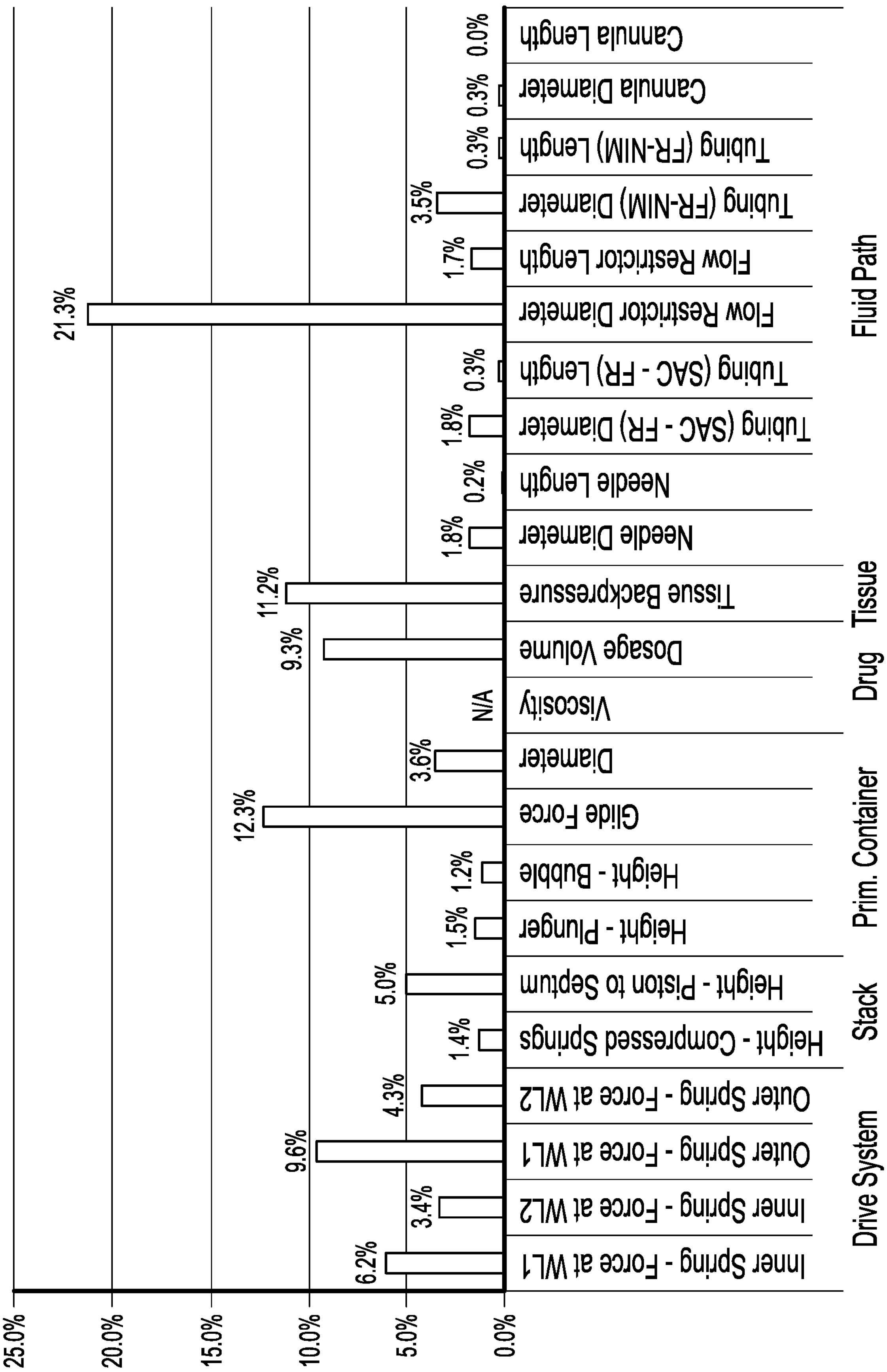
Figure 96:
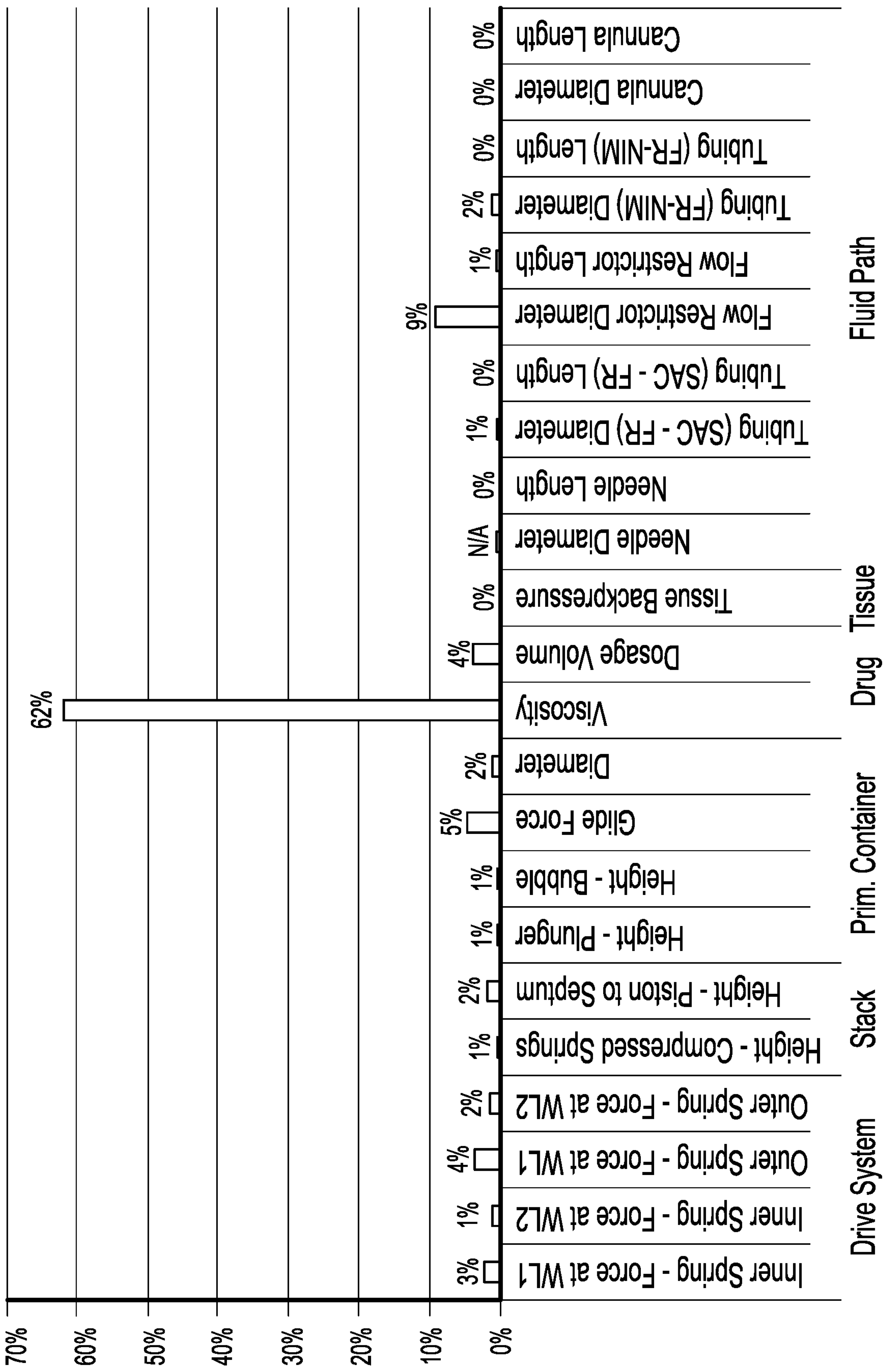
Figure 97:
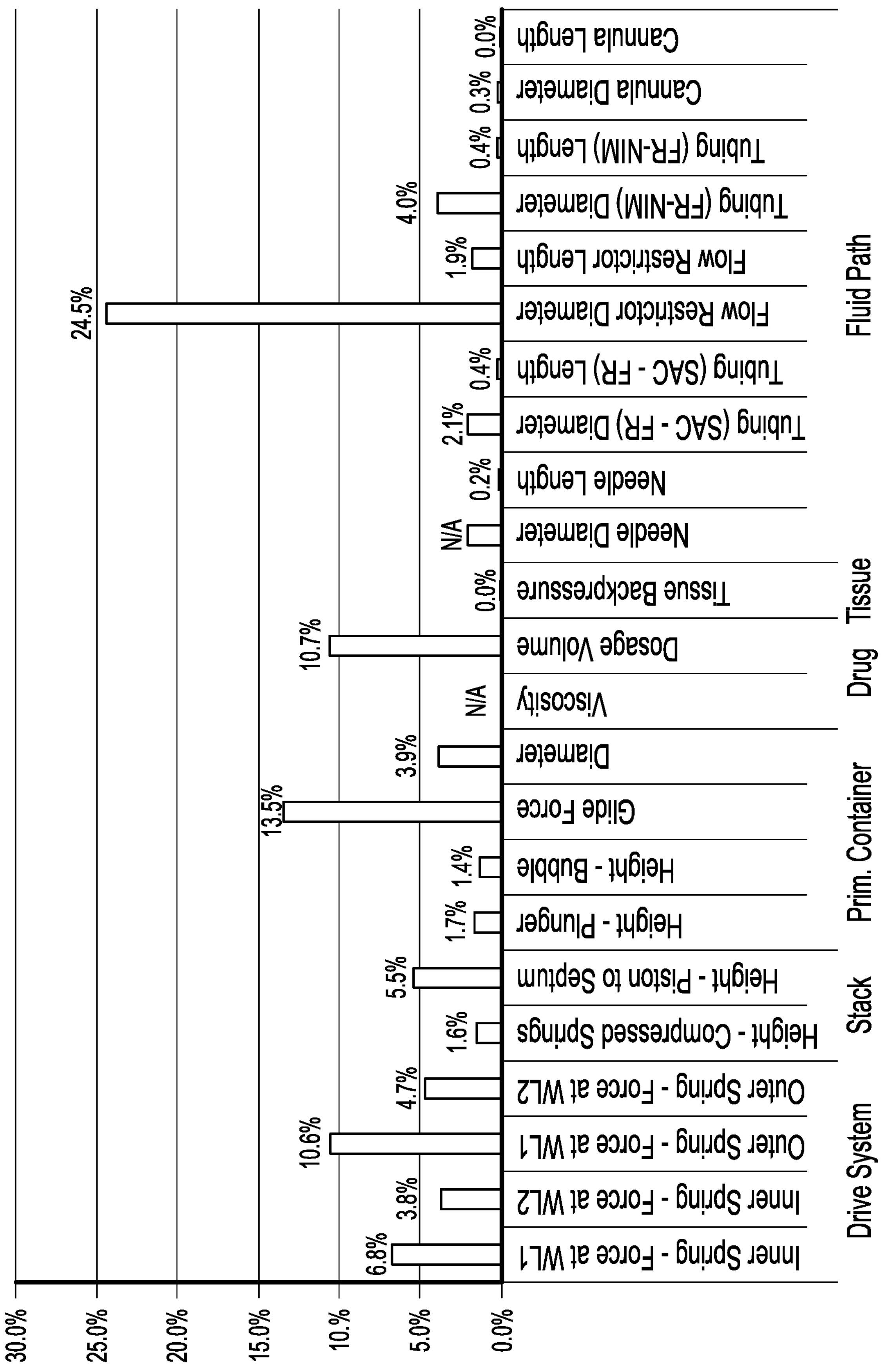
Figure 98:
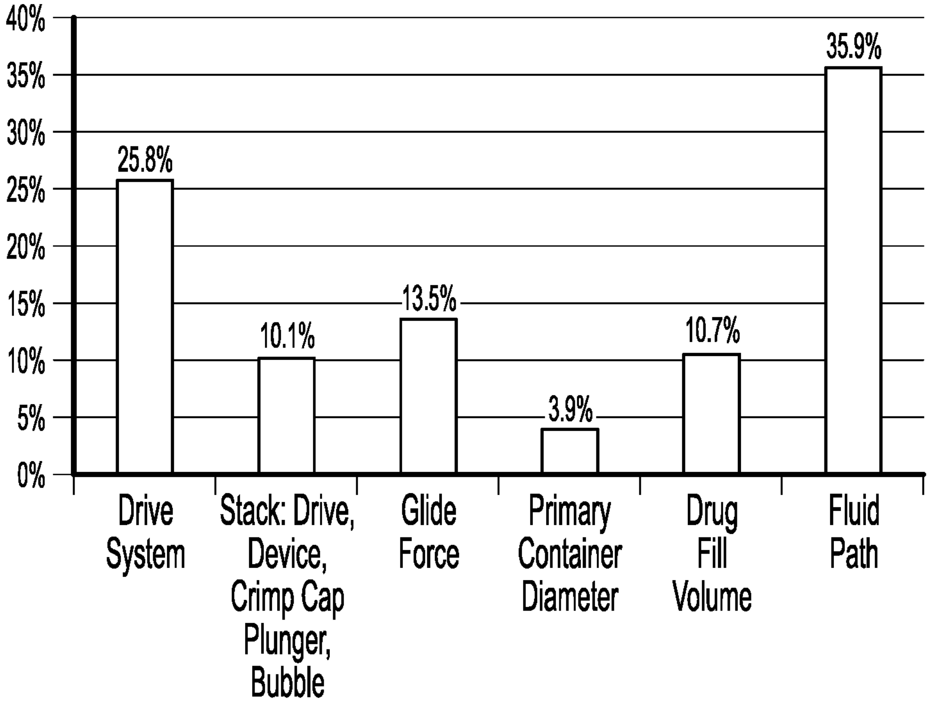
Figure 99:
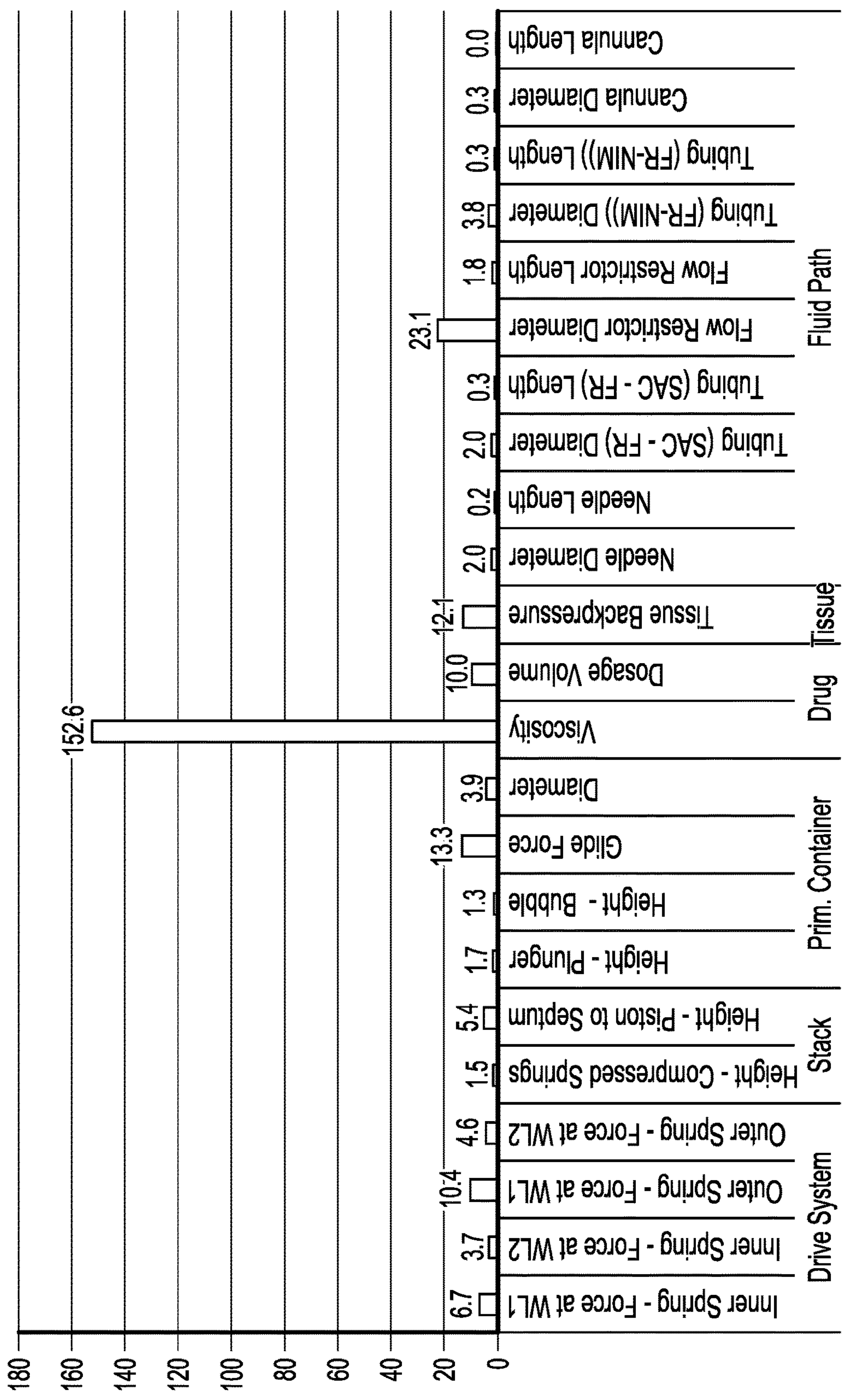
Figure 100A:
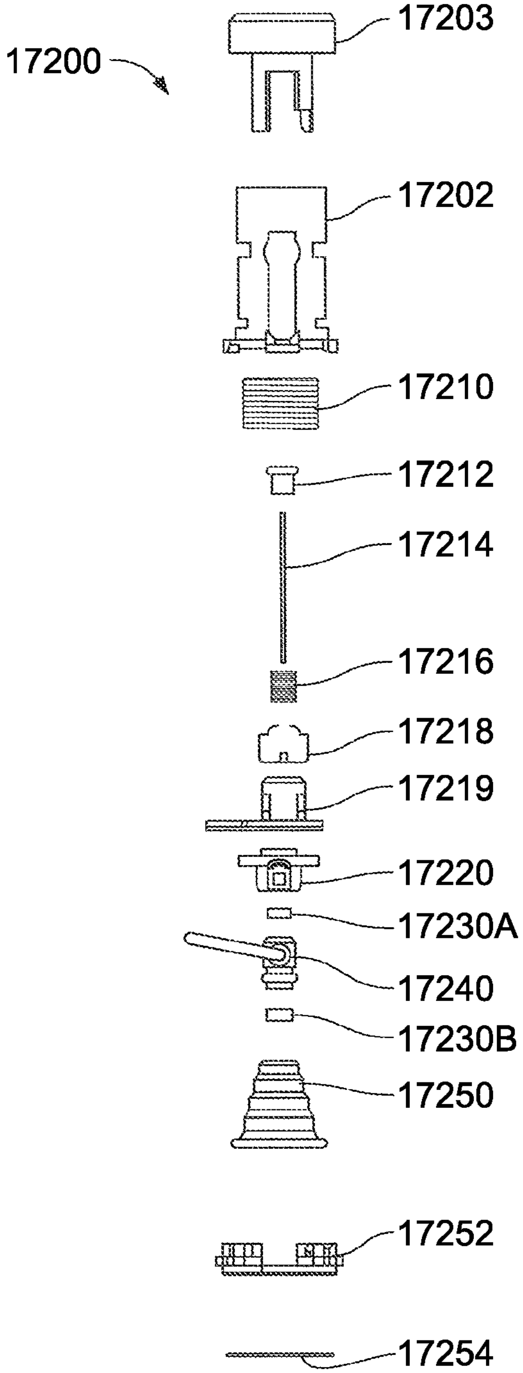
Figure 100B:
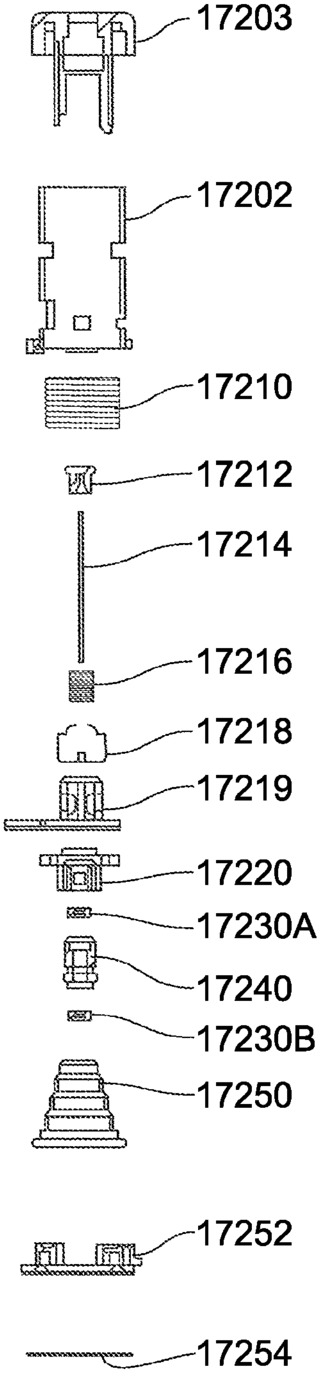
Figure 101:
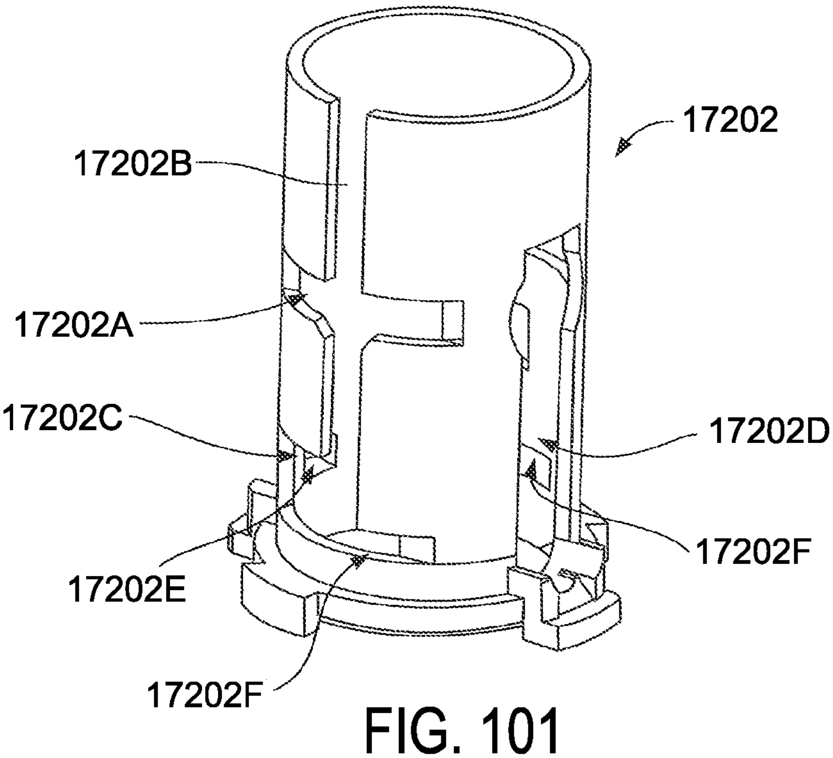
Figure 102:
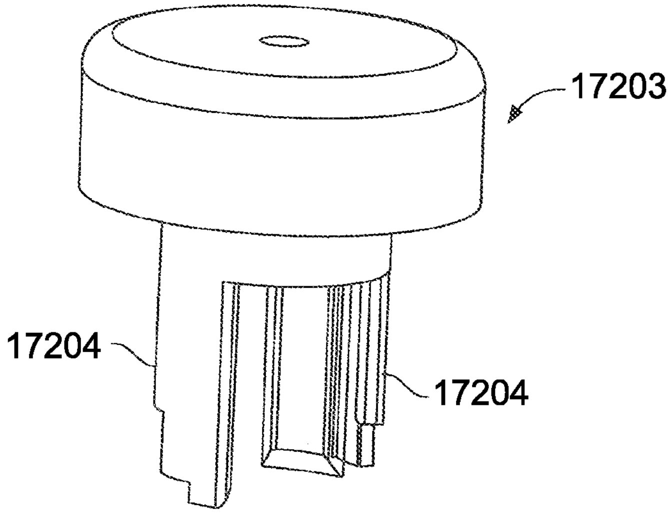
Figure 103:
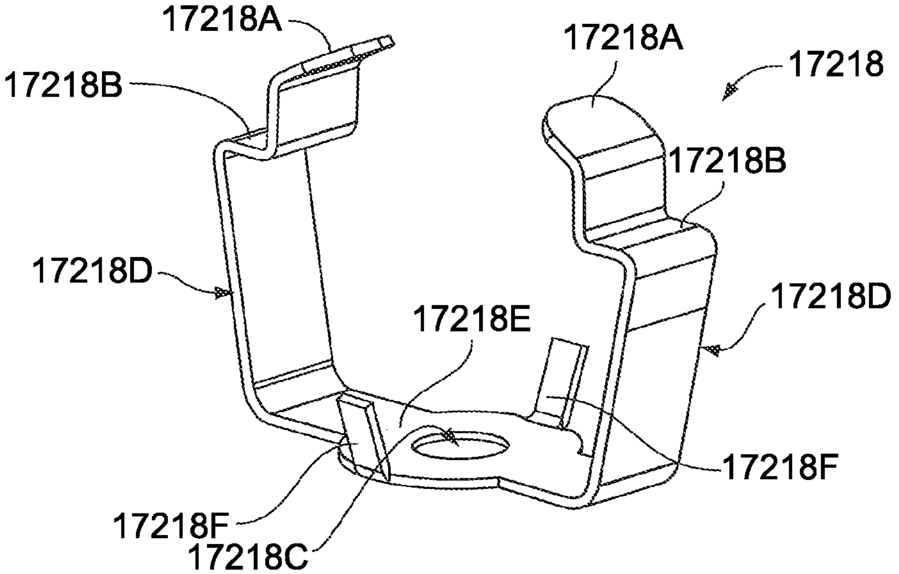
Figure 104:
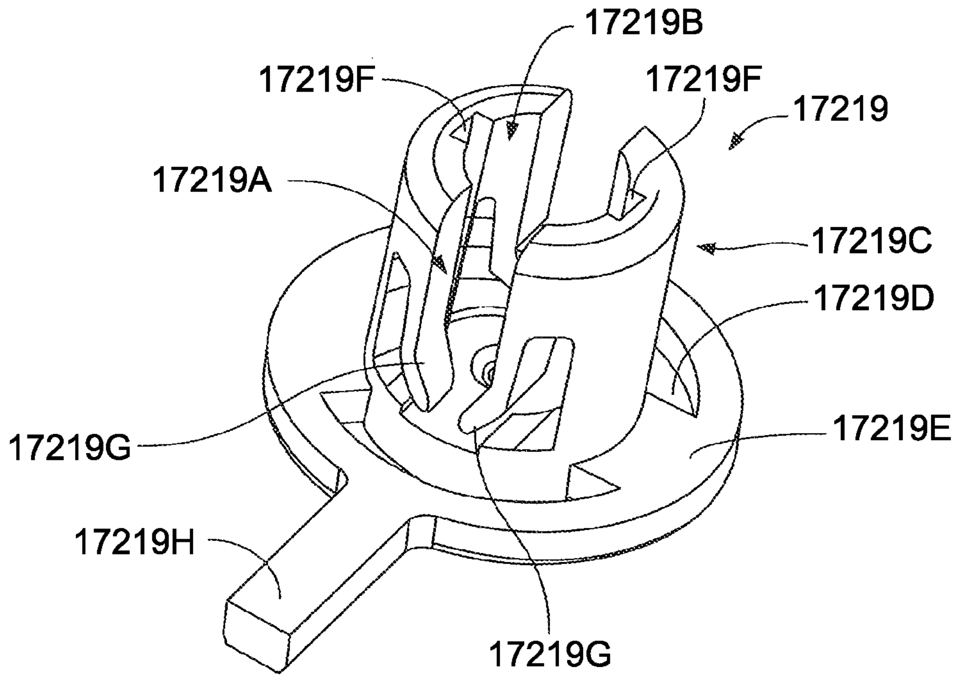
Figure 105:
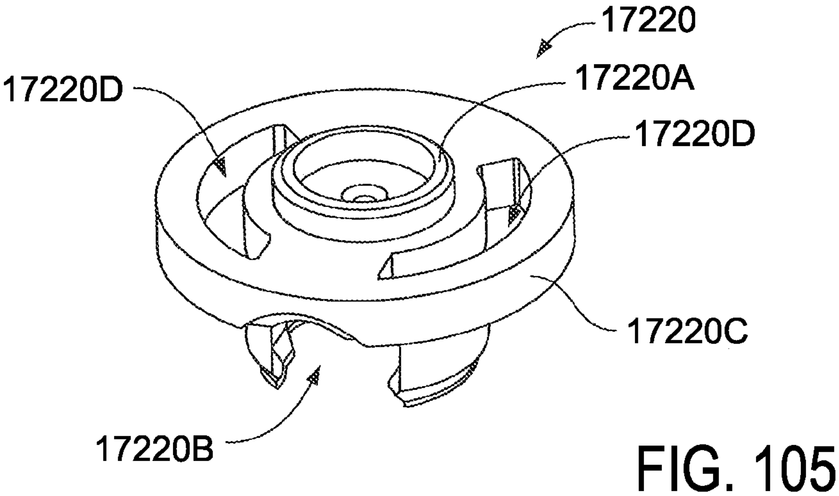
Figure 106:
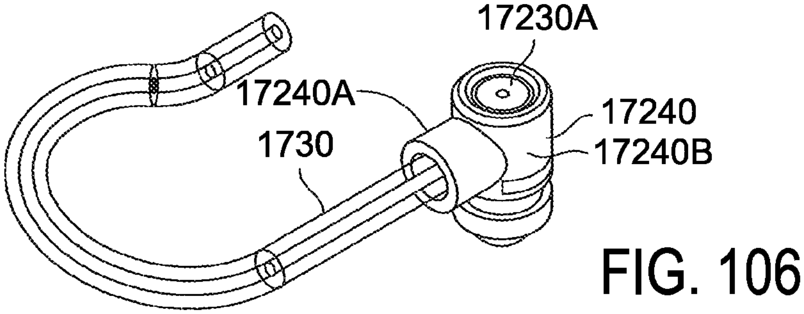
Figure 107:
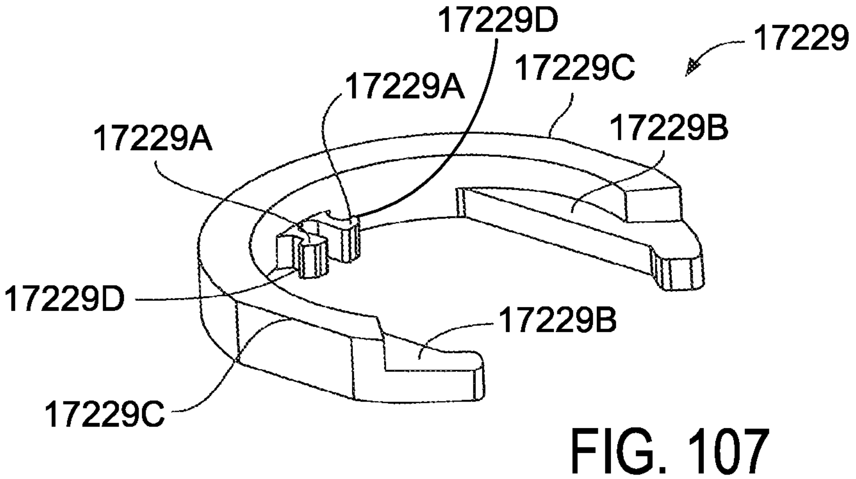
Figure 108A:
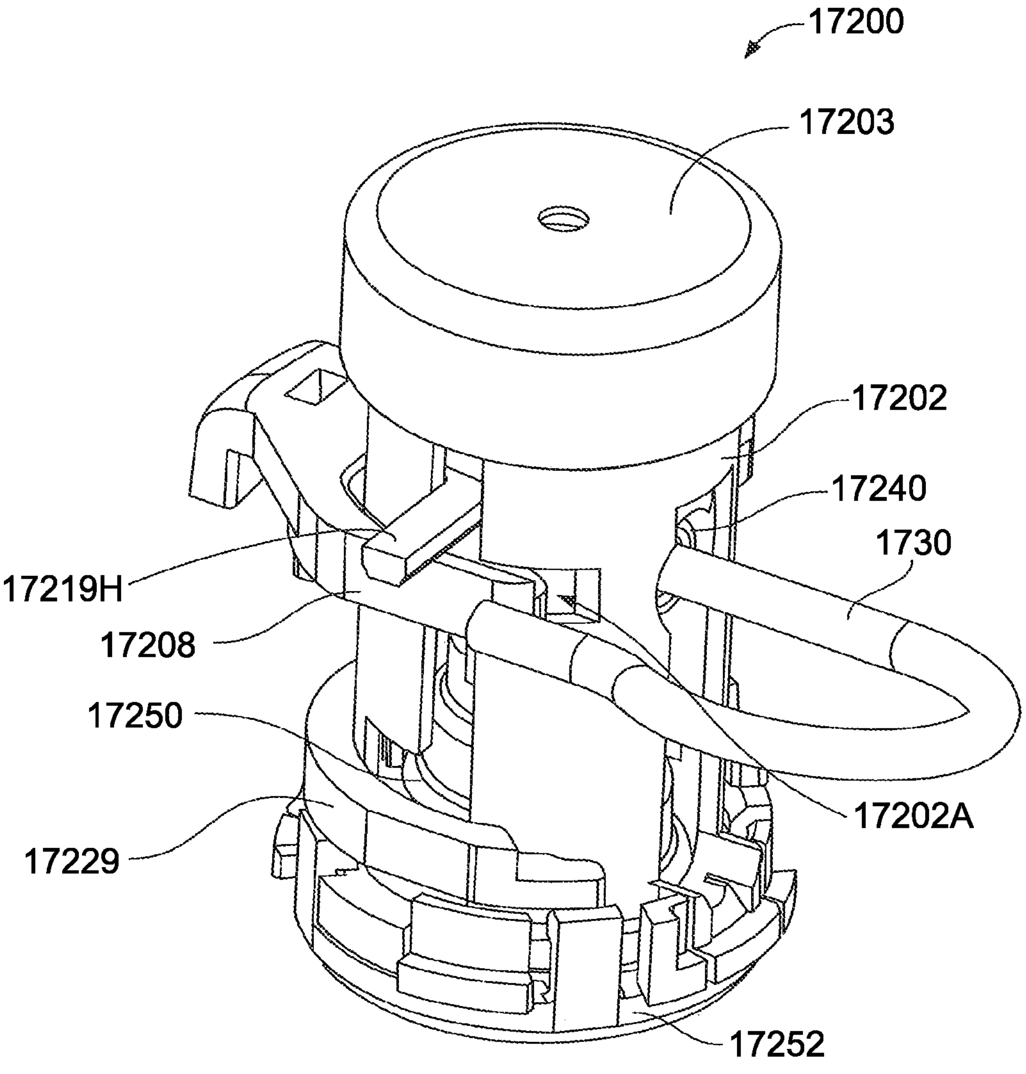
Figure 108B:
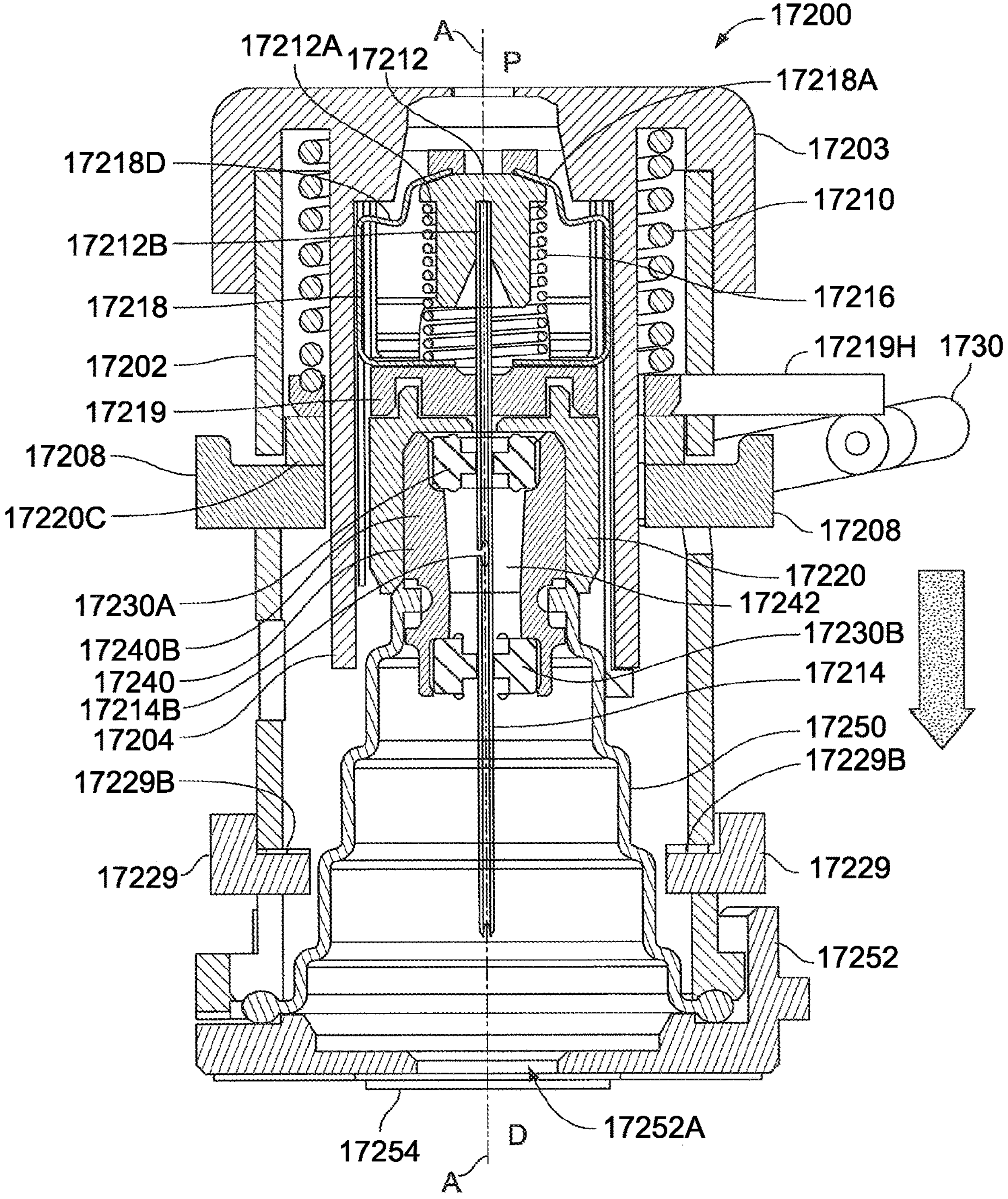
Figure 109A:
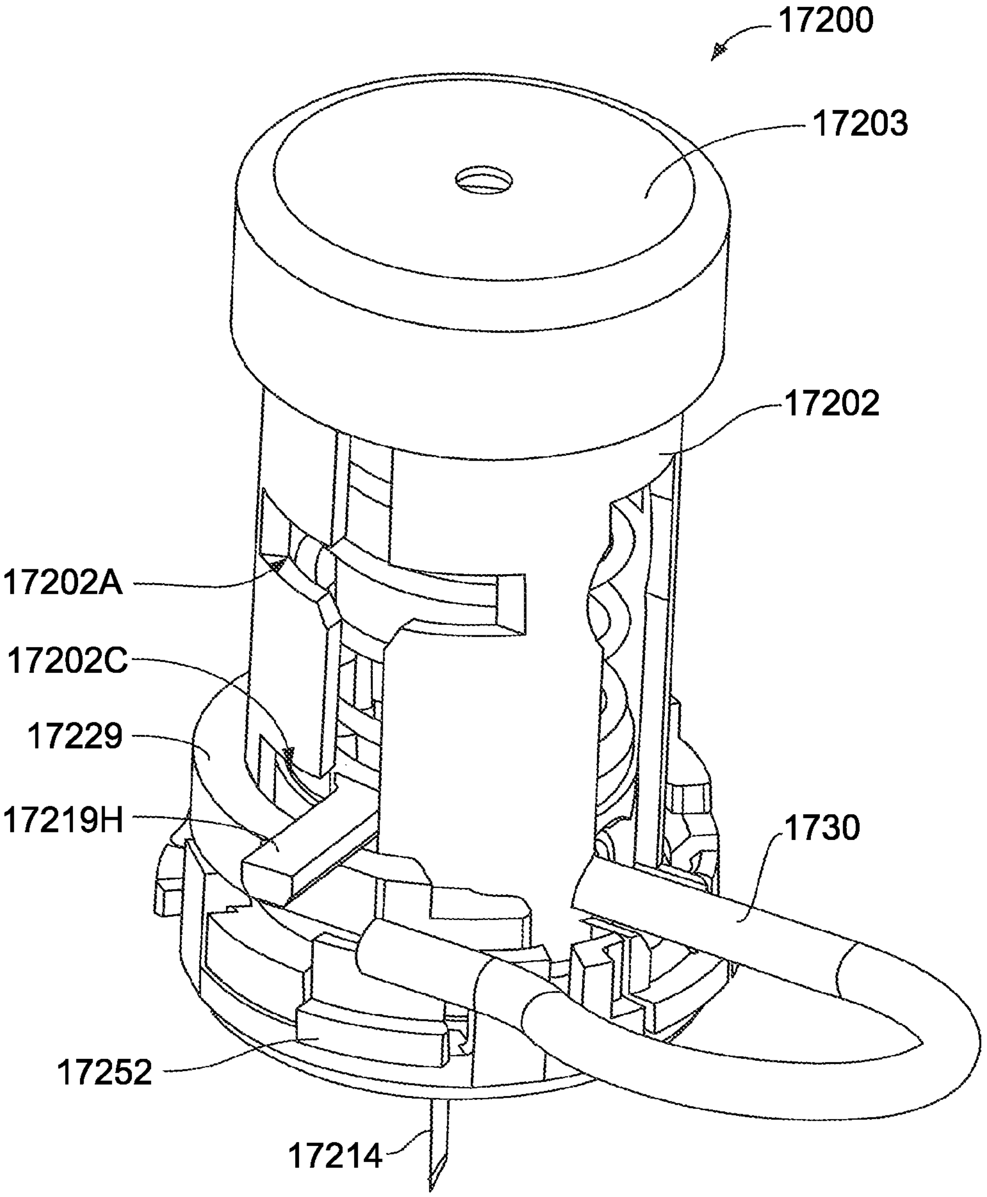
Figure 109B:
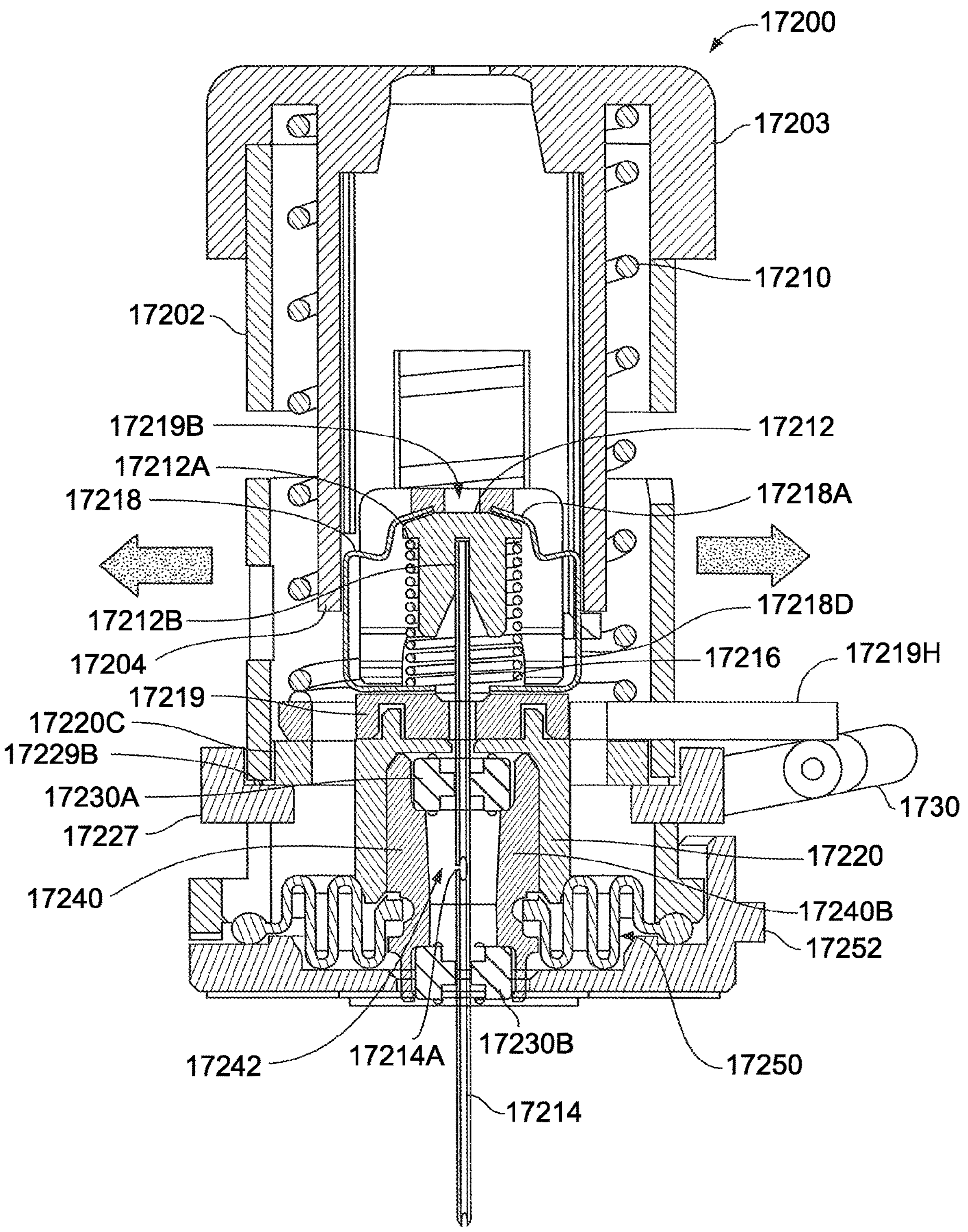
Figure 110A:
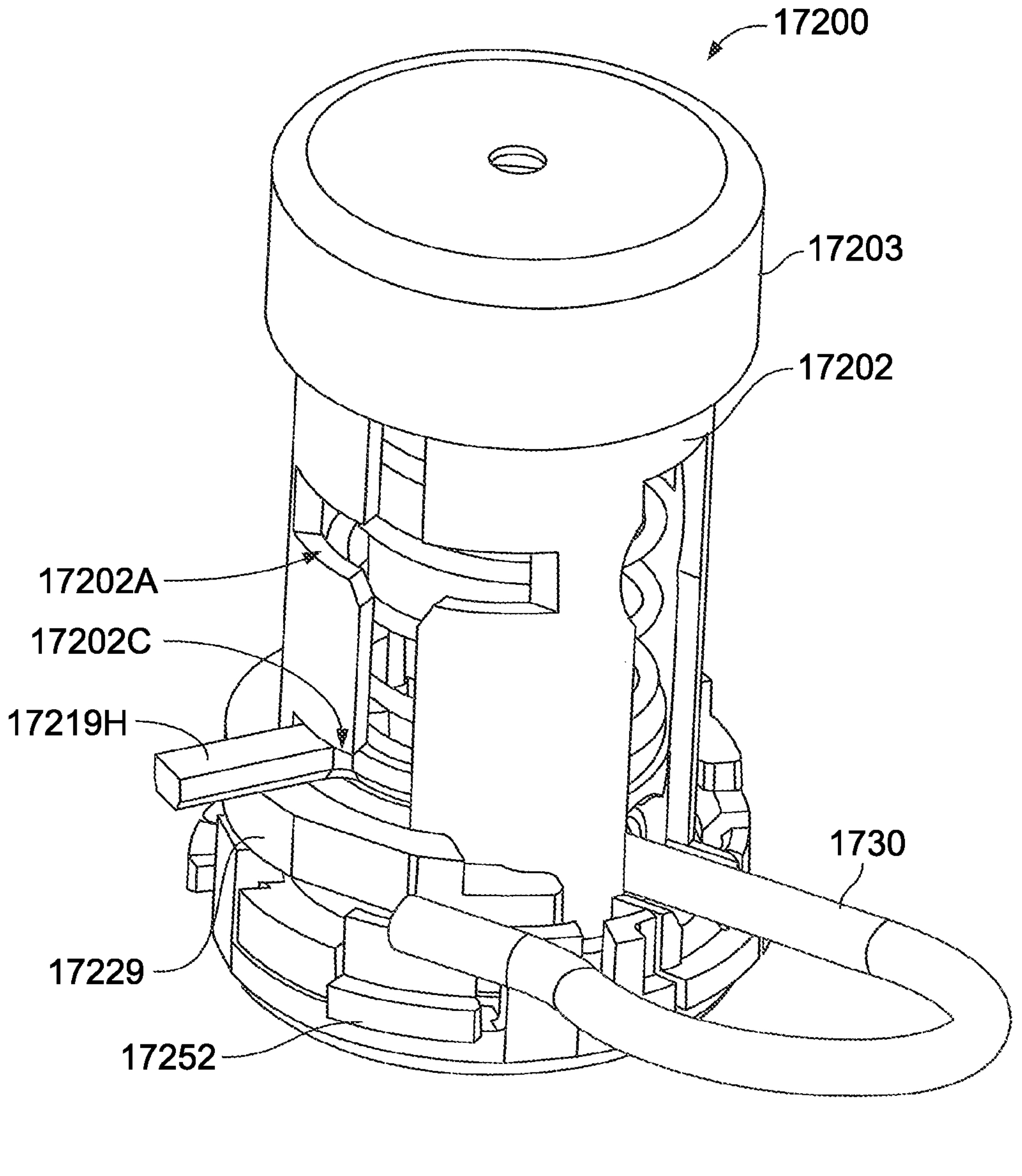
Figure 110B:
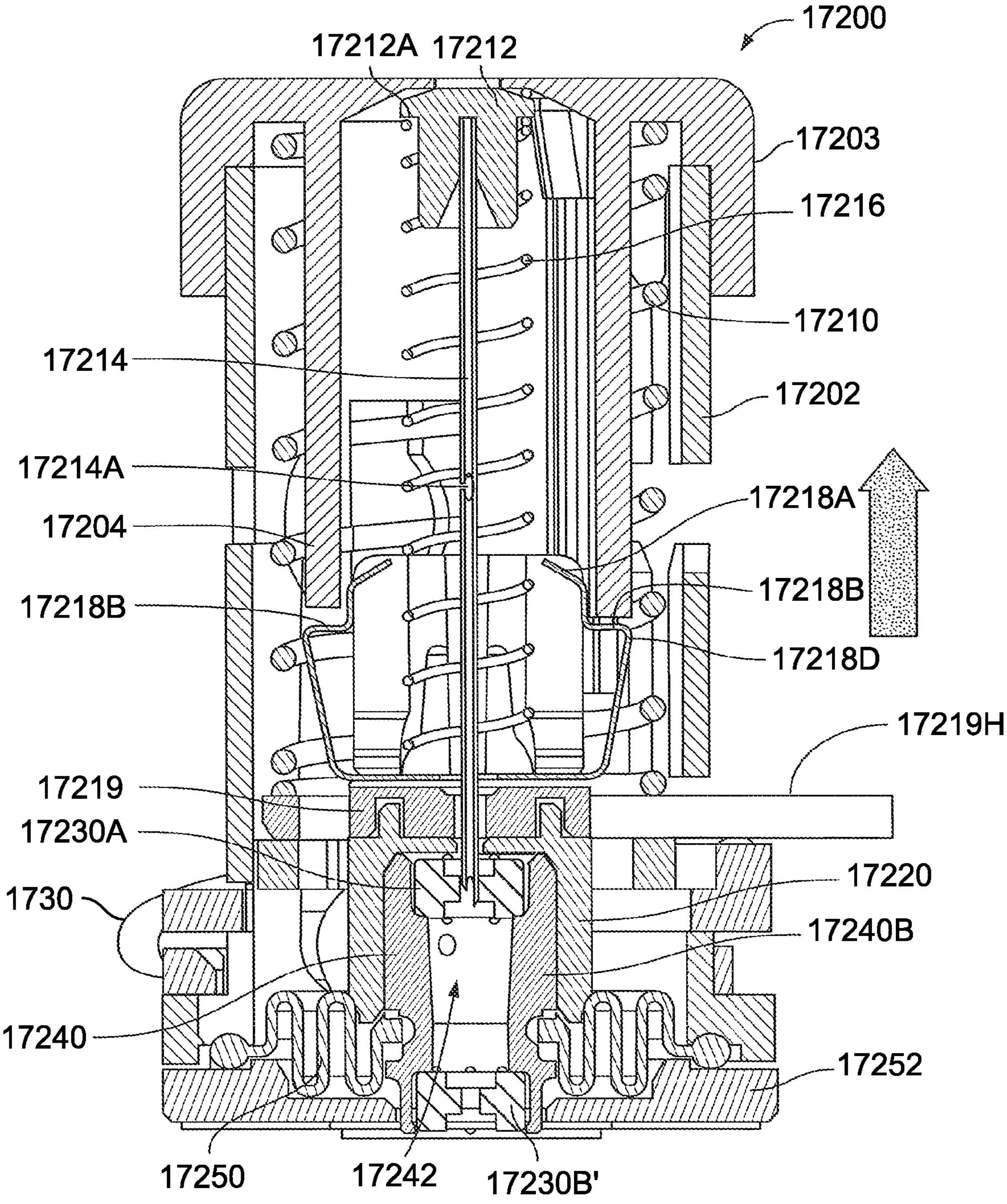
Figure 111A:
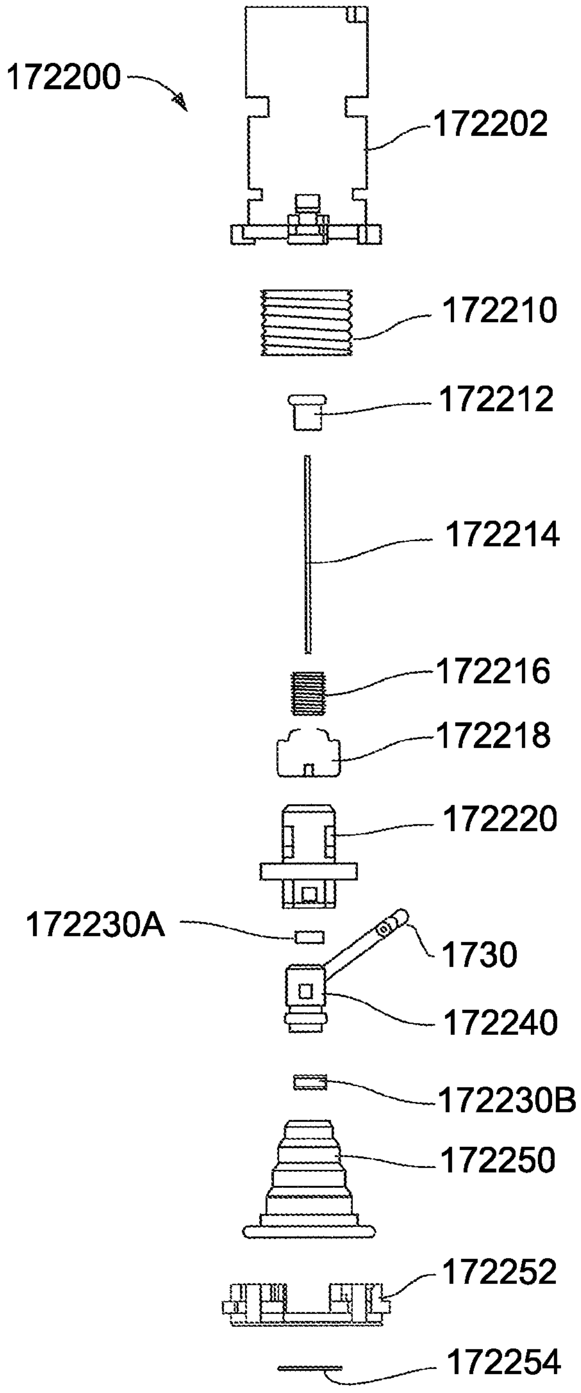
Figure 111B:
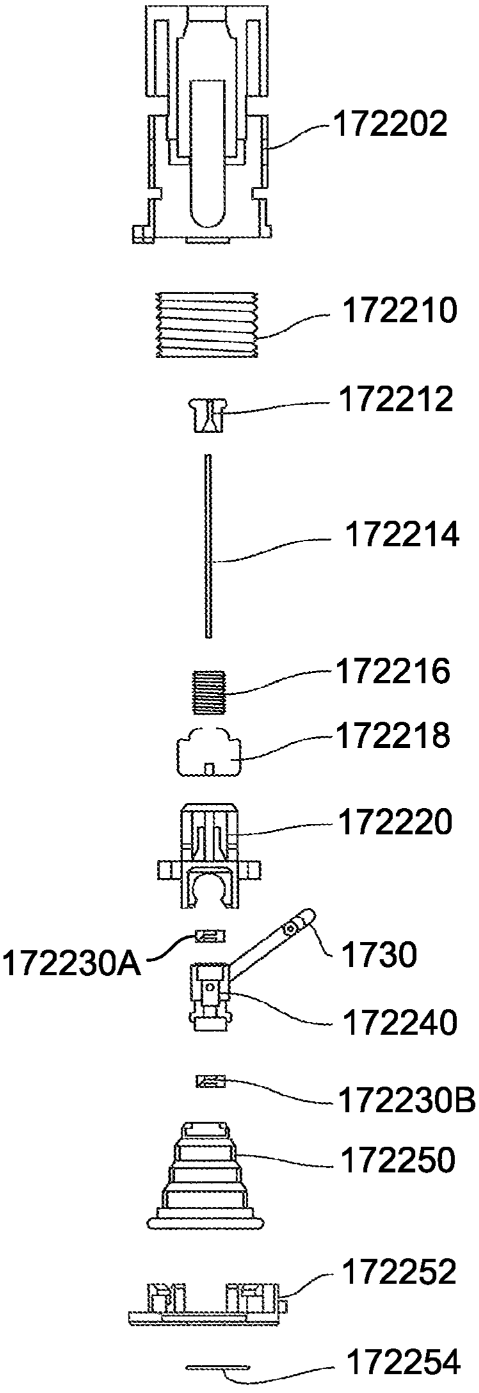
Figure 112:
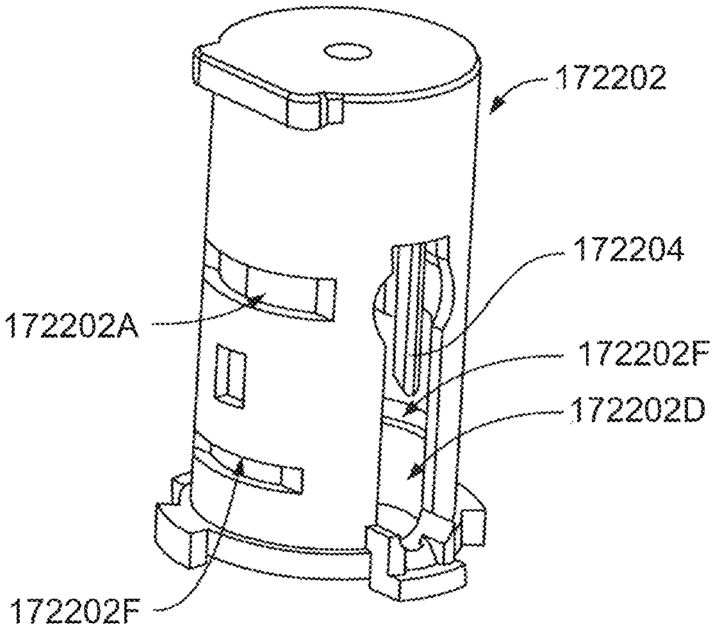
Figure 113:
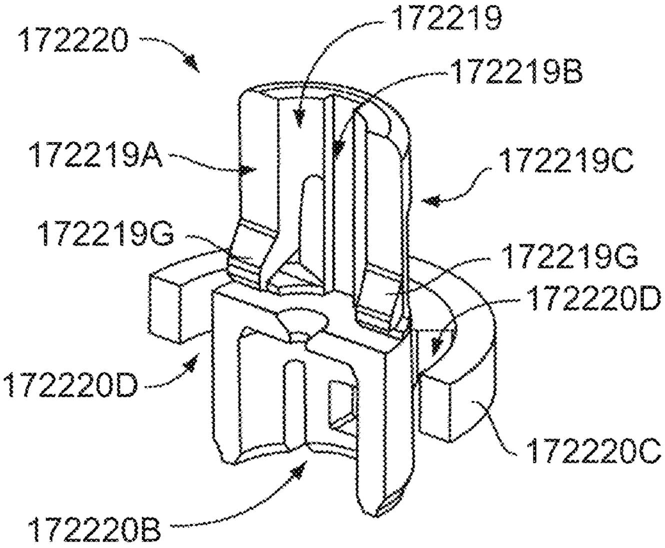
Figure 114:
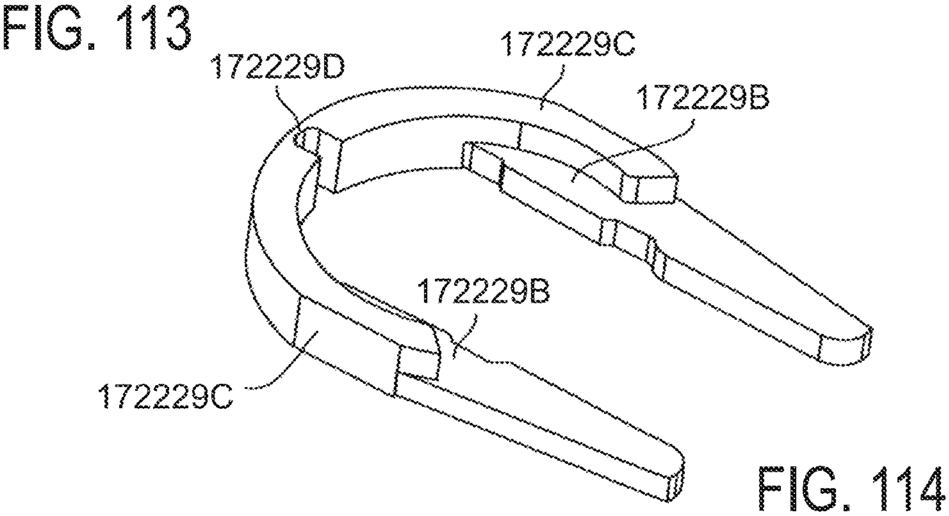
Figure 115A:
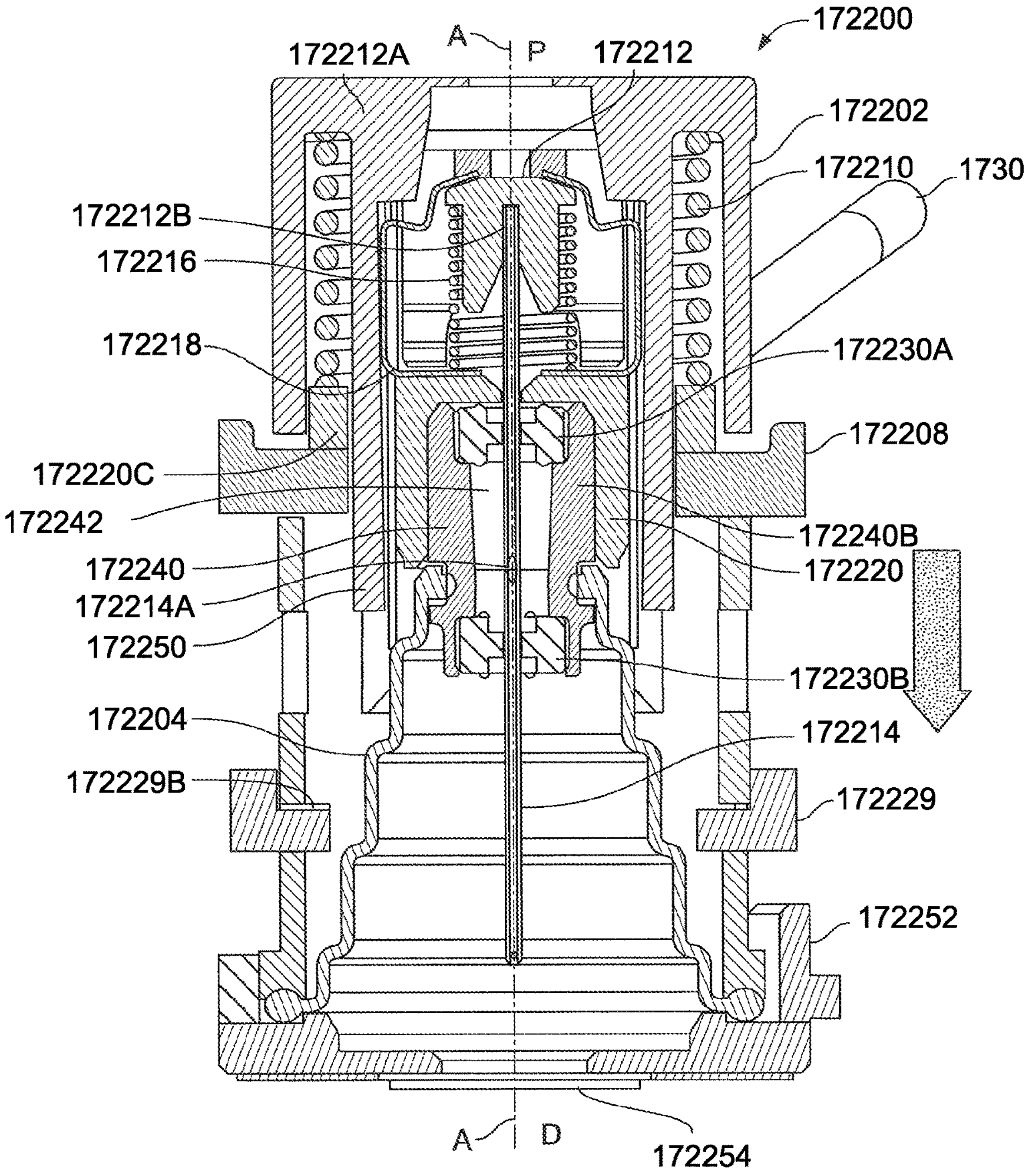
Figure 115B:
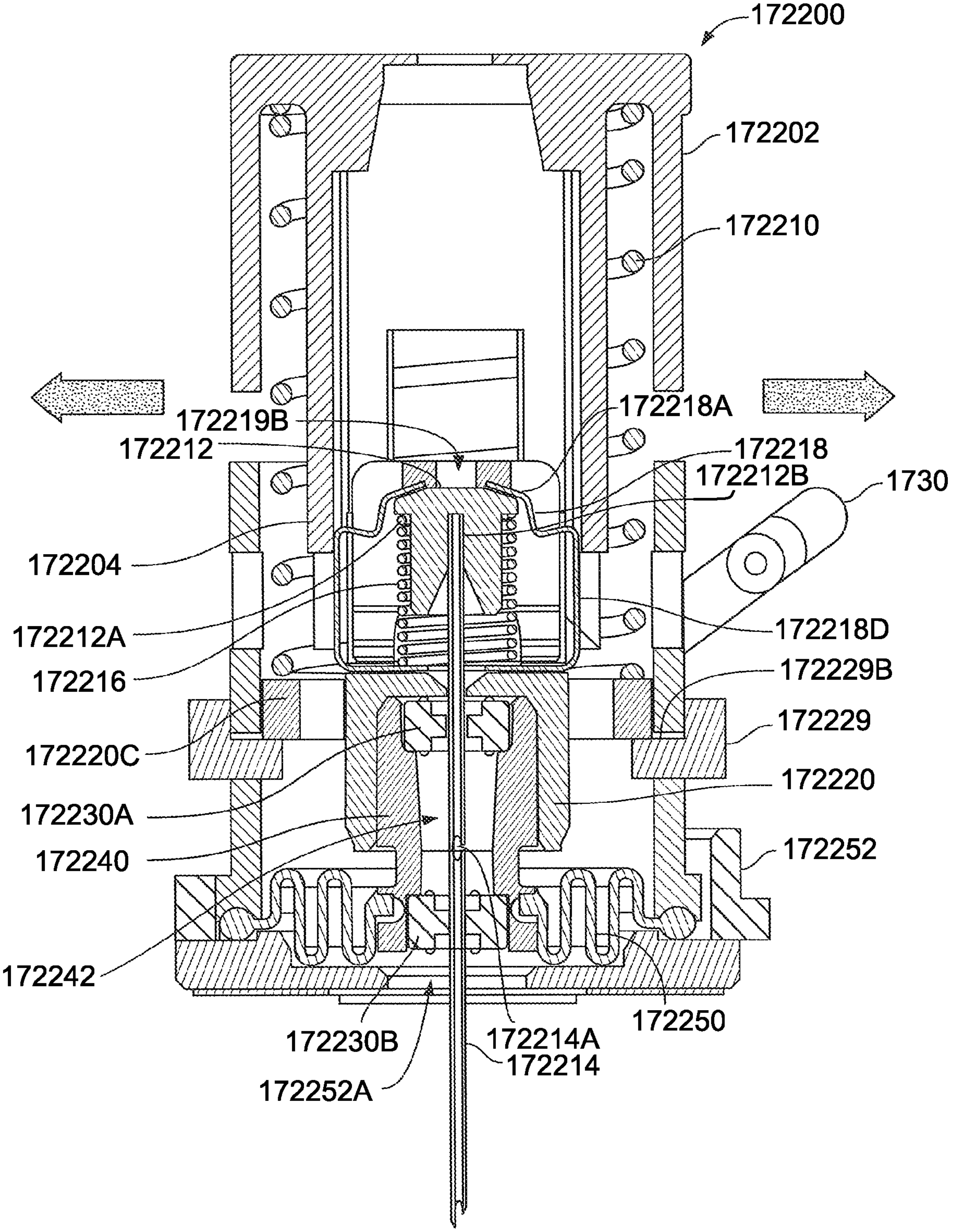
Figure 115C:
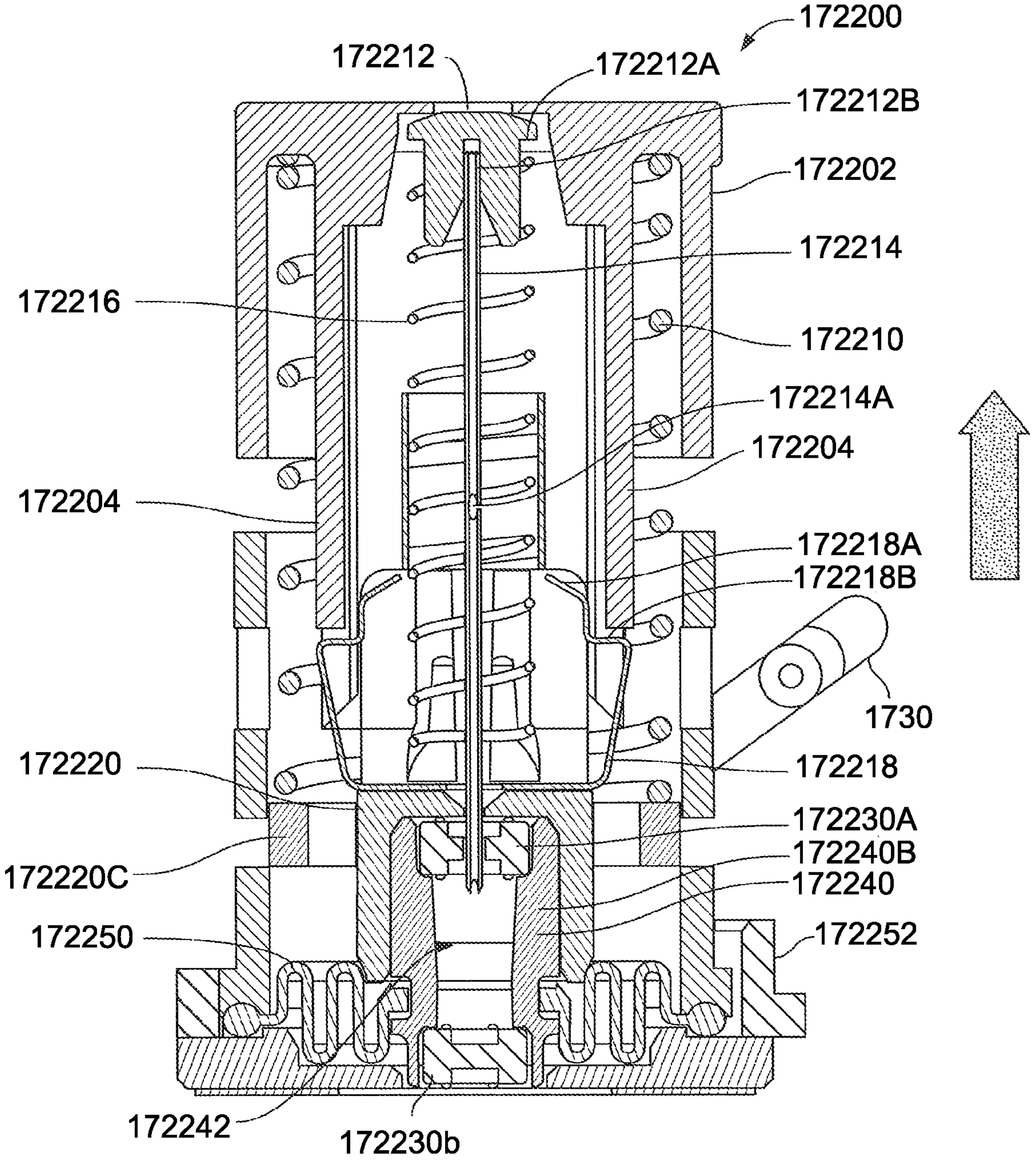
Figure 116:
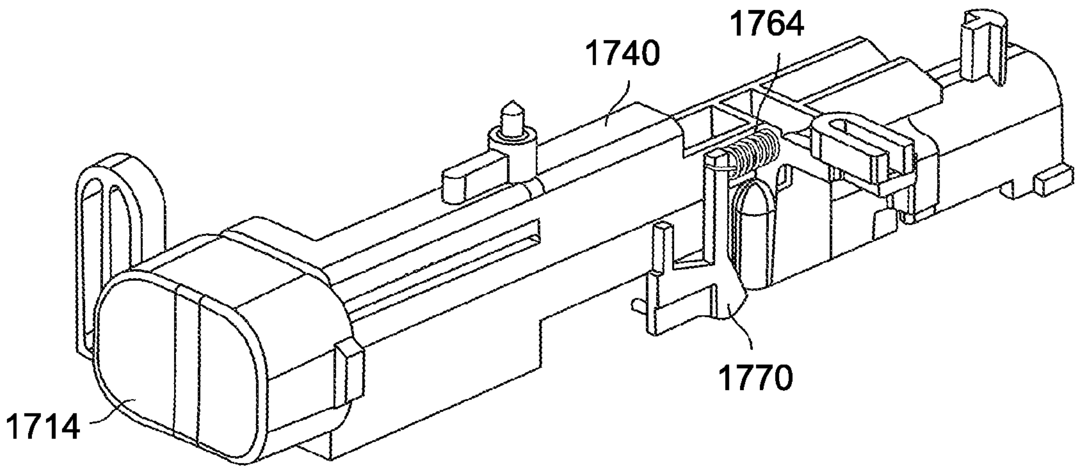
Figure 117:
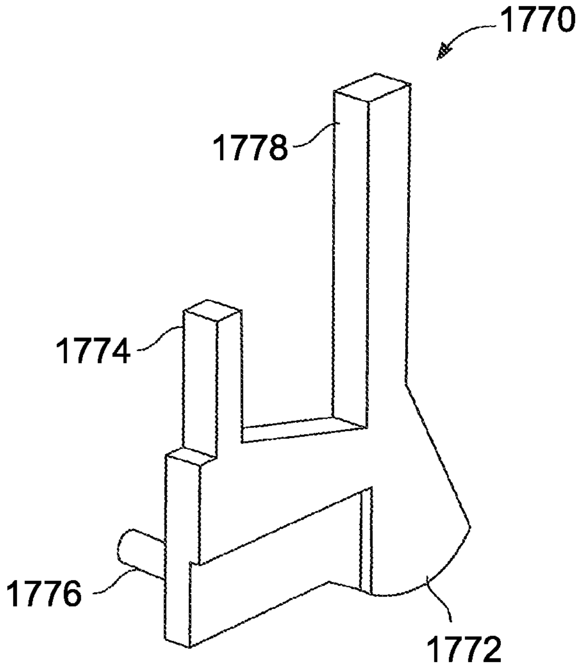

FIG. 76A is a cross-sectional view of an embodiment of a fluid pathway connector and drug container prior to drug delivery;

FIG. 76B is a cross-sectional view of the embodiment of a fluid pathway connector and drug container of FIG. 76A during drug delivery;

FIG. 76C is a cross-sectional view of the embodiment of a fluid pathway connector and drug container of FIG. 76A following completion of drug delivery;

FIG. 77 is a schematic illustration of a drug delivery device including a temperature control system, according to one embodiment of the present disclosure;

FIG. 78A illustrates an embodiment of an adhesive patch for a drug delivery device constructed in accordance with principles of the present disclosure;

FIG. 78B illustrates an embodiment of an adhesive patch for a drug delivery device constructed in accordance with principles of the present disclosure;

FIG. 79 depicts an embodiment of a non-adhesive patch liner in combination with a drug delivery device constructed in accordance with principles of the present disclosure;

FIG. 80A illustrates an exploded assembly view of an embodiment of an adhesive patch for a drug delivery device constructed in accordance with principles of the present disclosure;

FIG. 80B depicts the adhesive patch of FIG. 80A in an assembled form;

FIG. 81 illustrates an isometric view of a drug delivery device including an adhesive patch with stiffening members, according to one embodiment of the present disclosure;

FIG. 82 illustrates a bottom view an embodiment of a non-adhesive patch liner;

FIG. 83A-83C illustrate a process of attaching the drug delivery device of FIG. 81 to a patient's skin;

FIG. 84 is a schematic diagram of a drug delivery device in communication with a data processing network according to one embodiment of the present disclosure;

FIGS. 85A-85C are schematic diagrams illustrating the operation of an energy management system according to one embodiment of the present disclosure;

FIGS. 86A-86C are schematic diagrams illustrating the operation of an energy management system according to another embodiment of the present disclosure;

FIGS. 87A-87C are schematic diagrams illustrating the operation of an energy management system according to another embodiment of the present disclosure;

FIG. 88 is an isometric view of an energy management system according to another embodiment of the present disclosure;

FIG. 89 is an isometric view of an energy management system according to another embodiment of the present disclosure;

FIG. 90 is a cross-sectional view of an energy management system according to another embodiment of the present disclosure;

FIGS. 91A-91B are cross-sectional views illustrating the operation of an energy management system according to another embodiment of the present disclosure;

FIG. 92 is a bar graph showing delivery times, in seconds (y-axis), for various types of administration (y-axis). tsubQ=Delivery Time, Subcutaneous (SQ) Delivery, With Viscosity Tolerance (Case 1); tsubQvc=Delivery Time, Subcutaneous Delivery, Constant Viscosity (Case 2); tamb=Delivery Time, Ambient Delivery, With Viscosity Tolerance (Case 3); and tambvc=Delivery Time, Ambient Delivery, Constant Viscosity (Case 4). Error bars show min/max error;

FIG. 93 is a graph presenting drive system force profiles as a function of drive assembly force (N) (x-axis) over travel distance (mm) (y-axis). In FIG. 93, the line having squares indicates a minimum, the line having triangles indicates a maximum, and the lines having diamonds indicates a nominal;

FIG. 94 is a bar graph conveying the contribution (%) to delivery time variation of components (x-axis) in subcutaneous Case 1, SQ delivery and viscosity range. The y-axis shows relative time contribution as percent in seconds;

FIG. 95 is a bar graph conveying the contribution (%) to delivery time variation of components (x-axis) in Case 2, SQ delivery and viscosity constant. Relative contribution, in seconds, is shown as percent on the y-axis;

FIG. 96 is a bar graph conveying the contribution (%) to delivery time variation of components (x-axis) in Case 3, ambient delivery and viscosity range. Relative contribution, in seconds, is shown as percent on the y-axis;

FIG. 97 is a bar graph conveying the contribution (%) to delivery time variation of components (x-axis) in Case 4, ambient delivery and viscosity constant. Relative contribution, in seconds, is shown as percent on the y-axis;

FIG. 98 is a bar graph conveying the contribution (%) to delivery time variation of components (x-axis) in Case 4, ambient delivery and viscosity constant, by variable groups. Relative contribution, in seconds, is shown as percent on the y-axis;

FIG. 99 is a bar graph conveying the contribution (%) to delivery time variation of components (x-axis) in SubQ delivery;

FIG. 100A is an exploded view of an insertion mechanism, according to a first embodiment of the disclosure;

FIG. 100B is a cross-sectional exploded view of the insertion mechanism of FIG. 100A;

FIG. 101 is an isometric view of an insertion mechanism housing, according to at least one embodiment of the present disclosure;

FIG. 102 is an isometric view of an insertion mechanism housing cap, according to at least one embodiment of the present disclosure;

FIG. 103 is an isometric view of a clip, according to at least one embodiment of the present disclosure;

FIG. 104 is an isometric view of a clip retainer according to at least one embodiment of the present disclosure;

FIG. 105 is an isometric view of a manifold guide according to at least one embodiment of the present disclosure;

FIG. 106 is an isometric view of a manifold and fluid conduit according to at least one embodiment of the present disclosure;

FIG. 107 is an isometric view of a travel limiter according to at least one embodiment of the present disclosure;

FIG. 108A is an isometric view of a needle insertion mechanism in an initial configuration or initial locked configuration according to at least one embodiment of the present disclosure;

FIG. 108B is a cross-sectional view of the needle insertion mechanism of FIG. 108A;

FIG. 109A is an isometric view of the needle insertion mechanism of FIG. 108A in an administration configuration;

FIG. 109B is a cross-sectional view of the needle insertion mechanism of FIG. 108A in an administration configuration;

FIG. 110A is an isometric view of the needle insertion mechanism of FIG. 108A in a retracted configuration or unlocked configuration;

FIG. 110B is a cross-sectional view of the needle insertion mechanism of FIG. 110A in a retracted configuration or unlocked configuration;

FIG. 111A is an exploded view of an insertion mechanism, according to a second embodiment of the disclosure;

FIG. 111B is a cross-sectional exploded view of the insertion mechanism of FIG. 111A;

FIG. 112 is an isometric view of an insertion mechanism housing, according to at least one embodiment of the present disclosure;

FIG. 113 is an isometric view of a manifold guide according to at least one embodiment of the present disclosure;

FIG. 114 is an isometric view of a travel limiter of at least one embodiment of the present disclosure;

FIG. 115A is a cross-sectional view of a needle insertion mechanism in an initial configuration or initial locked configuration according to at least one embodiment of the present disclosure;

FIG. 115B is a cross-sectional view of the needle insertion mechanism of FIG. 115A in an administration configuration;

FIG. 115C is a cross-sectional view of the needle insertion mechanism of FIG. 115A in a retracted configuration or unlocked configuration;

FIG. 116 is an isometric view of a needle retraction release mechanism of at least one embodiment of the present disclosure;

FIG. 117 is an isometric view of a pivot of at least one embodiment of the present disclosure.

Figure 4A:
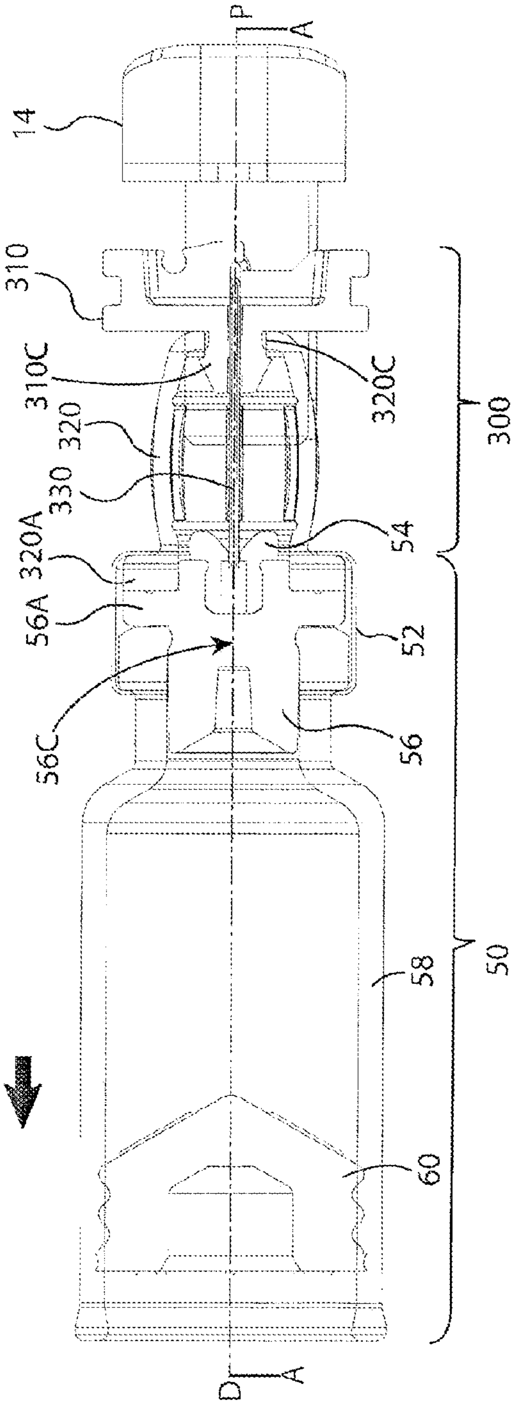
FIG. 4A shows a cross-sectional view of the fluid pathway connector attached to a drug container, as shown in FIG. 2B, prior to patient activation.
Figure 4B:
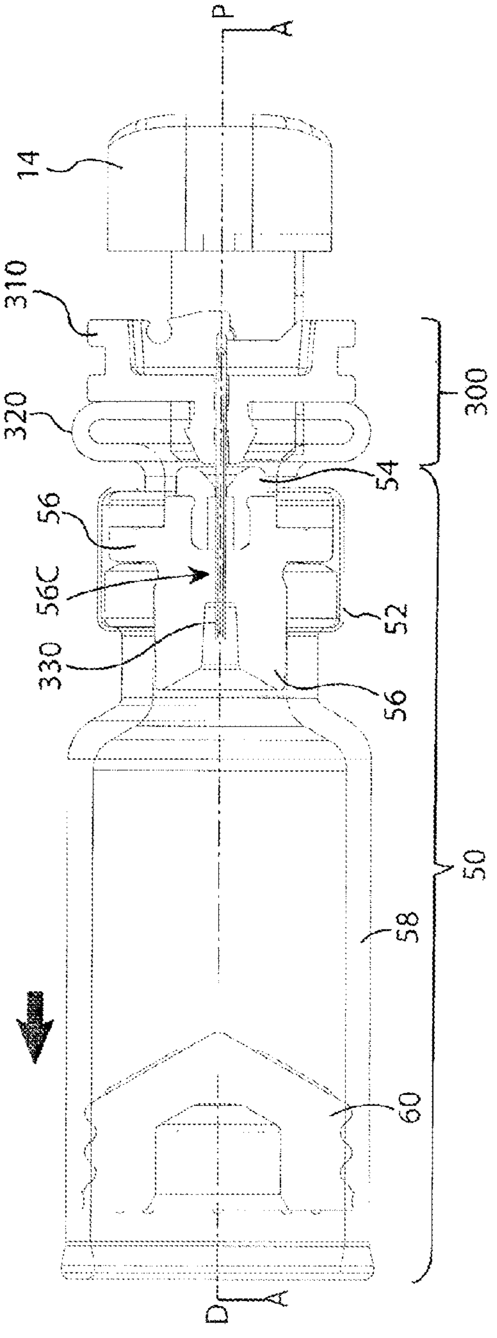
FIG. 4B shows a cross-sectional view of the fluid pathway connector attached to a drug container, as shown in FIG. 2B, with the fluid pathway connected by the patient.
Figure 118:
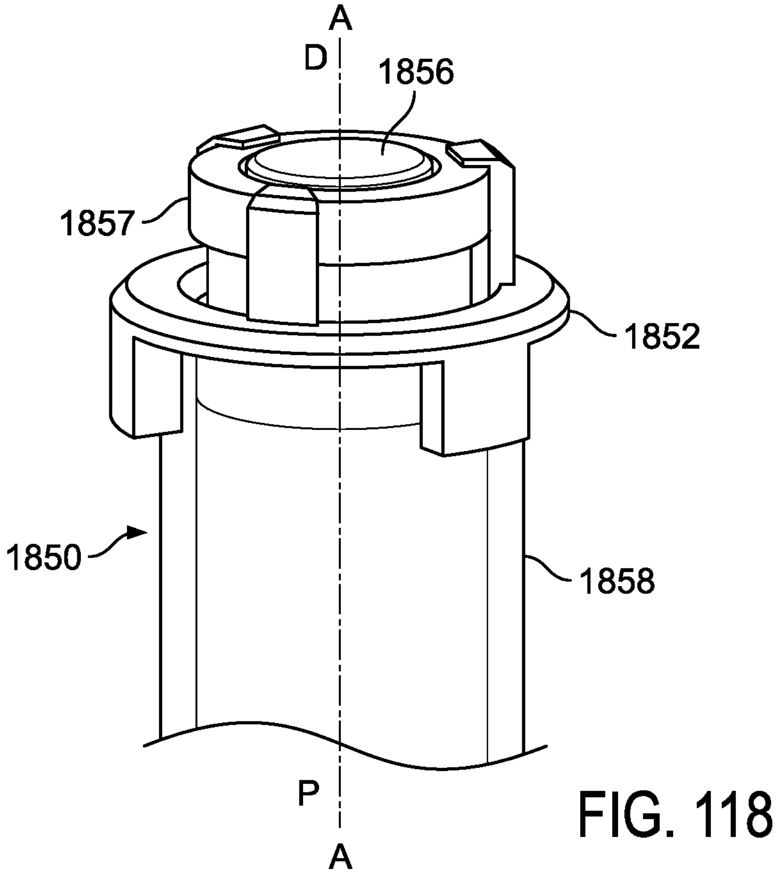
Figure 119:
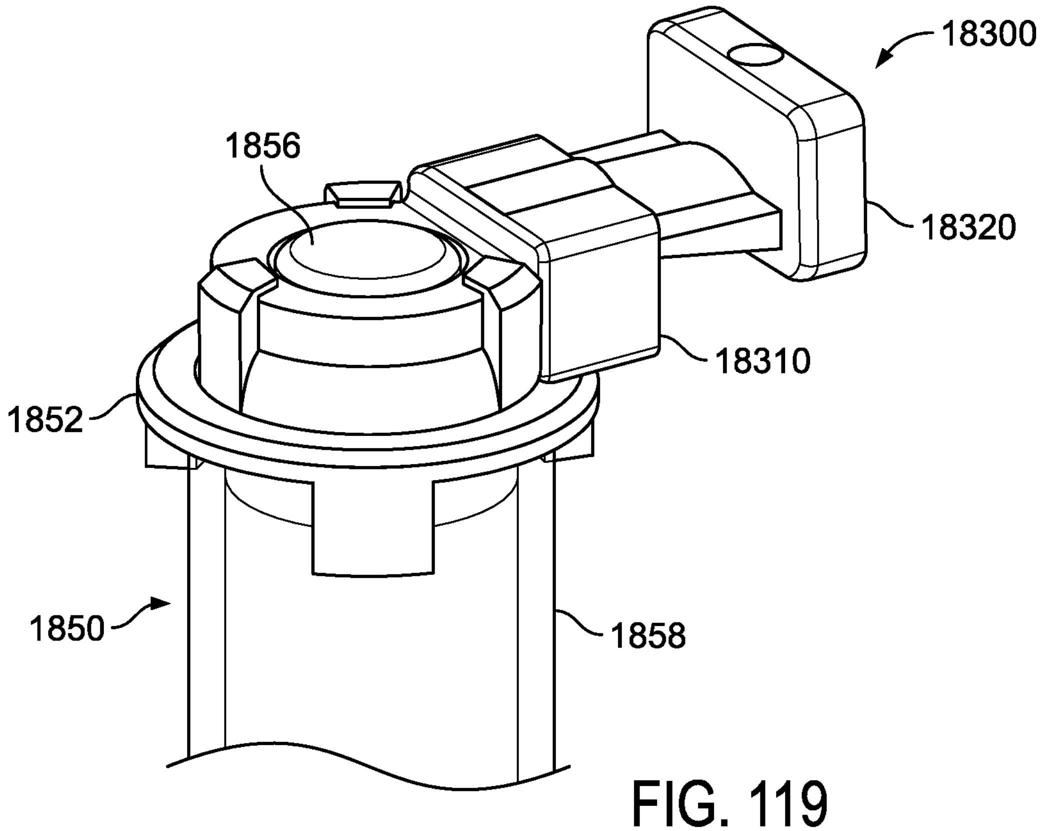
Figure 120A:
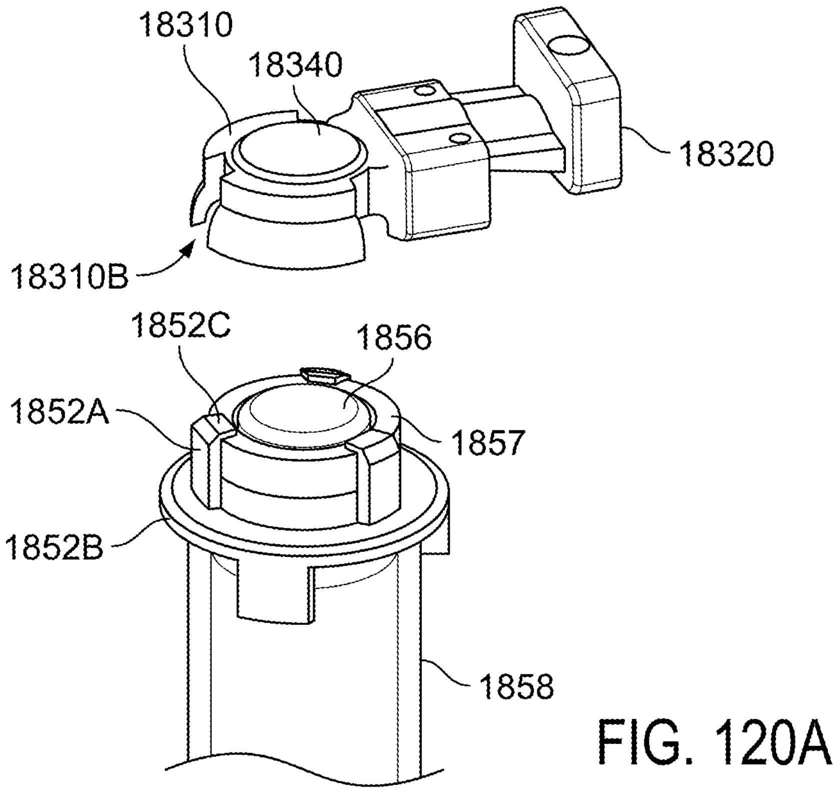
Figure 120B:
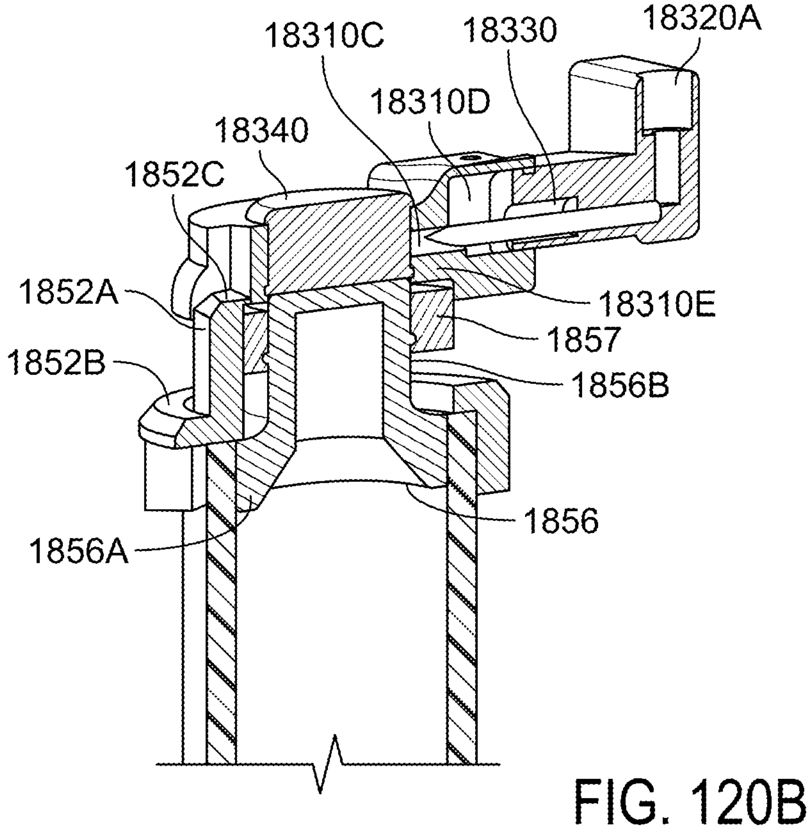
Figure 120C:
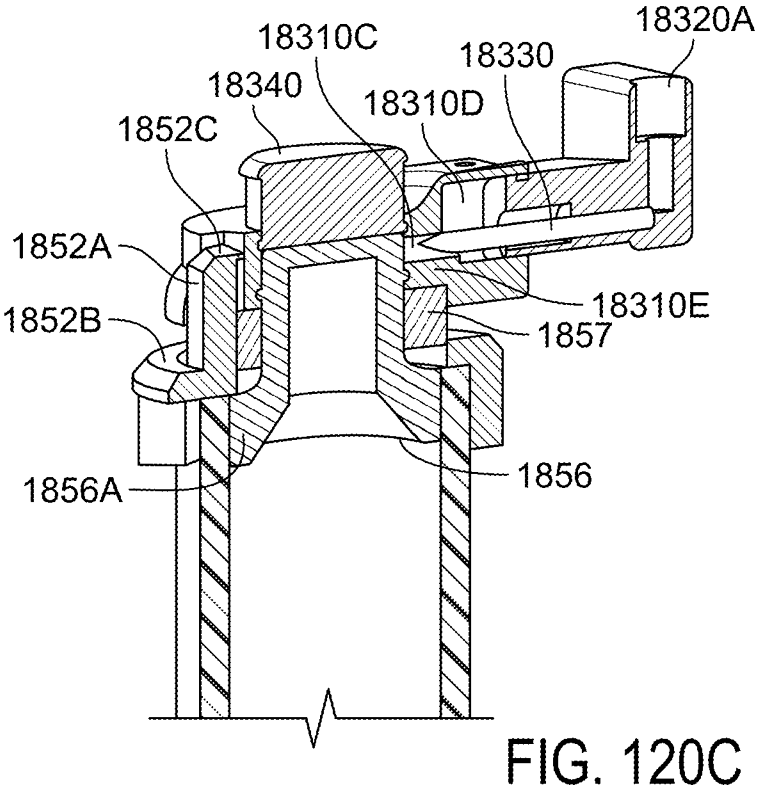
Figure 120D:
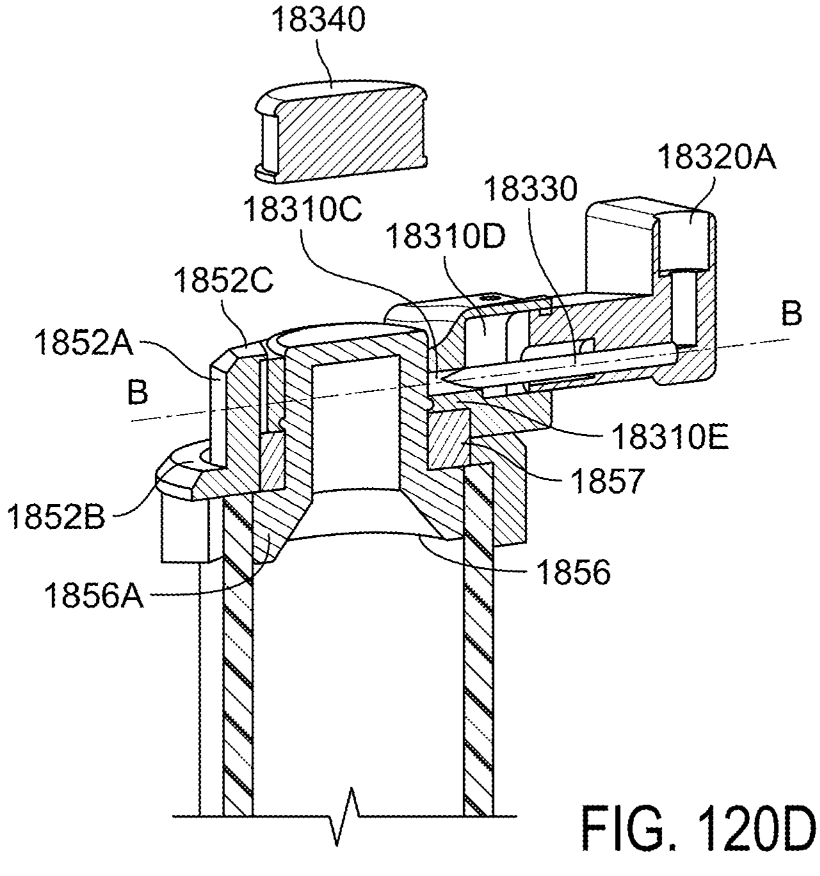
Figure 121A:
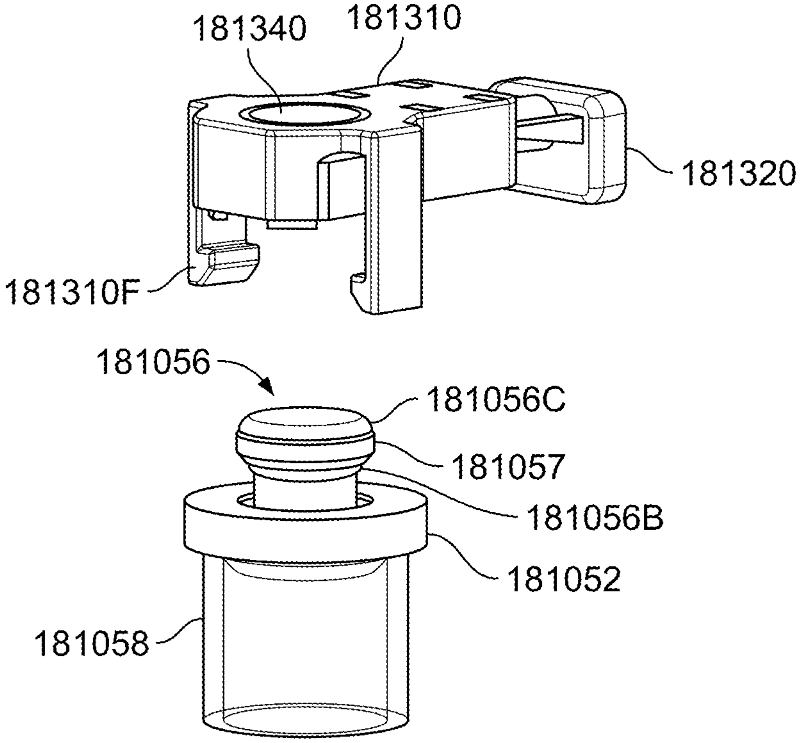
Figure 121B:
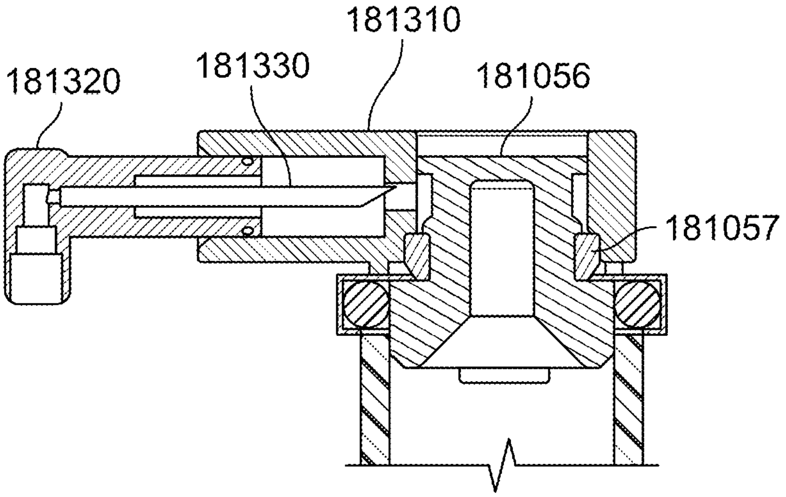
Figure 122:
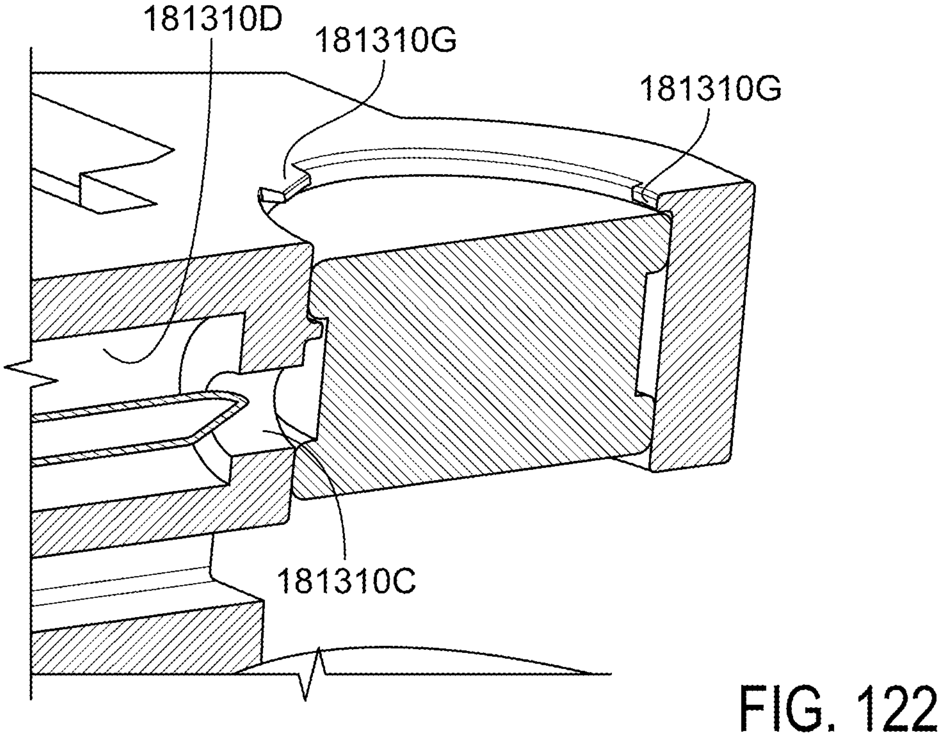
Figure 123:
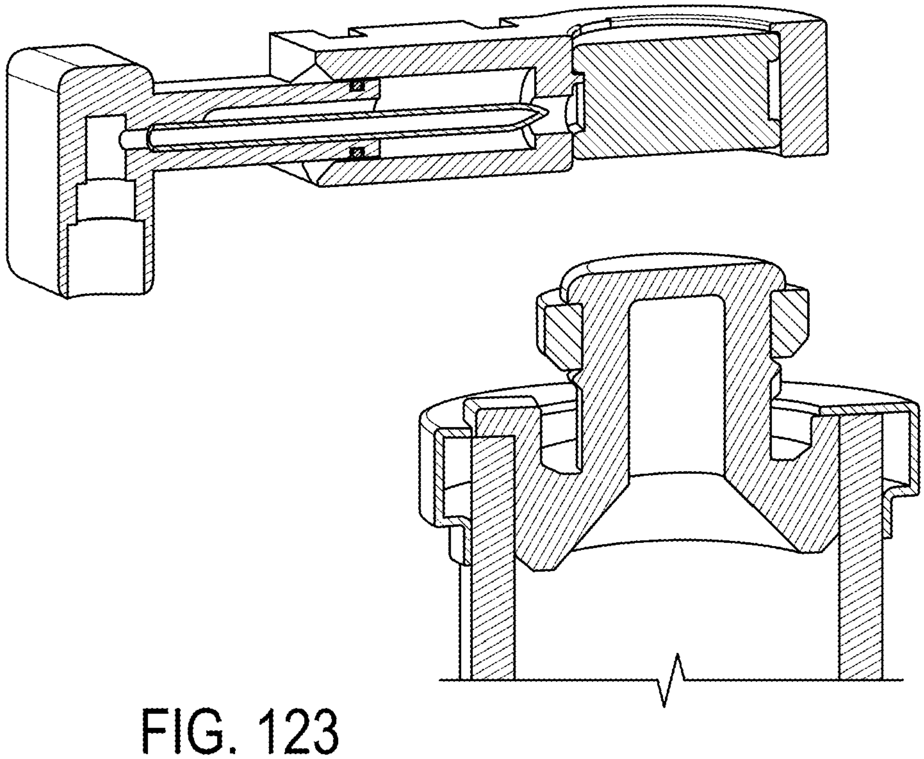
Figure 124:
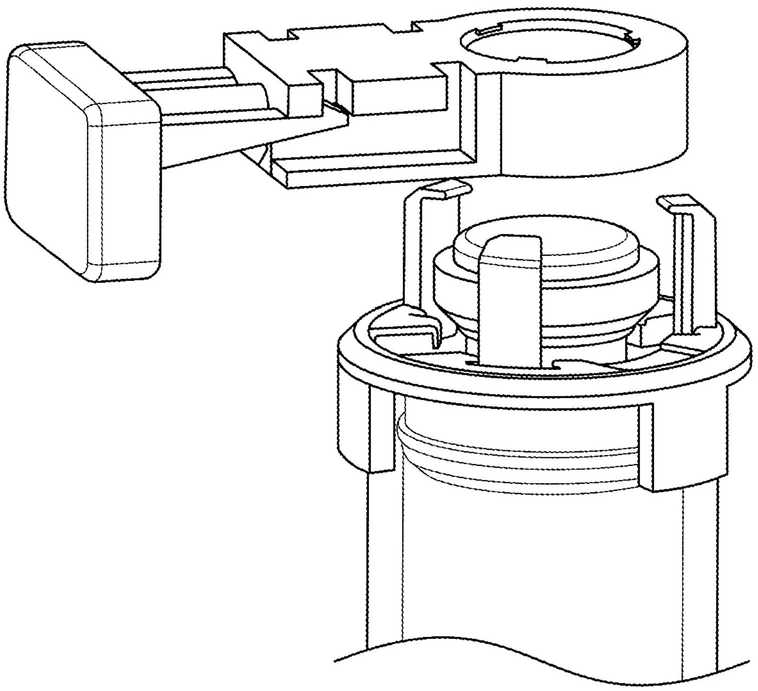
Figure 125:
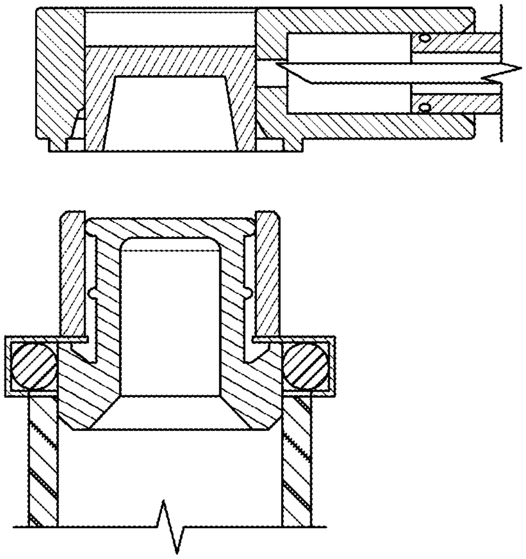
Figure 126:
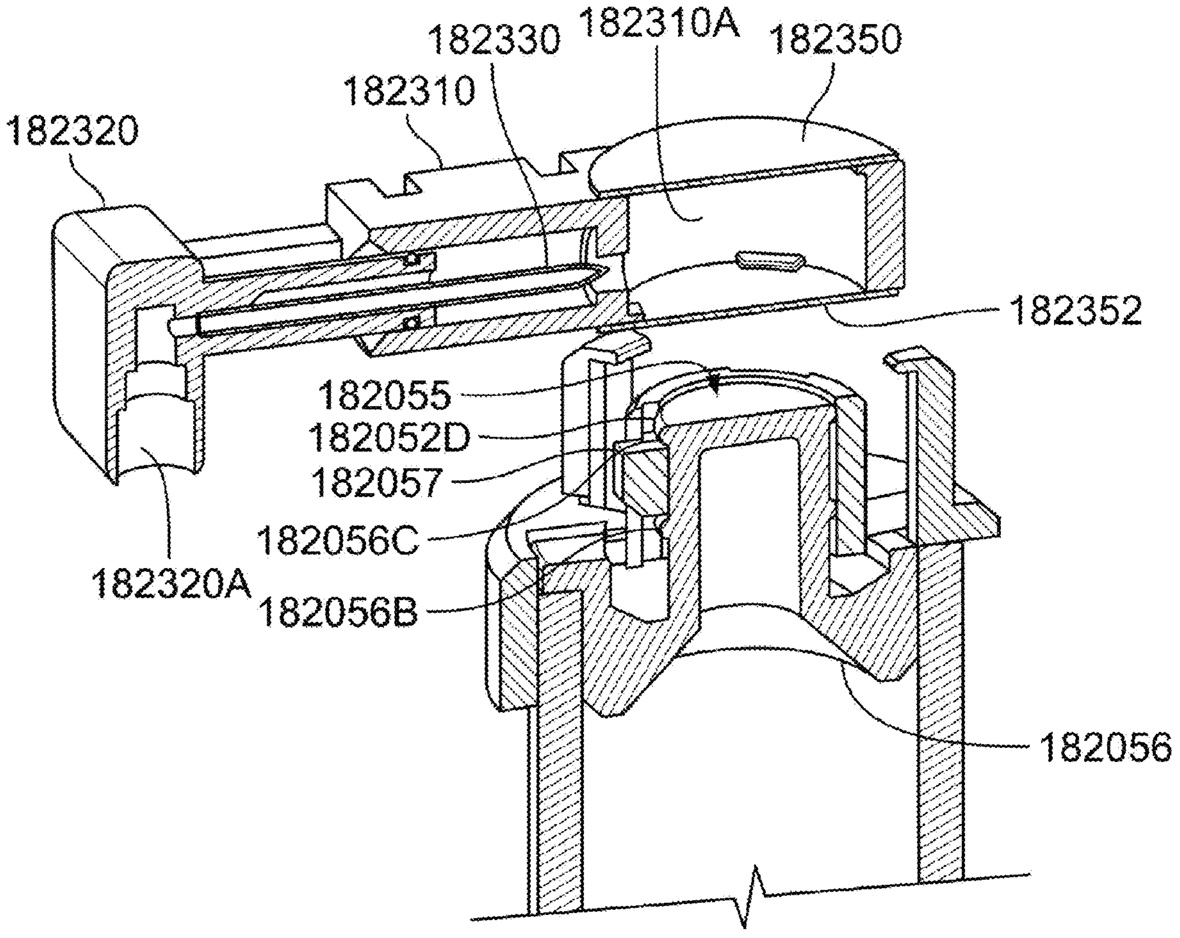
Figure 127B:
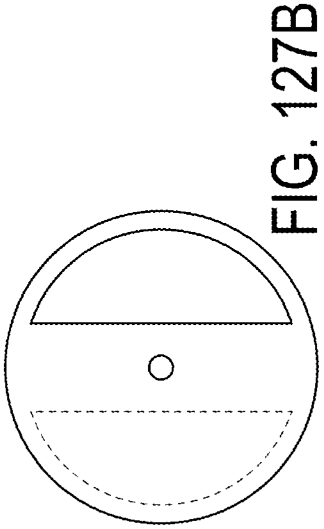
Figure 127C:
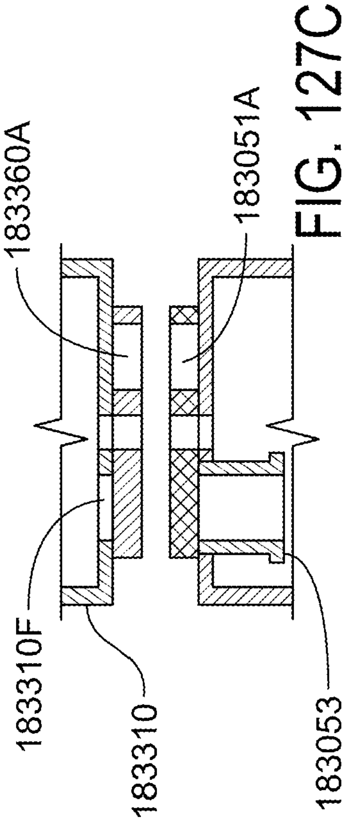
Figure 127D:
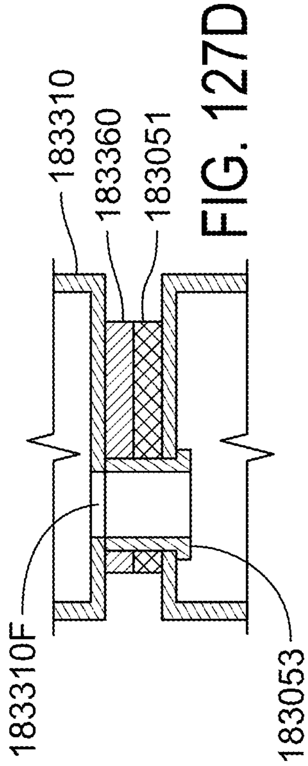
Figure 127A:
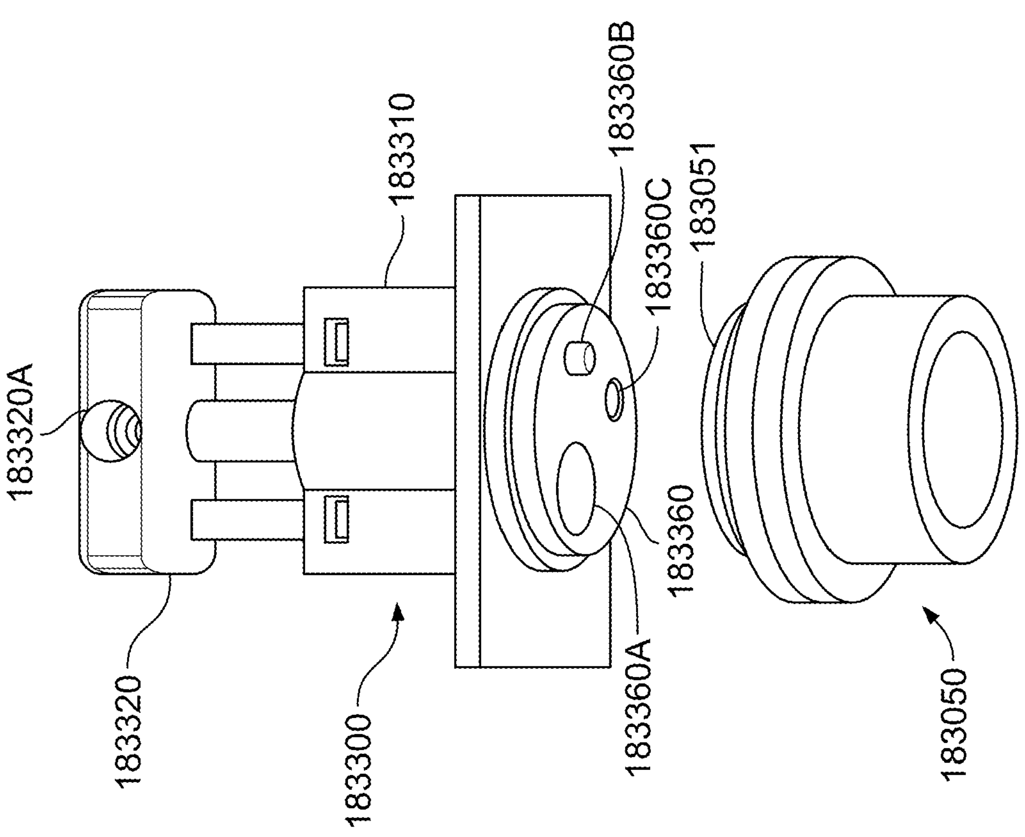
Figure 128A:
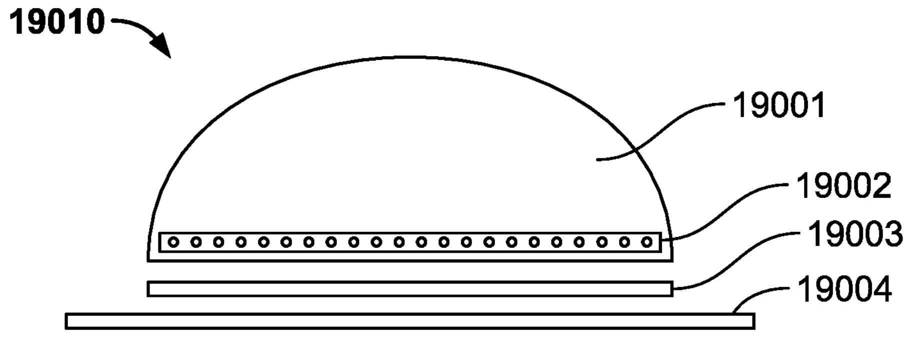
Figure 128B:
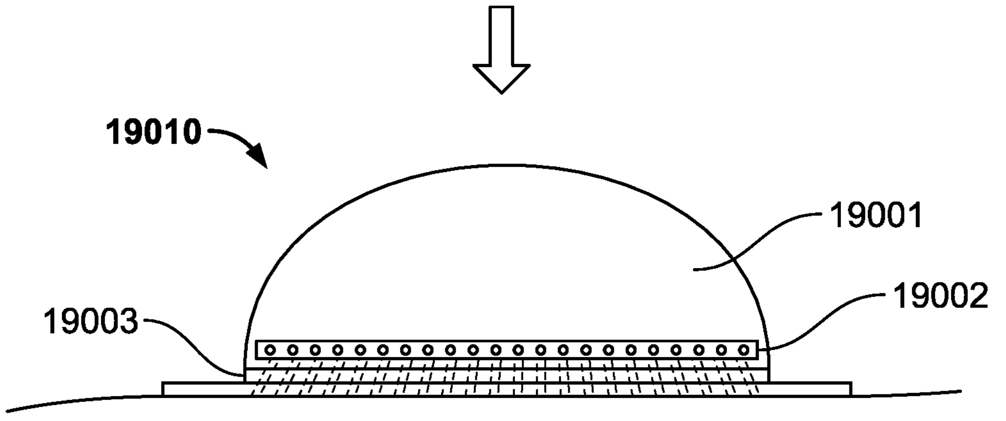
Figure 128C:
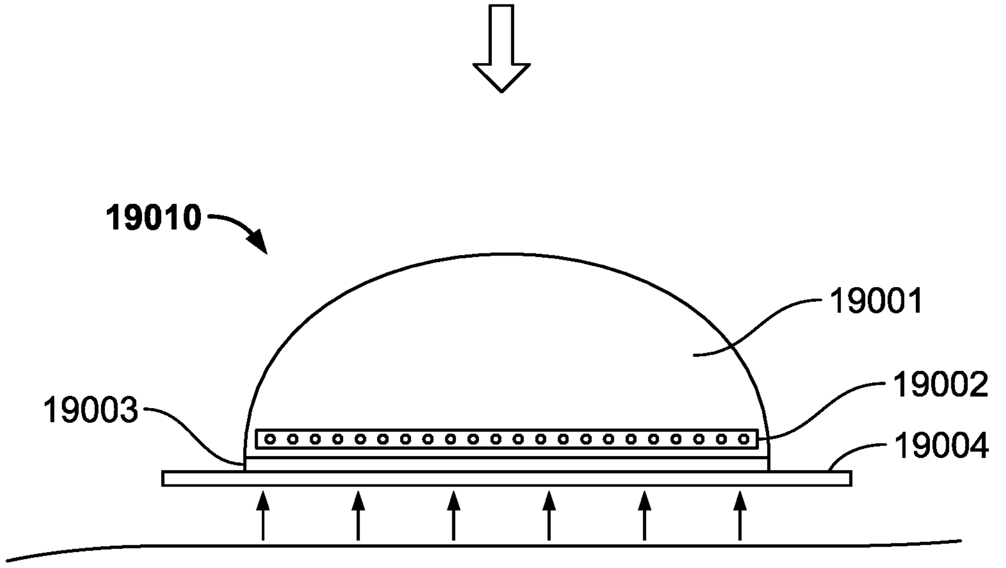
Figure 129A:
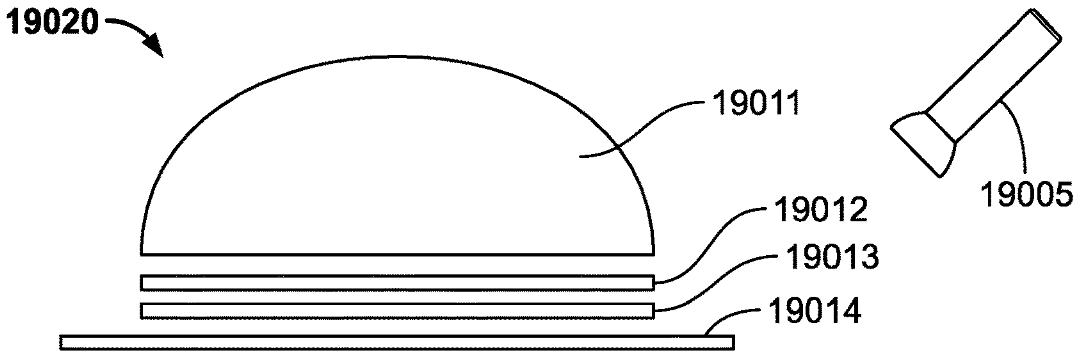
Figure 129B:
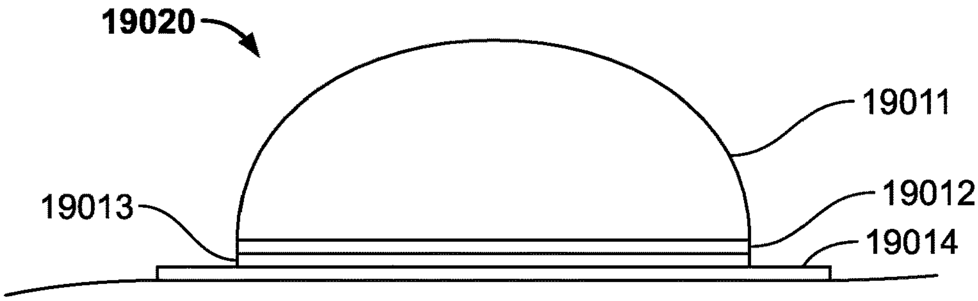
Figure 129C:
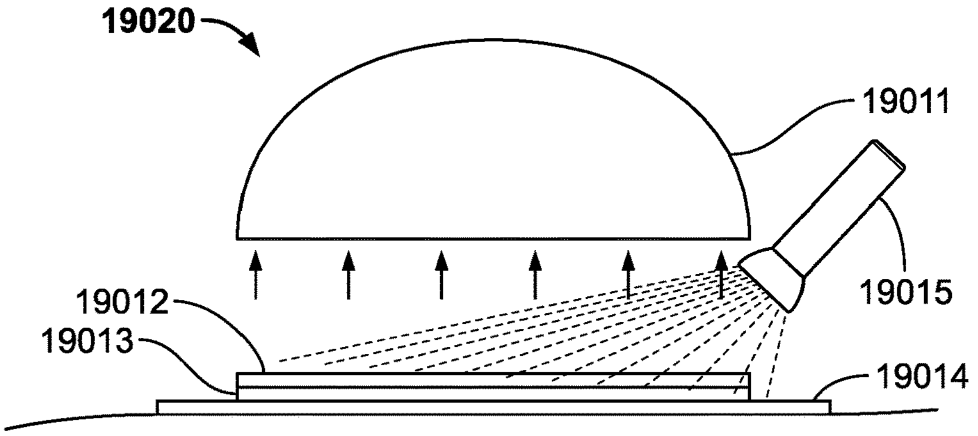
Figure 129D:
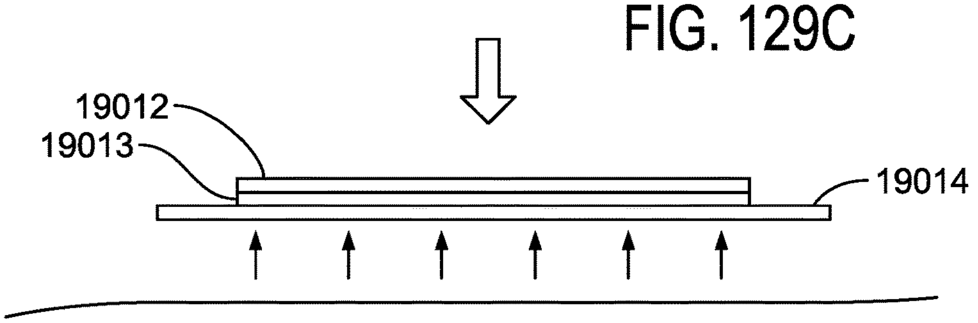
Figure 130:
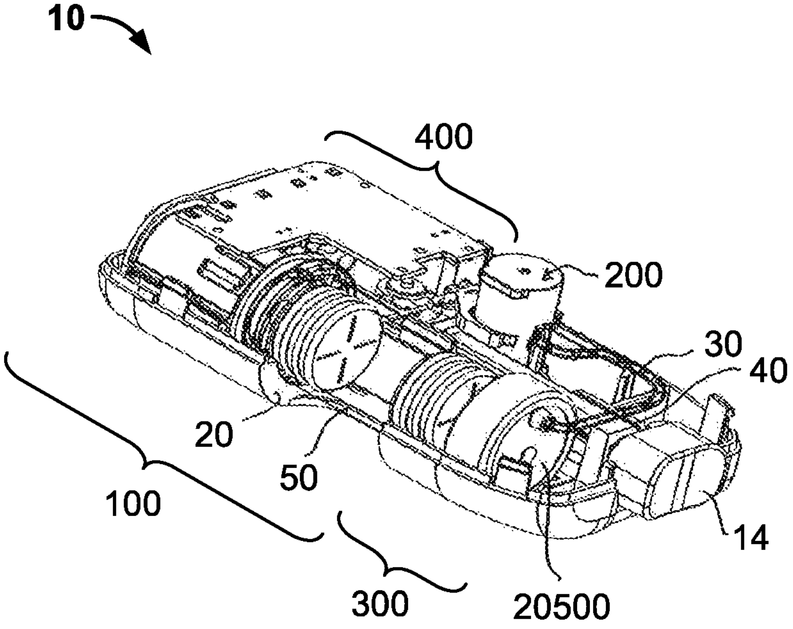
Figures 131A, 131B, 131C:
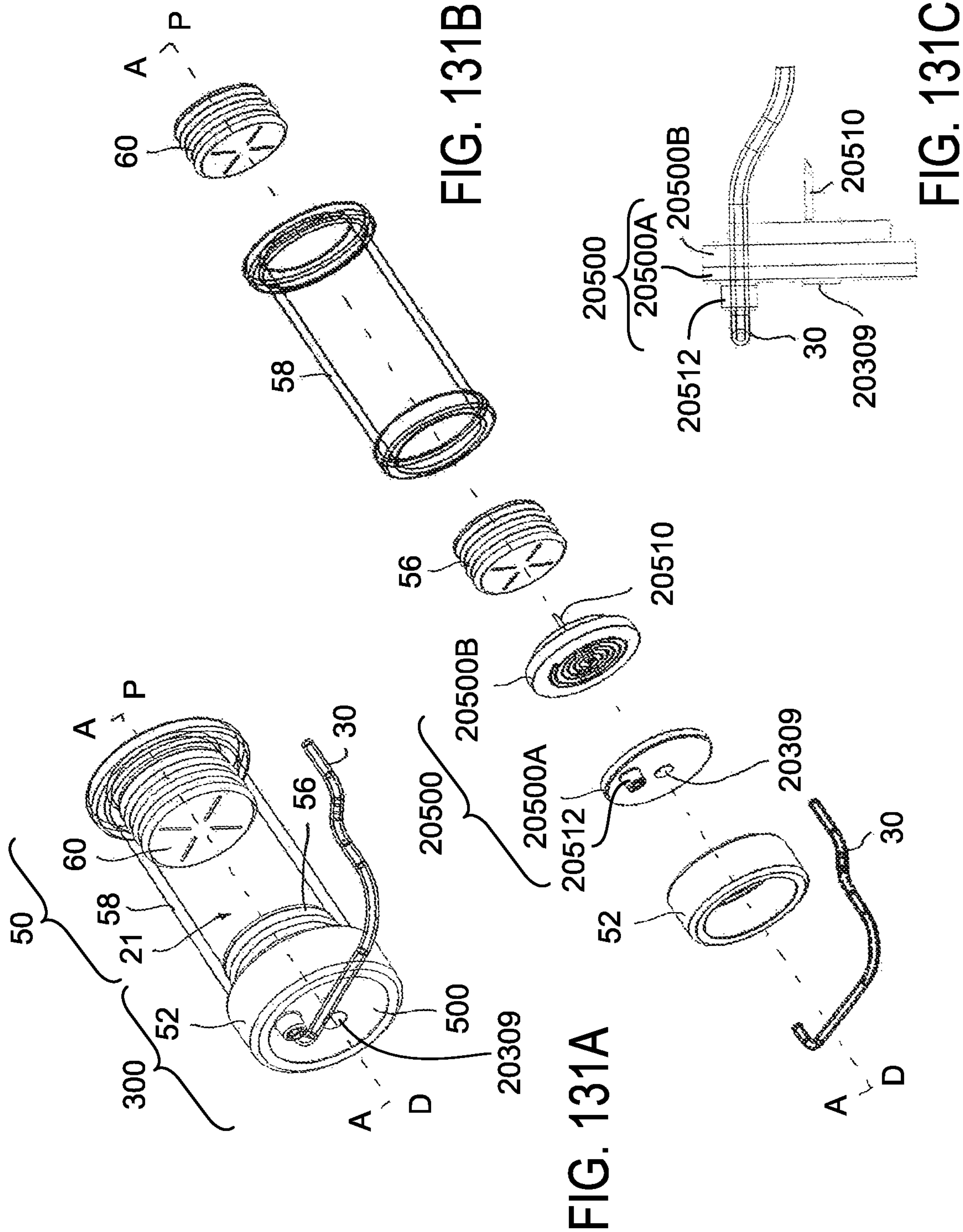
Figures 133A, 133B, 133C:
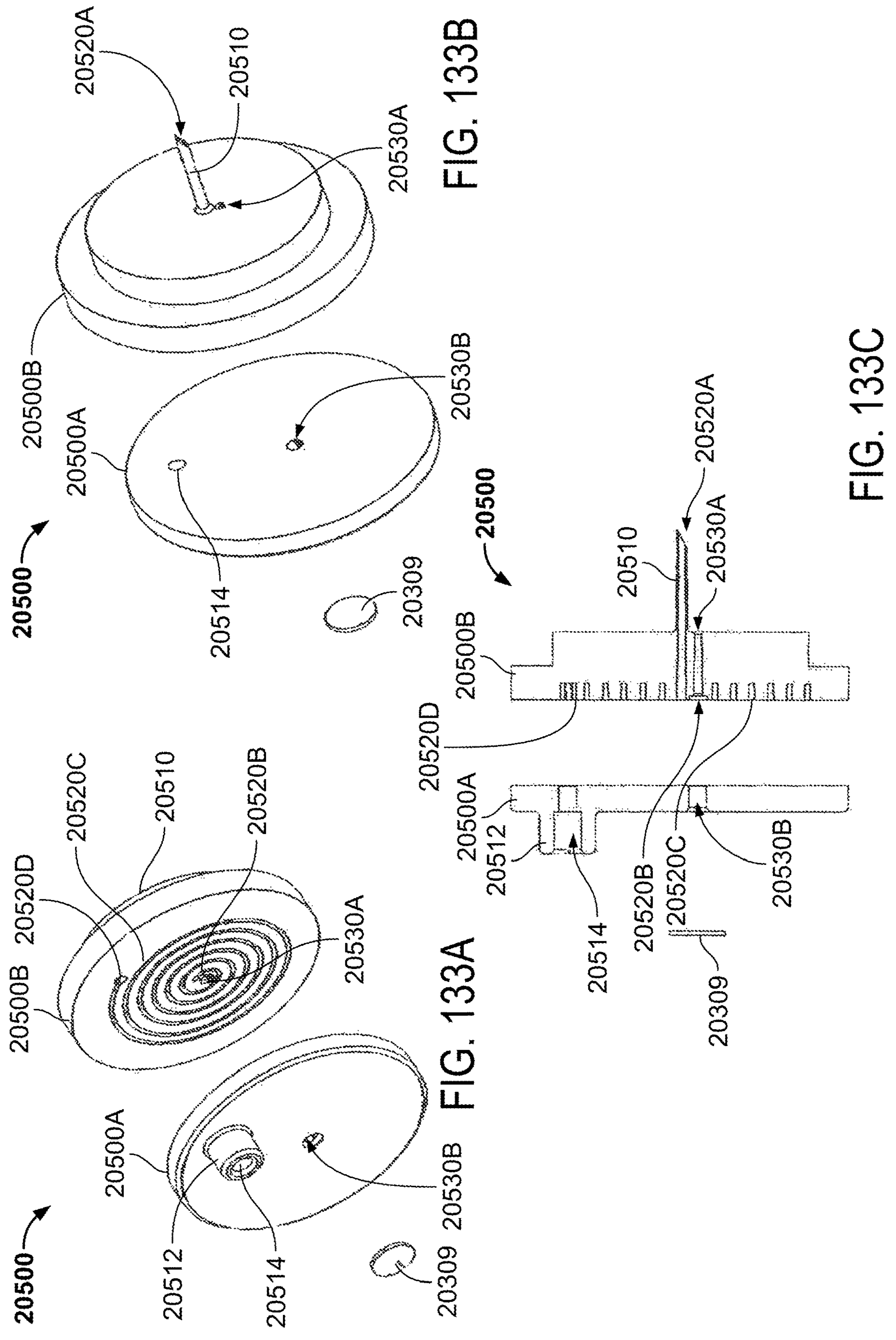
Figure 134A:
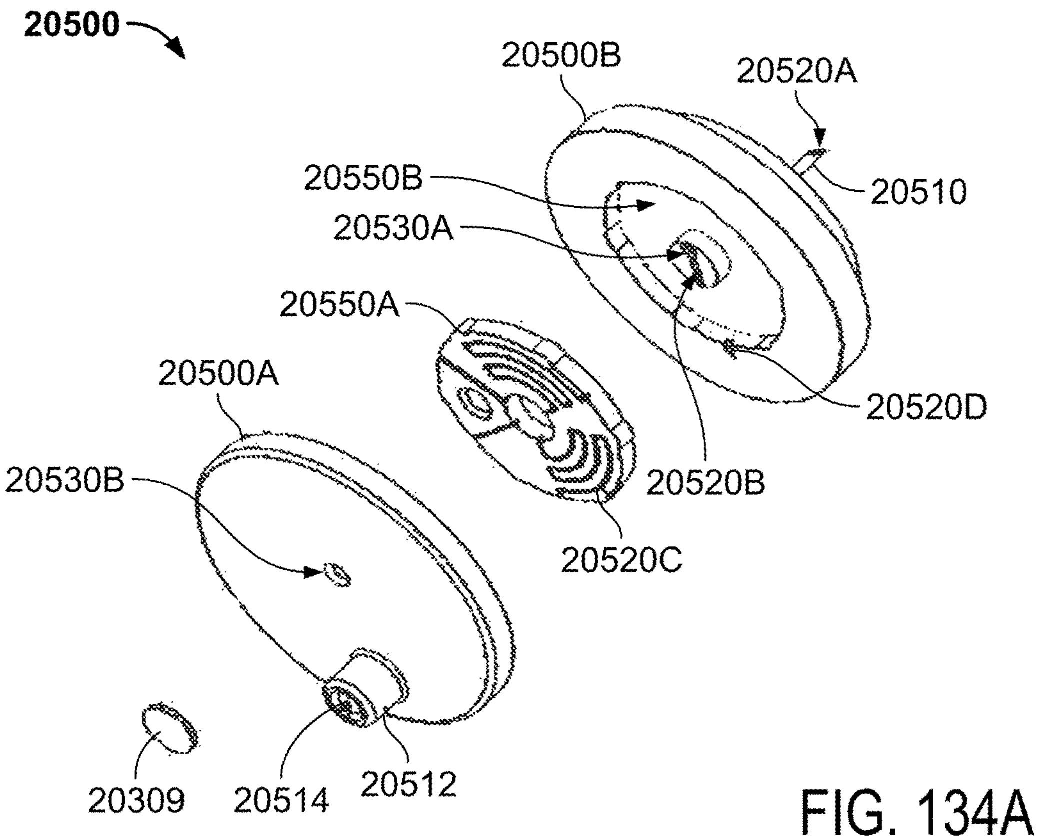
Figure 134B:
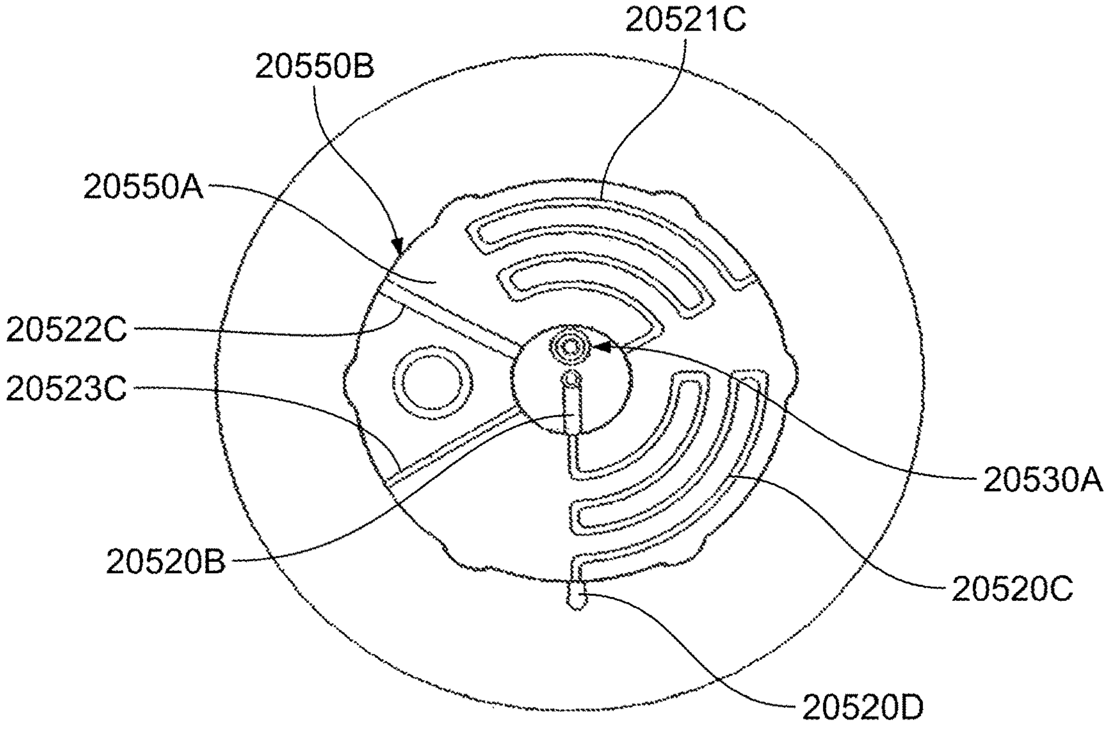
Figure 135A:
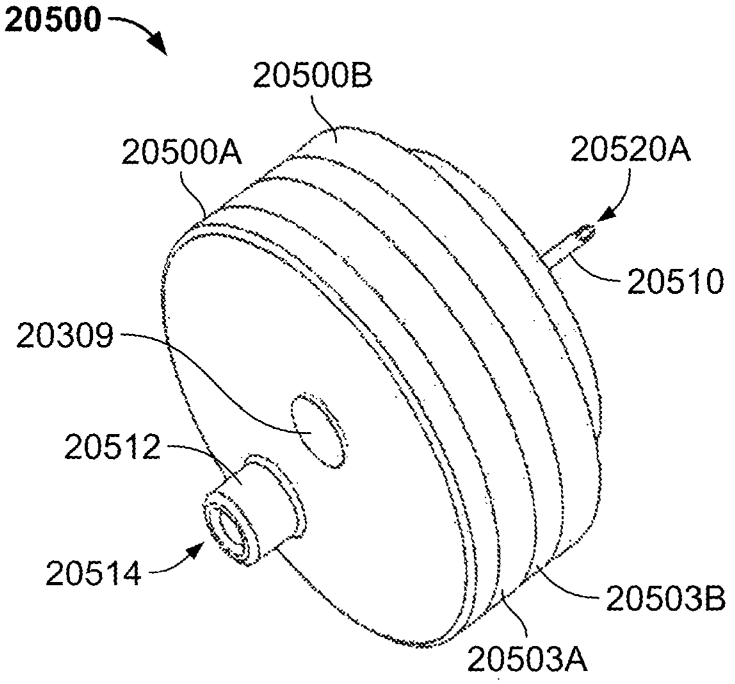
Figure 135B:
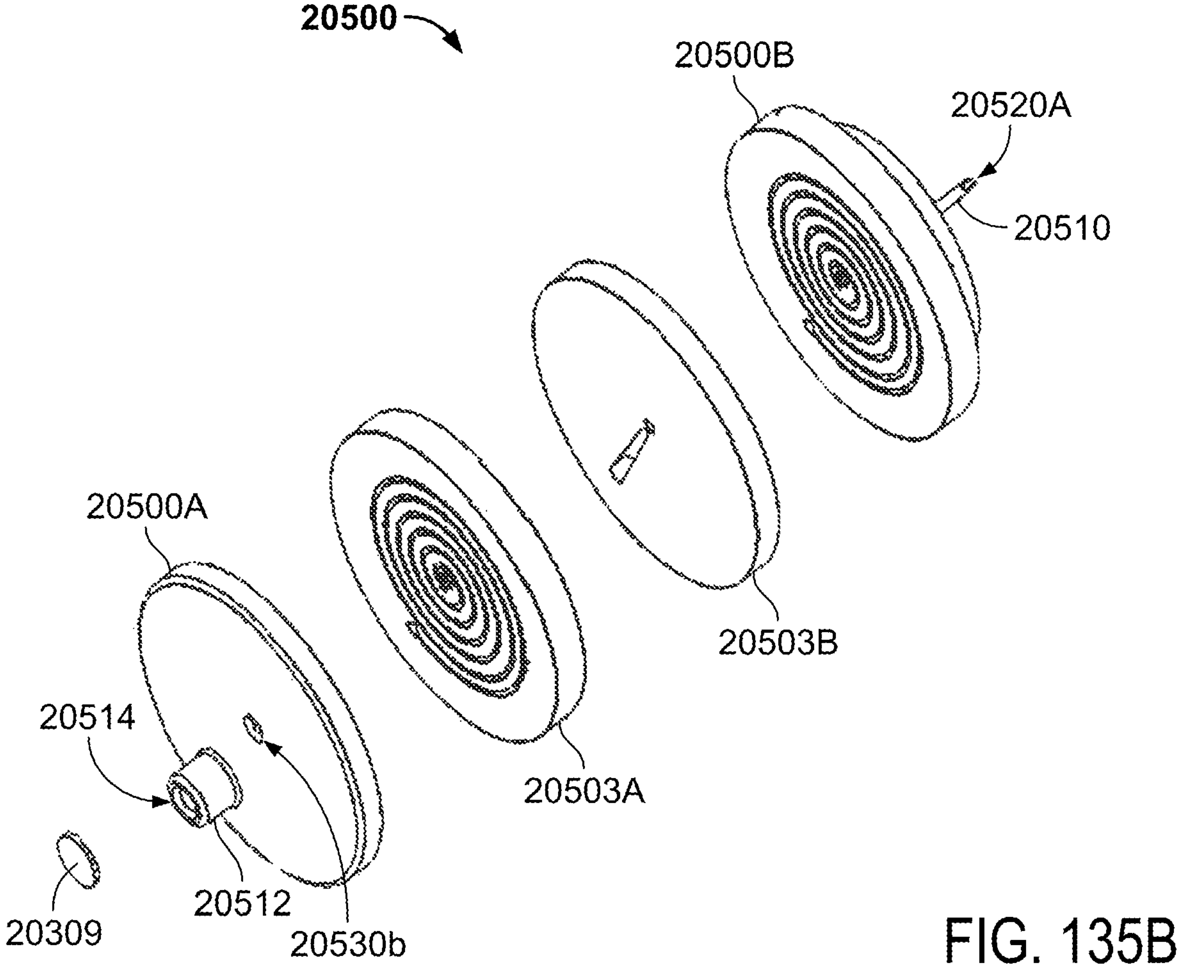
Figure 136A:
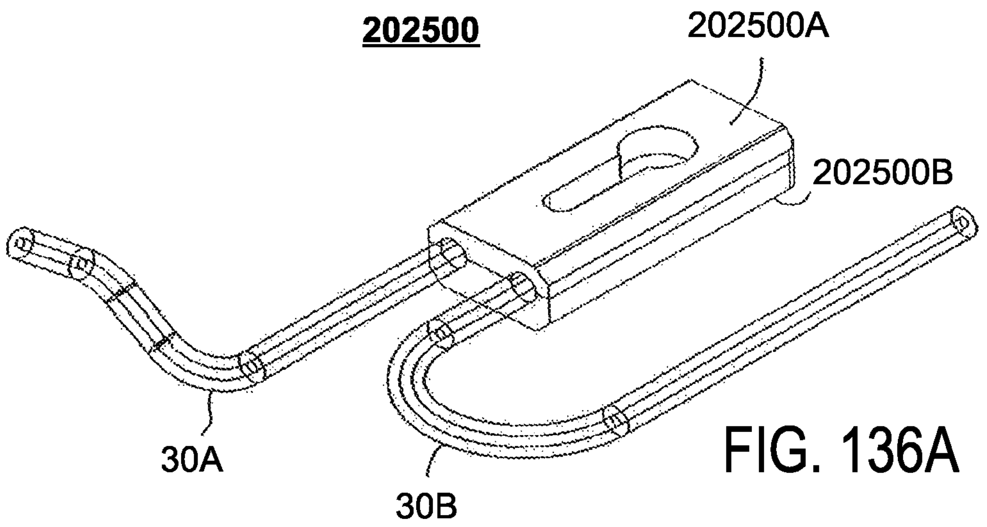
Figure 136B:
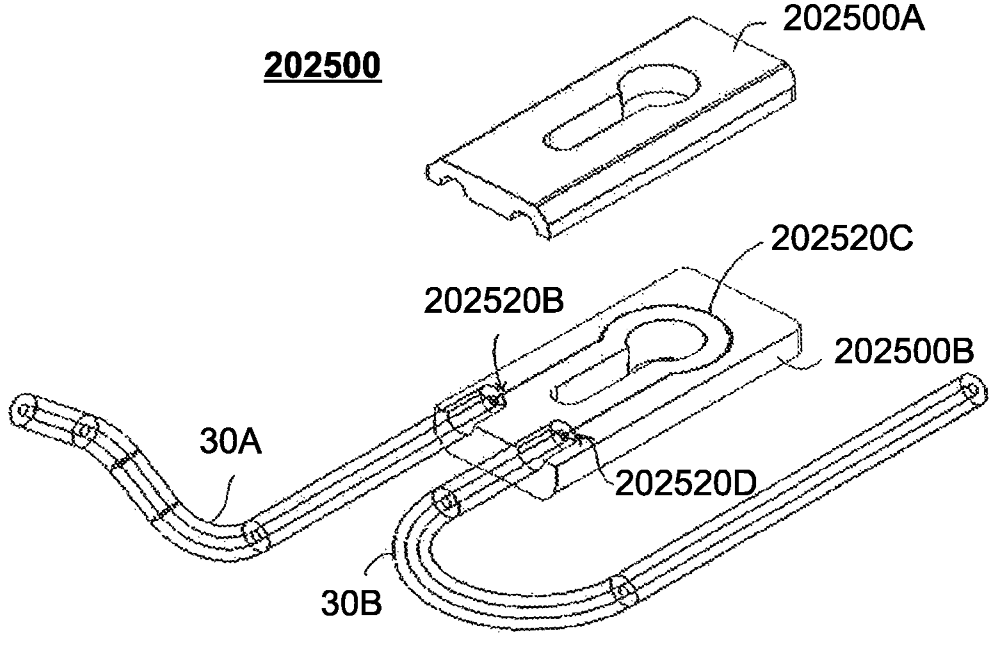
Figure 137A:
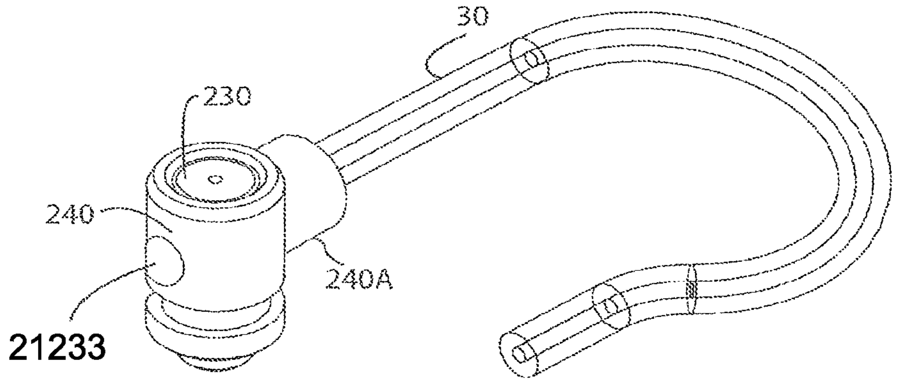
Figure 137B:
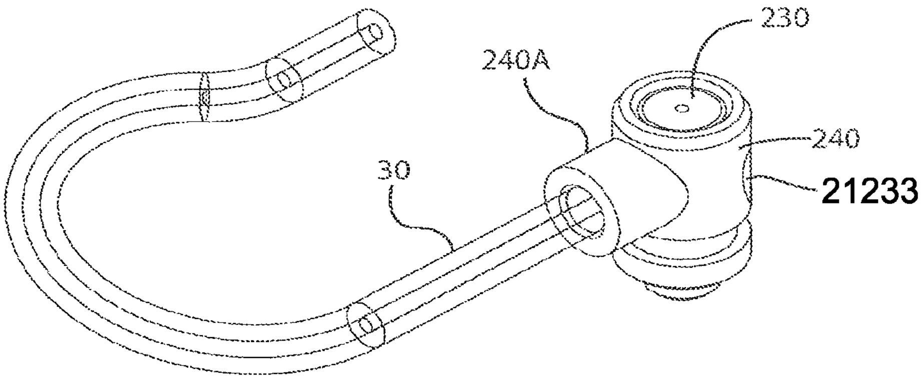
Figure 138A:
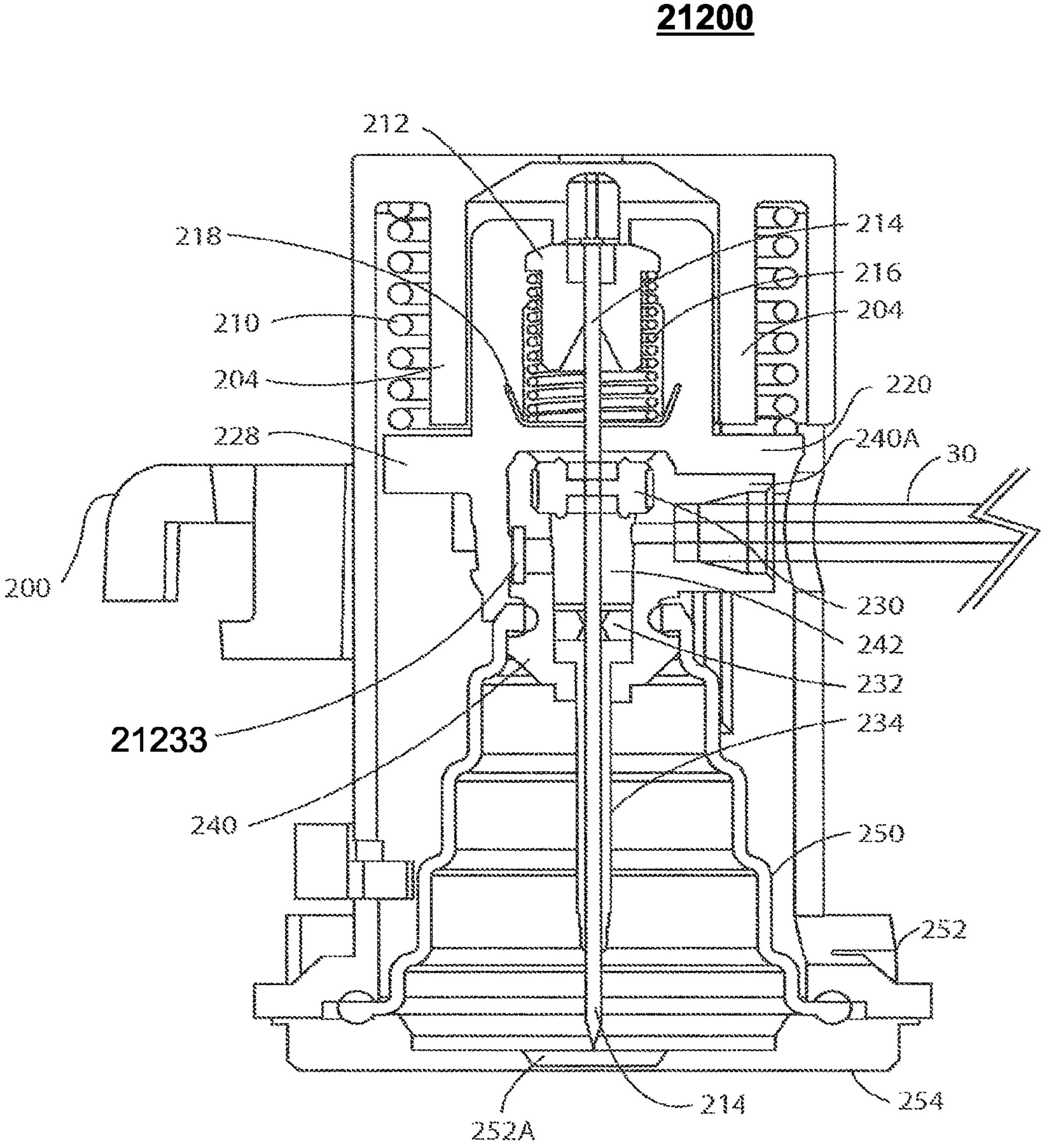
Figure 138B:
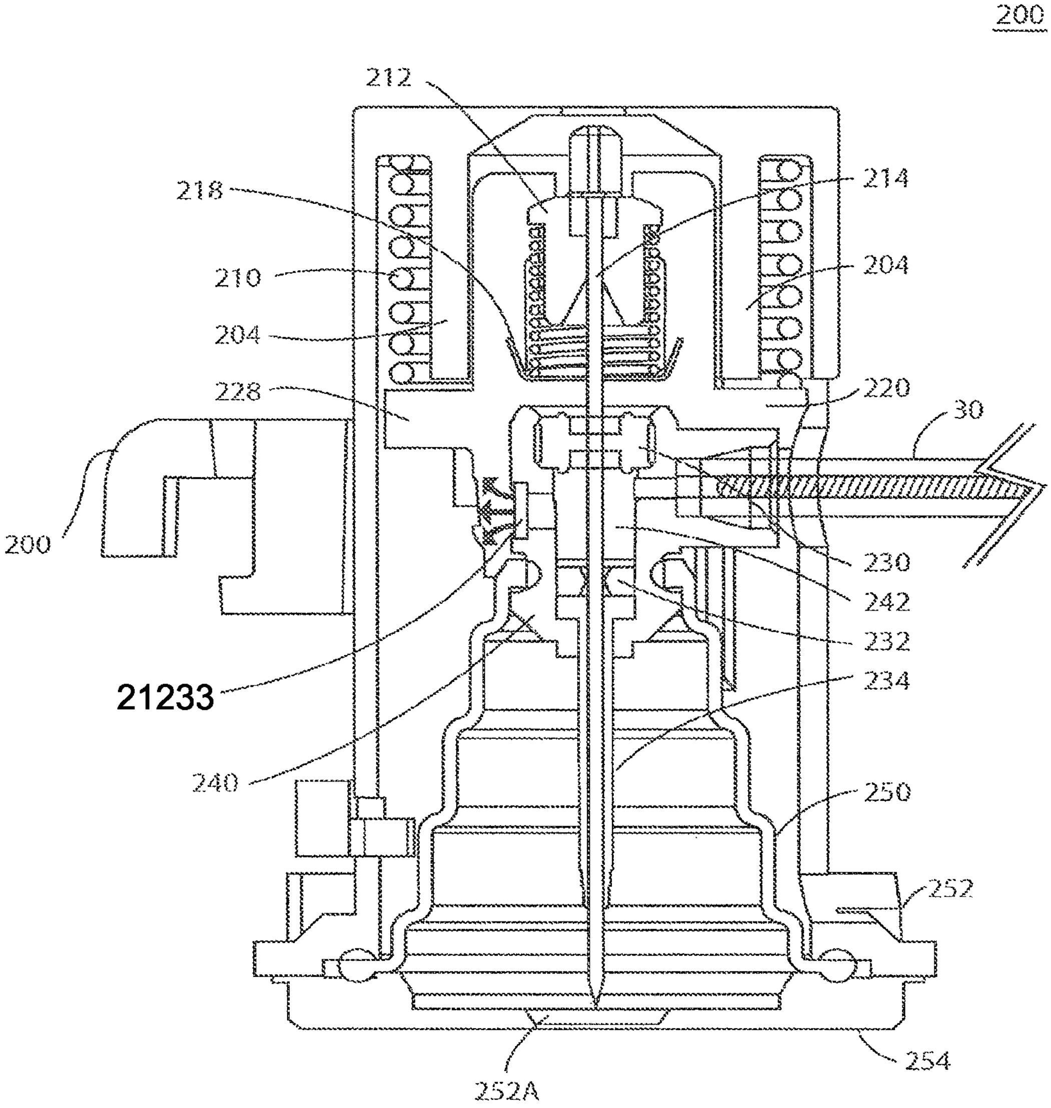
Figure 138C:
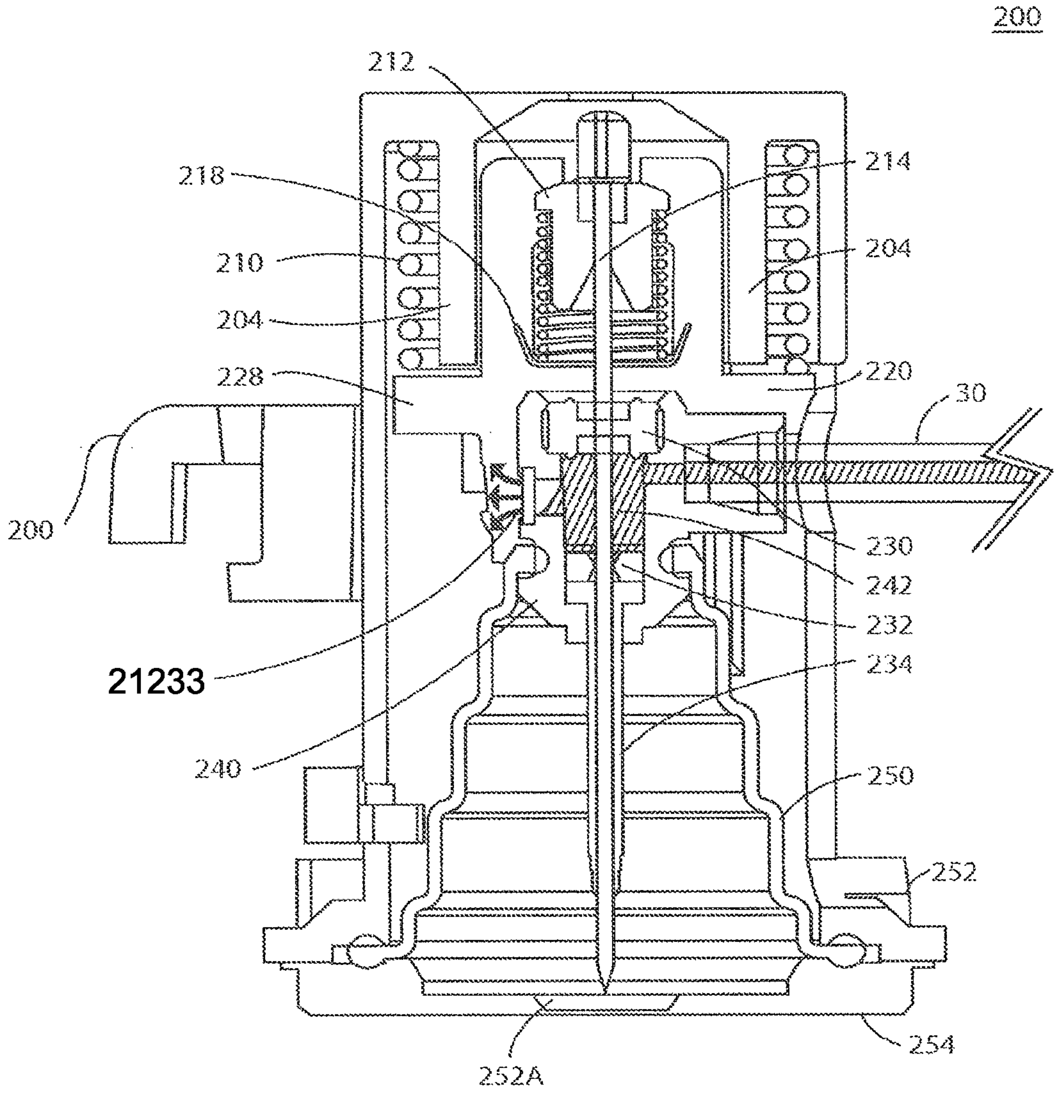
Figure 138D:
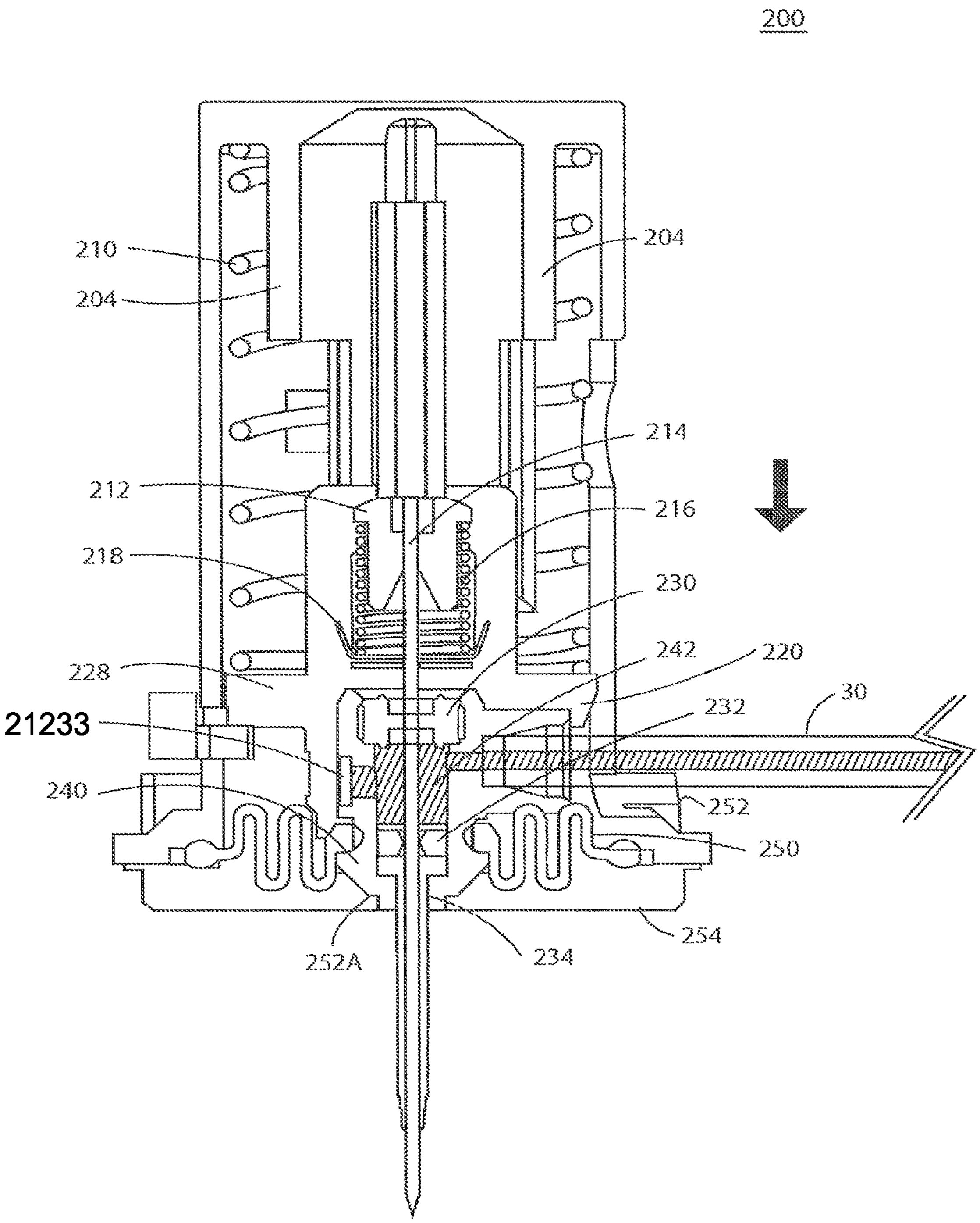
Figure 138E:
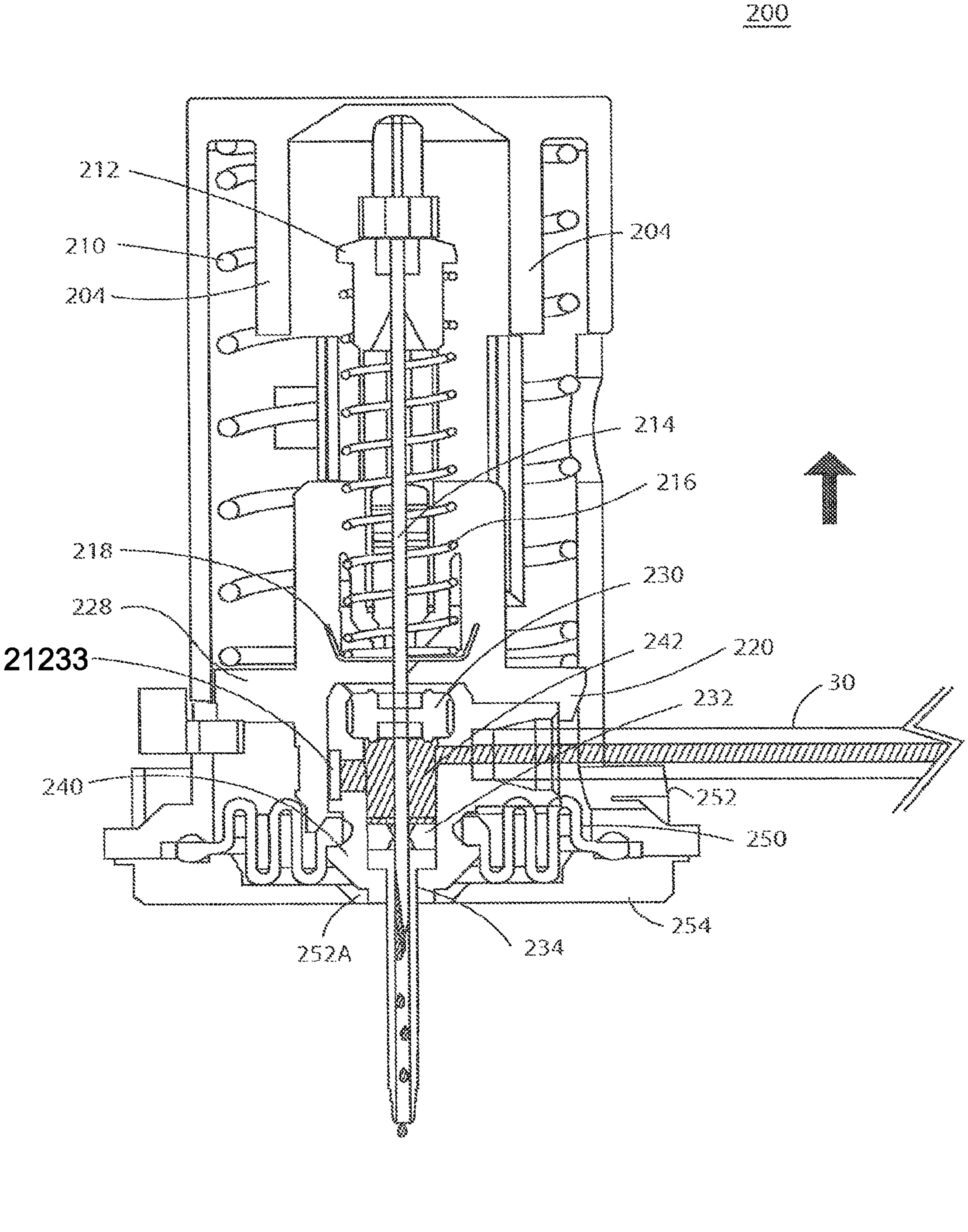
Figure 138F:
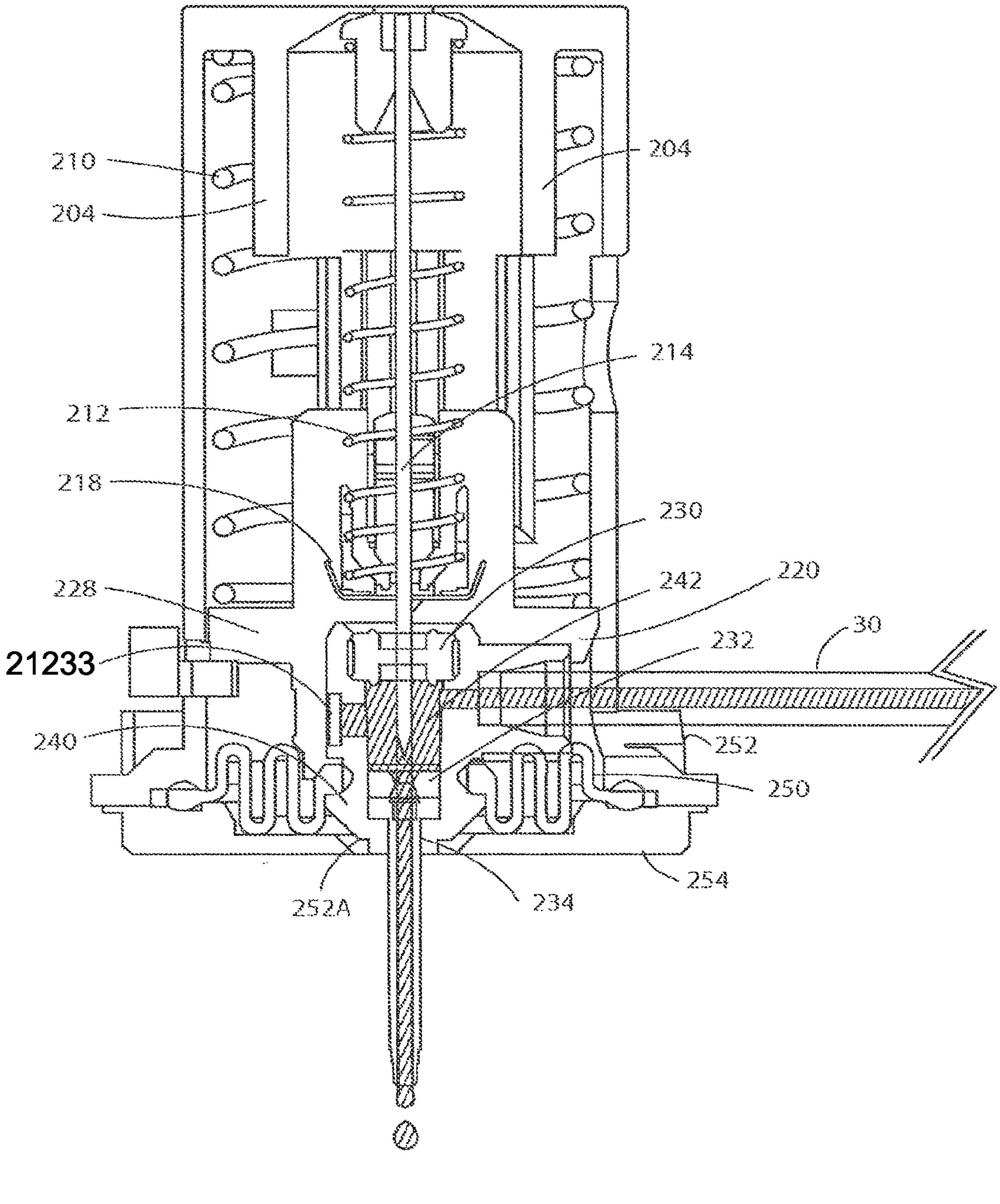
Figure 139A:
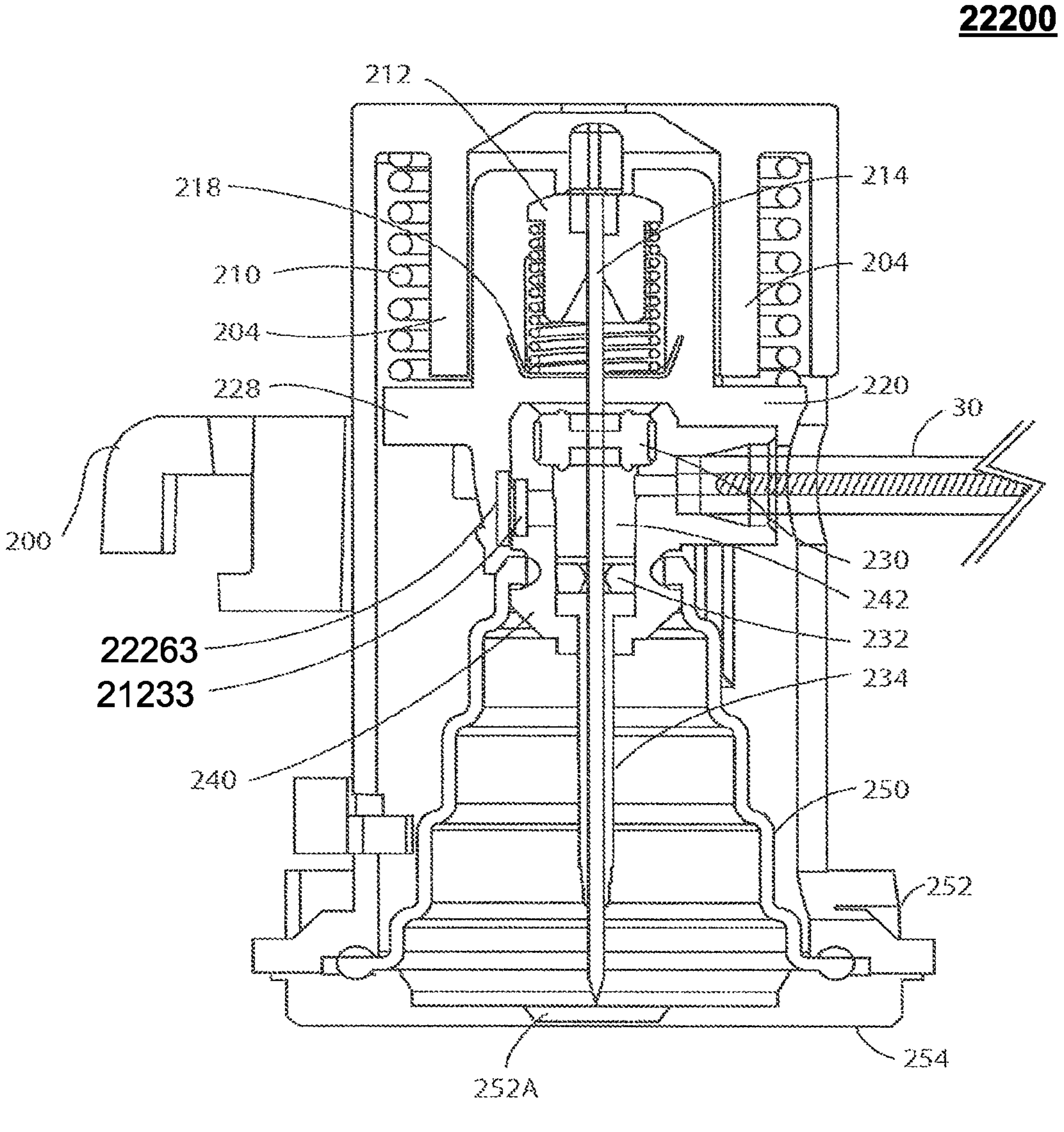
Figure 139B:
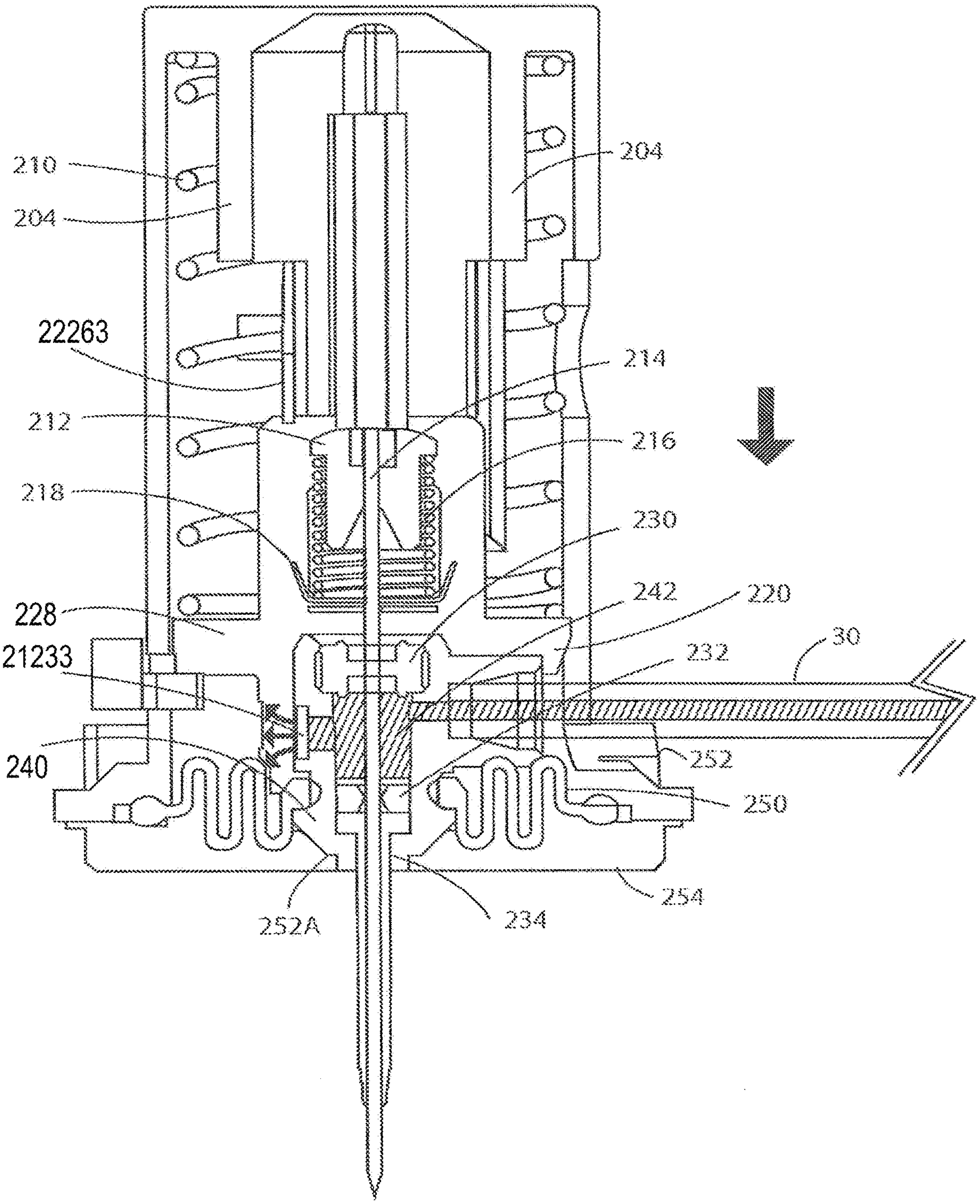
Figure 139C:
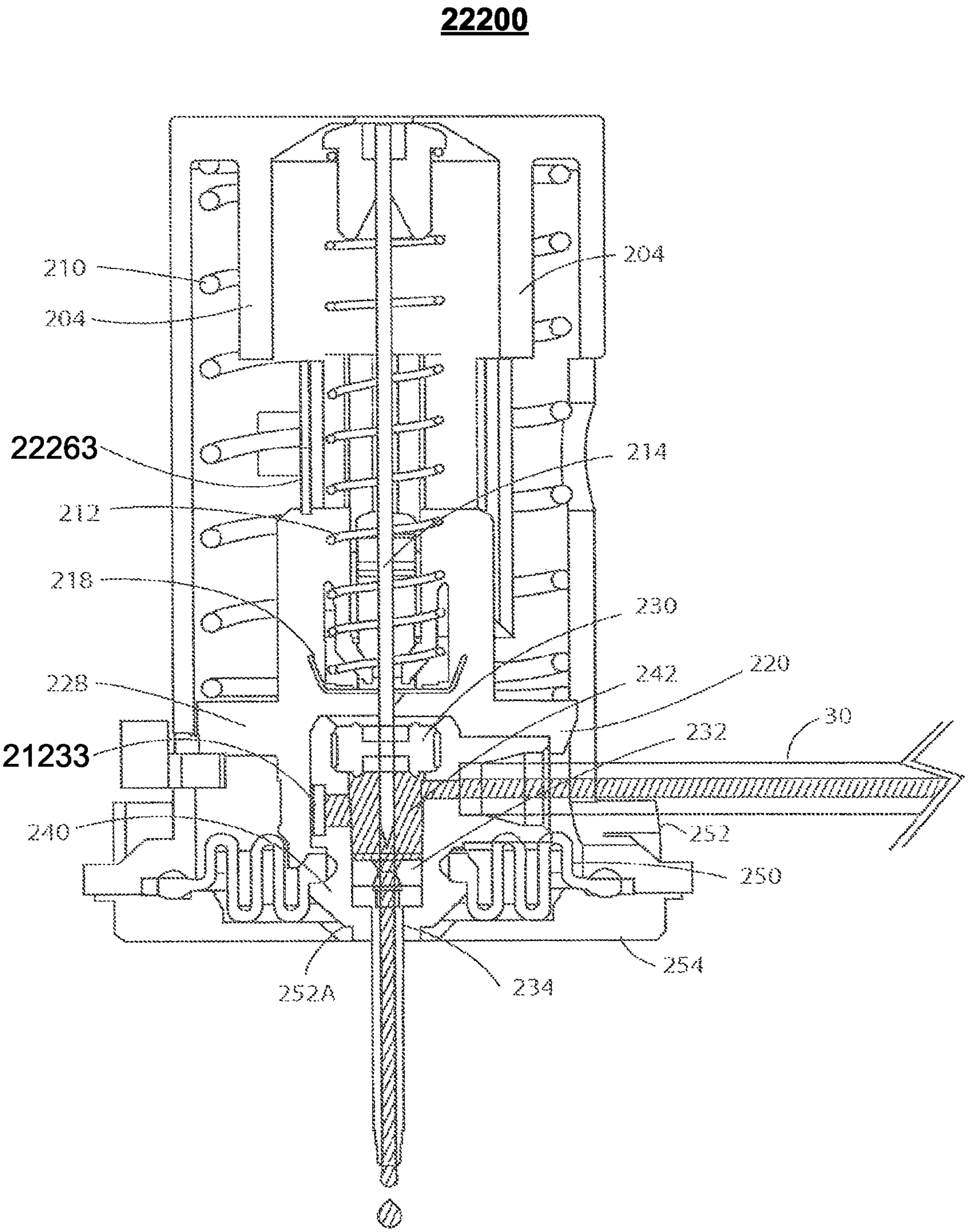
Figure 140A:
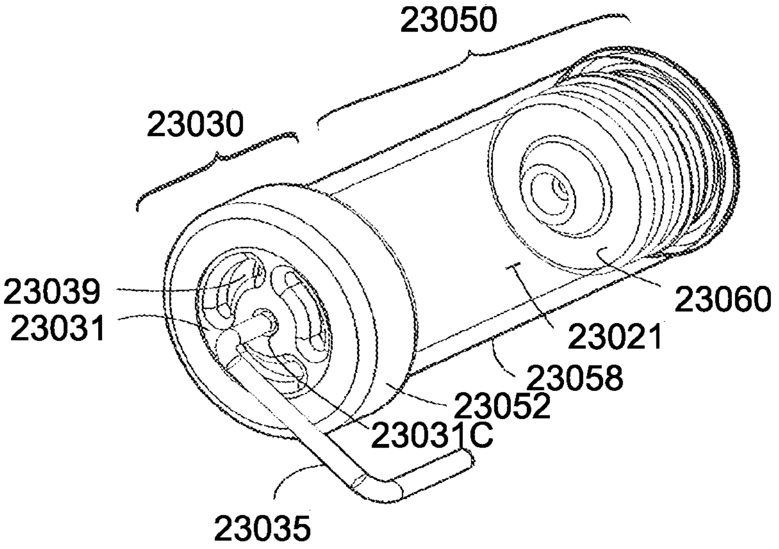
Figure 140B:
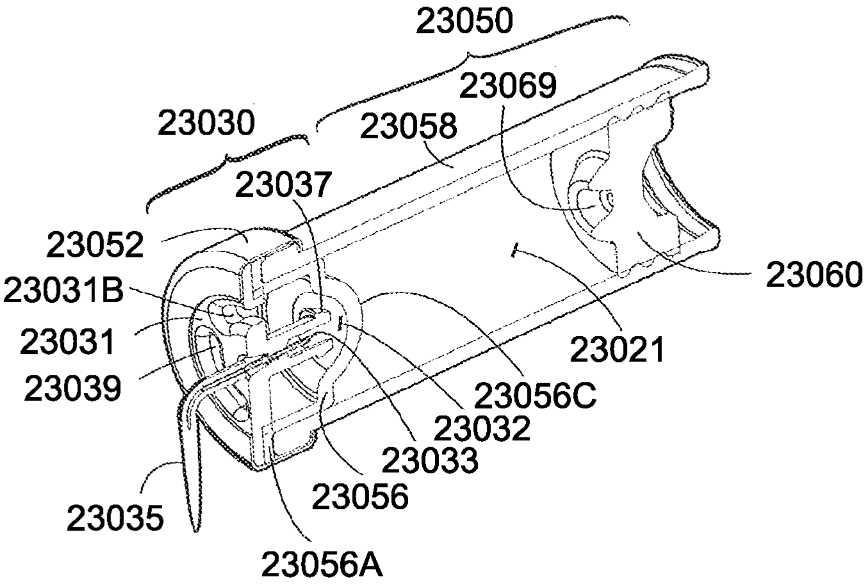
Figure 141A:
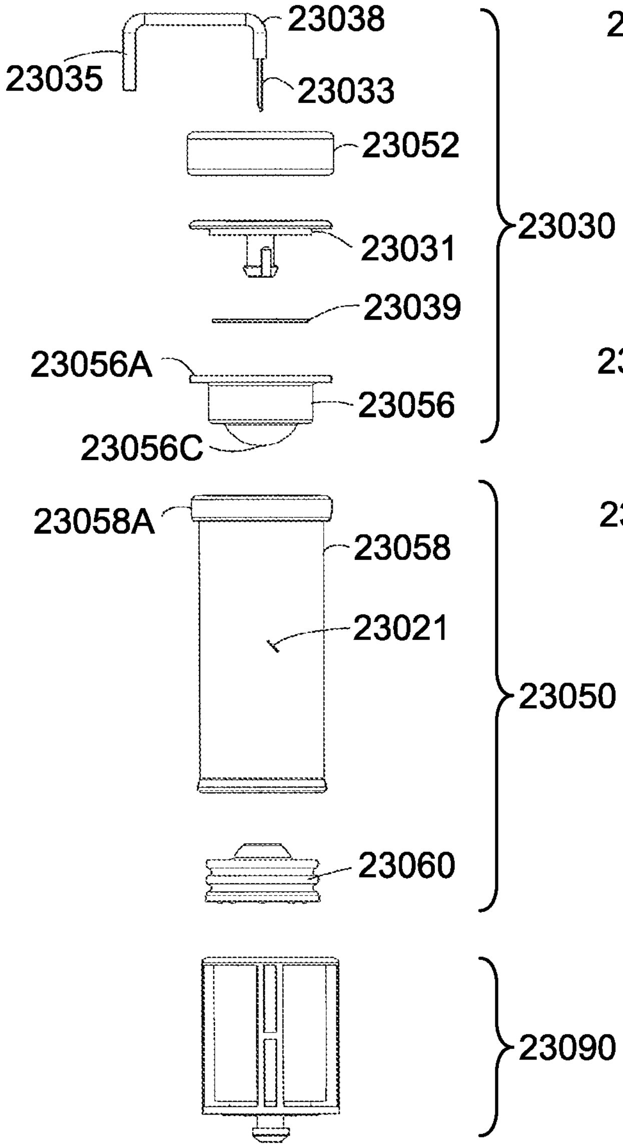
Figure 141B:
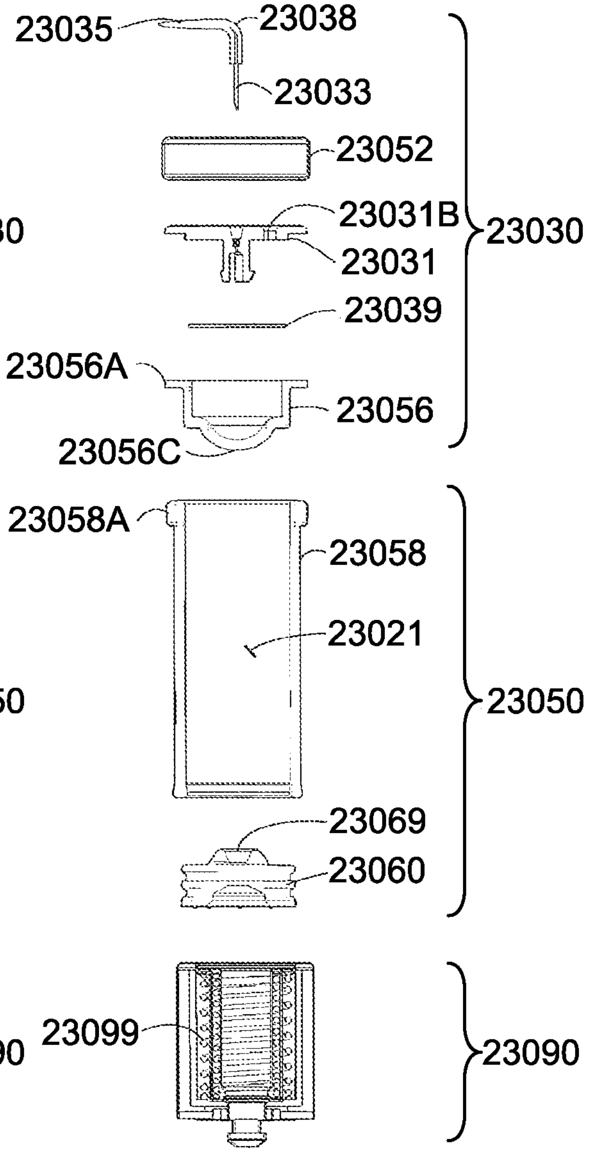
Figure 142B:
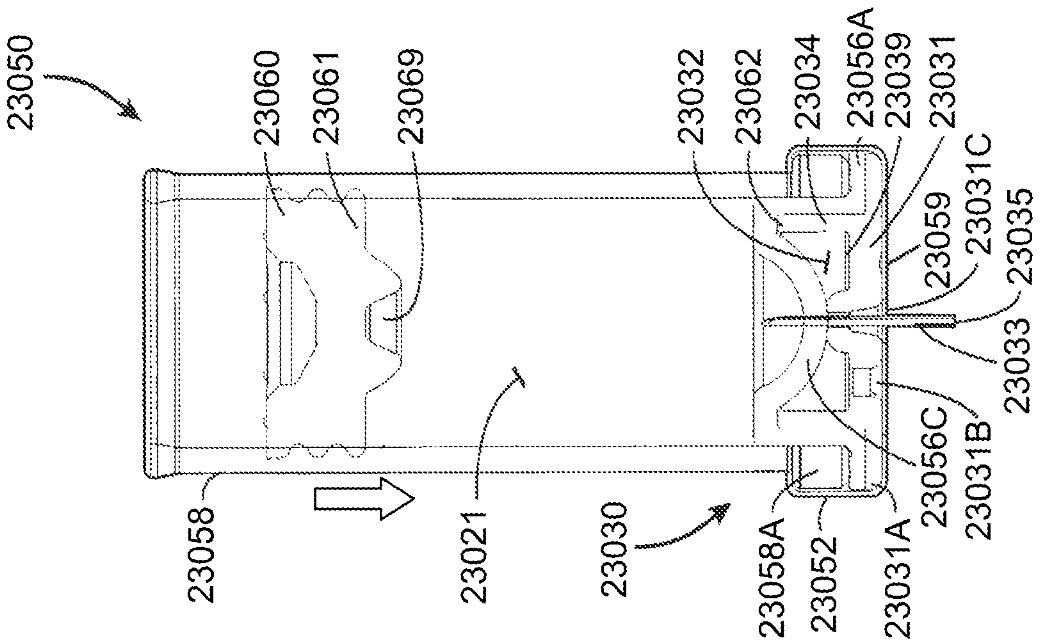
Figure 142A:
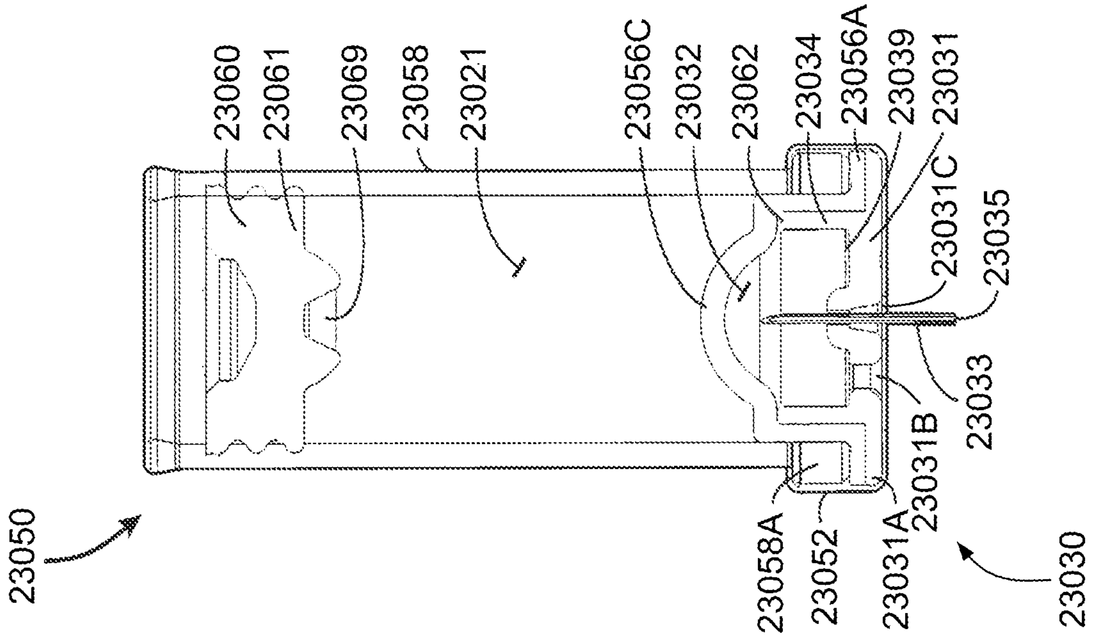
Figure 142C:
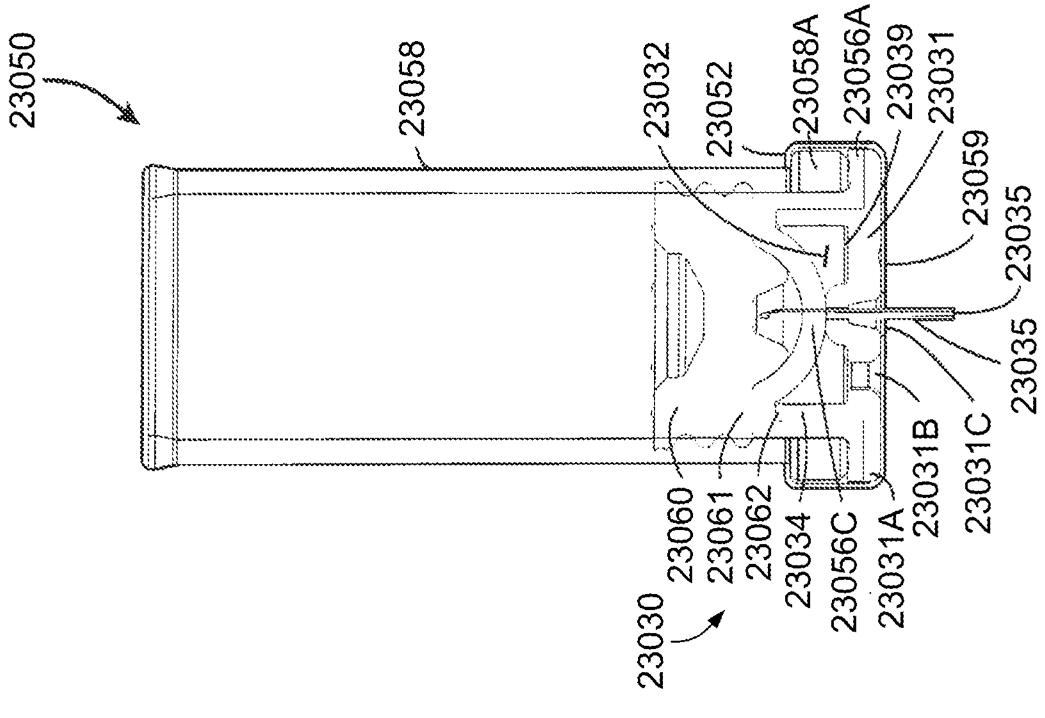
Figure 143A:
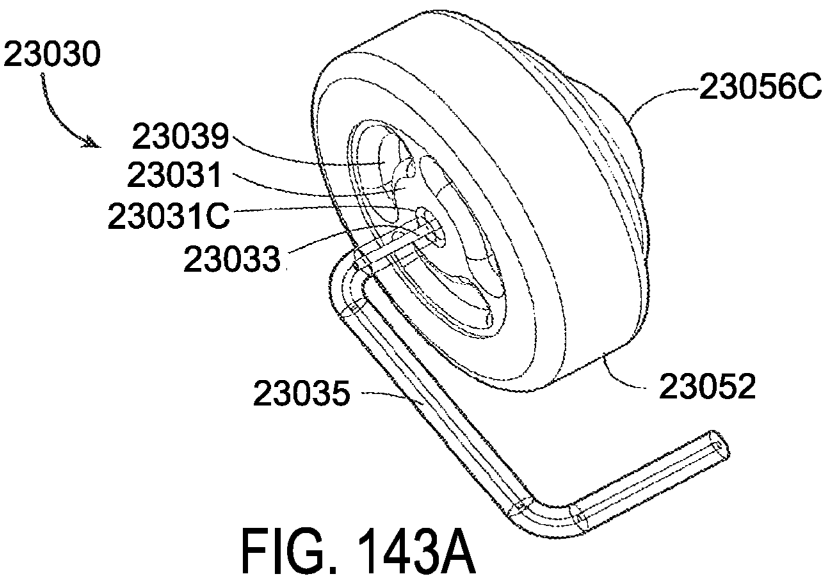
Figure 143B:
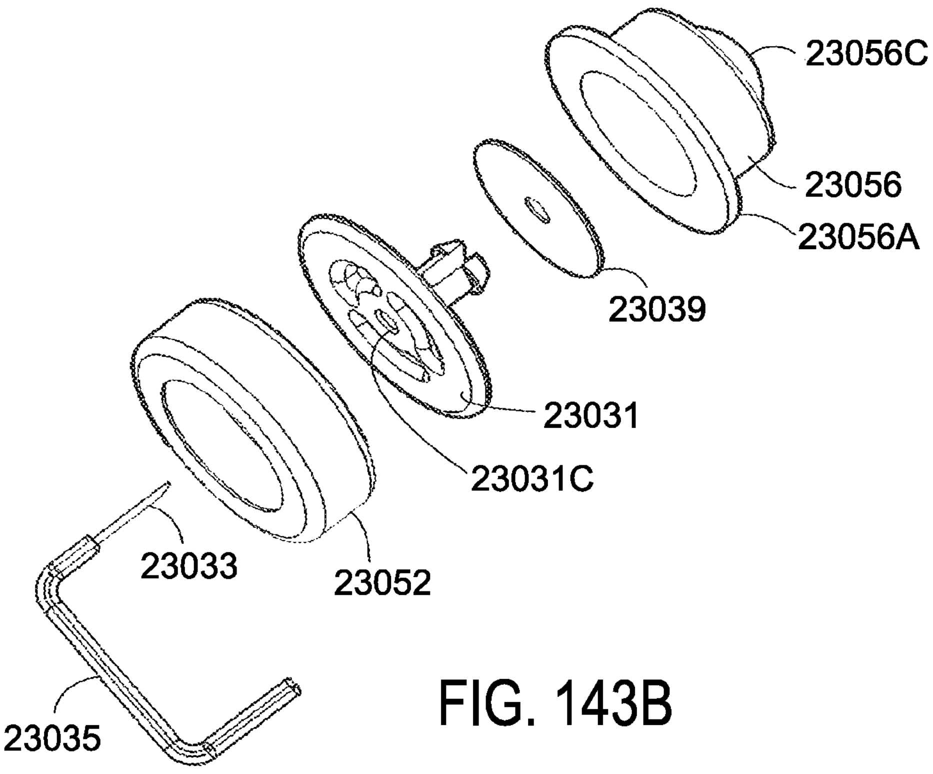
Figure 144A:
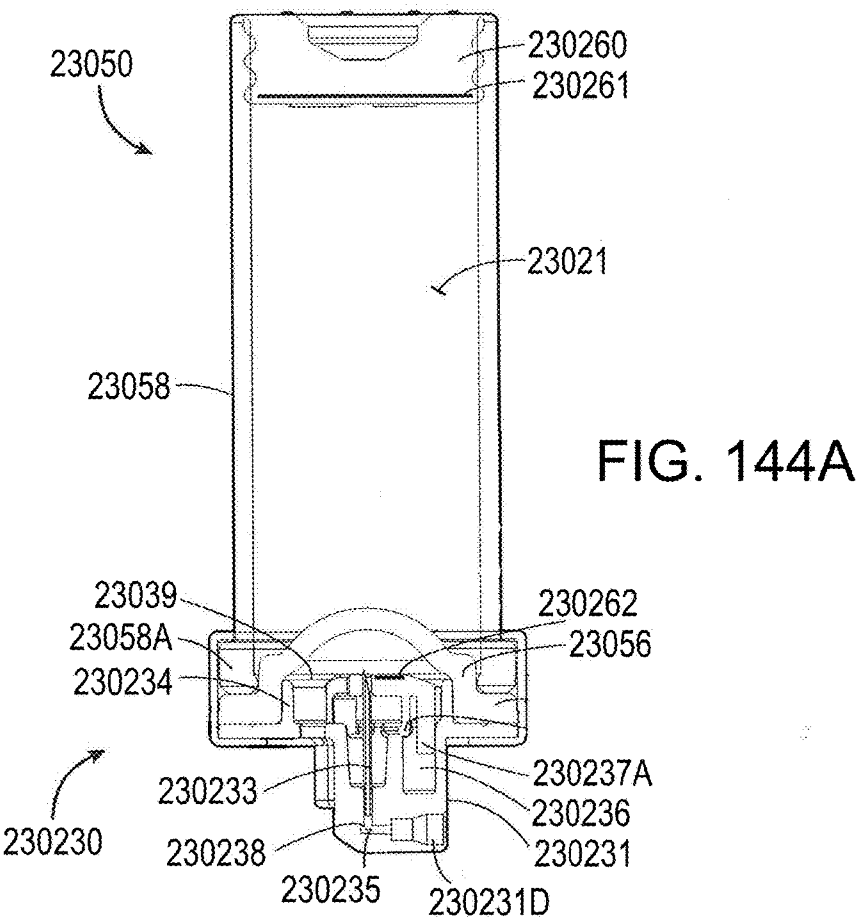
Figure 144B:
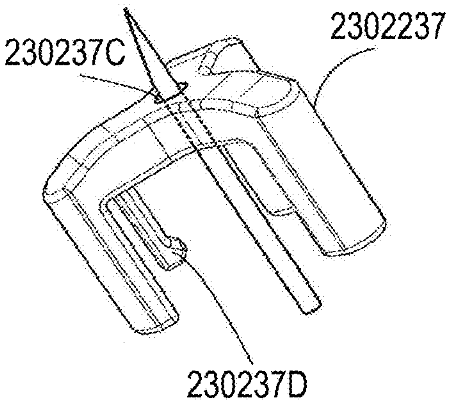
Figure 144C:
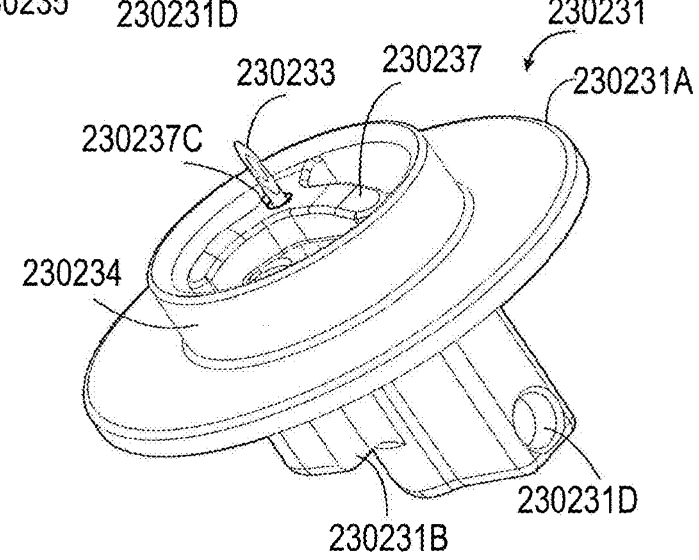
Figure 145:
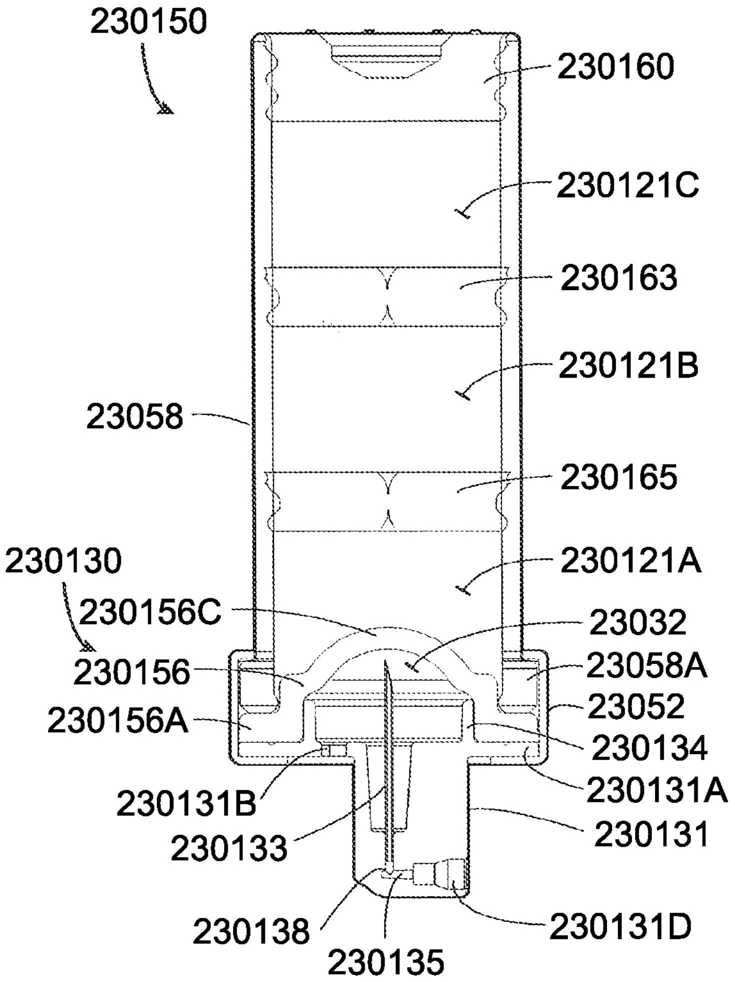
Figure 151A:
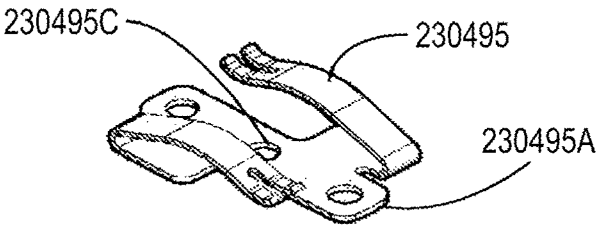
Figure 151B:
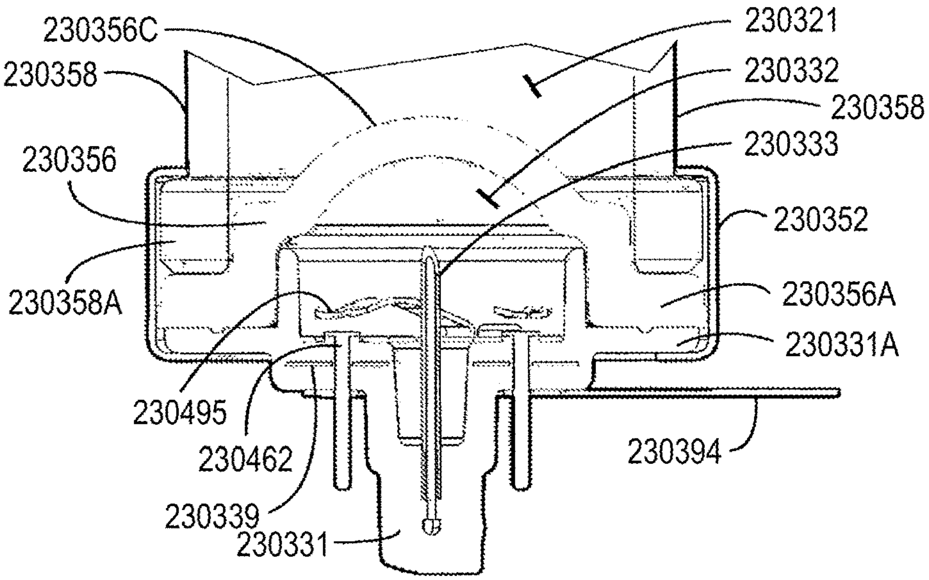
Figure 151C:
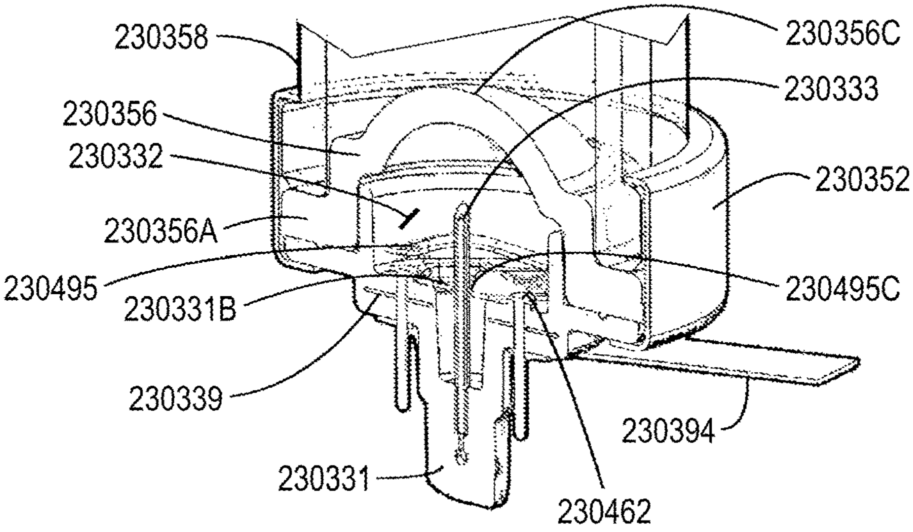
Figure 152A:
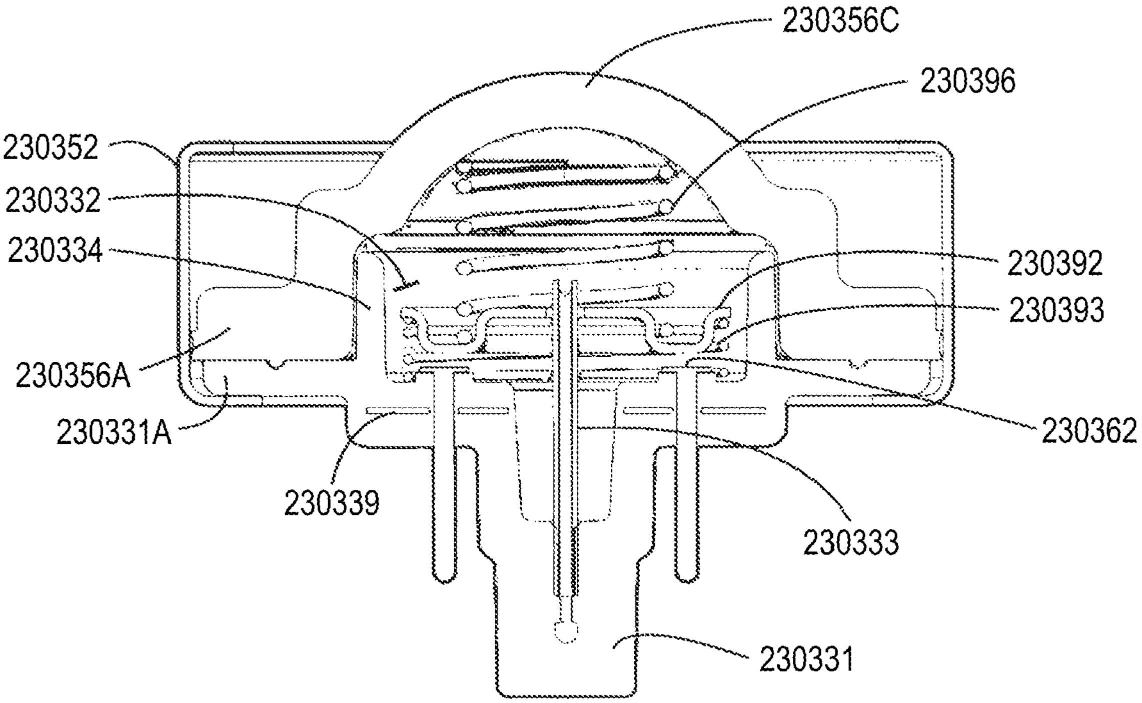
Figure 152B:
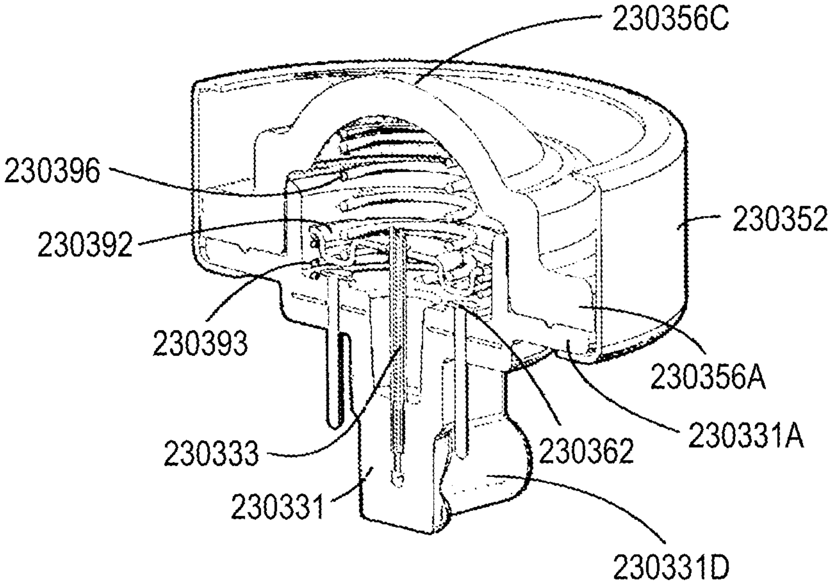
Figure 153A:
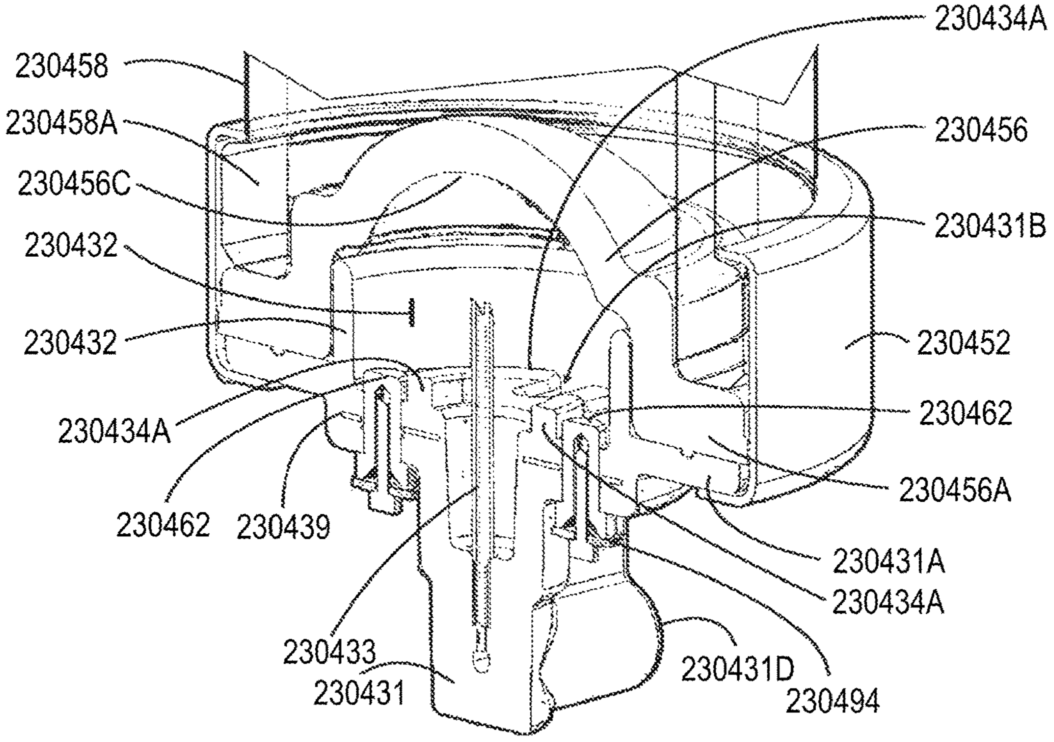
Figure 153B:
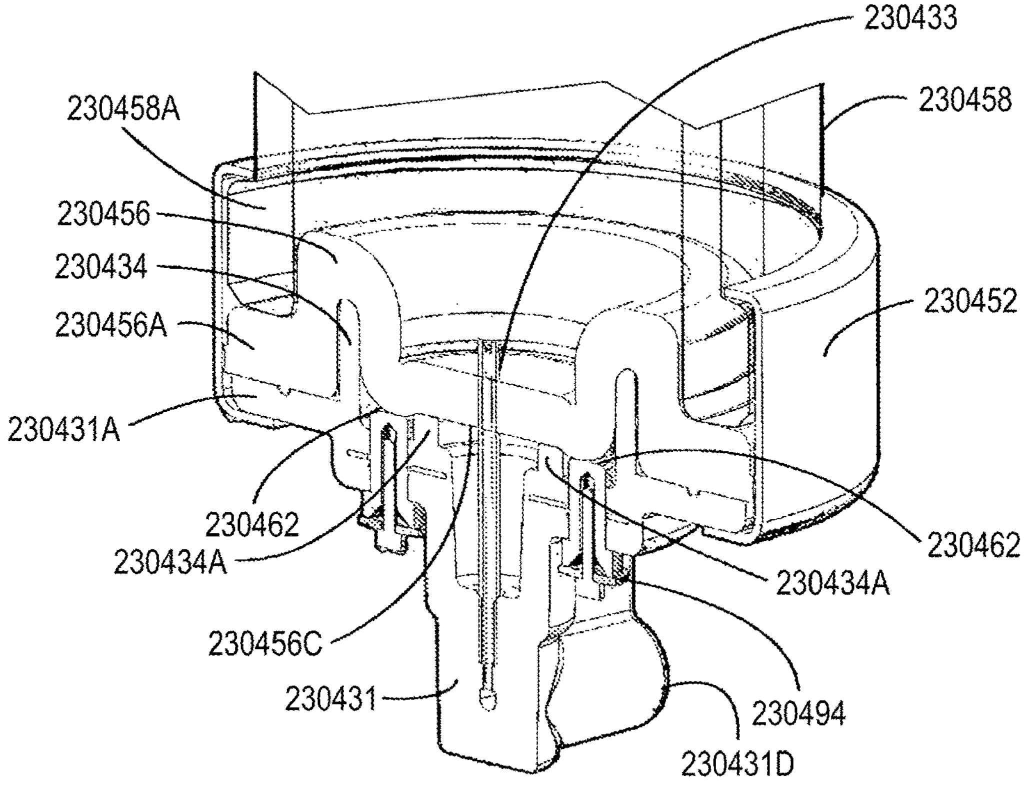
Figure 154:
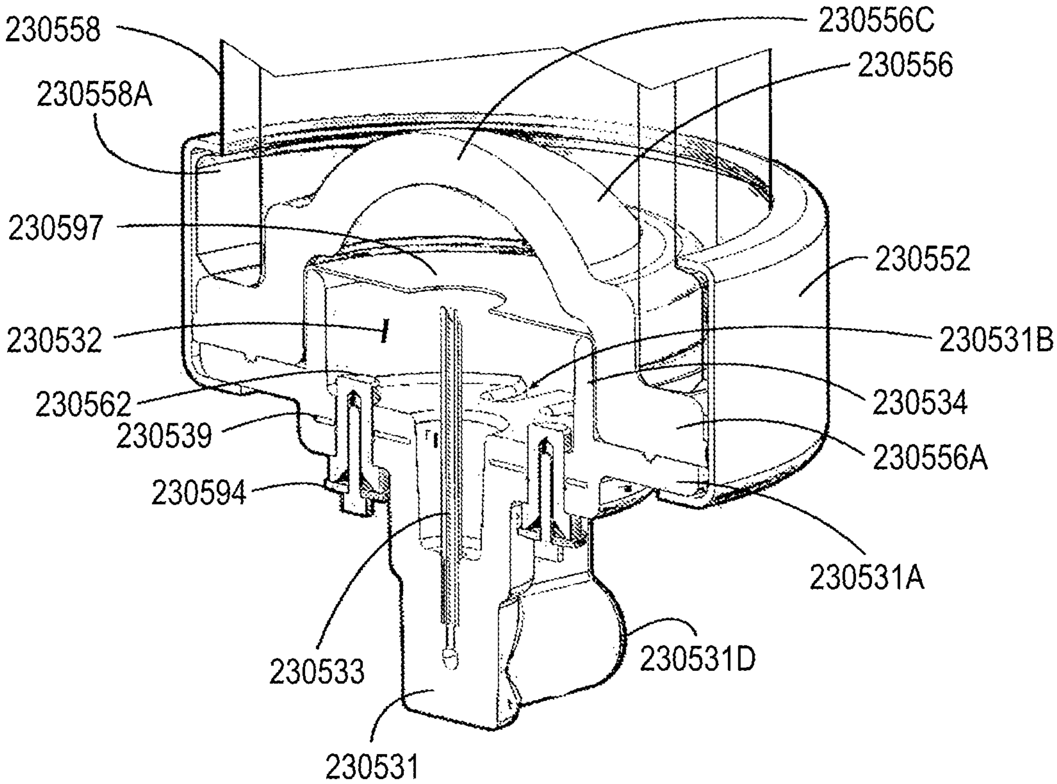
Figure 155:
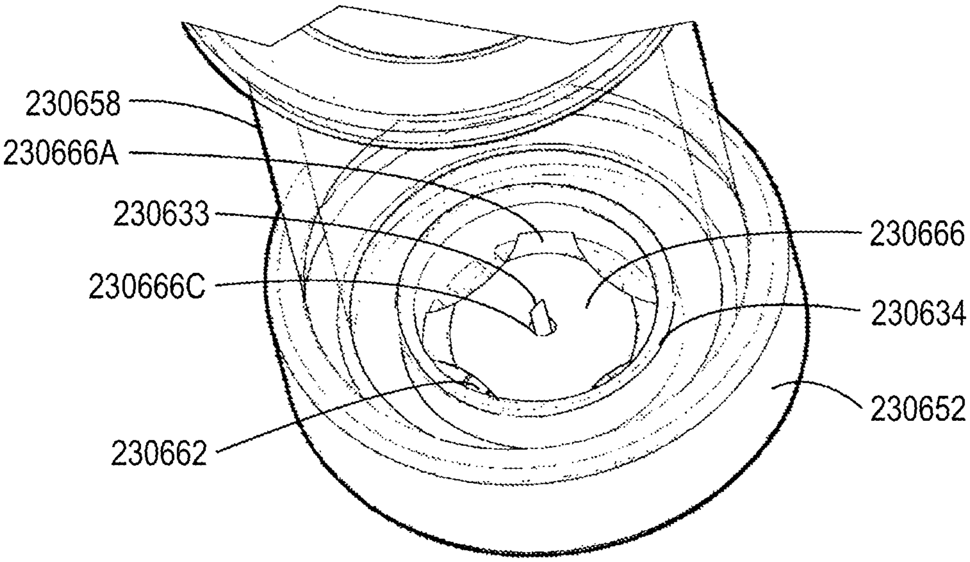
Figure 156:
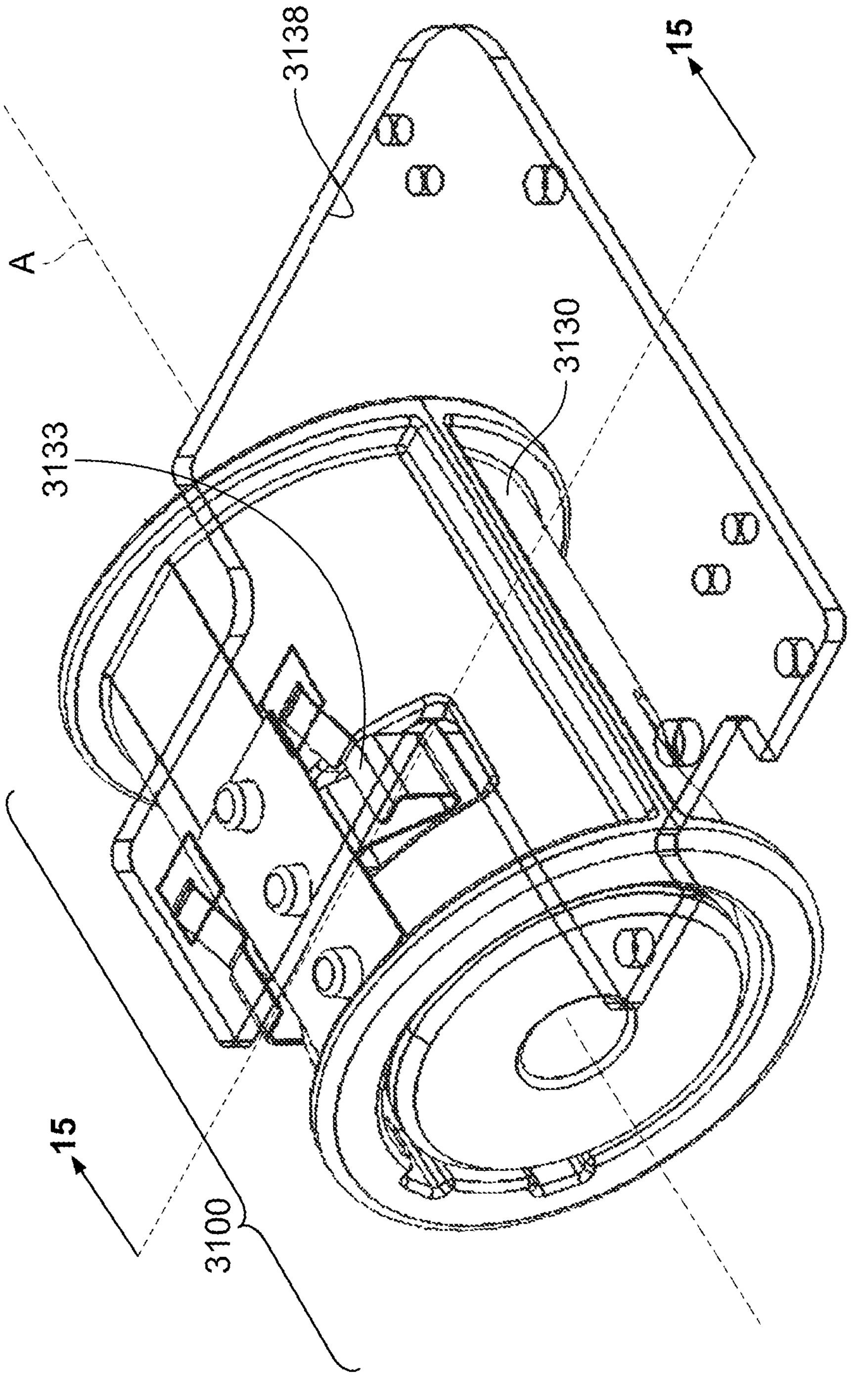
Figure 157A:
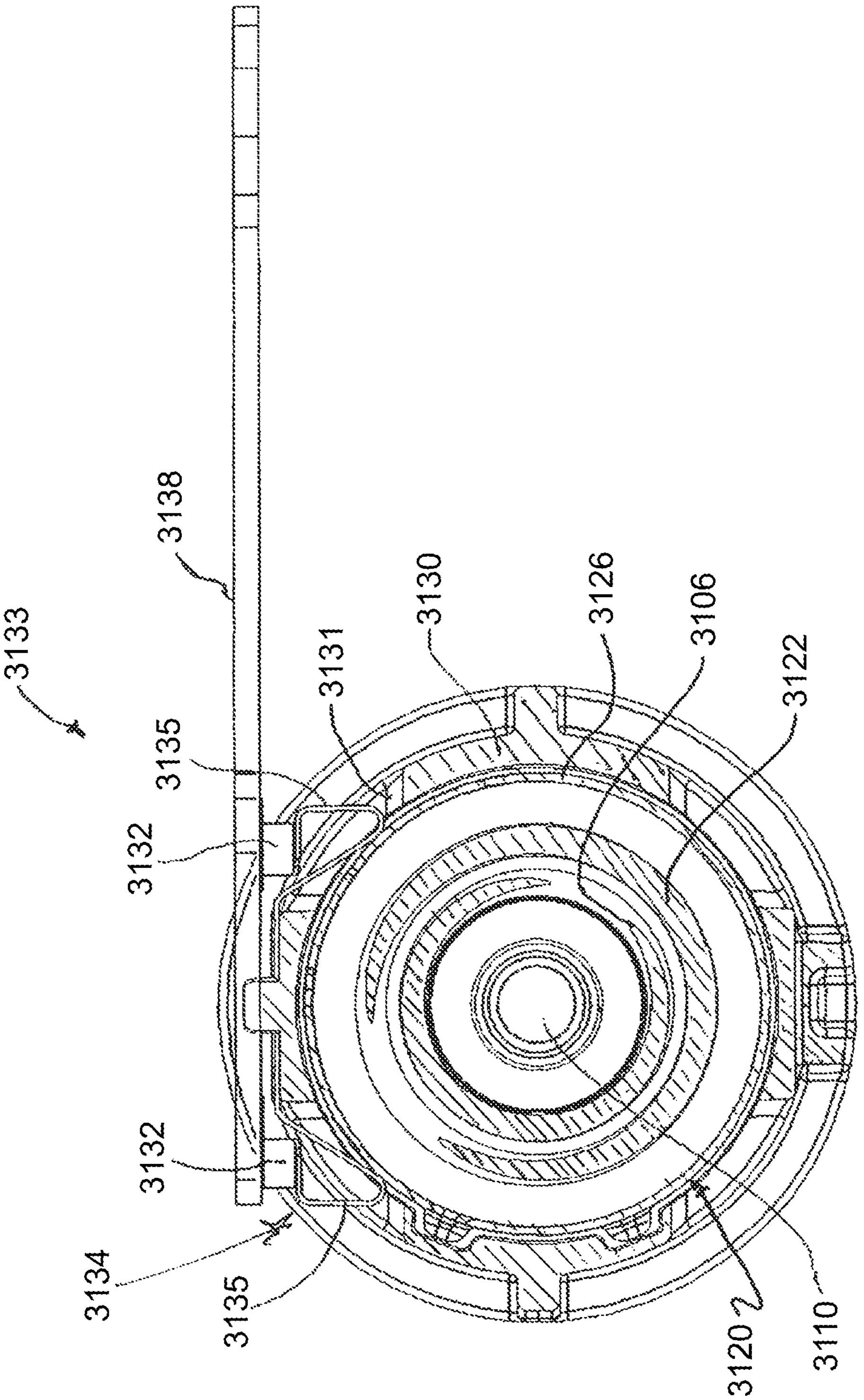
Figure 157B:
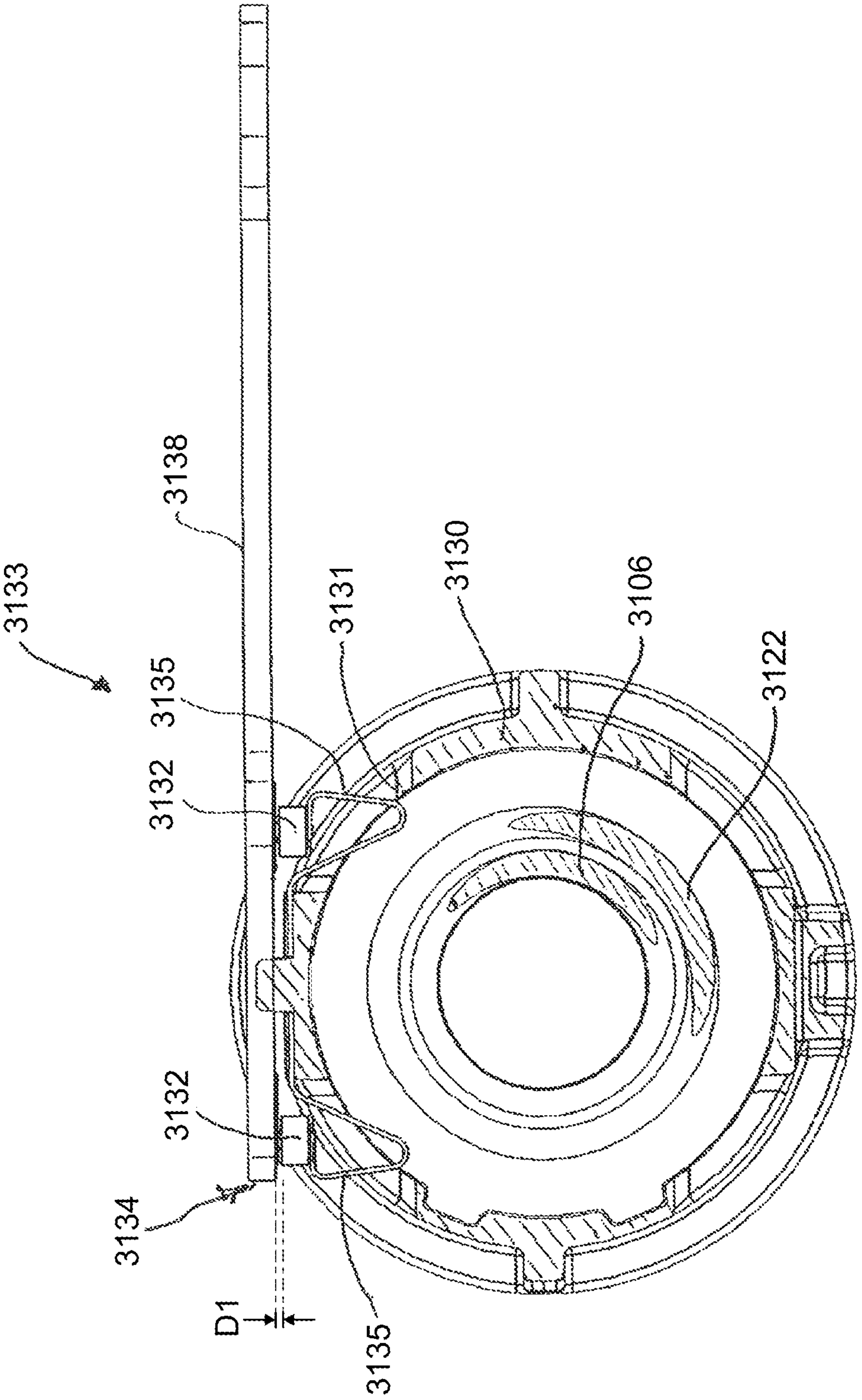

FIG. 118 shows an isometric view of a drug container according to at least one embodiment of the present disclosure;

FIG. 119 shows an isometric view of a drug container and a fluid pathway connection according to at least one embodiment of the present disclosure;

FIG. 120A shows an isometric view of the drug container and fluid pathway connection of FIG. 119 in an unmounted configuration;

FIG. 120B shows a cross-sectional isometric view of the drug container and fluid pathway connection of FIG. 119 in an initial mounting configuration;

FIG. 120C shows a cross-sectional isometric view of the drug container and fluid pathway connection of FIG. 119 in an intermediate mounting configuration;

FIG. 120D shows a cross-sectional isometric view of the drug container and fluid pathway connection of FIG. 119 in a mounted configuration;

FIG. 121A shows an isometric view of an embodiment of a drug container and fluid pathway connection in an unmounted configuration;

FIG. 121B shows a cross-sectional isometric view of the drug container and fluid pathway connection of FIG. 121A in a mounted configuration;

FIG. 122 shows a detail cross-sectional view of a fluid pathway connection according to at least one embodiment of the present disclosure;

FIG. 123 shows a cross-sectional isometric view of an embodiment of a drug container and fluid pathway connection in an unmounted configuration;

FIG. 124 shows an isometric view of an embodiment of a drug container and fluid pathway connection in an unmounted configuration;

FIG. 125 shows a cross-sectional view of an embodiment of a drug container and fluid pathway connection in an unmounted configuration;

FIG. 126 shows a cross-sectional isometric view of an embodiment of a drug container and fluid pathway connection in an unmounted configuration;

FIG. 127A shows an isometric view of an embodiment of a drug container and fluid pathway connection in an unmounted configuration;

FIG. 127B shows an end view of a drug container;

FIG. 127C shows a cross-sectional view of a drug container and fluid pathway connection in an unmounted configuration;

FIG. 127D shows a cross-sectional view of a drug container and fluid pathway connection in a connected configuration;

FIG. 128A shows an exploded view of a medical device with an integrated stimulant source according to at least one embodiment of the present invention;

FIG. 128B shows the medical device of the embodiment of FIG. 128A applied to a patient's skin and the stimulant source activated;

FIG. 128C shows the medical device of the embodiment of FIG. 128A after removal from the patient's skin;

FIG. 129A shows an exploded view of a medical device with an external stimulant source according to at least one embodiment of the present invention;

FIG. 129B shows the medical device of the embodiment of FIG. 129A applied to a patient's skin;

FIG. 129C shows the medical device of the embodiment of FIG. 129A after removal of the body of the medical device and the stimulant source activated;

FIG. 129D illustrates removal of the adhesive from the patient's skin;

FIG. 130 illustrates an isometric view of the interior components of the drug delivery device 10 (shown without the adhesive patch) installed with an embodiment of fluid restriction mechanism;

FIG. 131A shows an isometric view of a fluid restriction mechanism, according to at least one embodiment of the present invention, attached to an integrated sterile fluid pathway connection and drug container;

FIG. 131B shows an exploded isometric view of the fluid restriction mechanism, and integrated sterile fluid pathway connection and drug container, shown in FIG. 131A;

FIG. 131C shows a side view of the fluid restriction mechanism shown in FIG. 131A;

FIG. 132A shows an isometric view of a fluid restriction mechanism, according to another embodiment of the present invention, attached to a sterile fluid pathway connection which may or may not be integrated within the drug container;

FIG. 132B shows an exploded isometric view of the fluid restriction mechanism, and sterile fluid pathway connection and drug container, shown in FIG. 131A;

FIG. 132C shows a side view of the fluid restriction mechanism shown in FIG. 132A;

FIG. 133A shows an exploded isometric view of the fluid restriction mechanism shown in FIGS. 131A-131C;

FIG. 133B shows another angle of the exploded isometric view of the fluid restriction mechanism shown in FIG. 133A;

FIG. 133C shows a cross-sectional view of the fluid restriction mechanism shown in FIGS. 133A-4B;

FIG. 134A shows an exploded isometric view of a configurable fluid restriction mechanism, according to another embodiment of the present invention;

FIG. 134B shows a front view of the configurable fluid restriction mechanism shown in FIG. 134A;

FIG. 135A shows an isometric view of a stackable fluid restriction mechanism, according to another embodiment of the present invention;

FIG. 135B shows an exploded isometric view of the stackable fluid restriction mechanism shown in FIG. 135A;

FIG. 136A shows an isometric view of a fluid restriction mechanism, according to a further embodiment of the present invention;

FIG. 136B shows the isometric view of the fluid restriction mechanism shown in FIG. 136A, with the top component of the fluid restriction mechanism removed;

FIG. 137A shows an isometric view of a manifold having a vent, according to a first embodiment of the present disclosure;

FIG. 137B shows an isometric view of the components shown in FIG. 137A, rotated to show the manifold, manifold intake, and a fluid conduit of the insertion mechanism, according to a first embodiment of the present disclosure;

FIG. 138A shows a cross-sectional view of an insertion mechanism having a vented fluid pathway, according to a first embodiment of the present disclosure, in a locked and ready to use stage;

FIG. 138B shows a cross-sectional view of an insertion mechanism having a vented fluid pathway, according to a first embodiment of the present disclosure, as fluid passes through a conduit and into the manifold;

FIG. 138C shows a cross-sectional view of an insertion mechanism having a vented fluid pathway, according to a first embodiment of the present disclosure, as fluid fills the manifold and gas is pushed through the permeable membrane;

FIG. 138D shows a cross-sectional view of an insertion mechanism having a vented fluid pathway, according to a first embodiment of the present disclosure, in an unlocked and inserted stage;

FIG. 138E shows a cross-sectional view of an insertion mechanism having a vented fluid pathway, according to a first embodiment of the present disclosure, in a partially retracted stage as fluid begins exiting the manifold through the cannula;

FIG. 138F shows a cross-sectional view of an insertion mechanism having a vented fluid pathway, according to a first embodiment of the present disclosure, in a retracted stage for drug delivery;

FIGS. 139A-139C show cross-sectional views of an insertion mechanism having a vented fluid pathway, according to another embodiment of the present disclosure, as it progresses through the various stages of insertion, venting, and drug delivery;

FIG. 140A is an isometric view of an integrated sterile fluid pathway connection and drug container, according to an embodiment; and FIG. 140B is a sectional isometric view of the integrated sterile fluid pathway connection and drug container shown in FIG. 140A;

FIG. 141A is an exploded, side view of the components of an embodiment of an integrated sterile fluid pathway connection and drug container, exploded along a longitudinal axis; and FIG. 141B is a sectional exploded view of the embodiment of FIG. 141A;

FIG. 142A is a sectional view of an integrated sterile fluid pathway connection and drug container, as shown in FIG. 140A, prior to user activation; FIG. 142B is a sectional view of the embodiment with the fluid pathway connected; and FIG. 142C is a sectional view of the embodiment at the end of drug delivery;

FIG. 143A is an isometric perspective view, of the integrated sterile fluid pathway connection according to an embodiment of the present invention; and FIG. 143B is an exploded, perspective view of the components of the integrated sterile fluid pathway connection shown in FIG. 143A;

FIG. 144A is a sectional view of an embodiment of an integrated sterile fluid pathway connection, having a piercing member guide and drug container, prior to user activation; FIG. 144B shows an isometric perspective view of the piercing member guide and piercing member of the embodiment shown in FIG. 144A; and FIG. 144C is an isometric view of the piercing member guide, piercing member, and connector hub of the embodiment of FIG. 144A;

FIG. 145 is a cross-sectional view of an integrated sterile fluid pathway connection and drug container according to an embodiment prior to user activation, in which the drug container comprises more than one drug chamber, each drug chamber separated from the next by a pierceable membrane;

FIG. 146A to FIG. 146E are sectional views of an embodiment of a sterile fluid connector in which the pierceable seal is configured to maintain different positions within the connector in response to pneumatic and/or hydraulic pressure;

FIG. 147A to FIG. 147H are sectional and isometric sectional views of an embodiment of a sterile fluid connector in which the pierceable seal, in response to pneumatic and/or hydraulic pressure, engages or disengages a sensor mechanism that is capable of transmitting a signal indicating the status of fluid transfer from the sterile fluid container to the connector;

FIG. 148A to FIG. 148G are perspective and sectional views of another embodiment of a sterile fluid connector capable of transmitting a signal indicating the status of fluid transfer from the sterile fluid container to the connector;

FIG. 149A to FIG. 149D are sectional and isomeric sectional views of another embodiment of a sterile fluid connector capable of transmitting a signal indicating the status of fluid transfer from the sterile fluid container to the connector, showing more specific configurations of a sensor in the open and closed positions;

FIG. 150A to FIG. 150D are perspective and sectional views of an embodiment of a sterile fluid connector capable of transmitting a signal indicating the status of fluid transfer from the sterile fluid container to the connector, illustrating the unpressurized (FIG. 150B), pressurized (FIG. 150C), and end-of-delivery (FIG. 150D) positions of components of a sterile fluid connector;

FIG. 151A to FIG. 151C are perspective and sectional views of another embodiment of a sterile fluid connector capable of transmitting a signal indicating the status of fluid transfer from the sterile fluid container to the connector;

FIG. 152A is a sectional view; and FIG. 152B is an isometric sectional view of another embodiment of a sterile fluid connector capable of transmitting a signal indicating the status of fluid transfer from the sterile fluid container to the connector;

FIG. 153A and FIG. 153B are sectional isometric views of another embodiment of a sterile fluid connector capable of transmitting a signal indicating the status of fluid transfer from the sterile fluid container to the connector, in which the pierceable seal comprises a conductive material or coating;

FIG. 154 is a sectional isometric view of another an embodiment of a sterile fluid connector capable of transmitting a signal indicating the status of fluid transfer from the sterile fluid container to the connector, in which signal is mediated using an conductive elastomeric film;

FIG. 155 is a sectional isometric view of another embodiment of a sterile fluid connector capable of transmitting a signal indicating the status of fluid transfer from the sterile fluid container to the connector, in which signal is mediated using a dome switch;

FIG. 156 is an isometric view of a drive mechanism, according to yet another embodiment of the present invention;

FIG. 157A is a cross-sectional view of the drive mechanism taken along line 15-15 in FIG. 156; and FIG. 157B is a cross-sectional view of the drive mechanism similar to FIG. 157A, but after the activation of the sensor.

DETAILED DESCRIPTION

The present disclosure provides drug delivery devices having advantageous insertion mechanisms, drive mechanisms, sterile fluid pathway assemblies, status indicators, safety features, and other advantageous components. Such drug delivery devices are safe and easy to use, and are aesthetically and ergonomically appealing for self-administering patients. The drug delivery devices described herein incorporate features which make activation, operation, and lock-out of the drug delivery device simple for even untrained patients. The drug delivery devices of the present disclosure provide these desirable features without various problems associated with known prior art devices. Furthermore, the sterile fluid pathway assemblies of the present disclosure may filled with pharmaceutical treatments using standard filling equipment and systems. This advantage is enabled by the fill-finish cartridges of the present disclosure which function to maintain the sterility of the fluid pathway assemblies and allow them to nest, mount, or otherwise be removably inserted into trays for standard fill-finish processes, as discussed is more detail below.

As discussed in more detail below, the drug delivery devices of the present disclosure may contain a drug, which may also be also be referred to as a medication or a medicament. The drug may be, but is not limited to, various biologicals (e.g., peptides, peptibodies, or antibodies), biosimilars, large-molecule drugs (e.g., a drug with a molecular weight of greater than or equal to approximately 900 Daltons), small-molecule drugs (e.g., a drug with a molecular weight of less than or equal to approximately 900 Daltons), high viscosity drugs, low viscosity drugs, drugs exhibiting non-Newtonian fluid characteristics such as shear thinning, and/or drugs exhibiting Newtonian fluid characteristics. The drug may be in a fluid or liquid form, although the disclosure is not limited to a particular state (e.g., no differentiation is intended between a solution, a gel, or a lyophilized product for example).

One perceived disadvantage of certain known drug delivery devices is their inability to deliver highly viscous drugs such as certain biologics in a timely manner and/or with little patient discomfort. High viscosity drugs typically require more time for injection than low viscosity drugs. Patients may find it difficult and/or undesirable to hold an autoinjector or a syringe against their skin for the amount of time necessary to inject a high viscosity drug. While the injection time can be decreased by increasing the force of the drive mechanism, a more powerful drive mechanism increases the risk of breakage of the drug container and other internal components of the device. Also, a more powerful drive mechanism increases the possibility that the patient will experience an impulse or mechanical shockwave that may disturb or surprise the patient. As a result, the patient may attempt to pull the drug delivery device away from skin, which can compromise complete dosing.

Long injection times are more likely to be tolerated by patients if the drug is administered via a wearable drug delivery device. Unlike a syringe or an autoinjector, a wearable drug delivery device does not have to be held in place by the patient during drug delivery. Therefore, the patient can resume physical activities after the wearable drug delivery device has been placed on the skin and initiated or otherwise not burdened by holding the drug delivery device in place.

Certain aspects of wearable drug delivery devices, however, have discouraged their adoption in the field of high viscosity drugs. In order to achieve a compact design with a low profile that does not significantly protrude from the patient's body, wearable drug delivery devices oftentimes include a drug container that is offset and orthogonal to an insertion mechanism. This arrangement usually requires a tubular conduit with one of more turns to fluidly couple the drug container and the insertion mechanism. Therefore, as compared to syringes and autoinjectors, the internal fluid flowpath of wearable drug delivery devices tend to be relatively long and tortuous.

For drugs that behave as Newtonian fluids (i.e., fluids for which shear rate is directly proportional to flow rate), a longer flow path can result in a slower flow rate. Thus, wearable drug delivery devices, due to their long internal flowpaths, have the potential to exacerbate the injection problems associated with high viscosity drugs. The force of the drive mechanism can be increased to compensate for the reduction in flow rate, but a more powerful drive mechanism increases the risk of drug container breakage and therefore is typically considered undesirable. For at least these reasons, wearable drug delivery devices were viewed by some as not being particularly well suited for the delivery of high viscosity drugs.

The inventors of the present disclosure found that various high viscosity drugs (e.g., PCSK9 specific antibodies, G-CSFs, sclerostin antibodies, and CGRP antibodies) exhibit non-Newtonian fluid characteristics when injected via a wearable drug delivery device. One such characteristic is shear thinning, which is the ability of a non-Newtonian fluids to exhibit decreased viscosity when subjected to shear strain. Shear thinning reduces the viscosity of a fluid as it is pushed through a conduit. Accordingly, the force needed to push the fluid through a conduit is less than it would be if the fluid was Newtonian. In the context of wearable drug delivery devices, shear shinning mitigates the clogging effect of the device's long internal flowpath. Therefore, an unexpected benefit of wearable drug delivery devices found by the inventors of the present disclosure is that they are well suited for delivering high viscosity drugs having non-Newtonian characteristics such as shear thinning. The inventors of the present disclosure found that shear thinning oftentimes occurs in drugs such as biologics which have relatively large protein molecules with a molecular weight greater than or equal to approximately (e.g., ±10%) 900 daltons. Any of the wearable drug delivery devices described herein may have a drug container filled with a high viscosity drug having shear thinning capabilities, and therefore realize the unexpected benefits of shear thinning on the operation and use of the device.

Certain non-limiting embodiments of the drug delivery device and its respective components will now be described with reference to the accompanying figures.

As used herein to describe the drive mechanisms, the insertion mechanisms, fluid pathway connectors, drug delivery devices, or any of the relative positions of the components of the present disclosure, the terms "axial" or "axially" refer generally to a longitudinal axis "A" around which a component is preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. As used herein, "fluid" refers primarily to liquids, but can also include suspensions of solids dispersed in liquids, and gasses dissolved in or otherwise present together within liquids inside the fluid-containing portions of drug delivery devices. According to various aspects and embodiments described herein, reference is made to a "biasing member", such as in the context of one or more biasing members for insertion or retraction of the needle, trocar, and/or cannula. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present disclosure, the biasing member is a spring, preferably a compression spring. Also, as used herein, the term "drug delivery device" is intended to include any number of devices which are capable of dispensing a fluid to a patient upon activation. Such drug delivery devices include, for example, wearable drug delivery devices, on-body injectors, off-body injectors, autoinjectors, infusion pumps, bolus injectors, and the like. Furthermore, as used herein, the term "wearable drug delivery device" is intended to include any number of devices which are capable dispensing a fluid to a patient upon activation and capable of being attached to the patient's skin or clothing. Such wearable drug delivery devices include, for example, on-body injectors and off-body injectors.

I. Drug Delivery Device

Figure 1A:
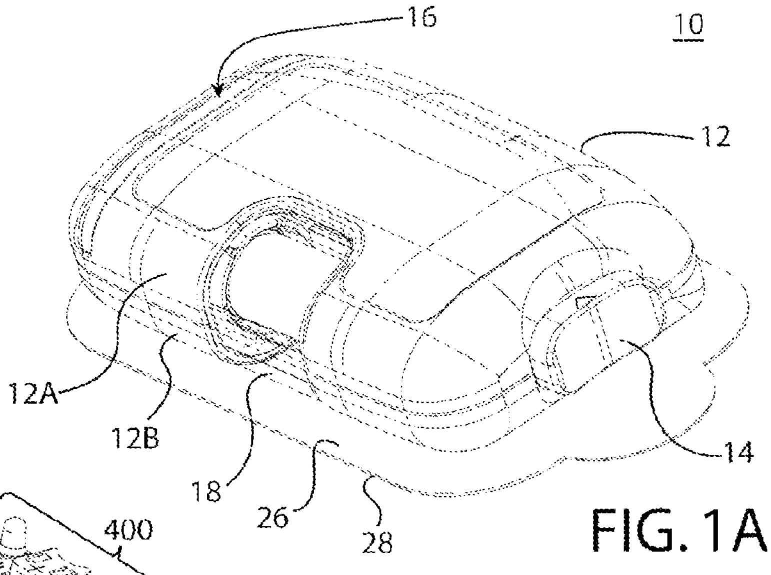
FIG. 1A shows an isometric view of a drug delivery device having safety integrated insertion mechanisms, according to one embodiment of the present disclosure.
Figure 1B:
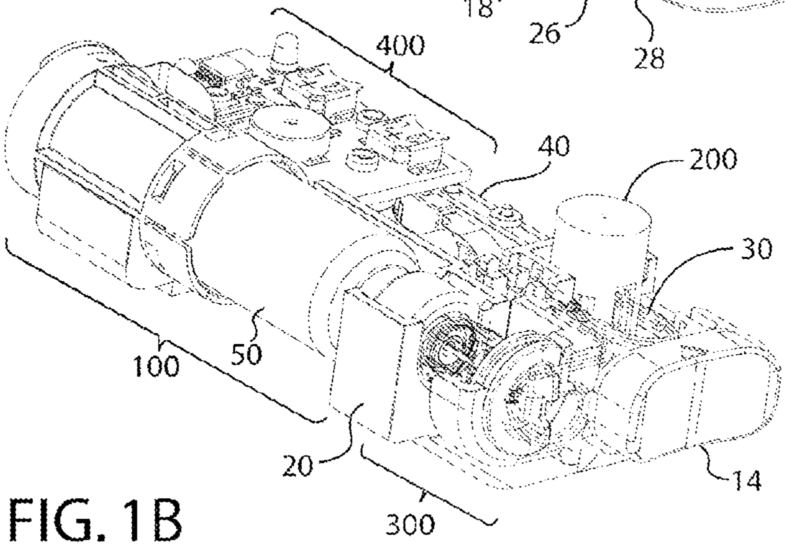
FIG. 1B shows an isometric view of the interior components of the drug delivery device shown in FIG. 1A.
Figure 1C:
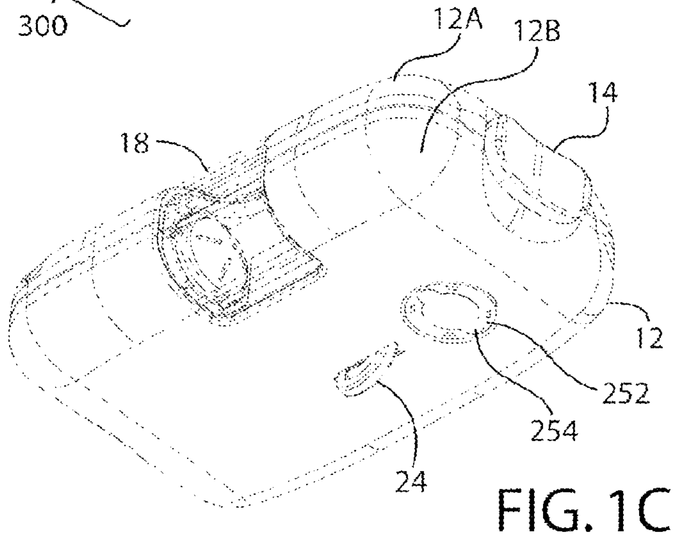
FIG. 1C shows an isometric view of the bottom of the drug delivery device shown in FIG. 1A.

FIGS. 1A-1C show an exemplary drug delivery device 10 according to at least one embodiment of the present disclosure. The drug delivery device 10 may be utilized to administer delivery of a drug treatment into a body of a patient. As shown in FIGS. 1A-1C, the drug delivery device 10 includes a housing 12. The housing 12 may include one or more housing subcomponents which are fixedly engageable to facilitate easier manufacturing, assembly, and operation of the drug delivery device 10. For example, drug delivery device 10 includes the housing 12 which includes an upper housing 12A and a lower housing 12B. The drug delivery device 10 may further include an activation mechanism 14, a status indicator 16, and a window 18. Window 18 may be any translucent or transmissive surface through which the operation of the drug delivery device 10 may be viewed. In at least one embodiment, the window 18 may be configured to connect and hold together the upper housing 12A and the lower housing 12B. As shown in FIG. 1B, drug delivery device 10 further includes assembly platform 20, sterile fluid conduit 30, drive mechanism 100 having drug container 50, insertion mechanism 200, fluid pathway connector 300, and power and control system 400. One or more of the components of the drug delivery device 10 may be modular in that they may be, for example, pre-assembled as separate components and configured into position onto the assembly platform 20 of the drug delivery device 10 during manufacturing.

The housing 12 may contain some or all of the device components. In some embodiments, the housing 12 may provide a means of removably attaching the drug delivery device 10 to the skin or clothing of the patient, thereby rending the drug delivery device 10 a wearable drug delivery device. In some embodiments, a layer of adhesive may be applied to an exterior surface of the housing 12, such as the surface through which a cannula protrudes during operation, for releasably attaching the drug delivery device 10 to a patient's skin.

The housing 12 also provides protection to the interior components of the drug delivery device 10 against environmental influences. The housing 12 is ergonomically and aesthetically designed in size, shape, and related features to facilitate easy packaging, storage, handling, and use by patients who may be untrained and/or physically impaired. Furthermore, the external surface of the housing 12 may be utilized to provide product labeling, safety instructions, and the like. Additionally, as described above, housing 12 may include certain components, such as status indicator 16 and window 18, which may provide operation feedback to the patient.

The container 50 may be configured to contain variety of different drug dose volumes, including drug dose volumes in a range of approximately (e.g., ±10%) 0.5-20 mL, or 1-10 mL, or 2-10 mL, or 2-8 mL, or 2-6 mL, or 2-4 mL, or 0.5-2 mL, or 0.5-1 mL, or 3.5 mL. The container 50 may be completely or partially filled with the drug.

In at least one embodiment, the drug delivery device 10 provides an activation mechanism that is displaced by the patient to trigger a start command to a power and control system 400. In a preferred embodiment, the activation mechanism is a start button 14 that is located through the housing 12, such as through an aperture between the upper housing 12A and the lower housing 12B, and which contacts a control arm 40 of the power and control system 400. In at least one embodiment, the start button 14 may be a push button, and in other embodiments, may be an on/off switch, a toggle, or any similar activation feature known in the art. The housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the patient when the drug delivery device 10 is placed on the body of the patient. Housing 12 is described in further detail hereinafter with reference to other components and embodiments of the present disclosure.

The drug delivery device 10 may be configured such that, upon activation by a patient by depression of the activation mechanism, the drug delivery device 10 is initiated to: insert a fluid pathway into the patient; enable, connect, or open necessary connections between a drug container, a fluid pathway, and a sterile fluid conduit; and force drug fluid stored in the drug container through the fluid pathway and fluid conduit for delivery into a patient. One or more optional safety mechanisms may be utilized, for example, to prevent premature activation of the drug delivery device 10. For example, an optional on-body sensor 24 (shown in FIG. 1C) may be provided in one embodiment as a safety feature to ensure that the power and control system 400, or the activation mechanism, cannot be engaged unless the drug delivery device 10 is in contact with the body of the patient. In one such embodiment, the on-body sensor 24 is located on the bottom of lower housing 12B where it may come in contact with the patient's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug delivery device 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. In at least one embodiment, such an electrically based on-body sensor may incorporate a resistor with an impedance of approximately (e.g., ±10%) 1 MΩ. These concepts are not mutually exclusive and one or more combinations may be utilized within the breadth of the present disclosure to prevent, for example, premature activation of the drug delivery device 10. In a preferred embodiment, the drug delivery device 10 utilizes one or more mechanical on-body sensors. Additional integrated safety mechanisms are described herein with reference to other components of the drug delivery device 10.

II. Power and Control System

The power and control system 400 includes a power source, which provides the energy for various electrical components within the drug delivery device 10, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the patient and interfaces with the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the housing 12, which may be a transmissive or translucent material which permits light transfer, to provide visual feedback to the patient. The power and control system 400 interfaces with the drive mechanism 100 through one or more interconnects to relay status indication, such as activation, drug delivery, and end-of-dose, to the patient. Such status indication may be presented to the patient via auditory tones, such as through the audible alarms, and/or via visual indicators, such as through the LEDs. In a preferred embodiment, the control interfaces between the power and control system and the other components of the drug delivery device 10 are not engaged or connected until activation by the patient. This is a desirable safety feature that prevents accidental operation of the drug delivery device 10 and may additionally maintain the energy contained in the power source during storage, transportation, and the like.

The power and control system 400 may be configured to provide a number of different status indicators to the patient. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the patient, the power and control system 400 will power the drive mechanism 100 to begin delivery of the drug treatment through the fluid pathway connector 300 and sterile fluid conduit 30. In a preferred embodiment of the present disclosure, the insertion mechanism 200 and the fluid pathway connector 300 may be caused to activate directly by patient operation of the activation mechanism 14. During the drug delivery process, the power and control system 400 is configured to provide a dispensing status signal via the status indicator 16. After the drug has been administered into the body of the patient and after the end of any additional dwell time, to ensure that substantially the entire dose has been delivered to the patient, the power and control system 400 may provide an okay-to-remove status signal via the status indicator 16. This may be independently verified by the patient by viewing the drive mechanism 100 and drug dose delivery through the window 18 of the housing 12. Additionally, the power and control system 400 may be configured to provide one or more alert signals via the status indicator 16, such as for example alerts indicative of fault or operation failure situations.

Other power and control system configurations may be utilized with the drug delivery device of the present disclosure. For example, certain activation delays may be utilized during drug delivery. As mentioned above, one such delay optionally included within the system configuration is a dwell time which ensures that substantially the entire drug dose has been delivered before signaling completion to the patient. Similarly, activation of the drug delivery device 10 may require a delayed depression (i.e., pushing) of the activation mechanism 14 of the drug delivery device 10. Additionally, the system may include a feature which permits the patient to respond to the end-of-dose signals and to deactivate or power-down the drug delivery device 10. Such a feature may similarly require a delayed depression of the activation mechanism, to prevent accidental deactivation of the device. Such features provide desirable safety integration and ease-of-use parameters to the drug delivery device 10. An additional safety feature may be integrated into the activation mechanism to prevent partial depression and, therefore, partial activation of the drug delivery device. For example, the activation mechanism and/or power and control system may be configured such that the device is either completely off or completely on, to prevent partial activation. Such features are described in further detail hereinafter with regard to other aspects of the drug delivery device 10.

III. Fluid Pathway Connector

Figure 2A:
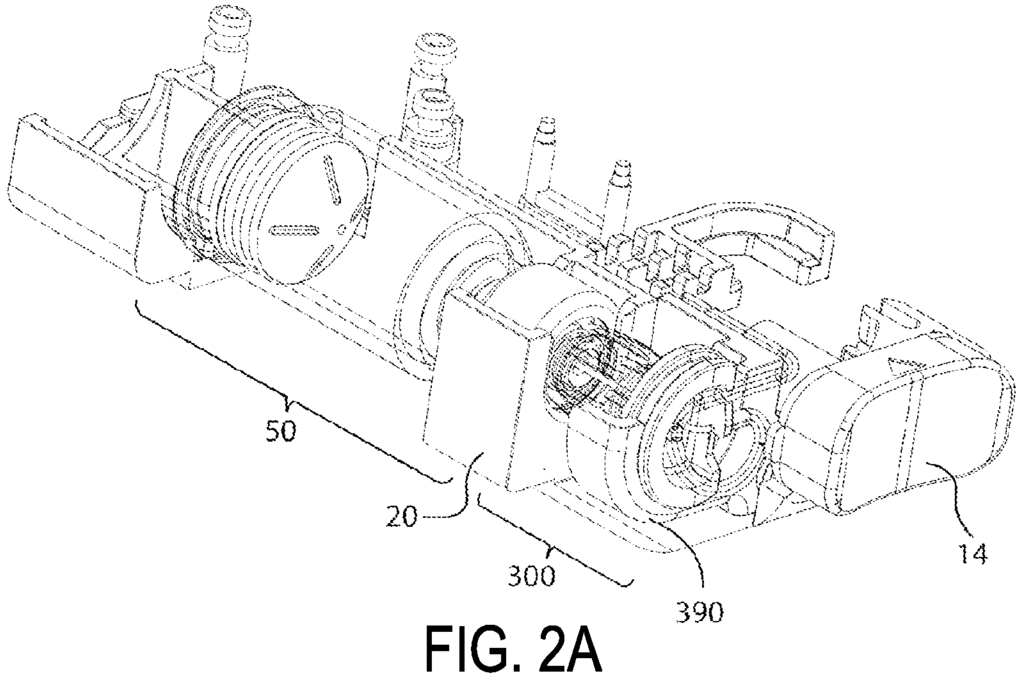
FIG. 2A shows an isometric view of the patient-initiated fluid pathway connectors to drug containers, according to one embodiment of the present disclosure.
Figure 2B:
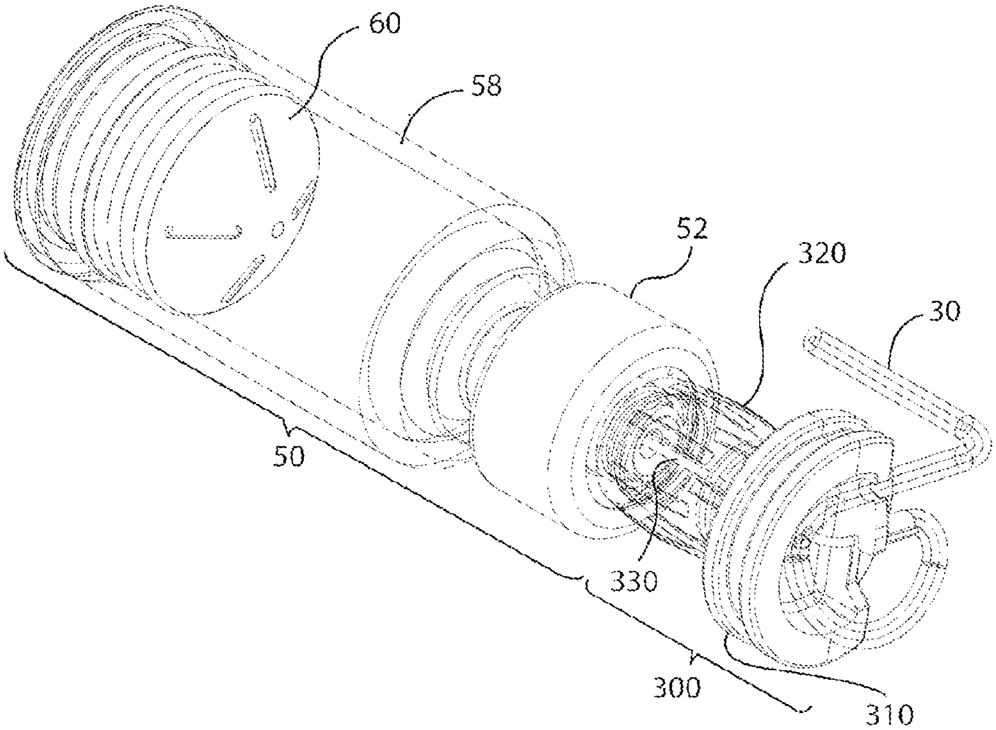
FIG. 2B shows an isometric view of the fluid pathway connector shown in FIG. 2A attached to a drug container.

The present disclosure provides patient-initiated fluid pathway connectors providing fluid communication with drug containers, and drug delivery devices which utilize fluid pathway connectors capable of maintaining the sterility of the fluid pathway before, during, and after operation of the drug delivery device, and which enable active safety controls for the device. In one embodiment, a fluid pathway connector 300 includes a sterile fluid conduit 30, a piercing member 330, a connection hub 310, and a sterile sleeve 320, as shown in FIGS. 2A and 2B. The fluid pathway connector 300 may, optionally, further include one or more flow restrictors. Upon proper activation of the drug delivery device 10 by the patient, the fluid pathway connector 300 is connected to a drug container 50, thereby enabling fluid flow from the drug container (as may be forced by the drive mechanism 100), through the fluid pathway connector 300, the fluid conduit 30, the insertion mechanism 200 and into the body of the patient. Such connection between the fluid pathway connector 300 and the drug container 50 may be facilitated by a piercing member 330, such as a needle, penetrating a pierceable seal 56 (shown in FIGS. 3A, 3B, 4A, and 4B) of the drug container 50. The sterility of this connection may be maintained by performing the connection within a flexible sterile sleeve 320. Upon substantially simultaneous activation of the insertion mechanism 200, the fluid pathway between drug container 50 and insertion mechanism 200 is complete to permit drug delivery into the body of the patient.

In at least one embodiment of the present disclosure, the piercing member 330 of the fluid pathway connector 300 is caused to penetrate the pierceable seal 56 of the drug container 50 of the drive mechanism 100 by direct action of the patient, such as by depression of the activation mechanism 14 by the patient. For example, the activation mechanism 14 itself may bear on the fluid pathway connector 300 such that displacement of the activation mechanism 14 from its original position also causes displacement of the fluid pathway connector 300. In a preferred embodiment, this connection is enabled by the patient depressing the activation mechanism 14 and, thereby, driving the piercing member 330 through the pierceable seal 56. Because the fluid pathway connector 300 is not connected to the drug container 50 until activation by the patient, fluid flow from the drug container 50 is prevented until desired by the patient. This provides an important safety feature to the patient while also maintaining the container integrity of the drug container 50 and sterility of the fluid pathway. In such an embodiment, a collapsible or compressible sterile sleeve 320 may be fixedly attached between a cap 52 of the drug container 50 and the connection hub 310 of the fluid pathway connector. The piercing member 330 may reside within the sterile sleeve 320 until a connection between the fluid pathway connector 300 and the drug container 50 is desired. The sterile sleeve 320 may be sterilized to ensure the sterility of the piercing member 330 and the fluid pathway prior to activation of the device and connection between the fluid pathway connector 300 and the drug container 50.

As shown in FIG. 2A, the fluid pathway connector 300 may be attached to a drug container 50 and mounted, by a number of known methods, either fixedly or removably to an assembly platform 20 and/or the housing 12 of the drug delivery device 10. The assembly platform may be a separate component from the housing, or may be a unified component of the housing such a pre-formed mounting aspect on the interior surfaces of the housing. In one embodiment, the drug container 50 may be mounted, connected, or otherwise attached to a fixed aspect of the assembly platform 20 or housing, while the fluid pathway connector 300 is mounted, connected, or otherwise attached to a movable guide 390 that is capable of being translated upon patient translation of the activation mechanism 14. In an alternative embodiment, this configuration can be reversed such that the drug container 50 is attached to a movable guide 390 and the fluid pathway connector 300 is attached to a fixed aspect of the assembly platform 20 or housing. In either configuration, the sterility of the fluid pathway is maintained, the pathway for fluid flow is not connected until desired by the patient, and patient-initiated activation causes the connection of the drug container and the fluid pathway connector. While the former configuration is preferred, the latter configuration may be desired in certain embodiments such as, for example, those which utilize cartridge-style drug containers. Patient translation or similar displacement of the activation mechanism 14 causes displacement, either directly or indirectly, of the guide 390 to enable a connection between the fluid pathway connector and the drug container. Such displacement of the guide 390 may optionally be assisted, for example to reduce the activation force needed by the patient acting upon the activation mechanism 14, by a number of different biasing members including compression springs, extension springs, elastic bands, or the like.

FIG. 2B shows the fluid pathway connector 300 and the drug container 50 apart from the housing, assembly platform, and other components of the drug delivery device 10. As stated above, drug container 50 may include barrel 58 having a plunger seal 60 at one end and a cap 52 at another end. The fluid pathway connector 300 may be mounted, connected, or otherwise attached to the drug container 50 at the cap 52. At least in an initial configuration, a piercing member 330 is maintained within a sterile sleeve 320 with a distal end adjacent to, or contacting, a pierceable seal of the drug container 50. The piercing member 330 may be a number of cannulas or conduits, such as rigid needles, and may be comprised of a number of materials, such as steel. In at least one embodiment, the piercing member 330 is a rigid steel needle. The sterile sleeve 320 is a compressible or collapsible membrane positioned between the drug container 50 and the connection hub 310 and provides a sterile environment within which the piercing member 330 may reside. The sterile sleeve 320 may be comprised of a number of materials which are compressible or collapsible, but preferably is an elastomeric membrane. The sterile sleeve 320 may be a number of different shapes or configurations, including cones, pyramids, ellipsoids, ovoids, spheres, octahedron (diamond-shaped), and the like, which are capable of being compressed, collapsed, or otherwise deformed to permit two adjacent components to become closer together while maintaining sterility of an interior environment within the sleeve. Similarly, the sterile sleeve 320 may have one or more aspects, such as longitudinal (i.e., axial) and/or latitudinal (i.e., radial) groove striations, ridges, valleys, accordion folds, and the like, which promote compressibility or collapsibility. Such aspects may be positioned equidistant or non-equidistant, and in a myriad of configurations including along the inner surface, the outer surface, or both surfaces of the sterile sleeve. FIG. 2B shows an embodiment having longitudinal grooves which are equidistant along the circumferential exterior surface of the sterile sleeve 320.

Figure 3A:
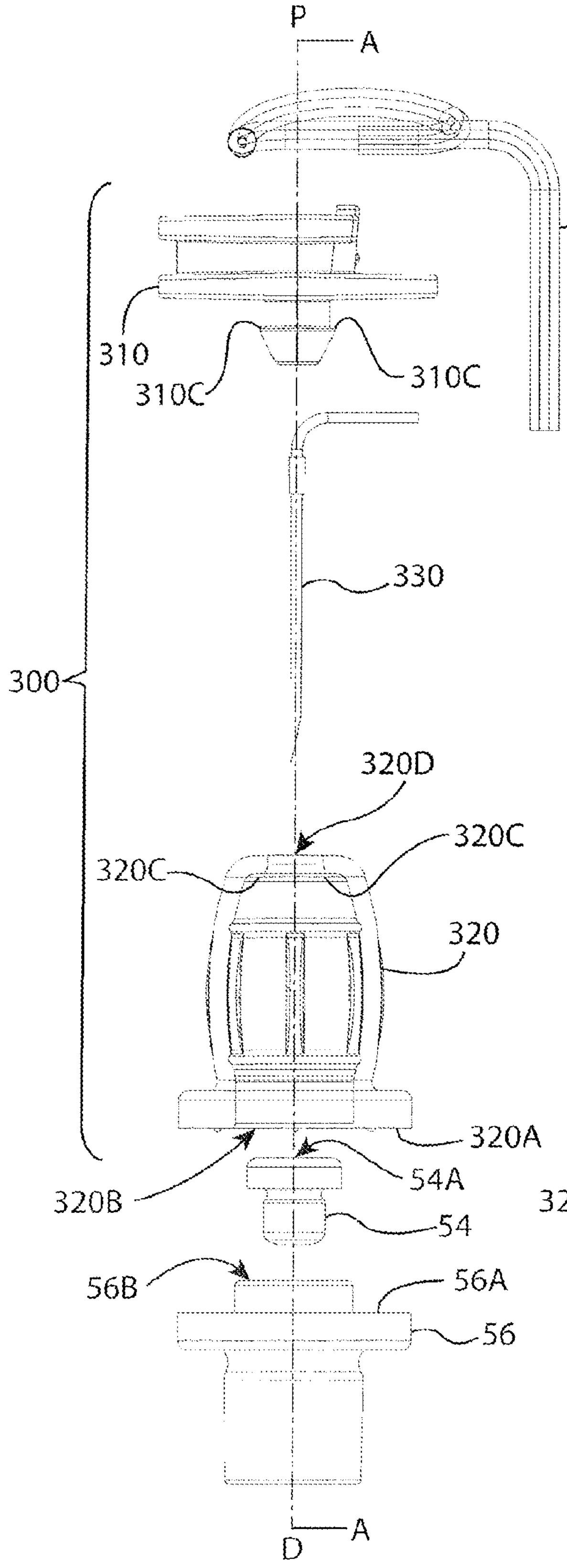
FIG. 3A shows an exploded view of the fluid pathway connector, exploded along a longitudinal axis "A," according to at least one embodiment of the present disclosure.
Figure 3B:
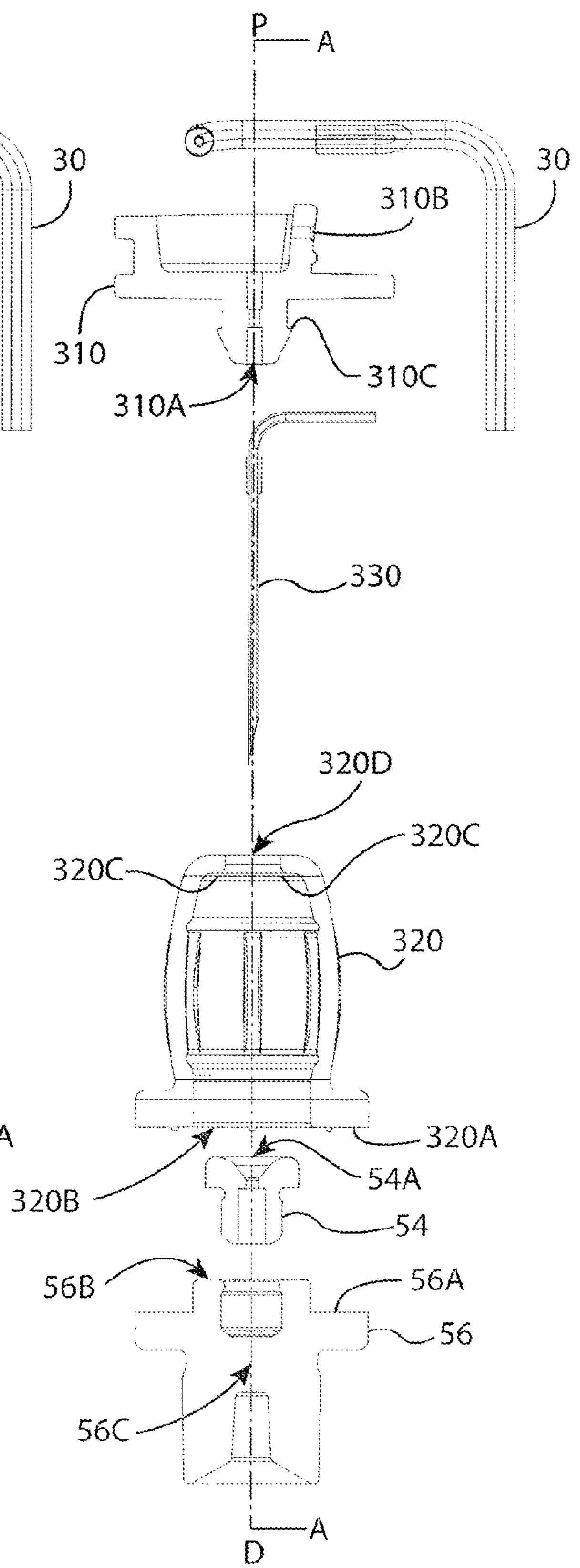
FIG. 3B shows a cross-sectional exploded view of the fluid pathway connector shown in FIG. 3A.

The piercing member 330 is maintained in a sterile environment within the sterile sleeve 320. This sterile environment is maintained between the connection hub 310 and the cap 52 of the drug container 50. FIG. 3A shows an exploded view of the arrangement of the components of the fluid pathway connector, according to at least one embodiment of the present disclosure, while FIG. 3B shows a cross-sectional exploded view. These figures include certain components of the drug container, specifically the pierceable seal 56 and the optional connection mount 54, as they relate to the connection of the fluid pathway connector 300. As shown, a sleeve interface surface 320A of the sterile sleeve 320 is caused to contact a seal interface surface 56A of pierceable seal 56 upon assembly. These corresponding interface surfaces may be retained in position and/or connection by cap 52, as shown in FIGS. 4A and 4B, such that a distal end of the sterile sleeve 320 may be held fixed within the cap 52 while the remainder of the sterile sleeve 320 is outside the cap 52. When utilized, the optional connection mount 54 may reside within a seal recess 56B of the pierceable seal 56, and within the sterile interior environment of the sterile sleeve 320. Alternatively, the pierceable seal 56 and the sterile sleeve 320 may be two aspects of a single pre-formed component (i.e., a unified component having two or more functions). In such a configuration, the cap 52 may similarly be utilized to hold the components in place at a proximal end of the drug container 50 (and attached to the proximal end of the barrel 58). In either of these embodiments, the sterile sleeve 320 may have a container connection opening 320B at a distal end through which the piercing member 330 may translate to pierce the pierceable seal 56 and enable the fluid flow connection with the drug container 50. Alternatively, the connection opening 320B may be a closed surface and function as a pierceable sealing membrane between the fluid pathway and the drug container. However, in at least a preferred embodiment of the present disclosure, pierceable seal 56 has a seal barrier 56C that would be pierced to open the drug container to the fluid pathway. In an initial position, the distal end of the piercing member 330 may reside adjacent to, or in contact with, the seal barrier 56C of the pierceable seal 56 to, for example, minimize the distance of translation of the fluid pathway connector 300 to pierce the pierceable seal 56 and open the drug container to the fluid pathway. In one particular embodiment, the distal end of the piercing member 330 may reside at least partially within the seal barrier 56C of the pierceable seal 56, yet not fully passing there-through until activation of the device by the patient. When an optional connection mount 54 is utilized, for example to ensure axial piercing of the pierceable seal 56, the piercing member 330 may pass through a piercing member recess 54A of the connection mount 54.

Figure 5A:
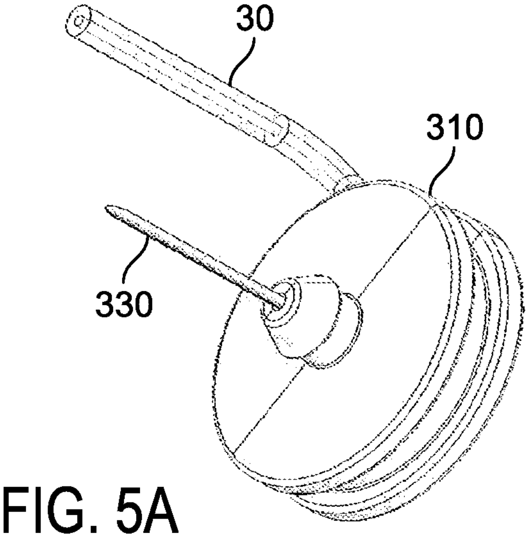
FIG. 5A shows an isometric view, from the distal perspective, of a connection hub, according to one embodiment of the present disclosure.
Figure 5B:
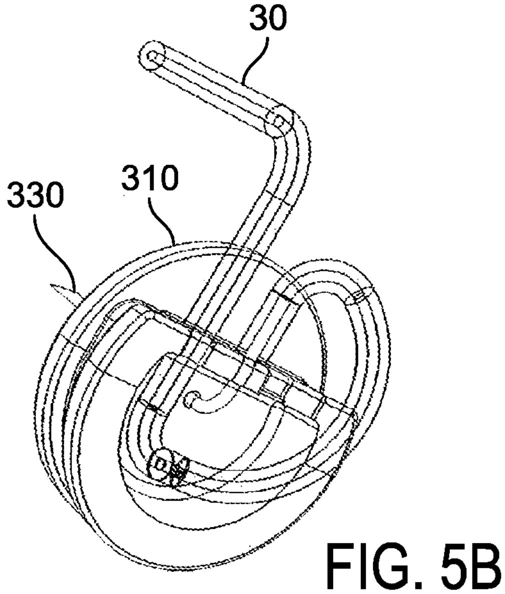
FIG. 5B shows an isometric view, from the proximal perspective, of the connection hub shown in FIG. 5A.
Figure 5C:
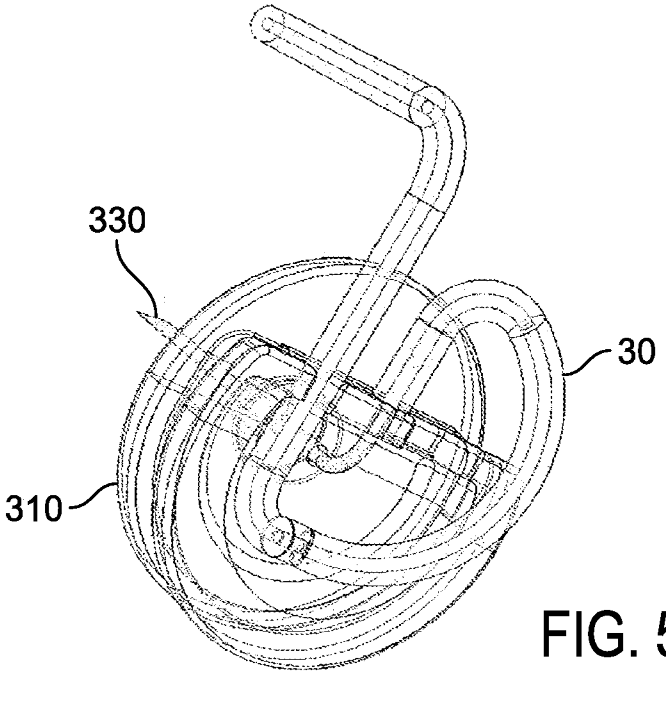
FIG. 5C shows a transparent view of the connection hub shown in FIG. 5B.

The sterile sleeve 320 is connected at a proximal end to a connection hub 310. In one embodiment, this connection is facilitated by engagement between hub connectors 320C of sterile sleeve 320 and corresponding sleeve connectors 310C of connection hub 310. This engagement can be a snap-fit, interference fit, screw fit, or a number of other connective linkages. The piercing member 330 passes through the connection hub 310 and is held in place at the piercing member connection aperture 310A. As described further below, in one embodiment the connection hub 310 is configured to accept a bent piercing member 330 such that the piercing member passes through and is held in place at both the piercing member connection aperture 310A and the conduit connection aperture 310B. The fluid conduit 30 is connected to the proximal end of the piercing member 330 at the conduit connection aperture 310B. As would be readily appreciated by an ordinary skilled artisan, a number of glues or adhesives, or other connection methods such as snap-fit, interference fit, screw fit, fusion joining, welding, ultrasonic welding, and the like may optionally be utilized to engage one or more of the components described herein. FIGS. 5A-5C, show a connection hub 310 according to one embodiment of the present disclosure, with a fluid conduit 30 and a piercing member 330 attached. FIGS. 5A and 5B show that the piercing member 330 may pass through the connection hub 310. FIG. 5C provides a transparent view of the connection hub 310, in an embodiment having a bent piercing member 330 which connects to the fluid conduit 30 as described above.

One or more optional flow restrictors may be utilized within the configurations of the fluid pathway connector described herein. For example, a flow restrictor may be utilized at the connection between the piercing member 330 and the fluid conduit 30. The drug delivery device 10 is capable of delivering a range of drugs with different viscosities and volumes. The drug delivery device 10 is capable of delivering a drug at a controlled flow rate (speed) and/or of a specified volume. In one embodiment, the drug delivery process is controlled by one or more flow restrictors within the fluid pathway connector and/or the sterile fluid conduit.

In other embodiments, other flow rates may be provided by varying the geometry of the fluid flow path or delivery conduit, varying the speed at which a component of the drive mechanism advances into the drug container to dispense the drug therein, or combinations thereof.

Figure 6A:
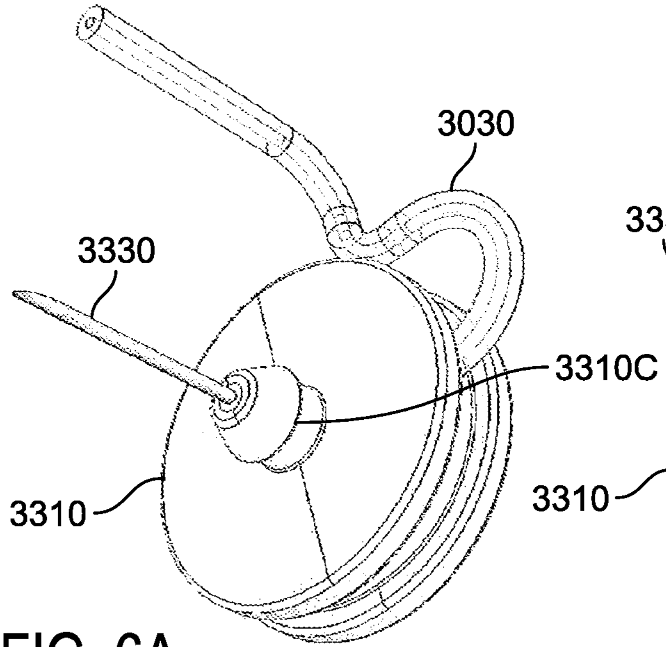
FIG. 6A shows an isometric view, from the distal perspective, of a connection hub, according to another embodiment of the present disclosure.
Figure 6B:
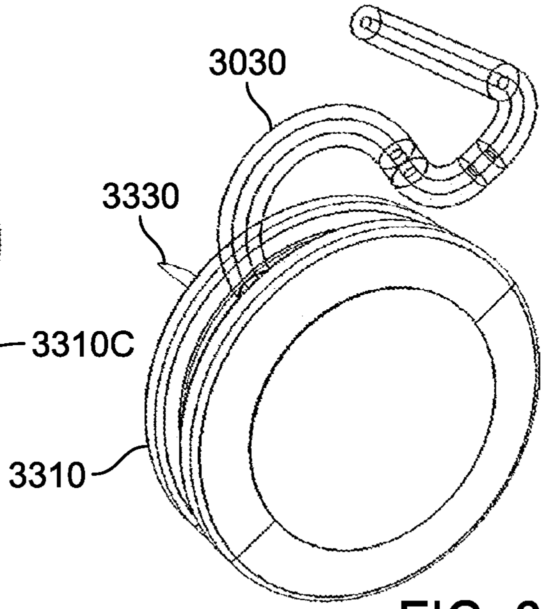
FIG. 6B shows an isometric view, from the proximal perspective, of the connection hub shown in FIG. 6A.
Figure 6C:
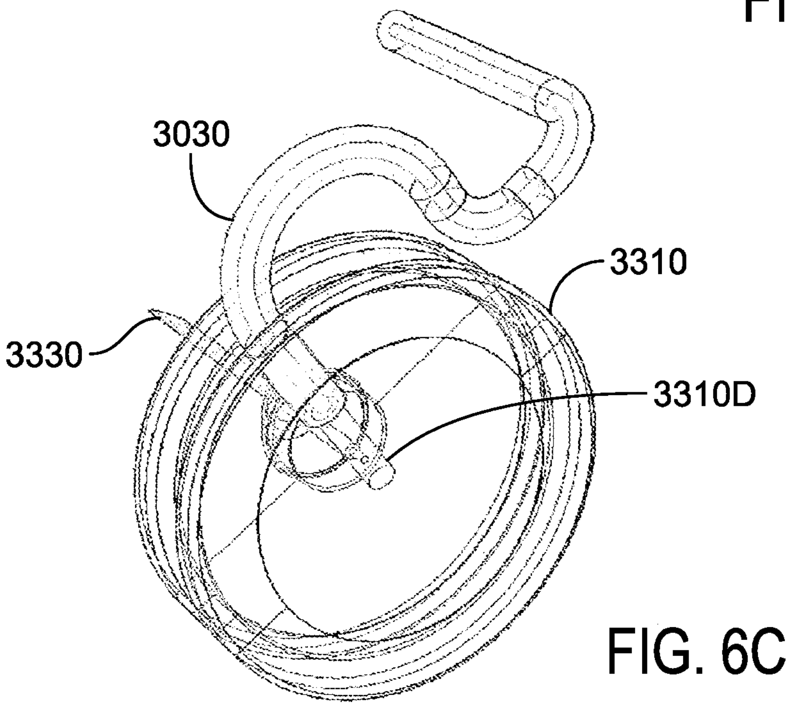
FIG. 6C shows a transparent view of the connection hub shown in FIG. 6B.

In one embodiment of the present disclosure, the connection hub itself may be utilized as part of the fluid path and may, optionally, function as a flow restrictor. FIGS. 6A and 6B show such an embodiment, where connection hub 3310 has a piercing member 3330 and a fluid conduit 3030 connected at opposite ends of an internal aperture 3310D of the connection hub 3310 (visible in the transparent view shown in FIG. 6C). Accordingly, the internal aperture 3310D functions as part of the fluid path and may be utilized to restrict or otherwise modify the flow of fluid from the drug container 50 to the insertion mechanism 200 for delivery of the drug fluid to the body of the patient. For example, the internal aperture 3310D may have a smaller diameter than the fluid conduit 30 to restrict the fluid flow through the fluid pathway connector 300. Additionally or alternatively, the internal aperture 3310D may be configured to extend the length of the fluid path to prolong the time it takes for drug to flow from the drug container to the patient. For example, while the embodiment shown in FIG. 6C shows a straight, short distance internal aperture 3310D, the internal aperture may be a circuitous or tortuous path within the connection hub which extends the fluid pathway and/or provides further flow restriction to the system. By utilizing one or more non-reactive materials and/or non-reactive polymers to form the connection hub 3310, the container integrity and sterility of the fluid path may be maintained.

Referring now to FIGS. 4A and 4B, upon displacement by the patient of the activation mechanism 14 (in the direction of the solid arrow) the piercing member 330 is caused to penetrate the pierceable seal 56 (through the seal barrier 56C) to open the fluid path from the drug container 50 to the fluid pathway connector 300. As described above, because the piercing member 330 is maintained in a sterile environment within the sterile sleeve 320, the sterility of the fluid path is not compromised. The compressible or collapsible sterile sleeve 320 is deformed to permit the translation or displacement of the fluid pathway connector 300 upon patient initiation. FIG. 4A shows an embodiment of the present disclosure which utilizes a sterile sleeve 320 and a pierceable seal 56 as separate components, attached to the proximal end of a barrel 58 of the drug container 50 by a cap 52. As described above, however, sterile sleeve 320 and pierceable seal 56 may be a unified component that provides two or more functions. An optional connection mount 54 is also shown to guide the piercing member 330 upon activation. In this embodiment, the sterile sleeve 320 is shown to deform radially as it is compressed in the axial direction. However, in other embodiments the sterile sleeve 320 may be caused to collapse upon itself in the axial direction such as in, for example, an accordion-style sterile sleeve 320. By keeping the fluid path disconnected until use by the patient, the sterility of the fluid pathway and the drug container are maintained. This novel configuration also provides an additional safety feature to the patient which prevents drug flow until desired, and actively initiated, by the patient.

As described herein, the fluid pathway connector, and specifically a sterile sleeve of the fluid pathway connector, may be connected to the cap and/or pierceable seal of the drug container upon patient-initiated activation of the device. A fluid conduit may be connected at one end to the fluid pathway connector and at another end to the insertion mechanism such that the fluid pathway, when opened, connected, or otherwise enabled travels directly from the drug container, fluid pathway connector, fluid conduit, insertion mechanism, and through the cannula for drug delivery into the body of a patient. The components which constitute the pathway for fluid flow are now assembled. These components may be sterilized, by a number of known methods, and then mounted either fixedly or removably to an assembly platform or housing of the drug delivery device 10, as shown in FIG. 1B.

Certain optional standard components or variations of sterile pathway connection 300 or drug delivery device 10 are contemplated while remaining within the breadth and scope of the present disclosure. For example, upper or lower housings may optionally contain one or more transparent or translucent windows 18, as shown in FIG. 1A, to enable the patient to view the operation of the drug delivery device 10 or verify that drug dose has completed. Additionally, the drug delivery device 10 may contain an adhesive patch 26 and a patch liner 28 on the bottom surface of the housing 12. The adhesive patch 26 may be utilized to adhere the drug delivery device 10 to the body of the patient for delivery of the drug dose. As would be readily understood by one having ordinary skill in the art, the adhesive patch 26 may have an adhesive surface for adhesion of the drug delivery device 10 to the body of the patient. The adhesive surface of the adhesive patch 26 may initially be covered by a non-adhesive patch liner 28, which is removed from the adhesive patch 26 prior to placement of the drug delivery device 10 in contact with the body of the patient. Removal of the patch liner 28 may further remove the sealing membrane 254 of the insertion mechanism 200, opening the insertion mechanism to the body of the patient for drug delivery (as shown in FIG. 1C). In some embodiments, removal of the patch liner 28 may also wake-up onboard electronics (e.g., the power and control system 400) by supplying them with electricity from an onboard battery. Furthermore, as described above, a number of flow restrictors may be optionally utilized to modify the flow of fluid within the fluid pathway connector.

Similarly, one or more of the components of fluid pathway connector 300 and drug delivery device 10 may be modified while remaining functionally within the breadth and scope of the present disclosure. For example, as described above, while the housing of drug delivery device 10 is shown as two separate components upper housing 12A and lower housing 12B, these components may be a single unified component. Similarly, while sterile sleeve 320 is shown as a separate component from pierceable seal 56, it may be a unified component pre-formed as part of pierceable seal. As discussed above, a glue, adhesive, or other known materials or methods may be utilized to affix one or more components of the fluid pathway connector and/or drug delivery device to each other. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the fluid pathway connectors and drug delivery devices disclosed herein provide an efficient and easily-operated system for automated drug delivery from a drug container. The present disclosure provides container connections which are patient-initiated and which maintain the sterility of the fluid pathway, and drug delivery devices which incorporate such sterile fluid pathway connectors to drug containers. Such devices are safe and easy to use, and are aesthetically and ergonomically appealing for self-administering patients. The devices described herein incorporate features which make activation, operation, and lock-out of the device simple for even untrained patients. Because the fluid path is disconnected until drug delivery is desired by the patient, the sterility of the fluid pathway connector, the drug container, the drug fluid, and the device as a whole is maintained. These aspects of the present disclosure provide highly desirable storage, transportation, and safety advantages to the patient. Furthermore, the novel configurations of the fluid pathway connectors and drug devices of the present disclosure maintain the sterility of the fluid path through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly. A further benefit of the present disclosure is that the components described herein are designed to be modular such that, for example, housing and other components of the drug delivery device may readily be configured to accept and operate connection hub 310, connection hub 3310, or a number of other variations of the components described herein.

Assembly and/or manufacturing of fluid pathway connector 300, drug delivery device 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The fluid pathway connector may be assembled in a number of methodologies. In one method of assembly, the drug container 50 may be assembled and filled with a volume of a fluid for delivery to the patient. The fluid may be one of the drugs described below, such as a granulocyte colony-stimulating factor (G-CSF) or a PCSK9 (Proprotein Convertase Subtilisin/Kexin Type 9) specific antibody, for example. In one method of assembly, after being filling with a drug, the drug container 50 may not be subjected to sterilization (e.g., radiation sterilization), so that the drug is not damaged by the high-energy rays typically used in sterilization. The drug container 50 includes a cap 52, a pierceable seal 56, a barrel 58, and a plunger seal 60. The pierceable seal 56 may be fixedly engaged between the cap 52 and the barrel 58, at a distal end of the barrel 58. The barrel 58 may be filled with a drug fluid through the open proximal end prior to insertion of the plunger seal 60 from the proximal end of the barrel 58. An optional connection mount 54 may be mounted to a distal end of the pierceable seal 56. The connection mount 54 to guide the insertion of the piercing member of the fluid pathway connector into the barrel 58 of the drug container 50. The drug container 50 may then be mounted to a distal end of drive housing 130. The sterile sleeve 320 may be connected to the pierceable seal 56 and held in fixed contact by the cap 52, as described above. The connection hub 310, fluid conduit 30, and piercing member 330 may be assembled together and then attached to the proximal end of the sterile sleeve 320 by engagement between hub connectors 320C of sterile sleeve 320 and corresponding sleeve connectors 310C of connection hub 310, as shown in FIG. 4A. The drive mechanism 100 may be attached to the distal end of the drug container 50. The insertion mechanism 200 may be assembled and attached to the other end of the fluid conduit 30. This entire sub-assembly, including drive mechanism 100, drug container 50, fluid pathway connector 300, fluid conduit 30, and insertion mechanism 200 may be sterilized, as described above, before assembly into the drug delivery device 10. Certain components of this sub-assembly may be mounted to the assembly platform 20 or directly to the interior of the housing 12, while other components are mounted to the guide 390 for activation by the patient.

Manufacturing of the drug delivery device 10 may further include the step of attaching both the fluid pathway connector 300 and the drug container 50, either separately or as a combined component, to the assembly platform 20 or the housing 12 of the drug delivery device 10. This step may be performed in a sterile or a non-sterile environment. It may be possible to perform this step in a non-sterile environment because the sterile fluid pathway from the drug container 50 to the insertion mechanism 200 may be been previously established. Accordingly, more flexibility may exist in choosing the manufacturing site for installing the combined assembly of the fluid pathway connector 300, the container 50, and the insertion mechanism 200 in the housing 12 of the drug delivery device 10. The method of manufacturing further includes attachment of the drive mechanism 100, container 50, and insertion mechanism 200 to the assembly platform 20 or housing 12. The additional components of the drug delivery device 10, as described above, including the power and control system 400, the activation mechanism 14, and the control arm 40 may be attached, preformed, or pre-assembled to the assembly platform 20 or housing 12. An adhesive patch and/or an patch liner may be attached to the exterior housing surface of the drug delivery device 10 that contacts the patient during operation of the device.

IV. Insertion Mechanism

Figure 7A:
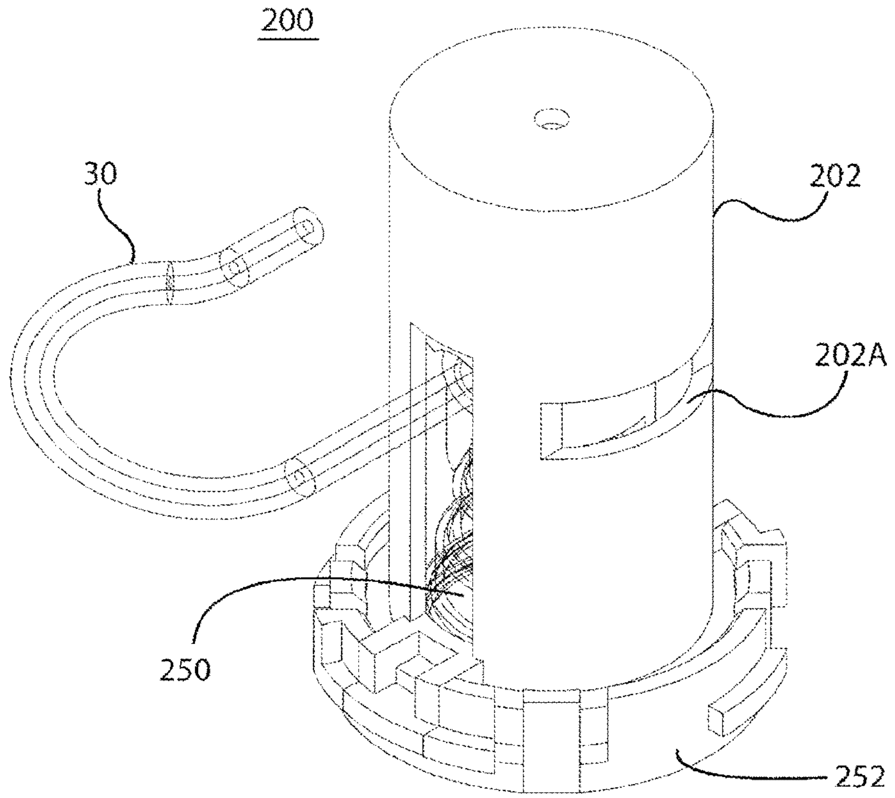
FIG. 7A shows an isometric view of an insertion mechanism, according to a first embodiment of the present disclosure.
Figure 8A:
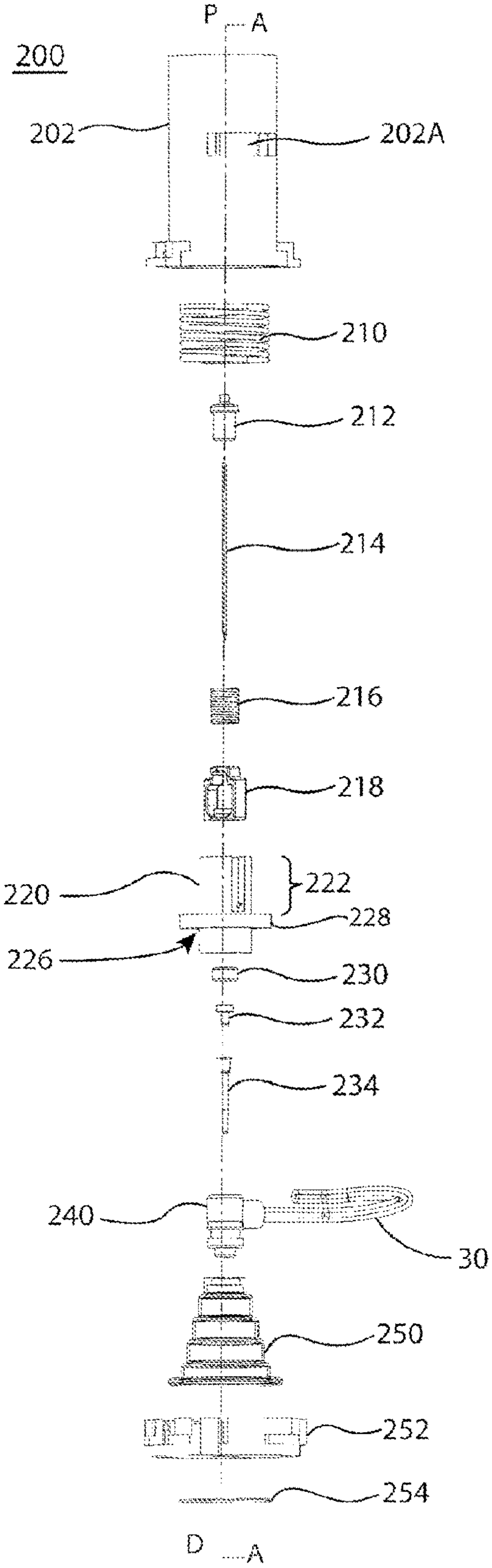
FIG. 8A shows an exploded view, exploded along an axis "A," of the insertion mechanism shown in FIG. 7A.
Figure 8B:
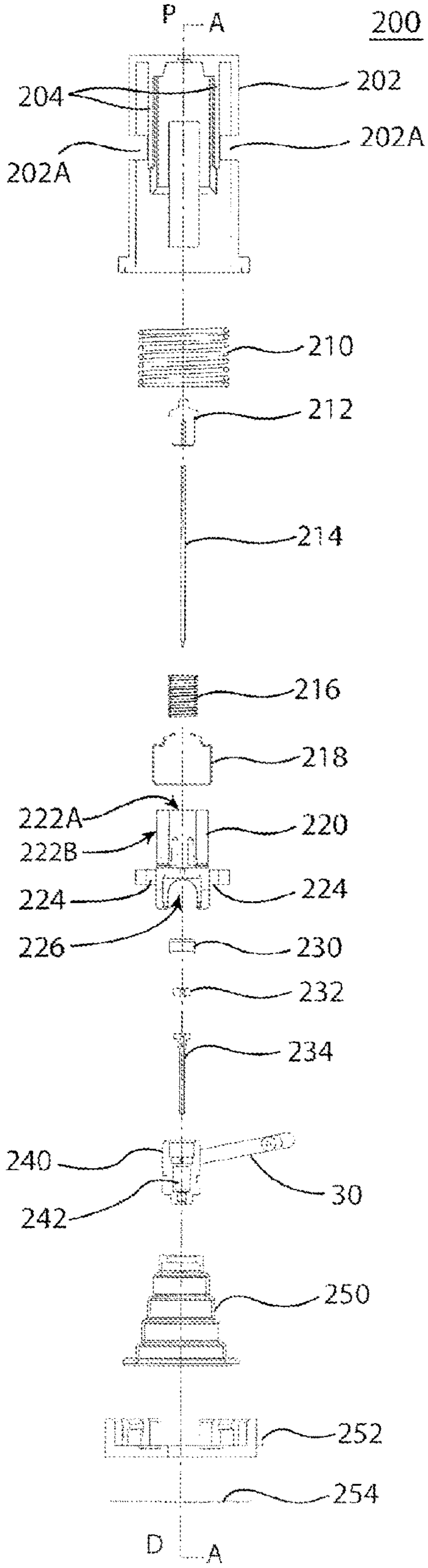
FIG. 8B shows a cross-sectional exploded view, exploded along an axis "A," of the insertion mechanism shown in FIG. 7A.

The insertion mechanism 200 includes an insertion mechanism housing 202 having one or more lockout windows 202A, a base 252, and a sterile boot 250, as shown in FIG. 7A. Base 252 may be connected to assembly platform 20 to integrate the insertion mechanism into the drug delivery device 10 (as shown in FIG. 1B). The connection of the base 252 to the assembly platform 20 may be, for example, such that the bottom of the base is permitted to pass-through a hole in the assembly platform to permit direct contact of the base to the body of the patient. In such configurations, the bottom of the base 252 may include a sealing membrane 254 that, at least in one embodiment, is removable prior to use of the drug delivery device 10. Alternatively, the sealing membrane 254 may remain attached to the bottom of the base 252 such that the needle 214 pierces the sealing membrane 254 during operation of the drug delivery device 10. As shown in FIGS. 8A and 8B, the insertion mechanism 200 may further include an insertion biasing member 210, a hub 212, a needle 214, a retraction biasing member 216, a clip 218, a manifold guide 220, a septum 230, a cannula 234, and a manifold 240. The manifold 240 may connect to sterile fluid conduit 30 to permit fluid flow through the manifold 240, cannula 234, and into the body of the patient during drug delivery, as will be described in further detail herein.

The manifold guide 220 may include an upper chamber 222 and a lower chamber 226 separated by a manifold guide ring 228. The upper chamber 222 may include a clip interface slot 220A for engageable retention of clip 218. The upper chamber 222 may have an inner upper chamber 222A, within which the retraction biasing member 216, the clip 218, and the hub 212 may reside during an initial locked stage of operation, and an outer upper chamber 222B, which interfaces with the insertion biasing member 210. In at least one embodiment, the insertion biasing member 210 and the retraction biasing member 216 are springs, preferably compression springs. The hub 212 may be engageably connected to a proximal end of needle 214, such that displacement or axial translation of the hub 212 causes related motion of the needle 214.

As used herein, "needle" is intended to refer to a variety of needles including but not limited to conventional hollow needles, such as a rigid hollow steel needles, and solid core needles more commonly referred to as a "trocars." In a preferred embodiment, the needle is a 27 gauge solid core trocar and in other embodiments, the needle may be any size needle suitable to insert the cannula 234 for the type of drug and drug administration (e.g., subcutaneous, intramuscular, intradermal, etc.) intended. Upon assembly, the proximal end of needle 214 is maintained in fixed contact with hub 212, while the remainder of needle 214 is permitted to pass-through retraction biasing member 216, an aperture 218C of clip 218 (shown in FIG. 10A), and manifold guide 220. The needle 214 may further pass-through septum 230, cannula 234, manifold 240 through manifold header 242, sterile boot 250, and base 252 through base opening 252A. The manifold header 242 may include an internal chamber defined by an interior wall of the manifold 240. The cannula 234 may be configured in fluid communication with the internal chamber of the manifold header 242. Septum 230, cannula 234, and manifold 240 may reside within lower chamber 226 of manifold guide 220 and within sterile boot 250 until operation of the insertion mechanism. In this position, the cannula 234 may reside over a distal portion of the needle 214 and held in place within the manifold header 242 of manifold 240 by a ferrule 232. Ferrule 232 ensures that cannula 234 remains substantially fixed and in sealed engagement within the manifold 240 to, for example, maintain the sterility of the manifold header 242. Similarly, septum 230 resides substantially fixed and in sealed engagement within the upper portion of the manifold 240 to maintain the sterility of the manifold header 242.

Figure 11A:
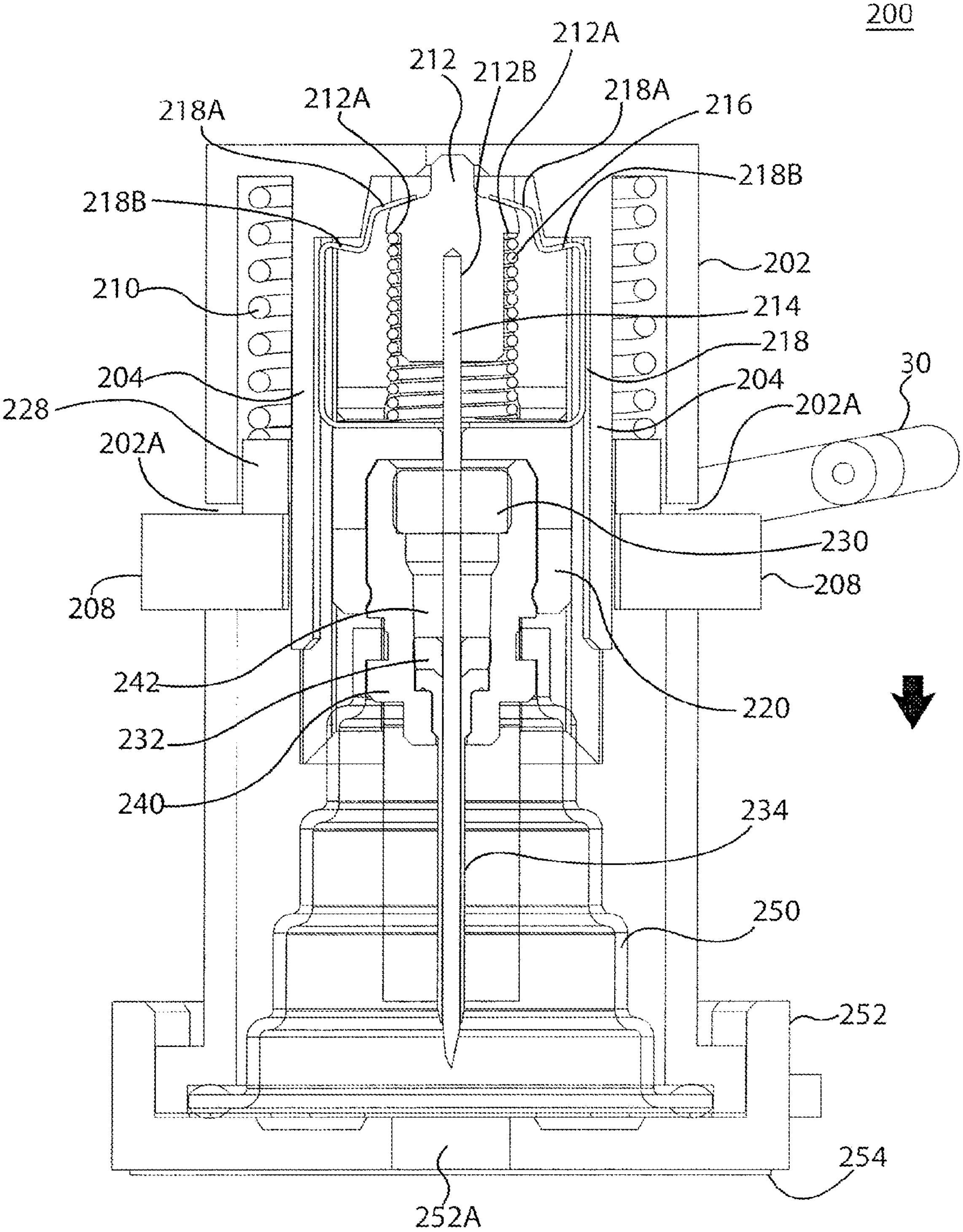
FIG. 11A shows a cross-sectional view of an insertion mechanism, according to a first embodiment of the present disclosure, in a locked and ready to use stage.

Sterile boot 250 is a collapsible or compressible sterile membrane that is in fixed engagement at a proximal end with the manifold 240 and at a distal end with the base 252. In at least on embodiment, the sterile boot 250 is maintained in fixed engagement at a distal end between base 252 and insertion mechanism housing 202, as shown in FIGS. 11A-116C. Base 252 includes a base opening 252A through which the needle and cannula may pass-through during operation of the insertion mechanism, as will be described further below. Sterility of the cannula and needle are maintained by their initial positioning within the sterile portions of the insertion mechanism. Specifically, as described above, needle 214 and cannula 234 are maintained in the sterile environment of the manifold header 242 and sterile boot 250. The base opening 252A of base 252 may be closed from non-sterile environments as well, such as by for example a sealing membrane 254.

Figure 9:
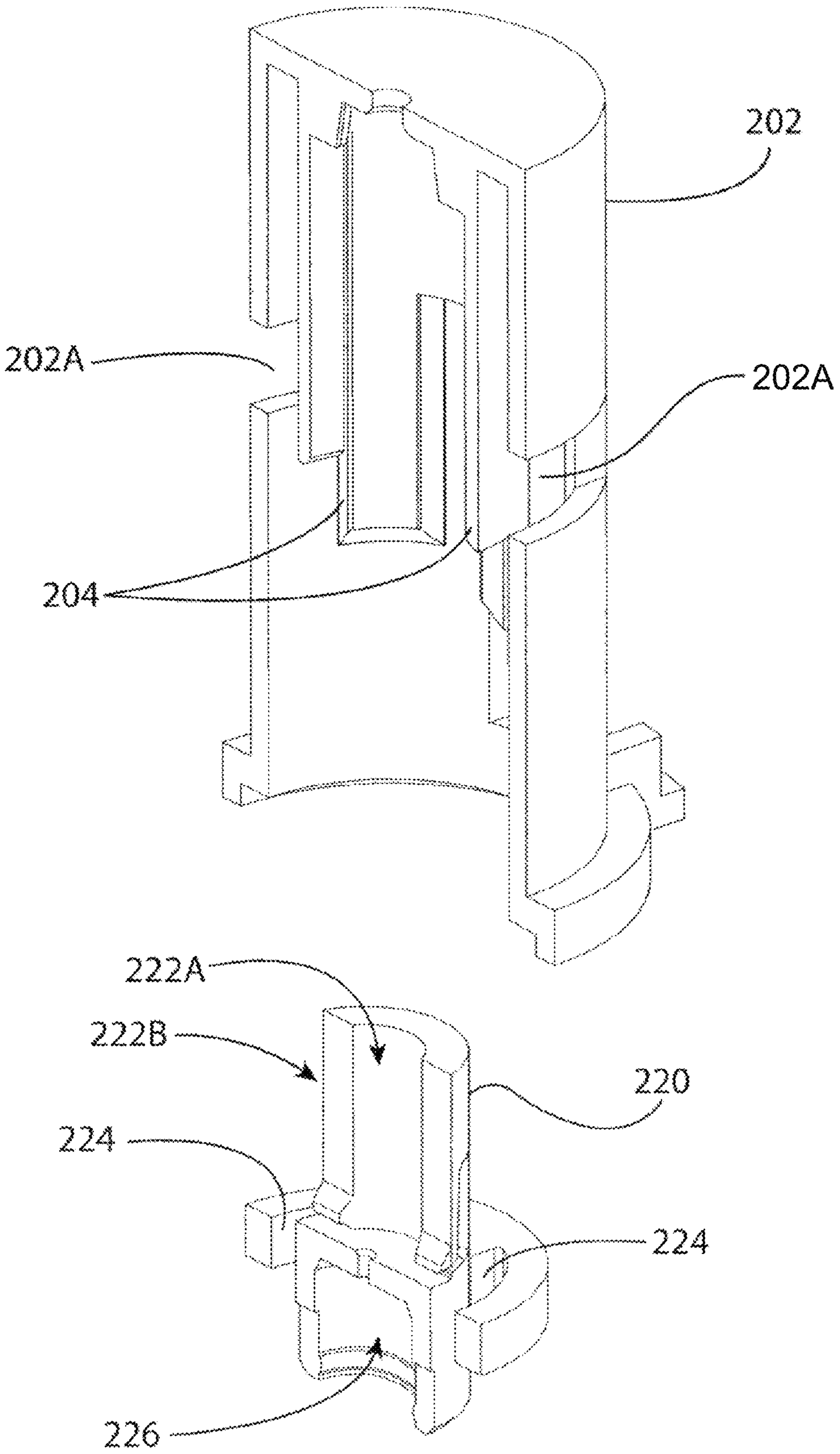
FIG. 9 shows a cross-section isometric view of the insertion mechanism housing and manifold guide of the insertion mechanism, according to a first embodiment of the present disclosure.

FIGS. 8A-8B, 9, and 10A-10C show the components of the insertion mechanism, according to at least a first embodiment, in greater detail. As shown in FIG. 9, insertion mechanism housing 202 may be a substantially cylindrical component having an inner chamber with guide protrusions 204. The guide protrusions 204 may be a pre-formed aspect on the interior of insertion mechanism housing 202, or may be a separate guide protrusion sleeve fixedly engaged to the interior proximal end of the insertion mechanism housing 202. The guide protrusions 204 slidably engage manifold guide 220 at pass-throughs 224 on manifold guide ring 228. The insertion biasing member 210 initially resides in an energized state between the guide protrusions 204 and inner surface of insertion mechanism housing 202 and between the interior proximal end of the insertion mechanism housing 202 and the manifold guide ring 228 of manifold guide 220. Therefore upon activation by the patient, as described further hereinafter, the insertion biasing member 210 is caused to bear against and exert force upon manifold guide ring 228 of manifold guide 220 as the insertion biasing member 210 decompresses and/or de-energizes, causing axial translation in the distal direction of the manifold guide 220 and the components retained within its lower chamber 226. Prior to activation, the insertion biasing member 210 is maintained substantially above locking windows 202A in a compressed, energized state.

Figure 7B:
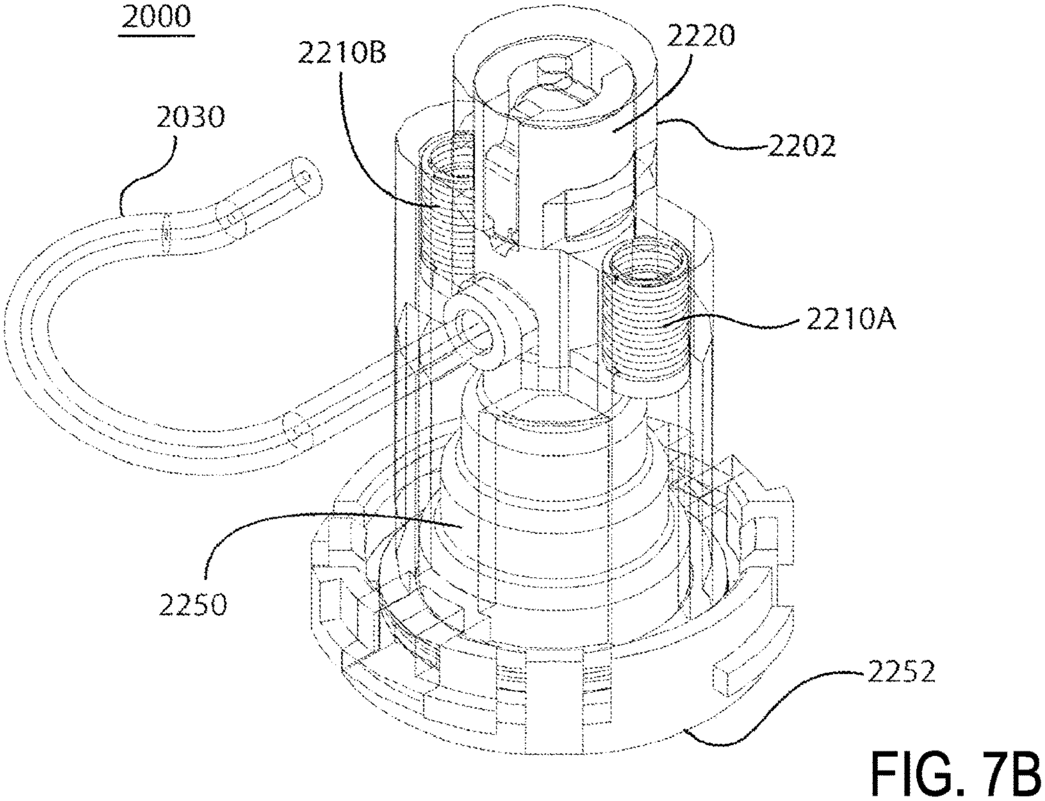
FIG. 7B shows an isometric view of an insertion mechanism, according to another embodiment of the present disclosure.

In an alternative embodiment of the insertion mechanism shown in FIG. 7B, the insertion mechanism 2000 may include two insertion biasing members 2210 A, B. Insertion mechanism 2000 further includes insertion mechanism housing 2202 (shown in transparent view), manifold guide 2220, sterile boot 2250, base 2252, and other components similar to those described above with reference to insertion mechanism 200. In the two insertion biasing members embodiment of the insertion mechanism shown in FIG. 7B, manifold guide ring includes two circular platforms upon which insertion biasing member 2210 A, B may bear. Insertion mechanism 2000 may function identically to insertion mechanism 200, but may provide additional insertion force through the use of multiple insertion biasing members 2210 A, B. The components and functions of the insertion mechanisms will be described further herein with the understanding that similar or identical components may be utilized for insertion mechanism 200, insertion mechanism 2000, and all reasonably understood variations thereof.

Figure 10A:
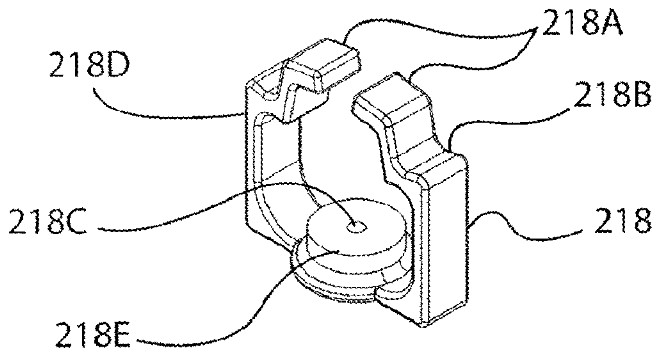
FIG. 10A shows an isometric view of a clip of the insertion mechanism, according to a first embodiment of the present disclosure.
Figure 10B:
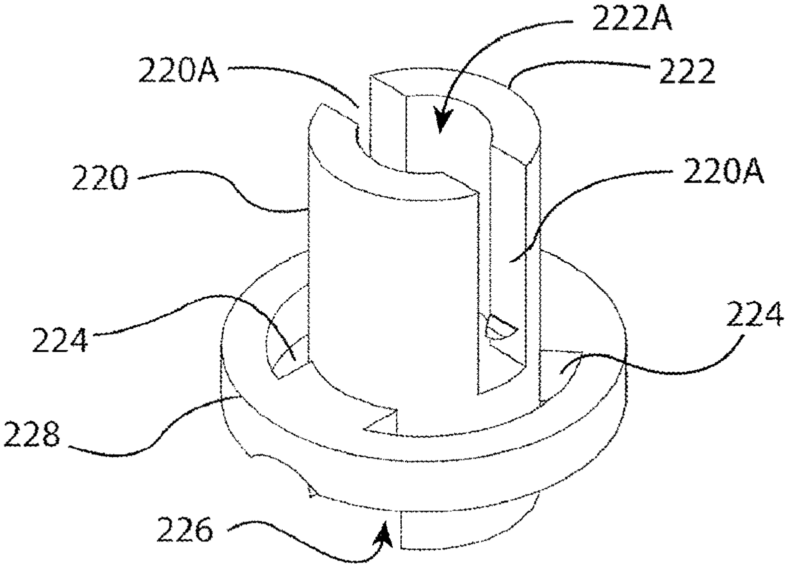
FIG. 10B shows an isometric view of the manifold guide shown in FIG. 9.

FIG. 10A shows a clip 218, according to one embodiment of the present disclosure. Clip 218 includes aperture 218C on platform 218E through which needle 214 may pass, and release surfaces 218A and lockout surfaces 218B of arms 218D. Clip 218 may be made of any number of resilient materials that are capable of flexing and returning to substantially their original form. In an original form, clip 218 may flex outwards such that anus 218D are not perpendicular with platform 218E. Clip 218 resides within clip interface slot 220A of manifold guide 220 such that clip 218 is in fixed engagement with manifold guide 220 but arms 218D are permitted to flex. In an initial locked stage, retraction biasing member 216 and hub 212 (with connected needle 214) are retained between release surfaces 218A and platform 218E of clip 218, and within inner upper chamber 222A of manifold guide 220 (shown in FIG. 9 and FIG. 10B). The needle may pass through aperture 218C of clip 218 and manifold guide 220 into septum 230 and manifold 240.

Figure 10C:
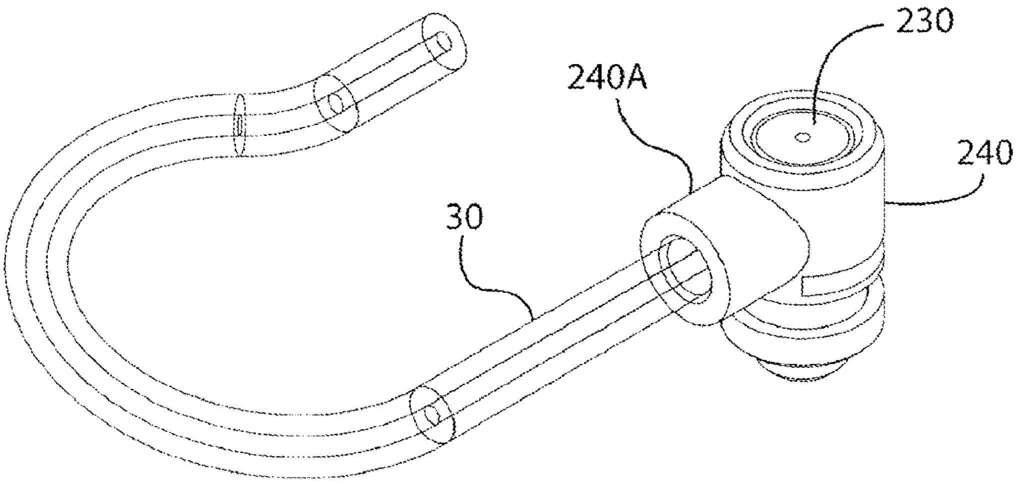
FIG. 10C shows an isometric view of a manifold, a manifold intake, and a fluid conduit of the insertion mechanism, according to a first embodiment of the present disclosure.

Septum 230 resides within manifold 240, as shown in FIG. 10C. Manifold 240 further includes a manifold intake 240A at which the sterile fluid conduit 30 may be connected. The manifold intake 240A may lead to the internal chamber of the manifold header 242 such that connecting the sterile fluid conduit 30 to the manifold intake 240A provides fluid communication between the sterile fluid conduit 30 and the internal chamber of the manifold head 242. Furthermore, the connection between the manifold intake 240A and the sterile fluid conduit 30 is such that the sterility is maintained from the drug container 50 of the drive mechanism 100, through the fluid pathway connector 300 and the sterile fluid conduit 30, into sterile manifold header 242 of manifold 240 and sterile boot 250 to maintain the sterility of the needle 214, cannula 234, and the fluid pathway until insertion into the patient for drug delivery.

Figure 11B:
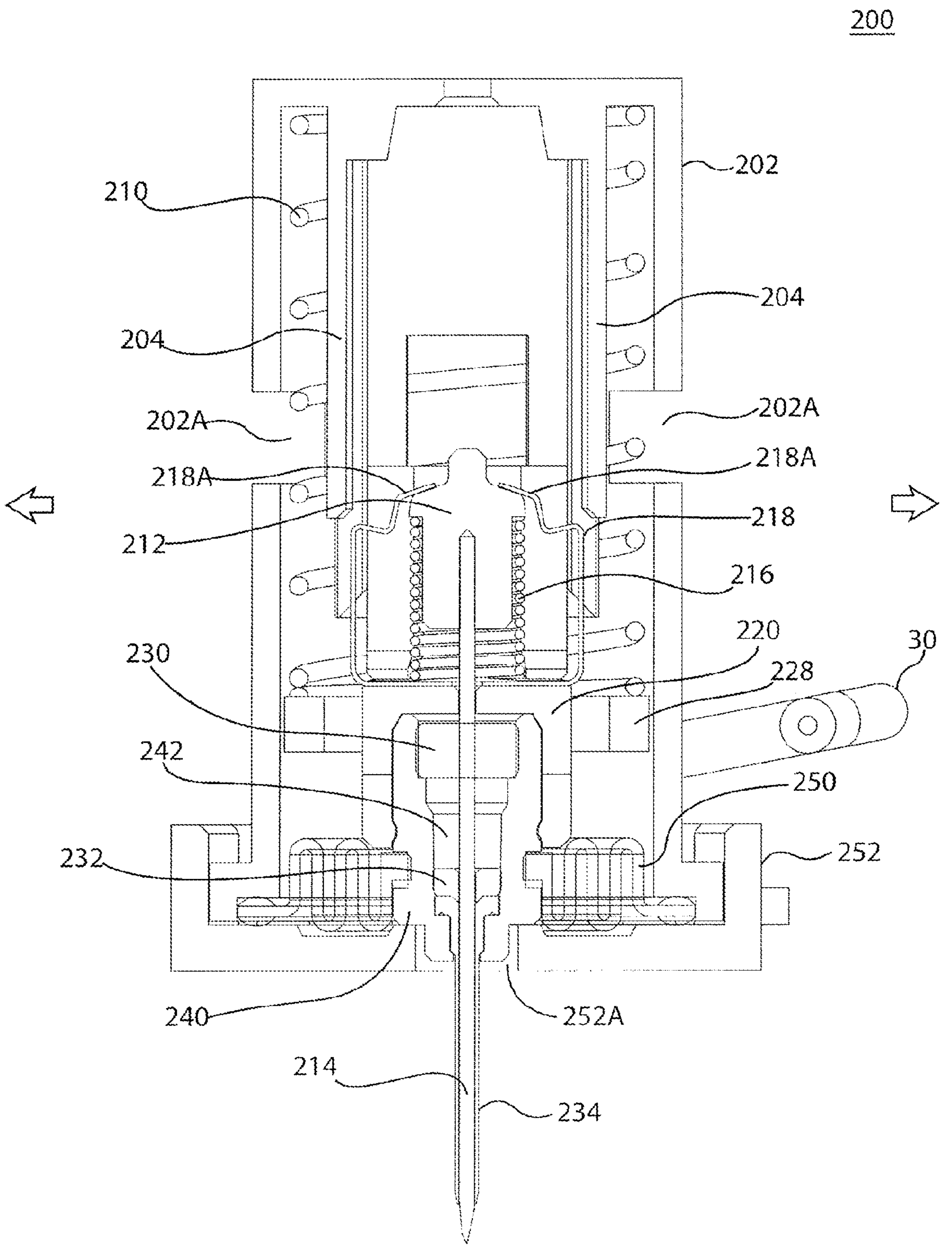
FIG. 11B shows a cross-sectional view of an insertion mechanism, according to a first embodiment of the present disclosure, in an unlocked and inserted stage.
Figure 11C:
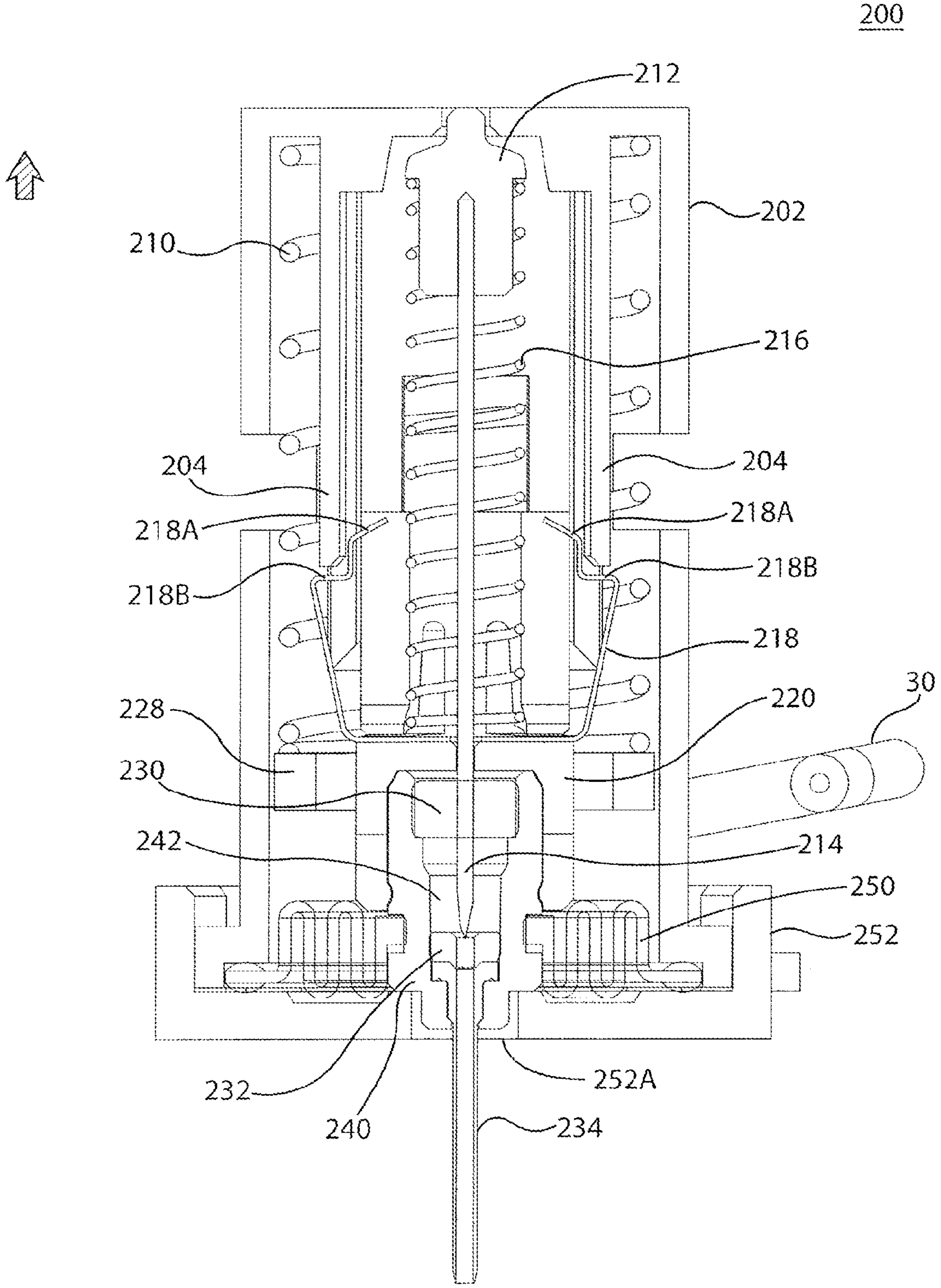
FIG. 11C shows a cross-sectional view of an insertion mechanism, according to a first embodiment of the present disclosure, in a retracted stage for drug delivery.

The operation of the insertion mechanism is described herein with reference to the above components, in view of FIGS. 11A-11C. FIG. 11A shows a cross-sectional view of the insertion mechanism, according to at least one embodiment of the present disclosure, in a locked and ready to use stage. Lockout pin(s) 208 are initially positioned within lockout windows 202A of insertion mechanism housing 202. In this initial position, manifold guide ring 228 of manifold guide 220, clip 218, and hub 212 are retained above lockout windows 202A and locking pin(s) 208. In this initial configuration, insertion biasing member 210 and retraction biasing member 216 are each retained in their compressed, energized states.

As shown in FIG. 11B, the lockout pin(s) 208 (not visible) may be directly displaced by patient depression of the activation mechanism 14. As the patient disengages any safety mechanisms, such as an optional on-body sensor 24 (shown in FIG. 11C), the activation mechanism 14 may be depressed to initiate the drug delivery device. Depression of the activation mechanism 14 may directly cause translation or displacement of control arm 40 and directly or indirectly cause displacement of lockout pin(s) 208 from their initial position within locking windows 202A of insertion mechanism housing 202. Displacement of the lockout pin(s) 208 permits insertion biasing member 210 to decompress and/or de-energize from its initial compressed, energized state. Accordingly, the lockout pin(s) 208 may function as a second retainer having: a second retainer retaining position (FIG. 11A), where the second retainer retains the insertion biasing member 210 in the energized state; and a second retainer releasing position (FIG. 12B), where the second retainer allows the insertion biasing member 210 to de-energize.

As shown in FIG. 11A, hub ledges 212A maintain retraction biasing member 216 in a compressed, energized state between hub 212 and manifold guide 220 within inner upper chamber 222A. The hub 212 fixedly engages proximal end of needle 214 at hub recess 212B. Prior to operation, sealing member 254 may be removed from bottom of base 252 and base 252 is placed in contact with the target injection site on the body of the patient. As lockout pin(s) 208 are displaced by the activation mechanism, as described above, and insertion biasing member 210 is permitted to expand axially in the distal direction (i.e., in the direction of the solid arrow in FIG. 11A), manifold ring guide 228 is forced by the decompression and/or de-energizing of the insertion biasing member 210 to translate axially in the distal direction to insert the needle 214 and cannula 234 into the body of the patient. The axial translation of the manifold guide is directed, and maintained in rotational alignment, by interaction between the guide protrusions 204 of the insertion mechanism housing 202 and corresponding pass-throughs 224 of the manifold guide 220. Release surfaces 218A of clip 218 engage hub 212 and retain the retraction biasing member 216 in a compressed, energized state while the manifold guide 220 travels axially in the distal direction until the clip 218 reaches the end of the guide protrusions 204 where the clip 218 is permitted to elastically flex outwards, as will be described further below.

FIG. 11B shows a cross-sectional view of an insertion mechanism in a needle inserted stage. As shown, sterile boot 250 is permitted to collapse as the insertion biasing member 210 expands and inserts the needle 214 and cannula 234 into the body of the patient. During expansion of the insertion biasing member 210, the manifold 240 moves in the distal direction, and because the cannula 234 and the sterile fluid conduit 30 are fixedly connected to the manifold 240, the cannula 234 and the sterile fluid conduit 30 also move in the distal direction, as seen in FIGS. 11A and 11B. At this stage, as illustrated in FIG. 11B, needle 218 is introduced into the body of the patient to place the cannula 234 into position for drug delivery. As shown in FIG. 11C, upon needle 214 and cannula 234 insertion by operation of the insertion biasing member 210 as described above, the needle 214 is retracted back (i.e., axially translated in the proximal direction) into the insertion mechanism housing 202. Manifold guide 220, clip 218, and guide protrusions 204 are dimensioned such that, as the manifold 240 substantially bottoms-out on base 252, i.e., reaches its full axial translation in the distal direction, the clip 218 escapes the guide protrusions 204 and is permitted to elastically flex outwards (i.e., in the direction of the hollow arrows shown in FIG. 11B) to disengage release surfaces 218A from hub 212. Upon disengagement of the release surfaces 218A from hub 212, retraction biasing member 216 is permitted to expand axially in the proximal direction (i.e., in the direction of hatched arrow in FIG. 11C) from its initial compressed, energized state. The clip 218 is prevented from retracting or axial translation in the proximal direction by contact between the lockout surfaces 218B and the distal ends of the guide protrusions 204, as shown in FIG. 11C. This lockout also prevents axial translation in the proximal direction of the manifold guide 220 and insertion mechanism components that are distal to (i.e., below) the manifold guide ring 228. Thus, the clip 218 may function as a third retainer having: a third retainer retaining position (FIGS. 11A and 11B), where the third retainer retains the retraction biasing member 216 in its energized state; and a third retainer releasing position (FIG. 11C), where the third retainer allows the retraction biasing member 216 to de-energize.

Expansion of the retraction biasing member 216 translates hub 212, and needle 214 to which it is connected, axially in the proximal direction. Ferrule 232 retains cannula 234 inserted within the body of the patient through base opening 252A. Upon retraction of the needle 214 from cannula 234, the fluid pathway from manifold header 242 to the body of the patient through the cannula 234 is opened. As the fluid pathway connector is made to the drug container and the drive mechanism is activated, the fluid drug treatment is forced from the drug container through the fluid pathway connector and the sterile fluid conduit into the manifold header 242 and through the cannula 234 for delivery into the body of the patient. Accordingly, activation of the insertion mechanism inserts the needle 214 and cannula 234 into the body of the patient, and sequentially retracts the needle 214 while maintaining the cannula 234 in fluid communication with the body of the patient. Retraction of the needle 214 also opens up the fluid pathway between the manifold header 242 and the body of the patient through the cannula 234. At the end of the drug dose delivery, the cannula 234 may be removed from the body of the patient by removal of the drug delivery device from contact with the patient.

In some embodiments, the cannula 234 is made of a relatively soft, flexible material (e.g., rubber or plastic), and the needle 214 may be constructed of a relatively hard, rigid material (e.g., metal). In some embodiments, the cannula 234 may be made of a more flexible material than the needle 214. The rigidity of the needle 214 may facilitate piercing the patient's skin, and the flexibility of the cannula 234 may facilitate patient comfort when the cannula 234 is disposed in the patient's body. Accordingly, the combination of the needle 214 and the cannula 234 may be effective in providing subcutaneous delivery of a drug over a duration of time (e.g., 10 of seconds, minutes, hours, or even days) with little or no patient discomfort, and without impeding the patient's physical activity.

A method of operating an insertion mechanism 200 according to one embodiment of the present disclosure includes: removing one or more of the lockout pins 208 from corresponding one or more locking windows 202A of the insertion mechanism housing 202, wherein removal of said lockout pins 208 permits the insertion biasing member 210 to expand from its initially energized state; driving, by expansion of the insertion biasing member 210, a manifold guide 220 axially in the distal direction to force the needle 214 and the cannula 234 at least partially out of the insertion mechanism 200 and into the body of the patient; permitting outwards flexion of the clip 218 retained in an upper chamber of the manifold guide 220, wherein said clip 210 initially retains the hub 212 and the retraction biasing member 216 in an energized state and wherein flexion disengages one or more release surfaces 218A of the clip 210 from contact with a hub 212 thereby permitting expansion of the retraction biasing member 216 axially in the proximal direction; and retracting the needle 214 upon retraction of the hub 212 through a fixed connection between the needle 214 and the hub 212, while maintaining the cannula 234 inserted into the body of the patient for fluid delivery.

Certain optional standard components or variations of insertion mechanism 200 or drug delivery device 10 are contemplated while remaining within the breadth and scope of the present disclosure. For example, upper or lower housings may optionally contain one or more transparent or translucent windows 18, as shown in FIGS. 1A-1C, to enable the patient to view the operation of the drug delivery device 10 or verify that drug dose has completed. Additionally, the drug delivery device 10 may contain an adhesive patch 26 and a patch liner 28 on the bottom surface of the housing 12. The adhesive patch 26 may be utilized to adhere the drug delivery device 10 to the body of the patient for delivery of the drug dose. As would be readily understood by one having ordinary skill in the art, the adhesive patch 26 may have an adhesive surface for adhesion of the drug delivery device to the body of the patient. The adhesive surface of the adhesive patch 26 may initially be covered by a non-adhesive patch liner 28, which is removed from the adhesive patch 26 prior to placement of the drug delivery device 10 in contact with the body of the patient. Adhesive patch 26 may optionally include a protective shroud that prevents actuation of the optional on-body sensor 24 and covers base opening 252A. Removal of the patch liner 28 may remove the protective shroud or the protective shroud may be removed separately. Removal of the patch liner 28 may further remove the sealing membrane 254 of the insertion mechanism 200, opening the insertion mechanism to the body of the patient for drug delivery. In some embodiments, removal of the patch liner 28 may also wake up onboard electronics (e.g., the power and control system 400) by supplying them with electricity from an onboard battery.

Similarly, one or more of the components of insertion mechanism 200 and drug delivery device 10 may be modified while remaining functionally within the breadth and scope of the present disclosure. For example, as described above, while the housing of drug delivery device 10 is shown as two separate components upper housing 12A and lower housing 12B, these components may be a single unified component. Similarly, while guide protrusions 204 are shown as a unified pre-formed component of insertion mechanism housing 202, it may be a separate component fixedly attached to the interior surface of the insertion mechanism housing 202. As discussed above, a glue, adhesive, or other known materials or methods may be utilized to affix one or more components of the insertion mechanism and/or drug delivery device to each other. Alternatively, one or more components of the insertion mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the insertion mechanisms and drug delivery devices disclosed herein provide an efficient and easily-operated system for automated drug delivery from a drug container. The novel embodiments described herein provide integrated safety features; enable direct patient activation of the insertion mechanism; and are configured to maintain the sterility of the fluid pathway. As described above, the integrated safety features include optional on-body sensors, redundant lockouts, automated needle insertion and retraction upon patient activation, and numerous patient feedback options, including visual and auditory feedback options. The novel insertion mechanisms of the present disclosure may be directly activated by the patient. For example, in at least one embodiment the lockout pin(s) which maintain the insertion mechanism in its locked, energized state are directly displaced from the corresponding lockout windows of the insertion mechanism housing by patient depression of the activation mechanism. Alternatively, one or more additional components may be included, such as a spring mechanism, which displaces the lockout pin(s) upon direct displacement of the activation mechanism by the patient without any intervening steps.

Furthermore, the novel configurations of the insertion mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control aim, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly. A further benefit of the present disclosure is that the components described herein are designed to be modular such that, for example, housing and other components of the drug delivery device may readily be configured to accept and operate insertion mechanism 200, insertion mechanism 2000, or a number of other variations of the insertion mechanism described herein.

Assembly and/or manufacturing of insertion mechanism 200, drug delivery device 10, or any of the individual components may utilize a number of known materials and methodologies in the art. For example, a number of known cleaning fluids such as isopropyl alcohol may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

The insertion mechanism may be assembled in a number of methodologies. In one method, a hub is initially connected to a proximal end of a needle. The hub and needle are inserted into an inner upper chamber of a manifold guide, wherein a retraction biasing member is maintained in an energized state between the manifold guide and the hub. The hub, needle, and retraction biasing member are held in this alignment by a clip, wherein the clip is fixedly and flexibly connected to the manifold guide at a clip interface. A cannula is inserted into a manifold and held in place by a ferrule. A septum is inserted into the manifold at an end opposing the cannula to create a manifold header therebetween. The manifold, septum, cannula, and ferrule are inserted into a lower chamber of the manifold guide such that the needle pierces through the septum and resides within the cannula. The needle extends beyond the distal end of the cannula to provide a piercing tip. A sterile boot is connected to the manifold, wherein the needle and cannula reside within the sterile boot when the latter is in an expanded configuration.

An insertion spring is inserted into insertion mechanism housing between the housing and one or more guide protrusions extending into the interior of the housing from the proximal end. The manifold guide, having the components attached thereto as described herein, is inserted into the insertion mechanism housing such that the guide protrusions extend through corresponding pass-throughs on a manifold guide ring aspect of the manifold guide. As the manifold guide is translated in the proximal direction, the insertion biasing member is caused to contact the manifold guide ring and become energized. As translation of the manifold guide and compression of the insertion biasing member reach a point above one or more lockout windows of the insertion mechanism housing, one or more corresponding lockout pin(s) may be inserted to retain the manifold guide in this position and the insertion biasing member in the compressed, energized state.

The distal end of the sterile boot may be positioned and held in fixed engagement with the distal end of the insertion mechanism housing by engagement of the housing with a base. In this position, the sterile boot is in an expanded configuration around the needle and cannula and creates an annular volume which may be sterile. A fluid conduit may be connected to the manifold at a manifold intake such that the fluid pathway, when open travels directly from the fluid conduit, through the manifold intake, into the manifold header, and through the cannula upon retraction of the needle. A fluid pathway connector may be attached to the opposite end of the fluid conduit. The fluid pathway connector, and specifically a sterile sleeve of the fluid pathway connector, may be connected to a cap and pierceable seal of the drug container. The plunger seal and drive mechanism may be connected to the drug container at an end opposing the fluid pathway connector. A sealing membrane may be attached to the bottom of the base to close of the insertion mechanism from the environment. The components which constitute the pathway for fluid flow are now assembled. These components may be sterilized, by a number of known methods, and then mounted either fixedly or removable to an assembly platform or housing of the drug delivery device.

Manufacturing of a drug delivery device 10 includes the step of attaching the base of the insertion mechanism 200 to the assembly platform 20 or housing 12 of the drug delivery device 10. In at least one embodiment, the attachment is such that the base of the insertion mechanism 200 is permitted to pass-through the assembly platform 20 and/or housing 12 to come in direct contact with the body of the patient. The method of manufacturing may further include attachment of the fluid pathway connector 300, drug container 50, and drive mechanism 100 to the assembly platform 20 or housing 12. The additional components of the drug delivery device, as described above, including the power and control system 400, the activation mechanism 14, and the control arm 40 may be attached, preformed, or pre-assembled to the assembly platform 20 or housing 12. An adhesive patch and/or patch liner may be attached to an exterior surface of the housing 12 that contacts the patient during operation of the drug delivery device 10.

A method of operating the drug delivery device 10 includes the steps of: activating, by a patient, the activation mechanism 14; displacing a control arm to actuate an insertion mechanism 200; displacing a guide to translate a fluid pathway connector 300; and actuating the power and control system 400 to activate the drive mechanism 100 to drive fluid drug flow through the drug delivery device 10, wherein translating the fluid pathway 300 connector causes the piercing member 330 to penetrate the pierceable seal 56 thereby opening a fluid path from the drug container 50 to the fluid pathway connector 300. The method may further include the step of engaging an optional on-body sensor prior to activating the activation mechanism 14. Furthermore, the method of operation may include translating the plunger seal 60 within the drive mechanism 100 to force the fluid drug to flow through the drug container 50, the fluid pathway connector 300, the sterile fluid conduit 30, and the insertion mechanism 200 for delivery of the fluid drug to the body of a patient. The method of operation of the drug delivery device 10 may be appreciated with reference to FIGS. 4A-4B and 11A-11C, as described above.

V. Drive Mechanism

Figure 12:
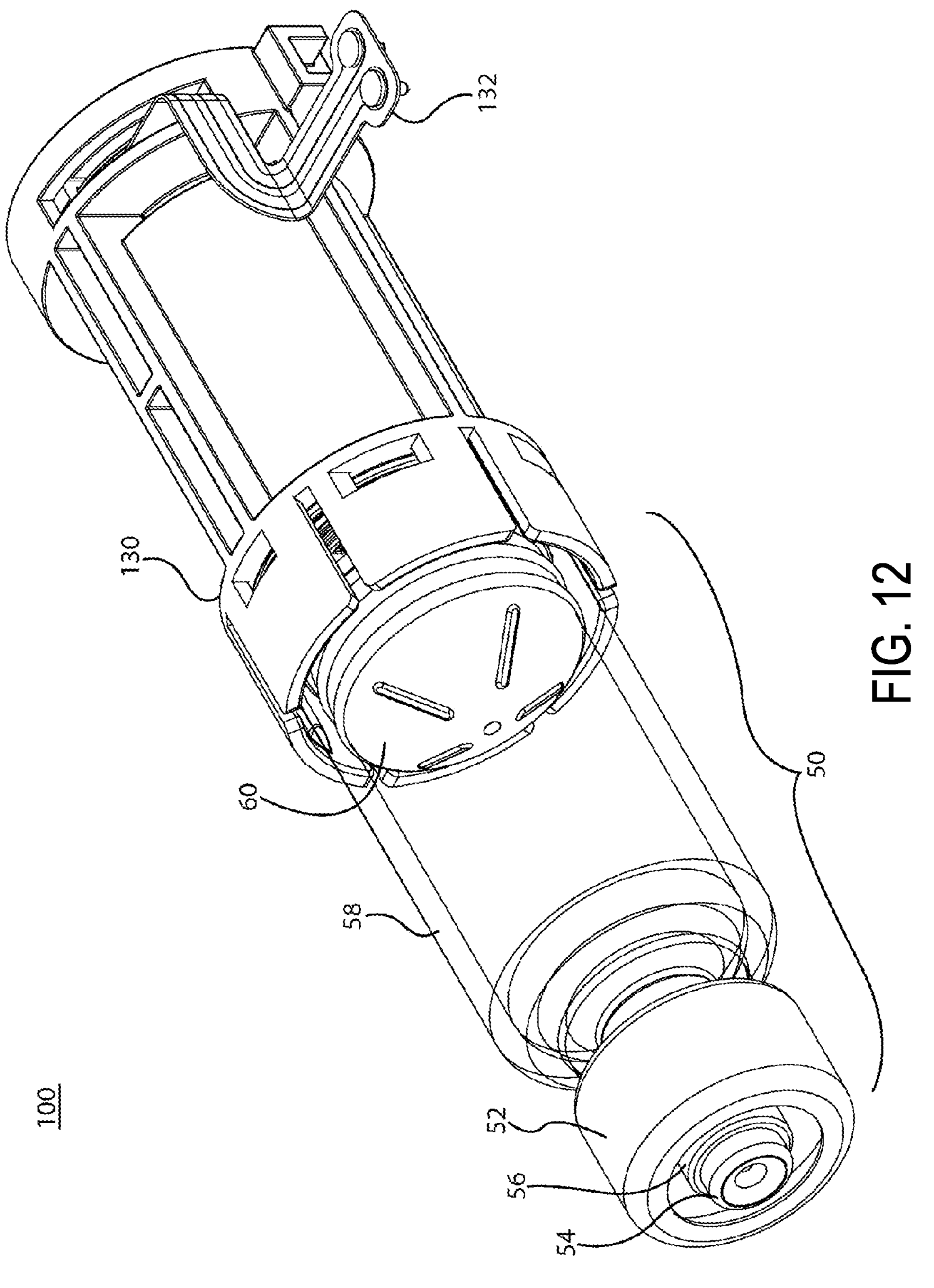
FIG. 12 shows an isometric view of a drive mechanism, according to at least one embodiment of the present disclosure.
Figure 13:
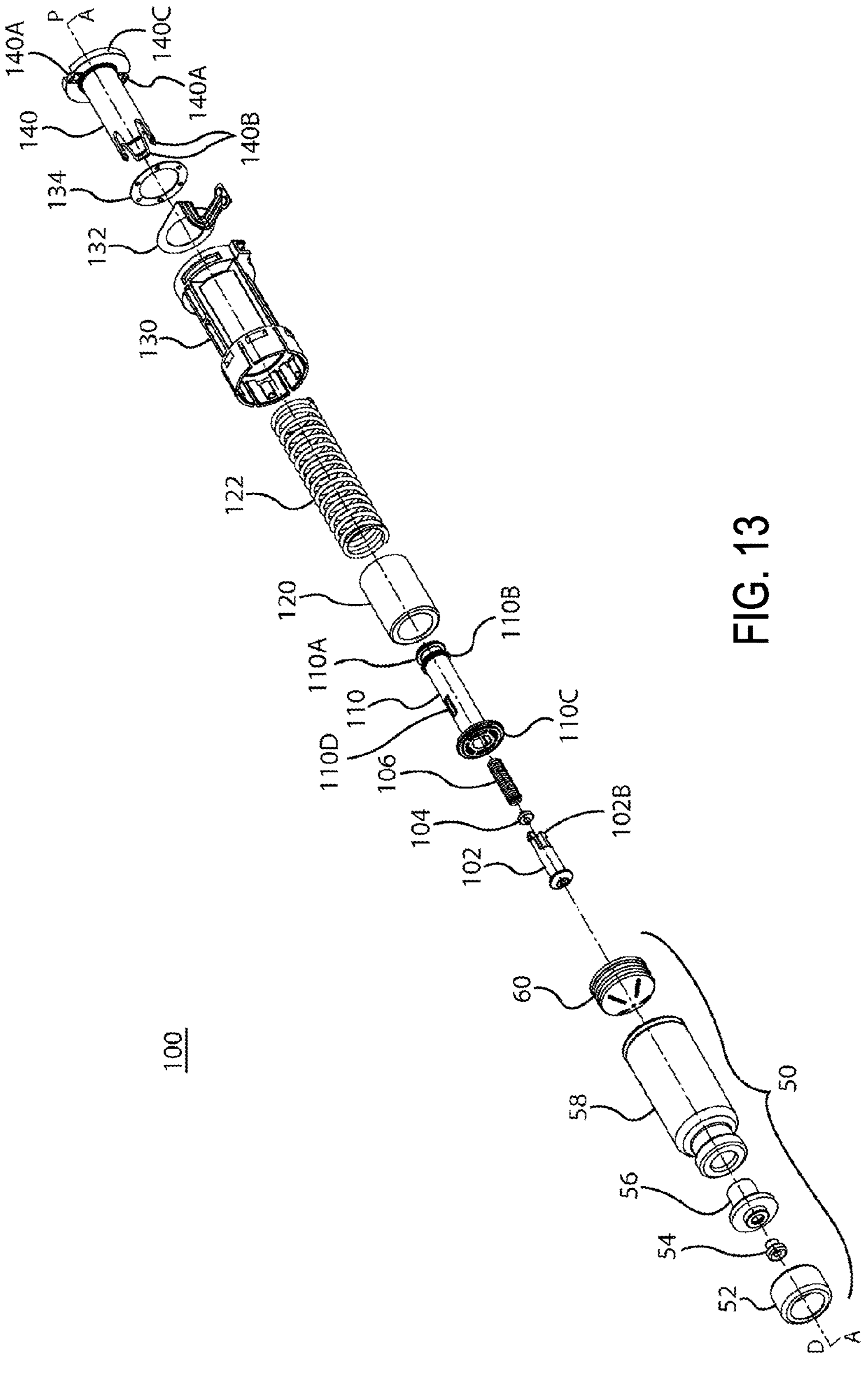
FIG. 13 shows an exploded view, along an axis “A,” of the drive mechanism shown in FIG. 12.

With reference to the embodiments shown in FIGS. 12 and 13, the drive mechanism 100 includes a drive housing 130, a status switch interconnect 132, and the drug container 50 having the cap 52, the pierceable seal 56, the barrel 58, and the plunger seal 60. The drug container 50 may contain a drug fluid, within the barrel between the pierceable seal and the plunger seal, for delivery through the insertion mechanism and drug delivery device 10 into the body of the patient. The seals described herein may be comprised of a number of materials but are, in a preferred embodiment, comprised of one or more elastomers or rubbers. The drive mechanism may further include a connection mount 54 to guide the insertion of the piercing member of the fluid pathway connector into the barrel 58 of the drug container 50. The drive mechanism 100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the patient.

The drive mechanism may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power control system 400. In at least one embodiment, as described further herein, the contact surfaces may be electrical contact surfaces which are initially disconnected and caused to come into engagement whereby, upon such engagement, contact surfaces are capable of continuing an energy pathway or otherwise relaying a signal to the power and control system 400. In another embodiment of the present disclosure, the contact surfaces are mechanical contact surfaces which are initially in contact and caused to disengage whereby, upon such disengagement, such disengagement is communicated to the power and control system 400. Such signals may be transferred across one or more interconnects 132 to the power and control system 400 or by mechanical action to the power and control system 400. Such components may be utilized within the drive mechanism to measure and relay information related to the status of operation of the drive mechanism, which may be converted by the power and control system 400 into tactile, auditory, and/or visual feedback to the patient. Such embodiments are described further herein. Regardless of the electrical or mechanical nature of the contact surfaces, the motion of the components which permits transmission of a signal to the power control system 400 is enabled by a biasing member 122 axially translating a contact sleeve 140 in the distal direction during operation of the device.

In one particular embodiment, the drive mechanism 100 employs one or more compression springs as the biasing member(s). Upon activation of the drug delivery device 10 by the patient, the power and control system may be actuated to directly or indirectly release the compression spring(s) from an energized state. Upon release, the compression spring(s) may bear against and act upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the patient for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

Referring now to the embodiment of the drive mechanism shown in FIG. 13, the drive mechanism 100 includes a drug container 50 having a cap 52, a pierceable seal 56, a barrel 58, and a plunger seal 60, and optionally a connection mount 54. The drug container 50 is mounted to a distal end of a drive housing 130. Compressed within the drive housing 130, between the drug container 50 and the proximal end of the housing 130, are a drive biasing member 122 and a piston 110, wherein the drive biasing member 122 is configured to bear upon an interface surface 110C of the piston 110, as described further herein. Optionally, a cover sleeve 120 may be utilized between the drive biasing member 122 and the interface surface 110C of the piston 110 to, for example, promote more even distribution of force from the drive biasing member 122 to the piston 110, prevent buckling of the drive biasing member 122, and/or hide biasing member from patient view. Interface surface 110C of piston 110 is caused to rest substantially adjacent to, or in contact with, a proximal end of seal 60.

The drive mechanism 100 further includes, mounted at a distal end, a status switch interconnect 132. A contact sleeve 140 is slidably mounted to the drive housing 130 through an axial aperture of the housing 130, such that sleeve hooks 140B at a distal end of the contact sleeve 140 are caused to contact the piston 110 between interface surface 110 and a contact protrusion 110B near the proximal end of the piston 110. Piston 110 also includes a locking groove 110A, between contact protrusion 110B and the proximal end of the piston 110. Contact sleeve 140 has a radially extending ring 140C at its proximal end, upon which resides one or more flex prongs 140A. An electrical contact 134 may be connected, mounted, printed, or otherwise mounted to ring 140C which, during operation of the drive mechanism, may come in contact with corresponding status switch interconnect 132 to complete an electrical circuit or otherwise permit a transmission to the power and control system to provide feedback to the patient.

The components of the drive mechanism 100, upon activation, may be used to drive axial translation in the distal direction of the plunger seal 60 of the drug container 50. Optionally, the drive mechanism 100 may include one or more compliance features which enable additional axial translation of the plunger seal 60 to, for example, ensure that substantially the entire drug dose has been delivered to the patient and make sure that the feedback contact mechanisms have connected. For example, in one embodiment of the present disclosure, the sleeve hooks 140B are flex aims which may permit, upon sufficient application of force by the drive biasing member 122 on the piston 110, to allow interface surface 110C to translate axially beyond sleeve hooks 140B to drive further axial translation of the plunger seal 60 for a compliance push of drug fluid from the drug container. Additionally or alternatively, the plunger seal 60, itself, may have some compressibility permitting a compliance push of drug fluid from the drug container.

In at least one embodiment of the present disclosure, a compliance push of drug fluid from the drug container is enabled by a piston extension 102. In such embodiments, the drive mechanism 100 further includes a piston extension 102 slidably mounted at a distal end and within an axial passthrough of piston 110. The piston extension 102 may be retained within piston 110 by interaction between extension arms 102B of the piston extension 102 and connection slots 110D of piston 110, as shown in FIGS. 14A-14E. Piston extension may be driven by a piston extension biasing member 106, which is mounted within the axial passthrough of piston 110 and initially compressed between piston extension 102 and piston 110. An optional piston biasing member support 104 may be utilized between piston extension biasing member 106 and piston extension 102 to, for example, promote more uniform distribution of force from piston extension biasing member 106 to piston extension 102. The function of the optional piston extension is described in further detail hereinafter.

The novel drive mechanisms of the present disclosure integrate status indication into the drug dose delivery. By use of one or more status switch interconnects and one or more corresponding electrical contacts, the status of the drive mechanism before, during, and after operation can be relayed to the power and control system to provide feedback to the patient. Such feedback may be tactile, visual, and/or auditory, as described above, and may be redundant such that more than one signals or types of feedback are provided to the patient during use of the device. For example, the patient may be provided an initial feedback to identify that the system is operational and ready for drug delivery. Upon activation, the system may then provide one or more drug delivery status indications to the patient. At completion of drug delivery, the drive mechanism and drug delivery device 10 may provide an end-of-dose indication. As the end-of-dose indication is tied to the piston reaching the end of its axial translation, the drive mechanism and drug delivery device 10 provide a true end-of-dose indication to the patient.

In at least one embodiment, as shown in FIG. 12 and FIG. 13, an end-of-dose status indication may be provided to the patient once the status switch interconnect 132 is caused to contact electrical contact 134 at the end of axial travel of the piston 110 and plunger 60 within the barrel 58 of the drug container 50. In a further embodiment, incremental status indication relaying various stages of drug delivery can be communicated to the patient during operation. In one such embodiment, sleeve hooks 140B of cover sleeve 120 may have one or more interconnects which come into contact with one or more electrical contacts on the outer surface of piston 110 during operation. As piston 110 translates axially in the distal direction to push plunger seal 60 distally, thereby pushing fluid out of the drug container through the pierceable seal end, the electrical contacts of the piston 110 may sequentially contact the interconnect on the sleeve hooks 140B to relay the incremental status of operation. Depending on the number of electrical contacts located on the outer surface of the piston 110, the frequency of the incremental status indication may be varied as desired. The location of the contacts and interconnects may be interchanged or in a number of other configurations which permit completion of an electrical circuit or otherwise permit a transmission between the components.

Figure 15:
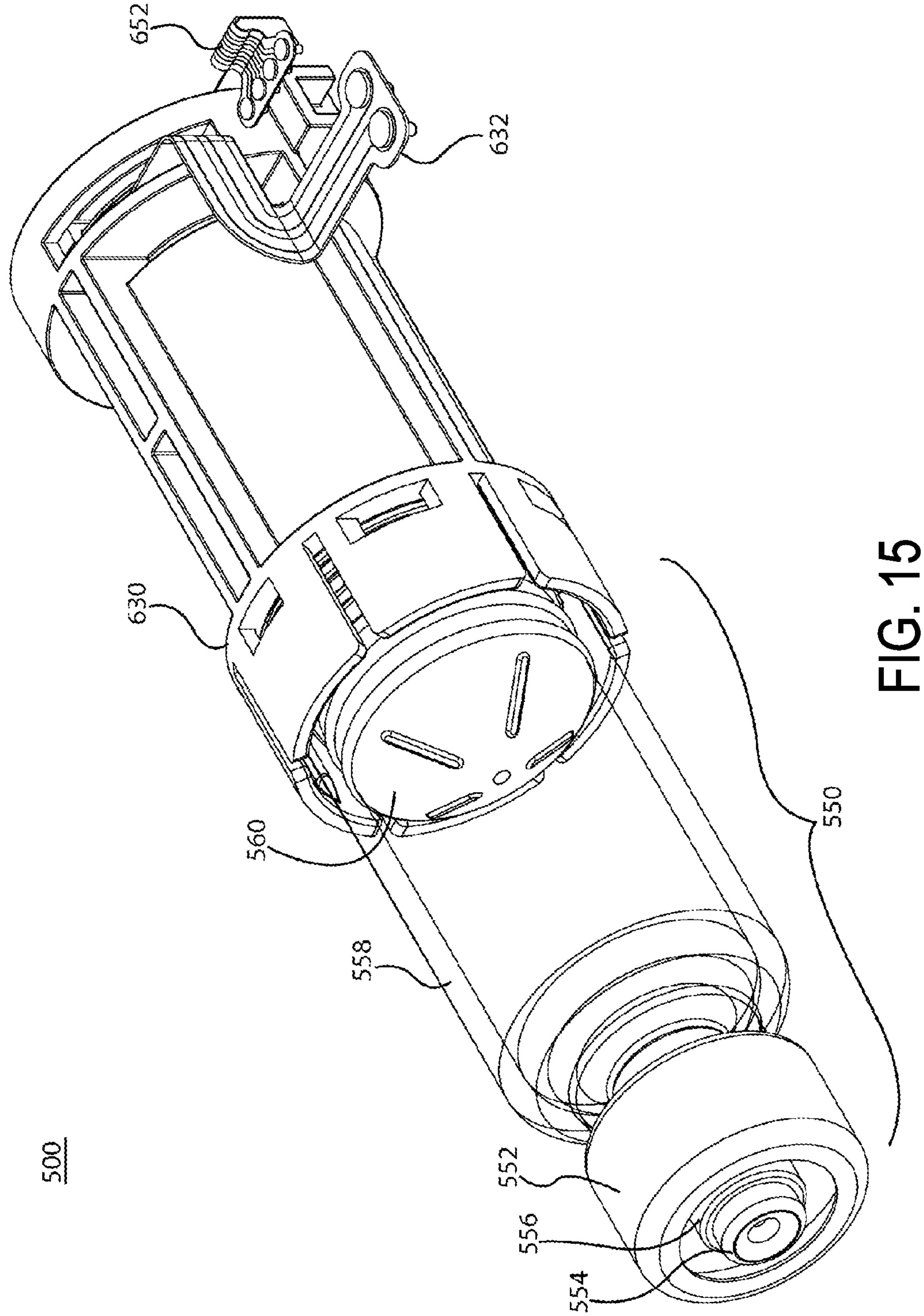
FIG. 15 shows an isometric view of a drive mechanism, according to a second embodiment of the present disclosure.
Figure 16:
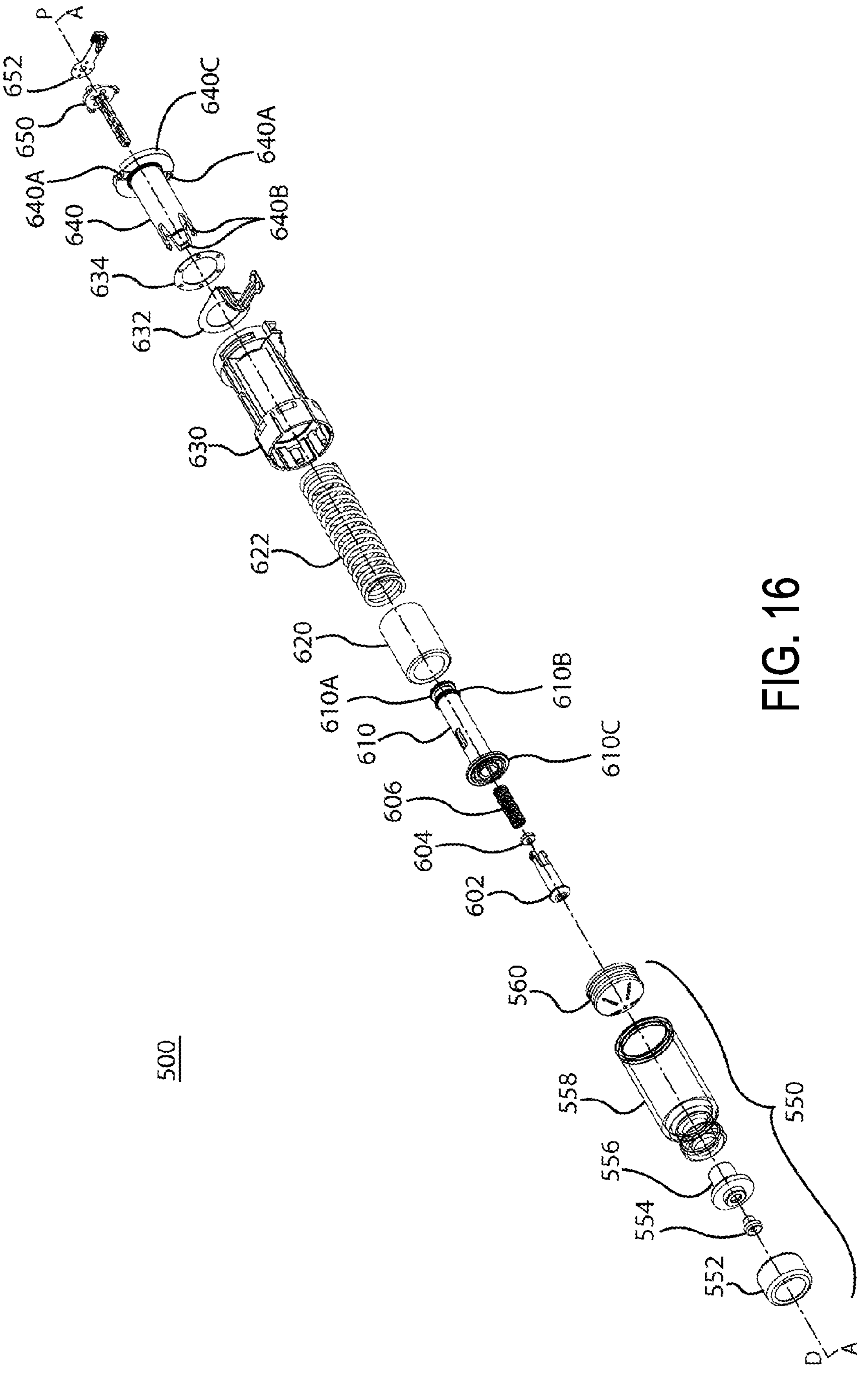
FIG. 16 shows an exploded view, along an axis “A,” of the drive mechanism shown in FIG. 15.

In another embodiment of the drive mechanism 500, shown in FIGS. 15 and 16, incremental status indication may be measured and relayed by a separate incremental status stem 650 and a corresponding stem interconnect 652. The stem interconnect 652 may be mounted, affixed, printed, or otherwise attached to incremental status stem 650. Incremental status stem 650 may be a static component, i.e., it does not move or translate, that is mounted to the distal end of contact sleeve 640 and/or the distal end of drive housing 630 such that the incremental status stem 650 resides within an axial pass-through of contact sleeve 640 and drive housing 630. The incremental status stem 650 further resides within an axial pass-through of piston 610. In such embodiments of the present disclosure, one or more contacts may be located on an inner surface of the piston 610 such that they sequentially interface with one or more corresponding interconnects on the incremental status stem 650. As piston 610 translates axially in the distal direction to push plunger seal 60 distally, thereby pushing fluid out of the drug container through the pierceable seal end, the electrical contacts of the piston 610 may sequentially contact the interconnect on the incremental status stem 650 to relay the incremental status of operation. Depending on the number of electrical contacts, the frequency of the incremental status indication may be varied as desired. The location of the contacts and interconnects may be interchanged or in a number of other configurations which permit completion of an electrical circuit or otherwise permit a transmission between the components.

Figure 17:
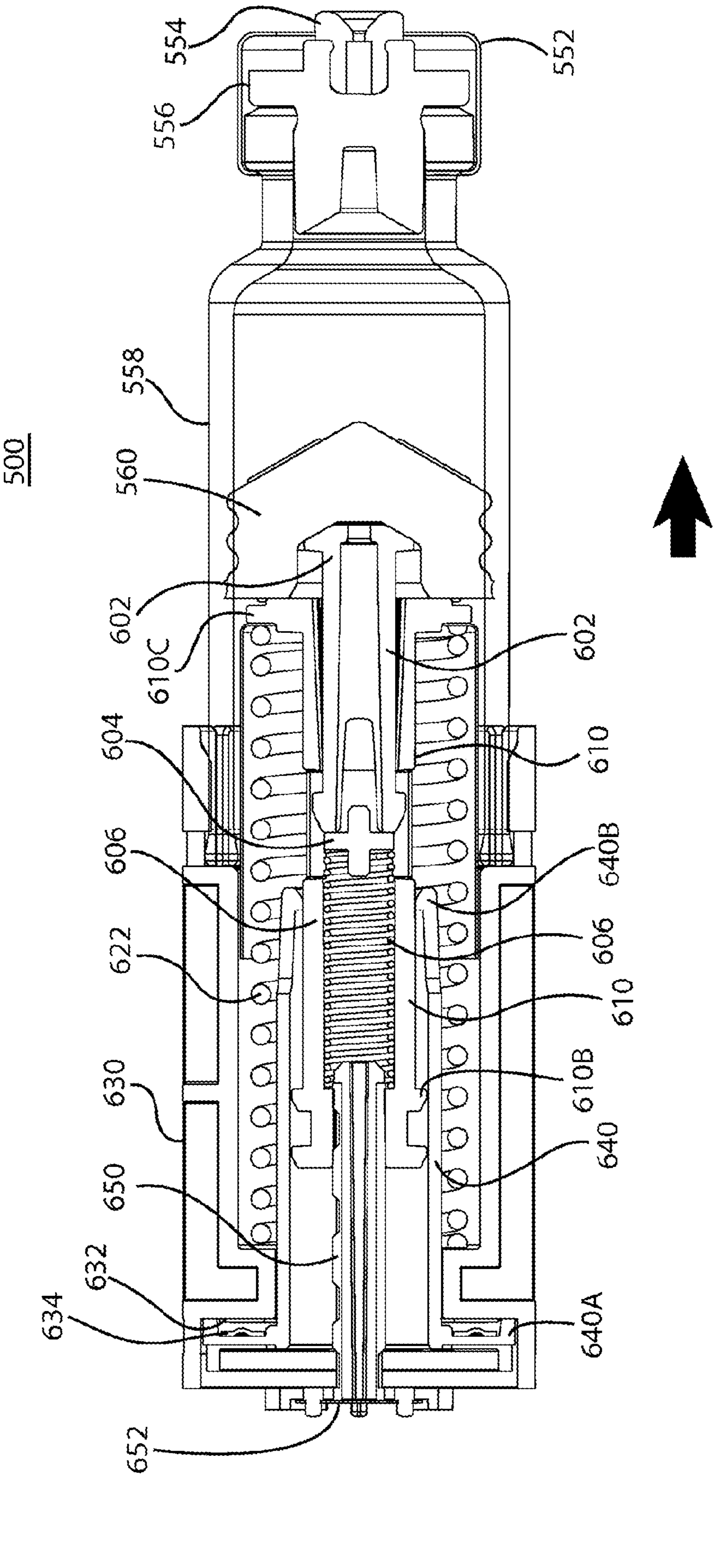
FIG. 17 shows a cross-sectional view of the drive mechanism shown in FIG. 15 in an actuated state.

FIG. 17 shows a cross-sectional view of the embodiment of the drive mechanism shown in FIG. 15 during operation of the drive mechanism. As shown, incremental status stem 650 may be a static component that is mounted to the distal end of contact sleeve 640 and/or the distal end of drive housing 630 such that the incremental status stem 650 resides within an axial pass-through of contact sleeve 640 and drive housing 630. As piston 610 translates axially in the distal direction (i.e., in the direction of the solid arrow) to push plunger seal 60 distally, the electrical contacts of the piston 610 may sequentially contact the interconnect on the incremental status stem 650 to relay the incremental status of operation through stem interconnect 652. Accordingly, incremental status of the drive mechanism, and therefore status of drug delivery, may be conveyed to the patient during use of the device.

Figure 14A:
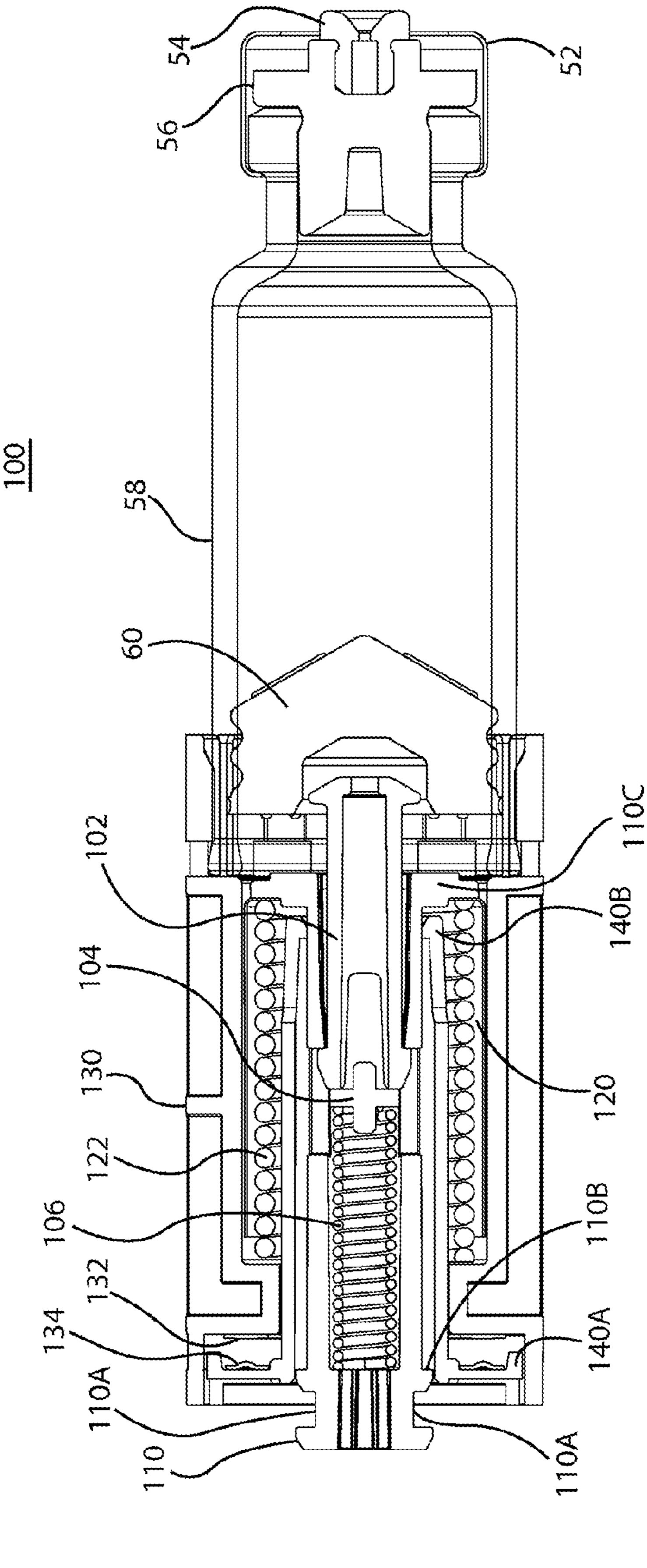
FIG. 14A shows a cross-sectional view of the drive mechanism shown in FIG. 12 in an initial inactive state.

Returning now to the embodiment shown in FIGS. 12 and 13, further aspects of the novel drive mechanism will be described with reference to FIGS. 14A-14E. One or more of these aspects may similarly be utilized in the embodiment shown in FIG. 15, or any other variation captured by the embodiments described herein. FIG. 14A shows a cross-sectional view of the drive mechanism, according to at least a first embodiment, during its initial locked stage. A fluid, such as a drug fluid, may be contained within barrel 58, between plunger seal 60 and pierceable seal 56, for delivery to a patient. Upon activation by the patient, a fluid pathway connector may be connected to the drug container through the pierceable seal 56. As described above, this fluid connection may be facilitated by a piercing member of the fluid pathway connector which pierces the pierceable seal and completes the fluid pathway from the drug container, through the fluid pathway connector, the fluid conduit, the insertion mechanism, and the cannula for delivery of the drug fluid to the body of the patient. Initially, one or more locking mechanisms (not shown) may reside within the locking grooves 110A of piston 110. Directly or indirectly upon activation of the device by the patient, the locking mechanism may be removed from the locking grooves 110A of piston 110, to permit operation of the drive mechanism. Such a locking mechanism may function as a first retainer having: a first retainer retaining position, where the first retainer retains the drive biasing member 122 in the energized state; and a first retainer releasing position, where the first retainer allows the drive biasing member 122 to de-energize. The first retainer may be structurally and functionally similar to the clip 2115 illustrated in FIGS. 22 and 23A and described in more detail below.

Figure 14B:
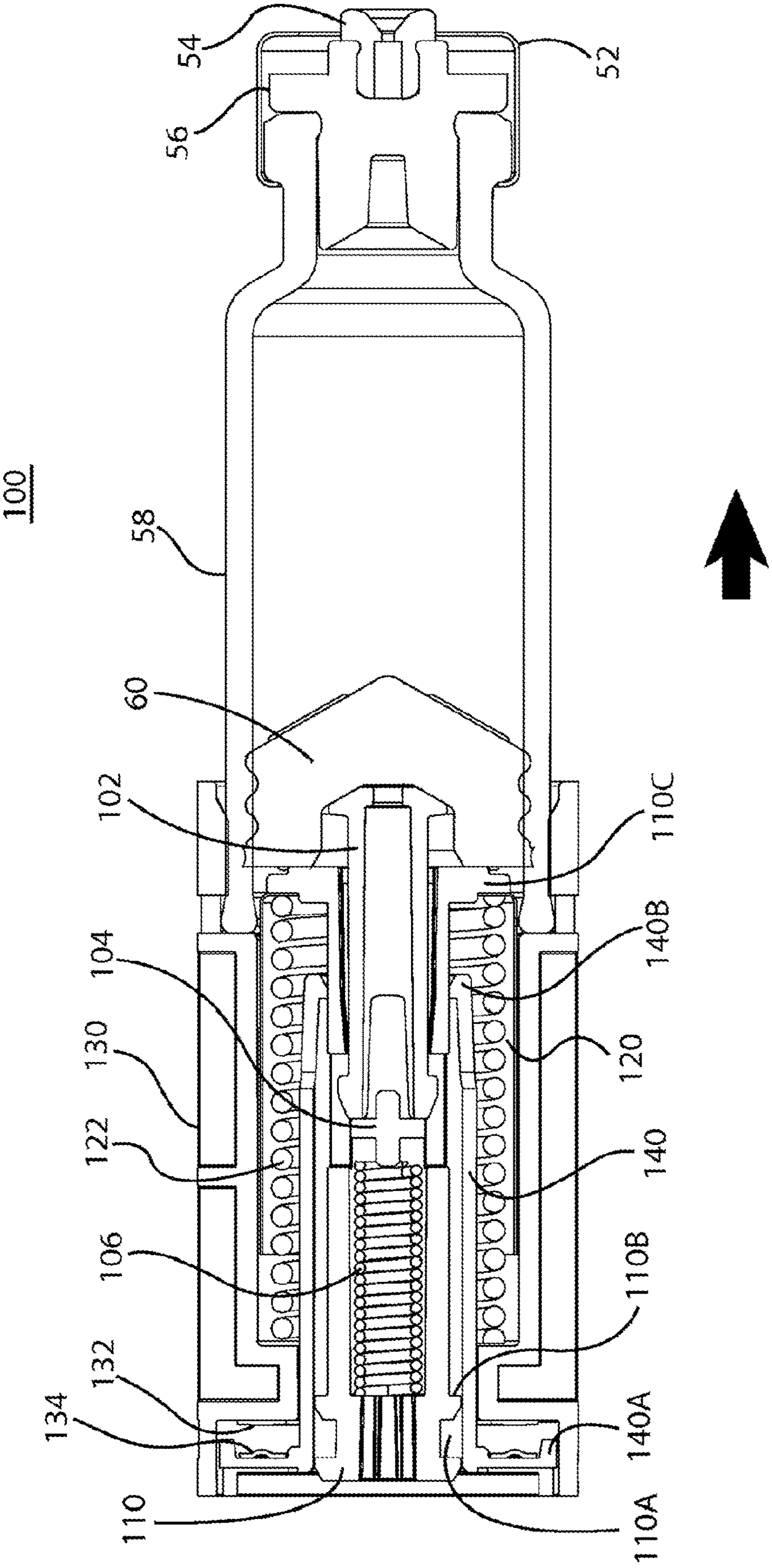
FIG. 14B shows a cross-sectional view of the drive mechanism shown in FIG. 12 in an actuated state.
Figure 14C:
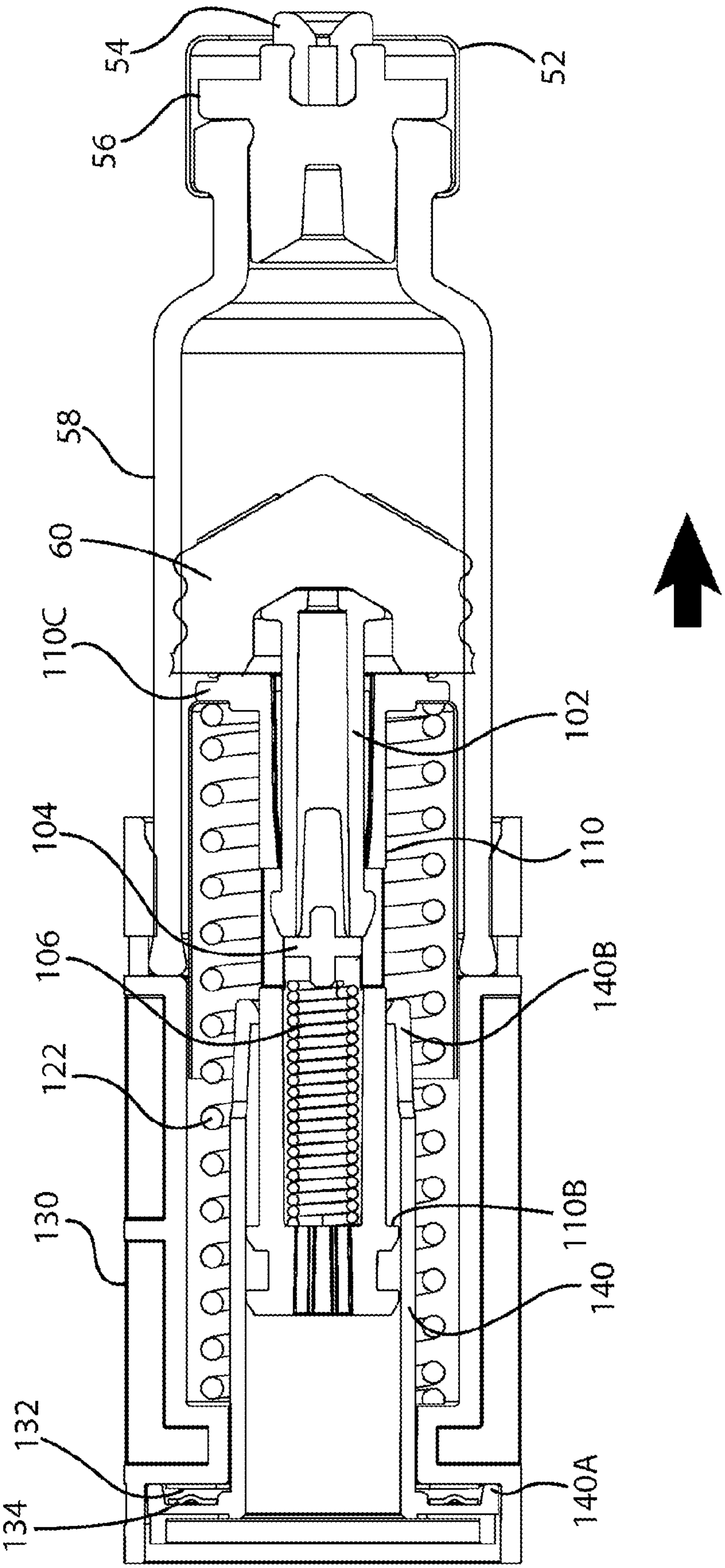
FIG. 14C shows a cross-sectional view of the drive mechanism shown in FIG. 12 in a further actuated state as drug delivery from the mechanism continues.

As shown in FIG. 14A, the piston extension biasing member 106 and drive biasing member 122 are both initially in a compressed, energized state. The drive biasing member 122 may be maintained in this state until activation of the device between internal features of drive housing 130 and interface surface 110C of piston 110. As the locking mechanism is removed from the locking groove 110A of piston 110, drive biasing member 122 is permitted to expand (i.e., decompress) axially in the distal direction (i.e., in the direction of the solid arrow). Such expansion causes the drive biasing member 122 to act upon and distally translate interface surface 110C and piston 110, thereby distally translating plunger 60 to push drug fluid out of the barrel 58. Distal translation of the piston 110 causes distal translation of the piston extension biasing member 106 and piston extension 102, when such optional features are incorporated into the device. As shown in FIG. 14B, such distal translation of the piston 110 and plunger seal 60 continues to force fluid flow out from barrel 58 through pierceable seal 56. Status switch interconnect 132 is prevented from prematurely contacting electrical contact 134 by one or more flex prongs 140A, as shown in FIG. 14C. Alternatively, low force springs or other resistance mechanisms may be utilized in addition to or alternatively from flex prongs 140A to achieve the same functions. During distal translation of the piston 110, sleeve hooks 140B may slidably contact the outer surface of piston 110. As described above, interconnects and electrical contacts may be located on these components to provide incremental status indication during operation of the drive mechanism.

As the drive mechanism 100 nears or reaches end-of-dose, flex prongs 140A may be caused to flex outwards (i.e., in the direction of the hollow arrows) by the decompression force of drive biasing member 122. Such flexion of the flex prongs 140A may permit status switch interconnect 132 to contact electrical contact 134, completing a circuit or otherwise permitting a transmission to the power and control system to provide feedback to the patient. At this stage, one or more delivery compliance mechanisms may be utilized to ensure that the status switch interconnect 132 has contacted electrical contact 134 and/or that substantially the entire drug dose has been delivered. For example, in one embodiment of the present disclosure, the sleeve hooks 140B are flex arms which may permit, upon sufficient application of force by the drive biasing member 122 on the piston 110, to allow interface surface 110C to translate axially beyond sleeve hooks 140B to drive further axial translation of the plunger seal 60 for a compliance push of drug fluid from the drug container. Additionally or alternatively, the plunger seal 60, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container.

Figure 14D:
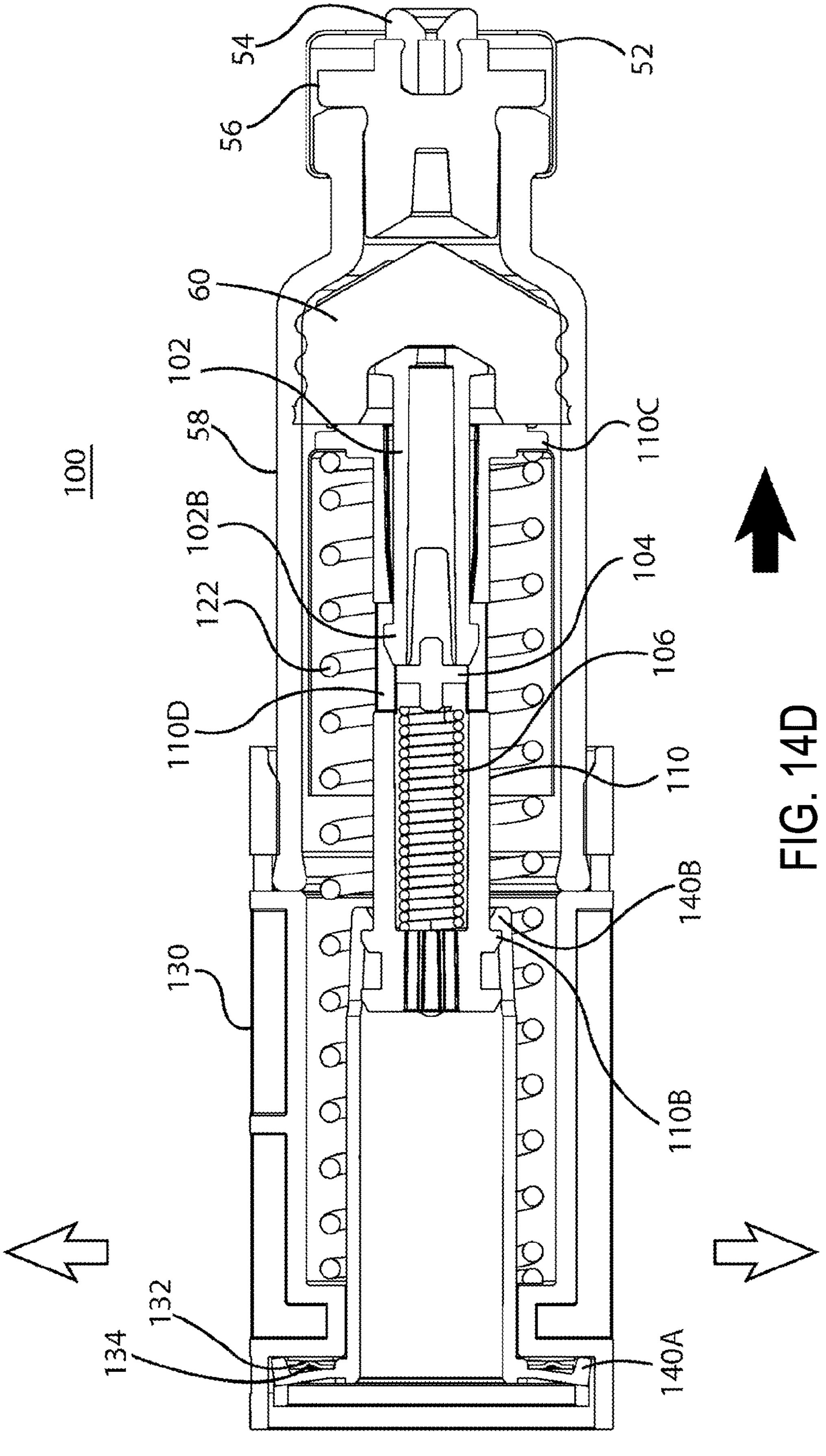
FIG. 14D shows a cross-sectional view of the drive mechanism shown in FIG. 12 as the mechanism nears completion of drug delivery.

In at least one embodiment of the present disclosure, a compliance push of drug fluid from the drug container is enabled by a piston extension 102. In such embodiments, the drive mechanism 100 further includes a piston extension 102 slidably mounted at a distal end and within an axial pass-through of piston 110. The piston extension 102 may be retained within piston 110 by interaction between extension arms 102B of the piston extension 102 and connection slots 110D of piston 110, as shown in FIG. 14D. Piston extension may be driven by a piston extension biasing member 106, which is mounted within the axial pass-through of piston 110 and initially compressed between piston extension 102 and piston 110. An optional piston biasing member support 104 may be utilized between piston extension biasing member 106 and piston extension 102 to, for example, promote more uniform distribution of force from piston extension biasing member 106 to piston extension 102.

Figure 14E:
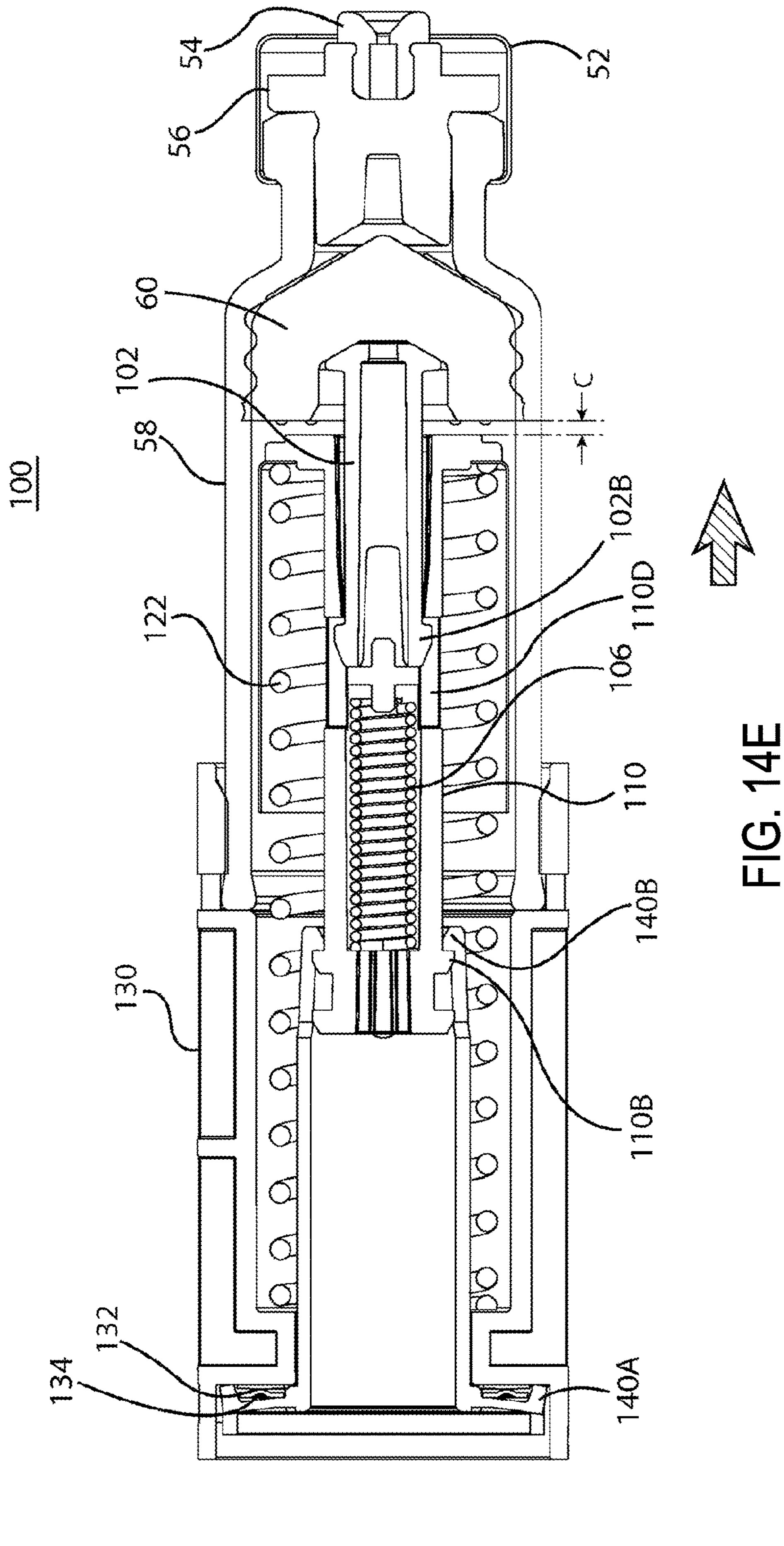
FIG. 14E shows a cross-sectional view of the drive mechanism shown in FIG. 12 as the mechanism performs a compliance push to ensure completion of drug delivery.

As the piston 110 reaches its end of travel within barrel 58, piston extension 102 may be permitted to axially travel in the distal direction by the force exerted by piston extension biasing member 106. At this stage, the piston extension biasing member 106 is permitted to expand (i.e., decompress) axially in the distal direction such that extension arms 102B of the piston extension 102 may translate distally (i.e., in the direction of the solid arrow) within connection slots 110D of piston 110, as shown in FIG. 14D. As shown in FIG. 14E, such distal translation (i.e., in the direction of the hatched arrow) of the piston extension 102 enables a compliance push (shown by dimension "C" in FIG. 14E) of drug fluid from the drug container. Piston extension 102 may be configured such that extension arms 102B may contact and apply force upon a distal end of connections slots 110D to distally translate piston 110 further (i.e., in the direction of the hatched arrow). This further distal translation of the piston 110 may be utilized to ensure that status switch interconnect 132 has engaged contact 134.

As described above, the novel drive mechanisms of the present disclosure integrate status indication into the drug dose delivery. Through integration of the end-of-dose status indication mechanisms to the axial translation of the piston, and thereby the plunger seal, true and accurate end-of-dose indication may be provided to the patient. By use of one or more contact surfaces on corresponding components, the status of the drive mechanism before, during, and after operation can be relayed to the power and control system to provide feedback to the patient. Such feedback may be tactile, visual, and/or auditory, as described above, and may be redundant such that more than one signals or types of feedback are provided to the patient during use of the device. FIGS. 14A-14E above show an arrangement which provide end-of-dose status indication to the patient once the status switch interconnect 132 is caused to contact electrical contact 134 at the end of axial travel of the piston 110 and plunger 60 within the barrel 58 of the drug container 50. As described above, the novel devices described herein may additionally provide incremental status indication to relay various stages of drug delivery to the patient during operation. In one such embodiment, sleeve hooks 140B of cover sleeve 120 may have one or more interconnects which come into contact with one or more electrical contacts on the outer surface of piston 110 during operation. A redundant end-of-dose indication may be utilized upon contact between sleeve hooks 140B of contact sleeve 140 and contact protrusion 110B of piston 110. Electrical contacts or interconnects along piston 110 may sequentially contact the corresponding interconnects or contacts on the sleeve hooks 140B to relay the incremental status of operation. Depending on the number of electrical contacts located on the outer surface of the piston 110, the frequency of the incremental status indication may be varied as desired. The location of the contacts and interconnects may be interchanged or in a number of other configurations which permit completion of an electrical circuit or otherwise permit a transmission between the components.

In another embodiment of the drive mechanism 500, shown in FIGS. 15-17, incremental status indication may be measured and relayed by a separate incremental status stem 650 and a corresponding stem interconnect 652. As shown in FIG. 17, incremental status stem 650 may be a static component that is mounted to the distal end of contact sleeve 640 and/or the distal end of drive housing 630 such that the incremental status stem 650 resides within an axial pass-through of contact sleeve 640 and drive housing 630. As piston 610 translates axially in the distal direction (i.e., in the direction of the solid arrow) to push plunger seal 60 distally, the electrical contacts of the piston 610 may sequentially contact the interconnect on the incremental status stem 650 to relay the incremental status of operation through stem interconnect 652. Depending on the number of electrical contacts, the frequency of the incremental status indication may be varied as desired. The location of the contacts and interconnects may be interchanged or in a number of other configurations which permit completion of an electrical circuit or otherwise permit a transmission between the components. Accordingly, incremental status of the drive mechanism, and therefore status of drug delivery, may be conveyed to the patient during use of the device.

Figure 18:
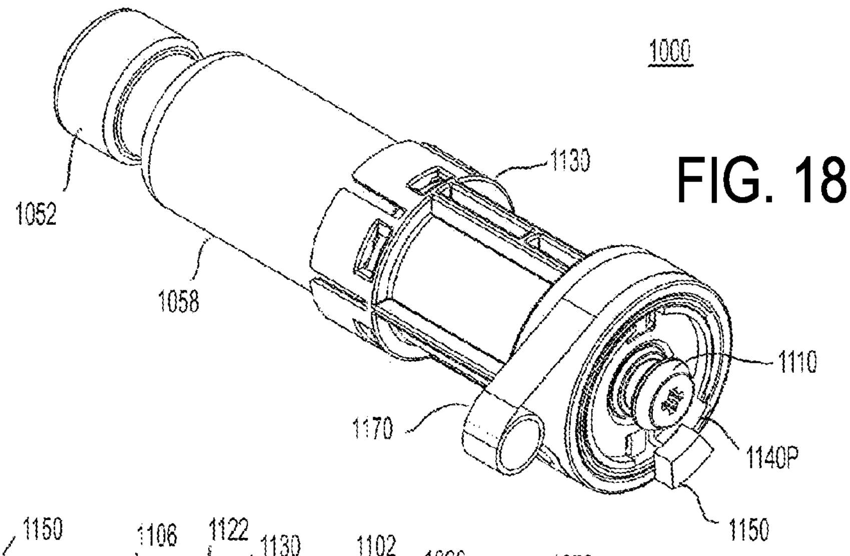
FIG. 18 shows an isometric view of the drive mechanism according to a further embodiment of the present disclosure.
Figure 19A:
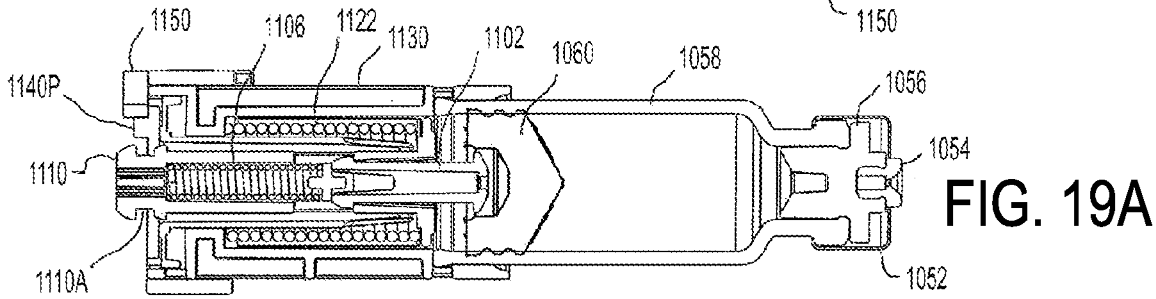
FIG. 19A shows a cross-sectional view of the drive mechanism shown in FIG. 18 in an initial inactive state.
Figure 19B:
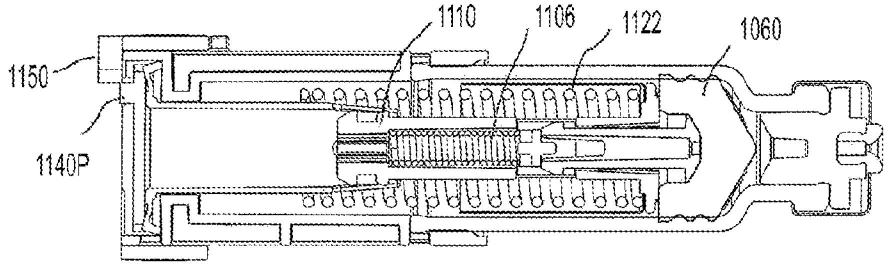
FIG. 19B shows a cross-sectional view of the drive mechanism shown in FIG. 18 in an actuated state and as the mechanism nears completion of drug delivery.
Figure 19C:
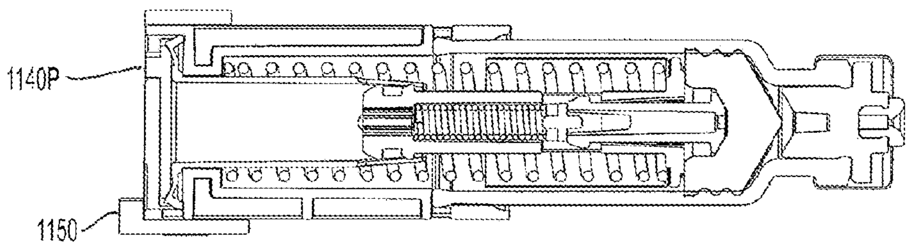
FIG. 19C shows a cross-sectional view of the drive mechanism shown in FIG. 18 as the mechanism completes drug delivery and triggers an end-of-dose signal.

In a further embodiment of the drive mechanism, shown in FIGS. 18 and 19A-19C, drive mechanism 1000 may be similar to mechanism 100 or mechanism 500, and incorporate the respective components and functions of such embodiments, but utilize mechanical contact surfaces instead of electrical contact surfaces, as described above. FIG. 18 shows an isometric view of the drive mechanism 1000 according to a further embodiment of the present disclosure. FIGS. 19A-19C show cross-sectional views of the drive mechanism shown in FIG. 18 in an initial inactive state, an actuated state and as the mechanism nears completion of drug delivery, and as the mechanism completes drug delivery and triggers an end-of-dose signal. In such embodiments, the status switch interconnect is a mechanical trigger 1150 and the contact surface is a pin 1140P. As shown in FIG. 19A, the optional piston extension biasing member 1106 and drive biasing member 1122 are both initially in a compressed, energized state. The drive biasing member 1122 may be maintained in this state until activation of the device between internal features of drive housing 1130 and interface surface 1110C of piston 1110. As the locking mechanism is removed from the locking groove 1110A of piston 1110, drive biasing member 1122 is permitted to expand (i.e., decompress) axially in the distal direction (i.e., in the direction of the solid arrow). Such expansion causes the drive biasing member 1122 to act upon and distally translate interface surface 1110C and piston 1110, thereby distally translating plunger 1060 to push drug fluid out of the barrel 1058. Distal translation of the piston 1110 causes distal translation of the piston extension biasing member 1106 and piston extension 1102, when such optional features are incorporated into the device.

As shown in FIG. 19B, such distal translation of the piston 1110 and plunger seal 1060 continues to force fluid flow out from barrel 1058 through pierceable seal 1056. As described above, interconnects and electrical contacts may be located on these components to provide incremental status indication during operation of the drive mechanism. As shown in FIG. 19C, as the drive mechanism 1000 reaches end-of-dose, pin 1140P disengages from mechanical trigger 1150 to permit a transmission to the power and control system 400 to provide feedback to the patient. In one such embodiment, disengagement of the pin 1140P from the mechanical trigger 1150 permits the trigger to rotate as it is biased by a biasing member, such as a constant-force spring 1170. Initially, the constant-force spring 1170 biases the mechanical trigger 1150 against the pin 1140P. Upon axial translation of the pin 1140P, as described above, pin 1140P disengages from mechanical trigger 1150 which then rotates or is otherwise displaced to permit transmission of feedback to the patient. At this stage, one or more delivery compliance mechanisms, as described above, may be utilized to ensure that the pin 1140P has disengaged mechanical trigger 1150 and/or that substantially the entire drug dose has been delivered.

Assembly and/or manufacturing of drive mechanism 100, drug delivery device 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 50 may first be assembled and filled with a fluid for delivery to the patient. The drug container 50 includes a cap 52, a pierceable seal 56, a barrel 58, and a plunger seal 60. The pierceable seal 56 may be fixedly engaged between the cap 52 and the barrel 58, at a distal end of the barrel 58. The barrel 58 may be filled with a drug fluid through the open proximal end prior to insertion of the plunger seal 60 from the proximal end of the barrel 58. An optional connection mount 54 may be mounted to a distal end of the pierceable seal 56. The connection mount 54 to guide the insertion of the piercing member of the fluid pathway connector into the barrel 58 of the drug container 50. The drug container 50 may then be mounted to a distal end of drive housing 130.

One or more switch status interconnects 132 may be mounted to a proximal end of drive housing 130. A contact sleeve 140, having one or more sleeve hooks 140B at a distal end and a ring 140C at a proximal end having an electrical contact 134 thereon, may be mounted to the drive housing 130 through an axial pass-through from the proximal end of the drive housing 130. A drive biasing member 122 may be inserted into a distal end of the drive housing 130. Optionally, a cover sleeve 120 may be inserted into a distal end of the drive housing 130 to substantially cover biasing member 122. A piston may be inserted into the distal end of the drive housing 130 and through an axial pass-through of contact sleeve 140, such that a contact protrusion 110B of piston 110 is proximal to the sleeve hooks 140B of contact sleeve 140. The piston 110 and drive biasing member 122, and optional cover sleeve 120, may be compressed into drive housing 130. Such assembly positions the drive biasing member 122 in an initial compressed, energized state and preferably places a piston interface surface 110C in contact with the proximal surface of the plunger seal 60 within the proximal end of barrel 58. When a piston extension 102 is employed, the piston extension 102 and piston extension biasing member 106, and optional piston biasing member support, may be compressed into an axial pass-through of piston 110. The piston, piston biasing member, contact sleeve, and optional components, may be compressed and locked into the ready-to-actuate state within the drive housing 130 prior to attachment or mounting of the drug container 50.

When one or more interconnects or contacts are utilized for status indication, such components may be mounted, connected, printed, or otherwise attached to their corresponding components prior to assembly of such components into the drive mechanism 100. When a separate incremental status stem 650 and a corresponding stem interconnect 652 are utilized for such incremental status indication, the stem interconnect 652 may be mounted, affixed, printed, or otherwise attached to incremental status stem 650. The incremental status stem 650 and stem interconnect 652 to the proximal end of the contact sleeve 640 and/or the proximal end of the drive housing 630 in a manner such that the incremental status stem 650 resides within an axial pass-through of contact sleeve 640 and drive housing 630. The incremental status stem 650 is further mounted to reside within an axial pass-through of piston 610.

It will be appreciated that the end-of-dose indicator or interconnects/contact may include any appropriate arrangement, including, for example, mechanical, electrical, electromechanical, ultrasonic, capacitive or magnetic arrangements. Similarly, the drive mechanism may be of any appropriate design.

Alternate arrangements of both the drive mechanism and end-of-dose indicator or interconnects/contact are illustrated, for example, in FIGS. 20A-24B. For the sake of clarity, the reference numbers utilized in FIGS. 20A-24B are similar to those of the embodiment of FIGS. 1A-11C, only preceded by the number "2" or "20" as appropriate to provide a reference number having four digits, i.e., 2XXX. For example, the drug delivery device 10 and drive mechanism of FIGS. 20A-24B will be designated by the numbers 2010 and 2100, respectively, as opposed to the drug delivery device 10 and drive mechanism 100 of FIGS. 1A-11C. This correlation, however, should not be taken as an indication that the components of FIGS. 20A-24B with reference numbers similar to those of the embodiment of FIGS. 1A-11C are exactly the same as the respective components of FIGS. 1A-11C.

Figure 20A:
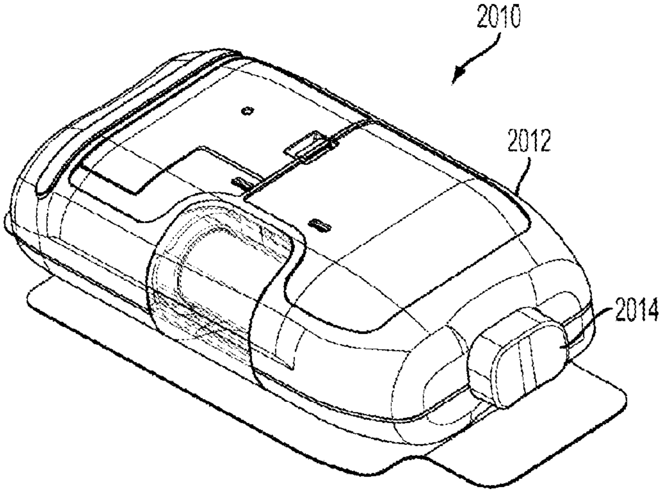
FIG. 20A is an isometric view of yet another embodiment of a drug delivery device having safety integrated insertion mechanisms in accordance with teachings of the present disclosure.
Figure 20B:
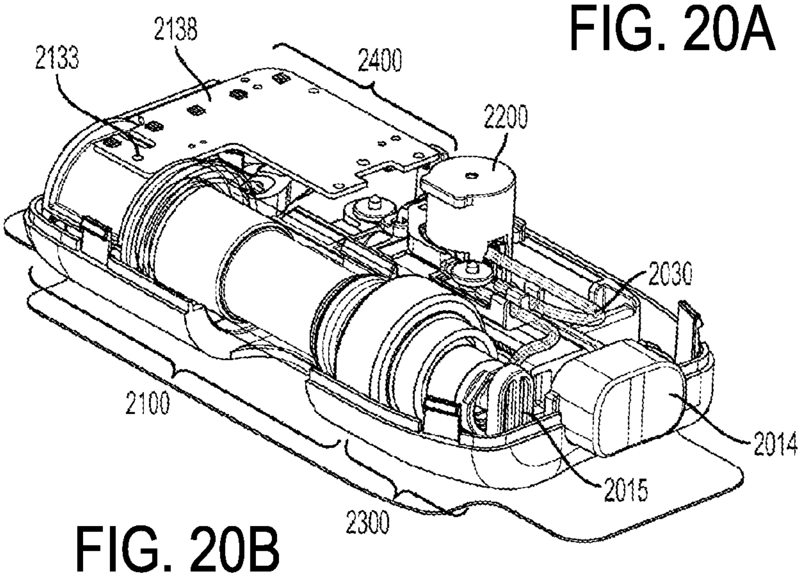
FIG. 20B is an isometric view of the interior components of the drug delivery device shown in FIG. 20A.
Figure 20C:
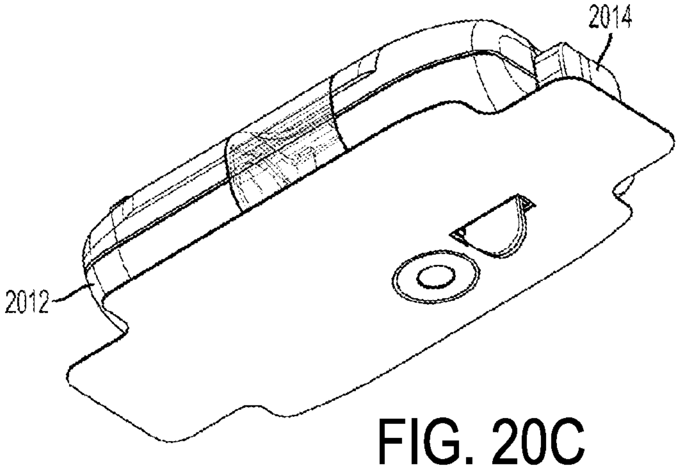
FIG. 20C is an isometric view of the bottom of the drug delivery device shown in FIG. 20A.

As shown in FIGS. 20A-20C, the drug delivery device 2010 includes a drive mechanism 2100 for receiving a drug container 2050, an insertion mechanism 2200, a fluid pathway connector 2300 including a fluid conduit 2030, and a power and control system 2400, all residing within a housing 2012, and an activation mechanism 2014 actuatable by a patient from the outside of the housing 2012. The housing 2012 may take any number of configurations and be facilitated by any number of components, such as a single-body or multi-component housing 2012. Certain other components, such as electronics for power and signaling, activation buttons, and safety sensors are also omitted for clarity, but are understood to be standard components within such drug delivery device 10 devices. While the housing 2012, insertion mechanism 2200, fluid pathway connector 2300, and power and control system 2500, as well as the activation mechanism 2014 are not discussed in detail, those of skill in the art will appreciate that they may be the same or similar to the components and systems discussed in detail with regard to the other embodiments disclosed herein.

Figure 21:
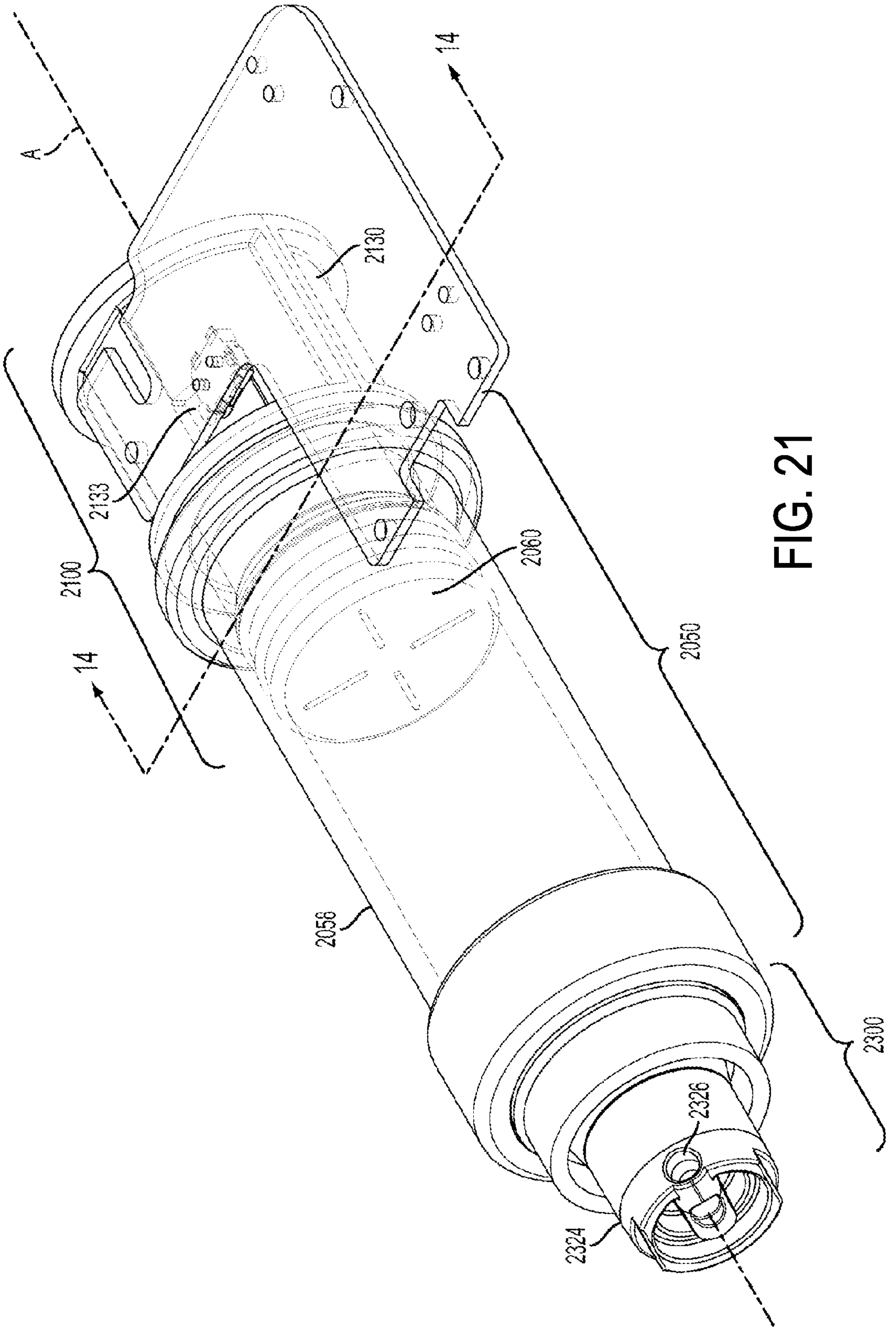
FIG. 21 is an isometric view of a drive mechanism, according to at the embodiment of FIGS. 20A-20C.
Figure 22:
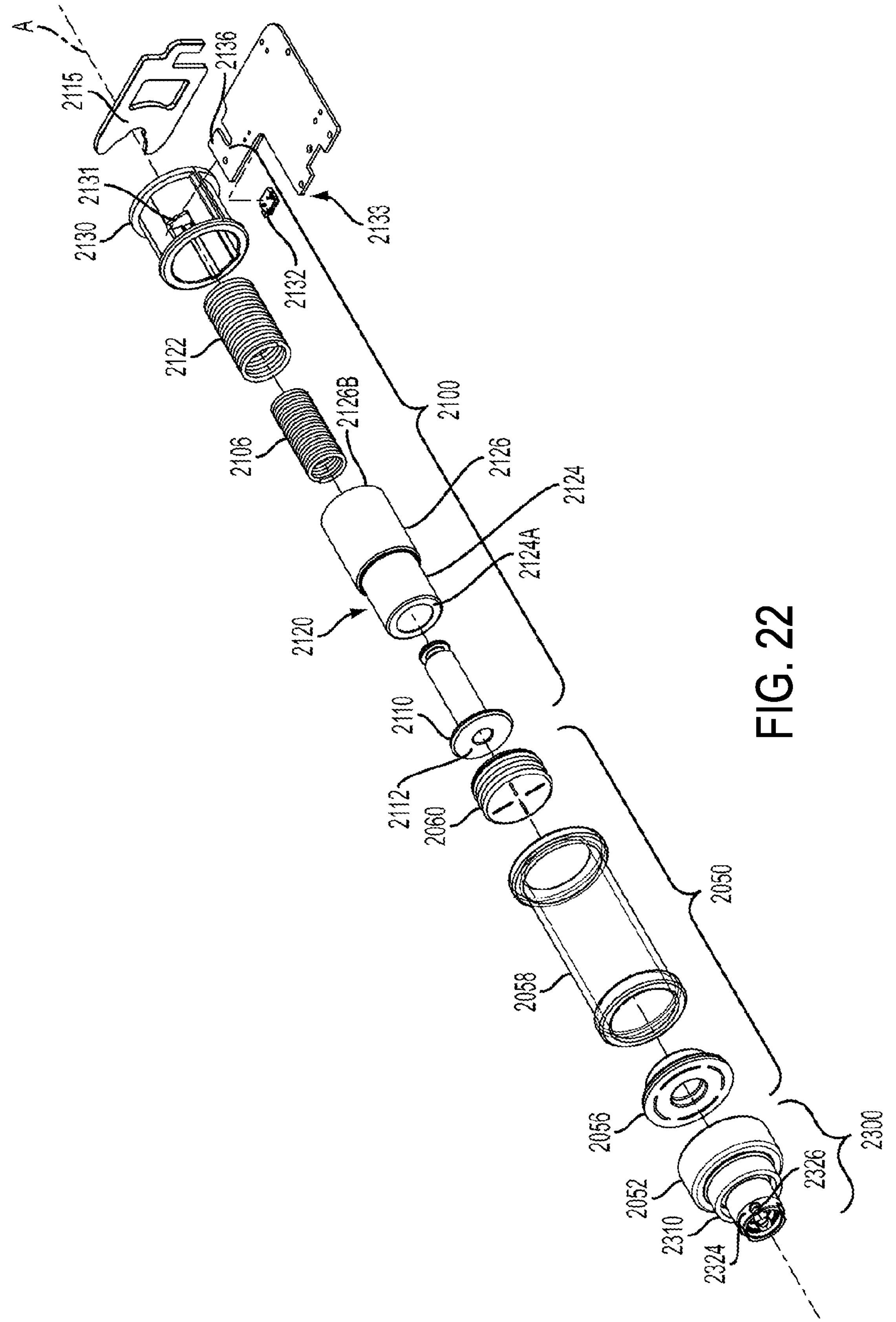
FIG. 22 is an exploded view, along an axis “A,” of the drive mechanism shown in FIG. 21.
Figure 23A:
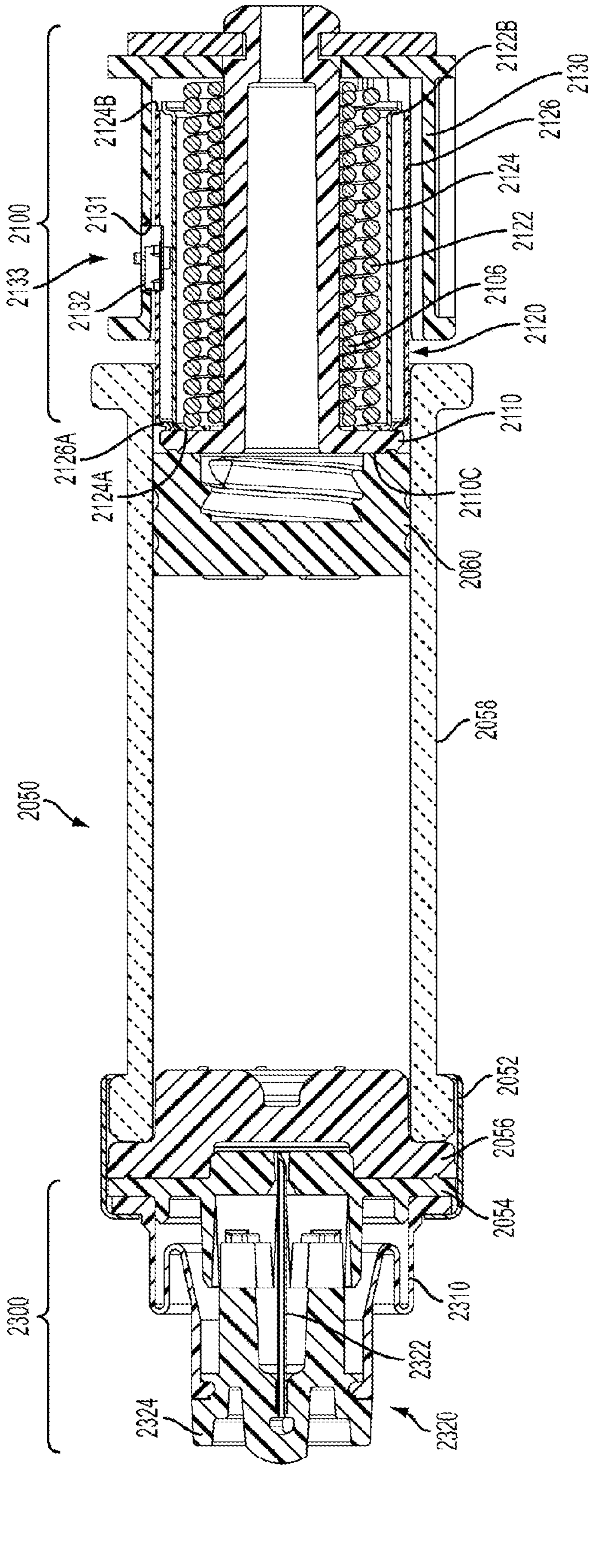
FIG. 23A is a cross-sectional view of the drive mechanism shown in FIG. 21 in an initial inactive state.
Figure 23B:
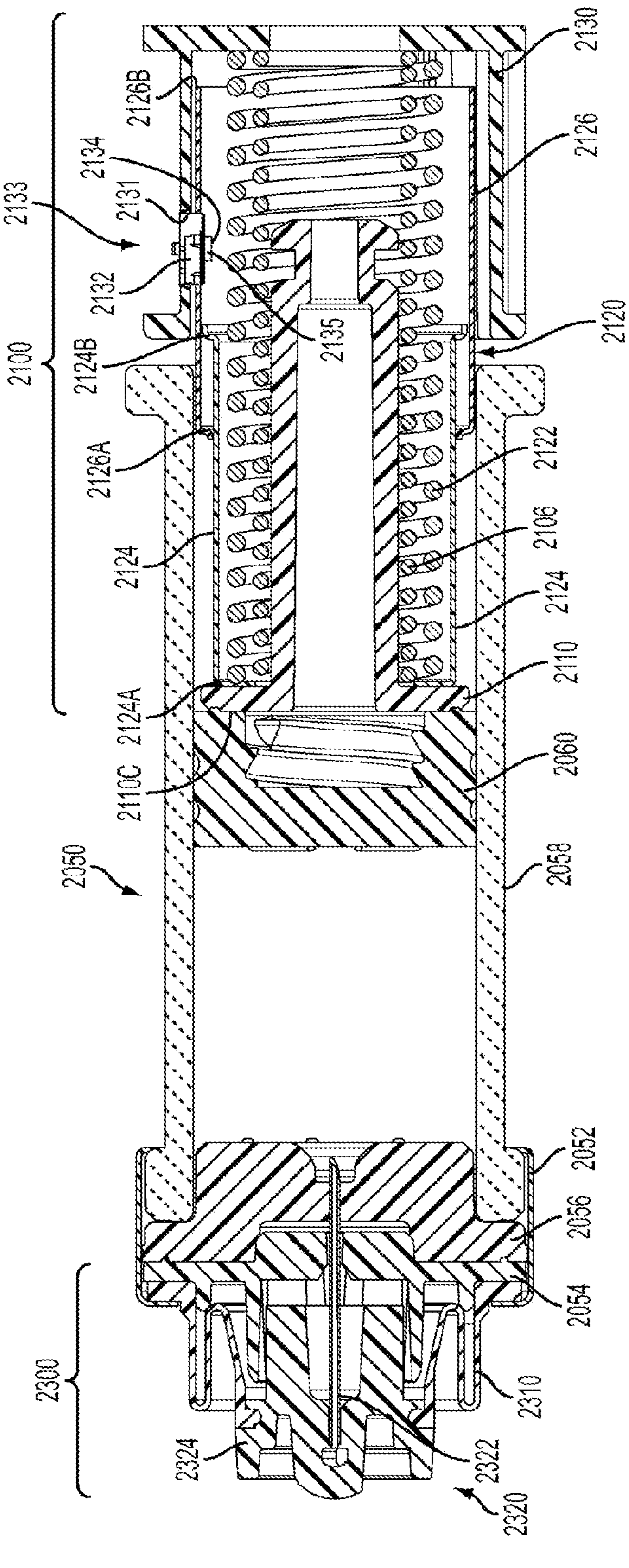
FIG. 23B is a cross-sectional view of the drive mechanism shown in FIG. 21 in an actuated state.
Figure 23C:
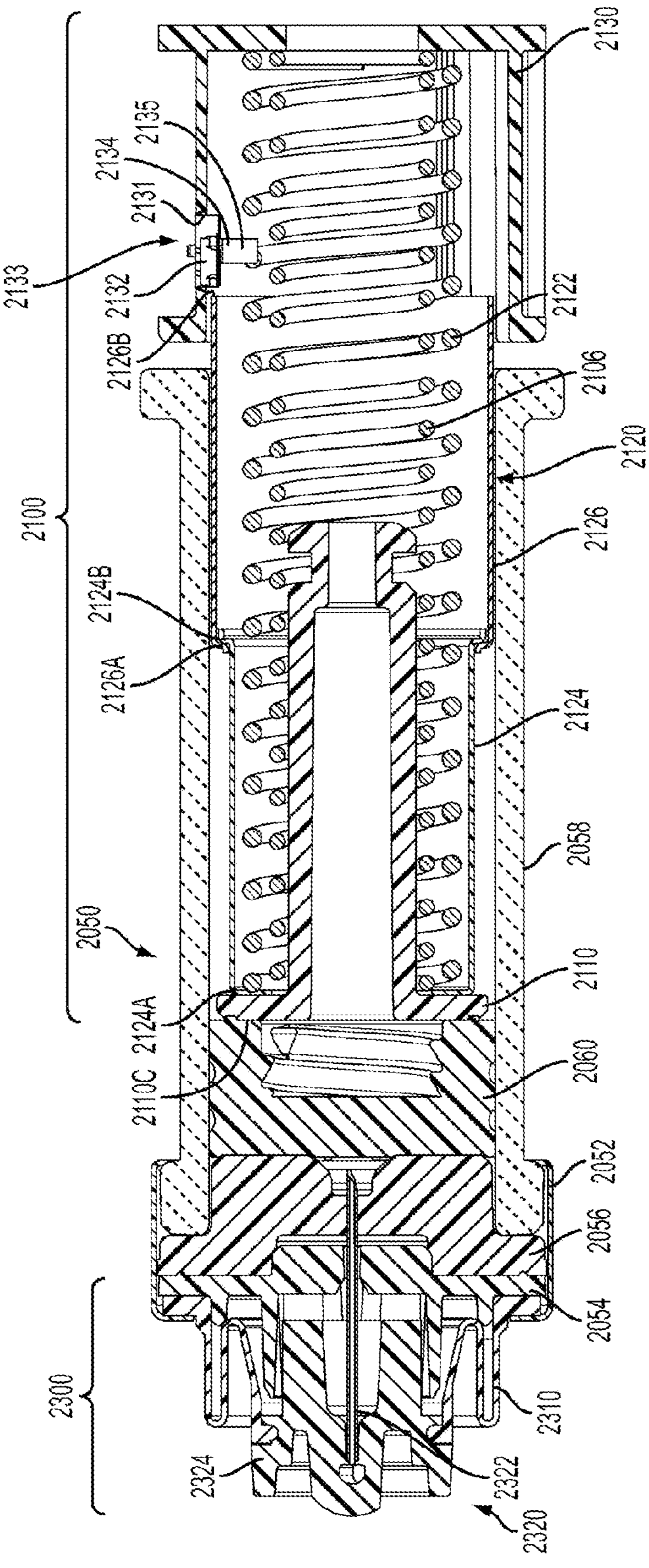
FIG. 23C is a cross-sectional view of the drive mechanism shown in FIG. 21 at the completion of drug delivery.
Figure 24A:
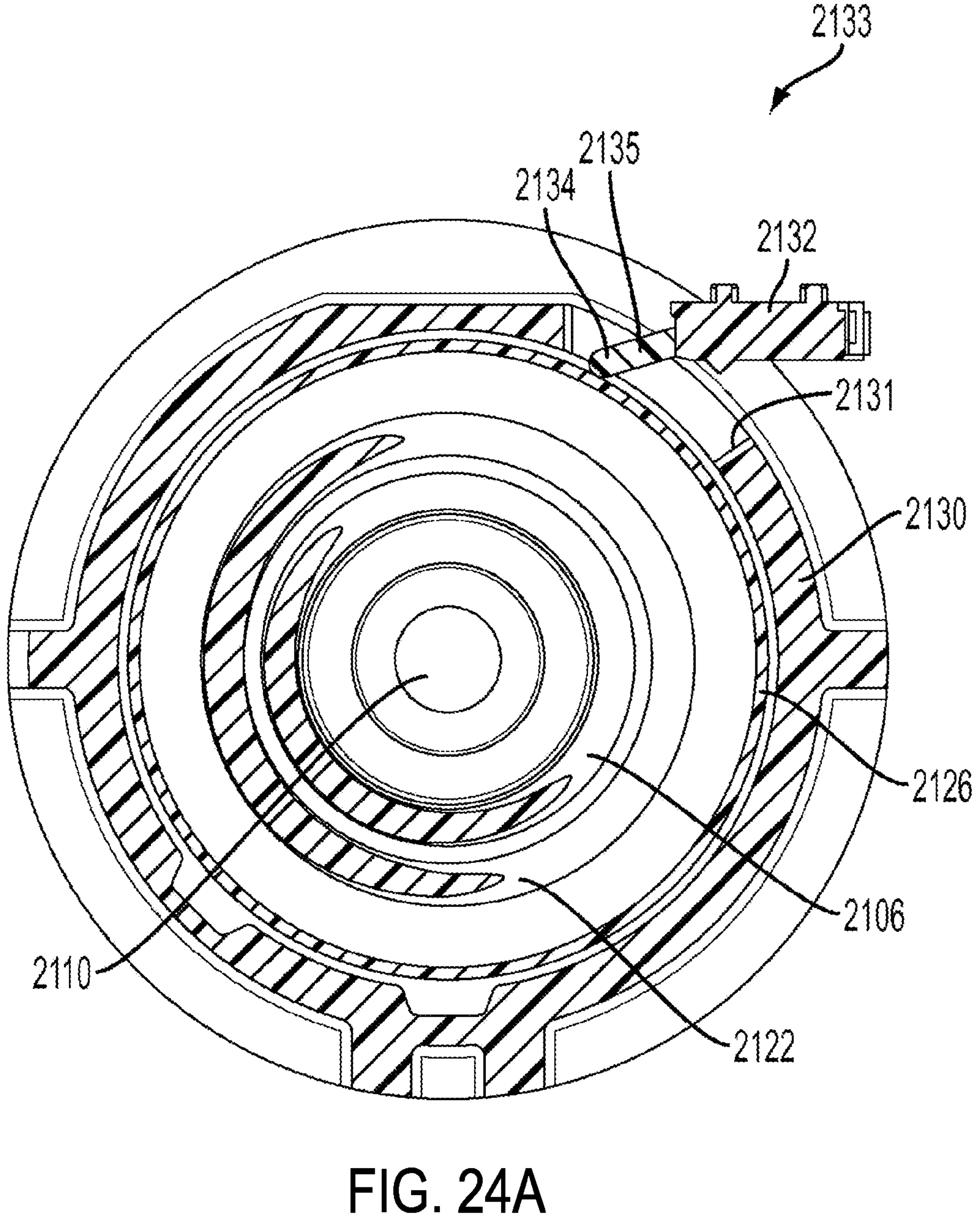
FIG. 24A is a cross-sectional view of the drive mechanism taken along line 14-14 in FIG. 21.
Figure 24B:
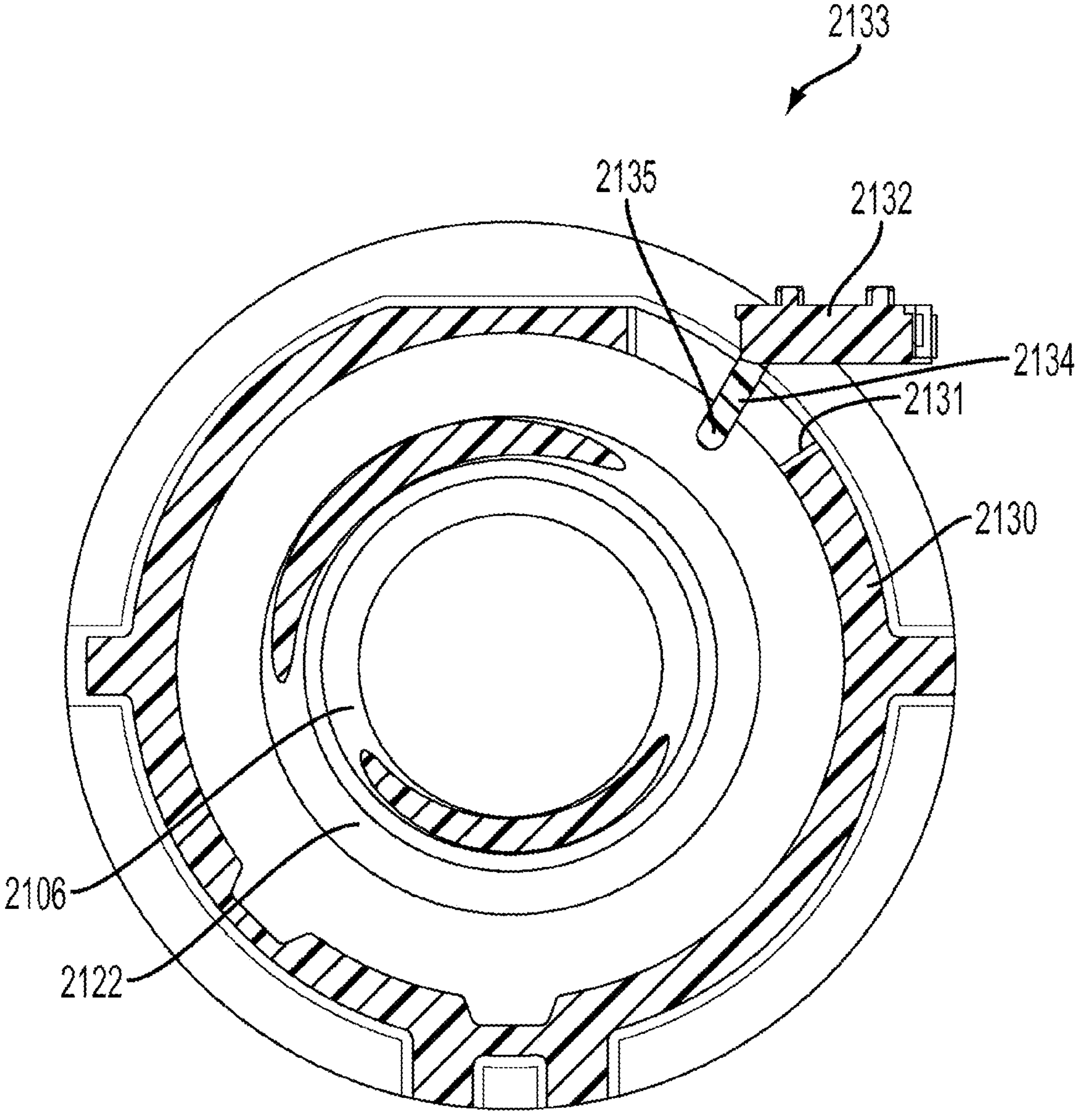
FIG. 24B is a cross-sectional view of the drive mechanism similar to FIG. 24A, but after the activation of the sensor.

The drive mechanism 2100, primary drug container 2050, and a portion of the fluid pathway connector 2300 are shown isometrically in FIG. 21 and exploded form in FIG. 22. FIGS. 23A-23C illustrate the drive mechanism 2100 in cross-section as it progresses through several stages of operation. FIGS. 24A-24B illustrate a lateral cross-section of the drive mechanism 2100 at several stages of operation.

The primary drug container 2050 retains the drug treatment that is to be injected or infused into the patient, and may be a vial or similar container from which a drug treatment can be dosed. To provide a sterile environment for the drug treatment, the drug container 2050 may include a cylindrical barrel 2058 with a pierceable seal 2056 disposed in a distal end and a plunger seal 2060 disposed within a proximal end. The pierceable seal 2056 and plunger seal 2060 may be formed of a number of materials, such as one or more elastomeric materials, and are sized and formulated to maintain a seal with the barrel 2058.

The portion of the fluid pathway connector 2300 illustrated in FIGS. 21-23C includes a connection mount 2054, a sterile boot 2310, and a piercing assembly 2320. The piercing assembly 2320 includes a piercing member 2322 extending from a hub 2324 which supports the piercing member 2322, and provides a fluid connection 2326 (see FIG. 21) to which the fluid conduit 2030 or other fluid connector may be fluidly coupled to fluidly couple the drug container 2050 to the insertion mechanism 2200. The connection mount 2054 is disposed adjacent the pierceable seal 2056 and includes an aperture adapted to guide the insertion of the piercing member 2322 of the fluid pathway connector into the pierceable seal 2056 of the drug container 2050. The sterile boot 2310 is disposed about the piercing assembly 2320 and provides a sterile environment for the completion of the fluid coupling of the fluid pathway connector 2300. A collar 2052 may be provided in order to secure a flange of the sterile boot 2310, the connection mount 2054, the pierceable seal, and the barrel 2058 in fixed relation to one another.

Referring to FIGS. 20A and 20B, in operation, when a patient activates the activation mechanism 2014, as by depressing the illustrated start button, an arm 2015 coupled to the activation mechanism 2014 exerts an axial force on the piercing assembly 2320 to move the piercing member 2322 axially to pierce the pierceable seal 2056. The drive mechanism 2100 is adapted for use in cooperation with the proximal end of the drug container 2050 to axially advance the plunger seal 2060 within the barrel 2058 to dispense the drug treatment through the fluid pathway connector 2300 once the pierceable seal 2056 has been pierced by the piercing member 2322.

The drive mechanism 2100 includes a drive housing 2130 having an axis that is coincident with the axis A of the drive mechanism 2100 (see FIG. 21). The axis A may be disposed in coincident with axes in the container 2050 and the plunger seal 2060. A piston 2110 is at least partially disposed within the drive housing 2130 for longitudinal movement along the axis of the drive mechanism 2100. It will be appreciated that the term "axis" when used in connection with the drive housing 2130 is not intended to require the axis to be in a central location of the drive housing 2130 or that the drive housing 2130 be round.

The piston 2110 is mounted to move between a retracted first position (illustrated in FIG. 23A), wherein the piston 2110 is at least partially disposed within the drive housing 2130, and an extended second position (illustrated in FIGS. 23B and 23C), wherein the piston 2110 extends axially outward from drive housing 2130. The piston 2110 includes an interface surface 2110C that is disposed to either directly confront the plunger seal 2060 when assembled with a drug container 2050, or to otherwise transmit an actuating force to the plunger seal 2060. In other words, the piston 2110 of the drive mechanism 2100 of FIGS. 20A-24B is adapted to exert a dispensing force on the plunger seal 2060 of the drug container 2050 and to translate outward from a distal end of a housing 2012 to advance the plunger seal 2060 within the drug container 2050 to dispense the drug. While the initial position shown in FIG. 23A illustrates the interface surface 2110C of the piston 2110 as disposed substantially adjacent the distal end of the housing 2012, it will be appreciated that, in alternate embodiments, the piston may be initially disposed in a position extending outside of the drive housing 2130. In such an arrangement, in initial assembly of the drive mechanism 2100 with a drug container 2050, the piston 2110 may be initially at least partially disposed within proximal end of the drug container 2050.

In order to impart axial movement to the piston 2010, the drive mechanism 2100 further includes a plurality of piston biasing members 2106, 2122 disposed to move from an energized first position when the piston 2110 is in the retracted first position to a de-energized second position when the piston 2110 is in an extended second position. It will be appreciated that, for the purposes of this disclosure and the accompanying claims, the term "de-energized second position" is a relative term. That is, the piston biasing members 2106, 2122 in the "de-energized second position" have less energy than the piston biasing members 2106, 2122 in the "energized first position." That is not to say, however, that the piston biasing members 2106, 2122 in the "de-energized second position" are necessarily completely de-energized or storing no energy.

So long as the piston 2110 is maintained in the retracted first position, biasing members 2106, 2122 are maintained in their energized first position (see FIG. 23A). The piston 2110 is maintained in the retracted first position by a retaining element or clip 2115. While any appropriate arrangement may be utilized to retain the piston 2110 in the retracted first position, the clip 2115 may bear against an outside surface of the drug delivery device 10 housing 2012 and be received in a locking groove 2110A of the piston 2110. FIG. 23A illustrates the clip 2115 disposed in such a retaining first position. It will thus be appreciated by those of skill in the art that the engagement of the retaining element or clip 2115 to maintain the piston 2110 in its retracted first position with the biasing members 2106, 2122 in their energized first position, allows the drive mechanism 2100 to be handled as a self-contained unit such that it may be assembled into the drug delivery device 2010 or in cooperation with a drug container 2050. In operation, however, once the clip 2115 is removed or moved to a releasing second position (see FIGS. 22B and 23C), the piston biasing members 2106, 2122 exert an axial dispensing force on the piston 2110 as they move to a de-energized second position and the piston moves to its extended second position. In at least one embodiment, clip 2115 may be removed through an action caused, directly or indirectly, by movement of the activation mechanism 2014. The action removing clip 2115 can be achieved in a number of ways. For example, with reference to FIG. 22, the action removing clip 2114 is a linear, perpendicular movement relative to the axis "A" of the drug container 2050.

In accordance with an aspect of the disclosure as illustrated in the embodiment of FIGS. 20A-24B, the drive mechanism 2100 is small in size and/or device footprint, yet capable of providing the dispensing force needed to push a drug fluid from a drug container 2050 through a fluid conduit 2030 for drug delivery via an insertion mechanism 2200. In this embodiment of the drive mechanism 2100, the piston biasing members 2106, 2122 are disposed in parallel, in contrast to the series disposal of the embodiments of FIGS. 1A-11C. It will thus be appreciated by those of skill in the art that the drive mechanism 2100 of FIGS. 20A-24B yields a significantly smaller footprint than prior art devices or even the drive mechanisms 100, 500, 1000 of the other embodiments herein.

For the purposes of this disclosure and its claims, when used in connection with biasing members, be it a specific embodiment of biasing members, such as springs, or the general use of the term "biasing members," the terms "parallel" are to be interpreted as they would by those of skill in the art. That is, the terms "series," "in series," or "disposed in series" is to be interpreted as springs disposed and operating as they would when connected end to end, and the terms "parallel," "in parallel," or "disposed in parallel" is to be interpreted as springs disposed and operating as they would in a side-by-side relationship.

Those of skill in the art will appreciate that for biasing members disposed in series, the inverse of equivalent spring constant will equal the sum of the respective inverses of the spring constants of the individual biasing members. In contrast, the equivalent spring constant of biasing members 2106, 2122 in a parallel relationship will be the sum of the spring constants of the individual biasing members. Similarly, the dispensing force exerted by the biasing members 2106, 2122 in a parallel relationship will be the sum of the forces exerted by the biasing members 2106, 2122 individually. As a result, the use of biasing members 2106, 2122 disposed in parallel provides the desired dispensing force in a substantially more compact package, allowing the drive mechanism 2100 to be more compact than the embodiments of FIGS. 1A-11C. By extension, the use of biasing members 2106, 2122 disposed in parallel may allow the entire drug delivery device 2010 to be substantially more compact than an arrangement wherein the biasing members are disposed in series.

In this embodiment, the biasing members 2106, 2122 are in the form of a pair of concentrically disposed compression springs. In some embodiments, the biasing members 2106, 2122 may be wound in opposite directions, thereby balancing any lateral forces created by the biasing members 2106, 2122. Alternate arrangements are also envisioned, however. For example, one or more of the biasing members could alternately, for example, be tension springs, depending upon the structure of the components of the drive mechanism. Moreover, in the illustrated drive mechanism 2100, the biasing members 2106, 2122 are disposed concentrically with respect to each other and the piston 2100. In an alternate embodiment, however, the biasing members may be alternately disposed, as, by way of example only, in a side by side arrangement, or on opposite sides of the piston. In still further embodiments, three or more biasing members could be provided and disposed in parallel in any appropriate configuration. It will further be appreciated, that an additional biasing member may be provided and disposed in series with one or more of the parallelly disposed biasing members. For example, in an embodiment where the piston includes an extension, similar to the piston extension 102 of the embodiment of FIGS. 1A-11C, for example, an additional biasing member may be provided to engage the piston extension.

Returning now to the embodiment of FIGS. 20A-24B, the drive mechanism 2100 includes an end-of-dose indicator 2133. The end-of-dose indicator 2133 includes a switch interconnect 2132 and a contact sleeve assembly 2120 adapted for movement with the piston 2110. Piston 2110 has an interface surface 2112 that is capable of contacting or otherwise bearing upon plunger seal 2060 to force drug fluid out of barrel 2058 through the fluid pathway connector 2300 for delivery to a patient. In order to provide access of the end-of-dose indicator 2133 to the interior of the drive housing 2130 includes an access window 2131, the significance of which will be described further below.

The contact sleeve assembly 2120 of the embodiment illustrated in FIGS. 21-23C includes a pair of telescoping sleeves 2124, 2126. The first sleeve 2124 is adapted for movement with the piston 2110 as the piston biasing members 2106, 2122 are de-energized. A distal, generally radially extending flange 2124A of the first sleeve 2124 is disposed subjacent the head 2111 of the piston 2110. In this way, one or both of the biasing members 2106, 2122 bear against the flange 2124A, which bears against the piston head 2111 to impart axial movement to the piston 2110. The second sleeve 2126 is slidably coupled to the first sleeve 2124, the first sleeve 2124 sliding distally outward from the second sleeve 2126. In order to permit the second sleeve 2126 to travel with the first sleeve 2124 when the first sleeve 2124 is fully extended from the second sleeve 2126, a coupling structure is provided. In the illustrated embodiment the sleeves 2124, 2126 include respective flanges 2124B, 2126A that engage as the proximal end of the first sleeve 2124 approaches the distal end of the second sleeve 2126 (see FIG. 23A) to cause the second sleeve 2126 to likewise move in an axial direction with the piston 2110 (see FIG. 23C).

It will be appreciated, however, that alternate arrangements are envisioned. By way of example only, the first sleeve 2124 could alternatively be integrally formed with the piston 2110. In this way, the first sleeve 2124 formed with the piston 2110 would telescope outward from a second sleeve 2126 in a manner similar to that described above. Moreover, while the sleeve assembly 2120 has been described as including a pair of telescoping sleeves, alternate numbers of sleeves may be used, such as three or more telescoping sleeves. The number of sleeves may be dependent upon the cooperative structures, however, such as the relative dimensions of the drive housing 2130, and the travel of the piston 2110. For example, in an embodiment utilizing a smaller drive housing, but having a similar piston travel, three or more telescoping sleeves may be desirable. In some embodiments where multiple sleeves are provided about the biasing members 2106, 2122, and the biasing members 2106, 2122 are in the form of compression springs, such as shown in the illustrated embodiment, the springs in a compressed, energized state may have a length equal to the untelescoped sleeves 2124, 2126, yet have an uncompressed, de-energized length that is equal to the length of the telescoped sleeves. Further, while the end-of-dose indicator 2133 is described in connection with a drive mechanism 2100 including a plurality of biasing members disposed in parallel, those of skill in the art will appreciate that the end-of-dose indicator 2133 could also be utilized in connection with a drive mechanism including a single biasing device or a plurality of biasing members disposed in series and/or parallel.

As the sleeve assembly 2120 moves axially outward, the proximal end 2126B of the sleeve assembly 2120 passes the window 2131 of the drive housing 2130. In the illustrated embodiment in particular, as the second sleeve 2126 moves axially outward, the proximal end 2126B of the second sleeve 2126 passes the window 2131 of the drive housing 2130.

The switch interconnect 2132 includes a sensor 2134 and an electronic coupling 2136 to the power and control system 2400. At least a portion of the sensor 2134 is disposed adjacent the window 2131, and is adapted to identify a change in the presence of the contact sleeve assembly 2120 proximal to the window 2131 within the drive housing 2130. For example, in the illustrated embodiment, the sensor 2134 may read that the sleeve assembly 2120 is no longer present proximal to the window 2131.

In order to better illustrate the relationship of the sensor 2134 and the sleeve assembly 2120 during movement of the sleeve assembly 2120, portions of the sleeve assembly 2120 are broken away in FIGS. 23A-23B; in FIGS. 24A-24B, the housing 2130, sleeve 2126, biasing members 2106, 2122, and end-of-dose indicator 2133 are shown in cross-section taken along line 14-14 in FIG. 11. In the illustrated embodiment, the sleeve assembly 1120 is disposed adjacent the window 2131 when the piston 2110 is in the retracted first position (see FIG. 23A), and as the sleeve assembly 1120 begins to telescope outward with the piston 2110 (see FIGS. 23B and 24A). Conversely, the sleeve assembly 1120 is not disposed adjacent the window 2131 when the piston 2110 is in a fully extended second position (see FIGS. 23C and 24B). As the proximal end 2126B of the second sleeve 2126 passes the window, the switch interconnect 2132 identifies that the sleeve assembly has passed the window 2131, and that the end of dose has occurred, and provides that information to the power and control system 2400. The electronic coupling 2136 may be of any appropriate design. In the illustrated embodiment, for example, the sensor 2134 connects directly to a PCB board 2138.

The switch interconnect 2132 illustrated includes a mechanical sensor 2134 in the form of a pivotably mounted trigger 2135, in essence, an on/off mechanical switch. The trigger 2135 is disposed in a first position in contact with the sleeve assembly 2120 when the piston 2110 is in a retracted first position. As the piston 2110 moves outward from the drive housing 2130, the trigger 2135 slides along the telescoping sleeve assembly 2120 until such time as the proximal end 2126B of the second sleeve 2126 passes the window 2131, that is, the trigger 2135. As the second sleeve 2126 passes the trigger 2135, the trigger 2135 moves to a second position. The movement of the trigger 2135 to the second position results in the electronic coupling 2135 providing a signal indicating the end of dose to the power and control system 2400.

The switch interconnect 2132 may be of any appropriate design, however. For example, the switch interconnect 2132 may include a sensor of an electromechanical nature, such as the one illustrated in FIGS. 20A-24B, or a sensor of an electrical nature, such as, for example, an optical reader or sensor. Additionally or alternatively, the switch interconnect 2132 may utilize an ultrasonic sensor, a capacitive sensor, a magnetic sensor, or a number of other types of sensors. Accordingly, the sensor may not require physical contact with the corresponding reference component. In an embodiment including an optical sensor, the sensor may read when the presence or absence of the sleeve assembly 2120, for example, reading the interior of the drive housing 2130 opposite the window 2131. The sensor may be configured to additionally or alternatively identify at least one of when the sleeve assembly is disposed subjacent the window and when the sleeve assembly is not disposed subjacent the window, the relative motion of the sleeve assembly with reference to the window or another reference component, the stoppage of such motion, and the rate or change of rate of motion.

Although illustrated as an electromechanical arrangement that reads the position of a telescoping sleeve, any appropriate arrangement may be provided to read the relative position of any appropriate component, the end-of-dose indicator providing a signal to the power and control system to indicate that all of the drug has been administered. Additionally, the switch interconnects and corresponding contacts and/or reference component may be utilized to provide incremental status indication in addition to an end-of-dose indication. For example, in the switch interconnect arrangement described above with reference to FIGS. 20A-23C, the switch interconnect 2132 may be an electromechanical sensor configured to recognize a number of bumps, ridges, or grooves, in the corresponding sleeve 2126 or any other reference component, the contact with which permits the switch interconnect to signal an incremental status indication (e.g., delivery initiation, amount of volumes delivered, duration of plunger travel, etc.) and a final end-of-dose indication. As described herein, similar incremental status indication may be provided in this configuration by utilizing a different type of sensor arrangement. For example, the switch interconnect 2132 may be an optical sensor configured to recognize a number of markings on the corresponding sleeve 2126 or any other reference component. As the optical sensor recognizes the number of markings, it permits the switch interconnect to signal an incremental status indication (e.g., delivery initiation, amount of volumes delivered, duration of plunger travel, etc.) and a final end-of-dose indication. Any appropriate arrangement may be provided to read the relative position of a number of markings, ridges, grooves, or respective indicators on any appropriate reference component, and recognition of such indicators by the switch interconnect permits it to provide a signal to the power and control system to indicate the incremental status of drug delivery, including the final status that all of the drug has been administered. As would be appreciated by an ordinarily skilled artisan in the relevant arts, the indicators may not necessarily be defined aspects on a reference component, and the switch interconnects may be configured to recognize the actual travel of the reference component itself. The switch interconnects may thus be configured to recognize the rate of change, the distance of travel, or other related measurements in the actual travel of the reference components and enable a signal to the power and control system to provide the patient with such information or feedback.

It will be appreciated by those of skill in the art that the embodiments of the present disclosure provide the necessary drive force to push a plunger seal and a drug fluid within a drug container, while reducing or minimizing the drive mechanism and overall device footprint. Accordingly, the present disclosure provides a drive mechanism which may be utilized within a more compact drug delivery device. The embodiments of the present disclosure may similarly be utilized to provide additional force, as may be needed for highly viscous drug fluids or for larger volume drug containers.

The embodiments shown and detailed herein disclose only a few possible variations of the present disclosure; other similar variations are contemplated and incorporated within the breadth of this disclosure.

The drive mechanism may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power control system 2400.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a patient. The components which constitute the pathway for fluid flow are now assembled. These components may be sterilized, by a number of known methods, and then mounted either fixedly or removably to an assembly platform or housing of the drug delivery device, as shown in FIG. 1B.

Certain optional standard components or variations of drive mechanism 100 or drug delivery device 10 are contemplated while remaining within the breadth and scope of the present disclosure. For example, upper or lower housings may optionally contain one or more transparent or translucent windows 18, as shown in FIG. 1A, to enable the patient to view the operation of the drug delivery device 10 or verify that drug dose has completed. Additionally, the drug delivery device 10 may contain an adhesive patch 26 and a patch liner 28 on the bottom surface of the housing 12. The adhesive patch 26 may be utilized to adhere the drug delivery device 10 to the body of the patient for delivery of the drug dose. As would be readily understood by one having ordinary skill in the art, the adhesive patch 26 may have an adhesive surface for adhesion of the drug delivery device 10 to the body of the patient. The adhesive surface of the adhesive patch 26 may initially be covered by a non-adhesive patch liner 28, which is removed from the adhesive patch 26 prior to placement of the drug delivery device 10 in contact with the body of the patient. Removal of the patch liner 28 may further remove the sealing membrane 254 of the insertion mechanism 200, opening the insertion mechanism to the body of the patient for drug delivery (as shown in FIG. 1C). In some embodiments, removal of the patch liner 28 may also wake up onboard electronics (e.g., the power and control system 400) by supplying them with electricity from an onboard battery.

Similarly, one or more of the components of drive mechanism 100 and drug delivery device 10 may be modified while remaining functionally within the breadth and scope of the present disclosure. For example, as described above, while the housing of drug delivery device 10 is shown as two separate components upper housing 12A and lower housing 12B, these components may be a single unified component. Similarly, while electrical contact 134 is shown as a separate component from contact sleeve 140, it may be a unified component printed onto the ring surface of the contact sleeve 140. As discussed above, a glue, adhesive, or other known materials or methods may be utilized to affix one or more components of the drive mechanism and/or drug delivery device 10 to each other. Alternatively, one or more components of the drive mechanism and/or drug delivery device 10 may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the drive mechanisms and drug delivery devices disclosed herein provide an efficient and easily-operated system for automated drug delivery from a drug container. The novel embodiments described herein provide integrated status indication to provide feedback to the patient. The novel drive mechanisms of the present disclosure may be directly or indirectly activated by the patient. For example, in at least one embodiment the lockout pin(s) which maintain the drive mechanism in its locked, energized state are directly displaced from the corresponding lockout grooves of the piston 110 by patient depression of the activation mechanism. Furthermore, the novel configurations of the drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device 10 do not need to be sterilized. This greatly improves the manufacturability of the device and reduces associated assembly costs. Accordingly, the devices of the present disclosure do not require terminal sterilization upon completion of assembly. A further benefit of the present disclosure is that the components described herein are designed to be modular such that, for example, housing and other components of the drug delivery device may readily be configured to accept and operate drive mechanism 100, drive mechanism 500, or a number of other variations of the drive mechanism described herein.

Manufacturing of a drug delivery device 10 includes the step of attaching both the drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device 10 that contacts the patient during operation of the device.

VI. Fill Finish Cartridge

The sterile fluid pathway assemblies described above may be filled with pharmaceutical treatments, such as the drugs described below, using standard filling equipment and systems. This advantage is enabled by the fill-finish cartridges described below which function to maintain the sterility of the fluid pathway assemblies and allow them to nest, mount, or otherwise be removably inserted into trays for standard fill-finish processes, as discussed further below. The drive mechanisms, fluid pathway connectors, insertion mechanisms, and other components and sub-components of the drug delivery devices described below in connection with FIGS. 25-47 may be implemented in any of the drug delivery devices described above in connection with FIGS. 1A-24B. Furthermore, any of the methods of manufacture and methods of use described below may be applied to the drug delivery devices described above in connection with FIGS. 1A-24B.

Turning to FIG. 25, there is illustrated a schematic representation of an example of a drug delivery device 10 incorporating aspects of the disclosure. The device 10 includes a housing 612 having an activation mechanism 614. For ease of understanding, the housing 612 is shown schematically. In accordance with the disclosure, the device further includes a fill-finish cartridge 616. The fill-finish cartridge 616 includes a drug container 618, a fluid pathway assembly 620 including a fluid pathway connector 622 and a needle insertion mechanism 624. The fluid pathway assembly 620 may include further structure that facilitates disposition of various components, including, for example, a fluid conduit 26. The fluid pathway connector 622 is disposed substantially adjacent a distal end 628 of the drug container 618, and the needle insertion mechanism 624 is disposed substantially adjacent a distal end 630 of the fluid pathway connector 622. In the illustrated embodiment, the drug container 618 is generally horizontally positioned and perpendicular from a vertically positioned needle insertion mechanism 624. It will be appreciated, however, that the components may be positioned in any appropriate manner.

Administration of a drug contained in the drug container 618 may be initiated by the activation mechanism 614. The activation mechanism 614 may include, for example, activation mechanisms that are manually actuated by a patient, or that are automatically actuated by, for example, a power and control module 632 that may include, by way of further example, a microprocessor or other automatic administration arrangement with appropriate connections. In this embodiment, the activation mechanism 614 is a button 634 that may be disposed, for example, along an outer surface of the housing 612, and may be selectively depressed by the patient. It will be appreciated that the drug delivery device 10 as well as the activation mechanism 614 may be of any appropriate design.

The power and control module 632, if included, may include a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control module 632 controls several device interactions with the patient and may interface with one or more other components of the drug delivery device 10. In one embodiment, the power and control module 632 may identify when an on-body sensor and/or the activation mechanism 614 have been activated. The power and control module 632 may also interface with a status indicator, which may be a transparent or translucent material which permits light transfer, to provide visual feedback to the patient. The power and control module 632 may interface with a drive mechanism and/or the integrated sterile fluid pathway connector and drug container 618 through one or more interconnects to relay status indication, such as activation, drug delivery, and/or end-of-dose, to the patient. Such status indication may be presented to the patient via tactile feedback, such as vibration; auditory tones, such as through the audible alarms; and/or via visual indicators, such as through the LEDs. In a preferred embodiment, the control interfaces between the power and control system and the other components of the drug delivery device are not engaged or connected until activation by the patient. This is a desirable safety feature that prevents accidental operation of the drug delivery device and may also maintain the energy stored in the power source during storage, transport, and the like.

The power and control module 632 may be configured to provide a number of different status indicators to the patient. For example, the power and control module 632 may be configured such that after the on-body sensor and/or trigger mechanism have been pressed, the power and control module 632 provides a ready-to-start status signal via the status indicator if device start-up checks provide no errors. After providing the ready-to-start status signal and, in an embodiment with the optional on-body sensor, if the on-body sensor remains in contact with the body of the patient, the power and control module 632 will power the drive mechanism to begin delivery of the drug treatment through the integrated sterile fluid pathway connector 622 and sterile fluid conduit 26. In a preferred embodiment of the present disclosure, the insertion mechanism 624 and the drive mechanism may be caused to activate directly by patient operation of the activation mechanism 614. The integrated sterile fluid pathway connector is connected (i.e., the fluid pathway is opened) by the pneumatic force of the drug fluid within the drug container 618 created by activation of the drive mechanism, as is detailed further herein. During the drug delivery process, the power and control module 632 is configured to provide a dispensing status signal via the status indicator. After the drug has been administered into the body of the patient and after the end of any additional dwell time, to ensure that substantially the entire dose has been delivered to the patient, the power and control module 632 may provide an okay-to-remove status signal via the status indicator. This may be independently verified by the patient by viewing the drive mechanism and delivery of the drug dose within the drug container through a window of the housing 612. Additionally, the power and control module 632 may be configured to provide one or more alert signals via the status indicator, such as for example alerts indicative of fault or operation failure situations.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the patient. Similarly, activation of the device may require a prolonged depression (i.e., pushing) of the activation mechanism 614 of the drug delivery device 10 prior to drug delivery device activation. Additionally, the system may include a feature which permits the patient to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

When included, the power and control module 632 may include a processor (not shown) and a memory component (not shown). The processor may be microprocessors or other processors as known in the art. In some embodiments the processor may be made up of multiple processors. The processor may execute instructions for generating administration signal and controlling administration of a drug contained in the drug container 618. Such instructions may be read into or incorporated into a computer readable medium, such as the memory component or provided external to processor. In alternative embodiments, hard-wired circuitry may be used in place of or in combination with software instructions to implement drug administration. Thus, embodiments are not limited to any specific combination of hardware circuitry and software.

The term "computer-readable medium" as used herein refers to any medium or combination of media that participates in providing instructions to processor for execution. Such a medium may take many forms. The memory component may include any form of computer-readable media as described above. The memory component may include multiple memory components.

The power and control module 632 may be enclosed in a single housing. In alternative embodiments, the power and control module 632 may include a plurality of components operably connected and enclosed in a plurality of housings.

The power and control module 632 may be configured to generate an administration signal as a function of patient actuation, preprogrammed actuation or remote actuation. The power and control module 632 may be communicatively coupled to fill-finish cartridge 616, and/or the drug container 618, the fluid pathway connector 622, and/or the needle insertion mechanism 624 individually.

In accordance with an aspect of embodiments of the disclosure, in the illustrated embodiment, actuation of the activation mechanism 614, here, depression of the button 634, results in engagement of the fluid pathway connector 622, as will be discussed in greater detail below. This same action by the patient may trigger the needle insertion mechanism 624 to inject a needle or cannula into the patient, as will likewise be explained in greater detail below. Thus, actuation of activation mechanism 614 results in the completion of a drug pathway from the drug container 618 through the fluid pathway connector 622, the fluid conduit 26, and the needle insertion mechanism 624 to the patient (not shown). Actuation of the activation mechanism 614 may also result in a drive mechanism acting upon structure associated with the drug container 618 to force fluid through the sterile pathway. In an embodiment of the present disclosure, the needle insertion mechanism 624 may be triggered to retract the needle from the patient, giving a clear end of dose delivery indication upon completion of drug delivery. The housing 612 may additionally include, for example, a window through which the drug container 618 may be viewed to confirm drug delivery.

According to an aspect of embodiments of the disclosure, the fill-finish cartridge 616 is constructed and filled prior to assembly into the housing 612 of the drug delivery device 10. In this regard, the fill-finish cartridge 616 is sufficiently robust to withstand procedures for sterilizing the fill-finish cartridge 616, in some embodiments prior to fill, and in some embodiments after fill. After the sterile construction and filling of the fill-finish cartridges 616, the device may be positioned as needed within a drug delivery device 10. In any event, the sterility of the fluid pathway assembly 620 and the drug container 618 are maintained through aspects of the assembly, filling, and manufacturing processes. Final assembly of the drug delivery device 10 can thus be performed outside of a sterile environment. Because only the components of the sterile fluid pathway assembly 620 need to be, and have been, sterilized, the remainder of the drug delivery device 10 does not need sterilization (i.e., terminal sterilization). This provides a number of advantages. Novel embodiments of the present disclosure may also alleviate the need to fill the drug delivery device at time-of-use, although some embodiments of the present disclosure may be utilized in devices configured for time-of-use filling as well.

Figure 26A:
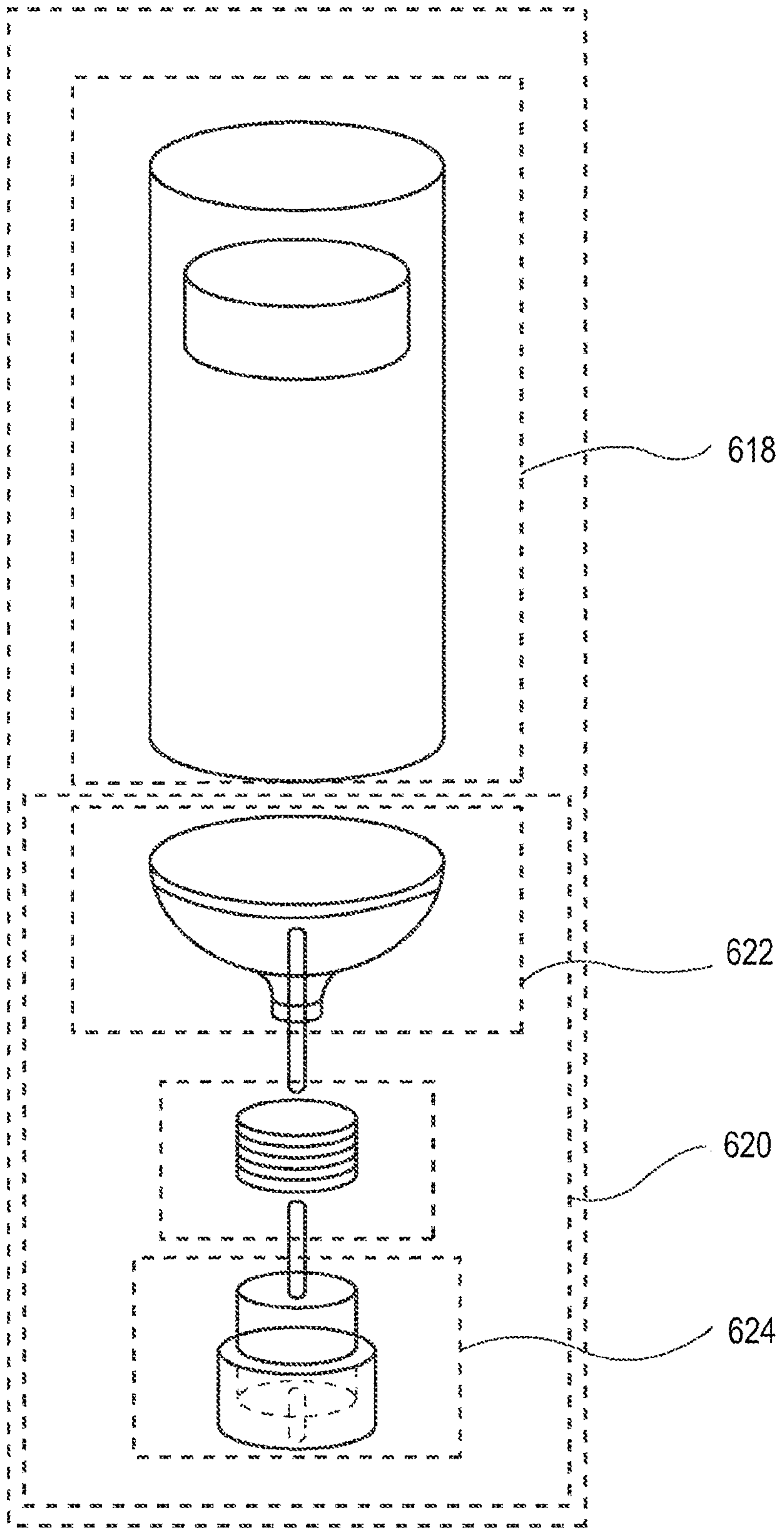
FIG. 26A is a schematic representation of an exemplary fill-finish cartridge of the present disclosure.

According to another aspect of embodiments of the disclosure, various embodiments of individual components of the fill-finish cartridge 616 may be assembled in various configurations to provide various embodiments of the fill-finish cartridge 616. The following disclosures disclose exemplary structures of individual elements that may be incorporated into the fill-finish cartridge 616, and are incorporated herein by reference for everything disclosed therein: U.S. application Ser. No. 13/600,114 filed Aug. 30, 2012; U.S. application Ser. No. 13/599,727 filed Aug. 30, 2012; U.S. application Ser. No. 13/612,203 filed Sep. 12, 2012; and Ser. No. 13/796,156 filed Mar. 12, 2013. FIG. 26B is a chart of examples of variables for possible structures of connections between individual components that may yield various configurations of embodiments of fill-finish cartridges 616, while FIG. 26A shows an example of a fill-finish cartridge 616 identifying aspects referenced in FIG. 26A. For ease of understanding, the same reference numbers are utilized as in FIG. 25. The individual components, as well as the interactions and connections between the individual components may have various designs. For example, the needle insertion mechanism 624 may be of any suitable design. Similarly, the container 618 and the fluid pathway connector 622 may each be of any appropriate design.

Likewise, the interactions between the components may be of any appropriate design. For example, the engagement of the fluid pathway connector 622 with the drug container 618 may include a threaded or snap connection, an interference fit, or an external support or other arrangement, so long as a tight seal is obtained. Similarly, the engagement of the fluid pathway connector 622 with the needle insertion mechanism 624 may include a threaded or snap connection, an interference fit, a tongue and groove arrangement, an external support, or some other arrangement including, but not limited to, utilizing a fluid conduit between the fluid pathway connector 622 and the needle insertion mechanism 624 for the connection. Moreover, in some embodiments, the engagement of the fluid pathway connector 622 with the needle insertion mechanism 624 may be disassembled following the fill-finish process in order to permit the needle insertion mechanism 624 to be oriented other than axially with the remainder of the fill-finish cartridge 616, so long as the sterile fluid connection is maintained.

In various embodiments, the fill-finish cartridge 616 may be maintained with the components in axial alignment during the fill-finish process, as well as in use with a drug delivery device 10. That is, for example, the needle insertion mechanism 624 may be disposed axially with the remainder of the fill-finish cartridge 616 during both the fill-finish process, such as is shown in FIG. 26B, and in use in a drug delivery. In other embodiments, the fill-finish cartridge 616 may be maintained with the components in axial alignment during the fill-finish process, such as is illustrated in FIG. 26B, while the components may be maintained in other than axial alignment in use with a drug delivery device 10. For example, as illustrated in FIG. 25, the needle insertion mechanism 624 is disposed spaced from the fluid pathway connector 622 and the drug container 618, and at a 90.degree. orientation. In other embodiments, the fill-finish cartridge may be maintained with the components in other than axial alignment during the fill-finish process, yet be axially aligned in use with a drug delivery device 10. In other embodiments, the fill-finish cartridge 616 may be maintained with the components in other than axial alignment during both the fill-finish process and in use with a drug delivery device 10.

Further, while not included in all embodiments, in order to provide added structural integrity to the fill-finish cartridge 616, a carrier may be provided, as will be explained in more detail below. Such a carrier may be integrated with the structure of the fill-finish cartridge 616 such that it is maintained about or along at least a portion of the fill-finish cartridge 616 in the drug delivery device 10, or such a carrier may be fully or partially disposable. A carrier may perform a number of functions, such as, the maintenance of the relative positions of various of the fill-finish cartridge components during assembly, a fill-finish process, or other operations performed on the fill-finish cartridge or a drug delivery device incorporating the same; a carrier or a portion of a carrier may be utilized in the interaction of the fill-finish cartridge with a drug delivery device 10, such as, in attachment of the fill-finish cartridge 616 into a drug delivery device 10 or in connection with operation of a drug delivery device 10. More detailed explanations of various examples of such structures in varied configurations follow; it is not the intention to limit the structures to those particular configurations. Rather, the individual arrangements explained are provided as examples of various possible configurations and structures within the purview of this disclosure.

Figure 27:
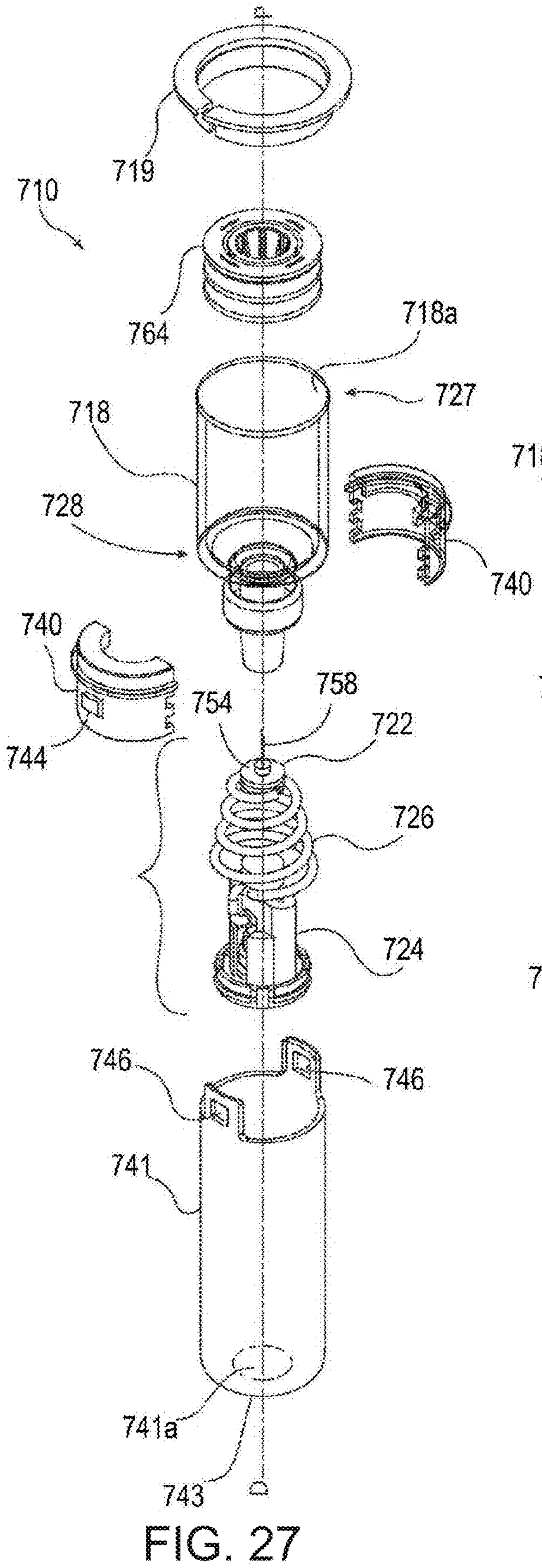
FIG. 27 is an exploded isometric view of a fill-finish cartridge, according to an embodiment of the disclosure.

FIG. 27 shows an exploded view of one embodiment of the fill-finish cartridge 716 of the present disclosure. For ease of understanding, the number utilized in FIG. 25 are utilized in further examples of embodiments of the disclosure with numerical prefixes; in this embodiment, 1XX will be utilized. The fill-finish cartridge 716 of this embodiment includes a fluid pathway assembly 720 connected to a drug container 718.

The fluid pathway assembly 720 includes a needle insertion mechanism 724 coupled to a fluid pathway connector 722 by a fluid conduit 726. A proximal end of the needle insertion mechanism 724 is connected to a distal end of a fluid conduit 726, which is connected at its proximal end to the fluid pathway connector 722.

The needle insertion mechanism 724 may be of any appropriate design so long as it may be sterilized prior to the placement of the fill-finish cartridge 716 in a drug delivery device. Examples of such needle insertion mechanisms 724 for implants and liquid drugs and are disclosed in U.S. application Ser. No. 13/599,727 filed Aug. 30, 2012, is incorporated herein by reference for everything disclosed therein. It will be noted that the needle insertion mechanism 724 of FIG. 27 includes an axial structure, such that the administration needle (not visible in FIG. 27) extends axially from a distal end of the fill-finish cartridge 716 for administration. It will be appreciated, however, that a needle insertion mechanism 724 that is disposed at an angle to an axis of the fluid pathway connector 722 and/or drug container 718 could alternately be utilized.

The components of the fluid pathway assembly 720, including the needle insertion mechanism 724, the fluid pathway connector 722, and the fluid conduit 726 are formed of materials that may be sterilized by conventional sterilization techniques and machinery. The fluid conduit 726 may be formed of any appropriate material, for example, a length of flexible tubing, such as plastic tubing. It will be appreciated, however, that fluid pathway connector 722 and the needle insertion mechanism 724 may be directly attached in some embodiments (not illustrated in FIGS. 27 and 28).

The components of the fluid pathway assembly 720 may be sterilized in advance of such connections, or may be connected prior to sterilization as a unified component. If sterilized in advance of such connections, the fluid pathway assembly 720 may include an additional seal at the fluid pathway connector 722, such as a permeable seal that may be pierced during assembly or actuation (not illustrated).

The drug container 718 of this and each of the embodiments may be of any appropriate material and of any appropriate shape and size, and may include a seal to maintain the integrity and sterility of a drug contained therein. For example, the drug container 718 may be formed of glass, plastic, or other appropriate material. The drug container 718 of this and each of the embodiments may include structure that facilitates handling, mounting within a drug delivery device, sterilization, and/or interface with other components of the fill-finish cartridge 716. For example, a flange 719 may be provided at any appropriate location along the drug container 716. Such a flange 719 may be integrally formed with the drug container 718 or may be a separate element that is secured to the drug container. In the illustrated embodiment, the flange 719 is a separate component that is coupled to a proximal end of the drug container 718.

It will be appreciated that any appropriate drive mechanism may be provided for moving the medication from the drug container 718 to the fluid pathway assembly 720 in embodiments of the disclosure. For example, U.S. application Ser. No. 13/600,114 filed Aug. 30, 2013, discloses an embodiment of a drive mechanism associated with a drug container, and is incorporated herein by reference for everything disclosed in that application.

In order to facilitate both filling the drug container 718 and administering medication from the drug delivery container, the drug container 718 may include openings 718*a*, 718*b* at the proximal and distal ends 6127, 728, respectively. In order to seal the drug container 718, a permeable seal 150 may be provided at a distal end 728 of the drug container 718. In this way, once filled, a drug contained within the drug container 718 may be maintained in a sterile environment until such time as the seal 150 is pierced by the fluid pathway connector 722 to complete the fluid pathway. The permeable seal 150 may be of any appropriate design and material.

Figure 28:
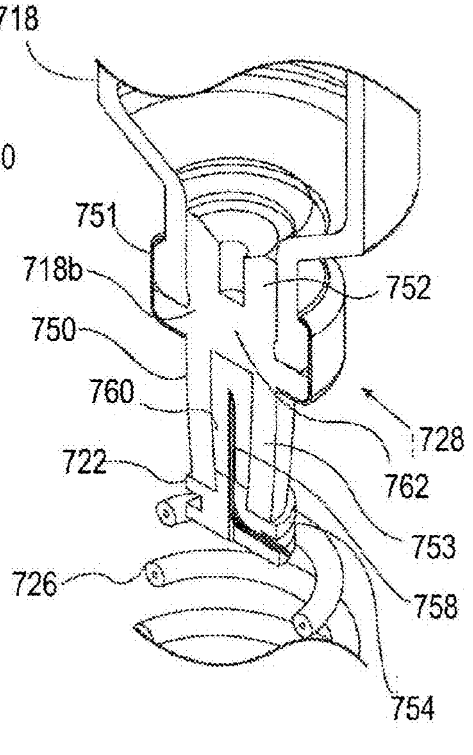
FIG. 28 is an enlarged fragmentary isometric cross-sectional view of the fluid pathway connector of the fill-finish cartridge shown in FIG. 27, cross-hatching being eliminated for the purposes of clarity.

The distal end 728 of the drug container 718 may be assembled with the fluid pathway assembly 720 for sterilization prior to or after fill, as will be explained in greater detail below. FIG. 28 shows an enlarged cross-sectional view of the fluid pathway connector 722 and the permeable seal 150 of FIG. 28, after these components are assembled and ready for sterilization. While the permeable seal 150 may be a single thin membrane 762 or the like across the opening 718*b* at the distal end 728 of the drug container 718, the permeable seal 150 may include further structure that facilitates connection with the drug container 718 and/or the fluid pathway connector 722. As shown, in at least one embodiment of the present disclosure, the permeable seal 150 is in the form of a container tip which caps the drug container 718, as well as provides support for the fluid pathway connector 722. In this embodiment, the permeable seal 150 may include a portion 152 that rests inside the drug container 718, providing a mating surface to mount the permeable seal 150 to the drug container 718. To assist in maintaining the connection of the seal 150 with the drug container 718 a cap 151 may be provided about portions of the permeable seal 150 and the drug container 718, such as around a lip on the drug container 718. Such a cap 151 may be of any appropriate material, such as a foil. While the drug container 718 necks in at the interface with the permeable seal 150, it will be appreciated that alternate designs may likewise be provided.

The permeable seal 150 may also have an extension 153 which facilitates mounting with the fluid pathway connector 722. In the embodiment shown in FIG. 28, the fluid pathway connector 722 includes a hub 154 through which a cannula 158 may extend. It will be appreciated by those of skill in the art that, as used herein the term "cannula" 158 includes a needle or a cannula that may be operative to provide the required fluid connection. The fluid conduit 726 is fluidly connected to the cannula 158 as it extends from a surface of the hub 154. The hub 154 of the fluid pathway connector 722 may be employed, as shown here, to mount, attach, or otherwise connect with the extension 153 of the permeable seal 150, the proximal end of the cannula 158 being disposed within a bore 760 of the extension 153. Prior to the completion of a fluid pathway between the drug container 718 and the fluid conduit 726, the cannula 158 is held in position as illustrated in FIG. 28.

The permeable seal 150 has a portion that acts as a membrane 762 that may be pierced by the cannula 158. In the embodiment of FIGS. 27 and 28, the membrane 762 is disposed generally perpendicular to the cannula 158 to close off the drug container 718 from the fluid pathway connector 722, thereby blocking the fluid pathway from the drug container 718 to the fluid conduit 726. Upon activation by the patient, a portion of the permeable seal 150 blocking the drug container 718, here, membrane 762, is caused to be pierced by the cannula 158 of the fluid pathway connector 722, thereby completing the fluid pathway and permitting drug fluid to pass from the container 718 to the cannula 158 and the fluid conduit 726, and on to the needle insertion mechanism 724. In order to facilitate piercing, the extension 153 of the permeable seal 150 may bow outward in response to sufficient axial pressure, for example, to allow the cannula 158 to pierce the membrane 762 to complete the fluid pathway.

Accordingly to another aspect of embodiments of the disclosure, the drug container 718, fluid pathway connector 722, and the needle insertion mechanism 724 of the fill-finish cartridge 716 exhibit sufficient structural integrity to be utilized in a fill-finish process and to be assembled into a housing of a drug delivery device. It will be appreciated that any appropriate fluid pathway connector 722 may be incorporated into embodiments of the disclosure. For example, a mounted fluid pathway connector, such as is disclosed, for example, in U.S. application Ser. No. 13/612,203 filed Sep. 12, 2012, may be utilized. Likewise, an integrated fluid pathway connector, such as is disclosed, for example, in U.S. application Ser. No. 13/796,156 filed Mar. 12, 2013, and may be utilized. Both of these applications are incorporated herein by reference.

Similarly, it will be appreciated that any appropriate connection may be provided between the fluid pathway connector 722 and the needle insertion mechanism 724. While examples of some connections are disclosed in detail herein, it is not the applicant's intention to limit the disclosure. Such a connection may include, for example, a snap connection (see FIGS. 45-47), a threaded connection (see FIGS. 40-44), an interference connection, a tongue and groove connection, an external support (see FIG. 27), or other appropriate connection.

Returning to FIG. 27, In order to provide further structural integrity to such an interface between the fluid pathway connector 722 and the permeable seal 150, and/or between the fluid pathway connector 722 and the needle insertion mechanism 724, a carrier 742 may be provided. The carrier 742 of this embodiment includes a connection collar 740 and a barrel 6141. For manufacturing purposes, the connection collar 740 may itself include multiple components, as illustrated in FIG. 27, that may be coupled together about the fluid pathway connector 722, the permeable seal 150, and a portion of the drug container 718 by any appropriate mechanism. It will be appreciated, however, that a unitary connection collar 740 could alternately be provided. It will further be appreciated that the connection collar 740 may not be required or desirable in all embodiments, and that such a connection collar 740 may be provided as an integrated part of the design, or may be fully or partially disposable during the assembly or sterilization processes.

Further structural integrity may be provided by the barrel 6141, which may support the fluid pathway assembly 720 during the sterilization and assembly processes. While any appropriate coupling may be provided, the connection collar 740 may facilitate coupling of the barrel 6141 about the fluid pathway assembly 720. In the illustrated embodiment, the connection collar 740 includes a pair of protrusions 744 (only one being visible in FIG. 27) that mate with a pair of recesses 746 in the barrel 6141. As with the connection collar 740, it will further be appreciated that the barrel 6141 may not be required or desirable in all embodiments, and that such a barrel 6141 may be provided as an integrated part of the design, or may be fully or partially disposable during the assembly or sterilization processes. In order to permit the needle insertion mechanism 724 to operate to administer medication, the barrel 6141 may include an opening 6 741*a* through which an administration needle may extend during use.

Figure 29:
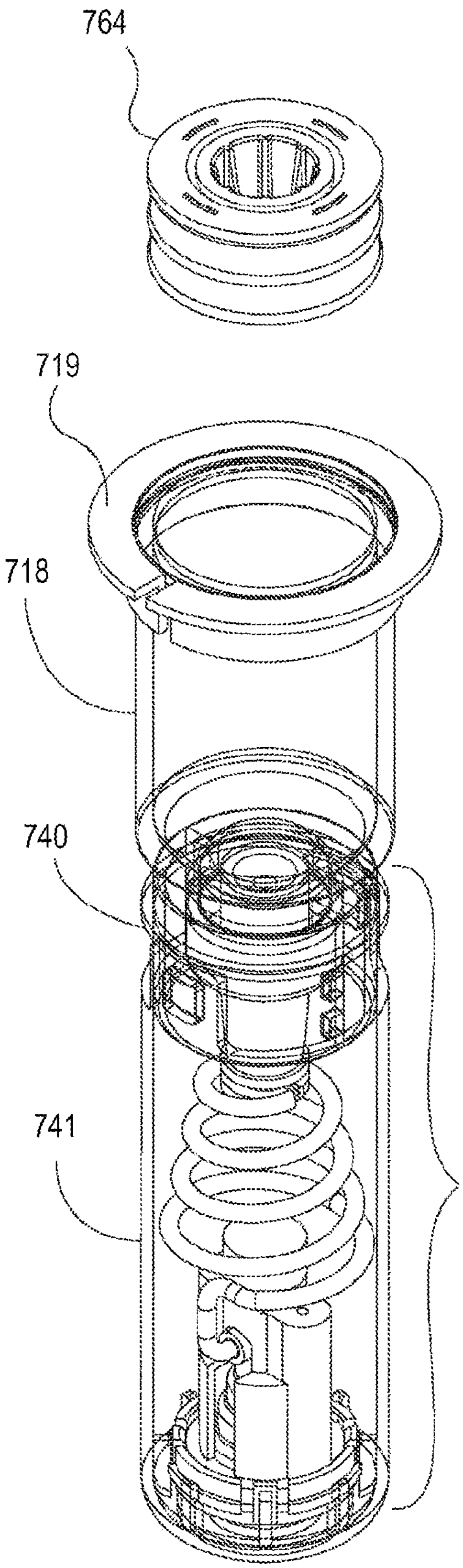
FIG. 29 is an isometric view of the fill-finish cartridge of FIG. 27 before insertion of a plunger seal, elements of FIG. 29 being shown in partial transparency.
Figure 30:
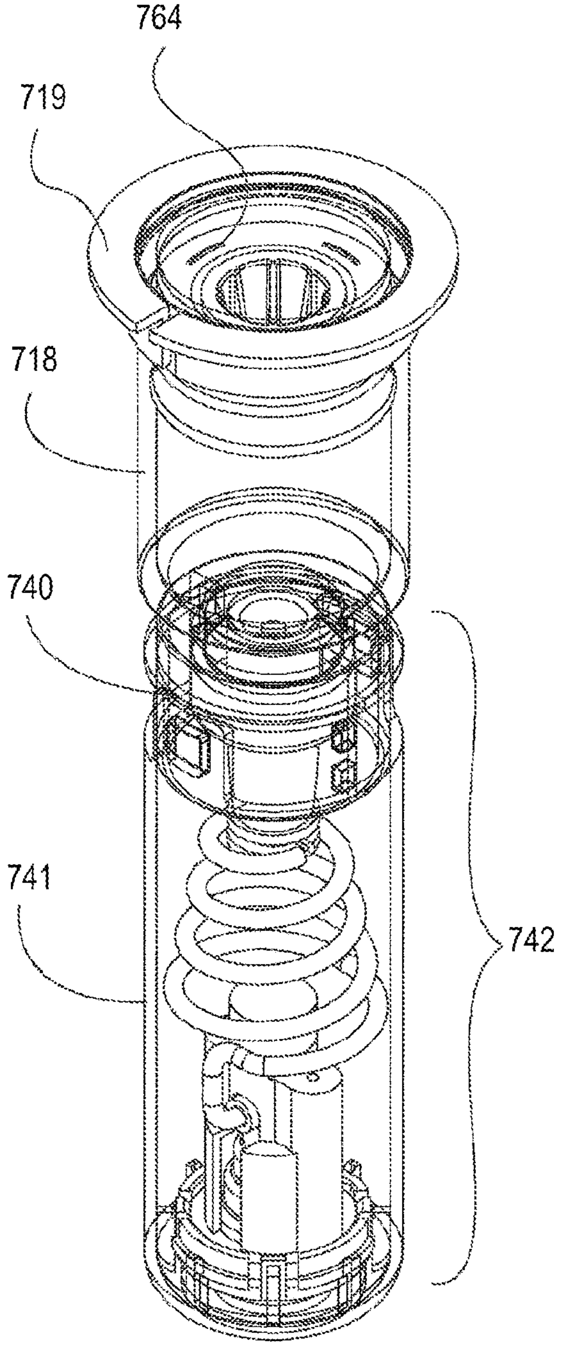
FIG. 30 is an isometric view of the fill-finish cartridge of FIG. 27 after insertion of a plunger seal, elements of FIG. 30 being shown in partial transparency.

For operational efficiency, the needle insertion mechanism 724 may be coupled to the fluid pathway connector 722, and the fluid pathway connector 722 may be connected to the permeable seal 150 with the needle insertion mechanism 724 maintained in the non-piercing configuration through the sterilization, filling, and assembly processes. In this way, the fill-finish cartridge 716 may appear as shown in FIG. 29, with the fluid pathway assembly 720 residing entirely hidden from the external environment by the carrier 742. Once the drug container 718 is filled with a pharmaceutical treatment, a seal 764 may be provided in the proximal end 6127 of the drug container 718 to provide a closed fill-finish cartridge 716 that may be inserted into an appropriate drug delivery device. In the embodiment illustrated in FIGS. 29-30, an elastomeric plunger seal 764 is inserted into the proximal end 6127 of the drug container 718. It will be appreciated, however, that other appropriate sealing arrangement may be provided. In FIGS. 29 and 30, the arrangement of the fluid pathway connector 722, the container 718, and the insertion mechanism 724 relative to each other may be considered to be a first configuration. The first configuration may facilitate the manufacturing process, for example, by enabling the use of standard filling equipment and systems. While the first configuration shown in FIGS. 29 and 30 involves the axial alignment of the container 718 and the insertion mechanism 724, in other embodiments, the first configuration may involve a non-axial alignment of the container 718 and the insertion mechanism 724, or any other relative positioning of the container 718 and the insertion mechanism 724. Subsequently, when assembled in the drug delivery device 610, as illustrated in FIG. 25, the fluid pathway connector 722, the container 718, and the insertion mechanism 724 may be arranged relative to each other such they have a second configuration. The second configuration may involve the non-alignment of the container 718 and the insertion mechanism 724 as illustrate in FIG. 25, or, in alternative embodiments, the axial alignment of the container 718 and the insertion mechanism 724, or any other relative positioning of the container 718 and the insertion mechanism 724. In some embodiments, the first configuration is different from the second configuration.

According to another aspect of the disclosure, the fluid pathway assemblies may be maintained in a sterile condition and the drug containers of each assembly may be filled with a pharmaceutical compound aseptically using processes similar to those known in the art. After a pharmaceutical treatment is filled into the drug container and the container is sealed, for example with the plunger seal 764 of the embodiment of FIGS. 27-30, the fill-finish cartridge 716 may be removed from the sterile filling environment without comprising the sterility or container integrity of the drug container 718, fluid pathway assembly 720, or their individual components.

Alternatively, the fill-finish process may be such that the plunger seal 764 is inserted to the proximal end of the drug container 718 prior to filling the container 718 with a pharmaceutical treatment. In such an embodiment, the pharmaceutical treatment may be filled from the distal end 728 of the drug container 718 prior to insertion and connection of the fluid pathway connector 722 and the fluid pathway assembly 720. Accordingly, the fill-finish cartridges of the present disclosure enable the fluid pathway assemblies of the present disclosure to be filled with pharmaceutical treatments in standard fill-finish processes, greatly reducing the complexities associated with manufacturing and operation of the components and the drug delivery devices in which they are incorporated.

Figure 32:
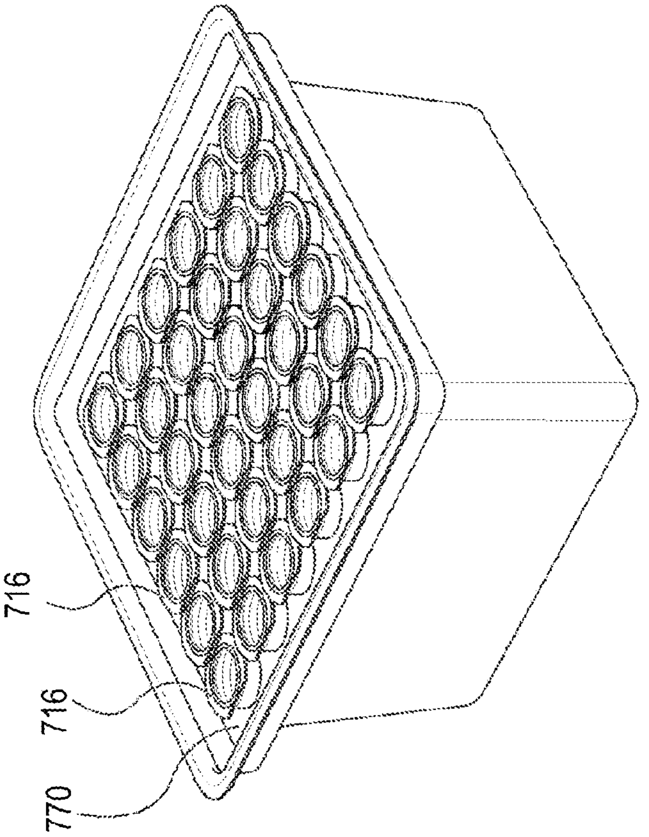
FIG. 32 is an isometric view of the a tray of FIG. 31 in an assembled form and holding a plurality of fill-finish cartridges for use in a fill-finish process.
Figure 31:
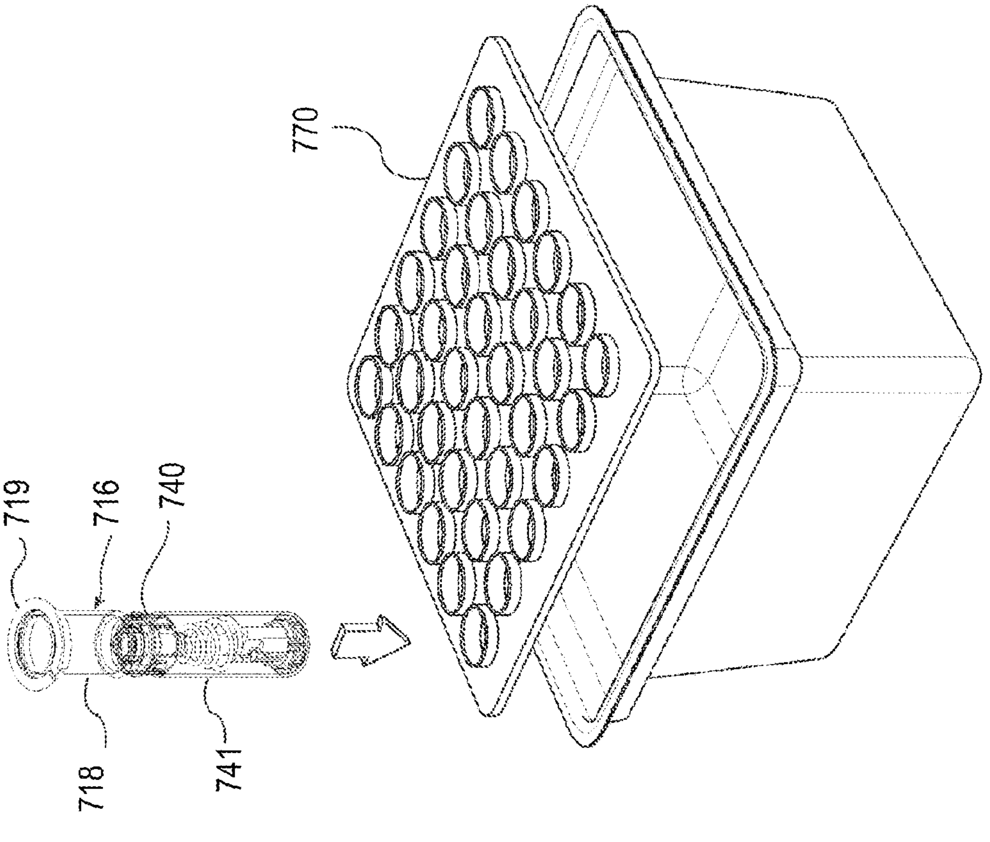
FIG. 31 is an exploded isometric view of a tray which may be utilized to retain a plurality of fill-finish cartridges for use in a fill-finish process, elements of FIG. 7 being shown in partial transparency; 31

According to another aspect of the disclosure, embodiments of the fill-finish cartridges of the present disclosure may enable the fluid pathways assemblies to be filled in standard fill-finish processes. In this regard, the fill-finish cartridges may utilize existing or standardized fill-finish equipment. A plurality of fill-finish cartridges 716, such as is illustrated in FIGS. 27-30, for example, may be removably mounted, mated, inserted, or otherwise placed into a standard fill-finish tray 770, such as illustrated in FIGS. 31-32, for filling with pharmaceutical treatments. As explained above, the flange 719 of the drug container 718 may assist in placement and handling of the fill-finish cartridges 716. The fill-finish tray 770 illustrated in FIGS. 31-32 is configured to hold thirty-six drug containers, here, fill-finish cartridges 716, but trays of any configuration or capable of holding any number of containers may be utilized.

According to another aspect of the disclosure, fill-finish cartridges may be configured to be fixed cartridges or adjustable cartridges. For example, the cartridges may have a flexible or adjustable portion that enables them to bend, rotate, expand, or contract to fit a number of different fluid pathway assemblies or to mate with fill-finish processing trays of different dimensions.

According to yet another aspect of the disclosure, components of some embodiments of the fill-finish cartridges may be incorporated into the drug delivery devices, while in other embodiments, components of the fill-finish cartridges may be utilized for the fill-finish process and then discarded upon mounting the fluid pathway assembly and drug container into a drug delivery device. For example, in an embodiment such as is illustrated in FIGS. 27-30 is utilized as shown in FIG. 25, by removing the barrel, the connection collar may be utilized to mount and/or brace the drug container into position within the drug delivery device, while the needle insertion mechanism is mounted remotely from and 90.degree. to the drug container.

Figure 33:
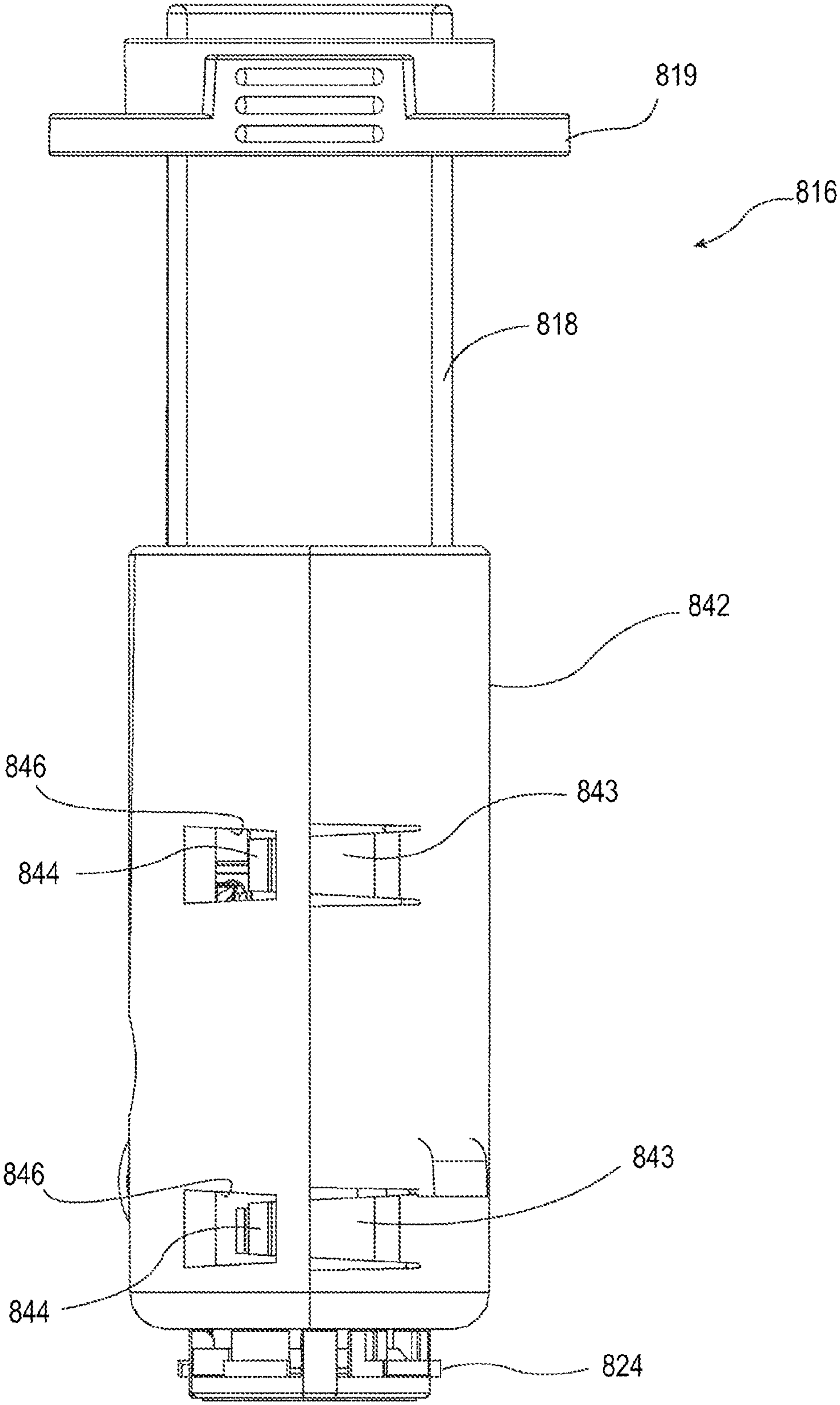
FIG. 33 is a side elevational view of another embodiment of a fill-finish cartridge, wherein the cartridge includes a fully disposable carrier.
Figure 34:
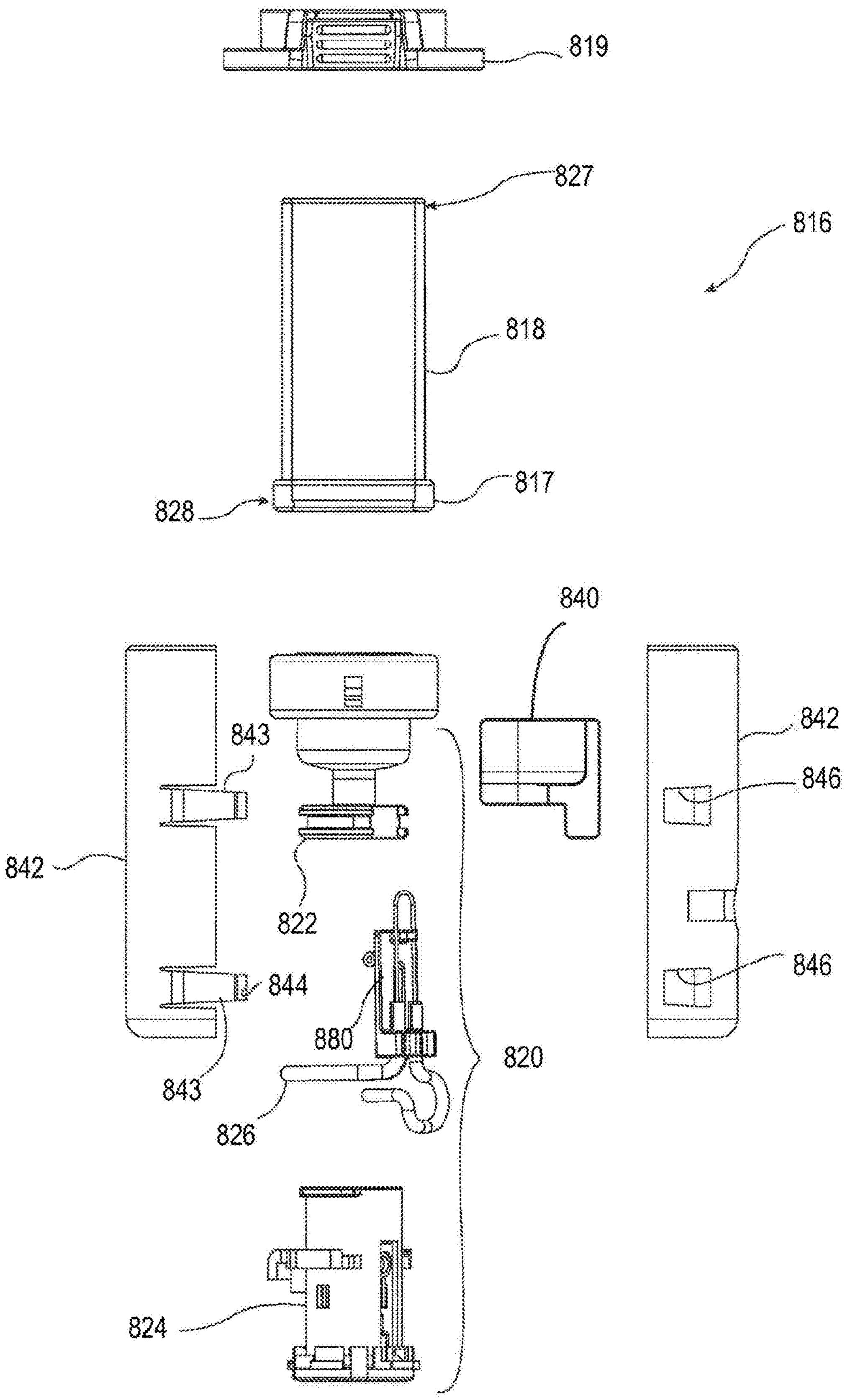
FIG. 34 is an exploded view of the fill-finish cartridge of FIG. 33.
Figure 35:
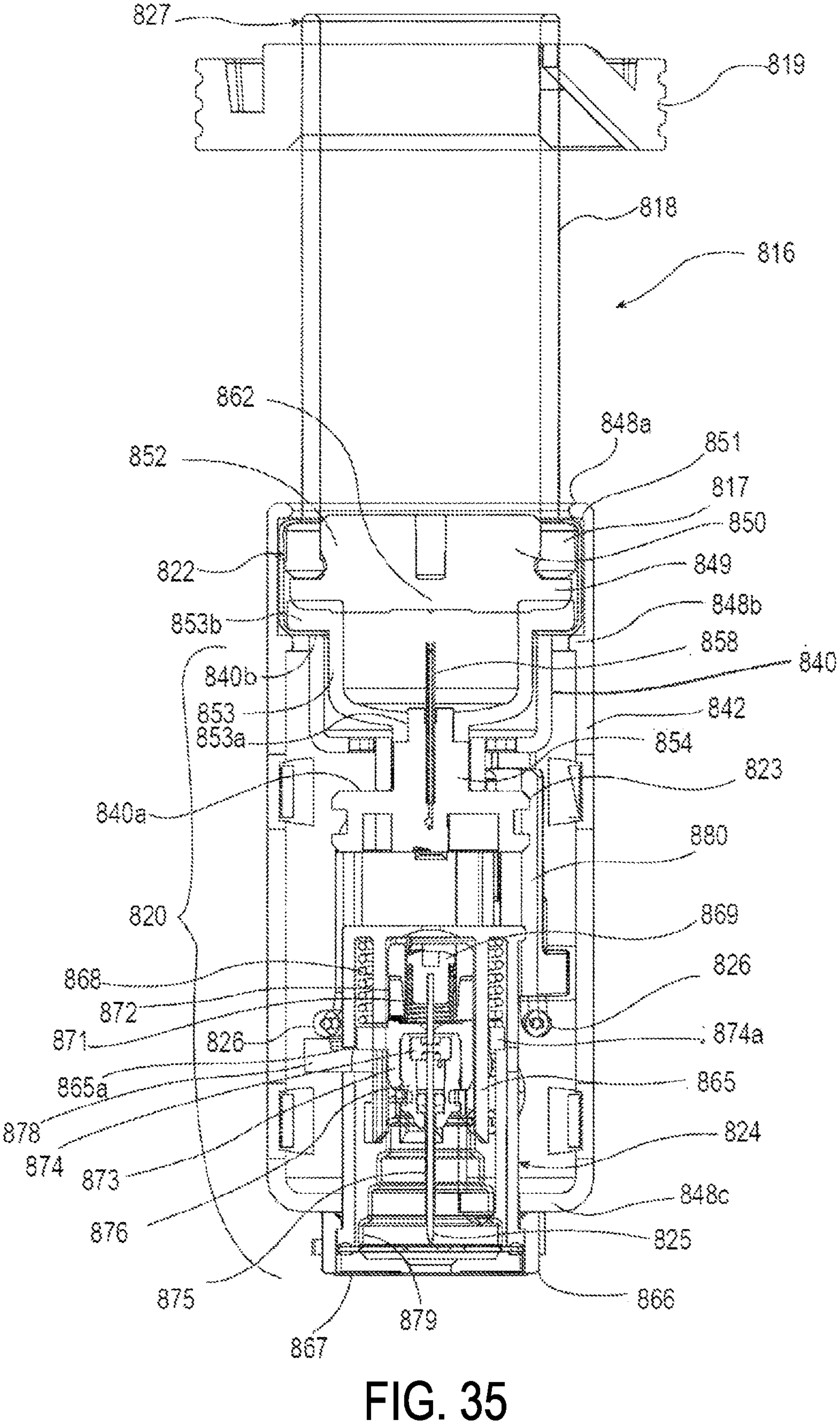
FIG. 35 is a cross-sectional view of the fill-finish cartridge of FIGS. 33 and 34, cross-hatching being eliminated for the purposes of clarity.
Figure 36:
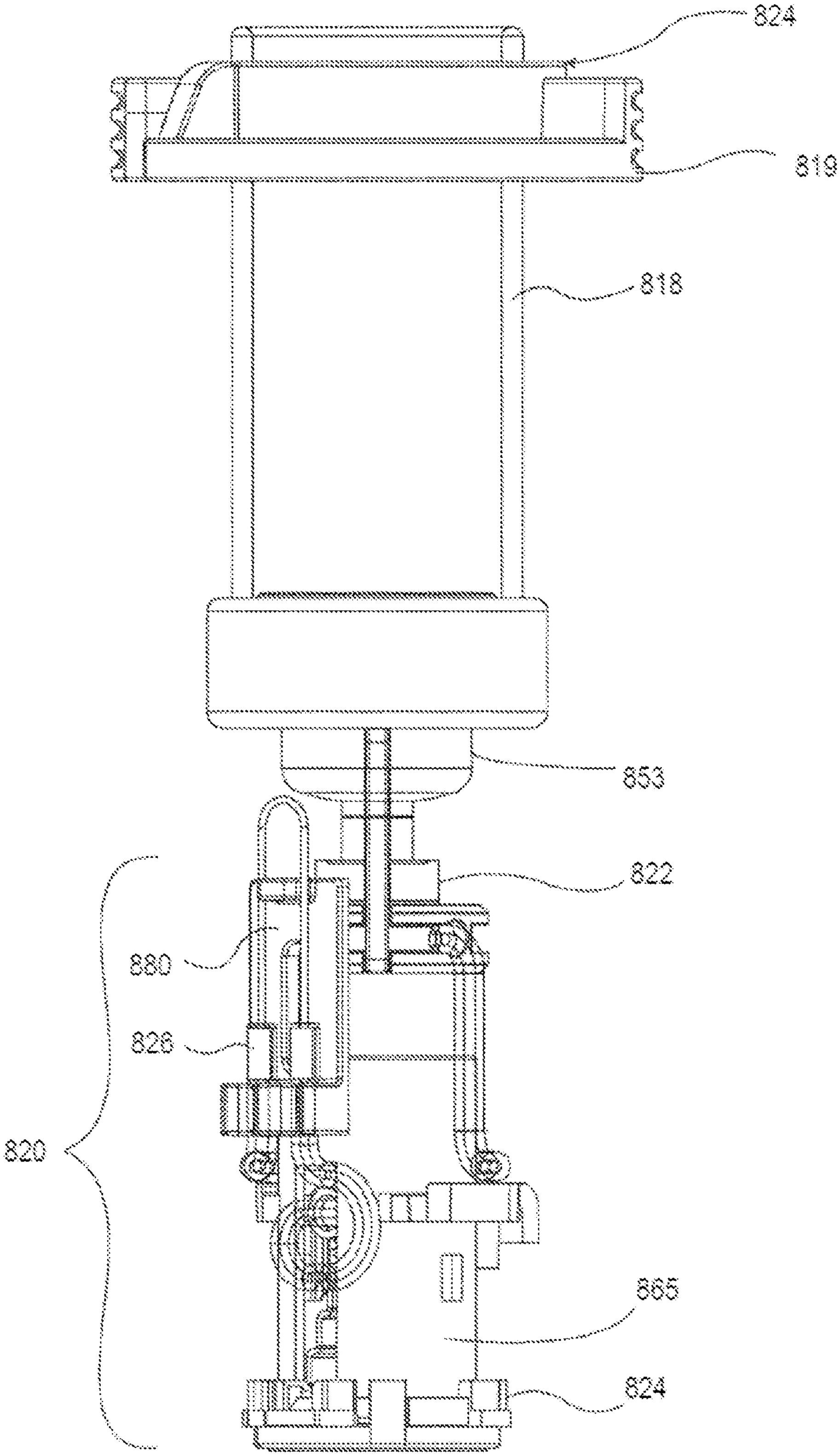
FIG. 36 is a side elevational view of the fill-finish cartridge of FIGS. 33-35 with the carrier removed.

In the embodiment of FIGS. 33-35, there is illustrated a fill-finish cartridge 816 that includes a carrier 842 that may be disposed of after the fill-finish process, that is prior to insertion into a drug delivery device. The fill-finish cartridge 816 of this embodiment includes a fluid pathway assembly 820 connected to a drug container 818. The fluid pathway assembly 820 includes a needle insertion mechanism 824 coupled to a fluid pathway connector 822 by a fluid conduit

826. A proximal end of the needle insertion mechanism 824 is connected to a distal end of a fluid conduit 826, which is connected at its proximal end to the fluid pathway connector 822. In order to provide further support to the fill-finish cartridge 816, the illustrated carrier 842 is disposed about portions of the drug container 818 and the fluid pathway assembly 820, that is, the fluid pathway connector 822, the fluid conduit 826, and a portion of the needle insertion mechanism 824.

The carrier 842 is generally an elongated tubular structure that may be fabricated in multiple components to facilitate assembly and disassembly, if desired. In the illustrated embodiment, one portion of the carrier 842 includes circumferentially extending arms 843 having protrusions 844, while a mating portion of the carrier 842 includes recesses or openings 846 through which the protrusions 844 may extend when assembled about the fill-finish cartridge 816.

In order to assist in maintaining the components of the fill-finish cartridge 816 in their relative positions, the carrier 842 may further include one or more radially projecting flanges 848*a*, 848*b*, 848*c*. As will be apparent from the explanation below, flanges 848*a* and 848*b* may be disposed to further secure aspects of the fluid pathway connector 822 and the drug container 818 in their relative positions. Further, as will likewise be apparent from the explanation below, flanges 848*b* and 848*c* may be disposed to maintain the fill-finish cartridge 816 in an un-actuated position during filling, and, optionally, placement within a drug delivery device. In order to permit actuation of the device, the carrier 842 may be removed from the fill-finish cartridge 816 and discarded. The carrier 842 may further include a removable brace 840. The removable brace 840 may have a generally U-shaped structure and surfaces that confront the surfaces of the fill-finish cartridge 816 to prevent premature completion of the fluid pathway from the drug container 818 to the fluid pathway connector 822. The removable brace 840 may remain with the fill-finish cartridge 816 as it is assembled into a housing of a drug delivery device; in some embodiments, structure within the housing of the drug delivery device may confront one or more surfaces of the removable brace 840 to cause the removable brace 840 to disengage from the fill-finish cartridge 816 as it is assembled into the housing.

The drug container 818 is an elongated, generally annular structure, although the drug container 818 may be of an alternate design. For example, a flange 819 may be provided at any appropriate location along the drug container 818. Such a flange 819 may be integrally formed with the drug container 818 or may be a separate element that is secured to the drug container 818. In the illustrated embodiment, the flange 819 is a separate component that is coupled to a proximal end 827 of the drug container 818. In an embodiment, the flange 819 may interface with a wall of a housing of a drug delivery device incorporating the fill-finish cartridge 816. Further, in this embodiment, a flange 817 is provided at the distal end 828 of the drug container 818. As illustrated in FIG. 35, the flange 817 may engage with flange 848*a* of the carrier 842 to facilitate the maintenance of the relative positions of the components of the fill-finish cartridge 816 during the fill-finish process and handling.

In order to seal the drug container 818, a permeable seal 850 may be provided at the distal end 828 of the drug container 818. In this way, a drug contained within the drug container 818 may be maintained in a sterile environment until such time as the seal 850 is pierced by the fluid pathway connector 822 to complete the fluid pathway. The drug container 818 may be assembled with the permeable seal 850 and the fluid pathway assembly 820 for sterilization prior to or after fill. The permeable seal 850 may be of any appropriate design and material. The permeable seal 850 includes a thin membrane 862 or the like that may be pierced in order to complete the fluid pathway from the drug container 818 through the fluid pathway connector 822 and fluid conduit 826 to the needle insertion assembly 824.

The permeable seal 850 may include structure that facilitates connection with the drug container 818 and/or the fluid pathway connector 822. For example, the permeable seal 850 may include a portion 852 that rests inside the drug container 818, providing a mating surface to mount the permeable seal 850 to the drug container 818.

The fluid pathway connector 822 maybe of any appropriate design. Such piercing arrangements are disclosed, for example, in U.S. application Ser. No. 13/612,203, and in U.S. application Ser. No. 13/796,156, both of which are incorporated herein by reference.

Referring to FIG. 35, the illustrated fluid pathway connector 822 includes a cannula 858 that is disposed to pierce the membrane 862 of the permeable seal 850 during actuation, the cannula 858 being spaced from the permeable seal 850 in the un-actuated position (see FIG. 35), and progressing respectively axially in a proximal direction to confront and pierce the membrane 862 as a result of actuation. In the embodiment shown in FIG. 35, the fluid pathway connector 822 includes a hub 854 through which the cannula 858 extends. A pathway from the cannula 858 secured within the hub 854 extends from the lumen of the cannula 858 to a lumen of the fluid conduit 826. Accordingly, when the cannula 858 pierces the membrane 862 of the permeable seal 850, the fluid pathway is provided between the drug container 818, the fluid conduit 826 and the needle 825 of the needle insertion mechanism 824.

In order to maintain the hub 854 and, therefore, the cannula 858 in a desired position relative to the permeable seal 850 closing the drug container 818, the fluid pathway connector 822 further includes a boot 853 formed of collapsible material, such as an elastomeric material. A distal end of the boot 853 includes a generally axially extending bore 853*a* that is disposed about a portion of the hub 854, while a proximal end of the boot 853 includes a generally radially extending flange 853*b*. The permeable seal 850 may also include a flange 849 that may be sandwiched between the flange 853*b* of the boot 853 of the fluid pathway connector 822 and the flange 817 at the distal end 828 of the drug container 818. As with the embodiment illustrated in FIGS. 27-30, a retaining structure, such as a cap 851 may be provided about the periphery of the flanges 817, 849, 853*b*.

The fluid pathway connector 822 of the fill-finish cartridge 816 may be caused to pierce the membrane 862 of the permeable seal 850 to complete the fluid pathway, for example, by manual depression of the proximal end 827 of the drug container 818 or by an alternate arrangement. During actuation, the boot 853 bows outward to allow relative axial movement between the hub 854 and the permeable seal 850 such that the cannula 858 pierces the membrane 862 of the permeable seal 850 to fluidly connect the drug container 818 to the delivery needle 825 of the needle insertion mechanism 824 via the fluid conduit 826.

In order to inhibit inadvertent activation of the fluid pathway connector 822 once the carrier 842 is removed, the removable brace 840 may be provided about a portion of the circumference of the sterile boot 853 and/or between surfaces that inhibit axial movement of the hub 854 relative to the drug container 818. The removable brace 840 may be a relatively rigid structure that confronts opposing surfaces

840*a*, 840*b*, for example, on a surface of the hub 854, and the flange 853*b* of the sterile boot 853 or, as here the cap 851 along the flange 853*b*; as a result, the removable brace 840 inhibits axial movement of hub 854 relative to the seal 850. The removable brace 840 illustrated also closely follows at least a portion of the periphery of the sterile boot 853; as a result, the removable brace 840 likewise prevents the sterile boot 853 from bowing outward as the cannula 858 moves axially to pierce the seal 850. In this embodiment, the removable brace 840 may be slid out of position on the sterile boot 853 by the patient prior to assembling the fill-finish cartridge 816 into the drug delivery device or by the action of placement into the drug delivery device, for example, as the removable brace 840 engages confronting surfaces of the housing of the delivery device (not illustrated).

The needle insertion mechanism 824 may be of any appropriate design. The needle insertion mechanism 824 illustrated in connection with the embodiment of FIGS. 33-36 likewise includes a needle retraction mechanism, and is shown and explained in greater detail in U.S. application Ser. No. 13/599,727, which is incorporated by reference.

The insertion mechanism 824 includes an insertion mechanism housing 865 having one or more lockout windows 865*a*, a base 866, and a sterile boot 879. The base 866 includes an opening to passage of the needle 825 and may include a sealing membrane 867 that, at least in one embodiment, is removable prior to use of the fill-finish cartridge 816. Alternatively, the sealing membrane 867 may remain attached to the bottom of the base 866 such that the needle 825 pierces the sealing membrane 867 during operation of the fill-finish cartridge 816 within the drug delivery device incorporating the same.

The insertion mechanism 824 may further include an insertion biasing member 868, a hub 869, a needle 825, a refraction biasing member 871, a clip 872, a manifold guide 873, a septum 874, a cannula 875, and a manifold 876. As illustrated in FIG. 35, both the insertion and retraction biasing members 868, 871 are held in energized states. The manifold 876 may connect to sterile fluid conduit 826 to permit fluid flow through the manifold 876, cannula 875, and into the body of the patient during drug delivery, as will be described in further detail herein.

As used herein, "needle 825" is intended to refer to a variety of needles including but not limited to conventional hollow needles, such as a rigid hollow steel needles, and solid core needles often referred to as "trocars." In an embodiment, the needle 825 may be a 27 gauge solid core trocar and in other embodiments, the needle may be any size needle suitable to insert the cannula for the type of drug and drug administration (e.g., subcutaneous, intramuscular, intradermal, etc.) intended.

Upon assembly, the proximal end of needle 825 is maintained in fixed contact with hub 869. The needle 825 may be positioned to move through a cannula 875, if provided, in order to further control movement of the needle 825. The hub 869, and therefore the needle 825, is maintained in selective contact with the manifold guide 873 by the clip 872. While biasing members 868 and 871 bear on the manifold guide 873, the manifold guide 873 is maintained in position by at least one lockout pin 878, which extends through window 865*a* of the housing 865.

Actuation of the needle insertion 824 device results from removal of the lockout pin 878. The lockout pin 878 may be removed from the window 865*a* either directly or indirectly as a result of actuation of the fill-finish cartridge 816. Upon removal of the lockout pin 878, the manifold guide 873 carrying the hub 869 and needle 825 is permitted to move axially under the biasing force of the injection biasing member 868. That is, the needle 825 moves into the injection position. As the hub 869 and needle 825 move to the injection position, the sterile boot 879 collapses.

In at least some embodiments, such as the embodiment shown in FIG. 35, the needle insertion mechanism 824 further includes a refraction mechanism that retracts the needle 825 following injection. Such a retraction mechanism may be of any appropriate design. As the manifold guide 873 moves axially in the distal direction, the clip 872 releases the hub 869. Upon release, the biasing force of the retraction biasing member 871 causes hub 869 and the associated needle 825 to retract.

As with the embodiment of FIGS. 27-30, the needle insertion mechanism 824 of FIGS. 33-36 includes an axially aligned structure, such that the administration needle 825 extends axially from a distal end of the fill-finish cartridge 816 during administration. It will be appreciated that the components may be secured together by any appropriate structure and method. The relative positions of the fluid pathway connector 822 and the needle insertion mechanism 824 may be maintained by, for example, a bracket 880, as may be seen in FIGS. 34-36. The illustrated bracket 880 extends between the hub 854 of the fluid pathway connector 822 and the insertion mechanism housing 865, as may best be seen in FIG. 35. The bracket 880 may perform additional functions such as, for example, management of the fluid conduit 826.

It will be appreciated that in some embodiments wherein the bracket 880 is removed from its connection with either of the fluid pathway connector 822 or the needle insertion mechanism 824, or wherein the fill-finish cartridge does not include the bracket 880, the fluid conduit 826 may provide a flexible fluid connection between the fluid pathway connector 822 and the needle insertion mechanism 824, allowing the needle insertion mechanism 824 and the fluid pathway connector 822 to be placed other than in axial alignment. Such embodiments are illustrated, for example, in FIG. 25 or FIGS. 37-40.

Figure 37:
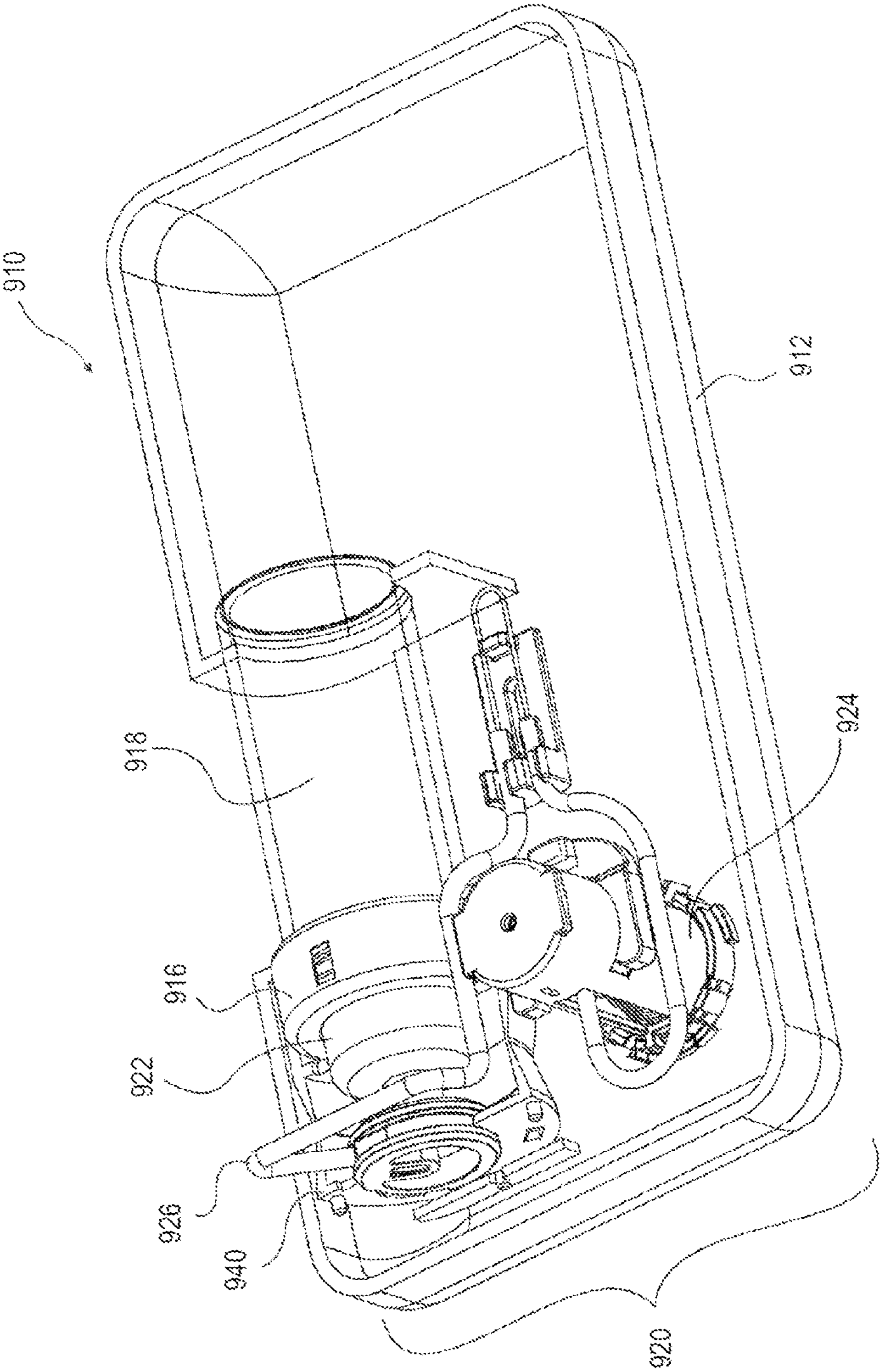
FIG. 37 is an isometric view of a drug delivery device incorporating another embodiment of a fill-finish cartridge according to the disclosure, a portion of a housing of the drug delivery device being removed.
Figure 38:
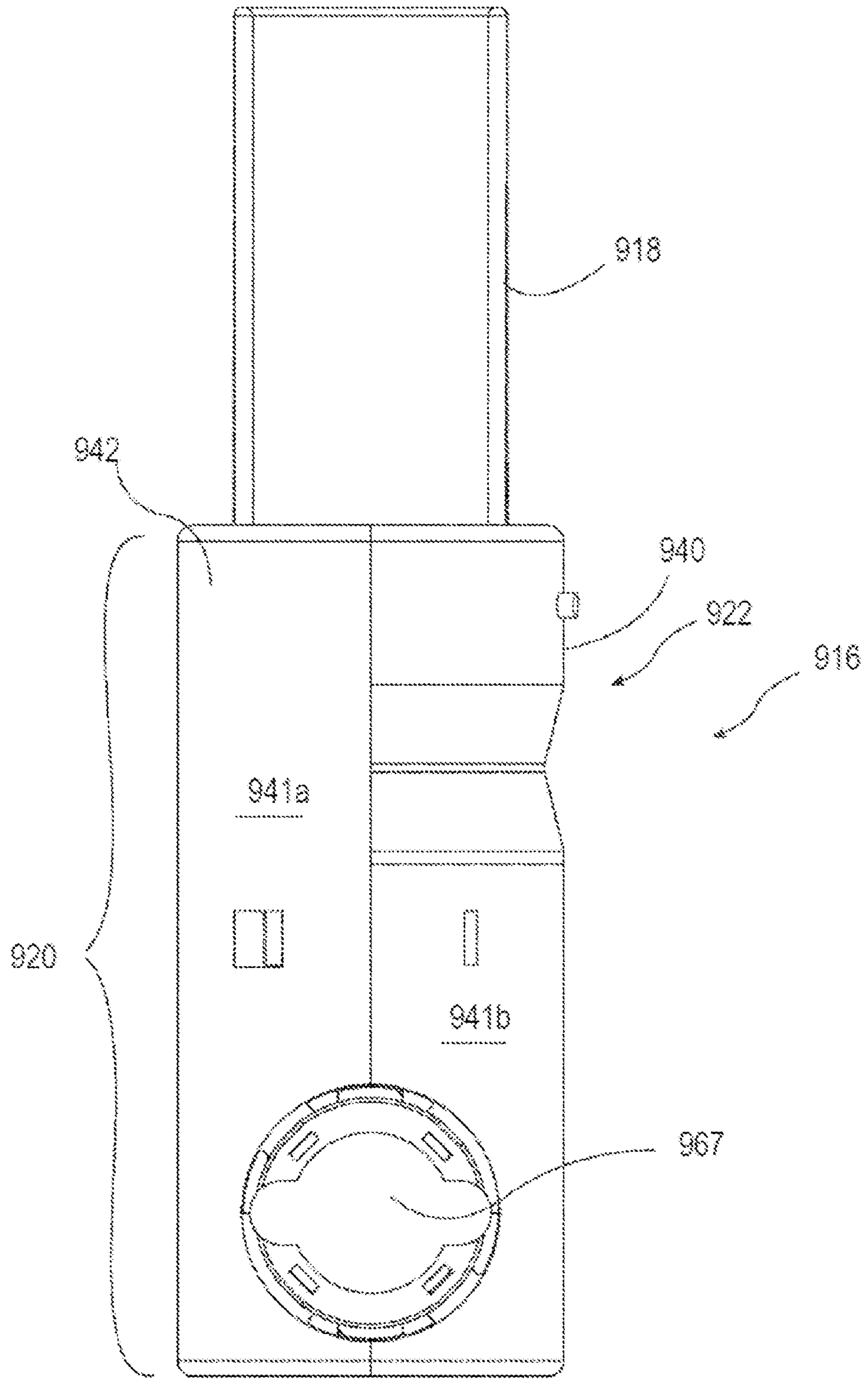
FIG. 38 is a side elevational view of the fill-finish cartridge of FIG. 37 prior to placement in the housing, and including partially disposable carrier.
Figure 39:
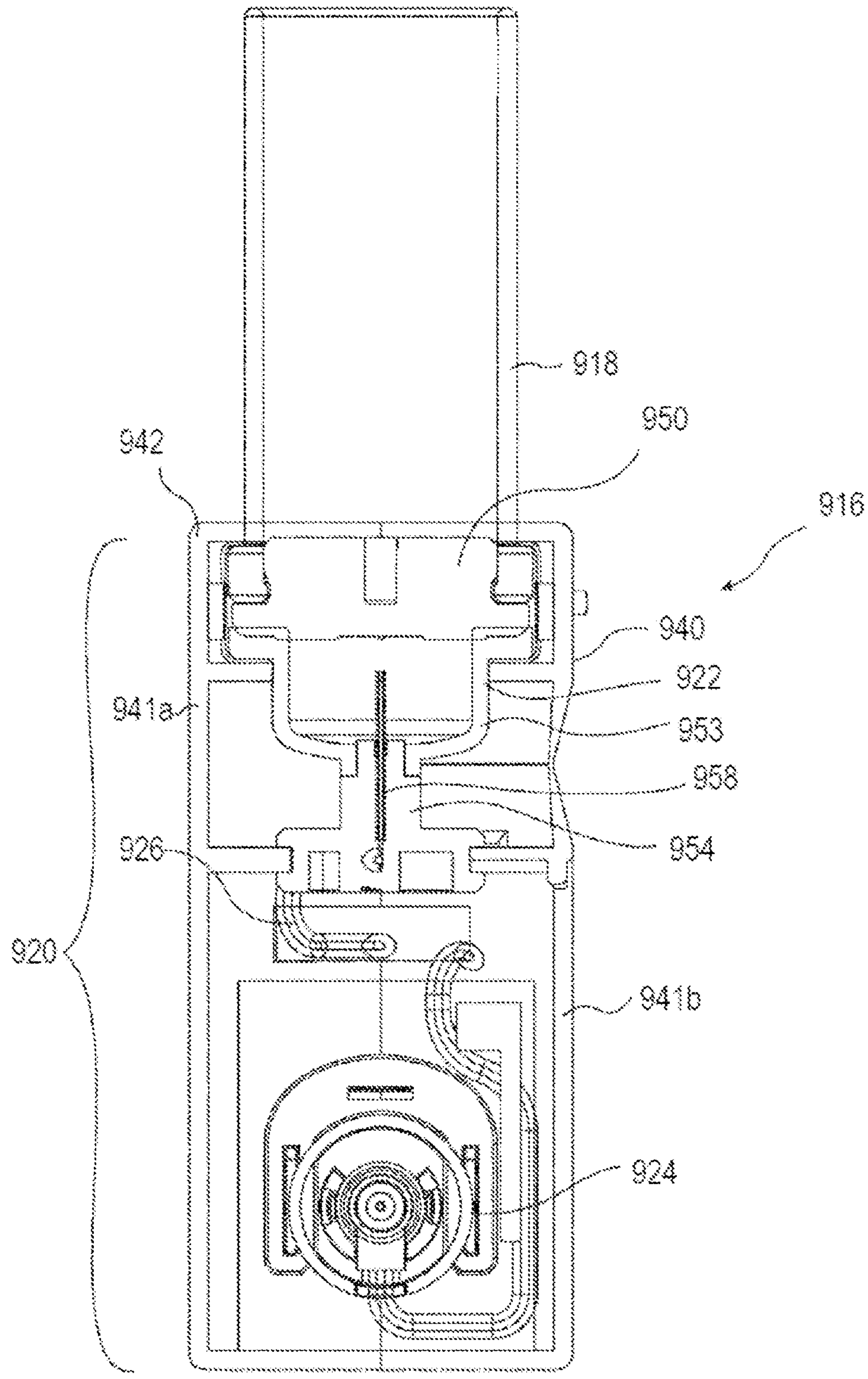
FIG. 39 is a cross-sectional view of the fill-finish cartridge of FIG. 37, cross-hatching being eliminated for the purposes of clarity.
Figure 40:
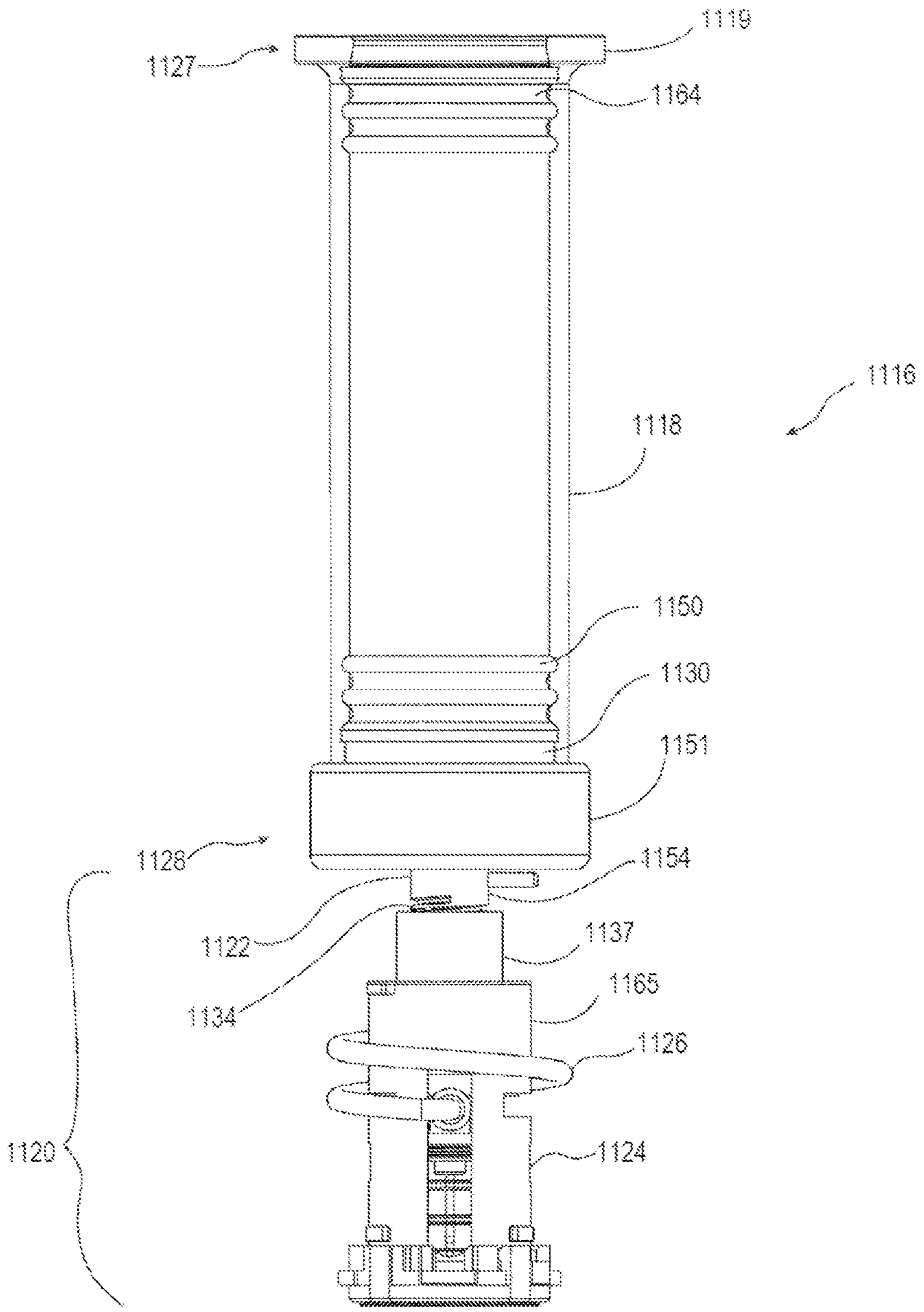
FIG. 40 is a side elevational view of another embodiment of a fill-finish cartridge in an assembled configuration.

Referring to FIG. 37, there is illustrated another embodiment of a drug delivery device 910 according to teachings of the disclosure. A portion of the housing 912 of the drug delivery device 910 is broken away in order to illustrate the relative positions of the components contained therein. The fill-finish cartridge 916 includes a drug container 918 to which a fluid pathway assembly 920 is coupled. The fluid pathway assembly 920 includes a fluid pathway connector 922, fluidly coupled to a needle insertion mechanism 924 by a fluid conduit 926. It will be appreciated that, in this embodiment, while they remain fluidly coupled, the needle insertion mechanism 924 is decoupled from the fluid pathway connector 922 of the fill-finish cartridge 916 when assembled into the housing 912. As shown in FIGS. 38 and 39, during the fill-finish process, the components are aligned to allow the fill-finish cartridge 916 to be readily placed in a tray, such as are illustrated in FIGS. 31 and 32. It is noted, however, that the components are not in axial alignment in the fill-finish cartridge 916 during the fill-finish process inasmuch as the axis of the needle insertion mechanism 924 extends perpendicular to the axis of the drug container 918 and fluid path connection 922. As may be best seen in FIG. 38, the needle insertion mechanism 924 may include a sealing membrane 967 that, at least in one embodiment, is removable prior to use of the fill-finish cartridge 916 within the drug delivery device to allow passage of a needle from the needle insertion mechanism 924. Alternatively, the sealing membrane 967 may remain attached to the bottom of the needle insertion mechanism 924 such that the needle pierces the sealing membrane 967 during operation of the fill-finish cartridge 916 within the drug delivery device 910 incorporating the same.

Referring to FIG. 38, there is illustrated the fill-finish cartridge 916 along with a carrier 942 that partially surrounds the assembled fill-finish cartridge 916 during the fill-finish process. As may be seen in FIG. 38, the carrier 942 substantially surrounds a distal portion of the drug container 918, the fluid pathway connector 922, and the needle insertion mechanism 924. The carrier 942 of this embodiment includes three separate sections, although a greater or lesser number may be provided. In this embodiment, a portion of the carrier 942 is disposable prior to placement of the fill-finish cartridge 916 into the housing 912 of the drug delivery device 910, while a portion remains on the fill-finish cartridge 916 when disposed in the housing 912, and may be utilized in operation of the device 910.

As may be seen in FIGS. 14 and 15, the carrier 942 includes a first barrel section 941*a* and a second barrel section 941*b*. The first and second barrel sections 941*a*, 941*b* may be selectively coupled together by any appropriate mechanism. In the illustrated embodiment, a coupling arrangement similar to that illustrated in FIGS. 33-35 is utilized such that the first and second sections 941*a*, 941*b* may be decoupled and removed prior to placement into the housing 912 of the drug delivery device 910. The carrier 942 further includes a collar 940 that, when assembled to the fill-finish cartridge 916, completes the barrel.

The fluid pathway connector 922 and the needle insertion mechanism 924 may be of any appropriate design. The illustrated fluid pathway connector 922, for example, is as explained with regard to FIGS. 33-36, and the needle insertion mechanism 924 may likewise be as described with regard to FIGS. 33-36. Referring to FIG. 39, in short, a permeable seal 950 is disposed between the drug container 918 and a sterile boot 953 of the fluid pathway connector 922. A cannula 958 extending from a hub 954 is axially disposed within the sterile boot 953. Continued relative axial, proximal movement of the cannula 958 toward the permeable seal 950 results in a piercing of the permeable seal 950, and completion of the fluid pathway to the needle insertion mechanism 924.

In assembly of the filled fill-finish cartridge 916 into the drug delivery device housing 912, the collar 940 remains coupled to the fluid pathway connector 922, as illustrated in FIG. 37. In some embodiments of the disclosure, the carrier, or a portion of the same such as the collar 940 here, may be utilized in the operation or actuation of the fill-finish cartridge 916. In this embodiment, an activation mechanism 914, such as a button, may be provided along an outer surface of the drug delivery device housing 912 in order to permit the patient to selectively provide medication. In this embodiment, the activation mechanism 914 asserts an axial, proximally directed force on the collar 940. The collar 940 further asserts an axial, proximally directed force on the hub 954, causing the cannula 958 to pierce the permeable seal 950 of the fluid pathway connector 922 to complete the fluid pathway from the drug container 918 to the needle insertion mechanism 924. The needle insertion mechanism 924 may be actuated by any appropriate operation. For example, the movement of a portion of the collar 940 may cause the dislodgement of the lockout pin, causing actuation of the needle insertion mechanism 924, as explained in greater detail with regard to the embodiment illustrated in FIGS. 33-36.

Turning now to the embodiment of FIGS. 40-46, the fill-finish cartridge 1116 includes a drug container 1118 having proximal and distal ends 1127, 1128. The proximal end 1127 may include a flange 1119 and is adapted to receive a plug or plunger seal 1164, while the distal end 1128 may include a flange 1117 and is adapted to receive a permeable seal 1150 in conjunction with a fluid pathway assembly 1120. The fluid pathway assembly 1120 includes a fluid pathway connector 1122 and a needle insertion mechanism 824 fluidly coupled by a fluid conduit 1126.

In this embodiment, the fluid pathway connector 1122 is integrated with the permeable seal of the drug container 1118. The fluid pathway connector 1122 may best be seen in the cross-sectional view of FIG. 41 and the exploded view of FIG. 43. The fluid pathway connector 1122 includes a hub assembly 1156 having a hub 1154 and a cap 1155. A cannula 1158 is secured to the hub 1154 to provide a fluid path therethrough. The fluid conduit 1126 may be coupled to the cannula 1158 by any appropriate structure. In this embodiment, the fluid conduit 1126 is coupled to a nipple 1159 that is fluidly open to the cannula 1158.

In order to maintain the hub assembly 1156 along with the associated cannula 1158 in position relative to the permeable seal 1150, a seal mount 1130 is provided. While the seal mount 1130 may be coupled to the permeable seal 1150 by any appropriate structure, in the illustrated embodiment, the permeable seal 1150 and the seal mount 1130 include mating structure in the form of respective interlocking flanges 1131, 1132.

Figure 41:
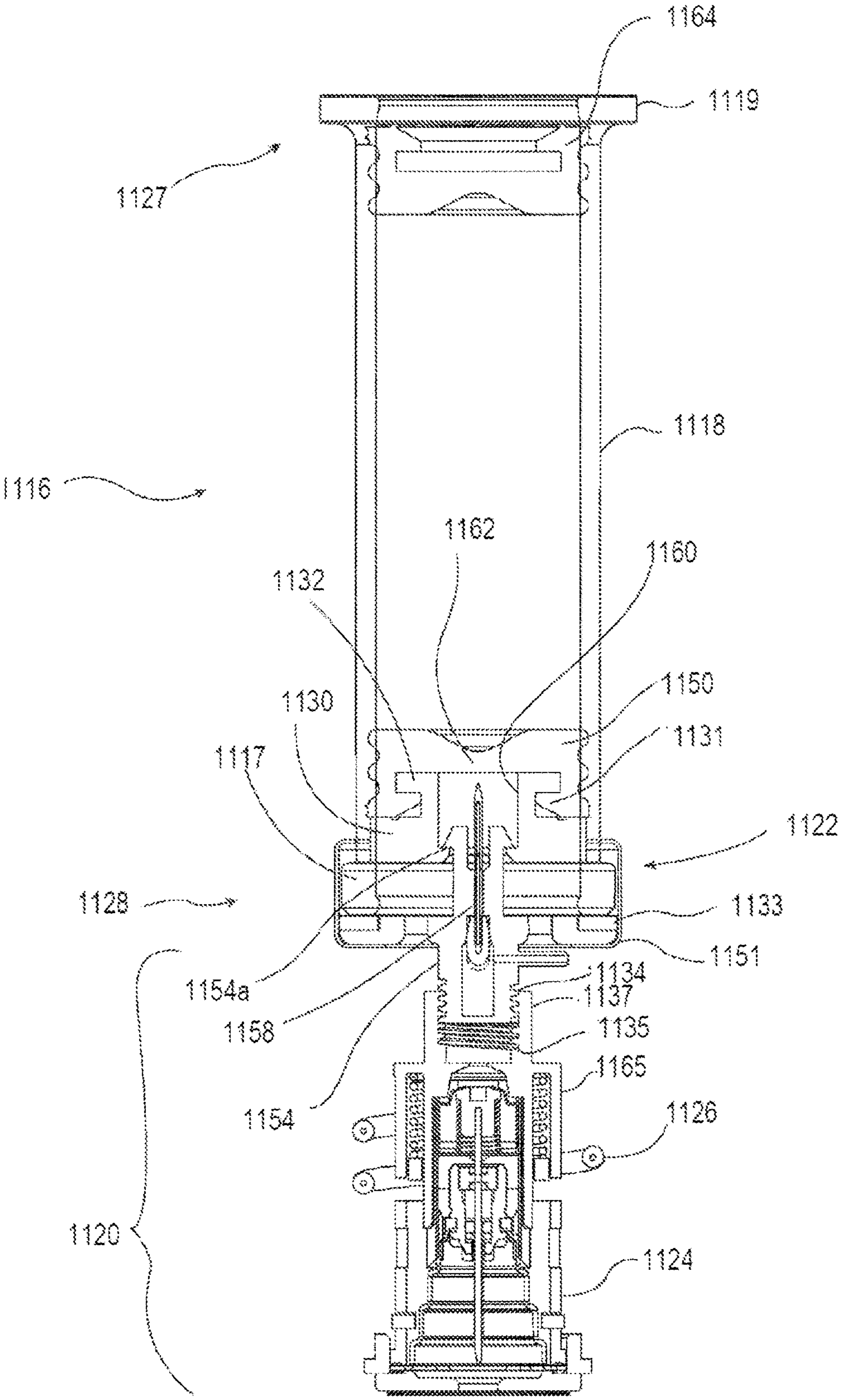
FIG. 41 is a cross-sectional view of the fill-finish cartridge of FIG. 40, cross-hatching being eliminated for the purposes of clarity.
Figure 42:
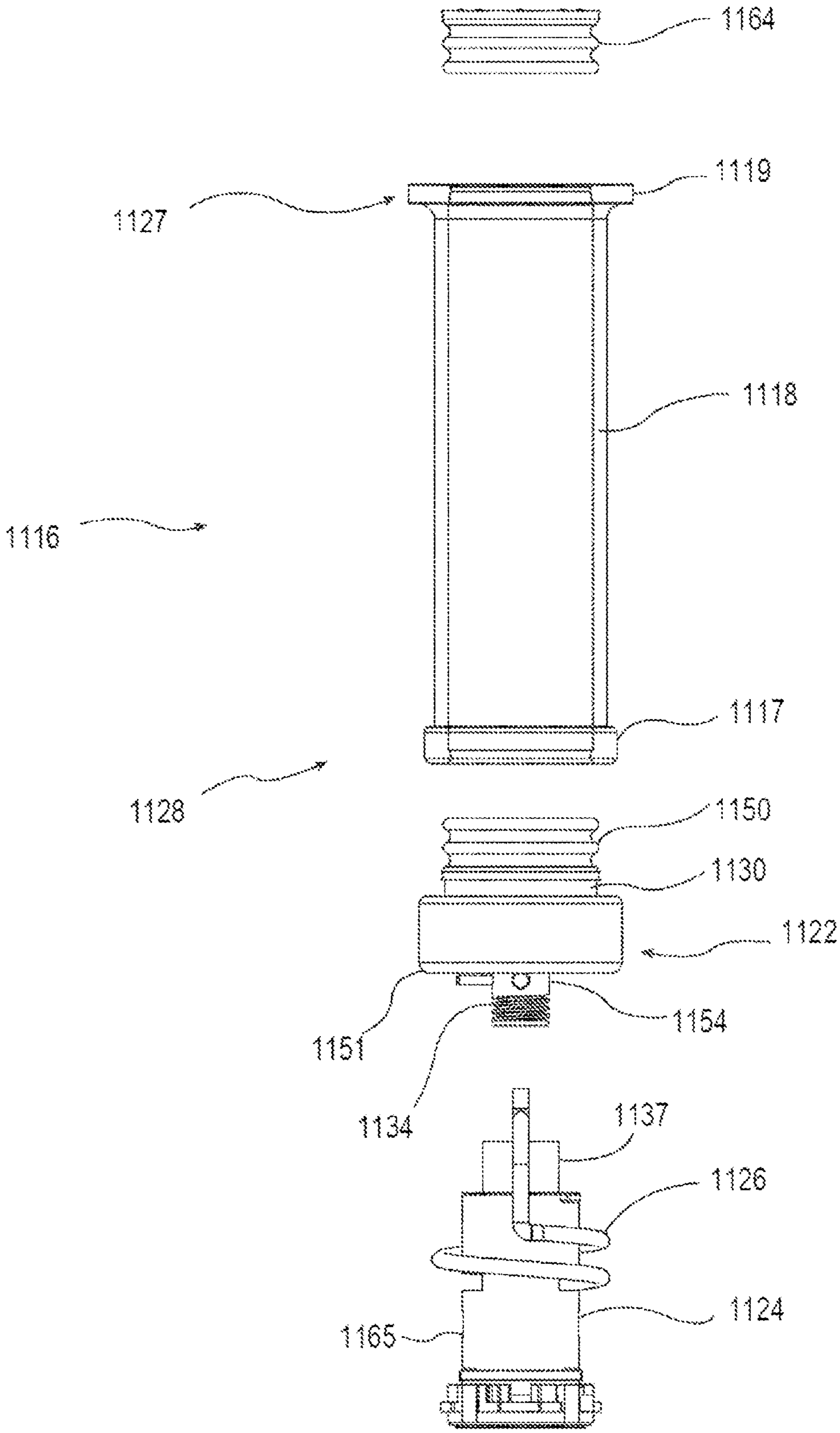
FIG. 42 is a partially exploded view of the fill-finish cartridge of FIGS. 40 and 41, showing a fluid conduit in the final configuration.
Figure 43:
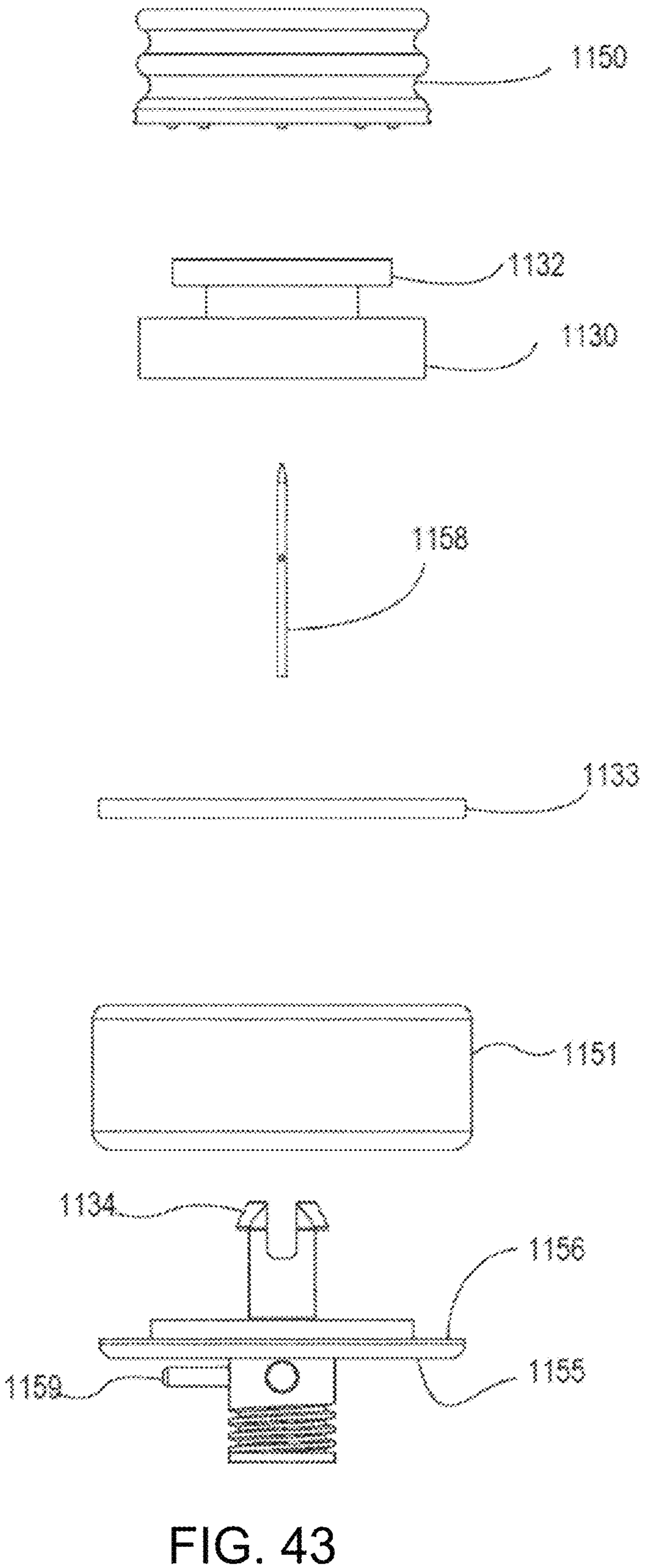
FIG. 43 is an exploded view of the fluid pathway connector of the fill-finish cartridge of FIGS. 40-42.

While the hub assembly 1156 may be assembled with the seal mount 1130 and permeable seal 1150 for coupling to the drug container 1118, the permeable seal 1150 and seal mount 1130 are slidably disposed relative to the hub assembly 1156. In order to allow this sliding, yet coupled relationship, the hub 1154 includes one or more resilient posts 1154*a* that present surfaces that interlock with a complimentarily disposed bore 1160 in the seal mount 1130. As shown in FIG. 41, the when assembled together, the cannula 1158 is disposed subjacent the membrane 1162 of the permeable seal 1150. In this way, the permeable seal 1150, the seal mount 1130 and the coupled hub assembly 1156 form an integrated fluid pathway connector 1122 that may be assembled into the distal end 1128 of the container 1118.

In order to further facilitate assembly of the fluid pathway connector 1122 to the container 1118, a cap 1151 may be provided. One or more gaskets 1133 may be provided between adjacent surfaces of the fluid pathway connector 1122 and, for example, the flange 1117 of the drug container 1118. One such gasket 1133 is illustrated in FIG. 41, although additional gaskets may be provided.

The needle insertion mechanism 1124 may be of any appropriate design, such as, for example, the needle insertion mechanism 1124 illustrated in FIG. 35. The cannula 1158 of the fluid pathway connector 1122 is fluidly connected to the needle 425 of the needle insertion mechanism 1124 by way of the fluid conduit 1126.

In this embodiment the fluid pathway connector 1122 and the needle insertion mechanism 1124 are coupled, for example by mechanical coupling, by way of complimentary threads 1134, 1135. In the illustrated embodiment, fluid pathway connector 1122, here, the hub 1154, includes external threads 1134, while the needle insertion mechanism 1124, here, a bore 436 of an extension 1137 of the insertion mechanism housing 1165, includes complimentary internal threads 1135. It will be appreciated that alternate arrangements are envisioned. For example, the threading arrangement could be reversed, the fluid pathway connector 1122 including internal threads and the needle insertion mechanism 1124 including external threads. Alternately, a threaded collar, or the like, could be provided to couple the components together.

Moreover, although the fluid pathway connector 1122 and the needle insertion mechanism 1124 are coupled in axial alignment in the fill-finish cartridge 1116 for the fill process, the components could be alternately disposed. For example, the axis of the needle insertion mechanism 1124 could be disposed at a right angle to the axis of the fluid pathway connector 1122 and the drug container 1118.

Figure 44:
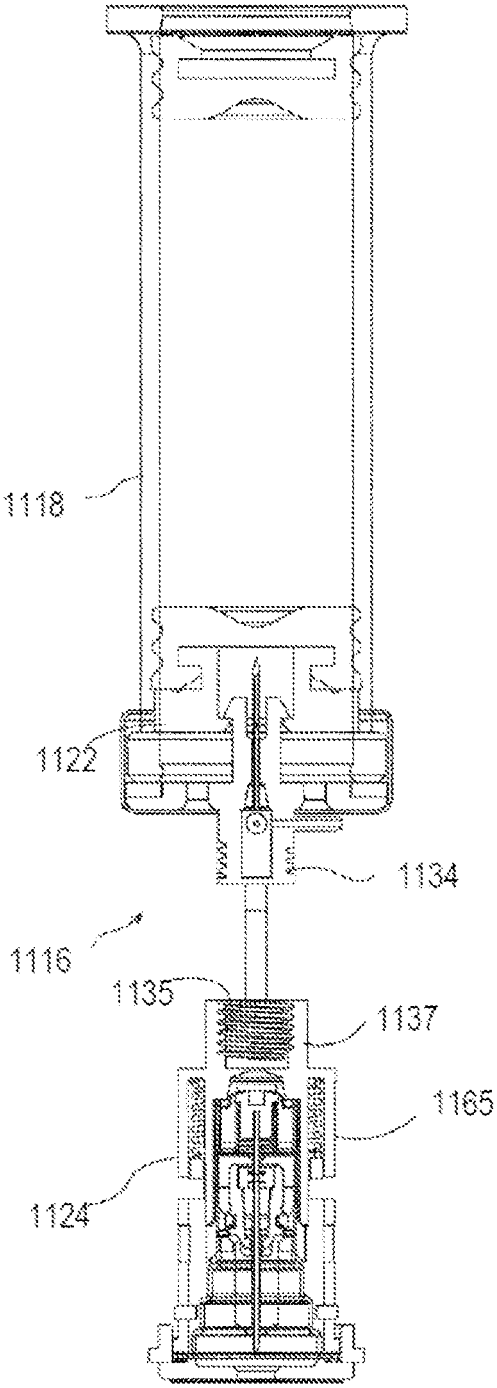
FIG. 44 is a cross-sectional view of the fill-finish cartridge of FIG. 40 similar to the view of FIG. 41, but prior to the coupling of the fluid pathway connector to the needle insertion mechanism, cross-hatching being eliminated for the purposes of clarity.

According to another aspect of the disclosure, the fill-finish cartridge 1116 provides controlled management of the fluid conduit 1126. In this embodiment, the threaded coupling of the needle insertion mechanism 1124 and the fluid pathway connector 1122 may provide controlled placement of the fluid conduit 1126. The uncoupled needle insertion mechanism 1124 and fluid pathway connector 1122 are illustrated in FIG. 44. As the needle insertion mechanism 1124 and the fluid pathway connector 1122 are threaded together to the positions illustrated in FIGS. 40 and 41, the fluid conduit 1126 winds about the housing 1165 of the needle insertion mechanism 1124. While the needle insertion mechanism 1124 and the fluid pathway connector 1122 are illustrated in a disassembled configuration with the fluid pathway connector 1122 being assembled to the container 1118 in FIG. 44, it will be appreciated that the components may be assembled in any order. For example, the needle insertion mechanism 1124 and the fluid pathway connector 1122 may be assembled together prior to coupling the fluid pathway connector 1122 to the container 1118 to form the fill-finish cartridge 1116.

Figure 45:
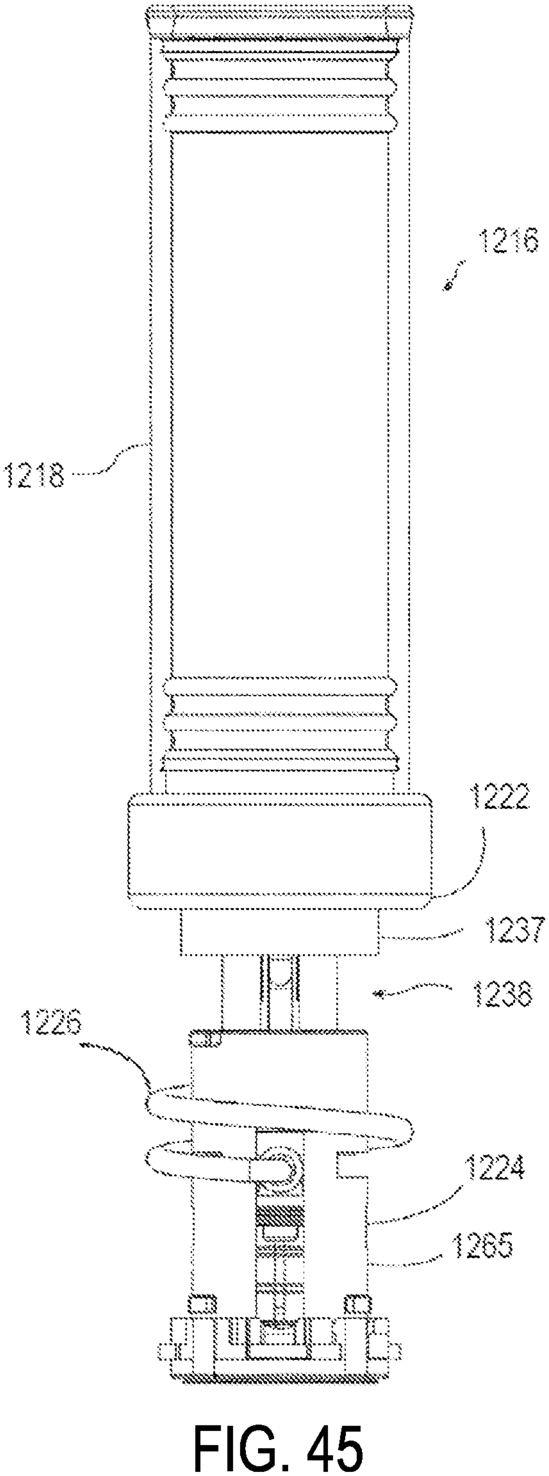
FIG. 45 is a side elevational view of another embodiment of a fill-finish cartridge in an assembled configuration.
Figure 46:
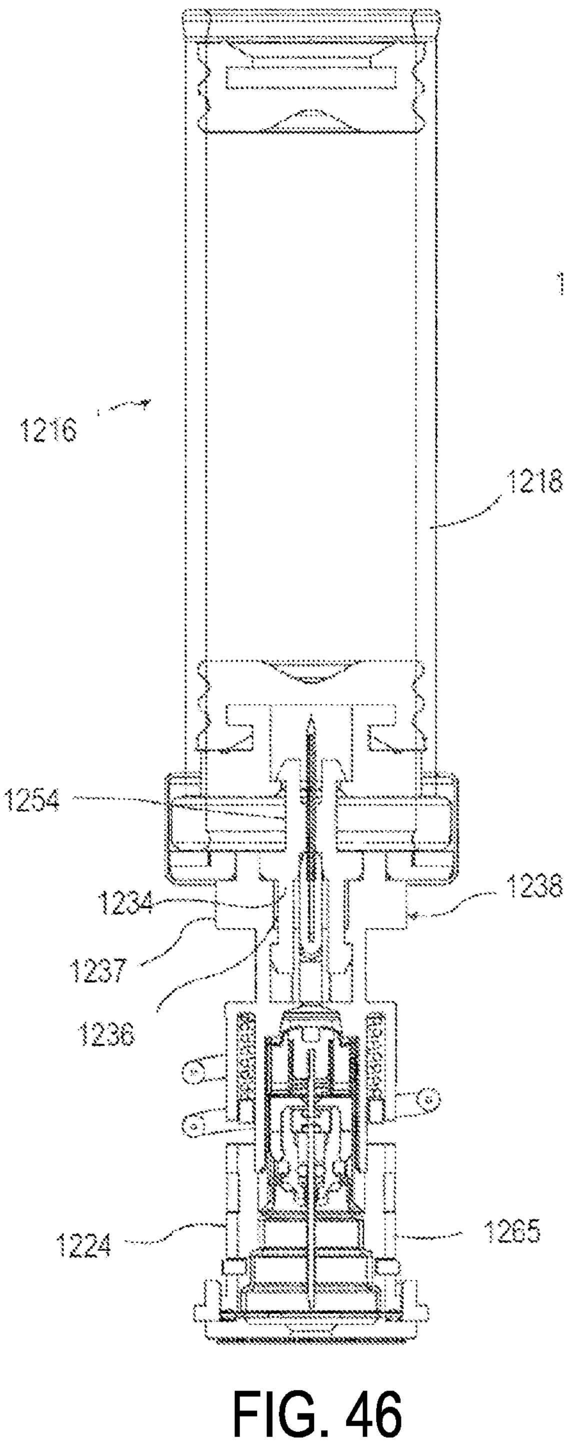
FIG. 46 is a cross-sectional view of the fill-finish cartridge of FIG. 41, cross-hatching being eliminated for the purposes of clarity.
Figure 47:
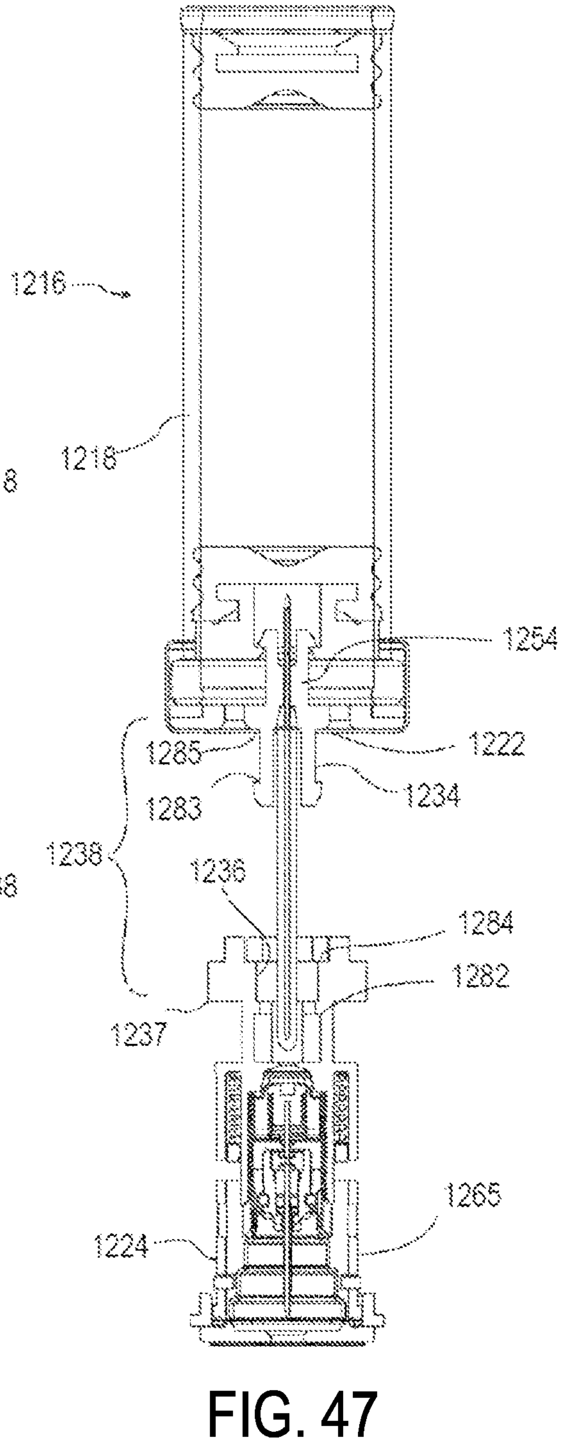
FIG. 47 is a cross-sectional view of the fill-finish cartridge of FIG. 41 similar to the view of FIG. 42, but prior to the coupling of the fluid pathway connector to the needle insertion mechanism, cross-hatching being eliminated for the purposes of clarity.

Turning to the embodiment illustrated in FIGS. 45-47, the fill-finish cartridge 1216 illustrated is similar in operation to the fill-finish cartridge 1116 of FIGS. 40-44. The fill-finish cartridge 1216 of FIGS. 45-47 differs, however, in that the fluid pathway connector 1222 is coupled to the needle insertion mechanism 1224 by way of a snap connection 1238, the needle insertion mechanism 1224 and the fluid pathway connector 1222 including complementary structure that allow the components to snap together. For example, the housing 1265 of the needle insertion mechanism 1224 may include an extension 1237 having a recess or bore 1236, or female portion, adapted to receive a corresponding male portion 1234 of the fluid pathway connector 1222. In order to ensure axial alignment of the extension 1237 and male portion 1234, each may present one or more confronting shoulders. For example, the recess 1236 of the may include shoulders 1282, 1284 against which one or more outwardly extending shoulders 1283, 1285 of the fluid pathway connector 1222 seat. To facilitate connection, the hub 1254 of the fluid pathway connector 1222 may include one or more resilient fingers 586 extending from the hub 1254. During assembly, the fingers 586 may flex such that the shoulders 1283 may move generally radially inward as the fingers 586 are moved through the recess or bore 1236, and snap outward into engagement with shoulders 1282 when the fluid pathway connector 1222 and the needle insertion mechanism 1224 are in their final assembled axial positions. It will be appreciated, however, that the snap connection 1238 may have alternate structure as, for example if the fluid pathway connector 1222 included a shouldered recess and the needle insertion mechanism 1224 included mating outwardly extending shoulders.

As with the embodiment of FIGS. 40-44, the embodiment of FIGS. 45-47 allows for controlled management of fluid conduit 1226 fluidly connecting the fluid pathway connector 1222 and the needle insertion mechanism 1224. For example, the conduit may be wound around the periphery of the housing 1265 of needle insertion mechanism 1224, as illustrated in FIG. 47, before, after, or during the engagement of the snap connection 1238.

While a threaded connection has been described with regard to FIGS. 40-44, and a snap connection with regard to FIGS. 45-47, it will be appreciated that alternate mechanical connections may be utilized to provide sufficient structural integrity to the cartridge to facilitate filling the container in a conventional fill-finish process. For example, a tongue and groove type connection may be utilized. Alternately, or additionally, an external support, such as the bracket 880 of FIGS. 33-36 may be utilized, or the relative positions may be maintained by way of a carrier, such as the carrier 742 of FIGS. 27-30. Other mechanical coupling arrangements are likewise within the purview of the disclosure.

It will thus be appreciated that the inventive arrangement described herein provide varied designs of components that may be assembled in various configurations to provide various designs of fill-finish cartridges that may be sterilized and filled in conventional fill finish processes.

As a further benefit, because the embodiments of the present disclosure enable the manufacture of pre-filled infusion or injection pumps, these pumps may be configured to be single-use or reusable pumps. For example, the fluid pathway assemblies and/or fill-finish cartridge of the present disclosure may be configured to be cartridges which can be replaced within reusable pump devices.

Some embodiments of the present disclosure enable the drug container to be filled in a standard fill-finish process, without the need to expose the drug treatment to the sterilization environment or conditions. Some drug treatments, however, are capable of withstanding the sterilization conditions without degrading, losing efficacy, or the like. Accordingly, in at least one embodiment of the present disclosure, sterilization of the fluid pathway assembly and/or the fill-finish cartridge may occur after the components have been assembled and the drug container has been filled with a pharmaceutical treatment. This method of manufacturing, filling, and using the novel embodiments of the present disclosure still may provide the benefit of being adaptable to a standard fill-finish process. Additionally, this method enables drug delivery device manufacturers and fillers the benefit of only needing to sterilize the components of the fluid pathway (i.e., components which may come in contact with the drug fluid). The fill-finish cartridges, fluid pathway assemblies, and individual components of the present disclosure may be sterilized prior to their integration in a drug delivery device. As such, the other components of the drug delivery device which generally never contact the drug fluid do not need to be sterilized because of the advantages offered by the present disclosure. Accordingly, the embodiments of the present disclosure enable more complex geometries and more standard materials, for example, to be employed for the manufacture of advanced drug delivery devices.

The novel configurations of the fluid pathway assemblies and the fill-finish cartridges of the present disclosure may provide substantial benefits in the marketplace. Embodiments of the present disclosure can readily be manufactured in a sterile environment, integrated into standard drug filling (e.g., fill-finish) process lines for aseptic filling of pharmaceutical treatments, and utilized for cost-effective assembly into drug delivery devices. Each of these advantages has substantial benefits over existing methodologies.

For example, because the fluid pathway assemblies themselves can be sterilized and maintained in a sterile condition during the filling and device assembly processes, the resulting drug delivery device does not need to be sterilized after assembly (i.e., terminally sterilized). This avoids a number of known challenges faced by existing methodologies for the manufacture of drug delivery devices.

Conventional drug delivery devices often require filling at time-of-use because the terminal sterilization of the device cannot be completed with the pharmaceutical drug within the drug container. Various pharmaceutical drugs cannot withstand the temperatures, pressures, and other conditions necessary for sterilization of the device after assembly. In other words, because existing manufacturing processes require sterilization of the entire device, the drug cannot be "pre-filled" into the device prior to sterilization. This adds a complex step after final assembly of the device, which often requires costly additional equipment, handling of separate drug containers, and/or training of the patient to perform the filling step themselves prior to injection. Instead, the embodiments of the present disclosure enable the manufacture, assembly, and use of pre-filled drug delivery devices which maintain the sterility of the fluid pathway assembly through the various manufacturing steps.

Additionally, because the drug delivery devices which incorporate the novel embodiments of the present disclosure do not need to be terminally sterilized, the components of the devices may comprise of other, often less expensive, materials which would not normally withstand the sterilization environment. For example, less expensive plastics may be utilized for certain device components because they do not need to be sterilized after assembly.

In other words, the embodiments of the present disclosure may allow the manufacturer to sterilize only the components which will be in contact with the drug fluid and/or which are necessary to maintain sterile fluid pathways. These embodiments may also allow the pharmaceutical filler to maintain the sterility of these components during the filling and finishing steps associated with the assembly of the drug delivery devices. Similarly, drug delivery devices which incorporate the fluid pathway assemblies of the present disclosure may have smaller or more efficient geometries as the device does not have to be configured for sterilization after assembly.

Additionally, the embodiments of the present disclosure allow for the utilization of standard fill-finish processes to fill the drug container. This greatly simplifies the manufacturing processes used to build drug delivery devices. Standard fill-finish processes utilize trays which hold multiple drug containers, such as syringes. The embodiments of the present disclosure enable a drug delivery device manufacturer, pharmaceutical company, or contract drug filler to fill the drug containers for infusion or injection pumps using the same standard fill-finish processes. These drug containers can be filled aseptically, as is common industry practice, in a cost-efficient manner that preserves the sterility of the fluid pathway assembly. After mounting of the fluid pathway connector mechanism, the combined assembly can then be mated into a drug delivery device without requiring the remainder of the device components to be sterilized. Accordingly, embodiments of the present disclosure may provide novel components which enable the fluid pathway assemblies to be sterilized, assembled, filling, and incorporated into drug delivery devices in a cost-efficient and streamlined process.

Additionally, the fluid pathway assemblies of the present disclosure utilize materials that are substantially non-reactive with therapeutic fluids or drugs, and are suitable for use in pharmaceutical grade applications. The novel fluid pathway assemblies and fill-finish cartridges are configured to minimize or eliminate the possibility of contact or interaction between degradable materials, such as certain plastics, with the therapeutic fluids or drugs. The fluid pathway assemblies, with adaptable needle injection and retraction mechanisms, also may provide fluid conduits from the drug container to the patient, through the needle or cannula, which are substantially absent of degradable materials. Such configurations, when integrated into the fill-finish cartridges or drug delivery devices, may provide increased stability and shelf-life parameters to the drug and drug delivery devices. These characteristics are thought to be highly desirable for generally all pharmaceutical treatments, but perhaps especially of value in drug delivery devices for use with biologics and other complex therapies.

One or more embodiments of the present disclosure may further include certain standard components. For example, the fill-finish cartridge configurations and drug delivery devices of the present disclosure may include one or more membranes. In at least one embodiment, one or more permeable membranes are employed to seal the drug container and/or to ensure a sterile environment and container integrity within the drug chamber. Similarly, the drug container may include a flange. The flange may be pre-formed along any portion of the container, or may be a separate component that is connected to or affixed to the container. In at least one embodiment, the flange is a removable connected component that is connected at the proximal end of the drug container. The flange may be configured to allow the fill-finish cartridge and drug container to rest within a fill-finish tray, for filling with a pharmaceutical compound within a standard fill-finish process. The position, shape, number, and materials for such components may vary, as would be readily appreciated by a skilled artisan, to meet any number of desired characteristics.

Similarly, while the components of the fill-finish cartridge and the fluid pathway assembly are described herein as separate components, it is within the contemplation of the present disclosure that certain groups of these components may be combined to form a single component capable of performing the functions of the individual components. In at least one embodiment the needle insertion and needle retraction mechanisms may be one unified component that may provide a dual function. Additionally, as would be appreciated by one having ordinary skill in the art, the components of the devices may be manufactured as individual components or as single components. For example, the flange may be a component that is pre-formed, during the manufacturing process, as a part of the drug container itself. Accordingly, in at least one embodiment, the flange may be a glass flange extension of the container. Furthermore, while the components of the fill-finish cartridge and fluid pathway assembly are described herein as separate components, they may be unified components having multiple functions. The configuration of the components and their assembly may vary based on the assembly process, the device parameters, and other desired characteristics.

Embodiments of the present disclosure may provide fluid pathway assemblies, fill-finish cartridges, methods of manufacturing such cartridges, and their methods of use. The fill-finish cartridges and fluid pathway assemblies may be utilized in a number of different configurations and may themselves comprise of one or more components. Such modifications are contemplated by and encompassed in the embodiments of the present disclosure. Other components may similarly be single components, unified components, or multi-purpose components, as described in the embodiments discussed above. Thus, it is intended that the present disclosure covers the modifications and variations of this disclosure, provided they come within the scope of the appended claims and their equivalents.

VII. Activation Mechanism

Figure 74:
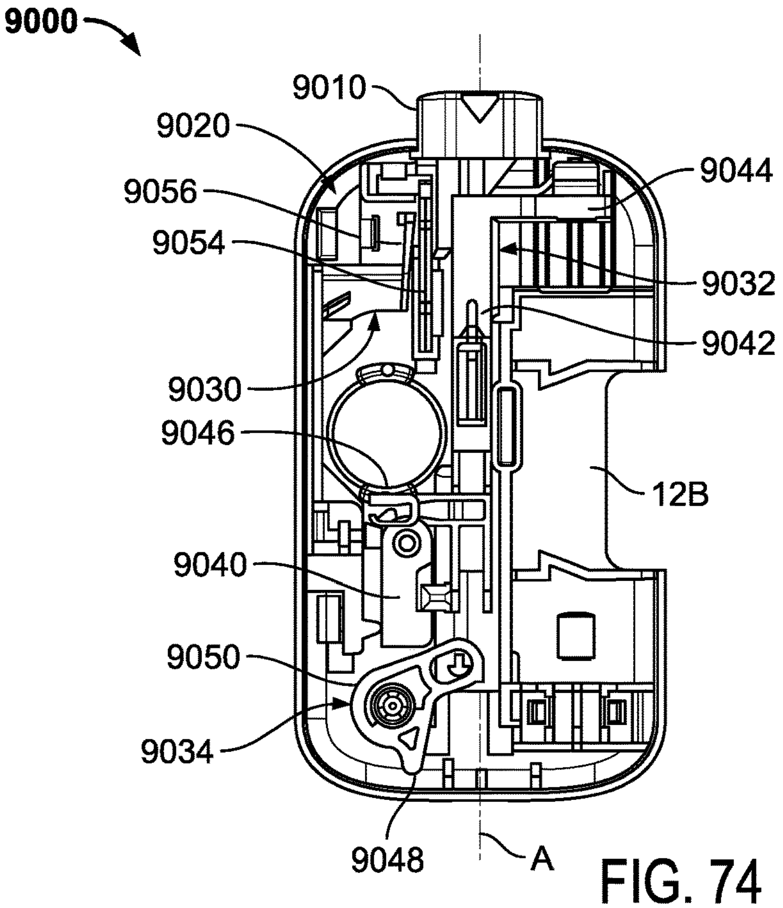
Figure 75:
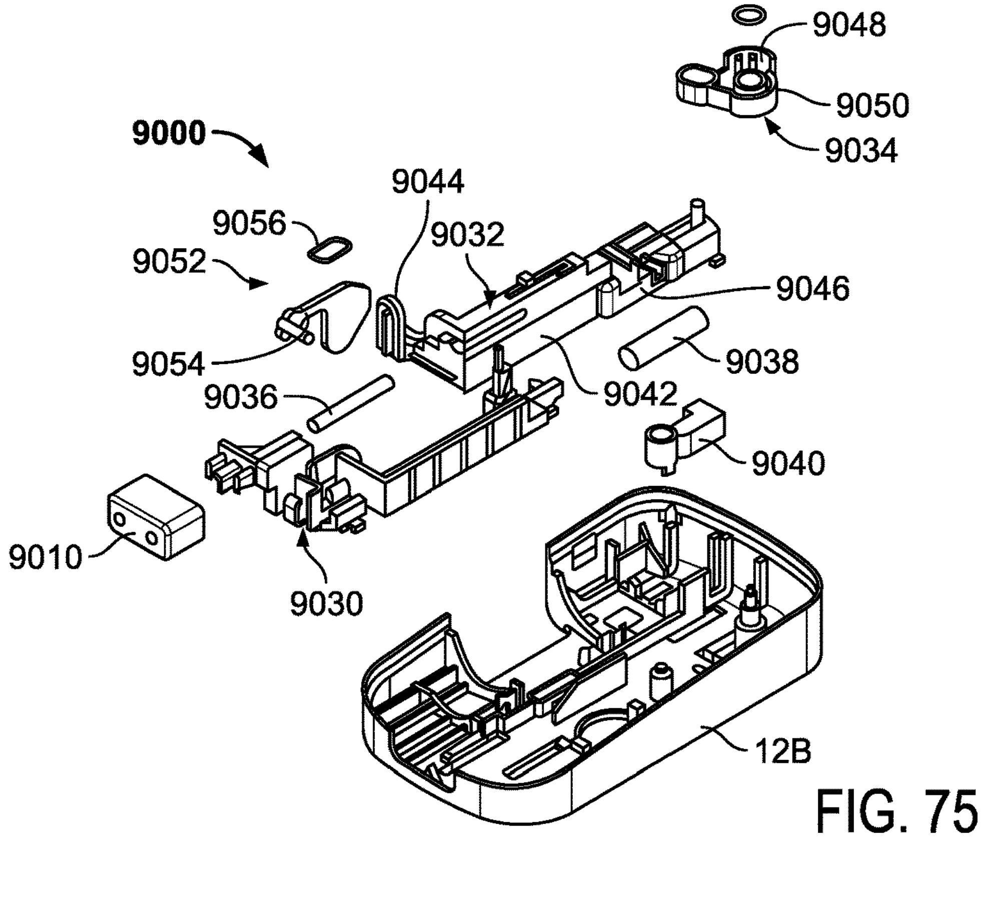

Described below in connection with FIGS. 74 and 75 is an activation mechanism 9000 enabling a user (e.g., a self-administering patient) to activate one or more mechanisms or subsystems of a drug delivery device disclosed herein (e.g., the drug delivery device 10, 910, 2010, 6000, or 8000). The activation mechanism 9000 may be configured to activate, simultaneously or sequentially, one or more of: a drive mechanism (e.g., the drive mechanism 100, 500, 1000, or 2100); a needle insertion mechanism (e.g., the needle insertion mechanism 200, 624, or 724); a fluid pathway connector (e.g., the fluid pathway connector 300, 622, 722, 822, 922, or 2300); and/or a power and control system (e.g., the power and control system 400 or 2400).

FIGS. 74 and 75 illustrate that the activation mechanism 9000 may include a button 9010, which may correspond to the start button 14 or 2014, and a trigger assembly 9020. The button 9010 may protrude from the housing 12, such as through an opening between the upper housing 12A and the lower housing 12B, and may be manually displaceable by a user, such that the button 9010 can be depressed into the housing 12 by the user. In at least one embodiment, the button 9010 may be configured to slide back-and-forth in a linear direction that is orthogonal to an exterior surface of the housing 12 from which the button 9010 protrudes.

In general, the trigger assembly 9020 may be configured to transfer, convert, and/or transmit motion of the button 9010 into motion that activates one or more of a drive mechanism, a needle insertion mechanism, a fluid pathway connector, and/or a power and control system. In at least one embodiment, in response to displacement of the button 9010 by the user, the trigger assembly 9020 may be configured to simultaneously or sequentially: (1) activate a needle insertion mechanism (e.g., the needle insertion mechanism 200, 624, or 724) so that the needle insertion mechanism inserts a needle (e.g., the needle 214) and/or a cannula (e.g., cannula 234) into a patient; (2) activate a fluid pathway connector (e.g., the fluid pathway connector 300, 622, 722, 822, 922, or 2300) to establish fluid communication between a drug container (e.g., the container 50, 618, 718, 818, 918, 1118, or 2050) and the insertion mechanism; (3) activate a drive mechanism (e.g., the drive mechanism 100, 500, 1000, or 2100) to force a drug (e.g., a PCSK9 specific antibody, a G-CSFs, a sclerostin antibody, a CGRP antibody, etc.) stored in the drug container through the fluid pathway connector and the insertion mechanism and ultimately into the patient. In at least one embodiment, displacement of the button 9010 by the user may also activate a power and control system (e.g., the power and control system 400 or 2400), either simultaneously or sequentially with the activation of the needle insertion mechanism, the fluid pathway connector, and/or the drive mechanism. Accordingly, the trigger assembly 9020 may permit a user to activate multiple mechanisms and/or subsystems with a single push of the button 9010, thereby simplifying operation of the drug delivery device for the user.

As shown in the exploded assembly view of FIG. 75, the trigger assembly 9020 may include a plurality of interconnected and/or cooperating components including a trigger arm 9030, a first control arm 9032, a second control arm 9034, a button spring 9036, a main slide spring 9038, and a latch 9040. The trigger arm 9030 may be connected directly to the button 9010 such that the trigger arm 9030 and the button 9010 move together as a single unit. The button spring 9036 may be disposed between the trigger arm 9030 and the first control arm 9032; and the main slide spring 9038 may be disposed between the first control arm 9032 and the housing 12. In at least one embodiment, the button spring 9036 and the main slide spring 9038 may be arranged in series and parallel to each other, with the first control arm 9032 arranged therebetween. The main slide spring 9038 may have a stiffness that is greater than the button spring 9036. Accordingly, initial displacement of the button 9010 by the user may cause the button spring 9036 to compress between the trigger arm 9030 and the first control arm 9032; however, due to its greater stiffness, the main slide spring 9038 may not compress between the first control arm 9032 and the housing 12 during the initial displacement of the button 9010. Further displacement of the button 9010 by the user may cause the individual coils of the button spring 9036 to contact each other, thus rendering additional compression of the button spring 9036 extremely difficult or impossible. Thus, further displacement of the button 9010 may cause the main slide spring 9038 to compress between the first control arm 9032 and the housing 12. Accordingly, the first control arm 9032 may move in response to displacement of the button 9010 only after the button spring 9036 has been sufficiently compressed. The interaction between the button spring 9036 and the main slide spring 9038, and the resulting movement of the first control arm 9032, may be referred to as a "point-of-no-return" feature of the button 9010.

The delay provided by the point-of-no-return feature of the button 9010 gives the user time to affirm his or her intent to activate the drug delivery device. Furthermore, the point-of-no-return feature of the button 9010 reduces the risk of accidental activation, and provides the user with tactile feedback that informs the user that he or she is approaching activation as the button spring 9036 becomes increasingly compressed.

The first control arm 9032 may be slidably connected to the housing 12 such that linear displacement of the button 9010 causes linear displacement of the first control arm 9032. The second control arm 9034 may be rotatably connected to the first control arm 9032 and rotatably connected to the housing 12 such that linear displacement of the first control arm 9032 causes rotation of the second control arm 9032 relative to the first control arm 9032 and the housing 12.

The first control arm 9032 may be configured to interact with and activate both the fluid pathway connector and the needle insertion mechanism. The first control arm 9032 may include a main body 9042 extending along a longitudinal axis A, and a first protrusion 9044 and a second protrusion 9046 extending from opposite sides of the main body 9042 away from the longitudinal axis A. During operation, the first control arm 9032 may slide in a direction that is parallel to the longitudinal axis A. In at least one embodiment, the first protrusion 9044 and the second protrusion 9046 each may extend orthogonally to the longitudinal axis A. By arranging the first and second protrusions 9044 and 9046 on opposite sides of the main body 9042, the first and second protrusions 9044 and 9046 can be used to activate mechanisms located on opposite sides of the drug delivery device. Accordingly, the first and second protrusions 9044 and 9046 may facilitate an arrangement that reduces the overall size of the drug delivery device.

The first protrusion 9044 of the first control arm 9032 may be configured to contact and move a portion of a fluid pathway connector such that fluid communication is established between a drug container and an insertion mechanism. For example, the first protrusion 9044 may be configured to contact and move the connection hub 310 of the fluid pathway connector 300 toward the drug container 50 in response to displacement of the button 9010. Consequently, the piercing member 330 mounted on the connection hub 310 may pierce the pierceable seal 56 and access the interior of the drug container 50, thereby establishing fluid communication between the drug container 50 and the needle insertion mechanism 200 via the fluid pathway connector 300. An example of linear movement imparted to the connection hub 310 by the first protrusion 9044 is illustrated by FIGS. 4A and 4B.

The second protrusion 9046 of the first control arm 9032 may be configured to contact and move a portion of a needle insertion mechanism such that the needle insertion mechanism inserts a needle and/or a cannula into the patient. For example, the second protrusion 9046 may be configured to contact and move lockout pin(s) 208 (i.e., the second retainer) so that they no longer occupy the retaining position illustrated in FIG. 11A. As a result, the insertion biasing member 210 may be allowed to de-energize and insert the needle 214 and the cannula 234 into the patient, as depicted in FIG. 11B.

The second control arm 9034 may be configured to contact and move a portion of a drive mechanism such that the drive mechanism discharges a drug from the container. For example, rotation of the second control arm 9034 caused by linear displacement of the first control arm 9032 may result in the second control arm 9034 to displace the clip 2115 (i.e., the first retainer) from its retaining position illustrated in FIG. 23A. Consequently, the piston biasing members 2106, 2122 may be allowed to de-energize and move the plunger seal 2060 to discharge drug from the distal end of the drug container 2050 and ultimately to the patient. In the embodiment illustrated in FIG. 74, linear movement of the first control arm 9032 away from the side of the housing 12 having the button 9010 may cause clockwise rotation of the second control arm 9034. A radial protrusion 9048 extending from a center portion 9050 of the control arm 9034 may be connected to the clip 2115 (not illustrated) such that the clockwise rotation of the radial protrusion 9048 moves the clip 2115 from its retaining position to its releasing position.

Still referring to FIGS. 74 and 75, the activation mechanism 9000 may incorporate one or more safety features to prevent premature and/or inadvertent activation of the drug delivery device. In at least one embodiment, the activation mechanism 9000 may include a body contact sensor 9052 to detect contact between the lower housing 12B and the patient's skin. In at least one embodiment, the body contact sensor 9052 may correspond to the on-body sensor 24 illustrated in FIG. 1C. The body contact sensor 9052 may include an interlock 9054 rotationally connected to the lower housing 12B and interlock spring 9056 configured to bias a portion of the interlock 9054 through an opening 9058 in the lower housing 12B. Contact between the lower housing 12B and the patient's skin may cause the interlock 9054 to retract into the housing 12 against the biasing force of the interlock spring 9056. When the interlock 9054 protrudes from the housing 12B through the opening 9058, the interlock 9054 may occupy a lock position in which the interlock 9054 obstructs linear displacement of the trigger arm 9030, as illustrated in FIG. 74. Accordingly, a user may be unable to depress the button 9010 when the interlock 9054 occupies its lock position. When the interlock 9054 retracts into the housing 12 due to contact with the patient's skin, the interlock 9054 may move to an unlock position in which the interlock 9054 does not obstruct movement of the trigger arm 9030. Accordingly, when the interlock 9054 occupies its unlock position, the user may be able to depress the button 9010 and activate, via the trigger assembly 9020, one or more of the drive mechanism, the needle insertion mechanism, the fluid pathway connector, and/or the power and control system.

While the body contact sensor 9052 functions primarily as a mechanical lockout mechanism, alternative embodiments may incorporate a body contact sensor that is electrically based such as, for example, a capacitive- or impedance-based sensor which must detect tissue before permitting activation of a power and control system. In at least one embodiment, such an electrically based on-body sensor may incorporate a resistor with an impedance of approximately (e.g., ±10%) 1 MΩ.

VIII. Additional Embodiments of Fluid Pathway Connector

At least some of the drug delivery devices described in this application, including at least those described in connection with FIGS. 1-47, 74, 75, and 77-91B, may be configured to incorporate the embodiments of the fluid pathway connector described below in connection with FIGS. 48-56 and 76A-76C.

Figure 48A:
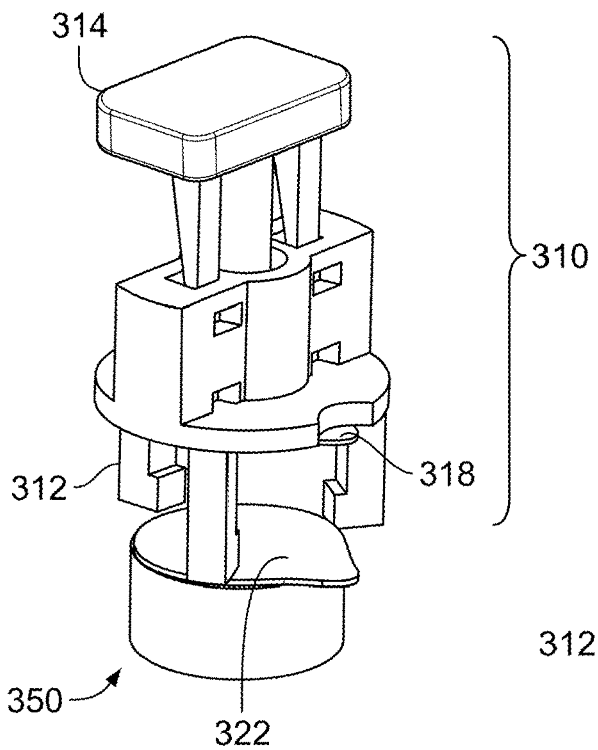
FIG. 48A is an isometric view of an embodiment of a fluid path connection assembly and drug container in an unmounted configuration.
Figure 48B:
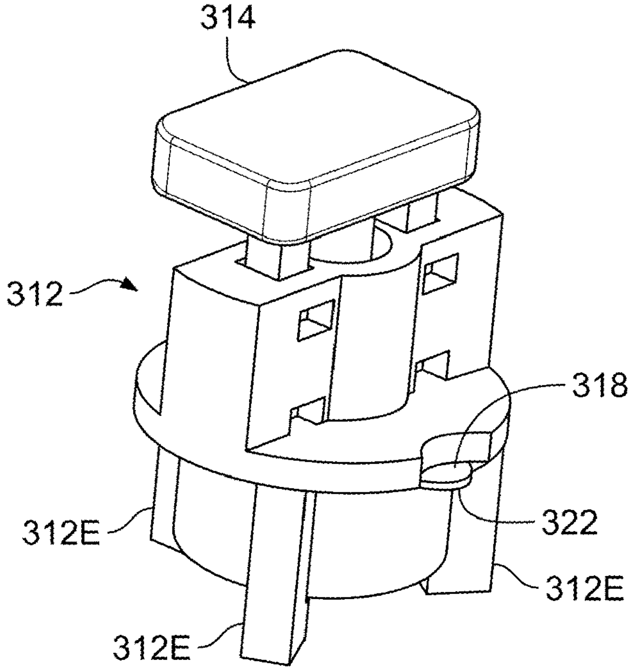
FIG. 48B is an isometric view of the embodiment shown in FIG. 48A in a mounted configuration.
Figure 48C:
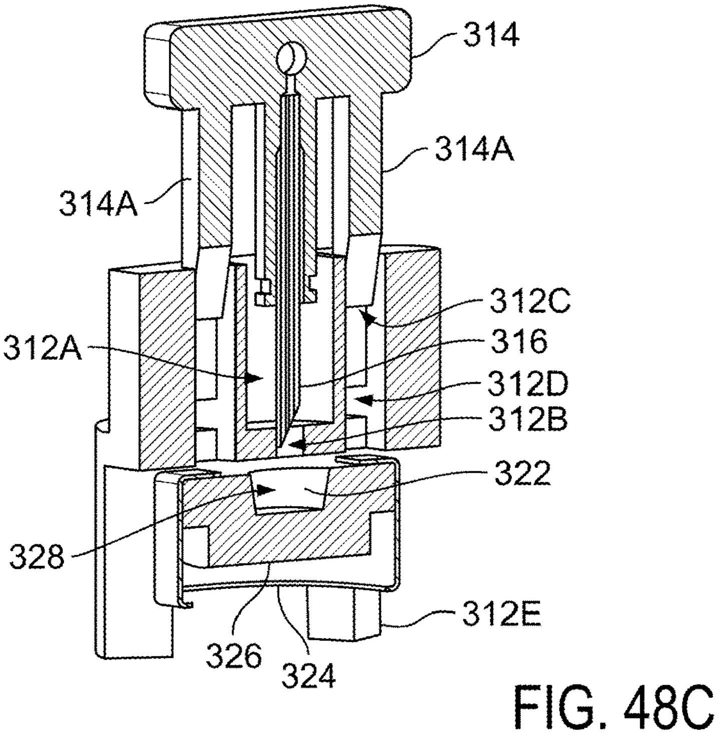
FIG. 48C is a cross-sectional isometric view of the embodiment shown in FIG. 48A in a mounted configuration.

In the processes of filling drug containers and other drug delivery devices, it is sometimes necessary to connect two or more sterile components or subassemblies. For example, wearable injectors or drug pumps may include a drug container which may be filled with a fluid drug using standard pharmaceutical fill-finish processes. After filling of the drug container, it may be necessary to connect the drug container to one or more additional components or subassemblies such that a fluid communication may be established between the drug container and these components. Maintaining the fluid path in an aseptic condition is critical, preventing the introduction of harmful microbes to the drug and/or fluid pathway. The connection of two or more aseptic components or subassemblies is typically performed in an aseptic environment, such as a clean room, thereby ensuring that no harmful microbes are introduced to the assembly. This, however, may lead to increased cost to manufacture the drug delivery devices Embodiments of the present disclosure allow aseptic connections to be made between two or components or subassemblies in a septic environment. As seen in FIGS. 48A-48C, the connection hub 310 of the fluid pathway connector may be connected to the drug container 350. FIG. 48A shows these components prior to connection. A first film 318 is in place on connection hub 312. First film 318 covers aperture 312B of connection hub 312 and prevents microbes from entering cavity 312A through aperture 312B, thereby maintaining cavity 312B and piercing member 316 in an aseptic condition. Piercing member 316 is partially disposed in cavity 312A and at least partially disposed in retainer 314. The piercing member may be a hollow needle. Retainer 314 is engaged with connection hub 312 and may be configured for translation with respect to the connection hub in a direction parallel to the long axis of piercing member 316. The retainer may include one or more locking arms 314A which may engage one or more first recesses 312C in connection hub 312. The locking arms may include protrusions at their lower end, which in the locked position are at least partially disposed in the upper recesses. The engagement of the flex arms maintains the spatial relationship of the retainer and the connection hub.

The drug container 350 may include a crimp cap 324 that maintains a connection between a pierceable seal 326 and a barrel (not shown). The pierceable seal maintains the fluid drug within the barrel and prevents microbes and other substances from entering the drug chamber. A recess 328 is formed by the geometry of the pierceable seal. A second film 322 is affixed to the drug container such that it encloses recess 328, thereby maintaining recess 328 in an aseptic condition. The first and second films may be constructed of any material capable of providing the barrier properties required to maintain the aseptic condition of the associated surfaces. In a preferred embodiment, the films are constructed from a foil material. Alternatively, the films may be any type of sterilizable membrane, film, or foil. Additionally, the film may be removable and/or pierceable as well as breathable and/or permeable.

An adhesive may be applied to the exterior surfaces of both first film 318 and second film 322 prior to joining the fluid pathway connector and the drug container 312. The adhesive may contain antimicrobial, antibacterial, and antiviral compounds to limit or reduce the number of such substances on the surface of the seals. During connection, flex arms 312E may engage crimp cap 324 or another portion of the drug container 312, thereby limiting axial translation of the fluid pathway connector with respect to the drug container 312. In this position, first film 318 and second film 322 are in contact with, or in close proximity to, one another. If an adhesive is present on the faces of one or more of the films the films may be bonded together.

After the fluid pathway connector and drug container 312 are joined, the retainer 314 may be translated axially with respect to the connection hub. Translation of the retainer causes locking arms 314A to flex and become disengaged from first recess 312C. Translation of the retainer causes needle 316 to also translate. This translation causes the needle to pierce first film 318 and second film 322. After translation of the retainer, the piercing member is at least partially disposed in recess 328 of pierceable seal 326. The retainer may be further translated, leading to the piercing of pierceable seal 326 by piercing member 316. After piercing of the pierceable seal a fluid path is established from the drug container and through the needle. The needle may also be in fluid communication with a conduit, the conduit being configured to carry the fluid contents to a delivery mechanism such as an insertion mechanism for delivery to a patient. Piercing of the first and second films may occur at the time of assembly. Alternatively, the piercing of the films may occur at or near the time-of-use of the drug delivery device. Piercing of the pierceable seal at or near the time-of-use may be initiated, by the patient, by interaction with an activation mechanism.

In some embodiments, the end of the piercing member may remain disposed within cavity 328 until time-of-use. The pierceable seal may be configured such that, in response to hydraulic and/or pneumatic pressure within the drug chamber, it deforms and is caused to come into contact with the piercing member. This deformation of the pierceable seal leads to the piercing of the seal by the piercing member.

Figure 49C:
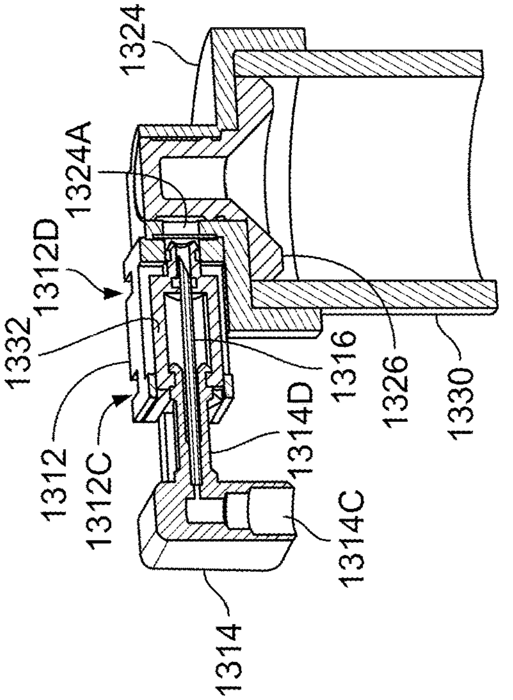
FIG. 49C is a cross-sectional isometric view of the embodiment shown in FIG. 49A in a mounted configuration.
Figure 49D:
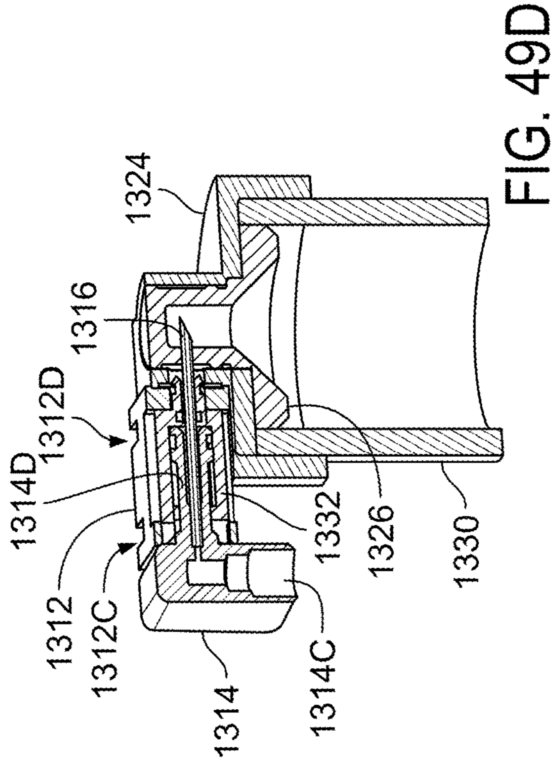
FIG. 49D is a cross-sectional isometric view of the embodiment shown in FIG. 49A after connection of the fluid path.
Figure 49A:
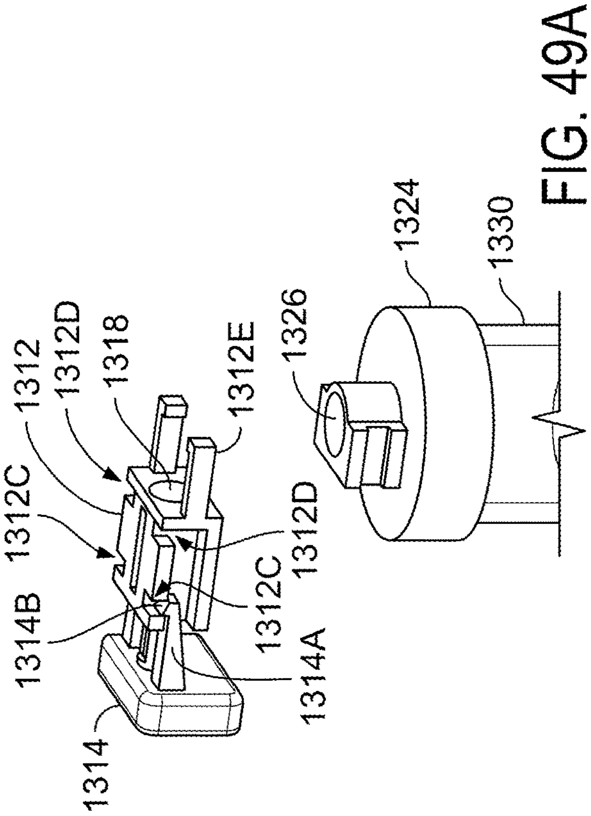
FIG. 49A is an isometric view of an embodiment of a fluid path connection assembly and a drug container in an unmounted configuration.
Figure 49B:
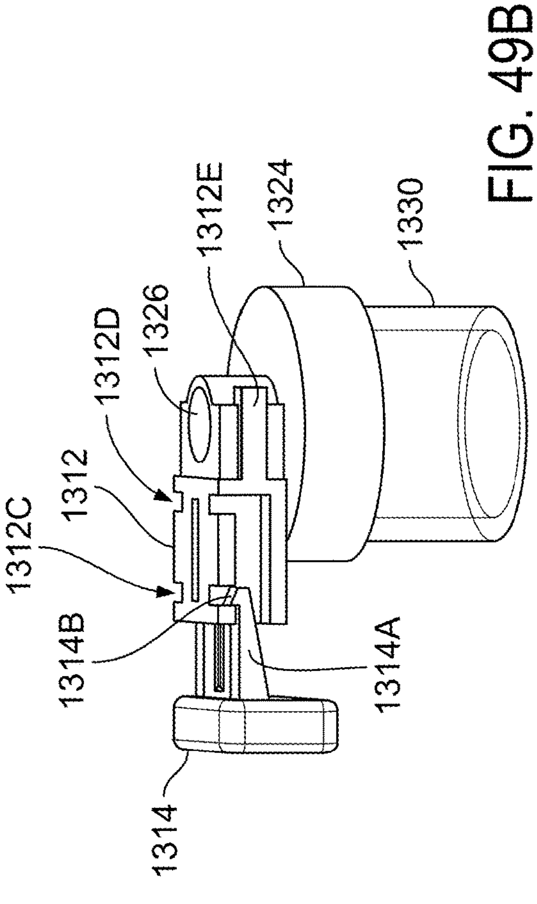
FIG. 49B is an isometric view of the embodiment shown in FIG. 49A in a mounted configuration.

FIGS. 49A-49D show an embodiment in which a connection hub 1312 of a fluid pathway connector is connected to a drug container such that the long axis of the piercing member 1316 is orthogonal to the long axis of the drug barrel 1330 of the drug container. As seen in FIG. 49B, flex arms 1312E engage a portion of cap 1324 to securely attach the fluid pathway connector to the drug container. The fluid pathway connector may further include insert 1332 disposed within connection hub 1312. Extension 1314D of retainer 1314 may be sealingly engaged with insert 1332 and be configured for axial translation with respect to the insert. Protrusions 1314B of retainer 1314 are initially disposed in first recesses 1312C of connection hub 1312. In this position, the piercing end of piercing member 1316 is disposed within insert 1332. FIG. 49C shows a cross-sectional view of the drug container and fluid pathway connector after assembly and before connection of the fluid path. As seen in the cross-section, cap 1324 may contain side port 1324A which allows the piercing member to access the pierceable seal. Also shown in FIG. 49C is conduit port 1314C which may be configured to allow a conduit to be connected to the retainer. This conduit may provide a fluid path that connects the drug container to a delivery mechanism for delivery of the fluid drug to the patient. FIG. 49D is a cross-section showing the assembly in an open fluid path configuration. As shown, retainer 1314 has been displaced toward the center axis of the drug container. Protrusions 1314B of flex arms 1314 have disengaged from first recesses 1312C and have engaged second recesses 1312D. Piercing member 1316 has pierced first film 1318, second film 1322, and pierceable seal 1326. The piercing of each of these may occur at time of use upon patient initiation. Alternatively, the first and second film may be pierced at time of assembly. This creates a fluid path from the drug container, through the piercing member, conduit, and insertion mechanism for delivery to the patient. The connection of the fluid pathway connector such that the long axis of the piercing member is orthogonal to the long axis of the drug container may allow for more compact packaging in a drug delivery device.

Figure 50A:
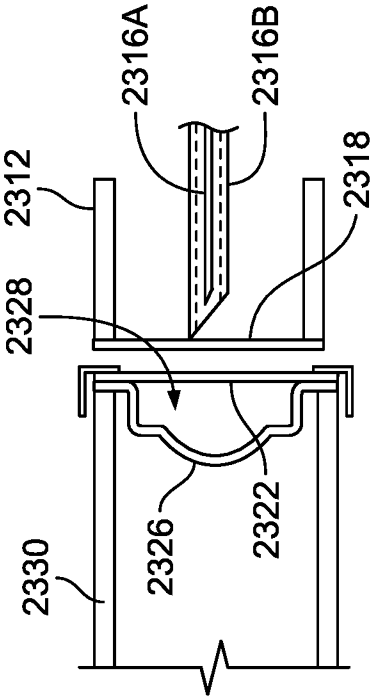
FIG. 50A is a cross-sectional side view of an embodiment of a fluid path connection assembly and a drug container in an mounted configuration.
Figure 50B:
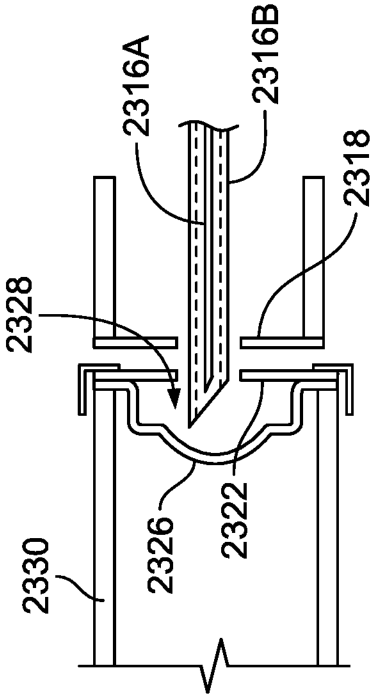
FIG. 50B is a cross-sectional side view of the embodiment shown in FIG. 50A after the first and second films have been pierced.
Figure 50C:
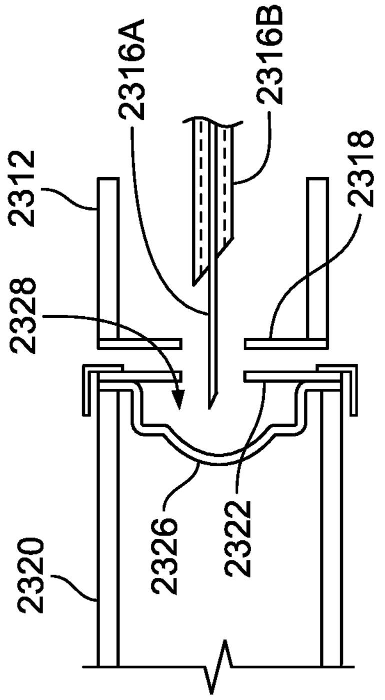
FIG. 50C is a cross-sectional side view of the embodiment shown in FIG. 50A after retraction of the outer piercing member.
Figure 50D:
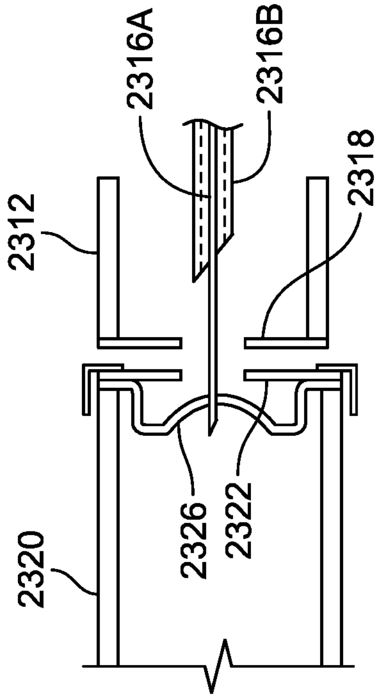
FIG. 50D is a cross-sectional side view of the embodiment shown in FIG. 50A after connection of the fluid path.
Figure 51A:
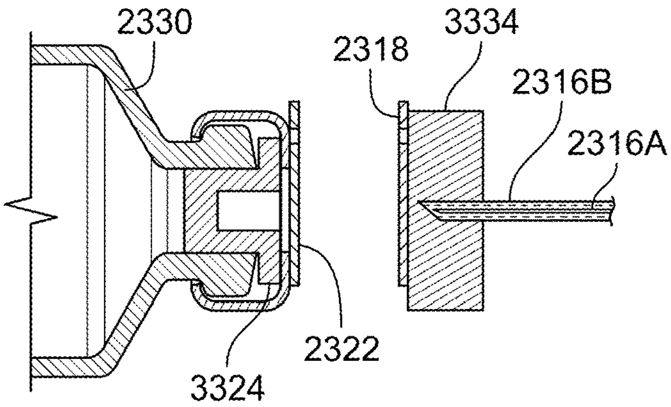
FIG. 51A is a cross-sectional side view of an embodiment of a fluid path connection mechanism and a drug container in an unmounted configuration.
Figure 51B:
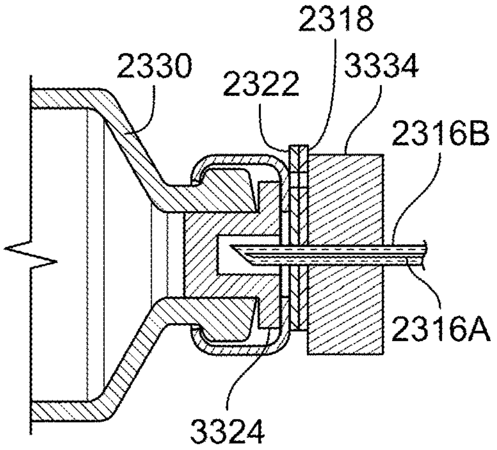
FIG. 51B is a cross-sectional side view of the embodiment shown in FIG. 51A after piercing of the first and second films by the outer piercing member.
Figure 51C:
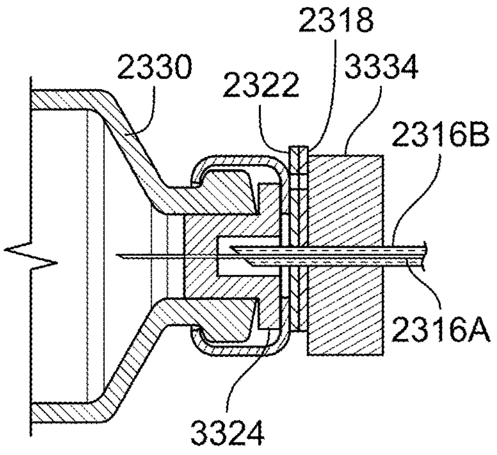
FIG. 51C is a cross-sectional side view of the embodiment shown in FIG. 51A after connection of the fluid path.
Figure 52A:
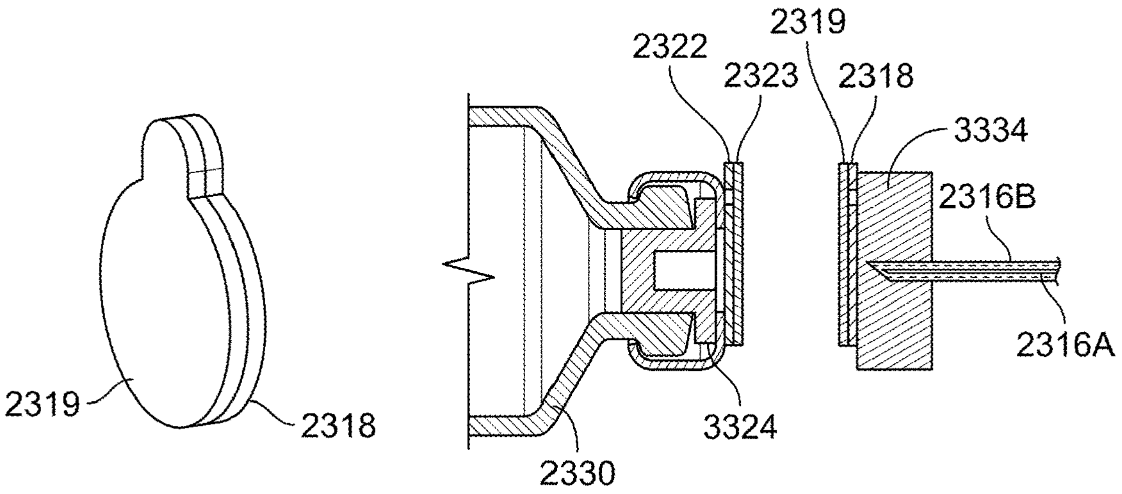
FIG. 52A is a cross-sectional side view of an embodiment of a fluid path connection mechanism and a drug container in an unmounted configuration.
Figure 52B:
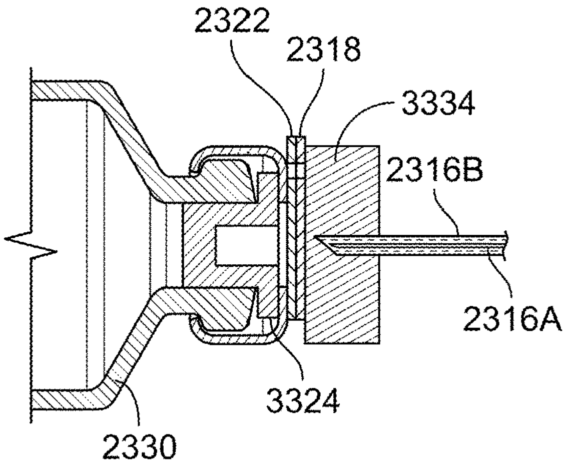
FIG. 52B is a cross-sectional side view of the embodiment shown in FIG. 52A in a mounted configuration.
Figure 52C:
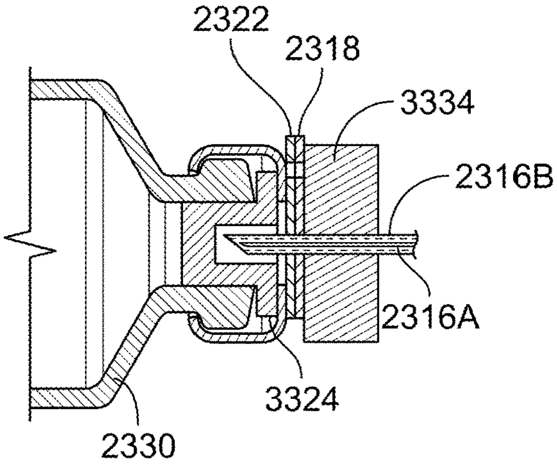
FIG. 52C is a cross-sectional side view of the embodiment shown in FIG. 52A after piercing of the first and second films by the outer piercing member.
Figure 52D:
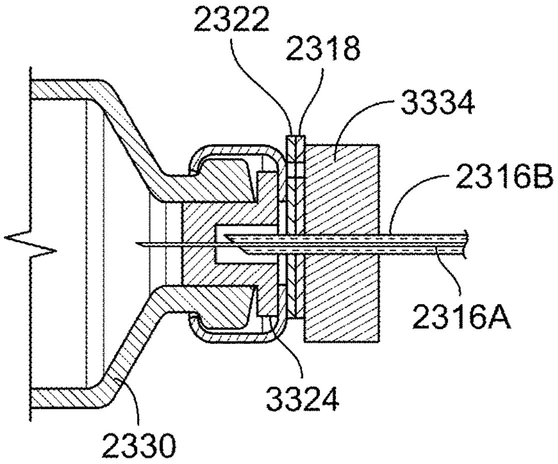
FIG. 52D is a cross-sectional side view of the embodiment shown in FIG. 52A after connection of the fluid path.

In other embodiments, shown in FIGS. 50A-50D, the piercing member includes an inner piercing member 2316A and an outer piercing member 2316B. The inner piercing member 2316A is disposed within the hollow outer piercing member 2316B. After connection of the connection hub 2312 to the drug container 2330, the outer piercing member 2316B pierces the first film 2318 covering terminal end of the connection hub 2312 and the second film 2318 covering the terminal end of the drug container 2330, while maintaining the inner piercing member 2316A within its hollow inner cavity. The piercing may be caused by joint motion of the piercing members 2316A and 2316B toward the drug container or, alternatively, may be caused by the drug container displacing the connection hub, thereby exposing the outer piercing member 2316B. Because the inner piercing member 2316A does not contact the first and second films 2318 and 2322, any contaminants present on the surface of the films 2318 and 2322 are not in contact with the inner piercing member 2316A. After piercing the films 2318 and 2322 the outer piercing member is retracted, thereby exposing the inner piercing member 2316A. In this position, shown in FIG. 50C, the end of the inner piercing member 2316A is disposed in the cavity 2328 created by the pierceable seal 2326. In response to increased hydraulic and/or pneumatic pressure within the drug container the pierceable seal 2326 may deform, as shown in FIG. 50D. The deformation of the pierceable seal 2326 causes the inner piercing member 2316A to pierce the pierceable seal 2326, thereby creating a fluid path from the drug container 2330 through the inner piercing member 2316A for delivery to the patient.

As shown in the alternative embodiment of FIGS. 51-52, the fluid pathway connector may include an elastomeric component 3334. At least a portion of the outer piercing member 2316B may be embedded in the elastomeric component 3334. The outer piercing member 2316B may be embedded in the elastomeric component 334 while in an aseptic environment. The aseptic condition of the embedded portion of the outer piercing member 2316B is maintained when the fluid path connection mechanism is transferred to a septic environment due to the sealing engagement of the outer piercing member 2316B with the elastomeric component 3334. Hence, after mounting the fluid pathway connector to the drug container, the fluid pathway connector may be transformed to the open configuration by initially piercing of the first and second films 2318 and 2322 with the outer piercing member 2316B, and then piercing the pierceable seal 3324 with the inner piercing member 2316A by moving the inner piercing member 2316A relative to the outer piercing member 2316B while keeping the outer piercing member 2316B stationary. In this way, the inner piercing member 2316A is not contaminated by touching the non-sterile exterior surfaces of the first and second foils 2318 and 2322. In alternative embodiments, the outer piercing member 2316B may be the sole piercing member and/or may pierce the pierceable seal 3324 in addition to the first and second films 2318 and 2322. As seen in the further alternative embodiment of FIGS. 52A-D, the first film 2318 and/or the second film 2322 may further include an adhesive containing antimicrobial agents as described above. Initially, the antimicrobial adhesive of the first film 2318 may be covered by a removable liner 2319 and the antimicrobial adhesive of the second film 2322 may be covered by a removable liner 2323. Prior to assembling the first film 2318 in engagement with the second film 2322, the removable liners 2319 and 2323 may be removed. This presence of the antimicrobial adhesive on the exterior surfaces of the first and second films 2318 and 2322 inhibits or prevents contamination of those surfaces if this step of the assembly is performed in a non-sterile environment.

Figure 53B:
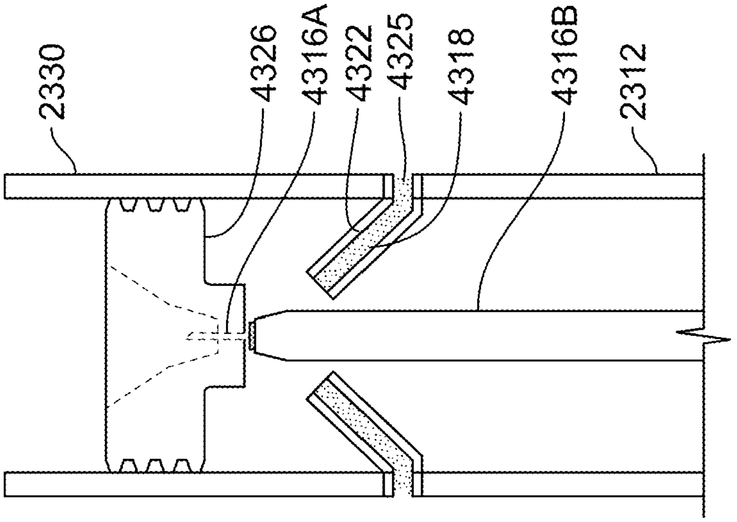
FIG. 53B is a cross-sectional side view of the embodiment of FIG. 53A after connection of the fluid path.
Figure 53A:
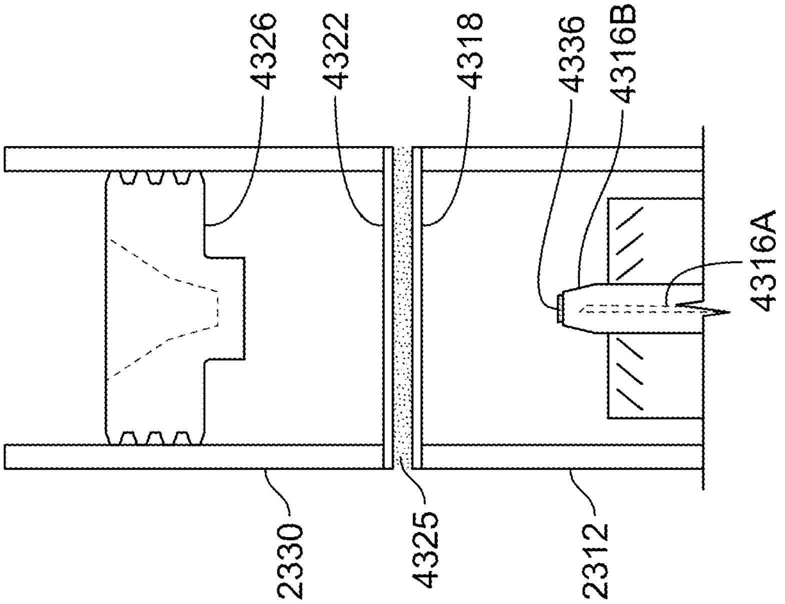
FIG. 53A is a cross-sectional side view of an embodiment of a fluid path connection mechanism and a drug container in a mounted configuration.

In some embodiments, as shown in FIGS. 53A-B, an additional film or seal 4336 may be present on the outer piercing member 4316B which further isolates the inner cavity of the outer piercing member 4316B and hence the inner piercing member 4316A. This seal 4336 may remain intact as the outer piercing member pierces first film 4318 and second film 4322. This may prevent any microbes that are present on the surfaces of the seals from coming in contact with the inner piercing member. After piercing the first and second films 4318 and 4322 the translation of the outer piercing member 4318B may be restricted prior to the outer piercing member piercing the piercable seal 4326. The inner piercing member 4316A continues to translate toward the drug container 2330 and pierces the first and second films 4318 and 4322 and the pierceable seal 4326, thereby opening the fluid path. Furthermore, in the embodiment shown in FIGS. 53A-B, an antimicrobial adhesive 4325 may initially cover the exterior surface(s) of the first film 4318 and/or the second film 4322.

Figure 54A:
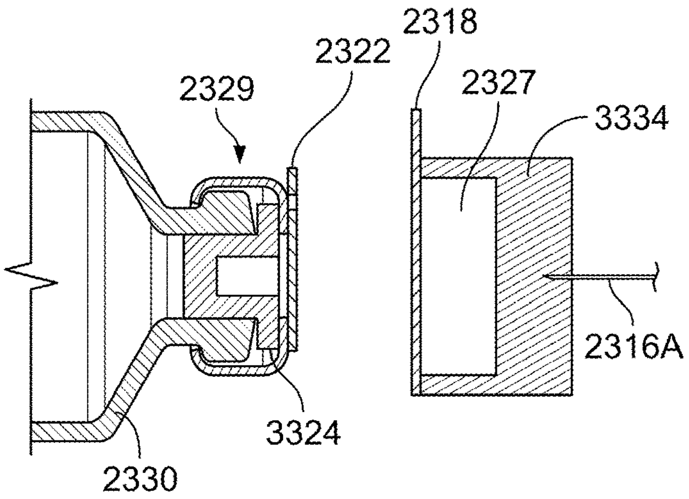
FIG. 54A is a cross-sectional side view of an embodiment of a fluid path connection mechanism and a drug container in an unmounted configuration.
Figure 54B:
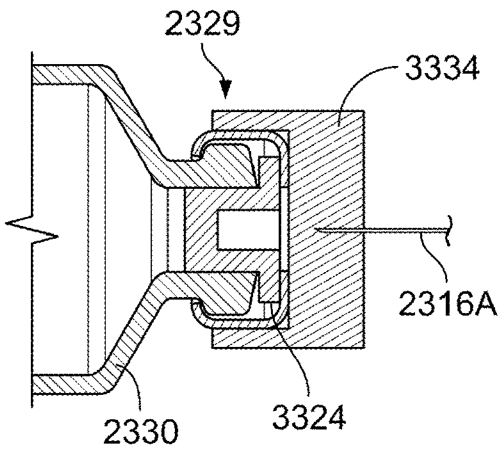
FIG. 54B is a cross-sectional side view of the embodiment shown in FIG. 54A in a mounted configuration.
Figure 54C:
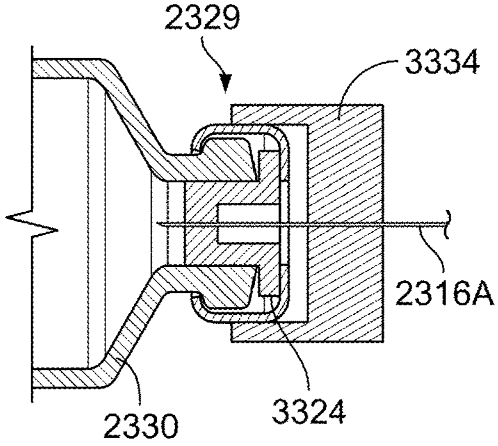
FIG. 54C is a cross-sectional side view of the embodiment shown in FIG. 54A after connection of the fluid path.
Figure 55A:
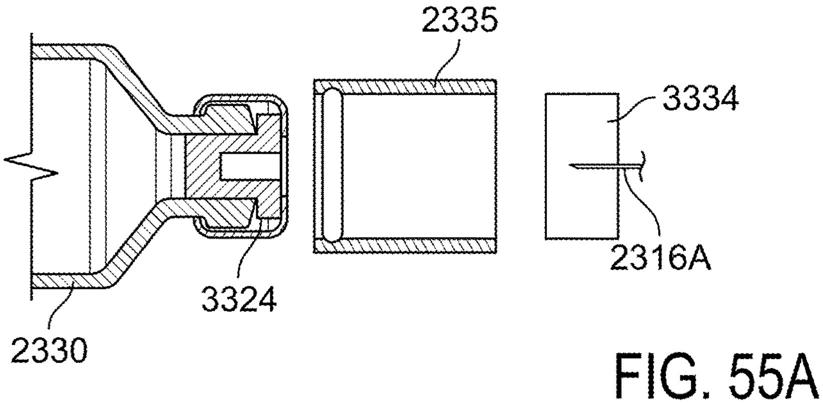
FIG. 55A is a cross-sectional side view of an embodiment of a fluid path connection mechanism and a drug container in an unmounted configuration.
Figure 55B:
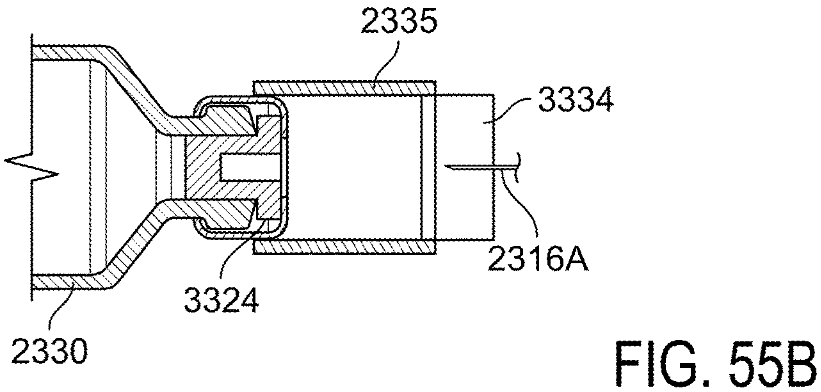
FIG. 55B is a cross-sectional side view of the embodiment shown in FIG. 55A in a mounted configuration.
Figure 55C:
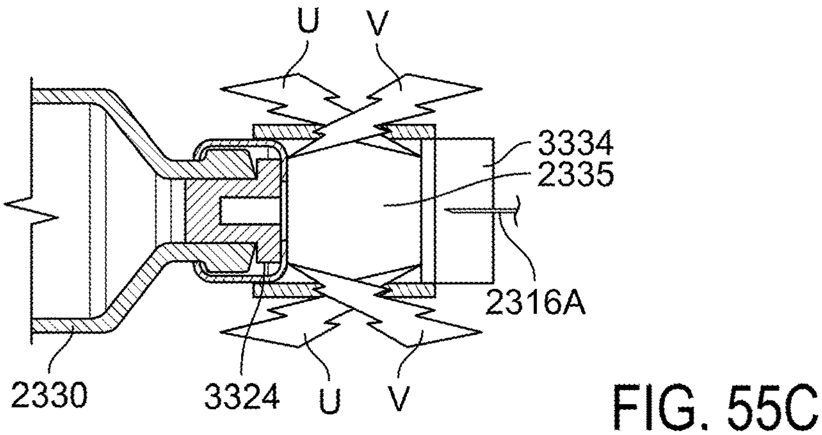
FIG. 55C is a cross-sectional side view of the embodiment shown in FIG. 55A during UV sterilization.
Figure 55D:
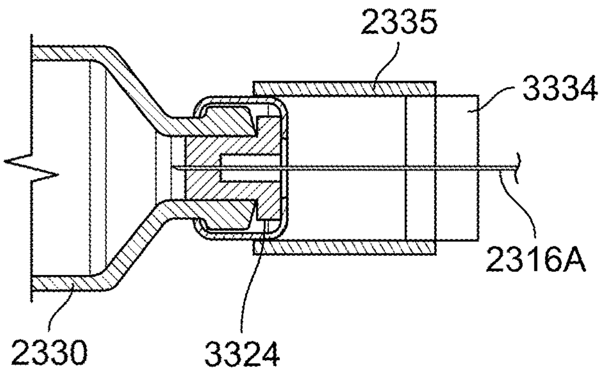
FIG. 55D is a cross-sectional side view of the embodiment shown in FIG. 55A after connection of the fluid path.

In other embodiments, shown in FIGS. 54A-C, the first and second films are removed from the fluid pathway connector and drug container just prior to mounting of the fluid pathway connector. Prior to removal of the films, their placement maintains the sterility of the pierceable seal of the drug container and the face of the elastomeric component of the fluid pathway connector. Except for the removal of the first and second films prior to connection of the fluid pathway connector and the drug container and the omission of the outer piercing member 2316B, the embodiment shown in FIGS. 54A-C includes same or similar elements as the embodiment shown in FIGS. 51A-C. Thus, same reference numerals are used to indicate same or similar elements in both sets of figures. It is noted that the outer piercing member 2316B of the embodiment shown in FIGS. 51A-C can be implemented in an alternative version of the embodiment shown n FIGS. 54A-C. Also, it is noted that the elastomeric component 3334 of the FIGS. 54A-C embodiment, unlike the elastomeric component 3334 of the FIGS. 51A-C embodiment, includes a recess or cavity 2327 configured to receive and form a tight fit (e.g., an airtight interference or press fit) with a distal end 2329 of the drug container 2330. This tight fit may prevent the ingress of contaminants and thereby maintain sterility of the interface between the drug container and the fluid pathway connector. In some embodiments, the distal end 2329 of the drug container 2330 may be inserted into the recess 2327 and the elastomeric component 3334 under non-sterile or aseptic conditions so that contaminants are not trapped between distal end 2329 of the drug container 2330 and the elastomeric component 3334 as the result of assembly.

As shown in the alternative embodiment of FIGS. 55A-D, the fluid pathway connector may also be mounted to the drug container 2330 using a glass tube 2335. After mounting, the glass tube 2335 and the surfaces of the elastomeric piercing member retainer or component 3334 and pierceable seal 3324 may be sterilized using UV sterilization (see FIG. 55C). The glass tube may be in sealing engagement (e.g., an airtight seal) with both the drug container 2330 and the elastomeric component 3334 of the fluid pathway connector such that after sterilization microbes and other foreign elements are unable to enter the glass tube, thereby maintaining the aseptic condition of the interior of the glass tube 2335. Except for the omission of the first and second foils 2318 and 2322 and the inclusion of the glass tube 2335, the embodiment shown in FIGS. 55A-D may include the same or similar elements as the embodiment shown in FIGS. 54A-C. Therefore, same reference numerals are used to indicate same or similar elements in both sets of figures.

Figure 56:
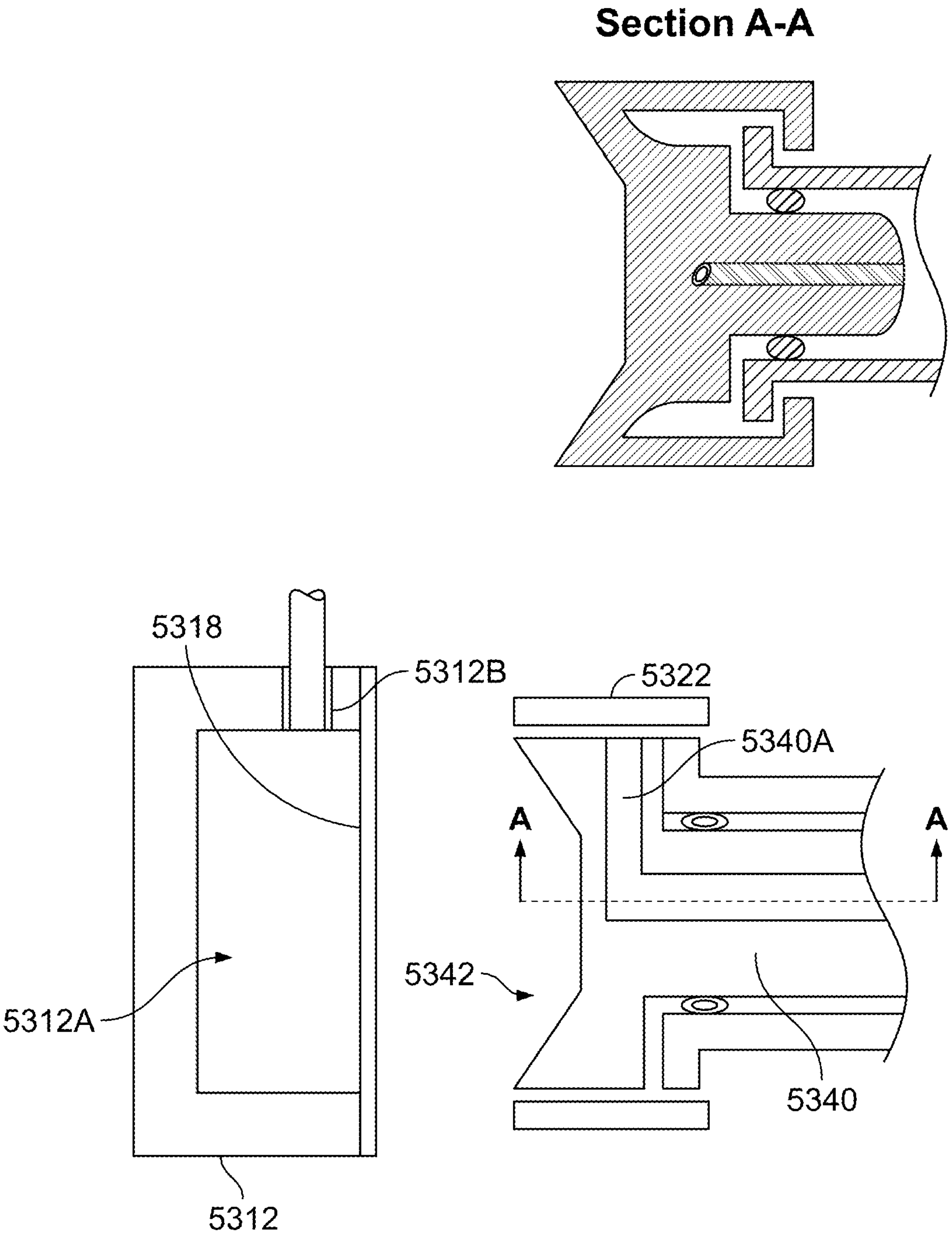
FIG. 56 shows a fluid path connection according to at least one embodiment of the present disclosure.

The embodiment shown in FIG. 56 shows a connection which is made orthogonal to the long axis of the drug container. In this embodiment, a first film 5318 is initially in place over and maintaining the sterility of a cavity 5312A of the connection hub 5312. During connection, the first film 5318 is pierced by an insert 5340 of the drug container. The pierced portion is retained within the concave portion 5342 of the insert after piercing. By retaining this pierced portion within the concave portion the non-aseptic surface of the first film is isolated and any substances present thereon are prevented from contaminating the drug fluid or fluid path. A second film 5322 is initially in place over an aperture 5340A in the insert 5340, maintaining the aseptic condition of the aperture. The second film 5322 may be a rigid or elastomeric component which is in tight conformity to the insert such that it prevents microbes and other contaminants from entering the aperture. Upon mounting of the connection hub to the drug container the second film may be displaced from its initial position, thereby allowing a fluid path to be established from the drug container through the fluid pathway connector. After mounting of the connection hub to the drug container the aperture 5340A in the insert 5340 is aligned with an aperture 5312B in the connection hub 5312. A pierceable seal may be in place over one or more of the apertures which may be pierced by a piercing member to establish a fluid path. One or more snap arms may retain the insert in position in relation to the drug barrel. The snap arms may connect to the drug barrel itself or another component of the drug container.

While many of the above-described embodiments of the fluid pathway connector incorporate a piercing member which moves to access the drug container upon activation of the drug delivery device, alternative embodiments of the fluid pathway connector, such as the embodiment illustrated in FIGS. 76A-76C, may include a piercing member that remains stationary throughout drug delivery. In such alternative embodiments, the drug container may move toward the stationary piercing member upon activation of the drug delivery device. The movement of the drug container may result in the stationary piercing member accessing the drug container through the pierceable seal located at the distal end of the drug container.

FIGS. 76A-76C illustrate a subassembly of a drug delivery device (e.g., the drug delivery device 10, 910, 2010, 6000, or 8000) including a drug container 10050 (which may be substituted for one or more the drug containers 50, 618, 718, 818, 918, 1118, 2050, or 6050), a drive mechanism 10100 (which may be substituted for one or more of the drive mechanisms 100, 500, 1000, or 2100) and a fluid pathway connector 10300. The drug container 10050 may include a barrel 10058, a plunger seal 10060 moveable through the barrel 10058, and a pierceable seal 10056 covering an open distal end of the barrel 10058 and controlling access to the interior of the barrel 10058.

The drive mechanism 10100 may include a drive housing 10130, a piston 10110 moveable relative to the drive housing 10130 and configured to impart movement to the plunger seal 10060, and a piston biasing member 10106 disposed between the drive housing 10130 and the piston 10110. Prior to delivery, the piston biasing member 10106 may be retained in a piston biasing member energized state, as depicted in FIG. 76A. When the piston biasing member 10106 is released and consequently de-energizes (as seen in FIGS. 76B and 76C), the piston biasing member 10106 may move the piston 10110 and/or the plunger seal 10060 toward the fluid pathway connector 10300.

The fluid pathway connector 10300 may define a sterile fluid flowpath between the drug container 10050 and an insertion mechanism (e.g., the needle insertion mechanism 200, 624, or 724). The fluid pathway connector 10300 may include a connection hub 10310, a tubular conduit (not illustrated) providing fluid communication between the connection hub 10310 and the insertion mechanism, a piercing member 10330 (e.g., a container access needle) configured to pierce the pierceable seal 10056 to establish fluid communication between the between the barrel 10058 and the tubular conduit during drug delivery, a barrel connector 10332, and a flexible sealing member 10334. In some embodiments, the tubular conduit may be a single, unitary tube made of a flexible material and may extend directly between the connection hub 10310 and the insertion mechanism. In other embodiments, depending on the need to regulate or modify the fluid pressure, fluid flow rate, or other characteristic of the drug, the tubular conduit may include one or more flow restrictors made of a relatively rigid material and connected at opposite ends via flexible tubes to the connection hub 10310 and the insertion mechanism, respectively.

Still referring to FIGS. 76A-76C, the flexible sealing member 10334 may define a sterile chamber 10062 with a collapsible volume between the distal end of the barrel 10058 and the connection hub 10310. In at least one embodiment, the flexible sealing member 10334 may have a generally conical shape and function as a flexible bellows. A proximal end of the flexible sealing member 10334 may be clamped between the barrel connector 10332 and a distal end surface of the barrel 10058. At its distal end, the flexible sealing member 10334 may be connected to the connection hub 10310.

The barrel connector 10332 may have a tubular body portion 10335 configured to fit snugly around a circumferential surface of the barrel 10058, and first and second radially inwardly depending annular protrusions 10336, 10338 at opposite ends of the tubular body portion 10335. The first annular protrusion 10336 may grip a neck of the barrel 10058, and the second annular protrusion 10338 may clamp the proximal end of the flexible sealing member 10334 against the distal end surface of the barrel 10332.

The connection hub 10310 may be fixed relative to a housing (e.g., the housing 12) of the drug delivery device such that the connection hub 10310 is prevented from moving relative to the housing of the drug delivery device. A distal end of the piercing member 10330 may be rigidly connected to the connection hub 10310 so that the piercing member 10330 is also fixed relative to the housing of the drug delivery device. The barrel 10058 may be slidably connected to the housing of the drug delivery device such that the barrel 10058 can move (e.g., translate in a linear direction) relative to the housing of the drug delivery device. As the barrel 10058 moves toward the connection hub 10310, the flexible sealing member 10334 may elastically or in-elastically deform such that the volume of the sterile chamber 10062 decreases, as illustrated in FIGS. 76B and 76C.

In a pre-delivery state (FIG. 76A), a proximal end of the piercing member 10330 may be disposed within the sterile chamber 10062 defined by the flexible sealing member 10334. Upon release of the piston biasing member 10106, the piston biasing member 10106 may begin to de-energize and thereby cause the piston 10110 and the plunger seal 10060 to move toward the piercing member 10330. Friction between the plunger seal 10060 and the inner wall of the barrel 10058 may cause the barrel 10058, which is slidably connected to the housing, to initially move in a distal direction together with the plunger seal 10060. The movement of the barrel 10058 causes the pierceable seal 10056 to be pierced by the piercing member 10330. As a result, the piercing member 10330 may access the interior of the barrel 10058 and establish fluid communication between the barrel 10058 and the connection hub 10310.

FIG. 76B shows that the barrel 10058 continues to move in the distal direction until it contacts a stopping member, which in the present embodiment corresponds to the connection hub 10310. The reaction force exerted on the barrel 10058 by the stopping member overcomes the frictional force between the plunger seal 10060 and the inner wall of the barrel 10058, thereby allowing the plunger seal 10060 to move relative to the barrel 10058 and discharge the drug from the barrel 10058 via the piercing member 10330. FIG. 76C shows that movement of the plunger seal 10060 is halted, thereby ending drug delivery, when the plunger seal 10060 impacts a portion of the inner wall of the barrel 10058 at the neck of the barrel 10058.

The combination of the fluid pathway connector 10300 having a stationary piercing member 10330 and the drug container 10050 having a moveable barrel 10058 removes the need for a separate mechanism to establish fluid communication with the interior of the barrel 10058 upon activation of the drug delivery device. Instead, the force of the piston biasing member 10106 is utilized to move the pierceable seal 10056 into the stationary piercing member 10330 to establish fluid communication with the interior of the barrel 10058. Accordingly, the design and manufacture of the drug delivery device may be simplified, and the overall size of the drug delivery device may be reduced.

IX. Motor-Driven Drug Delivery Device

Figure 57A:
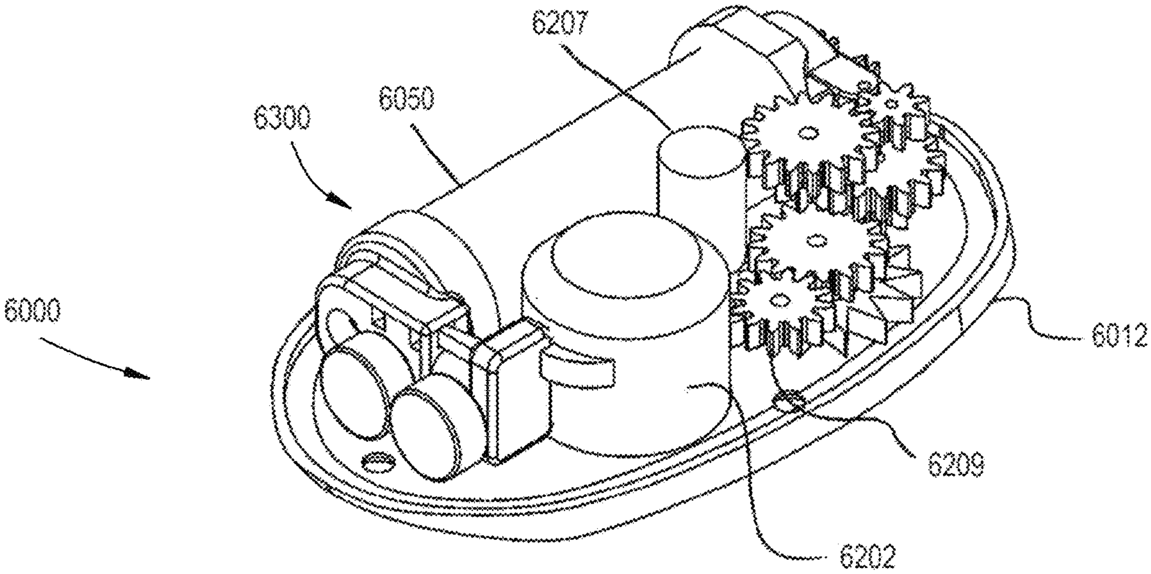
FIG. 57A shows an isometric view of the interior components of a second embodiment of a drug delivery device.
Figure 57B:
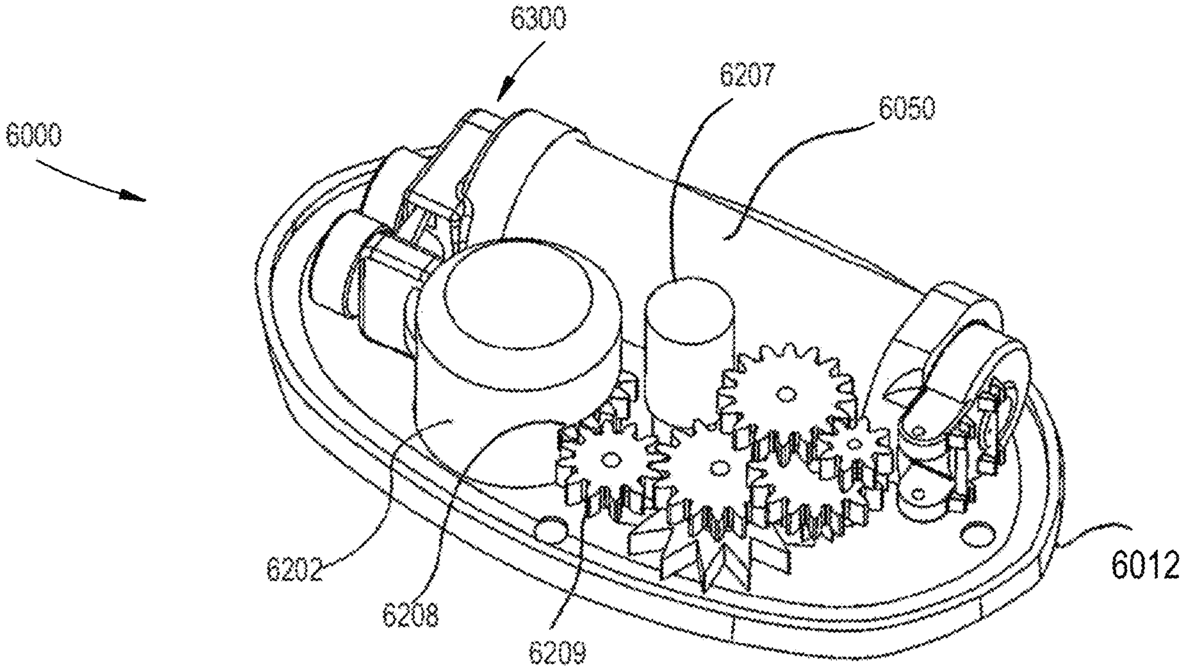
FIG. 57B shows a second view of the interior components of the drug delivery device shown in FIG. 57A.

Another embodiment of a drug delivery device 6000 is shown in FIGS. 57A-57B. The drug delivery device 6000 may include a container 6050 filled with a volume of a fluid(s) for delivery to a patient. The fluid(s) may include one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody. In drug delivery device 6000, one or more of an insertion mechanism, fluid pathway connector, and drug delivery drive mechanism are controlled by the rotation of a motor 6207. Additionally, or alternatively, an escapement mechanism may be used to control the rate of rotation of one or more gears. One of the gears may be engaged with teeth 6208 of an insertion mechanism housing 6202. As such, the rotation of the gear train controls the rotation of the insertion mechanism housing and, thereby, the insertion of the needle into the skin of the patient. The operation of the insertion mechanism will be described further herein.

X. Additional Embodiments of Insertion Mechanism

At least some of the drug delivery devices described in this application, including at least those described in connection with FIGS. 1-57B, may be configured to incorporate the embodiments of the insertion mechanism described below in connection with FIGS. 58A-68.

Figure 58A:
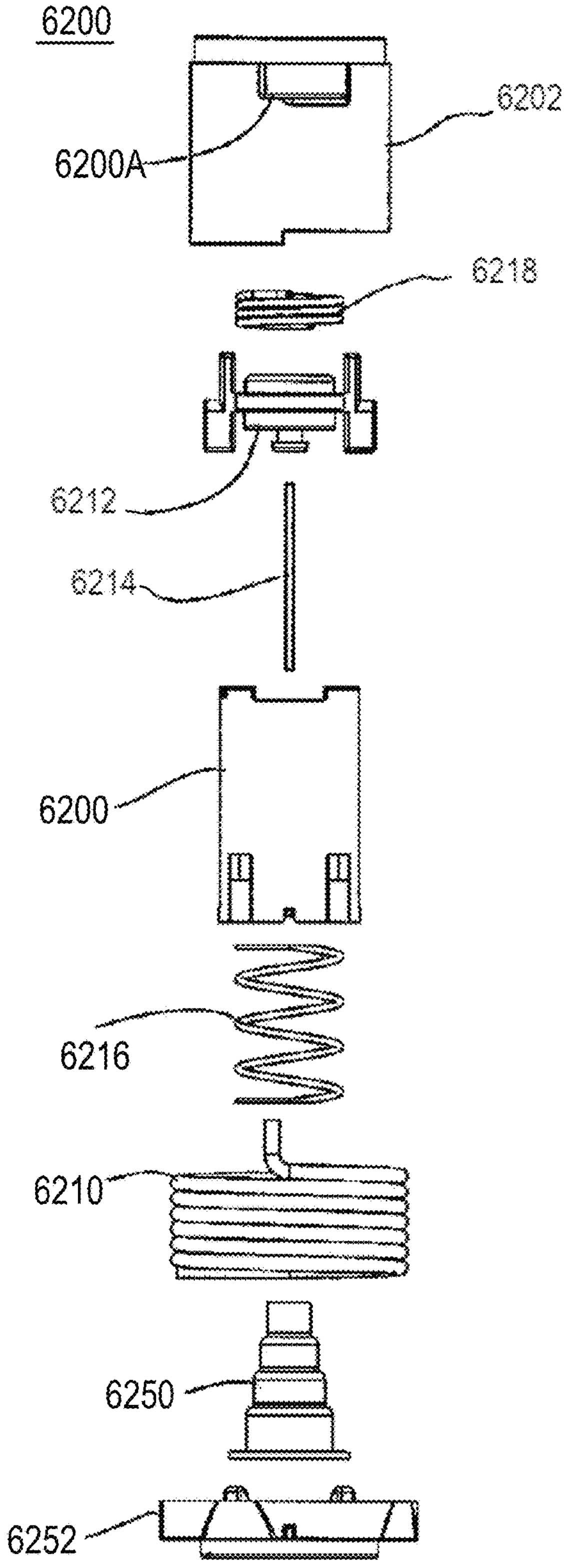
FIG. 58A shows an exploded view, exploded along an axis "A," of an insertion mechanism according to at least one embodiment of the present disclosure.
Figure 58B:
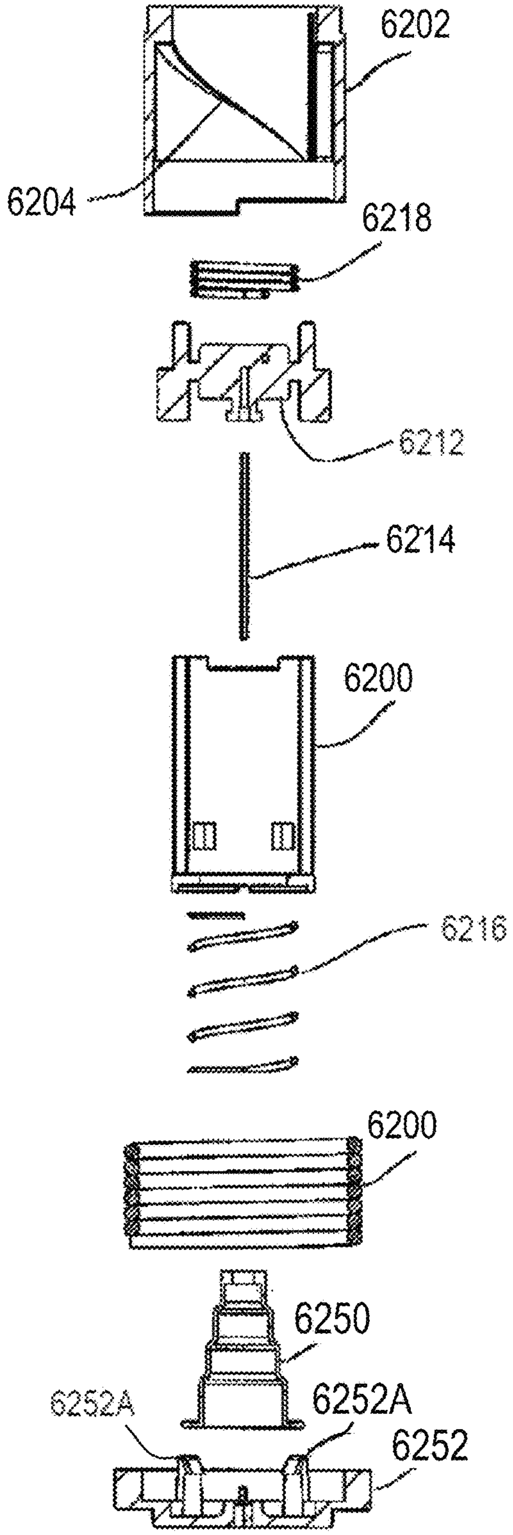
FIG. 58B shows a cross-sectional exploded view, exploded along an axis "A," of an insertion mechanism according to at least one embodiment of the present disclosure.

In one embodiment, the insertion mechanism 6200 includes an insertion mechanism housing 6202 having one or more extension arms 6202A, a base 6252, and a sterile boot 6250, as shown in the exploded view of FIGS. 58A and 58B. Base 6252 may be connected to assembly platform 20 to integrate the insertion mechanism into the drug delivery device 10 (as shown in FIG. 1B) or the or the drug delivery device 6000. The connection of the base 6252 to the assembly platform 20 may be, for example, such that the bottom of the base is permitted to pass-through a hole in the assembly platform to permit direct contact of the base to the body of the patient. In such configurations, the bottom of the base 6252 may include a sealing membrane 6254 that, at least in one embodiment, is removable prior to use of the drug delivery device 10 or the drug delivery device 6000. Alternatively, the sealing membrane 6254 may remain attached to the bottom of the base 6252 such that the needle 6214 pierces the sealing membrane 6254 during operation of the drug delivery device 10 or the drug delivery device 6000. As shown in FIGS. 58A and 58B, the insertion mechanism 6200 may further include a rotational biasing member 6210, a needle hub 6212, a needle 6214, a retraction biasing member 6216, a sleeve 6220, and a conduit 6218. The conduit 6218 may connect to sterile fluid conduit 30 or to sterile access connection 300 to permit fluid flow through the conduit 6218, needle 6214, and into the body of the patient during drug delivery, as will be described in further detail herein.

As used herein, "needle" is intended to refer to a variety of needles including but not limited to conventional hollow needles, such as a rigid hollow steel needles. Upon assembly, the proximal end of needle 6214 is maintained in fixed contact with hub 6212, while the remainder of needle 6214 is preferably located within sterile boot 6250. The needle 6214 may further pass-through base opening 6252E.

Sterile boot 6250 is a collapsible or compressible sterile membrane that is in fixed engagement at a proximal end with the hub 6212 and at a distal end with the sleeve 6220 and/or base 6252. The term "sterile boot" is used to describe a boot within which certain internal components may reside, at one or more stages of operation, in a sterile condition. The boot need not be sterile through the entire operation of the mechanism or drug delivery device and, in fact, may not be initially sterile until assembly and sterilization of certain components has occurred. Additionally, the term "boot" is not intended to mean any specific shape or configuration, but is instead utilized to describe a component that can provide an interior space within which other components may reside at one or more stages of operation. In at least one embodiment, the sterile boot 6250 is maintained in fixed engagement at a distal end between base 6252 and sleeve 6220. In other embodiments sterile boot 6250 is maintained in fixed engagement at a distal end between base 6252 and insertion mechanism housing 6202. Base 6252 includes a base opening 6252E through which the needle may pass during operation of the insertion mechanism, as will be described further below. Sterility of the needle is maintained by its initial positioning within the sterile portions of the insertion mechanism. Specifically, as described above, needle 6214 is maintained in the sterile environment of the sterile boot 6250. The base opening 6252E of base 6252 may be closed from non-sterile environments as well, such as by for example a sealing membrane 6254.

Figure 59A:
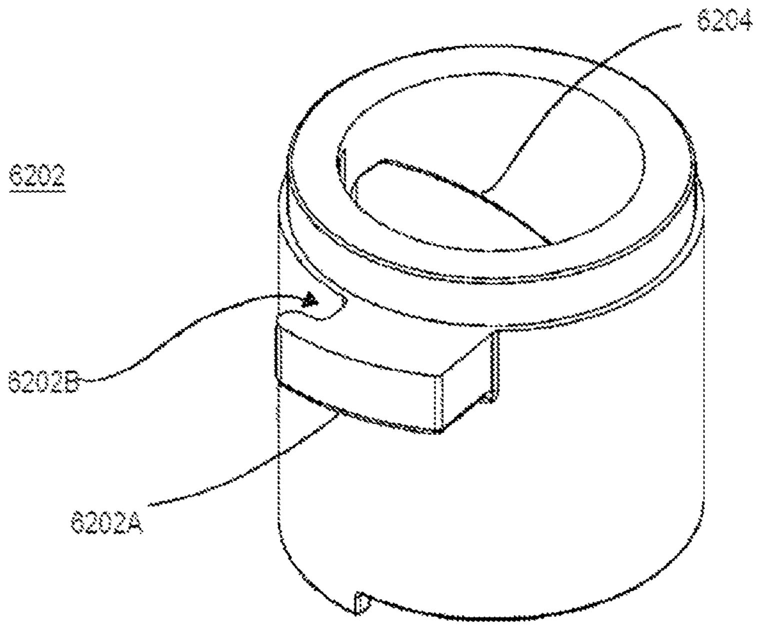
FIG. 59A shows an isometric view of an insertion mechanism housing according to at least one embodiment of the present disclosure.
Figure 59B:
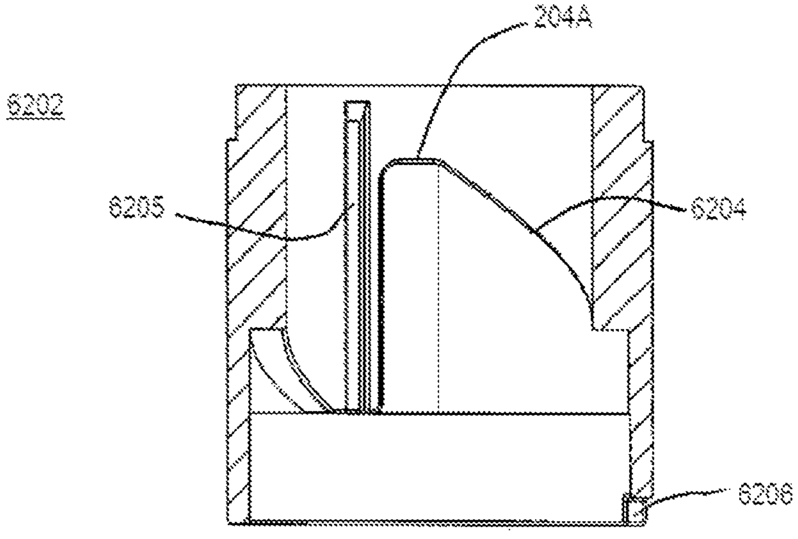
FIG. 59B shows a cross-section view of the insertion mechanism housing shown in FIG. 59A.

FIGS. 59A-59B and 60-62 show the components of the insertion mechanism, according to at least a first embodiment, in greater detail. As shown in FIGS. 59A-59B, insertion mechanism housing 6202 may be a substantially cylindrical component having an inner chamber within which conduit 6218, hub 6212, needle 6214, sleeve 6220, retraction biasing member 6216, and sterile boot 6250 are substantially disposed in an initial configuration. Guide surfaces 6204 (as best seen in FIG. 59B) are located on the inner surface of housing 6202 and are configured to interact with extension arms 6212A of hub 6212. As will be described in further detail hereinafter rotation of housing 6202 is transferred to axial movement of hub 6212 by interaction of guide surfaces 6204 with extension arms 6212A of hub 6212. Housing 6202 may further include one or more protrusions 6202A. Protrusion 6202A is configured to engage a proximal end of rotational biasing member 6210. Protrusion 6202A may form recess 6202B in which the proximal end of rotational biasing member 6210 may be disposed. In this way, unwinding and/or de-energizing of rotational biasing member 6210 causes rotation of housing 6202 about axis A. Rotational biasing member 6210 may be located on the outside of housing 6202 in a substantially concentric relationship. The distal end of the rotational biasing member may be engaged with base 6252 or another feature of the drug delivery device 10 or the drug delivery device 6000 such that movement of the distal end of rotational biasing member 6210 is restricted. Protrusion 6202A, or another feature, may further contact a portion of the sterile access connection during rotation of housing 6202. This contact, in conjunction with rotation of housing 6202, may be used to initiate the piercing of the pierceable seal and thereby allow the contents of the drug container to flow through the conduit.

Figure 60:
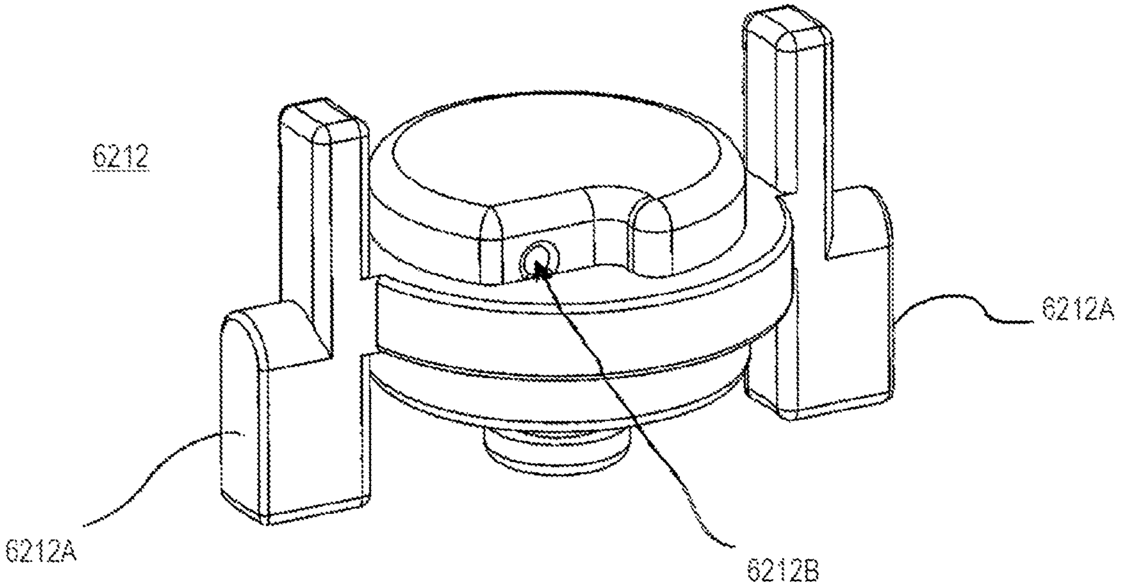
FIG. 60 shows an isometric view of a hub according to at least one embodiment of the present disclosure.

Hub 6212, as seen in FIG. 60, includes extension arms 6212A as described above. It further includes aperture 6212B configured to receive a portion of conduit 6218.

Aperture 6212B allows conduit 6218 to be in fluid communication with needle 6214 for delivery of the fluid drug to the patient. Needle 6214 is securely engaged with hub 6212 by bonding, press-fit or other means known to one skilled in the art.

Figure 61:
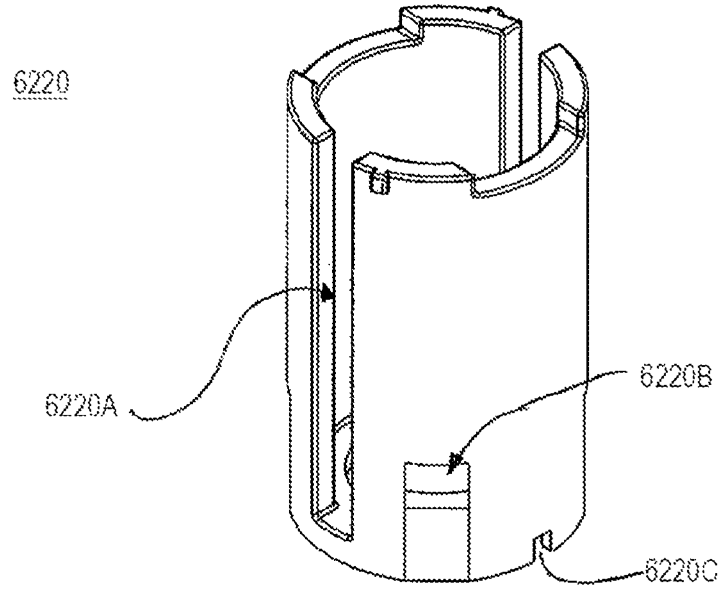
FIG. 61 shows an isometric view of a sleeve according to at least one embodiment of the present disclosure.
Figure 62:
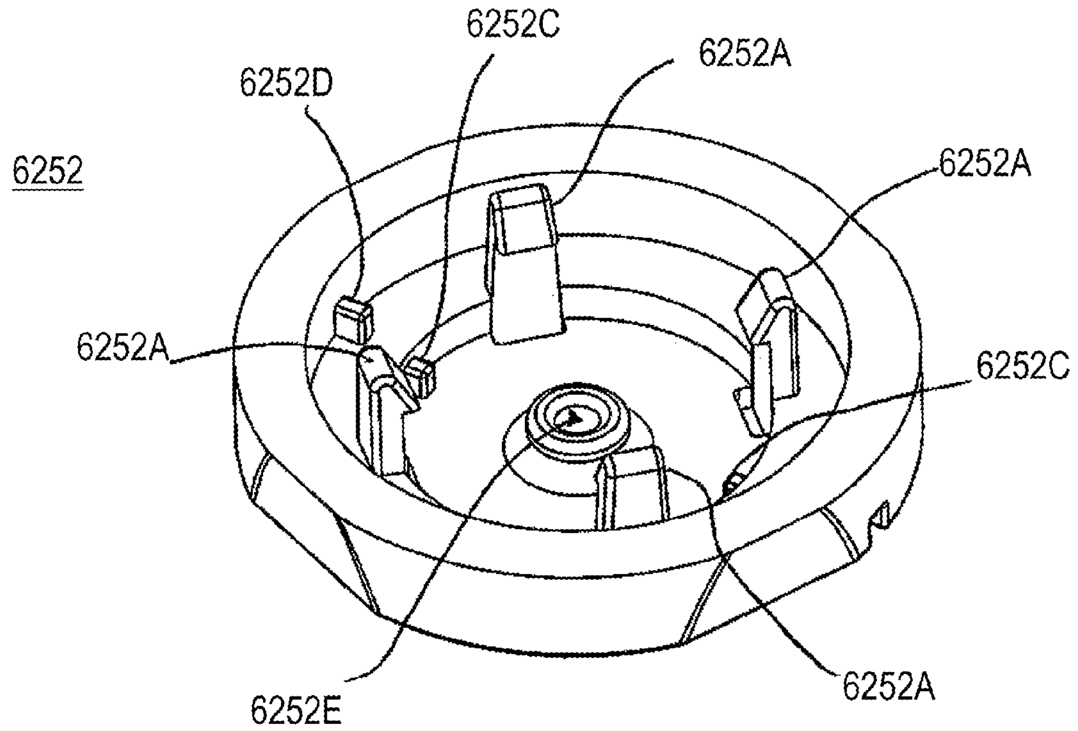
FIG. 62 shows an embodiment of a base of an insertion mechanism according to at least one embodiment of the present disclosure.

Sleeve 6220, as shown in FIG. 61, includes slots 6220A within which extension arms 6212A of hub 6212 are at least partially disposed during operation of the insertion mechanism. These slots restrict the ability of hub 6212 to rotate. Sleeve 6220 further includes one or more apertures 6220B which are configured to interface with flex arms 6252A of base 6252. During assembly, flex arms 6252A engage apertures 6220B, thereby restricting movement of sleeve 6220 with respect to base 6252. Base 6252, as shown in FIG. 62, may further include one or more lower alignment members 6252C configured to engage one or more alignment notches 6220C of sleeve 6220. This engagement aligns sleeve 6220 to base 6252 and limits rotation of sleeve 6220 with respect to base 6252. Base 6252 may also include one or more upper alignment members 6252D configured to engage face 206 of housing 6202 during installation, thereby positioning housing 6202 with respect to base 6252.

Figure 63A:
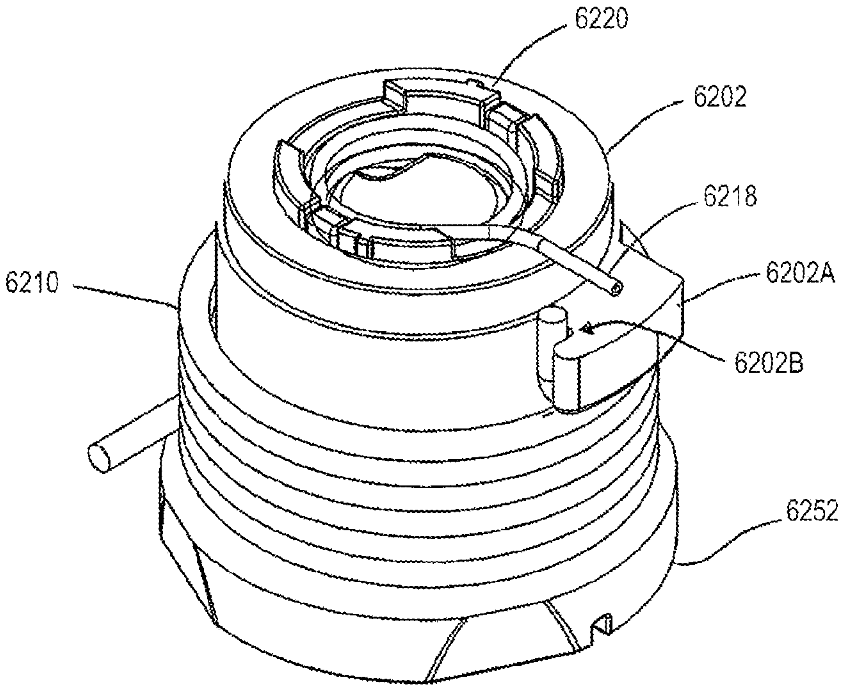
FIG. 63A shows an isometric view of an insertion mechanism according to at least one embodiment of the present disclosure in an initial configuration.
Figure 63B:
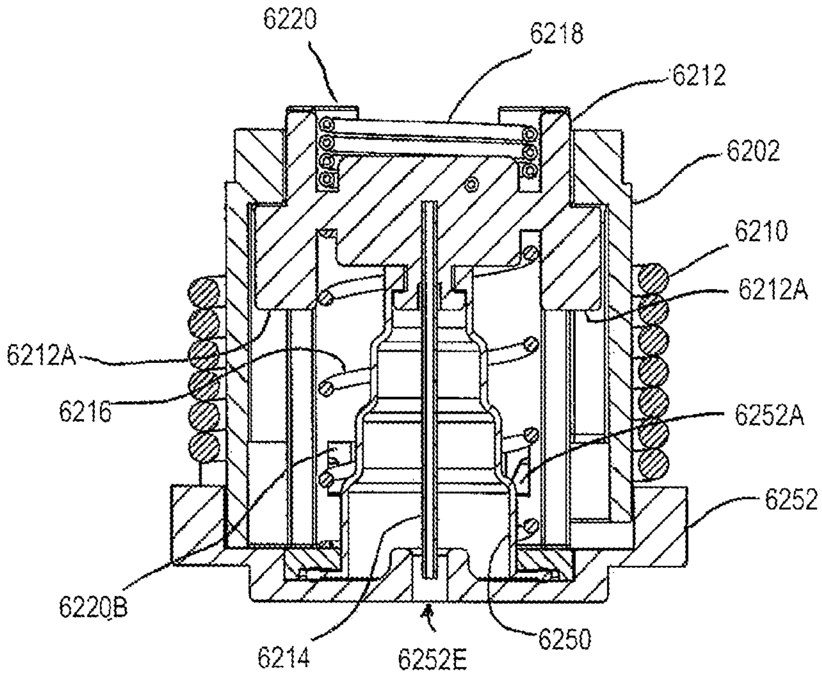
FIG. 63B shows a cross-sectional view of an insertion mechanism according to at least one embodiment of the present disclosure in an initial configuration.

The operation of the insertion mechanism is described herein with reference to the above components, in view of FIGS. 63-65. FIG. 63A shows an isometric view and FIG. 63B shows a cross-sectional view of the insertion mechanism, according to at least one embodiment of the present disclosure, in a locked and ready to use stage. The proximal end of rotational biasing member 6210 is disposed in recess 6202B of housing 6202 and rotational biasing member 6210 is in an energized state. In this initial position, hub 6212 is in a retracted, proximal position such that needle 6214 does not extend past opening 6252E of base 6252. Sterile boot 6250 is in an extended configuration with one end engaged with hub 6212 and the other engaged with shell 6220 and base 6252. Retraction biasing member 6216 is in a relatively decompressed and/or de-energized state. Extension arms 6212A of hub 6212 are located within or substantially adjacent to proximal portion 6204A of guide surfaces 6204. Coiled fluid conduit 6218 may be located proximally to hub 6212. Fluid conduit 6218 may be connected at one end to hub 6212, allowing fluid drug contents to pass from the drug container 50 to needle 6214 for delivery to the patient.

Insertion mechanism 6200 may be held in this initial configuration by interaction with other components of the drug delivery device 10 or the drug delivery device 6000. By way of example, activation member 14 may be engaged with a slide which, in an initial configuration, prevents rotation of housing 6202 by interaction with extension arm 6202A. Depression of trigger member 14 may displace the slide, disengaging the slide from the extension arm 6202A of housing 6202, thereby allowing rotation of housing 6202. In an alternative embodiment, shown in FIGS. 57A-57B, a portion of housing 6202 may have gear teeth 6208 configured to interact with a gear 6209 which prevents rotation of the housing. In this configuration, the gear may be connected to a motor 6207 which controls the rotation of the gear and therefore the housing. The housing may be able to be disengaged from the gear, thereby allowing free rotation of the housing in response to de-energizing of the rotational biasing member. Gear 6209 may be connected to motor 6207 through a gear train, the gear train controlling the relationship between rotation of motor 6207 and gear 6209. Additionally, or alternatively, an escapement mechanism may be used to control rotation of the gear train.

Figure 64A:
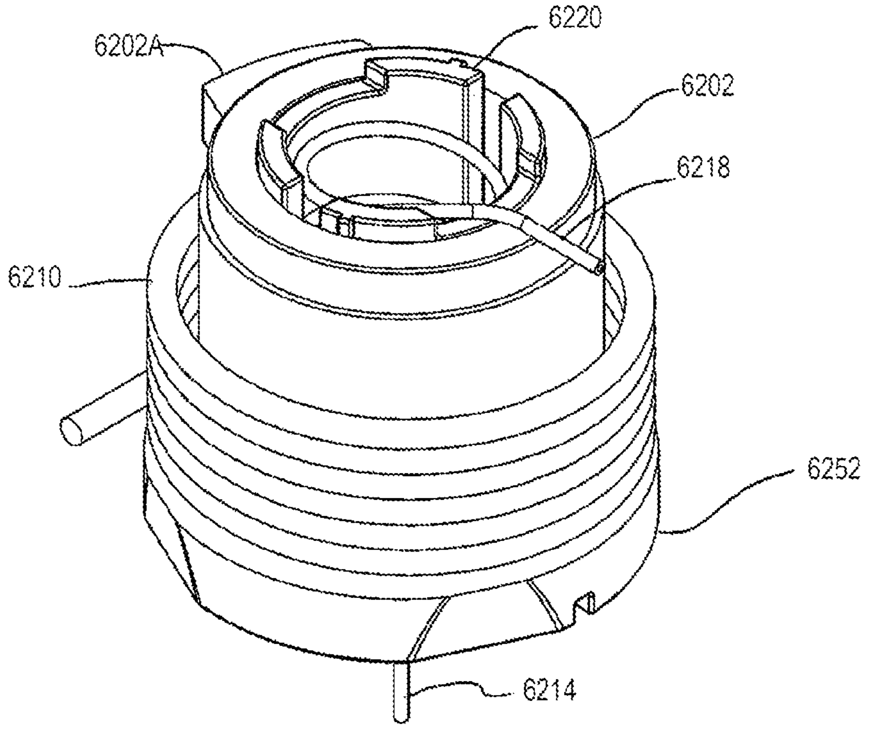
FIG. 64A shows an isometric view of an insertion mechanism according to at least one embodiment of the present disclosure in a needle inserted configuration.
Figure 64B:
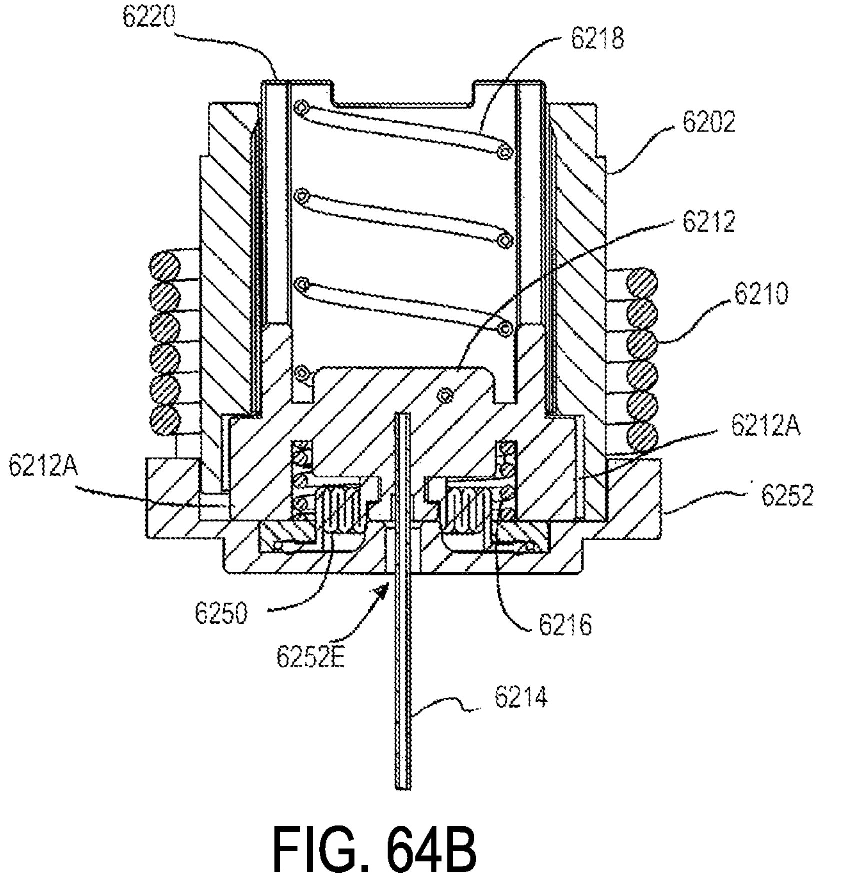
FIG. 64B shows a cross-sectional view of an insertion mechanism according to at least one embodiment of the present disclosure in a needle inserted configuration.

FIG. 64A shows an isometric view and FIG. 64B shows a cross-sectional view of an insertion mechanism in a needle inserted stage. As shown in FIG. 63A unwinding and/or de-energizing of rotational biasing member 6210 causes housing 6202 to rotate about axis A. As housing 6202 rotates contact of guide surfaces 6204 with extension arms 6212A of hub 6212 causes hub 6212 to translate in the distal direction. Hub 6212 is prevented from rotating by interaction between extension arms 6212A and slots 6220A of sleeve 6220. Sleeve 6220 is connected to base 6252 by engagement of flex arms 6252B with apertures 6220B. As shown, sterile boot 6250 is permitted to collapse as housing 6202 rotates and hub 6212 translates in the distal direction and inserts the needle 6214 into the body of the patient. At this stage, shown in FIG. 63B, needle 6214 is introduced into the body of the patient for drug delivery. Due to the distal translation of hub 6212, retraction biasing member 6216 is compressed or energized. Rotation of housing 6202 is preferably limited or stopped at a position in which guide surfaces 6204 retain hub 6212 in a distal position. Rotation of housing 6202 may be stopped at this position by interaction between protrusion 6202A and a stop component of the drug delivery device 10 or the drug delivery device 6000. Alternatively, a stop component may interact with another portion of housing 6202. Upon insertion of the needle 6214, the fluid pathway from the conduit to the body of the patient through the needle 6214 is opened. As the fluid pathway connector is made to the drug container and the drive mechanism is activated, the fluid drug treatment is forced from the drug container through the fluid pathway connector and the sterile fluid conduit into the needle 6214 for delivery into the body of the patient.

Figure 65A:
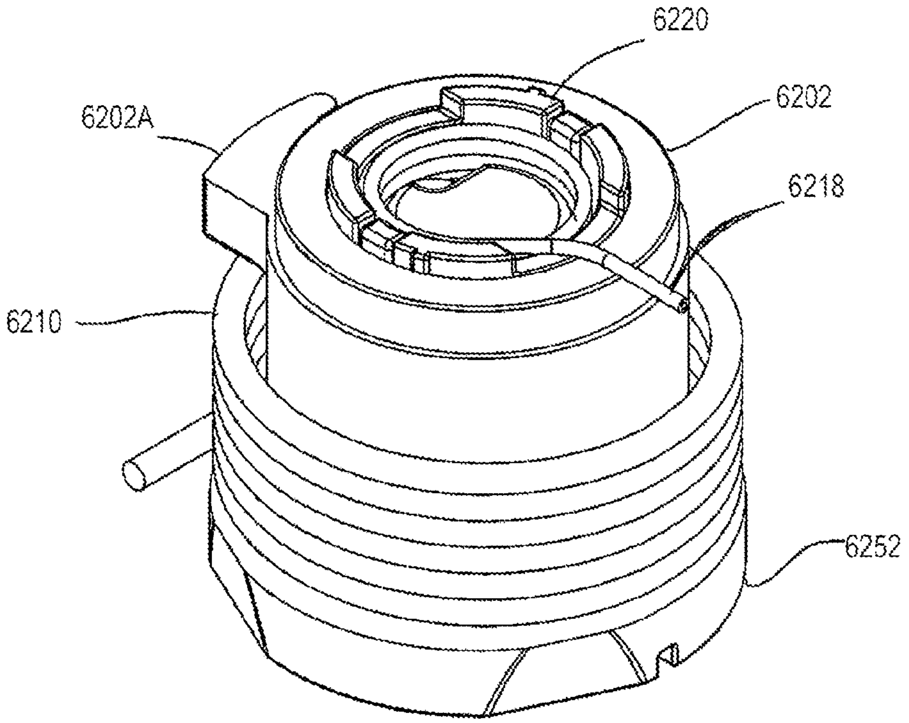
FIG. 65A shows an isometric view of an insertion mechanism according to at least one embodiment of the present disclosure in a needle retracted configuration.
Figure 65B:
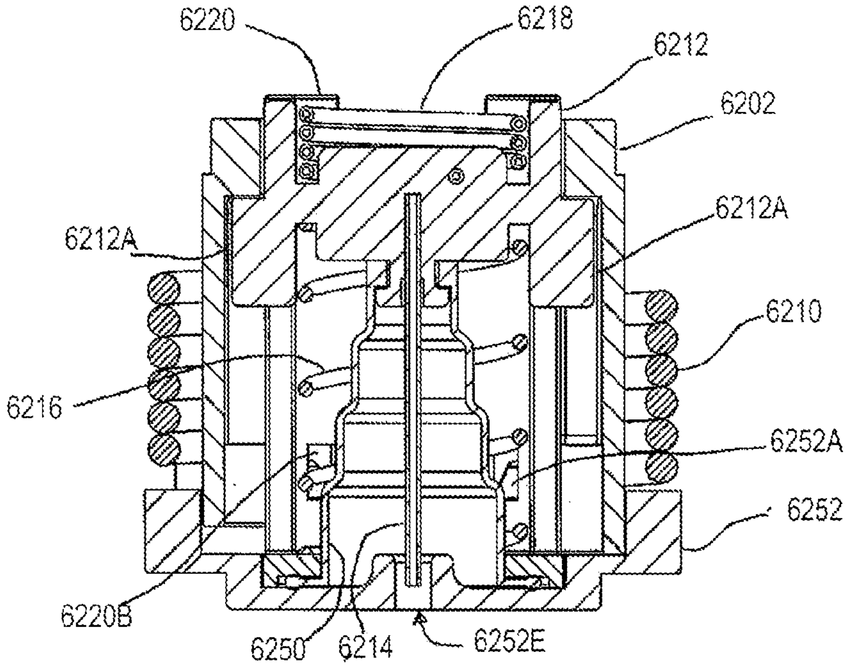
FIG. 65B shows a cross-sectional view of an insertion mechanism according to at least one embodiment of the present disclosure in a needle retracted configuration.

As shown in FIGS. 65A and 65B, upon completion of drug delivery, the needle 6214 is retracted back (i.e., axially translated in the proximal direction) into the insertion mechanism housing 6202. Continued rotation of housing 6202 aligns the proximal portion 6204A of guide surfaces 6204 with extension arms 6212A of hub 6212 such that proximal translation of hub 6212 is no longer restricted. In this position, retraction biasing member 6216 is able to decompress or de-energize. Expansion of the retraction biasing member 6216 translates hub 6212, and needle 6214 to which it is connected, axially in the proximal direction. Accordingly, activation of the insertion mechanism inserts the needle 6214 into the body of the patient, and sequentially retracts the needle 6214 after completion of drug delivery or upon some other retraction initiation mechanism.

Figure 66:
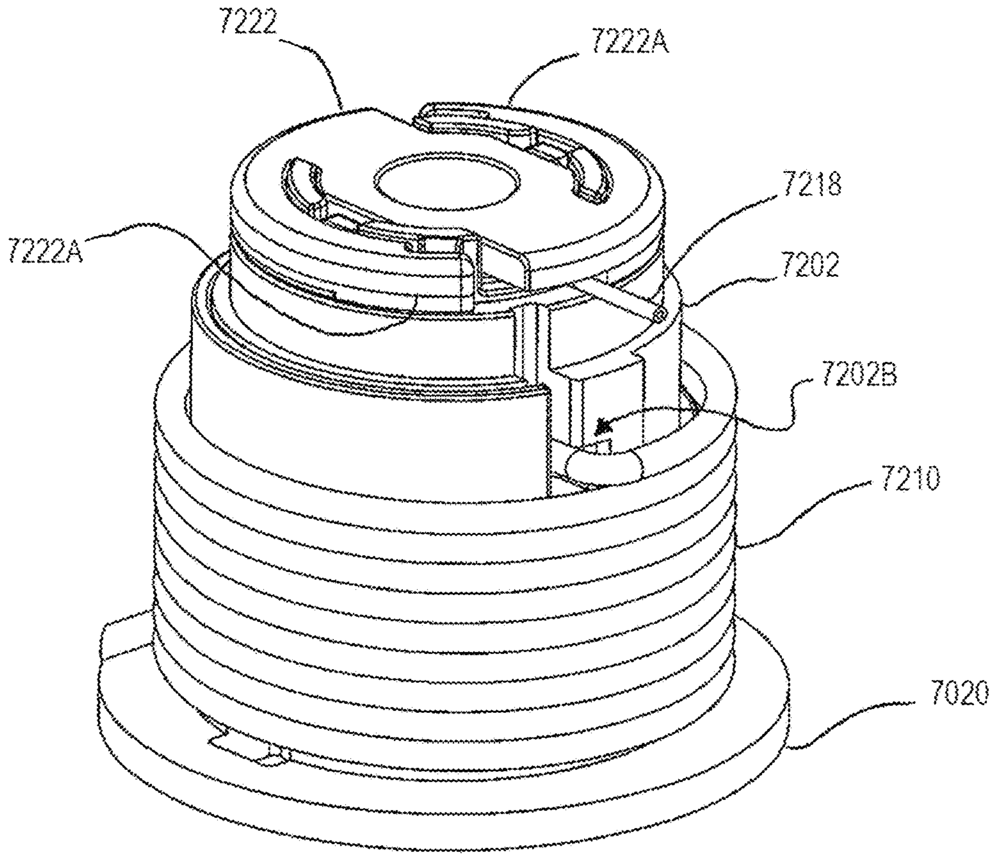
FIG. 66 shows an isometric view of an insertion mechanism according to at least one embodiment of the present disclosure.
Figure 67:
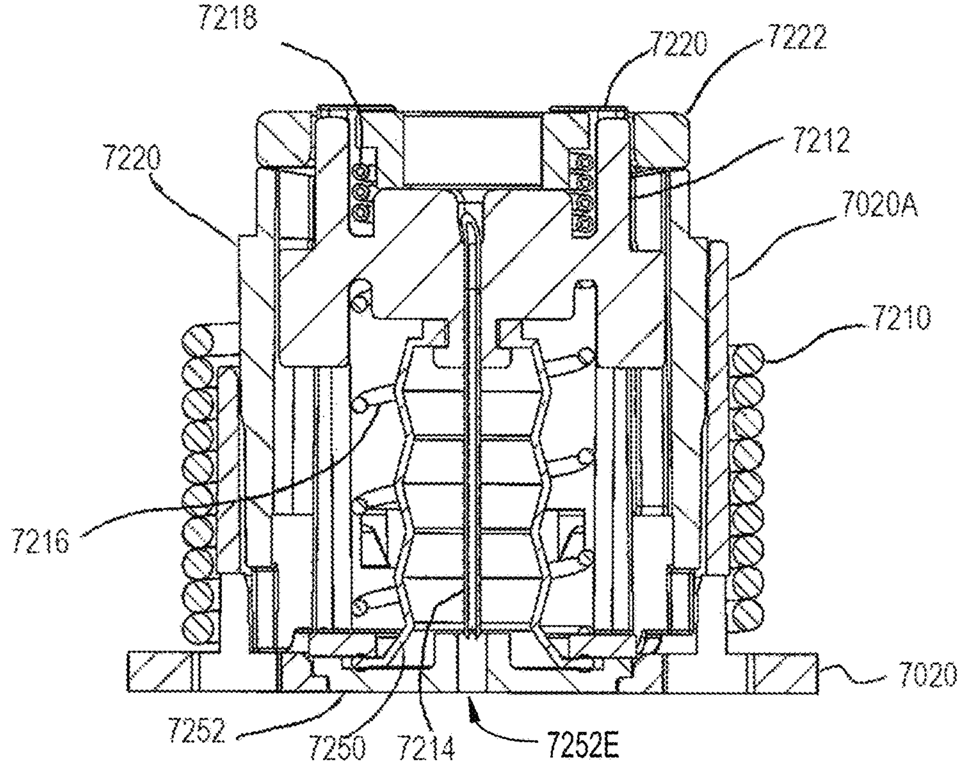
FIG. 67 shows a cross-sectional side view of the embodiment of FIG. 66.
Figure 68:
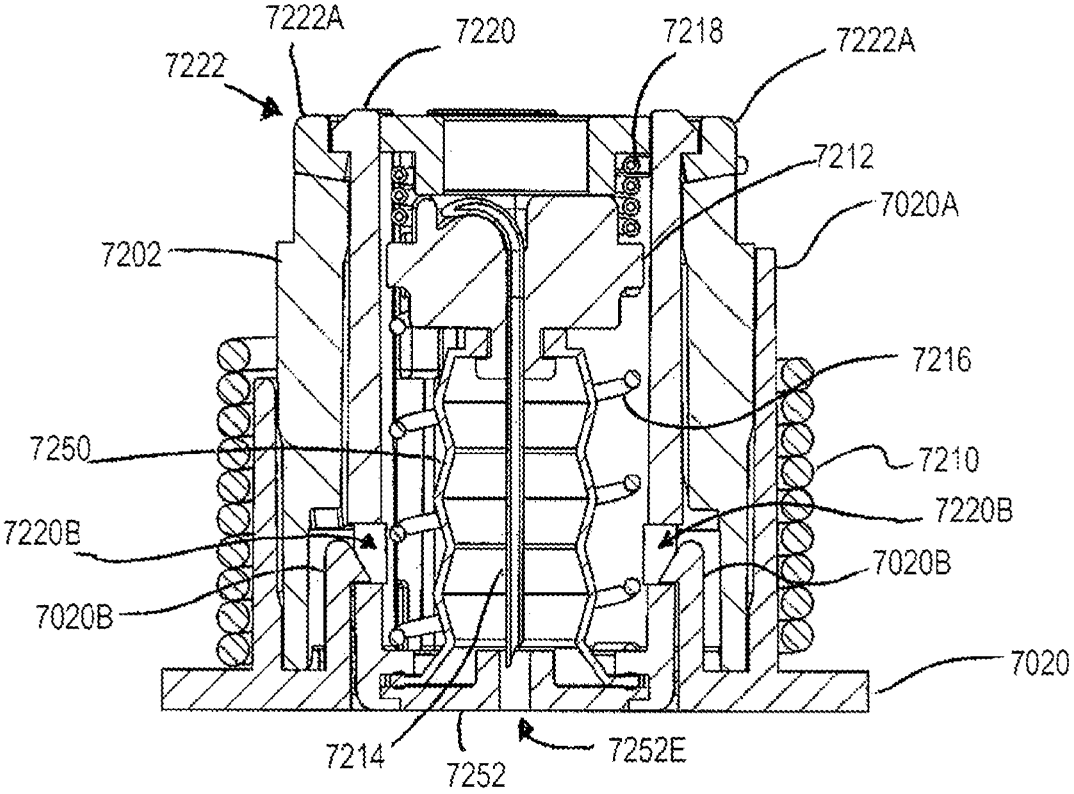
FIG. 68 shows a cross-sectional front view of the embodiment of FIG. 66.

FIGS. 11-13 show another embodiment of an insertion mechanism. As shown in FIG. 66, one end of the rotational biasing member 7210 is disposed in a recess 7202B formed in the housing 7202 of the insertion mechanism. By engaging the housing in this way the requirement for a protrusion extending outwardly from the housing is eliminated, thereby allowing the overall size of the insertion mechanism to be reduced. Further, as shown in FIG. 67 the sterile boot 7250 may be configured in an “accordion” configuration, which may allow the diameter of the sterile boot to be less than the sterile boot shown in previous embodiments. It may also be seen in FIG. 67 that platform 7020 may have upwardly extending boss 7020A that aids in locating and retaining the needle insertion mechanism. The rotational biasing member 7210 may be positioned around the outside of boss 7020A. The needle insertion mechanism may also include cap 7222. The cap may engage the shell 7220 and act to retain the components of the needle insertion mechanism in place. Specifically, the cap may retain the conduit in position within housing 7202. The cap may include one or more circumferential flex arms 7222A which, during installation, may flex outward in response to contact with protrusions of the shell 7220. The flex arms may then return to their natural position and thereby be retained in place with respect to the shell as seen best in the cross-section view of FIG. 68. Also seen in FIG. 68, one or more flex arms 7020B of platform 7020 may engage apertures 7220B of the housing 7220. This engagement retains and positions the insertion mechanism with respect to platform 7020. The platform 7020 of the drug delivery device may further include locking arms 7020B which are configured to engage apertures 7220B of the shell. This engagement retains the insertion mechanism in position with respect to the drug delivery device. The stages of operation of this embodiment may be substantially similar to those described above (i.e., de-energizing of the rotational biasing member leads to insertion of the needle and de-energizing of the retraction biasing member leads to retraction of the needle).

In some embodiments, retraction is activated upon removal of the drug delivery device from the patient's body. In other embodiments, retraction is activated if it is determined that an error has occurred in the delivery of the substances to the patient. For example, an occlusion of the drug delivery pathway which prevents the flow of medicament may be detected by a sensing function of the drug delivery device. Upon the sensing of the occlusion an electrical or mechanical input may be used to initiate retraction of the needle.

Activating retraction of the needle may be accomplished through many mechanisms. For example, a button may be provided on the outside of housing 12 which, when depressed by the patient, activates retraction of the needle from the patient's body. For example, in one embodiment, depressing the button may allow housing 6202 to rotate, hence allowing retraction biasing member 6216 to expand and retract needle 6214. Actuation of the button may be spring assisted such that the travel and/or force required to depress the button is reduced. Alternatively, or additionally, upon drive mechanism 100 reaching end-of-dose an electrical or mechanical actuator may cause activation of retraction. For example, upon end-of-dose, an electrical connection may be made such that a current is applied to a nitinol component. Upon application of the current the nitinol component's temperature rises. Because of nitinol's shape memory characteristics this component may be configured, upon an increase in temperature, to transform from a first configuration to a second configuration. In this second configuration, the nitinol component may allow or cause the actuation of the retraction of the needle by, for example, allowing rotation of housing 6202.

Alternatively, or additionally, a sensor such as on-body sensor 24 may, when drug delivery device 10 is removed from the patient's body, cause or allow activation of the retraction of the needle. For example, when drug delivery device 10 is installed on the patient the position of on-body sensor 24 may prevent rotation of housing 6202 to the retraction position. Upon removal from the patient a change in configuration of on-body sensor 24 may allow rotation. In another embodiment, a light sensor may be placed on drug delivery device 10 near to base opening 6252. When drug delivery device 10 is in place on the patient's body light would be substantially blocked from entering the light sensor. Upon removal of drug delivery device 10 from the patient's body light may be sensed by the light sensor and the light sensor may trigger an electromechanical actuator to allow or cause activation of retraction. In other embodiments, a pin-type press-fit interconnect is used to initiate retraction of the needle. The pin may be biased to at least partially protrude from housing 12 and be displaced upon placement of drug delivery device 10 on the patient. When displaced, the pin may engage a female hole on a PCB which may be a part of power and control system 400. Upon removal of drug delivery device 10 from the patient, the biased pin disengages the female PCB hole, thereby causing a signal to activate the retraction of the needle.

Certain optional standard components or variations of insertion mechanism 6200 or the drug delivery devices 10 or 6000 are contemplated while remaining within the breadth and scope of the present disclosure. For example, upper or lower housings may optionally contain one or more transparent or translucent windows 18, as shown in FIGS. 1A-1C, to enable the patient to view the operation of the drug delivery device 10 or verify that drug dose has completed. Additionally, the drug delivery device 10 may contain an adhesive patch 26 and a patch liner 28 on the bottom surface of the housing 12. The adhesive patch 26 may be utilized to adhere the drug delivery device 10 to the body of the patient for delivery of the drug dose. As would be readily understood by one having ordinary skill in the art, the adhesive patch 26 may have an adhesive surface for adhesion of the drug delivery device to the body of the patient. The adhesive surface of the adhesive patch 26 may initially be covered by a non-adhesive patch liner 28, which is removed from the adhesive patch 26 prior to placement of the drug delivery device 10 in contact with the body of the patient. Adhesive patch 26 may optionally include a protective shroud that prevents actuation of the optional on-body sensor 24 and covers base opening 6252E. Removal of the patch liner 28 may remove the protective shroud or the protective shroud may be removed separately. Removal of the patch liner 28 may further remove the sealing membrane 6254 of the insertion mechanism 6200, opening the insertion mechanism to the body of the patient for drug delivery.

Similarly, one or more of the components of insertion mechanism 6200 and the drug delivery devices 10 and 6000 may be modified while remaining functionally within the breadth and scope of the present disclosure. For example, as described above, while the housing of drug delivery device 10 is shown as two separate components upper housing 12A and lower housing 12B, these components may be a single unified component. As discussed above, a glue, adhesive, or other known materials or methods may be utilized to affix one or more components of the insertion mechanism and/or drug delivery device to each other. Alternatively, one or more components of the insertion mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the insertion mechanisms and drug delivery devices disclosed herein provide an efficient and easily-operated system for automated drug delivery from a drug container. The novel embodiments described herein provide integrated safety features; enable direct patient activation of the insertion mechanism; and are configured to maintain the sterility of the fluid pathway. As described above, the integrated safety features include optional on-body sensors, redundant lock-outs, automated needle insertion and retraction upon patient activation, and numerous patient feedback options, including visual and auditory feedback options. The novel insertion mechanisms of the present disclosure may be directly activated by the patient. For example, in at least one embodiment the rotation prevention feature, whether it is a stop component configured to engage protrusion 6202A or a gear engaged with teeth of housing 6202, which maintain the insertion mechanism in its locked, retracted state is directly displaced from its locked position by patient depression of the activation mechanism. Alternatively, one or more additional components may be included, such as a spring mechanism, which displaces the rotation prevention feature upon direct displacement of the activation mechanism by the patient without any intervening steps. In at least one configuration, rotation of a motor causes or allows rotation of a gear, thereby allowing rotation of the housing of the insertion mechanism.

Furthermore, the novel configurations of the insertion mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly. A further benefit of the present disclosure is that the components described herein are designed to be modular such that, for example, the housing and other components of the drug delivery device may readily be configured to accept and operate insertion mechanism 6200 or a number of other variations of the insertion mechanism described herein.

Assembly and/or manufacturing of insertion mechanism 6200, drug delivery devices 10 or 6000, or any of the individual components may utilize a number of known materials and methodologies in the art. For example, a number of known cleaning fluids such as isopropyl alcohol may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

In a further embodiment, the present disclosure provides a method of assembling the insertion mechanism including the steps of: connecting a hub to a proximal end of a needle; connecting a conduit to the hub; connecting a sterile boot to the hub; inserting a retraction biasing member into a sleeve of the needle insertion mechanism; inserting the hub, needle, conduit, and sterile boot into the sleeve (in this position, the retraction biasing member is constrained between the hub at one end and the shell at the other end); placing a housing around the sleeve; inserting a retraction biasing member into the sleeve; and connecting a base to the sleeve by engagement of flex arms with apertures in the housing. A rotational biasing member may be placed around the housing such that a portion of the rotational biasing member is engaged with a portion of the housing, thereby coupling de-energizing of the biasing member with rotation of the housing.

The distal end of the sterile boot may be positioned and held in fixed engagement with the distal end of the insertion mechanism housing by engagement of the housing with a base. In this position, the sterile boot is in an expanded configuration around the needle and creates an annular volume which may be sterile. A fluid conduit may be connected to the hub such that the fluid pathway, when open, travels directly from the fluid conduit, through the hub, and through the needle. A fluid pathway connector may be attached to the opposite end of the fluid conduit. The fluid pathway connector, and specifically a sterile sleeve of the fluid pathway connector, may be connected to a cap and pierceable seal of the drug container. The plunger seal and drive mechanism may be connected to the drug container at an end opposing the fluid pathway connector. A sealing membrane may be attached to the bottom of the base to close off the insertion mechanism from the environment. The components which constitute the pathway for fluid flow are now assembled. These components may be sterilized, by a number of known methods, and then mounted either fixedly or removably to an assembly platform or housing of the drug delivery device.

Manufacturing of a drug delivery device includes the step of attaching the base of the insertion mechanism to an assembly platform or housing of the drug delivery device. In at least one embodiment, the attachment is such that the base of the insertion mechanism is permitted to pass-through the assembly platform and/or housing to come in direct contact with the body of the patient. The method of manufacturing further includes attachment of the fluid pathway connector, drug container, and drive mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the patient during operation of the device.

A method of operating the drug delivery device may include the steps of: activating, by a patient, the activation mechanism; displacing a control arm to actuate an insertion mechanism; and actuating a power and control system to activate a drive control mechanism to drive fluid drug flow through the drug delivery device. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the drive control mechanism and drug container to force fluid drug flow through the drug container, the fluid pathway connector, a sterile fluid conduit, and the insertion mechanism for delivery of the fluid drug to the body of a patient.

XI. Drug Delivery Device with Multi-Function Drive Mechanism

Another embodiment of a drug delivery device 8000 is illustrated in FIGS. 69A-73D. Various aspects, components, mechanisms, assemblies, methods of manufacture, and methods of use associated with the drug delivery devices described in connection with FIGS. 1-68 may be incorporated into and/or applied to the drug delivery device 8000 to the extent they do not conflict with aspects, components, mechanisms, assemblies, methods of manufacture, and methods of use associated with the drug delivery device 8000, and vice versa. Furthermore, the drug delivery device 8000 may include a container 8050 filled with a volume of a fluid for delivery to a patient. The fluid may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

The present disclosure provides multi-function drive mechanisms for the controlled delivery of drug substances, controlled drug delivery pumps with such drive mechanisms, the methods of operating such devices, and the methods of assembling such devices. Notably, the multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a patient; and (iii) connecting a sterile fluid pathway to a drug container to permit fluid flow from the drug container to the needle insertion mechanism for delivery to the patient. The novel embodiments of the present disclosure thus are capable of delivering drug substances at variable rates. The drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the patient before, during, and after drug delivery. For example, the patient may be provided an initial feedback to identify that the system is operational and ready for drug delivery. Upon activation, the system may then provide one or more drug delivery status indications to the patient. At completion of drug delivery, the drive mechanism and drug delivery device may provide an end-of-dose indication. Because the end-of-dose indication is related to the physical end of axial translation and/or travel of one or more components of the drive mechanism, the drive mechanism and drug delivery device provide a true end-of-dose indication to the patient. Through these mechanisms, confirmation of drug dose delivery can accurately be provided to the patient or administrator. Accordingly, the novel devices of the present disclosure alleviate one or more of the problems associated with prior art devices, such as those referred to above.

In a first embodiment, the present disclosure provides a multi-function drive mechanism which includes an actuator, a gear assembly including a main gear, a drive housing, and a drug container having a cap, a pierceable seal (not visible), a barrel, and a plunger seal. The main gear may be, for example, a star gear disposed to contact multiple secondary gears or gear surfaces. A drug chamber, located within the barrel between the pierceable seal and the plunger seal, may contain a drug fluid for delivery through the insertion mechanism and drug delivery device into the body of the patient. A piston, and one or more biasing members, wherein the one or more biasing members are initially retained in an energized state and is configured to bear upon an interface surface of the piston, may also be incorporated in the multi-function drive mechanism. The piston is configured to translate substantially axially within a drug container having a plunger seal and a barrel. A tether is connected at one end to the piston and at another end to a winch drum/gear of a regulating mechanism, wherein the tether restrains the free expansion of the biasing member from its initial energized state and the free axial translation of the piston upon which the biasing member bears upon. The drug container may contain a drug fluid within a drug chamber for delivery to a patient. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of a regulating mechanism of the multi-function drive mechanism to meter the free expansion of the biasing member from its initial energized state and the free axial translation of the piston upon which the biasing member bears upon.

In at least one embodiment of the present disclosure, the regulating mechanism is gear assembly driven by an actuator of the multi-function drive mechanism. The regulating mechanism retards or restrains the distribution of tether, only allowing it to advance at a regulated or desired rate. This restricts movement of piston within barrel, which is pushed by one or more biasing members, hence controlling the movement of plunger seal and delivery of the drug contained in chamber. As the plunger seal advances in the drug container, the drug substance is dispensed through the sterile pathway connection, conduit, insertion mechanism, and into the body of the patient for drug delivery. The actuator may be a number of power/motion sources including, for example, a motor (e.g., a DC motor, AC motor, or stepper motor) or a solenoid (e.g., linear solenoid, rotary solenoid). In a particular embodiment, the actuator is a rotational stepper motor with a notch that corresponds with the gear teeth of the main/star gear.

The regulating mechanism may further include one or more gears of a gear assembly. One or more of the gears may be, for example, compound gears having a small diameter gear attached at a shared center point to a large diameter gear. The gear assembly may include a winch gear coupled to a winch drum/gear upon which the tether may be releasably wound. Accordingly, rotation of the gear assembly initiated by the actuator may be coupled to winch drum/gear (i.e., through the gear assembly), thereby controlling the distribution of tether, the rate of expansion of the biasing members and the axial translation of the piston, and the rate of movement of plunger seal within barrel to force a fluid from drug chamber. The rotational movement of the winch drum/gear, and thus the axial translation of the piston and plunger seal, are metered, restrained, or otherwise prevented from free axial translation by other components of the regulating element, as described herein. Notably, the regulating mechanisms of the present disclosure do not drive the delivery of fluid substances from the drug chamber. The delivery of fluid substances from the drug chamber is caused by the expansion of the biasing member from its initial energized state acting upon the piston and plunger seal. The regulating mechanisms instead function to provide resistance to the free motion of the piston and plunger seal as they are pushed by the expansion of the biasing member from its initial energized state. The regulating mechanism does not drive the delivery but only controls the delivery motion. The tether limits or otherwise restrains the motion of the piston and plunger seal, but does not apply the force for the delivery.

In addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a patient; and connecting a sterile fluid pathway to a drug container to permit fluid flow from the drug container to the needle insertion mechanism for delivery to the patient. In at least one embodiment, initial motion by the actuator of the multi-function drive mechanism causes rotation of main/star gear. In one manner, main/star gear conveys motion to the regulating mechanism through gear assembly. In another manner, main/star gear conveys motion to the needle insertion mechanism through gear. As gear is rotated by main/star gear, gear engages the needle insertion mechanism to initiate the fluid pathway connector into the patient, as described in detail above. In one particular embodiment, needle insertion mechanism is a rotational needle insertion mechanism. Accordingly, gear is configured to engage a corresponding gear surface of the needle insertion mechanism. Rotation of gear causes rotation of needle insertion mechanism through the gear interaction between gear of the drive mechanism and corresponding gear surface of the needle insertion mechanism. Once suitable rotation of the needle insertion mechanism occurs, the needle insertion mechanism may be initiated to create the fluid pathway connector into the patient, as described in detail herein.

In at least one embodiment, rotation of the needle insertion mechanism in this manner may also cause a connection of a sterile fluid pathway to a drug container to permit fluid flow from the drug container to the needle insertion mechanism for delivery to the patient. Ramp aspect of needle insertion mechanism is caused to bear upon a movable connection hub of the sterile fluid pathway connector. As the needle insertion mechanism is rotated by the multi-function drive mechanism, ramp aspect of needle insertion mechanism bears upon and translates movable connection hub of the sterile fluid pathway connector to facilitate a fluid connection therein. In at least one embodiment, the needle insertion mechanism may be configured such that a particular degree of rotation enables the needle/trocar to retract as detailed above. Additionally or alternatively, such needle/trocar retraction may be configured to occur upon a patient-activity or upon movement or function of another component of the drug delivery device. In at least one embodiment, needle/trocar retraction may be configured to occur upon end-of-drug-delivery, as triggered by, for example, the regulating mechanism and/or one or more of the status readers as described herein.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a patient. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present disclosure provides a drug delivery pump with controlled drug delivery. The drug delivery pump having a housing and an assembly platform, upon which an activation mechanism, an insertion mechanism, a fluid pathway connector, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum/gear of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a patient. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of the delivery regulating mechanism to meter the free expansion of the biasing member from its initial energized state and the free axial translation of the piston upon which the biasing member bears upon.

In another embodiment, the drug delivery device further includes a gear assembly. The gear assembly may include a winch gear connected to a winch drum/gear upon which the tether may be releasably wound, rotation of the winch drum/gear releases the tether from the winch drum/gear to meter the free expansion of the biasing member from its initial energized state and the free axial translation of the piston upon which the biasing member bears upon. The metering of the tether controls the rate or profile of drug delivery to a patient. The piston may be one or more parts and connects to a distal end of the tether. The winch drum/gear is coupled to a regulating mechanism which controls rotation of the winch drum/gear and hence metering of the translation of the piston.

In yet another embodiment, the drug delivery device may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a patient. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug delivery device is configured to receive one or more inputs to meter the release of the tether by the winch drum/gear and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch drum/gear on the free axial translation of the piston upon which the biasing member bears upon to meet a desired drug delivery rate or profile, to change the dose volume for delivery to the patient, and/or to otherwise start, stop, or pause operation of the drive mechanism.

The novel embodiments of the present disclosure provide drive mechanisms which are capable of metering, providing resistance, or otherwise preventing free axial translation of the plunger seal utilized to force a drug substance out of a drug container and, thereby, controlling the rate of delivery of drug substances. The novel control delivery drive mechanisms are additionally capable of providing the incremental status of the drug delivery before, during, and after operation of the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present disclosure may include one or more additional components which may be considered standard components in the industry of medical devices. For example, the embodiments may include one or more batteries utilized to power the motor, drive mechanisms, and drug delivery devices of the present disclosure. The components, and the embodiments containing such components, are within the contemplation of the present disclosure and are to be understood as falling within the breadth and scope of the present disclosure.

The present disclosure provides multi-function drive mechanisms for the controlled delivery of drug substances and drug delivery pumps which incorporate such multi-function drive mechanisms. The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a patient; and (iii) connecting a sterile fluid pathway to a drug container to permit fluid flow from the drug container to the needle insertion mechanism for delivery to the patient. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the patient before, during, and after drug delivery. For example, the patient may be provided an initial feedback to identify that the system is operational and ready for drug delivery. Upon activation, the system may then provide one or more drug delivery status indications to the patient. At completion of drug delivery, the drive mechanism and drug delivery device may provide an end-of-dose indication.

The novel devices of the present disclosure provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained patients. The novel devices of the present disclosure provide these desirable features without any of the problems associated with known prior art devices. Certain non-limiting embodiments of the novel drug delivery pumps, drive mechanisms, and their respective components are described further herein with reference to the accompanying Figures.

Figure 69A:
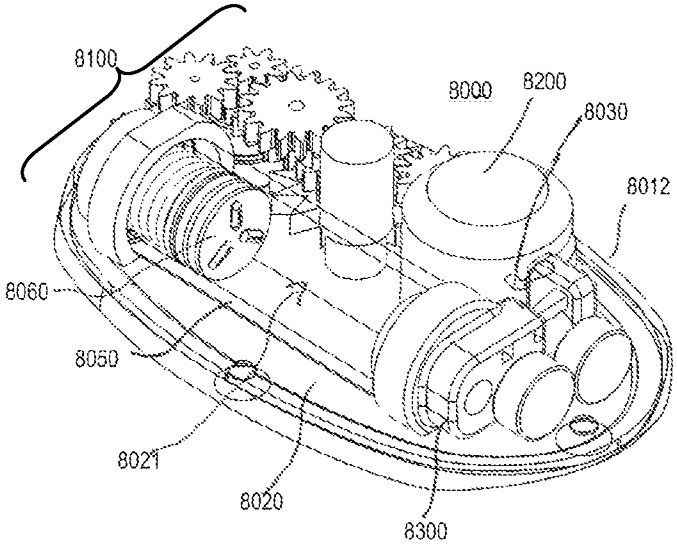
FIG. 69A shows an isometric view of the interior components of a drug delivery device having a multi-function drive mechanism, according to one embodiment of the present disclosure (shown without the adhesive patch)
Figure 69B:
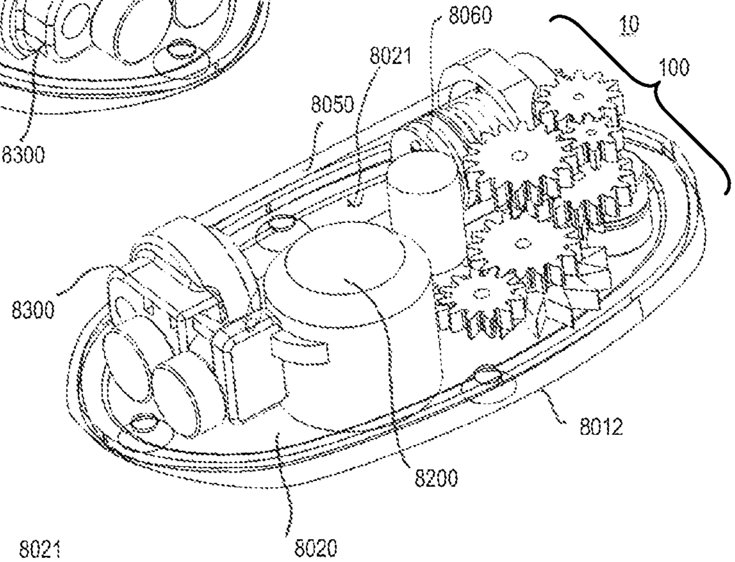
FIG. 69B shows an isometric view of the interior components of the drug delivery device shown in FIG. 69A (shown without the adhesive patch) from another viewpoint.
Figure 69C:
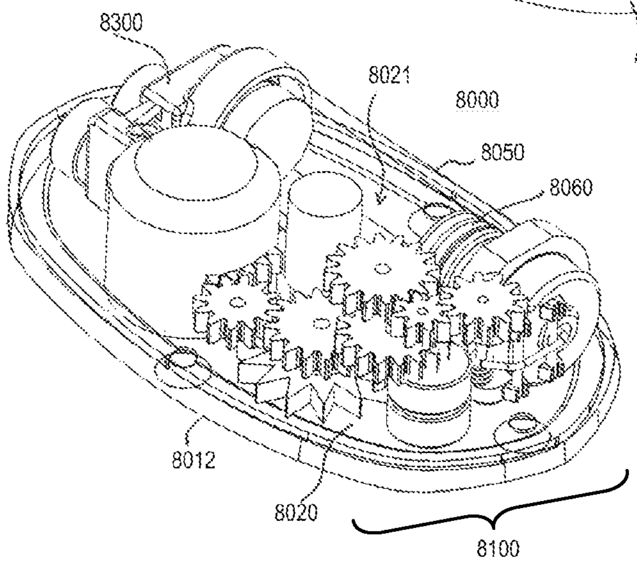
Figure 69D:
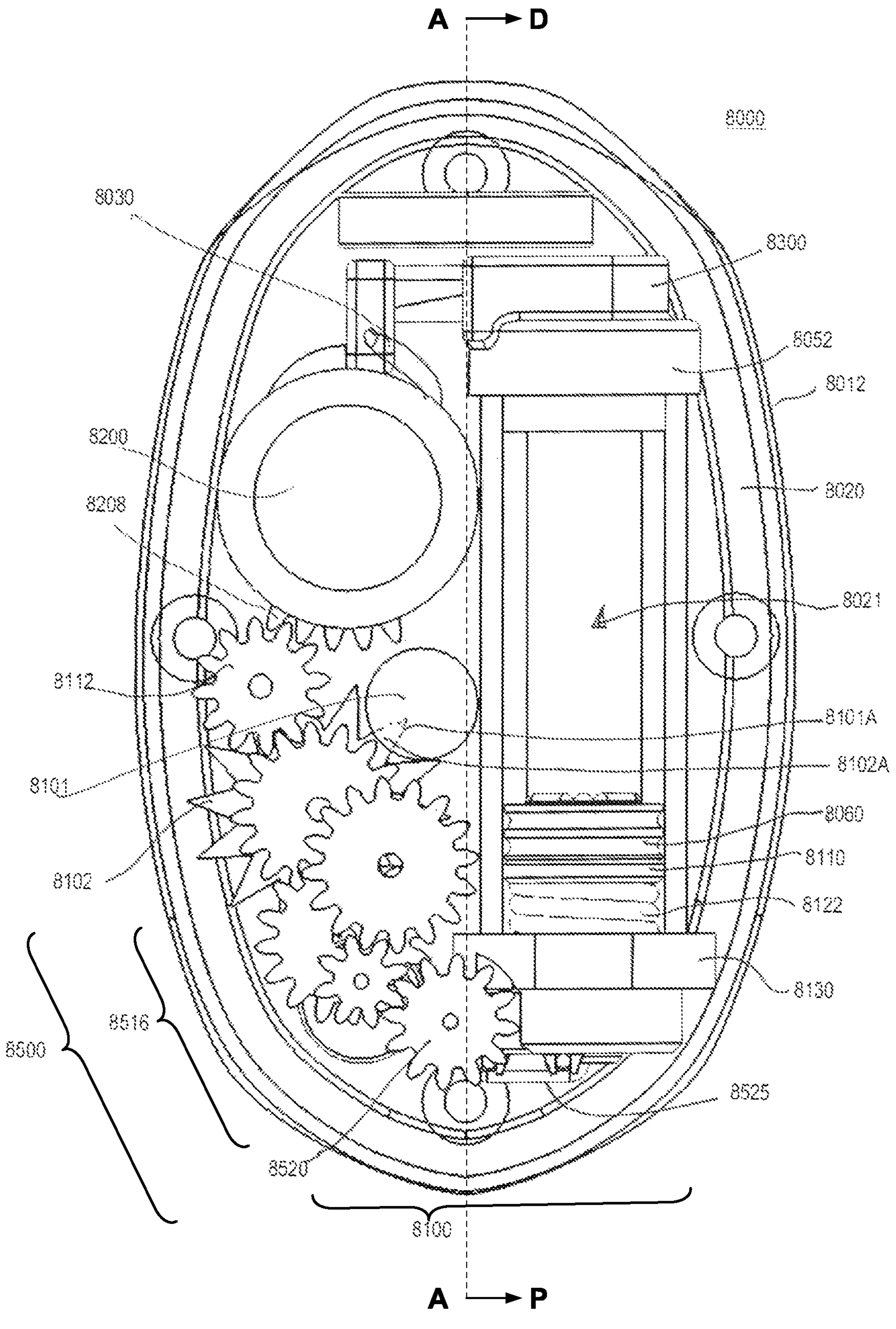

FIGS. 1A-1C show an exemplary drug delivery device according to at least one embodiment of the present disclosure with the top housing removed so that the internal components are visible. The drug delivery device may be utilized to administer delivery of a drug treatment into a body of a patient. As shown in FIGS. 69A-69C, the drug delivery device 8000 includes a pump housing 8012. Pump housing 8012 may include one or more housing subcomponents which are fixedly engageable to facilitate easier manufacturing, assembly, and operation of the drug delivery device. For example, drug delivery device 8000 includes a pump housing 8012 which may include an upper housing and a lower housing (not shown for ease of viewing internal components). The drug delivery device may further include an activation mechanism, a status indicator, and a window. Window may be any translucent or transmissive surface through which the operation of the drug delivery device may be viewed. As shown in FIG. 69B, drug delivery device 8000 further includes assembly platform 8020, sterile fluid conduit 8030, drive mechanism 8100 having drug container 8050, insertion mechanism 8200, fluid pathway connector 8300, and a power and control system (not shown). One or more of the components of such drug delivery devices may be modular in that they may be, for example, pre-assembled as separate components and configured into position onto the assembly platform 8020 of the drug delivery device 8000 during manufacturing.

The pump housing 8012 contains all of the device components and provides a means of removably attaching the device 8000 to the skin of the patient. The pump housing 8012 also provides protection to the interior components of the device 8000 against environmental influences. The pump housing 8012 is ergonomically and aesthetically designed in size, shape, and related features to facilitate easy packaging, storage, handling, and use by patients who may be untrained and/or physically impaired. Furthermore, the external surface of the pump housing 8012 may be utilized to provide product labeling, safety instructions, and the like. Additionally, as described above, housing 8012 may include certain components, such as one or more status indicators and windows, which may provide operation feedback to the patient.

In at least one embodiment, the drug delivery device 8000 provides an activation mechanism that is displaced by the patient to trigger the start command to the power and control system. In a preferred embodiment, the activation mechanism is a start button that is located through the pump housing 8012, such as through an aperture between upper housing and lower housing, and which contacts either directly or indirectly the power and control system. In at least one embodiment, the start button may be a push button, and in other embodiments, may be an on/off switch, a toggle, or any similar activation feature known in the art. The pump housing 8012 also provides one or more status indicators and windows. In other embodiments, one or more of the activation mechanism, the status indicator, the window, and combinations thereof may be provided on the upper housing or the lower housing such as, for example, on a side visible to the patient when the drug delivery device 8000 is placed on the body of the patient. Housing 8012 is described in further detail hereinafter with reference to other components and embodiments of the present disclosure.

Drug delivery device 8000 is configured such that, upon activation by a patient by depression of the activation mechanism, the multi-function drive mechanism is activated to: insert a fluid pathway into the patient; enable, connect, or open necessary connections between a drug container, a fluid pathway, and a sterile fluid conduit; and force drug fluid stored in the drug container through the fluid pathway and fluid conduit for delivery into a patient. In at least one embodiment, such delivery of drug fluid into a patient is performed by the multi-function drive mechanism in a controlled manner. One or more optional safety mechanisms may be utilized, for example, to prevent premature activation of the drug delivery device. For example, an optional on-body sensor (not visible) may be provided in one embodiment as a safety feature to ensure that the power and control system, or the activation mechanism, cannot be engaged unless the drug delivery device 8000 is in contact with the body of the patient. In one such embodiment, the on-body sensor is located on the bottom of lower housing where it may come in contact with the patient's body. Upon displacement of the on-body sensor, depression of the activation mechanism is permitted. Accordingly, in at least one embodiment the on-body sensor is a mechanical safety mechanism, such as for example a mechanical lock out, that prevents triggering of the drug delivery device 8000 by the activation mechanism. In another embodiment, the on-body sensor may be an electro-mechanical sensor such as a mechanical lock out that sends a signal to the power and control system to permit activation. In still other embodiments, the on-body sensor can be electrically based such as, for example, a capacitive- or impedance-based sensor which must detect tissue before permitting activation of the power and control system. In at least one embodiment, such an an electrically based on-body sensor may incorporate a resistor with an impedance of approximately (e.g., ±10%) 1 MΩ. These concepts are not mutually exclusive and one or more combinations may be utilized within the breadth of the present disclosure to prevent, for example, premature activation of the drug delivery device. In a preferred embodiment, the drug delivery device 8000 utilizes one or more mechanical on-body sensors. Additional integrated safety mechanisms are described herein with reference to other components of the novel drug delivery devices.

XI.A. Power and Control System

The power and control system may include a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the patient and interfaces with the drive mechanism 8100. In one embodiment, the power and control system interfaces either directly or indirectly with the on-body sensor 24 to identify when the device is in contact with the patient and/or the activation mechanism to identify when the device has been activated. The power and control system may also interface with the status indicator of the pump housing 8012, which may be a transmissive or translucent material which permits light transfer, to provide visual feedback to the patient. The power and control system interfaces with the drive mechanism 8100 through one or more interconnects to relay status indication, such as activation, drug delivery, and end-of-dose, to the patient. Such status indication may be presented to the patient via auditory tones, such as through the audible alarms, and/or via visual indicators, such as through the LEDs. In a preferred embodiment, the control interfaces between the power and control system and the other components of the drug delivery device are not engaged or connected until activation by the patient. This is a desirable safety feature that prevents accidental operation of the drug delivery device and may additionally maintain the energy contained in the power source during storage, transportation, and the like.

The power and control system may be configured to provide a number of different status indicators to the patient. For example, the power and control system may be configured such that after the on-body sensor and/or trigger mechanism have been pressed, the power and control system provides a ready-to-start status signal via the status indicator if device start-up checks provide no errors. After providing the ready-to-start status signal and, in an embodiment with the optional on-body sensor, if the on-body sensor remains in contact with the body of the patient, the power and control system will power the drive mechanism 8100 to begin delivery of the drug treatment through the fluid pathway connector 8300 and sterile fluid conduit 8030 (not shown).

Additionally, the power and control system may be configured to identify removal of the drug delivery device from its packaging. The power and control system may be mechanically, electronically, or electro-mechanically connected to the packaging such that removal of the drug delivery device from the packaging may activate or power-on the power and control system for use, or simply enable the power and control system to be powered-on by the patient. In such an embodiment, without removal of the drug delivery device from the packaging the drug delivery device cannot be activated. This provides an additional safety mechanism of the drug delivery device and for the patient. In at least one embodiment, the drug delivery device or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between. Additionally or alternatively, the drug delivery device or the power and control system may be mechanically connected to the packaging, such as by a pin and slot relationship which activates the system when the pin is removed (i.e., once the drug delivery device is removed from the packaging).

In a preferred embodiment of the present disclosure, once the power and control system has been activated, the multi-function drive mechanism is initiated to actuate the insertion mechanism 8200 and the fluid pathway connector 8300, while also permitting the drug fluid to be forced from the drug container. During the drug delivery process, the power and control system is configured to provide a dispensing status signal via the status indicator. After the drug has been administered into the body of the patient and after the end of any additional dwell time, to ensure that substantially the entire dose has been delivered to the patient, the power and control system may provide an okay-to-remove status signal via the status indicator. This may be independently verified by the patient by viewing the drive mechanism and drug dose delivery through the window of the pump housing 8012. Additionally, the power and control system may be configured to provide one or more alert signals via the status indicator, such as for example alerts indicative of fault or operation failure situations.

The power and control system may additionally be configured to accept various inputs from the patient to dynamically control the drive mechanisms 8100 to meet a desired drug delivery rate or profile. For example, the power and control system may receive inputs, such as from partial or full activation, depression, and/or release of the activation mechanism, to set, initiate, stop, or otherwise adjust the control of the drive mechanism 8100 via the power and control system to meet the desired drug delivery rate or profile. Similarly, the power and control system may be configured to receive such inputs to adjust the drug dose volume; to prime the drive mechanism, fluid pathway connector, and fluid conduit; and/or to start, stop, or pause operation of the drive mechanism 8100. Such inputs may be received by the patient directly acting on the drug delivery device 8000, such as by use of the activation mechanism 8014 or a different control interface, or the power and control system may be configured to receive such inputs from a remote control device. Additionally or alternatively, such inputs may be pre-programmed.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the patient. Similarly, activation of the device may require a delayed depression (i.e., pushing) of the activation mechanism of the drug delivery device 8000 prior to drug delivery device activation. Additionally, the system may include a feature which permits the patient to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

XI.B. Insertion Mechanism

A number of insertion mechanisms may be utilized within the drug delivery devices of the present disclosure. The pump-type delivery devices of the present disclosure may be connected in fluid flow communication to a patient or patient, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure, including a rigid needle insertion mechanism and/or a rotational needle insertion mechanism as described by the present disclosure.

In at least one embodiment, the insertion mechanism 8200 includes an insertion mechanism housing having one or more lockout windows, and a base for connection to the assembly platform and/or pump housing (as shown in FIG. 69B and FIG. 69C). The connection of the base to the assembly platform 8020 may be, for example, such that the bottom of the base is permitted to pass-through a hole in the assembly platform to permit direct contact of the base to the body of the patient. In such configurations, the bottom of the base may include a sealing membrane that is removable prior to use of the drug delivery device 8000. The insertion mechanism may further include one or more insertion biasing members, a needle, a retraction biasing member, a cannula, and a manifold. The manifold may connect to sterile fluid conduit 8030 to permit fluid flow through the manifold, cannula, and into the body of the patient during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane (not visible).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. Displacement of the lockout pin(s), by one or more methods such as pulling, pushing, sliding, and/or rotation, permits insertion biasing member to decompress from its initial compressed, energized state. This decompression of the insertion biasing member drives the needle and, optionally, the cannula into the body of the patient. At the end of the insertion stage or at the end of drug delivery (as triggered by the multi-function drive mechanism), the retraction biasing member is permitted to expand in the proximal direction from its initial energized state. This axial expansion in the proximal direction of the retraction biasing member retracts the needle. If an inserter needle/trocar and cannula configuration are utilized, retraction of the needle may occur while maintaining the cannula in fluid communication with the body of the patient. Accordingly, the insertion mechanism may be used to insert a needle and cannula into the patient and, subsequently, retract the needle while retaining the cannula in position for drug delivery to the body of the patient.

XI.C. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 8000, the fluid pathway connector 8300 is enabled to connect the sterile fluid conduit 8030 to the drug container of the drive mechanism 8100. Such connection may be facilitated by a piercing member, such as a needle, penetrating a pierceable seal of the drug container of the drive mechanism 8100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the patient. In one such embodiment, the fluid pathway connector may be substantially similar to that described in International Patent Application No. PCT/US2012/054861, which is included by reference herein in its entirety for all purposes. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Applications No. PCT/US2013/030478 or No. PCT/US2014/052329, for example, which are included by reference herein in their entirety for all purposes. According to such an embodiment, a drug container may have a drug chamber within a barrel between a pierceable seal and a plunger seal. A drug fluid is contained in the drug chamber. Upon activation of the device by the patient, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the patient for drug delivery. In at least one embodiment, the fluid flows through only a manifold and a cannula and/or needle of the insertion mechanism, thereby maintaining the sterility of the fluid pathway before and during drug delivery.

In a preferred embodiment, the sterile fluid pathway connector is initiated by movement of the needle insertion mechanism, which itself is initiated by the multi-function drive mechanism. Additionally or alternatively, the sterile fluid pathway connector is initiated by movement directly of the multi-function drive mechanism. For example, the multi-function drive mechanism may include a rotational gear, such as the star gear described in detail herein, that acts concurrently or sequentially to control the rate of drug delivery, to actuate the needle insertion mechanism, and/or initiate the sterile fluid pathway connector. In one particular embodiment, shown in FIGS. 69A-69C, the multi-function drive mechanism performs all of these steps substantially concurrently. The multi-function drive mechanism rotates a gear that acts upon several other components. The gear acts on a gear assembly to control the rate of drug delivery, while also contacting a needle insertion mechanism to introduce a fluid pathway into the patient. As the needle insertion mechanism is initiated, the sterile fluid connection is made to permit drug fluid flow from the drug container, through the fluid conduit, into the needle insertion mechanism, for delivery into the patient as the gear and gear assembly of the multi-function drive mechanism control the rate of drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 8300 and the sterile fluid conduit 8030 are provided hereinafter in later sections in reference to other embodiments.

XI.D. Multi-Function Drive Mechanism

The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a patient; and (iii) connecting a sterile fluid pathway to a drug container to permit fluid flow from the drug container to the needle insertion mechanism for delivery to the patient. With reference to the embodiments shown in FIGS. 70A-70D and 71A-71D, multi-function drive mechanism 8100 includes an actuator 8101, a gear assembly 8110 including a main gear 8102, a drive housing 8130, and a drug container 8050 having a cap 8052, a pierceable seal (not visible), a barrel 8058, and a plunger seal 8060. The main gear 8102 may be, for example, a star gear disposed to contact multiple secondary gears or gear surfaces. A drug chamber 8021, located within the barrel 8058 between the pierceable seal and the plunger seal 8060, may contain a drug fluid for delivery through the insertion mechanism and drug delivery device into the body of the patient. The seals described herein may be comprised of a number of materials but are, in a preferred embodiment, comprised of one or more elastomers or rubbers. The drive mechanism 8100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the patient.

In one particular embodiment, the drive mechanism 8100 employs one or more compression springs as the biasing member(s). Upon activation of the drug delivery device by the patient, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the patient for drug delivery. In at least one embodiment, the fluid flows through only a manifold and a cannula of the insertion mechanism, thereby maintaining the sterility of the fluid pathway before and during drug delivery. Such components and their functions are described in further detail herein.

Referring now to the embodiment of the multi-function drive mechanism shown in FIGS. 70A-70D and 70A-70D, multi-function drive mechanism 8100 includes an actuator 8101, a gear assembly 8110 including a main gear 8102, a drive housing 8130, and a drug container 8050 having a cap 8052, a pierceable seal (not visible), a barrel 8058, and a plunger seal 8060. The main gear 8102 may be, for example, a star gear disposed to contact multiple secondary gears or gear surfaces. A drug chamber 8021, located within the barrel 8058 between the pierceable seal and the plunger seal 8060, may contain a drug fluid for delivery through the insertion mechanism and drug delivery device into the body of the patient. Compressed within the drive housing 8130, between the drug container 8050 and the proximal end of the housing 8130, are one or more drive biasing members 8122 and a piston 8110, wherein the drive biasing members 8122 are configured to bear upon an interface surface 8110C of the piston 8110, as described further herein. Optionally, a cover sleeve (not shown) may be utilized between the drive biasing members 8122 and the interface surface 8110C of the piston 8110 to, for example, promote more even distribution of force from the drive biasing member 8122 to the piston 8110, prevent buckling of the drive biasing members 8122, and/or hide biasing members 8122 from patient view. Interface surface 8110C of piston 8110 is caused to rest substantially adjacent to, or in contact with, a proximal end of seal 8060. Although the embodiments shown in FIGS. 70A-70D and 71A-71D show a singular biasing member it is also contemplated that one or more biasing members disposed to act in parallel may be used.

Figure 70A:
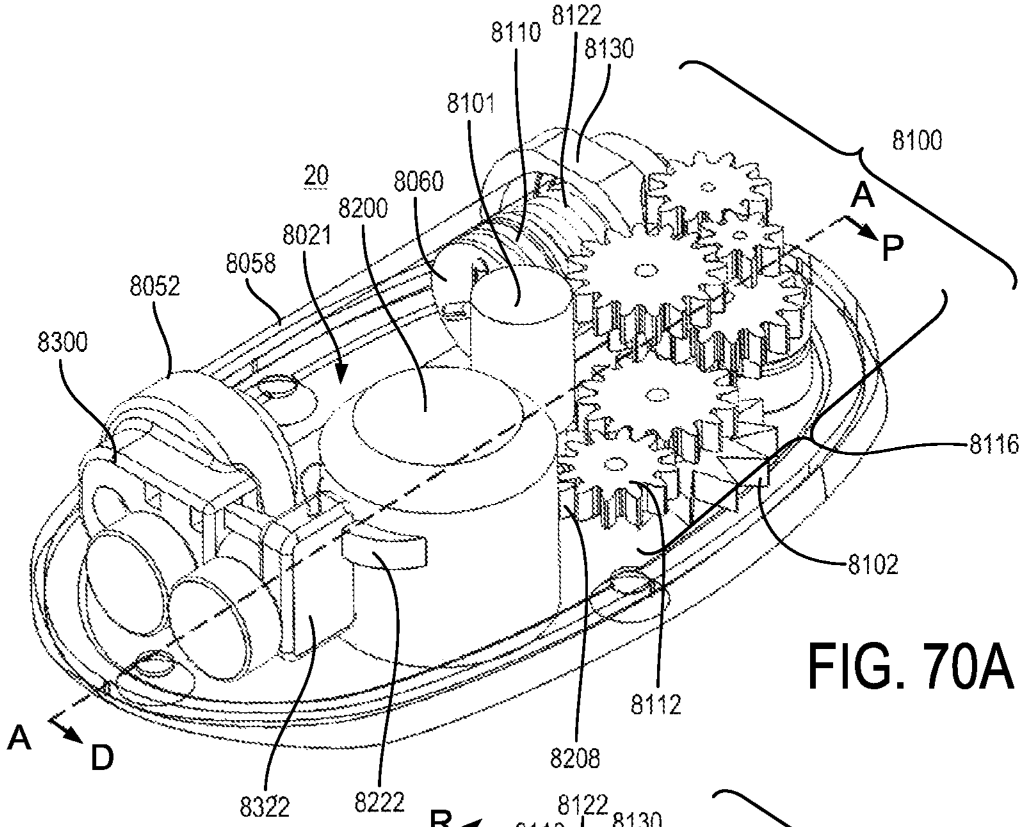
Figure 70B:
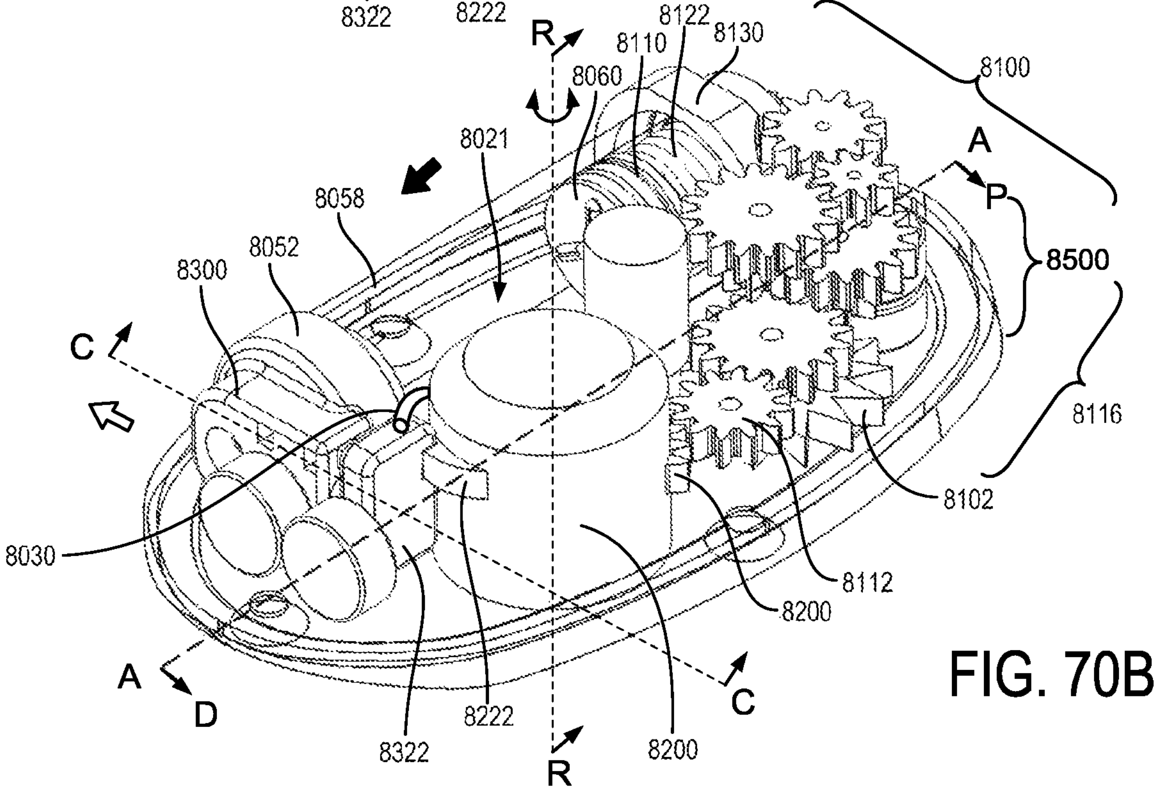
Figure 70C:
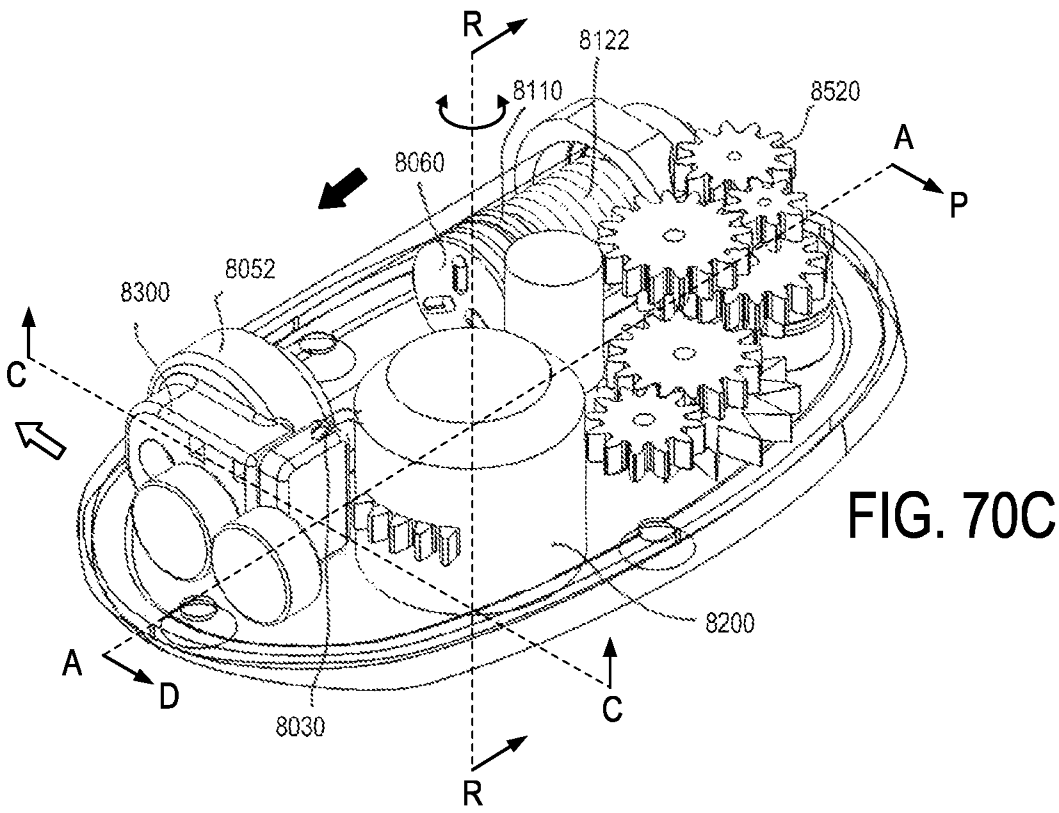
Figure 70D:
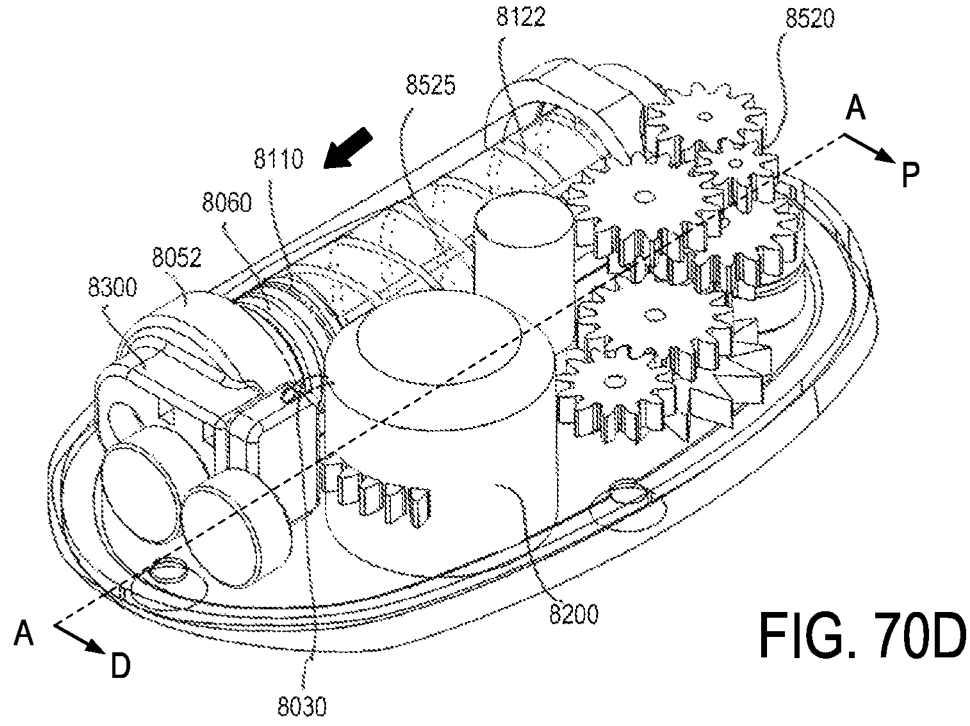
Figure 71A:
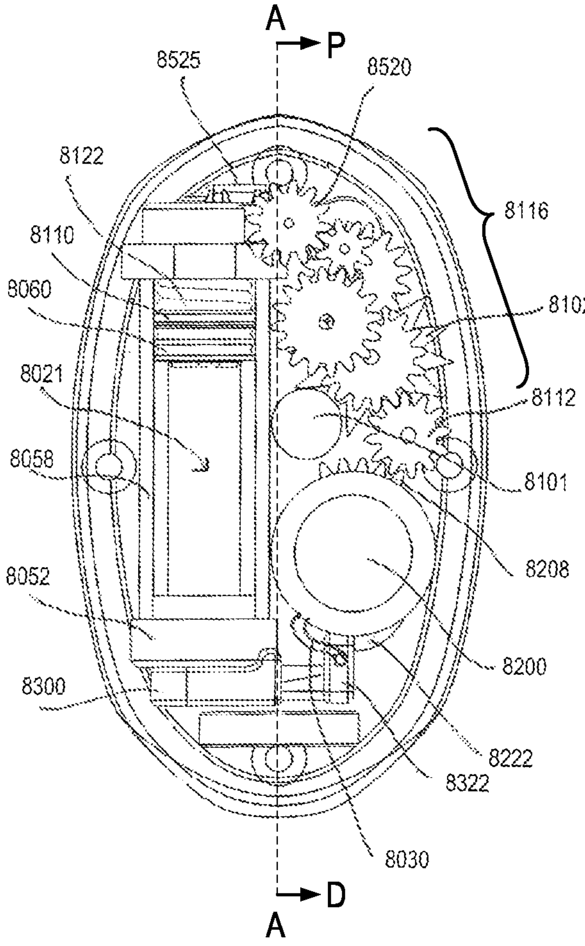
Figure 71B:
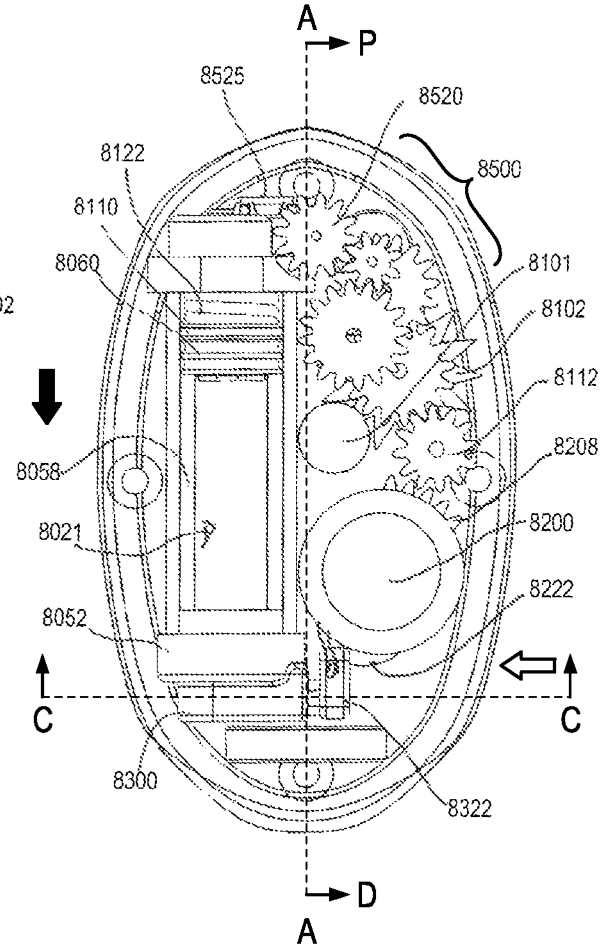
Figure 71C:
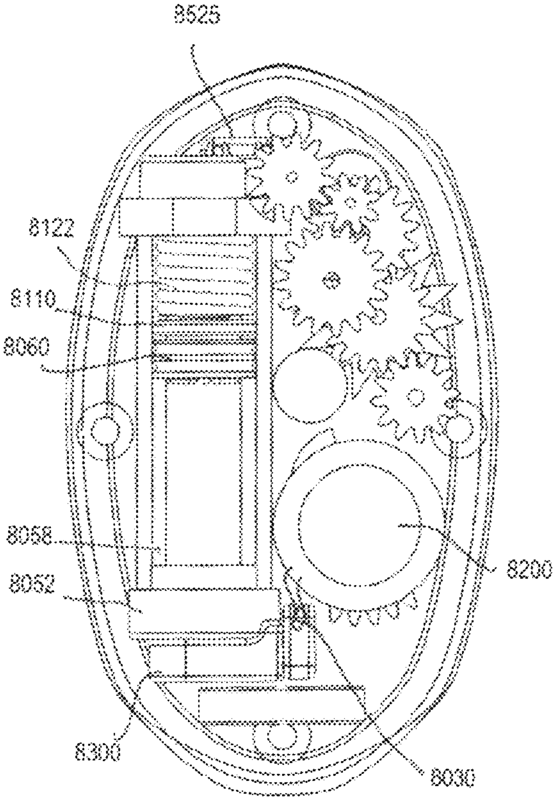
Figure 71D:
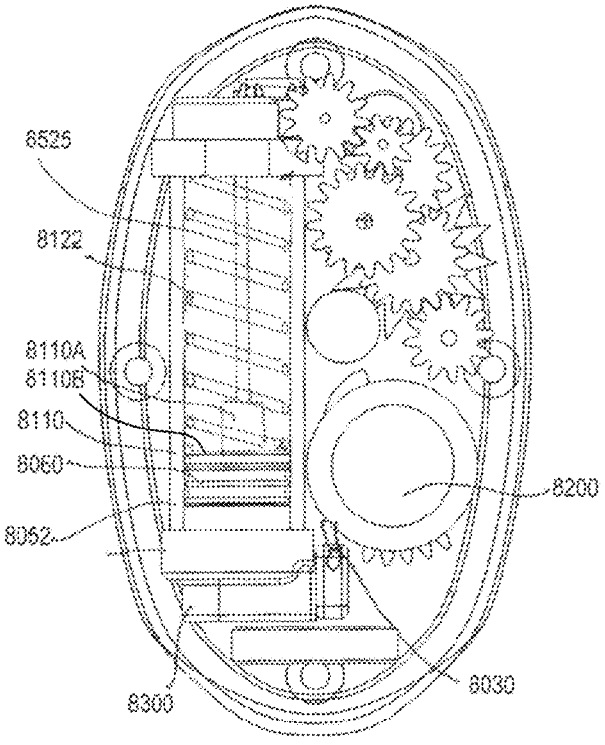

As best shown in FIG. 70D and FIG. 71D, the piston 8110 may be comprised of two components 8110A and 8110B and have an interface surface 8110C to contact the plunger seal. A tether, ribbon, string, or other retention strap (referred to herein as the "tether" 8525) may be connected at one end to the piston 8110A, 8110B. For example, the tether 8525 may be connected to the piston 8110A, 8110B by retention between the two components of the piston 8110A, 8110B when assembled. The tether 8525 is connected at another end to a winch drum/gear 8520 of a delivery control mechanism 8500. Through the use of the winch drum/gear 8520 connected to one end of the tether 8525, and the tether 8525 connected at another end to the piston 8110A, 8110B, the regulating mechanism 8500 functions to control, meter, provide resistance, or otherwise prevent free axial translation of the piston 8110A, 8110B and plunger seal 8060 utilized to force a drug substance out of a drug container 8050. Accordingly, the regulating mechanism 8500 is a portion of the gear assembly 8116 aspect of the multi-function drive mechanism, which together function to control the rate or profile of drug delivery to the patient.

Figure 72:
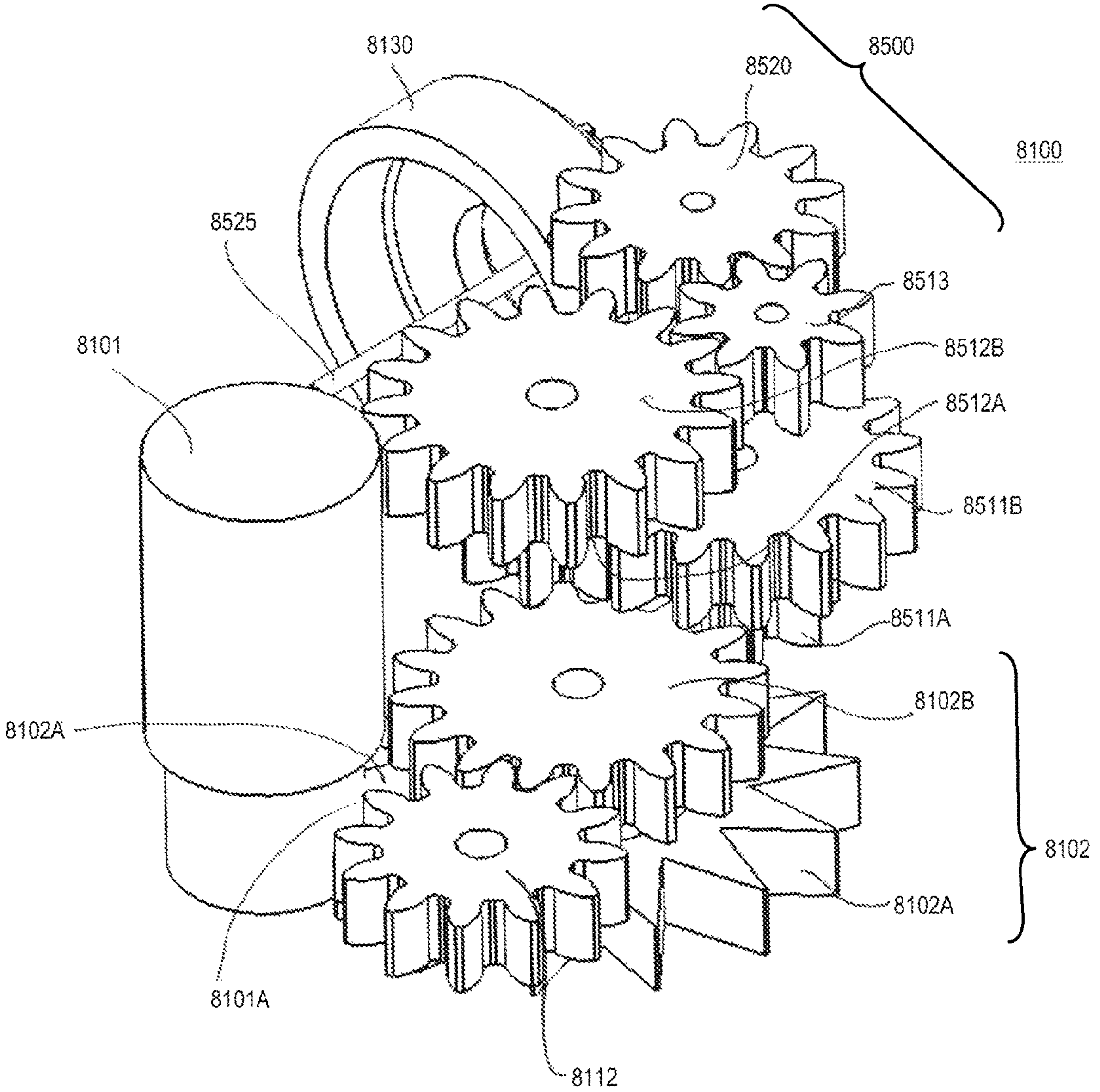
Figure 73A:
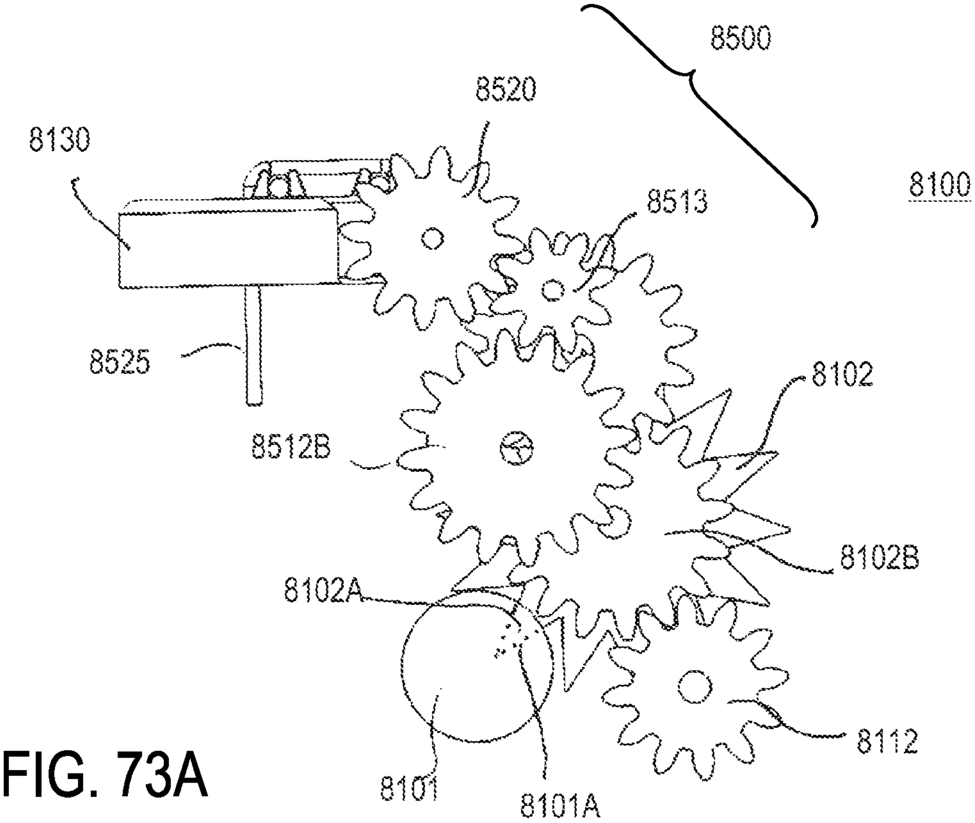
Figure 73B:
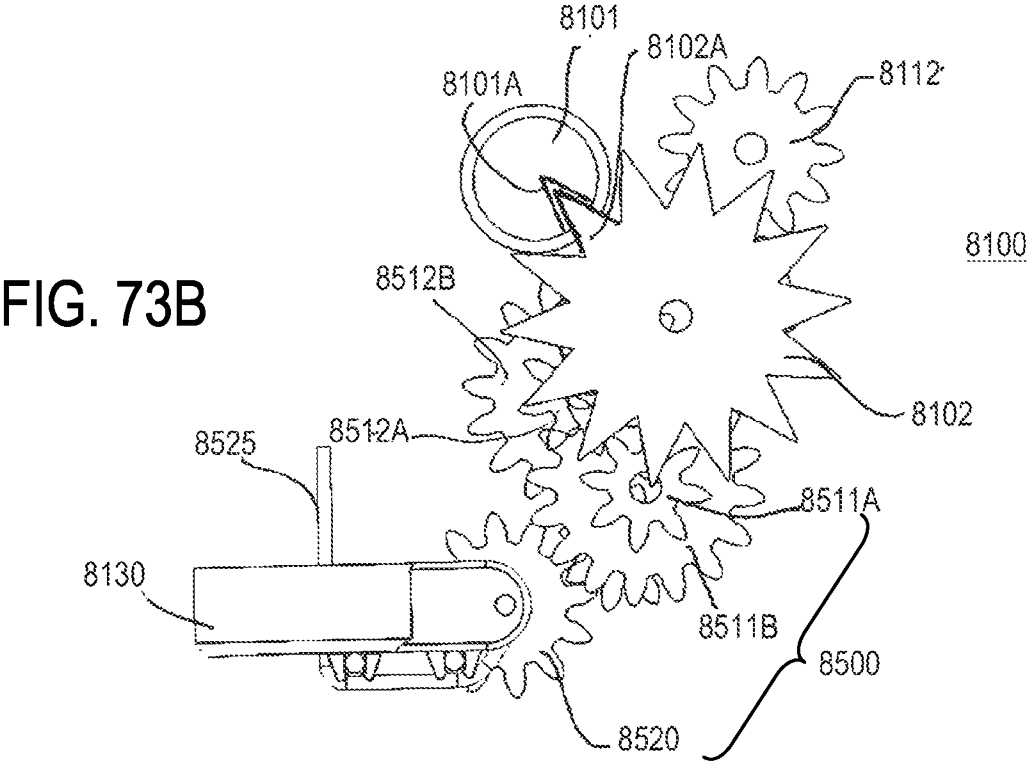
Figure 73C:
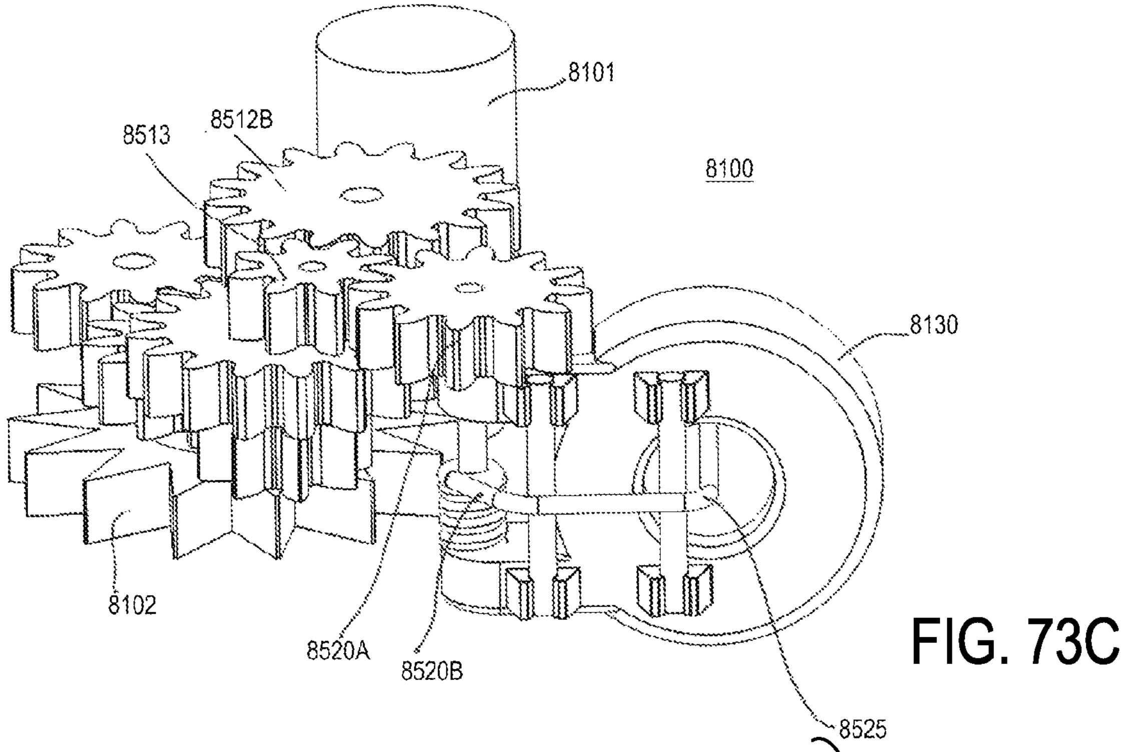
Figure 73D:
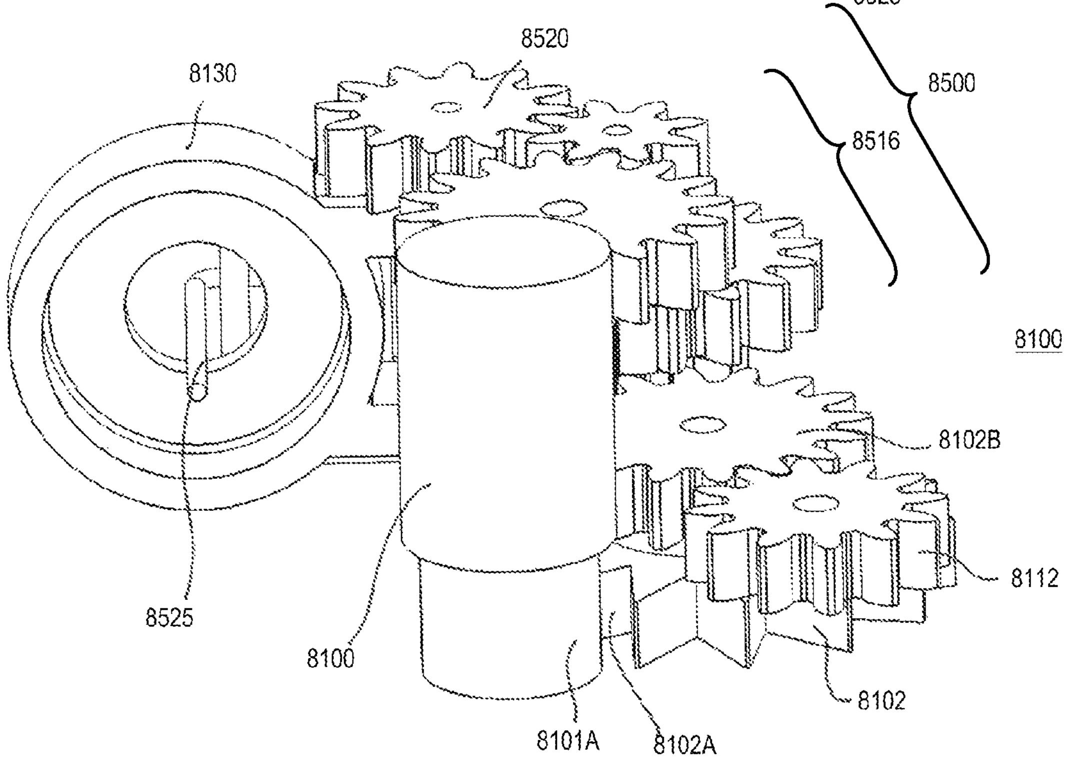

As shown in FIGS. 70A-70D and 71A-71D, and in isolation in FIGS. 72 and 73A-73B, in the embodiments of the present disclosure, the regulating mechanism 8500 is gear assembly driven by an actuator 8101 of the multi-function drive mechanism 8100. The regulating mechanism retards or restrains the distribution of tether 8525, only allowing it to advance at a regulated or desired rate. This restricts movement of piston 8110 within barrel 8058, which is pushed by one or more biasing members 8122, hence controlling the movement of plunger seal 8060 and delivery of the drug contained in chamber 8021. As the plunger seal 8060 advances in the drug container 8050, the drug substance is dispensed through the sterile pathway connection 8300, conduit 8030, insertion mechanism 8200, and into the body of the patient for drug delivery. The actuator 8101 may be a number of power/motion sources including, for example, a solenoid, a stepper motor, or a rotational drive motor. In a particular embodiment, the actuator 8101 is a rotational stepper motor with a notch that corresponds with the gear teeth of the main/star gear 8102. Commonly, such a rotational stepper motor may be referred to as a Pac-Man' motor. In at least one embodiment, the Pac-Man motor has a gear interface within which one or more teeth of the main gear may partially reside during operation of the system. This is more clearly visible in FIGS. 73A-73B. When the gear interface 8101A of the Pac-Man motor 8101 is in alignment with a tooth 8102A of the main gear 8102, rotational motion of the Pac-Man motor 8101 causes gear interface rotation of the main gear 8102. When the Pac-Man motor 8101 is between gear teeth of the main gear, it may act as a resistance for, for example, back-spinning or unwinding of the gear assembly 8116. Further detail about the gear assembly 8116, regulating mechanism 8500, and multi-function drive mechanism 8100 are provided herein.

In a particular embodiment shown in FIGS. 73A-73B, the regulating element 8500 further includes one or more gears 8511, 8512, 8513, 8514, of a gear assembly 8516. One or more of the gears 8511, 8512, 8513, 8514 may be, for example, compound gears having a small diameter gear attached at a shared center point to a large diameter gear.

Gear 8513 may be rotationally coupled to winch drum/gear 8520, for example by a keyed shaft, thereby coupling rotation of gear assembly 8516 to winch drum/gear 8520. Compound gear 8512 engages the small diameter gear 8513 such that rotational movement of the compound gear aspect 8512B is conveyed by engagement of the gears (such as by engagement of corresponding gear teeth) to gear 8513. Compound gear aspect 8512A, the rotation of which is coupled to gear aspect 8512B, is caused to rotate by action of compound gear aspect 8102B of the main/star gear 8102. Compound gear aspect 8102B, the rotation of which is coupled to main/star gear 8102, is caused to rotate by interaction between main/star gear 8102A and interface 8101A of the actuator 8101. Thus, rotation of main/star gear 8102 is conveyed to winch drum/gear 8520. Accordingly, rotation of the gear assembly 8516 initiated by the actuator 8101 may be coupled to winch drum/gear 8520 (i.e., through the gear assembly 8516), thereby controlling the distribution of tether 8525, and the rate of movement of plunger seal 8060 within barrel 8058 to force a fluid from drug chamber 8021. The rotational movement of the winch drum/gear 8520, and thus the axial translation of the piston 8110 and plunger seal 8060, are metered, restrained, or otherwise prevented from free axial translation by other components of the regulating element 8500, as described herein. As described above, the actuator 8101 may be a number of known power/motion sources including, for example, a motor (e.g., a DC motor, AC motor, or stepper motor) or a solenoid (e.g., linear solenoid, rotary solenoid).

Notably, the regulating mechanisms 8500 of the present disclosure do not drive the delivery of fluid substances from the drug chamber 8021. The delivery of fluid substances from the drug chamber 8021 is caused by the expansion of the biasing member 8122 from its initial energized state acting upon the piston 8110A, 8110B and plunger seal 8060. The regulating mechanisms 8500 instead function to provide resistance to the free motion of the piston 8110A, 8110B and plunger seal 8060 as they are pushed by the expansion of the biasing member 8122 from its initial energized state. The regulating mechanism 8500 does not drive the delivery but only controls the delivery motion. The tether limits or otherwise restrains the motion of the piston 8110 and plunger seal 8060, but does not apply the force for the delivery. According to a preferred embodiment, the controlled delivery drive mechanisms and drug delivery devices of the present disclosure include a regulating mechanism indirectly or directly connected to a tether metering the axial translation of the piston 8110A, 8110B and plunger seal 8060, which are being driven to axially translate by the biasing member 8122. The rate of drug delivery as controlled by the regulating mechanism may be determined by: selection of the gear ratio of gear assembly 8516; selection of the main/star gear 8102; selection of the diameter of winding drum/gear 8520; using electromechanical actuator 8101 to control the rate of rotation of the main/star gear 8102; or any other method known to one skilled in the art. By using electromechanical actuator 8101 the rate of rotation of the main/star gear 8102 it may be possible to configure a drug delivery device to provide a variable dose rate (i.e., the rate of drug delivery is varied during a treatment).

In another embodiment, the power and control system of the drug delivery device is configured to receive one or more inputs to meter the release of the tether 8525 by the winch drum/gear 8520 and thereby permit axial translation of the piston 8110 by the biasing member 8122 to translate a plunger seal 8060 within a barrel 8058. The one or more inputs may be provided by the actuation of the activation mechanism, a control interface, and/or a remote control mechanism. The power and control system may be configured to receive one or more inputs to adjust the restraint provided by the tether 8525 and winch drum/gear 8520 on the free axial translation of the piston 8110 upon which the biasing member 8122 bears upon to meet a desired drug delivery rate or profile, to change the dose volume for delivery to the patient, and/or to otherwise start, stop, or pause operation of the drive mechanism.

The components of the drive mechanism 8100, upon activation, may be used to drive axial translation in the distal direction of the plunger seal 8060 of the drug container 8050. Optionally, the drive mechanism 8100 may include one or more compliance features which enable additional axial translation of the plunger seal 8060 to, for example, ensure that substantially the entire drug dose has been delivered to the patient. For example, the plunger seal 8060, itself, may have some compressibility permitting a compliance push of drug fluid from the drug container.

The novel controlled delivery drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the patient. Such feedback may be tactile, visual, and/or auditory, as described above, and may be redundant such that more than one signal or type of feedback is provided to the patient during use of the device. For example, the patient may be provided an initial feedback to identify that the system is operational and ready for drug delivery. Upon activation, the system may then provide one or more drug delivery status indications to the patient. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the patient.

The tether 8525 may have one or more status triggers, such as electrical contacts, optical markings, or electromechanical pins or recesses, which are capable of contacting or being recognized by a status reader. In at least one embodiment, an end-of-dose status indication may be provided to the patient once the status reader contacts or recognizes the final status trigger positioned on the tether 8525 that would contact the status reader at the end of axial travel of the piston 8110A, 8110B and plunger 8060 within the barrel 8058 of the drug container 8050. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 8525 to be read or recognized at positions which correspond with the beginning and end of drug delivery, as well as at desired increments during drug delivery. As the drug delivery device is activated and drug delivery is begun by release of the biasing member 8122 and the resulting force applied to the piston 8110A, 8110B and plunger seal 8060, the rate or profile of drug delivery to the patient is controlled by the regulating mechanism 8500, gear assembly 8516, and winch drum/gear 8520 releasing the tether 8525 and permitting expansion of the biasing member 8122 and axial translation of the piston 8110A, 8110B and plunger seal 8060. As this occurs, the status triggers of the tether 8525 are contacted or recognized by the status reader and the status of the drive mechanism before, during, and after operation can be relayed to the power and control system to provide feedback to the patient. Depending on the number of status triggers located on the tether 8525, the frequency of the incremental status indication may be varied as desired. As described above, a range of status readers may be utilized depending on the status triggers utilized by the system.

In a preferred embodiment, the status reader may apply a tensioning force to the tether 8525. When the system reaches end-of-dose, the tether 8525 goes slack and the status reader 8544 is permitted to rotate about a fulcrum. This rotation may operate an electrical or electromechanical switch, for example a switch, signaling slack in the tether 8525 to the power and control system. Additionally, a gear 8511 of gear assembly 8516 may act as an encoder along with a sensor. The sensor/encoder combination is used to provide feedback of gear assembly rotation, which in turn can be calibrated to the position of piston 8110 when there is no slack in the tether 8525. Together, the status reader and sensor/encoder may provide positional feedback, end-of-dose signal, and error indication, such as an occlusion, by observing slack in the tether 8525 prior to reaching the expected number of motor rotations as counted by the sensor/encoder.

Referring back to FIGS. 70A-70D and 71A-71D, in addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a patient; and connecting a sterile fluid pathway to a drug container to permit fluid flow from the drug container to the needle insertion mechanism for delivery to the patient. In at least one embodiment, as shown in FIGS. 70A-70D and 71A-71D, initial motion by the actuator 8101 of the multi-function drive mechanism 8100 causes rotation of main/star gear 8102. Main/star gear 8102 is shown as a compound gear with aspects 8102A and 8102B (see FIG. 72). In one manner, main/star gear 8102 conveys motion to the regulating mechanism 8500 through gear assembly 8516. In another manner, main/star gear 8102 conveys motion to the needle insertion mechanism 8200 through gear 8112. As gear 8112 is rotated by main/star gear 8102, gear 8112 engages the needle insertion mechanism 8200 to initiate the fluid pathway connector into the patient, as described in detail above. In one particular embodiment, needle insertion mechanism 8200 is a rotational needle insertion mechanism. Accordingly, gear 8112 is configured to engage a corresponding gear surface 8208 of the needle insertion mechanism 8200. Rotation of gear 8112 causes rotation of needle insertion mechanism 8200 through the gear interaction between gear 8112 of the drive mechanism 8100 and corresponding gear surface 8208 of the needle insertion mechanism 8200. Once suitable rotation of the needle insertion mechanism 8200 occurs, for example rotation along axis 'R' shown in FIG. 70B-70C, the needle insertion mechanism may be initiated to create the fluid pathway connector into the patient, as described in detail above.

As shown in FIGS. 70A-70D and 71A-71D, rotation of the needle insertion mechanism 8200 in this manner may also cause a connection of a sterile fluid pathway to a drug container to permit fluid flow from the drug container to the needle insertion mechanism for delivery to the patient. Ramp aspect 8222 of needle insertion mechanism 8200 is caused to bear upon a movable connection hub 322 of the sterile fluid pathway connector 8300. As the needle insertion mechanism 8200 is rotated by the multi-function drive mechanism 8100, ramp aspect 8222 of needle insertion mechanism 8200 bears upon and translates movable connection hub 322 of the sterile fluid pathway connector 8300 to facilitate a fluid connection therein. Such translation may occur, for example, in the direction of the hollow arrow along axis 'C' shown in FIGS. 70B and 71B. In at least one embodiment, the needle insertion mechanism 8200 may be configured such that a particular degree of rotation upon rotational axis 'R' (shown in FIGS. 70B-70C) enables the needle/trocar to retract as detailed above. Additionally or alternatively, such needle/trocar retraction may be configured to occur upon a patient-activity or upon movement or function of another component of the drug delivery device. In at least one embodiment, needle/trocar retraction may be configured to occur upon end-of-drug-delivery, as triggered by, for example, the regulating mechanism 8500 and/or one or more of the status readers as described above. During these stages of operation, delivery of fluid substances from the drug chamber 8021 may be initiated, on-going, and/or completed by the expansion of the biasing member 8122 from its initial energized state acting upon the piston 8110A, 8110B and plunger seal 8060. As described above, the regulating mechanisms 8500 function to provide resistance to the free motion of the piston 8110A, 8110B and plunger seal 8060 as they are pushed by the expansion of the biasing member 8122 from its initial energized state. The regulating mechanism 8500 does not drive the delivery but only controls the delivery motion. The tether limits or otherwise restrains the motion of the piston 8110 and plunger seal 8060, but does not apply the force for the delivery. This is visible through the progression of the components shown in FIGS. 70A-70D and 71A-71D. The motion of the piston 8110A, 8110B and plunger seal 8060 as they are pushed by the expansion of the biasing member 8122 from its initial energized state are shown in the direction of the solid arrow along axis 'A' from proximal or first position 'F' to the distal or second position 'D', as shown in the transition of FIGS. 70A-70D and 71A-71D.

Further aspects of the novel drive mechanism will be described with reference to FIG. 72 and FIGS. 73A-73B. FIG. 4 shows a perspective view of the multi-function drive mechanism, according to at least a first embodiment, during its initial locked stage. Initially, the tether 8525 may retain the biasing member 8122 in an initial energized position within piston 8110A, 8110B. Directly or indirectly upon activation of the device by the patient, the multi-function drive mechanism 8100 may be activated to permit the biasing member to impart a force to piston 8110 and therefore to tether 8525. This force on tether 8525 imparts a torque on winding drum 8520 which causes the gear assembly 8516 and regulating mechanism 8500 to begin motion. As shown in FIG. 73A, the piston 8110 and biasing member 8122 are both initially in a compressed, energized state behind the plunger seal 8060. The biasing member 8122 may be maintained in this state until activation of the device between internal features of drive housing 8130 and interface surface 8110C of piston 8110A, 8110B. As the drug delivery device 8000 is activated and the drive mechanism 8100 is triggered to operate, biasing member 8122 is permitted to expand (i.e., decompress) axially in the distal direction (i.e., in the direction of the solid arrow shown in FIGS. 70A-70D and FIGS. 71A-71D). Such expansion causes the biasing member 8122 to act upon and distally translate interface surface 8110C and piston 8110, thereby distally translating plunger seal 8060 to push drug fluid out of the drug chamber 8021 of barrel 8058. In at least one embodiment, an end-of-dose status indication may be provided to the patient once the status reader contacts or recognizes a status trigger positioned on the tether 8525 to substantially correspond with the end of axial travel of the piston 8110A, 8110B and plunger seal 8060 within the barrel 8058 of the drug container 8050. The status triggers may be positioned along the tether 8525 at various increments, such as increments which correspond to certain volume measurement, to provide incremental status indication to the patient. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 8525 to be read or recognized at positions which correspond with the beginning and end of drug delivery, as well as at desired increments during drug delivery. As shown, tether 8525 passes substantially axially through the drive mechanism housing 8130, the biasing member 8122, and connects to the piston 8110A, 8110B to restrict the axial translation of the piston 8110A, 8110B and the plunger seal 8060 that resides adjacent thereto.

The novel embodiments of the present disclosure may be utilized to meter, restrain, or otherwise prevent free rotational movement of winding drum 8520 and, thus, axial translation of the components of the controlled delivery drive mechanism 8100. Accordingly, the regulating mechanism 8500 only controls the motion of the drive mechanism, but does not apply the force for the drug delivery. One or more additional biasing members 8122, such as compression springs, may be utilized to drive or assist the driving of the piston 8110. For example, a compression spring may be utilized within the drive housing 8130 for this purpose. The regulating mechanism 8500 only controls, meters, or regulates such action. The controlled delivery drive mechanisms and/or drug delivery devices of the present disclosure may additionally enable a compliance push to ensure that substantially all of the drug substance has been pushed out of the drug chamber 8021. The plunger seal 8060, itself, may have some compressibility permitting a compliance push of drug fluid from the drug container. For example, when a pop-out plunger seal is employed, i.e., a plunger seal that is deformable from an initial state, the plunger seal may be caused to deform or “pop-out” to provide a compliance push of drug fluid from the drug container. Additionally or alternatively, an electromechanical status switch and interconnect assembly may be utilized to contact, connect, or otherwise enable a transmission to the power and control system to signal end-of-dose to the patient. This configuration further enables true end-of-dose indication to the patient.

In at least one embodiment, incremental status indication may be provided to the patient by reading or recognizing the rotational movement of one or more gears of gear assembly 8516. As the gear assembly 8516 rotates, a status reader may read or recognize one or more corresponding status triggers on one of the gears in the gear assembly to provide incremental status indication before, during, and after operation of the variable rate controlled delivery drive mechanism. A number of status readers may be utilized within the embodiments of the present disclosure. For example, the drive mechanism may utilize a mechanical status reader which is physically contacted by gear teeth of one of the gears of the gear assembly. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the patient. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear assembly (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the patient.

As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the patient. While the drive mechanisms of the present disclosure are described with reference to the gear assembly and regulating mechanism shown in the Figures, a range of configurations may be acceptable and capable of being employed within the embodiments of the present disclosure, as would readily be appreciated by an ordinarily skilled artisan. Accordingly, the embodiments of the present disclosure are not limited to the specific gear assembly and regulating mechanism described herein, which is provided as an exemplary embodiment of such mechanisms for employment within the controlled delivery drive mechanisms and drug delivery pumps.

Assembly and/or manufacturing of controlled delivery drive mechanism 8100, drug delivery drug delivery device 8000, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 8050 may first be assembled and filled with a fluid for delivery to the patient. The drug container 8050 includes a cap 8052, a pierceable seal 8056, a barrel 8058, and a plunger seal 8060. The pierceable seal 8056 may be fixedly engaged between the cap 8052 and the barrel 8058, at a distal end of the barrel 8058. The barrel 8058 may be filled with a drug fluid through the open proximal end prior to insertion of the plunger seal 8060 from the proximal end of the barrel 8058. An optional connection mount 854 may be mounted to a distal end of the pierceable seal 8056. The connection mount 854 may guide the insertion of the piercing member of the fluid pathway connector into the barrel 8058 of the drug container 8050. The drug container 8050 may then be mounted to a distal end of drive housing 8130.

One or more drive biasing members 8122 may be inserted into a distal end of the drive housing 8130. Optionally, a cover sleeve 8140 may be inserted into a distal end of the drive housing 8130 to substantially cover biasing member 8122. A piston may be inserted into the distal end of the drive housing 8130 such that it resides at least partially within an axial pass-through of the biasing member 8122 and the biasing member 8122 is permitted to contact a piston interface surface 8110C of piston 8110A, 8110B at the distal end of the biasing member 8122. An optional cover sleeve 8140 may be utilized to enclose the biasing member 8122 and contact the piston interface surface 8110C of piston 8110A, 8110B. The piston 8110A, 8110B and drive biasing member 8122, and optional cover sleeve 8140, may be compressed into drive housing 8130. Such assembly positions the drive biasing member 8122 in an initial compressed, energized state and preferably places a piston interface surface 8110C in contact with the proximal surface of the plunger seal 8060 within the proximal end of barrel 8058. The piston, piston biasing member, contact sleeve, and optional components, may be compressed and locked into the ready-to-actuate state within the drive housing 8130 prior to attachment or mounting of the drug container 8050. The tether 8525 is pre-connected to the proximal end of the piston 8110A, 8110B and passed through the axial aperture of the biasing member 8122 and drive mechanism 8130, and then wound through the interior of the drug delivery device with the other end of the tether 8525 wrapped around the winch drum/gear 8520 of the regulating mechanism 8500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a patient. The components which constitute the pathway for fluid flow are now assembled. These components may be sterilized, by a number of known methods, and then mounted either fixedly or removably to an assembly platform or housing of the drug delivery device, as shown in FIG. 69B.

Certain optional standard components or variations of drive mechanism 8100 or drug delivery device 8000 are contemplated while remaining within the breadth and scope of the present disclosure. For example, the embodiments may include one or more batteries utilized to power a motor or solenoid, drive mechanisms, and drug delivery devices of the present disclosure. A range of batteries known in the art may be utilized for this purpose. Additionally, upper or lower housings may optionally contain one or more transparent or translucent windows 18 to enable the patient to view the operation of the drug delivery device 8000 or verify that drug dose has completed. Similarly, the drug delivery device 8000 may contain an adhesive patch 8026 and a patch liner 8028 on the bottom surface of the housing 8012. The adhesive patch 8026 may be utilized to adhere the drug delivery device 8000 to the body of the patient for delivery of the drug dose. As would be readily understood by one having ordinary skill in the art, the adhesive patch 8026 may have an adhesive surface for adhesion of the drug delivery device to the body of the patient. The adhesive surface of the adhesive patch 8026 may initially be covered by a non-adhesive patch liner 8028, which is removed from the adhesive patch 8026 prior to placement of the drug delivery device 8000 in contact with the body of the patient. Removal of the patch liner 8028 may further remove the sealing membrane 254 of the insertion mechanism 8200, opening the insertion mechanism to the body of the patient for drug delivery (as shown in FIG. 69C). In some embodiments, removal of the patch liner 8028 may also wake-up onboard electronics (e.g., the power and control system 2400) by supplying them with electricity from an onboard battery.

Similarly, one or more of the components of controlled delivery drive mechanism 8100 and drug delivery device 8000 may be modified while remaining functionally within the breadth and scope of the present disclosure. For example, as described above, while the housing of drug delivery device 8000 is shown as two separate components upper housing 8012A and lower housing 8012B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may provide integrated status indication features which provide feedback to the patient before, during, and after drug delivery. For example, the patient may be provided an initial feedback to identify that the system is operational and ready for drug delivery. Upon activation, the system may then provide one or more drug delivery status indications to the patient. At completion of drug delivery, the drive mechanism and drug delivery device may provide an end-of-dose indication. The novel controlled delivery drive mechanisms of the present disclosure may be directly or indirectly activated by the patient. Furthermore, the novel configurations of the controlled delivery drive mechanism and drug delivery devices of the present disclosure maintain the sterility of the fluid pathway during storage, transportation, and through operation of the device.

Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the patient during operation of the device.

A method of operating the drug delivery device includes the steps of: activating, by a patient, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connector, a sterile fluid conduit, and the insertion mechanism for delivery of the fluid drug to the body of a patient, wherein a regulating mechanism acting to restrain the distribution of a tether is utilized to meter the free axial translation of the piston. The method of operation of the drive mechanism and the drug delivery device may be better appreciated with reference to FIGS. 70A-70D and FIGS. 71A-71D, as described above.

XII. Temperature Control System

For some drugs, temperature is an important consideration both during and prior to patient delivery. Biologic drugs, for example, oftentimes require refrigeration or frozen storage prior to patient delivery. While cold temperatures may help extend the shelf life of the drug, they can result in an increased viscosity of the drug. A more viscous drug may take longer to inject and/or require additional injection force. Furthermore, injecting a cold drug can be uncomfortable, and potentially even painful, for some patients. Therefore, a drug which has been stored in a cold state usually is allowed to warm to near room temperature prior to patient delivery. This warming up period can take upwards of 30 minutes, which can be inconvenient to the patient and consequently have an adverse impact on patient compliance rates.

The drug delivery devices of the present disclosure can be configured to include a temperature control system for monitoring and/or controlling the temperature of the drug within the device. One embodiment of a drug delivery device, denoted by reference numeral 11010, incorporating a temperature control system 11600 according to principles of the present disclosure is illustrated by FIG. 77. While the temperature control system 11600 is described in conjunction with particular elements and features of the drug delivery device 11010, the temperature control system 11600 can be implemented, where appropriate, in any one of the drug delivery devices disclosed herein, including, but not limited to, any one of the drug delivery devices 10, 910, 2010, 6000, or 8000. Various elements of the drug delivery device 11010 are similar in structure and/or function to those previously described in connection with the drug delivery device 10. These elements are assigned reference numbers similar to those previously provided with the addition of the two-digit suffix "11," and, for the sake of brevity, are not described in detail below. For example, the drug delivery device 11010 includes a needle insertion mechanism 11200 which bears at least some similarities in structure and/or function to the needle insertion mechanism 200 of the drug delivery device 10. It should be noted, however, that the temperature control system 11600 is not limited to being used in conjunction with elements of the drug delivery device 10, and can be implemented in any one of the drug delivery devices disclosed herein, where appropriate.

Turning to FIG. 77, the drug delivery device 11600 may include a start button 11014, a drug container 11050, a drive mechanism 11100, a needle insertion mechanism 11200, a fluid pathway connector 11300, a power and control system 11400, and a temperature control system 11600. The drug container 11050 may include a barrel 11058 and a plunger seal 11060 moveable through the barrel 11058 to discharge a drug from the barrel 11058, and a pierceable seal (not illustrated) controlling access to an interior of the barrel 11058. The drive mechanism 11100 may include a drive housing 11130, a piston 11110 moveable relative to the drive housing 11130 and configured to impart movement to the plunger seal 11060, and a piston biasing member 11106 disposed between the drive housing 11130 and the piston 11110. The fluid pathway connector 11300 may define a sterile fluid flowpath between the drug container 11050 and the insertion mechanism 11200. The fluid pathway connector 11300 may include a connection hub 11310, a tubular conduit 11030 providing fluid communication between the connection hub 11310 and the insertion mechanism 11200, and a piercing member (not illustrated) configured to pierce the pierceable seal to establish fluid communication between the between the barrel 11058 and the tubular conduit 11030 during drug delivery.

The tubular conduit 11030 may include a first flexible tube 11032, a second flexible tube 11034, and a rigid tube 11036 connected and providing fluid communication between the first and second flexible tubes 11032 and 11034. The first flexible tube 11032 may fluidly connect the connection hub 11310 with a proximal end 11037 of the rigid tube 11036, and the second flexible tube 11032 may fluidly connect the needle insertion mechanism 11200 with a distal end 11038 of the rigid tube 11036. The first and second flexible tubes 11032 and 11034 each may be made of a material that is more flexible than the material used to construct the rigid tube 11036. In at least one embodiment, the first and second flexible tubes 11032, 11034 are made of a polymeric material, and the rigid tube 11036 is made of metal. As described below, the material used to construct the rigid tube 11036 may possess a relatively high thermal conductivity such that heat can be transferred from a heating element to a drug flowing through the rigid tube 11036 during delivery.

An inner diameter of the rigid tube 11036 may be less than an inner diameter of the first flexible tube 11032 and/or the second flexible tube 11034. Accordingly, the rigid tube 11036 may serve as a flow restrictor that reduces and/or regulates the flow rate of the drug during delivery. The rigid tube 11036 may be replaced with other rigid tubes having different inner diameters depending on the target flow rate. Furthermore, the inclusion of a flow restrictor may provide broadened design space when coupled with other contributing elements such as a drive spring. In an alternative embodiment, the rigid tube 11036 may have an inner diameter that is equal to that of the first flexible tube 11032 and/or the second flexible tube 11034.

Still referring to FIG. 77, the temperature control system 11600 may include a heating element 11602, a first temperature sensor 11604, and a second temperature sensor 11606. In the illustrated embodiment, the heating element 11602 includes an electrically-conductive coil that is wrapped around and contacts an exterior of the rigid tube 10036. The heating element 11602 may be electrically connected to the power and control system 11400, such that the heating element 11602 is supplied with electricity from the power and control system 11400 in a controlled manner. The impedance of the material used to construct the heating element 11602 may cause the heating element 11602 to convert at least some of the electricity it is supplied with into heat. Due to the contact or close proximity of the heating element 11602 to the rigid tube 11036, the heat generated by the heating element 11602 may warm the rigid tube 11036, and due to the thermal conductivity of the rigid tube 11036, warm a drug flowing through the rigid tube 11036.

The inclusion of the heating element 11602 may eliminate the need for a pre-delivery warming period in the case where the drug delivery device 11010 has been removed from cold storage. Furthermore, heat transfer from the heating element 11602 to the drug may be relatively efficient, because the volume of drug per unit length of the rigid tube 11036 is relatively small. Therefore, it may be possible to warm the drug to a target temperature without reducing the flow rate or increasing the length of the flow path. Accordingly, it may be possible to heat the drug during delivery without altering the duration of delivery. Moreover, the heating element 11602 can be installed with little or no modifications to a pre-existing fluid pathway connector, thereby reducing manufacturing and/or design costs.

In some embodiments, the heating element 11602 may be dynamically controlled based on real-time drug temperature measurements to ensure that the drug is delivered to the patient at a desired temperature. As shown in FIG. 77, the first temperature sensor 11604 may be connected to the proximal end 11037 of the rigid tube 11036 so that the first temperature sensor 11604 can measure the temperature of the drug flowing into the rigid tube 11036. The second temperature sensor 11606 may be connected to the distal end 11038 of the rigid tube 11036 so that the second temperature sensor 11606 can measure the temperature of the drug flowing out of the rigid tube 11036. In some embodiments, the first and second temperature sensors 11604 and 11606 may not directly measure the temperature of the drug. Rather, the first and second temperatures sensors 11604 and 11060 may measure the temperature of, respectively, the inlet and outlet portions of the rigid tube 11036 (or other portions of the drug delivery device proximate to the drug). These temperatures measurements could be used to extrapolate the temperature of the drug based on heat transfer characteristics of the material used to construct the rigid tube 11036 (or the other portions of the drug delivery device proximate to the drug).

The first and second temperature sensors 11604 and 11606 may be output their temperature measurements to the power and control system 11400, which may analyze the temperature measurements to determine an amount of electricity that must be supplied to the heating element 11602 to achieve a target drug temperature. Additionally, the temperature measurements of the first and second temperature sensors 11604 and 11606 may be analyzed by the power and control system 11400 according to thermal dilution techniques in order to determine the flow rate of the drug. Furthermore, in an embodiment where the drug delivery device incorporates a motor-controlled regulating mechanism to control the expansion of the piston biasing member (e.g., akin to the drug delivery device 6000 or 8000), the power and control system 11400 may control the motor based on the output of the first and second temperature sensors 11604 and 11606 to reduce the flow rate if the drug has not been sufficiently warmed by the heating element 11602, so that the patient does not experience a painful injection due to cold temperatures. Furthermore, input from the first and second temperature sensors 11604 and 11606 may be used to determine if the drug has been overheated by the heating element 11602 and therefore no longer suitable for injection, in which case the drive mechanism 11100 may be locked out. Additional temperature sensors may be included to monitor the temperature of the drug in the container during, for example, storage to determine if the drug has been stored at an appropriate temperature. If not, the power and control system 11400 may lockout the device and/or alert the patient that the drug is no longer viable.

The temperature control system 11600 may additionally include temperature indicators (e.g., lights, sounds, graphical displays, etc.) for informing the user of the drug temperature and/or whether the drug temperature is suitable for injection.

While the embodiment of the tubular conduit illustrated in FIG. 77 incorporates two flexible tubes and a rigid tube connected therebetween, alternative embodiments may forgo the rigid tube so that the tubular conduit is formed by a single, unitary flexible tube. In such an embodiment, the heating element 11602 may be wrapped around the single, unitary flexible tube.

In one alternative embodiment, the power and control system 11400 may serve as the heating element 11602, or as a supplemental heating element. The power and control system 11400 may include a circuit board and/or other electronics that heat up while performing their data processing functions. By positioning the circuit board and/or other electronics immediately adjacent to the tubular conduit 11030 (e.g., immediately above the tubular conduit 11030), the heat generated by the circuit board and/or other electronics can be used to warm the drug as it flows through the tubular conduit 11030. Also, in some embodiments, it may be desirable that the heat generated by the power and control system 11400 is not permitted to warm the drug. In such embodiments, the power and control system 11400 may include a heat sink that is remote from the drug container, the fluid pathway connector, and/or the insertion mechanism, so that the heat sink can draw heat away from regions of the drug delivery device including the drug.

While the heating element 11602 described above generates heat primarily through electrical resistance, other embodiments of the heating element may generate heat through other means, including, but not limited to, induction, the Peltier effect, and/or a chemical reaction.

Furthermore, other embodiments of the temperature control system 11600 may include a cooling system (not illustrated) for lowering the temperature of the drug while it is disposed in the container 11050 and/or flows through the tubular conduit 11030. Such a cooling system may employ a fan which draws in cool air from outside the drug delivery device and/or expels warm air from inside the drug delivery device. Alternatively, or additionally, the cooling system may employ the following to reduce the temperature of the drug: a thermoelectric cooling element the exploits the Peltier effect and/or a chemical reaction.

XIII. Skin Attachment

The drug delivery devices of the present disclosure may be configured for temporary attachment to a patient's body tissue (e.g., the patient's skin) while the drug is delivered. The drug delivery device may be attached to the tissue of the patient's abdomen, thigh, arm or some other portion of the patient's body. As described above, an adhesive patch (e.g., the adhesive patch 26) may be disposed on or over a base of the housing to adhere the drug delivery device to the patient's body tissue. The adhesive surface of the adhesive patch may initially be covered by a non-adhesive patch liner (e.g., the non-adhesive patch liner 28), which is removed from the adhesive patch 26 prior to placement of the drug delivery device in contact with the patient's body tissue.

Disengaging the adhesive from the patient's body tissue may cause to patient discomfort, particularly if the adhesive engages a large surface area of the patient's body tissue. Therefore, to reduce the amount of body tissue in contact with adhesive, only a limited portion of drug delivery device's base may be covered with adhesive. FIGS. 78A and 78B illustrate, respectively, adhesive patches 12000 and 12100 which reduce the amount body tissue in contact with adhesive, yet still provide adequate adhesion to secure the drug delivery device to the patient's body tissue during drug delivery. The adhesive patches 12000 and 12100 each may be applied to the base of any one of the drug delivery devices disclosed herein, including, but not limited to, any one of the drug delivery devices 10, 910, 2010, 6000, or 8000.

FIG. 78A shows that the adhesive patch 12000 includes a pattern of adhesive dots 12002 with non-adhesive regions 12004 located therebetween. The illustrated pattern is symmetric and includes equally-spaced rows and columns of circular adhesive dots 12202. Alternative embodiments may have a non-symmetric pattern and/or non-circular adhesive dots. The adhesive patch 12000 includes a base 12006 having a first side (not illustrated) for attachment to the drug delivery device and an opposite second side 12006 including the pattern of adhesive dots 12002. In alternative embodiments, the base 12006 may be omitted, and the pattern of adhesive dots 12002 may be applied directly to an exterior surface of the drug delivery device.

Instead of adhesive dots, the adhesive patch 12100 shown in FIG. 78B includes a plurality of adhesive strips 12102, with non-adhesive regions 12104 located therebetween. The adhesive strips 12102 are equally-spaced and extend lengthwise across the adhesive patch 12100. Alternative embodiments may have non-linear (e.g., curved) adhesive strips and/or the adhesive strips may extend widthwise across the adhesive patch 12100. The adhesive patch 12100 includes a base 12106 having a first side (not illustrated) for attachment to the drug delivery device and an opposite second side 12106 including the adhesive strips 12102. In alternative embodiments, the base 12106 may be omitted, and the pattern of adhesive strips 12102 may be applied directly to an exterior surface of the drug delivery device. A non-adhesive patch liner (e.g., the non-adhesive patch liner 28) may be used to cover the adhesive sides of each of the adhesive patches 12100 and 12200 prior to use.

FIG. 79 illustrates an embodiment of a non-adhesive patch liner, denoted by reference numeral 12300, including stiffening members 12310 for imparting rigidity to the non-adhesive patch liner 12300 as well as an adhesive patch (e.g., the adhesive patch 28, 12100, or 12200) covered by the non-adhesive patch liner 12300. A body 12312 of the non-adhesive patch liner 12300 may be co-extensive with the adhesive patch to prevent unintended adhesion prior to use of the drug delivery device. The stiffening members 12310 may each be made of a more rigid material (e.g., metal or hardened plastic) than the body 12312 of the non-adhesive patch liner 12300. Additionally, as shown in FIG. 79, each of the stiffening members 12310 may have a tapered shape, with a width that narrows as the stiffening member 12310 approaches the outer peripheral edge of the body 12312. The rigidity imparted by the stiffening members 12300 to the outer peripheral edge of the adhesive patch, which may extend beyond the outer edge of the body of the drug delivery 12340 device as shown in FIG. 79, renders the outer peripheral edge of the adhesive patch less likely to experience curling. Accordingly, the stiffening members 12310 may help the adhesive patch retain its planar shape so that the patient can press the adhesive patch flushly against the patient's body tissue upon removal of the non-adhesive patch liner 12300.

While the embodiment of the non-adhesive patch liner illustrated in FIG. 79 includes stiffening members located at discrete points around the periphery of the non-adhesive patch liner, other embodiments of the non-adhesive patch liner may include a stiffening member that extends continuously around the periphery of the non-adhesive patch liner. FIG. 80A illustrates an exploded assembly view of a non-adhesive patch liner 12400, an adhesive patch 12500, and a base 12600 of a drug delivery device. The adhesive patch 12500 may be similar to one of the adhesive patches disclosed herein, including, but not limited to, any one of the adhesive patches 28, 12100, or 12200. The non-adhesive patch liner 12400 may include a central body portion 12402 and a ring-shaped stiffening portion 12404 positioned around the periphery of the central body portion 12402 (as seen in the assembled view shown in FIG. 80B). The central body portion 12402 may cover a central portion of the adhesive patch 12500, leaving an outer peripheral edge of the adhesive patch 12500 exposed. The ring-shaped stiffening portion 12404 may be used to cover this exposed outer peripheral edge of the adhesive patch 12500, thereby preventing it from curling. In some embodiments, the ring-shaped stiffening portion 12404 may cover and contact each of: an outer peripheral edge of the central body portion 12402, an outer peripheral edge of the adhesive patch 12500, and a portion of the base 12600 of the drug delivery device surrounding the adhesive patch 12500. In such an embodiment, the underside of the ring-shaped stiffening portion 12404 may be include an adhesive for adhering the ring-shaped stiffening portion 12404 directly to the base 12600 of the drug delivery device and the central body portion 12402.

As such, removing the central body portion 12402 (e.g., by pulling a tab extending from the central body 12402) may disengage the ring-shaped stiffening portion 12404 from the base 12600 of the drug delivery device as well as the adhesive patch 12500.

While the stiffening members described above may be attached to or integrally formed with the non-adhesive patch liner, alternative embodiments of the stiffening members may be attached to or integrally formed with the adhesive patch. FIG. 81 illustrates a drug delivery device 12710 (which may correspond to any one of the drug delivery devices disclosed herein, including, but not limited to, any one of the drug delivery devices 10, 910, 2010, 6000, or 8000) including a housing 12712, an adhesive patch 12726 attached to the underside of the housing 12712, and a non-adhesive patch liner 12728 removably attached to the underside of the adhesive patch 12726.

The adhesive patch 12726 may include a base 12730 and a plurality of stiffening members 12732. The base 12730 may have an upper surface 12734 rigidly attached to the underside of the housing 12712 and a lower surface (hidden in FIG. 81) covered with a skin adhesive. The base 12730 may have a larger footprint than the housing 12712 such that an outer peripheral portion 12736 of the base 12730 forms a skirt that extends beyond the outer edge of the housing 12712.

Still referring to FIG. 81, the stiffening members 12732 may be formed in the outer peripheral portion 12736 of the base 12730. In the illustrated embodiment, the stiffening members 12732 and the base 12730 are integrally formed such that the stiffening members 12732 and the base 12730 form a single, unitary structure made of a single material. Alternatively, the stiffening members 12732 may be distinct structures from the base 12730. As illustrated in FIG. 81, the stiffening members 12732 may be designed as a plurality of equally spaced ribs located at discrete locations around the periphery of the base 12730. Furthermore, the stiffening members 12732 may protrude upwardly from the upper surface 12734 of the outer peripheral portion 12736 of the base 12730. Nevertheless, the height of the stiffening members 12732 may be such that the tops of the stiffening members 12732 are located below the bottom surface of the housing 12712.

The stiffening members 12732 may impart rigidity to the adhesive patch 12726 so that the adhesive patch 12726 can retain its generally planar shape. Accordingly, the periphery of the adhesive patch 12726 is less likely to fold over on itself, or experience, curling when the drug delivery device 12710 is being applied to the patient's skin or when the non-adhesive patch liner 12728 is being removed.

Referring to FIG. 82, in at least one embodiment, the non-adhesive patch liner 12728 may be comprised of separate first and second sections 12740 and 12742 covering respective portions of the underside of the adhesive patch 12726. The first section 12740 may have a first tab 12744 which protrudes outwardly from a side of the adhesive patch 12726, and the second section 12742 may have a second tab 12746 which protrudes outwardly from an opposite side of the adhesive patch 12726. The first and second sections 12740 and 12742 may be removed separately by pulling, respectively, on the first and second tabs 12744 and 12746, as described below with reference to FIGS. 83A-83C.

In at least one embodiment, the process of attaching the drug delivery device 12710 to the patient's skin 12750 may involve the following steps. Initially, the non-adhesive patch liner 12728 may be disposed against the patient's skin 12750. Next, while the user or patient pushes down on a first end 12752 of the housing 12712 (opposite to the first tab 12744), the first tab 12744 may be pulled outwardly to remove the first section 12740 of the non-adhesive patch liner 12728 from the adhesive patch 12726, as illustrated in FIG. 83A. Subsequently, while the user or patient pushes down on a second end 12754 of the housing 12712 (opposite to the second tab 12746), the second tab 12746 may be pulled outwardly to remove the second section 12742 of the non-adhesive patch liner 12728 from the adhesive patch 12726, as seen in FIG. 83B. This will result in the adhesive patch 12726 being flush with the patient's skin 12750, as shown in FIG. 83C.

In some embodiments, such as the one illustrated in FIGS. 83A-83C, the first tab 12744 may be formed by a portion of the first section 12740 of the non-adhesive patch liner 12728 that is folded back on itself. More particularly, the first section 12740 may have a first end 12760 in contact with the adhesive patch 12726 and a second end 12762 folded over the first end 12760 and configured to initially contact the patient's skin 12750. The second end 12762 may include the first tab 12744. By pulling the first tab 12744 outwardly, the first end 12760 of the first section 12740 may unroll such that it is peeled away from the adhesive patch 12726. This configuration of the first section 12740 of the non-adhesive patch liner 12728 may facilitate the removal of the first section 12740 from the adhesive patch 12726 despite the drug delivery device 12710 being push against the patient's skin 12750, as shown in FIG. 83A.

Similarly, the second tab 12746 may be formed a portion of the second section 12742 of the non-adhesive patch liner 12728 that is folded back on itself. More particularly, the second section 12742 may have a first end 12770 in contact with the adhesive patch 12726 and a second end 12772 folded over the first end 12770 and configured to initially contact the patient's skin 12750. The second end 12772 may include the second tab 12746. By pulling the second tab 12746 outwardly, the second end 12770 of the second section 12746 may unroll such that it is peeled away from the adhesive patch 12726. Like the first section 12740, this configuration of the second section 12742 of the non-adhesive patch liner 12728 may facilitate the removal of the second section 12742 from the adhesive patch 12728 despite the drug delivery device 12710 being push against the patient's skin 12750, as shown in FIG. 83B.

Attachment of the drug delivery devices disclosed herein to the patient's body tissue is not limited to adhesive means. Instead of an adhesive patch, or as a supplement to an adhesive patch, the drug delivery device may incorporate a pneumatic system for temporarily attaching the drug delivery device to the patient's body tissue. Such a pneumatic system may include at least one pressure communication channel or aperture which extends through a base of the drug delivery device and distributes a negative fluid pressure across the base that draws body tissue against the base. Embodiments of such adhesive and/or pneumatic systems for temporarily attaching a drug delivery device to body tissue are described in U.S. Provisional Patent Application No. 62/117,420 entitled "DRUG DELIVERY DEVICE WITH VACUUM ASSISTED SECUREMENT AND/OR FEEDBACK", which is hereby incorporated by reference in its entirety for all purposes. Any one of the drug delivery devices disclosed herein, including, but not limited to, any one of the drug delivery devices 10, 910, 2010, 6000, or 8000, may be configured to incorporate one or more of the embodiments of the adhesive and/or pneumatic systems for temporarily attaching a drug delivery device to body tissue as described in U.S. Provisional Patent Application No. 62/117,420.

In yet still further embodiments, the drug delivery devices disclosed herein may be temporarily attached to a patient's soft body tissue by way of a mechanism (e.g., a strap) that clamps or squeezes the drug delivery device between the patient's soft body tissue and bones or other more rigid anatomical structures behind the soft body tissue.

XIV. Connectivity Aspects

The drug delivery devices of the present disclosure may be configured to include various data processing functionalities and/or operate within various data processing networks. Embodiments of such data processing functionalities and networks related to drug delivery devices are disclosed in International Patent Application Publication No. WO/2015/187793, International Patent Application Publication No. WO/2015/187797, International Patent Application Publication No. WO/2015/187799, International Patent Application Publication No. WO/2015/187802, and International Patent Application Publication No. WO/2015/187805, each of which is hereby incorporated by reference in its entirety for all purposes. Any one of the drug delivery devices disclosed herein, including, but not limited to, any one of the drug delivery devices 10, 910, 2010, 6000, or 8000, may be configured to incorporate one or more of the data processing functionalities and/or operate within one or more of the data processing networks disclosed in International Patent Application Publication No. WO/2015/187793, International Patent Application Publication No. WO/2015/187797, International Patent Application Publication No. WO/2015/187799, International Patent Application Publication No. WO/2015/187802, and International Patent Application Publication No. WO/2015/187805.

The presently-disclosed drug delivery devices, or data processing systems in communication with the presently-disclosed drug delivery devices, may be configured to determine of one or more states of the drug delivery device, which states may be determined through the use of one or more sensors in combination with one or more controllers. The sensors may rely on mechanical, electrical or chemical sensing mechanisms, and the controllers may be mechanical, electrical, and/or electro-mechanical. By way of example and not by way of limitation, the states may relate to the operation of the drug delivery device, and/or to the condition of the drug delivery device. The drug delivery device, or data processing system in communication with the drug delivery device, may use the state determination to control the operation of the drug delivery device, and/or may communicate the state determination to other devices, such as third-party servers that may collect, process, and/or further disseminate the state determinations received from the drug delivery device. In at least one embodiment, the drug delivery device may communicate the state determination to one or more local computing devices, such as a mobile computing device (e.g., smartphone, smartwatch, tablet, laptop, etc.).

In at least one embodiment, a drug delivery device according to the present disclosure may communicate data related to the device or the patient to a social support network. For example, the drug delivery device may monitor a patient's use of the device with sensors or other means, and link the patient to a support group who can encourage the patient to comply with a treatment regimen (e.g., a therapeutic regimen). In this way, the drug delivery device may leverage the capabilities of social networking services (e.g., Facebook, Twitter, etc.) to identify a support group whose advice the patient is likely to follow, thereby increasing the likelihood of the patient's compliance with his or her treatment regimen.

FIG. 84 illustrates an embodiment of a data processing network 13000 in communication with a drug delivery device 13100 corresponding to any one of the other drug delivery device disclosed herein (including, but not limited to, any one of the drug delivery devices 10, 910, 2010, 6000, or 8000). The drug delivery device 13100 is associated with a patient 13102 who may use the drug delivery device 13100 to inject a drug as part of a treatment regime. The drug delivery device 13100 may communicate with a server 13104 via one or more intermediate computing devices and/or one or more networks. In turn, the server 13104 may communicate with the drug delivery device 13100, the patient 13102, and one or more computing devices (with their associated parties) via one or more intermediate computing devices and/or one or more networks. As is also illustrated in FIG. 84, the server 13104 may communicate directly and/or wirelessly with the wearable drug delivery device 13100, using a 4G antenna for example.

Still referring to FIG. 84, the drug delivery device 13100 is illustrated as communicating with a mobile computing device 13110 (e.g., a smartphone) via a first communication link 13112, and with a computing device (e.g., a personal computer or dedicated hub) 13114 via a second communication link 13116. Both links 13112 and 13116 may operate according to a near field communication protocol, such as Bluetooth, for example. The mobile computing device 13110 may communicate with a cellular network 13118 via a communication link 13120, while the computing device 13114 may communicate with a hard-wired network (e.g., local area network or wide area network) 13122 via a communication link 13124. These networks 13118 and 122 may also communicate with the server 13104.

The networks 13118 and 13122 may facilitate communication between the server 13104 and one or more parties associated with the patient 13102, such as his or her caregiver 13130, support giver 13132, and healthcare provider 13134, via their mobile computing devices (e.g., smartphones). The server 13104 may also be in communication with one or more computing devices (e.g., servers) associated with one or more additional parties associated with the patient 13102. For example, a healthcare system server 13140, a payment server 13142, a pharmacy server 13144, a distributor server 13146, and a governmental agency server 13148 are illustrated in communication with the server 13104 via the network 13122. It will also be recognized that the networks 13118 and 13122 may be in communication with each other.

In at least one embodiment, the mobile computing device 13110 may include a processor (e.g., microprocessor) and a memory (e.g., a random access memory (RAM), a non-volatile memory such as a hard disk, a flash memory, a removable memory, a non-removable memory, etc.) for storing computer-executable instructions to be executed by the processor. In some embodiments, the computer-executable instructions may be included in a software application (e.g., a mobile software application, also commonly referred to as a "mobile app") stored in the memory of the mobile computing device 13110. The software application may be installed on the mobile computing device 13110 as one or more downloaded files, such as an executable package installation file downloaded from a suitable application store via a connection to the Internet. Examples of package download files may include downloads via the iTunes store, the Google Play Store, the Windows Phone Store, downloading a package installation file from another computing device, etc. The software application may be developed for a mobile operating system such as Android™ or iOS®, developed by Google and Apple, respectively. In some embodiments, the application may be initiated by a user selecting an icon shown on a home screen of a display (e.g., a touchscreen) of the mobile computing device 13110. Various displays, including those having informational prompts and/or instructional prompts similar to those shown in the figures of International Patent Application Publication No. WO/2015/187797, may be generated in the software application and displayed to a user and/or patient via the display of the mobile computing device 13110.

XV. Energy Management

As described above, the drug delivery devices of the present disclosure may incorporate a drive mechanism including one or more springs to provide energy for moving a plunger seal to expel a drug from a container. The use of springs can offer benefits of simplicity and low cost, but can have certain limitations.

There is a linear relationship between force and displacement in spring actuators. To provide sufficient energy for drug delivery at the end of the stroke of the plunger seal, an excessive amount of energy may be input to the system as drug delivery commences.

Further, as higher viscosity drugs are delivered via drug delivery devices, requisite spring forces can increase. Springs with higher spring constants transmit more force to the drug product and container. Because kinetic energy is proportional to velocity squared, even incremental increases in the spring constant can result in large changes in the net kinetic energy applied to the drug and container.

The patient may feel this excessive energy as a "slap" or similar physical "bump", as the spring-driven piston impacts the plunger seal of the container storing the drug. It is known that such mechanical bumps can also be distracting or disturbing to users of the injectors and can therefore prevent proper dose completion. It is therefore desirable to eliminate such disturbances.

Accordingly, a need exists for a drug delivery device with an energy management system which can maintain the intended spring force load of the drive mechanism while reducing the transmitted force and resultant energy to the drug product, thereby reducing the potential for structural damage to the container or other components of the drug delivery device. Such a drug delivery device may be potentially more comfortable and safer to use, and applicable to a greater range of drugs.

The drug delivery devices of the present disclosure may be configured to include an energy management system that maintains the intended spring force load of the drive mechanism while reducing the transmitted force and resultant energy to the drug product. Embodiments of such energy management systems are disclosed in International Patent Application No. PCT/US15/29485 entitled "AUTOINJECTOR WITH SHOCK REDUCING ELEMENTS" and International Patent Application Publication No. WO/2016/003813, International Patent Application Publication No. WO/2015/187799, each of which is hereby incorporated by reference in its entirety for all purposes. Any one of the drug delivery devices disclosed herein, including, but not limited to, any one of the drug delivery devices 10, 910, 2010, 6000, or 8000, may be configured to incorporate one or more of aspects, features, and/or functionalities of the energy management systems disclosed in International Patent Application No. PCT/US15/29485 and International Patent Application Publication No. WO/2015/187799.

FIGS. 85A-85C, 86A-86C, and 87A-87C illustrate, respectively, assemblies **14000*a*, 14000*b*, 14000*c*, each of which includes a drug container 14050 (which may correspond to, but is not limited to, any one of the containers 50, 618, 718, 818, 918, 1118, or 2050), a drive mechanism 14100 (which may correspond to, but is not limited to, any one of the drive mechanisms 100, 500, 1000, or 2100), a fluid pathway connector 14300 (which may correspond to, but is not limited to, any one of the fluid pathway connector 300, 622, 722, 822, 922, or 2300), and a drive damper mechanism 14170*a*, 14170*b*, or 14170*c* that functions as an energy management system. The assemblies 14000*a*, 14000*b*, and 14000*c* each may be implemented in any one of the drug delivery devices disclosed herein, including, but not limited to, any one of the drug delivery devices 10, 910, 2010, 6000, or 8000**.

The drug container 14050 may include a barrel 14058 and a plunger seal 14060 moveable through the barrel 14058 to discharge a drug 14038 from the barrel 14058, and a pierceable seal (not illustrated) controlling access to an interior of the barrel 14058. The drive mechanism 14100 may include a drive housing 14130, a piston 14110 moveable relative to the drive housing 14130 and configured to impart movement to the plunger seal 14060, and a piston biasing member 14106 disposed between the drive housing 14130 and the piston 14110. The piston 14110 may include a head member 14148 disposed at its distal end.

The drive damper mechanism 14170 reduces the velocity of the piston 14110 while retaining the intended force of the drive mechanism 14100, before the piston 14110 begins to move the plunger seal 14060 distally through the barrel 14058. By reducing the velocity of the piston 14110, the damper mechanism 14170 essentially operates as a shock reducing element, as it reduces the kinetic energy applied to the drug 14038 and the drug container 14050. The damper mechanism 14170 can be adapted to reduce the velocity of the piston 14110 to ensure that pressure delivered to the system does not induce syringe breakage, pressure delivered to the system prevents appreciable "slap" or discomfort to the patient, and/or pressure delivered to the drug 14038 prevents shear forces from damaging the drug 14038.

In some embodiments, the drive damper mechanism can be adapted to reduce the velocity of the piston by less than 1%. In other embodiments, the drive damper mechanism can be adapted to reduce the velocity of the piston by about 1-5%. In further embodiments, the drive damper mechanism can be adapted to reduce the velocity of the piston by about 5-10%. In further embodiments, the drive damper mechanism can be adapted to reduce the velocity of the piston by about 10-15%. In further embodiments, the drive damper mechanism can be adapted to reduce the velocity of the piston by about 15-20%. In further embodiments, the drive damper mechanism can be adapted to reduce the velocity of the piston by about 20-30%. In still further embodiments, the drive damper mechanism can be adapted to reduce the velocity of the piston by about 30-50%. In yet further embodiments, the drive damper mechanism can be adapted to reduce the velocity of the piston by about 51%-100%. The reduction in velocity provided by the drive damper mechanism can be selected to prevent a physical disturbance and/or discomfort to the patient by preventing appreciable "slap", and/or reduce breakage of the drug storage device, and/or reduce drug product damage caused by shear load, and/or allow the injection device to be used for injecting drugs with higher viscosities.

As shown in FIGS. 85A-85C, the damper mechanism 14170 can be disposed inline between the plunger seal 14060 of the drug container 14050 and the plunger head 14148 of the piston 14110 to minimize the size of the assembly 14000*a* and to more effectively damp the motion of piston 14110 at the plunger head/stopper interface. In other embodiments, as shown in FIGS. 86A-86C, the drive damper mechanism can be disposed inline between the proximal end of the piston 14110 of the drive mechanism and the main housing of the drug delivery device. In further embodiments, the drive damper mechanism can be integrated into the piston.

In accordance with various embodiments of the assembly 14000*a*, the damper mechanism 14170 may comprise a dashpot. The dashpot uses viscous friction to resist the motion of the piston 14110, thereby reducing the velocity of the piston 14110. FIGS. 85A-85C depict an exemplary embodiment of a linear dashpot 14172 that can be used in the assembly 14000*a*. As shown, the linear dashpot 14172 includes a drive damping mechanism housing 14174, a working fluid 14178 contained inside the housing 14174, and a piston assembly 14176 movably disposed within the housing 14174. The housing 14174 can comprise a cylindrical sidewall 14174*sw* that is closed at each of its first and second ends by an end wall 14174*ew*. In some embodiments, the housing 14174 can be made of a rigid material, such as a plastic or a metal. The working fluid 14178 contained within the housing 14174 can comprise, without limitation, oil (e.g., mineral oil), silicone material, water or air.

As shown in FIGS. 85A-85C, the piston assembly 14176 may comprise a piston 14180 and a rod 14184 for pushing the piston 14180 through the housing 14174. In other embodiments, such as shown in FIGS. 86A-86C, the piston rod can be configured and adapted to pull the piston through the dashpot housing 14174. As shown in FIGS. 85A-85C, the piston 14180 can comprise a single disc-like structure or member 14182 (piston disc member 14182) having leading and trailing surfaces 141821 and 14182*t*, respectively. The piston rod 14184 extends through an aperture 14174*a* in one of the end walls 14174*ew* of the housing 14174 and can have one end attached to or unitary with the leading surface 141821 or trailing surface 14182*t* of the piston disc member 14182, depending upon whether it pushes (see FIGS. 85A-85C) or pulls (FIGS. 86A-86C) the piston disc member 14182 in the damping stroke. The free end of the piston rod 14184, which is typically disposed external to the housing 14174, can be attached to the plunger head 14148, as shown in FIGS. 85A-85C. A seal, such as an O-ring (not visible), may be provided in or adjacent to the aperture 14174*a* to prevent the working fluid 14178 from leaking out of the housing 14174 between the piston rod 14184 and the aperture 14174*a* in the end wall 14174*ew* of the housing 14174. In some embodiments, the piston assembly 14176 can be made of a rigid material, such as a plastic or a metal. In other embodiments, the piston assembly 14176 can be made of a resilient material, such as a natural or synthetic polymer. In still further embodiments, the piston assembly 14176 can be made of a porous, rigid material.

FIGS. 85A-85C depict one exemplary mode of operation of the dashpot 14172. As shown in FIG. 85A, upon the actuation of the drive triggering mechanism, the energy source (e.g., piston biasing member 14106) of the drive mechanism 14100 advances the piston 14110 toward plunger seal 14060 disposed in the barrel 14058 of the drug container 14050. Once the linear dashpot 14172 contacts the plunger seal 14060, as shown in FIG. 85B, the load from the piston biasing member 14106 begins to be transmitted to the linear dashpot 14172, thereby causing the working fluid 178 located in front of the dashpot piston disc member 14182 to be pushed or displaced through one or more constrictions to a location behind the piston disc member 14182 as the piston disc member 14182 moves from one end of the housing 14174 to the other. The flow of the working fluid 14178 through the one or more constrictions generates a viscous friction, which resists the movement of the piston disc member 14182, thereby damping plunger motion. In some embodiments in which the piston disc member 14182 is made of a rigid material, the constriction(s) can comprise a small gap (not shown) between the peripheral edge of the piston disc member 14182 and the sidewall 174*sw* of the dashpot housing 14174. In other embodiments, the constriction(s) further or alternatively comprise one or more grooves 14186 provided in the peripheral edge of the piston disc member and/or one or more openings extending through the piston disc member 14182 through which the working fluid 178 flows as it is displaced from in front of the piston disc member 14182, to behind the piston disc member 14182. In other embodiments in which the piston disc member 14182 is made of a resilient material, the peripheral edge of the piston disc member 14182 can bend backwards enough to generate a narrow gap or constriction between the peripheral edge of the piston disc member 14182 and the sidewall 174*sw* of the dashpot housing 14174 (not shown) so that the working fluid 178 can flow therethrough. In other embodiments in which the piston disc member 14182 is made of a porous material, the working fluid 178 will flow through the pores (constrictions) of the piston disc member 14182. In each of these embodiments, the one or more constrictions of the linear dashpot 14172 provide a velocity-dependent resistance to the force of the energy source 144 (e.g., piston biasing member 14106) acting on the piston 14110. This resistance, when coupled to the piston 14110, reduces the velocity of the piston 14110 while maintaining the force of the energy source 144 (e.g., piston biasing member 14106) before the piston 14110 starts to move the plunger seal 14060. The size, number and type of constrictions, the type of working fluid 178 used in the linear dashpot 14172, the configuration of the housing 14174 and piston assembly 14176, and any combination thereof, can be adjusted and/or selected to allow the damping characteristics of the damper mechanism 14170 to be tuned to properly damp the shock characteristics of the drive mechanism 14100.

As shown in FIG. 85C, the piston disc member 14182 engages the leading one of the end walls of the dashpot housing 14174, and the force of the piston biasing member 14106 moves the plunger seal 14060, linear dashpot 14172 and piston 14110 distally through the barrel 14058 of the drug container 14050 at a reduced velocity, to expel the drug 14038 from the barrel 14058.

FIGS. 86A-86C depict one exemplary mode of operation of a dashpot 14192 disposed inline between the proximal end 14146*pe* of the piston rod 14146 of the injection drive mechanism and the main housing of the drug delivery device. In this embodiment, the dashpot housing 14194 can be retained in a tubular support member 14122 of the main housing by a detent 14123 integrally formed with the tubular support member 14122. Such an arrangement can be provided on a cantilever spring 14125 defined in the tubular support member 14122. The end of the piston rod 14204 disposed within the dashpot housing 14194 can be attached to the leading surface 142021 of the piston disc member 14202 and the free end of the piston rod 14204 can be attached to the proximal end 14146*pe* of the piston rod 14146 such that as the piston rod 14146 is driven distally by the energy source (e.g., piston biasing member 14106). The piston rod 14204 pulls the piston disc member 14202 through the dashpot housing 14194.

As shown in FIGS. 86A-86C, upon the actuation of the drive triggering mechanism, the energy source (e.g., piston biasing member 14106) of the injection drive mechanism begins to advance the piston 14110 toward the plunger seal 14060 disposed in the barrel 14058 of the drug container 14050. The load applied by the piston biasing member 14106 to the piston 14110 can be transmitted to the dashpot 14192. The working fluid 194 located in front of the piston disc member 14202 is pushed or displaced through the one or more constrictions to a location behind the piston disc member 14202, as the piston disc member 14202 is pulled from one end of the dashpot housing 14194 to the other. The resistance generated by the working fluid 14198 flowing through the one or more constrictions maintains the force of the piston biasing member 14106 while reducing the velocity of the piston 14110 before the head member of the piston 14110 impacts the plunger seal 14060. The head member of the piston 14110 impacts the plunger seal 14060 at the reduced velocity, and the force of the energy source (e.g., piston biasing member 14106) begins to move the plunger seal 14060 and piston 14110 distally through the barrel 14058 of the drug container 14050, to expel the drug 14038 from the barrel 14058. At about the same time, the piston disc member 14202 of the dashpot 14192 reaches the end of its stroke and engages the leading end wall 194*ew* of the dashpot housing 14194. The energy source (e.g., piston biasing member 14106) can be selected to apply enough energy to the piston 14110 to overcome the detent and cantilever arrangement 123/125 so that it releases the dashpot 14192 from the tubular support member 14122 to allow for movement of the piston 14110 as the energy source (e.g., piston biasing member 14106) drives the piston 14110, plunger seal 14060, and drug 14038 through the barrel 14058 of the drug container 14050. The release of the dashpot 14192 from the tubular support member 14122 reduces the duration of engagement, which allows the overall length of the injection device to be reduced.

FIGS. 87A-87C depict an exemplary mode of operation of dashpot 14212 that is integrated into piston 14242. As shown in FIGS. 87A-87C, the integrated dashpot 14212 includes a housing 14214 formed by a tubular wall 14214*t* and plunger head 14248, which closes the open distal end of the tubular wall 14214*t*. The dashpot 14212 further includes a piston formed by a distal end wall 14220 of hollow plunger rod 14246, which is initially disposed in the open proximal end of the tubular wall 14214*t* of the dashpot housing 14214. The working fluid 14218 of the dashpot 14212 is initially provided in the dashpot housing 14214, in front of the distal end wall 14220 of the plunger rod 14246. As shown in FIG. 87A, upon actuation of the drive triggering mechanism (not shown), the energy source (e.g., spring 14244*s*) of the injection drive mechanism applies a force to the plunger rod 14246 and advances the piston 14242 toward plunger seal 14060 disposed in the barrel 14058 of the drug container 14050. Once the plunger head 14248 makes contact with the plunger seal 14060, as shown in FIG. 87B, the load from the spring 14244*s* is transmitted to the dashpot 14212 integrally formed in the piston 14242. The working fluid 14218 located in front of the end wall 220 of the plunger rod 14246 is pushed or displaced through one or more constrictions (as previously described) provided in the end wall 220 and into the space defined by the hollow plunger rod 14246, behind the end wall 220 as it moves distally into the dashpot housing 14214. The resistance or damping provided by dashpot 14212 reduces the velocity of the plunger rod 14246 before the plunger rod 14246 engages the plunger head 14248 to move the plunger seal 14060, and performs the damping while maintaining the force of the spring 14244*s*.

As shown in FIG. 87C, the end wall 220 of the plunger rod 14246 engages the plunger head 14248, which marks the end of the damping stroke of the dashpot. The spring 14244*s* then propels or forces the plunger rod 14246 and plunger head 14248 as a single component (i.e., the plunger) against the plunger seal 14060 to drive the plunger seal 14060 distally through the barrel 14058 of the drug container 14050, to expel the drug 14038 from the barrel 14058.

FIG. 88 shows another exemplary embodiment of the dashpot. The dashpot 14270 is substantially similar to the dashpots previously described except that the piston of the piston assembly 14276 comprises two or more disc members 14282 spaced apart from one another along the piston rod 14284. The two or more piston disc members 14282 and the previously described constrictions, which may be associated with each piston disc member 14282, provide a series of resistances to piston movement, where each of the resistances can be the same and/or different. The series resistance of the dashpot 14270 allows the velocity of the plunger to be reduced in stages or increments while maintaining the force of the energy source (e.g. spring 14144*s*). In some embodiments, the multi-disc piston assembly 14276 can be made of a rigid material, such as a plastic or a metal. In such embodiments, the constriction(s), which control or define the resistance provided by each piston disc member 14282, can comprise a small gap (not shown) between the peripheral edge of one or more of the piston disc members 14282 and the sidewall 14274*sw* of the dashpot housing 14274. In other such embodiments, the constriction(s) can comprise one or more grooves provided in the peripheral edge of one or more of the piston disc members 14182 or one or more openings 14188 extending through the one or more piston disc members 14182, forming one or more of the piston disc members as porous discs, and any combination thereof. In other embodiments, the multi-disc piston assembly 14276 can be made of a resilient material, such as a natural or synthetic elastomer, such that the marginal peripheral edge of each piston disc member 14282 can bend backwards enough to generate a narrow gap or constriction between the peripheral edge of the piston disc members 14282 and the sidewall 14274*sw* of the dashpot housing 14274 so that the working fluid can flow therethrough. If air is used as the working fluid, the resilient piston disc members 282 of the piston assembly 276 may be used to create a squeeze-film damping effect. Any of the dashpots described above with respect to FIGS. 85A-85C, 86A-86C, and 87A-87C, can utilize the piston assembly 14276 of FIG. 88.

FIG. 89 shows an exemplary embodiment of the dashpot of the present disclosure. The dashpot 14370 comprises a housing 14374 and a piston assembly 14376 comprising a hollow piston rod 14384 and a piston configured as a bellows-like structure (bellows piston structure) attached to an end of the piston rod 14384 disposed within the housing 14374. The hollow piston rod 14384 may have an aperture 14384*a* for exhausting working fluid (not shown) flowing through the hollow piston rod 14384 outside of the dashpot housing 14374. The bellows piston structure can comprise one or more collapsible lobes that contain the working fluid, which fluid can be air or any other suitable working fluid. An opening 14386 (constriction) can be provided in the portions of the lobe walls connecting each adjacent pair lobes of the bellows piston structure to one another and to the hollow piston rod 14384. The openings 14386 allow the working fluid contained in the lobes to flow from one lobe to another, thereby functioning as constrictions. The dashpot 14370 provides damping when the bellows piston structure is pushed or pulled into the end wall 14374*ew* of the dashpot housing 14374 and collapsed by the force acting on the plunger 14142 supplied by the energy source (e.g., spring 14144*s*) of the drive plunger mechanism. The damping action is provided as the working fluid contained inside the lobes flows through the openings 14386, the hollow piston rod 14384 and the rod aperture 14384*a* as the lobes of the bellows piston structure are collapsed. Any of the dashpots embodiments described above with respect to FIGS. 85A-85C, 86A-86C, and 87A-87C, can utilize the piston assembly 14376 of FIG. 89.

Turning to FIG. 90, illustrated is the drive mechanism 100 and drug container 50 of FIG. 14A, outfitted with an energy management system 15000. The energy management system 15000 includes a plurality of damping members 15010*a-e*. The damping members 15010*a-e* may be made of a shock absorbing material such as rubber, plastic, or any other suitable material. The damping member 15010*a* is positioned at the interface between the piston extension 102 and the plunger seal 60. The damping members 15010*b* and 15010*c* are disposed on the exterior of the neck of the barrel 58. In an alternative embodiment, the damping members 15010*b* and 15010*c* are replaced with a single ring-shaped damping member disposed around the neck of the barrel 58. The damping members 15010*d* and 15010*e* are disposed on the distal end surface of the cap 52. In an alternative embodiment, the damping members 15010*d* and 15010*e* are replaced with a single ring-shaped damping member disposed on the distal end surface of the cap 52. In use, the damping members 15010*a-e* may dampen a shockwave created when the when the piston 110 impacts the plunger seal 60, thereby reducing the likelihood of the barrel 58 shattering and/or the user experiencing a discomforting mechanical bump or slapping sound.

Looking to FIGS. 91A and 91B, illustrated is the drive mechanism 2100, drug container 2150, and the fluid pathway connector 2300 of FIGS. 23A and 23B, outfitted with an energy management system 16000. The energy management system 16000 includes a plurality of damping members 16010*a-c*. The damping members 16010*a-c* may be made of a shock absorbing material such as rubber, plastic, or any other suitable material. The damping member 16010*a* is positioned at the interface between the piston 2110 and the plunger seal 2060. The damping members 16010*b* and 16010*c* are disposed on the distal end surface of the cap 23152. In an alternative embodiment, the damping members 16010*b* and 16010*c* are replaced with a single ring-shaped damping member disposed on the distal end surface of the cap 2052. In use, the damping members 16010*a-c* may dampen a shockwave created when the when the piston 2110 impacts the plunger seal 2060, thereby reducing the likelihood of the barrel 2058 shattering and/or the user experiencing a discomforting mechanical bump or slapping sound.

XVI. Viscosity Modeling

At least some embodiments described above or below may provide delivery devices capable of delivering a viscous fluid dosage form to a subject. At least some of these embodiments provide for subcutaneous (SQ) injection of a large volume dose (e.g., 2 mL to 2.5 mL, or 2 mL to 3 mL) of a fairly viscous fluid with a tolerable level of pain to a subject. Accordingly, at least some of the embodiments disclosed herein can administer the large volume viscous dosage form at a rate such that pain does not negatively impact compliance with the prescribed dosing regimen. Furthermore, at least some embodiments disclosed herein provide delivery devices capable of delivering a fluid dosage form (including a large-volume dosage form) comprising an antibody, protein, peptide, or nucleic acid, for example.

At least one embodiment provides a delivery device comprising an insertion mechanism, a drive mechanism, and a sterile fluid pathway, wherein said device is configured to deliver to a human patient from about 1.0 mL to about 2.5 mL, inclusive, of a viscous dosage form at rate of up to about 12 mL per minute. In certain embodiments, the delivery is SQ injection. In at least one embodiment, the drug delivery device is an on-body or wearable device. In particular embodiments, the device is preloaded with a dosage form. In some embodiments, the dosage form comprises a biologic, such as an antibody, or antigen-binding portion thereof. In some embodiments, the dosage form comprises about 50 mg to about 400 mg, inclusive, of a biologic. In some aspects, the drug is administered at a fixed dose. In specific aspects, the drug is administered at a fixed dose selected from about 50 mg to about 400 mg, inclusive; such as a fixed dose of about 50 mg, about 100 mg, about 150 mg, about 175 mg, about 200 mg, about 300 mg, or about 325 mg drug/dose. In some aspects, the drug is administered in two or more doses. In other aspects, the drug is administered weekly, biweekly, or monthly. In certain aspects, the drug is administered biweekly. In some embodiments, the device is configured for SQ delivery of about 2 mL of a dosage form comprising about 300 mg drug. In some embodiments, the device is configured for delivery of the dosage form once-daily, twice a week (semiweekly), once-weekly, biweekly (fortnightly), once monthly, twice monthly (semimonthly), every two months (bimonthly), or at a frequency determined by a health care professional. In some embodiments, the delivery device is configured to deliver the dosage form at a preselected flow rate from, the rate chosen from a range of about 0.167 mL per minute to about 12 mL per minute, inclusive. In some embodiments, the delivery device is configured to deliver the dosage form at a flow rate of about 12 mL per minute. In some embodiments, the delivery device is configured to deliver the dosage form at a flow rate of about 2 mL per minute. In some embodiments, the delivery device is configured to deliver the dosage form at a flow rate of about 0.167 mL per minute. In some embodiments, the device is disposable.

At least one embodiment provides a drug delivery device comprising means for delivering to a human subject a volume of about 1 mL to about 2.5 mL, inclusive, of a viscous dosage form at a flow rate of up to about 12 mL per minute. In certain embodiments, the delivery is SQ injection. In some embodiments, the dosage form comprises a biologic. The biologic may be an antibody. In some embodiments, the dosage form comprises about 100 mg to about 400 mg, inclusive, of a biologic. In particular embodiments, the device is preloaded with a dosage form comprising a biologic, such as an antibody. In some embodiments, the device is configured for SQ delivery of about 2 mL of a drug. In some embodiments, the device is configured for delivery of the dosage form on a once-daily basis. In some embodiments, the delivery device is configured to deliver the dosage form at a flow rate ranging from about 0.167 mL per minute to about 12 mL per minute, inclusive. In some embodiments, the delivery device is configured to deliver the dosage form at a flow rate of about 12 mL per minute. In some embodiments, the delivery device is configured to deliver the dosage form at a flow rate of about 2 mL per minute. In some embodiments, the delivery device is configured to deliver the dosage form at a flow rate of about 0.167 mL per minute.

At least one embodiment provides for a method for administering to a human subject in need thereof a dosage form comprising a viscous pharmaceutical dosage form, comprising contacting a human patient with a drug delivery device configured to deliver from about 1.0 mL to about 2.5 mL, inclusive, of a viscous dosage form at a flow rate of up to about 12 mL per minute, and actuating said device to deliver said dosage form. In certain embodiments, the delivery is SQ injection. In some embodiments, the viscous dosage form comprises a biologic, such as an antibody. In some embodiments, the device is configured for SQ delivery of about 2 mL of a dosage form. In some embodiments, the device is actuated once daily. In some embodiments, the delivery (administration) rate is from a range of about 0.167 mL per minute to about 12 mL per minute, inclusive. In some embodiments, the delivery rate is about 12 mL per minute. In some embodiments, the delivery device is configured to deliver the dosage form at a flow rate of about 2 mL per minute. In some embodiments, the delivery device is configured to deliver the dosage form at a flow rate of about 0.167 mL per minute.

At least one embodiment provides for a delivery device comprising an insertion mechanism, a drive mechanism, and a sterile fluid pathway, wherein said device is configured to deliver to a human patient about 2 mL of a dosage form comprising a drug at a flow rate of up to about 12 mL per minute. In certain embodiments, the delivery is subcutaneous injection. In particular embodiments, the device is preloaded with a dosage form comprising a drug. In some embodiments, the dosage form comprises about 300 mg of a drug. In some embodiments, the device is configured for delivery of the dosage form comprising a drug on a once-daily basis. In some embodiments, the delivery device is configured to deliver the dosage form at a flow rate ranging from about 0.167 mL per minute to about 12 mL per minute, inclusive. In some embodiments, the delivery device is configured to deliver the dosage form at a flow rate of about 12 mL per minute. In some embodiments, the delivery device is configured to deliver the dosage form at a flow rate of about 2 mL per minute. In some embodiments, the delivery device is configured to deliver the dosage form at a flow rate of about 0.167 mL per minute.

At least one embodiment provides for a drug delivery device comprising a means for delivering a dosage form to a human patient of about 2 mL, comprising a drug, at a flow rate of up to about 12 mL per minute. In certain embodiments, the delivery is subcutaneous injection. In some embodiments, the dosage form comprises about 300 mg of a drug. In particular embodiments, the device is preloaded with a dosage form comprising a drug. In some embodiments, the device is configured for delivery of the dosage form comprising a drug on a once-daily basis. In some embodiments, the delivery device is configured to deliver the dosage form at a flow rate ranging from about 0.167 mL per minute to about 12 mL per minute, inclusive. In some embodiments, the delivery device is configured to deliver the dosage form at a flow rate of about 12 mL per minute. In some embodiments, the delivery device is configured to deliver the dosage form at a flow rate of about 2 mL per minute. In some embodiments, the delivery device is configured to deliver the dosage form at a flow rate of about 0.167 mL per minute.

At least one embodiment provides for a method for administering to a human patient in need thereof a dosage form comprising a drug comprising contacting a human patient with a drug delivery device configured to deliver about 2 mL of a dosage form comprising a drug at a flow rate of up to about 12 mL per minute, and actuating said device to deliver said dosage form. In certain embodiments, the delivery is subcutaneous injection. In some embodiments, the device is actuated once daily. In some embodiments, the dosage form comprises about 300 mg of a drug. In some embodiments, the device is configured for delivery of the dosage form comprising a drug on a once-daily basis. In some embodiments, the delivery (administration) rates ranges from about 0.167 mL per minute to about 12 mL per minute, inclusive. In some embodiments, the delivery rate is about 12 mL per minute. In some embodiments, the delivery device is configured to deliver the dosage form at a flow rate of about 2 mL per minute. In some embodiments, the delivery device is configured to deliver the dosage form at a flow rate of about 0.167 mL per minute.

As used herein, "viscosity" refers in general to the state of being thick, sticky, and semifluid in consistency, corresponding to the informal concept of "thickness." In particular, however, "viscosity" of a fluid is a measure of its resistance to gradual deformation by shear stress or tensile stress. Viscosity can be expressed as the magnitude of force needed to overcome internal friction, for example, as measured by the force per unit area resisting a flow, in which parallel layers a unit distance apart have a unit speed relative to one another. The viscosity of a Newtonian fluid is dependent only on temperature, and not on shear rate and time. The viscosity of non-Newtonian fluids, time dependent, depends on temperature, shear rate and time; depending on how viscosity changes with time the fluid behavior can be characterized as thixotropic (time thinning, i.e., viscosity decreases with time), rheopetic (time thickening, i.e., viscosity increases with time), or rheomaiaxis (time thinning correlates with breakdown of structure). The viscosity of Non-Newtonian fluids, time independent, depends not only on temperature but also on shear rate. Viscosity may be measured as centipoise (cps), in which water is the standard at 1 cps. Blood has an approximate viscosity of 10 cps; maple syrup 150 cps to 200 cps; motor oil SAE60 1000 cps to 2000 cps; ketchup 50,000 cps to 70,000 cps; peanut butter 150,000 csp to 250,000 cps; caulking compound 5,000,000 cps to 10,000,000 cps.

As noted above, temperature can be a factor in viscosity fluid mechanics, but for the purposes of the analytical modeling discussed herein, temperature is assumed to be ambient and remain substantially so for the course of drug delivery. Those of skill in the art armed with this specification can adjust configuration of a drug delivery device to control, manage, or harness changes in viscosity attributed to temperature. The viscous liquid as envisioned herein may be in liquid form or reconstituted from lyophilized form. Non-limiting examples of viscous fluids include those with at least about 10 cps or about 100 cps at a shear rate of 0.1/second. An example viscosity can in the range of from about 80,000 cps to about 300,000 cps, inclusive, or the viscosity be in the range of from about 140,000 cps to about 280,000 cps, inclusive, at a shear rate of 0.1/second at 25° C., or a viscosity range from about 100 cps to about 1,000 cps, inclusive, ata shear rate 0.1/second at 25° C. Viscosity can be measured by a rheometer.

The embodiments described herein provide for a drug delivery device capable of SQ delivery of a 2 mL dosage form comprising 300 mg of a drug with acceptable pharmacokinetics and tolerability. In some embodiments, the pharmacokinetics and tolerability of the 2 mL injection are comparable with two 150 mg drug/1 mL SQ injections. Tolerability factors include local injection site pain and injection site pruritus post-injection; local injection site reactions (e.g., erythema, bleeding, rash, etc.) post-injection; presence of fluid leakage immediately post-injection; and incidence of treatment-emergent adverse events including clinically significant changes in vital signs, physical examinations, and laboratory parameters. Additionally, biomarkers relevant to the mechanism of action of a drug, and the presence of anti-drug antibodies may be found acceptable relative to the two-injection regimen. Thus, the present embodiments provide for drug delivery devices that allow for a reduction in the number of injections by the administration of a larger dose volume of a rather viscous dosage form over longer injection times, still satisfying pharmacokinetic requirements as well as patient tolerance of pain.

Analytical models for delivery time (i.e., speed), drive system forces, and primary container pressures can be useful in implementing some of the embodiments described herein. For instance, in fluid mechanics, the Reynolds number is a dimensionless quantity that is used to help predict similar flow patterns in different fluid flow situations. The Reynolds number is defined as the ratio of momentum forces (or inertial forces) to viscous forces, and quantifies the relative importance of these two types of forces for given flow conditions. Reynolds numbers are useful when performing scaling of fluid dynamics modeling, and as such can be used to determine dynamic similitude between two different cases of fluid flow. This and other equations relating to such analytical models include the following formulae:

$$t_d = \frac{\mu R_g A_{pc}^2}{-k_{ds}} \ln\left(\frac{Z_{1subQ} + T_f}{Z_{1subQ} + T_i}\right) \quad \text{Formula 1}$$

in which td is delivery time and Rg is geometrical fluid resistance. Apc is the primary container area in m2; kds is event spring constant in N/m; Z1subQ is grouping term 1 "SubQ delivery," in mm; Tf is travel in final position (end of dose) in mm; Ti is travel at initial delivery (after bubble compression) in mm.

$$Z_{1rubQ} = \frac{F_0 - F_{fg} - P_{tb} A_{pc}}{-k_{ds}} \quad \text{Formula 2}$$

in which Z1subQ is grouping term 1 "SubQ delivery," in mm; Fo is loaded housing force in N; Ffg is glide force in N; ND is tissue back-pressure in psi; Apc is the primary container area in m2; and kds is event spring constant in N/m.

$$R_g = \left(\frac{128L_n}{\pi D_n^4} + \frac{128L_t}{\pi D_t^4} + \frac{128L_{fr}}{\pi D_{fr}^4} + \frac{128L_c}{\pi D_c^4}\right) \quad \text{Formula 3}$$

in which Rg is geometrical fluid resistance; Ln is needle length in mm; Lt is tubing length; Lfr is flow restrictor length in mm; Lc is cannula length in mm; Dn is needle diameter in mm; Dt is tubing diameter in mm; Dfr is flow restrictor diameter in mm; and Dc is cannula diameter in mm.

$$Re = \frac{4Q_\rho}{\pi \mu D} \quad \text{Formula 4}$$

in which Re is Reynolds number; Q is the flow rate in mL per minute; p is fluid density in kg/m3; μ is dynamic viscosity in cP (may also be calculated in Pa·s, N·s/$m^2$, or kg/(m·s)); and D is the hydraulic diameter in mm (the "wetted perimeter," total perimeter of all the channels in contact with the flow [the inside pipe diameter]). It may be convenient to assume the fluid has a density of 1.0 g/mL. Flow is laminar if the value is <2300.

Charts and bar graphs depicting variables, components, and delivery times per example embodiments are shown in FIG. 92 to FIG. 99. For example, FIG. 98 shows the contribution to delivery time of groups of component parts that have been described in more detail above. Further data related to the delivery time, described in the tables above for four models (see Output: Delivery Time, Case 1 to Case 4), appears as a bar graph in FIG. 92. The relationship between drive system force and the travel distance of the fluid delivered is shown in FIG. 93. The four models are further analyzed for component contribution to the time of delivery in FIG. 94 (Case 1), FIG. 95 (Case 2), FIG. 96 (Case 3), FIG. 97 (Case 4), and FIG. 99 (Case 1). FIG. 94 and FIG. 99 allow comparison of component contribution in the delivery of fluids with different viscosities.

In one aspect of the present disclosure, a drug delivery device comprises an insertion mechanism, a drive mechanism, a sterile fluid pathway, and a drug container comprising a dosage form comprising a drug, wherein said device is configured to deliver to a human patient about 2 mL of the dosage form at a flow rate of up to about 12 mL per minute. Additionally, the drug delivery device may configured for subcutaneous delivery. In addition, the drug delivery device may be configured to deliver about 300 mg of a drug. In addition, the drug delivery device may be configured for delivery of the dosage form comprising a drug on a once-daily basis. In addition, the drug delivery device may be configured to deliver the dosage form at a flow rate ranging from about 0.167 mL per minute to about 12 mL per minute, inclusive. In addition, the drug delivery device may be configured deliver the dosage form at a flow rate of about 12 mL per minute. In addition, the drug delivery device may be configured to deliver the dosage form at a flow rate of about 2 mL per minute. In addition, the drug delivery device may be configured to deliver the dosage form at a flow rate of about 0.167 mL per minute. In addition, the drug delivery device may include a means for delivering a dosage form to a human patient of about 2 mL, comprising a drug, at a flow rate of up to about 12 mL per minute.

In another aspect of the present disclosure, a method includes administering to a human subject in need thereof a dosage form comprising a drug comprising contacting a human patient with a drug delivery device configured to deliver about 2 mL of a dosage form comprising a drug at a flow rate of up to about 12 mL per minute, and actuating said device to deliver said dosage form. Additionally, the method may have the delivery administer a dosage form comprising about 300 mg of a drug. Additionally, the method have the delivery be a subcutaneous injection.

Additionally, the actuating step of the method may be carried out on a once-daily basis. Additionally, the delivery rate of the method may be from about 0.167 mL per minute to about 12 mL per minute, inclusive. Additionally, the delivery rate of the method may be about 12 mL per minute, about 2 mL per minute, or about 0.167 mL per minute.

XVII. Additional Embodiments of Insertion Mechanism

At least some of the drug delivery devices described in this application, including at least those described in connection with FIGS. 1-56, 74-91B and 118-127D, may be configured to incorporate the embodiments of the insertion mechanism described below in connection with FIGS. 100A-117. The embodiments of the insertion mechanism described below in connection with FIGS. 100A-117 may be used to replace, in its entirety or partially, the above-described insertion mechanism 200, the insertion mechanism 2000, or any other insertion mechanism described herein, where appropriate.

In one embodiment, the insertion mechanism 17200 includes an insertion mechanism housing 17202, a housing cap 17203, a base 17252, and a sterile boot 17250, as shown in FIG. 100A. Base 17252 may be connected to assembly platform 1720 to integrate the insertion mechanism into the drug delivery device 10 (as shown in FIG. 1A-1C). The connection of the base 17252 to the assembly platform 1720 may be, for example, such that the bottom of the base is permitted to pass through a hole in the assembly platform to permit direct contact of the base to the target. In such configurations, the bottom of the base 17252 may include a sealing membrane 17254 that, at least in one embodiment, is removable prior to use of the drug delivery device 10. Alternatively, the sealing membrane 17254 may remain attached to the bottom of the base 17252 such that the hollow needle 17214 pierces the sealing membrane 17254 during operation of the drug delivery device 10. As shown in FIGS. 100A and 100B, the insertion mechanism 17200 may further include an insertion biasing member 17210, a hub 17212, a needle 17214, a retraction biasing member 17216, a clip 17218, a clip retainer 17219, a manifold guide 17220, septa 17230A and 17230B, and a manifold body 17240. The manifold 17240 may connect to sterile fluid conduit 30 to permit fluid flow through the manifold 17240, into an interior of the hollow needle 17214, and into the target during drug delivery, as will be described in further detail herein.

FIGS. 101-117 show the components of the insertion mechanism, according to at least a first embodiment, in greater detail. As shown in FIG. 101, insertion mechanism housing 17202 may be a substantially cylindrical component having an inner chamber within which the components of the insertion mechanism are substantially housed. Housing 17202 further includes axial slot 17202B within which protrusion 17219H of clip retainer 17219 slidably translates during insertion as will be described in greater detail hereinafter. Housing 17202 may further include circumferential slot 17202C which allows protrusion 17219H to be rotated to allow retraction biasing member 17216 to retract needle 17214. Housing 17202 may further include axial slot 17202D within which sterile fluid conduit 30 may translate during needle insertion. Housing 17202 further includes one or more lockout windows 17202A which are configured to engage lockout pins 17208 in an initial, locked configuration. Lockout pins 17208 may pass through windows 17202A to the interior of housing 17202 such that manifold guide ring 17220C may rest upon lockout pins 17208 in an initial, locked configuration. Housing 17202 may additionally include limiter slots 17202F and aperture 17202E which are configured to accept and engage travel limiter 17229. Alternatively, the protrusion 17219H may be replaced by a manual button or the like, or an automated or automatic mechanism that responds to a timer or other control system or method (not shown).

Housing cap 17203, shown in FIG. 102, contains guide protrusions 17204. Guide protrusions 17204 may, alternatively, be a pre-formed aspect on the interior of insertion mechanism housing 17202. The guide protrusions 17204 slidably engage clip retainer 17219 at pass throughs 17219D and may slidably engage manifold guide 17220 at pass-throughs 17220D on manifold guide ring 17220C. The insertion biasing member 17210 initially resides in an energized state between the guide protrusions 17204 and inner surface of insertion mechanism housing 17202 and between the interior proximal end of the insertion mechanism housing cap 17203 and the flange 17219E of clip retainer 17219. Therefore upon activation by the user, as described further hereinafter, the insertion biasing member 17210 is caused to bear against and exert force upon flange 17219E of clip retainer 17219 as the insertion biasing member 17210 decompresses and/or de-energizes, causing axial translation in the distal direction of the clip retainer 17219, clip 17218, hub 17212, retraction biasing member 17216, manifold guide 17220 and the components retained within manifold guide lower chamber 17220E. Prior to activation, the insertion biasing member 17210 is maintained substantially above locking windows 17202A in a compressed, energized state. Housing cap 17203 may be mounted to housing 17202 by any means known to one skilled in the art such as threading, bonding, ultrasonic welding, press-fit, snap-fit, etc.

FIG. 103 shows a clip 17218, according to one embodiment of the present disclosure. Clip 17218 includes aperture 17218C through face 17218E through which needle 17214 may pass, and release surfaces 17218A and lockout surfaces 17218B of arms 17218D. Clip 17218 further includes prongs 17218F. Clip 17218 may be made of any number of resilient materials that are capable of flexing and returning to substantially their original form. In an original form, clip 17218 may flex outwards such that arms 17218D are not perpendicular with face 17218E. Clip 17218 resides within clip retainer 17219 such that clip 17218 is in fixed engagement with clip retainer 17219 but arms 17218D are permitted to flex within slots 17219A. Prongs 17218F are configured to engage slots 17219F of clip retainer 17219, thus coupling rotation of clip 17218 and clip retainer 17219. In an initial locked stage, retraction biasing member 17216 and hub 17212 (with connected needle 17214) are retained between release surfaces 17218A and face 17218E of clip 17218, and within inner chamber 17219B of clip retainer 17219. The needle may pass through aperture 17218C of clip 17218, through aperture 17219G of clip retainer 17219, and through manifold guide 17220 into septa 17230 and manifold 17240. Septa 17230 reside within manifold 17240, as shown in FIG. 106. Manifold 17240 further includes a manifold body 17240B having a manifold intake 17240A at which the sterile fluid conduit 30 may be connected. This connection is such that the sterility is maintained from the drug container 50 of the drive mechanism 100, through the fluid pathway connection 300 and the sterile fluid conduit 30, into sterile manifold header 17242 of manifold 17240 and sterile boot 17250 to maintain the sterility of the needle 17214, and the fluid pathway until insertion into the target for drug delivery.

The clip retainer 17219, shown in FIG. 104 may include a clip interface slot 17219A for engageable retention of clip 17218, shown in FIG. 103. Flexible extensions 17219G may be configured to flex outward during installation of clip 17218 into clip interface slot 17219A and, upon clip insertion, return to their natural positions. Hence, the clip 17218 is substantially retained in axial position with respect to clip retainer 17219. The clip retainer 17219 may have an inner chamber 17219B, within which the retraction biasing member 17216, the clip 17218, and the hub 17212 may reside during an initial locked stage of operation, and an outer upper chamber 17219C, which interfaces with the insertion biasing member 17210. In at least one embodiment, the insertion biasing member 17210 and the retraction biasing member 17216 are springs, preferably compression springs. The hub 17212 may be engageably connected to a proximal end of needle 17214, such that displacement or axial translation of the hub 17212 causes related motion of the needle 17214.

The manifold guide 17220, shown in FIG. 105, may include an upper protrusion 17220A and a lower chamber 17220B separated by a manifold guide ring 17220C. Upper protrusion 17220A is configured to engage manifold 17240. Manifold guide ring 17220C is configured to be supported by lockout pins 17208 in an initial, locked stage of operation.

As used herein, "needle" is intended to refer to a variety of needles including but not limited to conventional hollow needles, such as a rigid hollow steel needles, and solid core needles more commonly referred to as a "trocars." The needle 17214 may include at least one side port 17214A for admitting fluid into the hollow interior thereof. While one such side port 17214A is illustrated, it will be appreciated that a plurality of side ports may be provided for admitting fluid into the hollow interior of the needle 17214. The needle may be any size needle suitable for the type of drug and drug administration (e.g., subcutaneous, intramuscular, intradermal, etc.) intended.

Upon assembly, the proximal end of needle 17214 is maintained in fixed contact with hub 17212; the proximal end of the needle may be filled with a plug (e.g., a plastic plug, a plug of bonding agent) or may be encapsulated within hub 17212. By plugging the proximal end of needle 17214 fluid is prevented from flowing out of the needle in this direction during drug delivery. The remainder of needle 17214 is permitted to pass through retraction biasing member 17216, an aperture 17218C of clip 17218, clip retainer 17219, and manifold guide 17220. The needle 17214 may further pass through septa 17230, manifold body 17240B through manifold header 17242, sterile boot 17250, and base 17252 through base opening 17252A. Septa 17230 and manifold body 17240B may reside within lower chamber 17220B of manifold guide 17220 and within sterile boot 17250 until operation of the insertion mechanism. Similarly, septum 17230A resides substantially fixed and in sealed engagement within the upper portion of the manifold body 17240B and septum 17230B resides substantially fixed and in sealed engagement within the lower portion of the manifold body 17240B to maintain the sterility of the manifold header 17242. Upon insertion of needle 17214 into the target, port 17214A is located within manifold 17220 between the upper and lower septa. This allows fluid to pass into the needle for delivery into the target.

Sterile boot 17250 is a collapsible or compressible sterile membrane that is in fixed engagement at a proximal end with the manifold 17240 and at a distal end with the base 17252. In at least on embodiment, the sterile boot 17250 is maintained in fixed engagement at a distal end between base 17252 and insertion mechanism housing 17202, as shown in FIGS. 108C, 109C, and 110C. Base 17252 includes a base opening 17252A through which the needle may pass through during operation of the insertion mechanism, as will be described further below. Sterility of the needle is maintained by their initial positioning within the sterile portions of the insertion mechanism. Specifically, as described above, needle 17214 is maintained in the sterile environment of the manifold header 17242 and sterile boot 17250. The base opening 17252A of base 17252 may be closed from non-sterile environments as well, such as by for example a sealing membrane 17254.

FIG. 107 shows a travel limiter 17229, according to at least one embodiment of the present disclosure. Travel limiter 17229 includes prongs 17229A and arms 17229C. Travel limiter 17229 is configured to engage housing 17202 such that arms 17229C are at least partially disposed within one or more lower circumferential slots 17202F of housing 17202. Prongs 17229A are configured to engage aperture 17202E of housing 17202. Prongs 17229A flex inward during insertion through aperture 17202E due to interference with the walls of aperture 17202E. After protrusions 17229D fully pass through aperture 17202E prongs 17229A flex outward, thereafter substantially fixing travel limiter 17229 in place with respect to housing 17202. One or more proximal faces 17229B are used to restrict the movement of manifold guide 17220 and/or clip retainer 17219 as will be described in more detail hereinafter.

The operation of the insertion mechanism is described herein with reference to the above components, in view of FIGS. 108-110. FIG. 108A shows an isometric view and FIG. 108B shows a cross-sectional view of the insertion mechanism, according to at least one embodiment of the present disclosure, in a locked and ready to use stage. Lockout pin(s) 17208 are initially positioned within lockout windows 17202A of insertion mechanism housing 17202. In this initial position, manifold guide ring 17220C of manifold guide 17220, clip retainer, 17219, clip 17218, and hub 17212 are retained above lockout windows 17202A and locking pin(s) 17208. In this initial configuration, insertion biasing member 17210 and retraction biasing member 17216 are each retained in their compressed, energized states. Protrusion 17219H is located within slot 17202B of housing 17202.

As shown in FIG. 1B, the lockout pin(s) 17208 (not visible) may be directly displaced by user depression of the activation mechanism 14. As the user disengages any safety mechanisms, such as an optional sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 17208 from their initial position within locking windows 17202A of insertion mechanism housing 17202. Displacement of the lockout pin(s) 17208 permits insertion biasing member 17210 to decompress and/or de-energize from its initial compressed, energized state.

As shown in FIG. 108B, hub ledges 17212A maintain retraction biasing member 17216 in a compressed, energized state between hub 17212 and clip retainer 17219 within chamber 17219B. The hub 17212 fixedly engages proximal end of needle 17214 at hub recess 17212B, positioning the hub 17212 and needle 17214 in an initial position. Prior to operation, sealing member 17254 may be removed from bottom of base 17252 and base 17252 is placed in contact with the target injection site on the target. As lockout pin(s) 17208 are displaced by the activation mechanism, as described above, and insertion biasing member 17210 is permitted to expand axially in the distal direction (i.e., in the direction of the solid arrow in FIG. 108B), flange 17219E is forced by the decompression and/or de-energizing of the insertion biasing member 17210 to translate axially in the distal direction to insert the needle 17214 into the target. The axial translation of the clip retainer and manifold guide is directed, and maintained in rotational alignment, by interaction between the guide protrusions 17204 of the insertion mechanism housing cap 17203 and corresponding pass-throughs 17219D and 17220D of the clip retainer 17219 and manifold guide 17220. Release surfaces 17218A of clip 17218 engage hub 17212 and retain the retraction biasing member 17216 in a compressed, energized state while the manifold guide 17220 travels axially in the distal direction.

FIG. 109A shows an isometric and FIG. 109B shows a cross-sectional view of an insertion mechanism in an administration configuration, that is, with the needle 17214 and hub 17212 in an administration position. In this position, manifold guide 17220 is in contact with proximal surfaces 17229B of travel limiter 17229. As shown, sterile boot 17250 is permitted to collapse as the insertion biasing member 17210 expands and inserts the needle 17214 into the target. At this stage, shown in FIG. 109, needle 17214 is introduced into the target for drug delivery. As the fluid pathway connection is made to the drug container and the drive mechanism is activated, the fluid drug treatment is forced from the drug container through the fluid pathway connection and the sterile fluid conduit into the manifold header 17242 and through the needle 17214 for delivery into the target. Accordingly, activation of the insertion mechanism inserts the needle 17214 into a target or the target placing the fluid pathway in communication with the target. As can be seen in FIG. 109B arms 17218D are flexed inward due to contact with guide protrusions 17204. Hence, release surfaces 17218A maintain contact with hub 17212 and prevent retraction biasing member 17216 from decompressing or de-energizing.

As shown in FIG. 110A-110B, needle 17214 is retracted back (i.e., axially translated in the proximal direction) into the insertion mechanism housing 17202. FIG. 110A shows an isometric view of the insertion mechanism in this configuration and FIG. 110B shows a cross-sectional view. The plane of cross-section in FIG. 110B is not the same as that of FIG. 108B and FIG. 109B but is rotated with respect to the cross-sectional plane of those views. This retraction may be triggered by user activation, automatic retraction at completion of dose delivery, failure or fault of the drive mechanism, or upon activation by one or more sensors. Upon full distal displacement of insertion biasing member 17210, protrusion 17219H is substantially aligned with circumferential slot 17202C of housing 17202 and arms 17218D are constrained by guide protrusions 17204 as shown in FIGS. 11A-11B (position A). In this position clip retainer 17219 is able to rotate with respect to housing 17202, housing cap 17203, and guide protrusions 17204 to a position B as shown in FIGS. 110A-B. The rotation of clip retainer 17219 is transmitted to clip 17218. In position B, arms 17218D of clip 17218 are no longer restrained by guide protrusions 17204, hence, arms 17218D flex radially outward (i.e., in the direction of the hollow arrows shown in FIG. 109B) due to their outward bias. This causes release surfaces 17218A to disengage from hub 17212. Upon disengagement of the release surfaces 17218A from hub 17212, retraction biasing member 17216 is permitted to expand axially in the proximal direction (i.e., in the direction of hatched arrow in FIG. 110B) from its initial compressed, energized state. The clip 17218 is prevented from retracting or axial translation in the proximal direction by contact between the lockout surfaces 17218B and the distal ends of the guide protrusions 17204, as shown in FIG. 110B. This lockout also prevents axial translation in the proximal direction of the clip retainer 17219, manifold guide 17220 and insertion mechanism components that are distal to (i.e., below) the manifold guide ring 17220C. In this configuration, needle 17214 is no longer exposed, therefore making pump 10 safe to handle.

In a second embodiment, shown in FIG. 111, the insertion mechanism 172200 includes an insertion mechanism housing 172202, a base 172252, and a sterile boot 172250, as shown in FIGS. 111A and 111B. Base 172252 may be connected to assembly platform 1720 to integrate the insertion mechanism into the drug delivery device 10 (as shown in FIGS. 1A-1C). The connection of the base 172252 to the assembly platform 1720 may be, for example, such that the bottom of the base is permitted to pass through a hole in the assembly platform to permit direct contact of the base to the target. In such configurations, the bottom of the base 172252 may include a sealing membrane 172254 that, at least in one embodiment, is removable prior to use of the drug pump 10. Alternatively, the sealing membrane 172254 may remain attached to the bottom of the base 172252 such that the needle 172214 pierces the sealing membrane 172254 during operation of the drug pump 10. As shown in FIGS. 111A and 111B, the insertion mechanism 172200 may further include an insertion biasing member 172210, a hub 172212, a needle 172214, a retraction biasing member 172216, a clip 172218, a manifold guide 172220, a travel limiter 172229, and a manifold 172240 including a manifold body 172240B, septa 172230A and 172230B. The manifold 172240 may connect to sterile fluid conduit 30 to permit fluid flow through the manifold 172240, needle 172214, and into the target during drug delivery, as will be described in further detail herein.

As shown in FIG. 112, insertion mechanism housing 172202 may be a substantially cylindrical component having an inner chamber within which the components of the insertion mechanism are substantially housed. Housing 172202 may further include axial slot 172202D within which sterile fluid conduit 30 may translate during needle insertion as will be described hereinafter. Housing 17202 further includes one or more lockout windows 172202A which are configured to engage lockout pins 17208 in an initial, locked configuration. Lockout pins 17208 may pass through windows 172202A to the interior of housing 172202 such that manifold guide ring 172220C may rest upon lockout pins 17208 in an initial, locked configuration. Housing 172202 may additionally include limiter slots 172202F which are configured to accept and engage travel limiter 172229.

Housing 172202 may additionally include guide protrusions 172204. Guide protrusions 172204 may, alternatively, be a portion of a separate component located within housing 172202. The guide protrusions 172204 slidably engage manifold guide 172220 at pass-throughs 172220D on manifold guide ring 172220C. The insertion biasing member 172210 initially resides in an energized state between the guide protrusions 172204 and inner surface of insertion mechanism housing 172202 and between the interior proximal end of the insertion mechanism housing 172202 and the manifold guide ring 172220C. Therefore upon activation by the user, as described further hereinafter, the insertion biasing member 172210 is caused to bear against and exert force upon manifold guide ring 172220C as the insertion biasing member 172210 decompresses and/or de-energizes, causing axial translation in the distal direction of the manifold guide 172220 and the components retained within manifold guide 172220. Prior to activation, the insertion biasing member 172210 is maintained substantially above locking windows 172202A in a compressed, energized state.

The manifold guide 172220, shown in FIG. 113, may include an upper, clip retainer or clip retaining portion 172219 and a lower chamber 172220B separated by a guide ring 172220C. The clip retainer or clip retaining portion 172219 may include a clip interface slot 172219A for engageable retention of clip 172218. Flexible extensions 172219G may be configured to flex outward during installation of clip 172218 into clip interface slot 172219A and, upon clip insertion, return to their natural positions. Hence, the clip 172218 is substantially retained in axial position with respect to manifold guide 172220. The clip retainer or clip retaining portion 172219 may have an inner chamber 172219B, within which the retraction biasing member 172216, the clip 172218, and the hub 172212 may reside during an initial locked stage of operation, and an outer upper chamber 172219C, which interfaces with the insertion biasing member 172210. In at least one embodiment, the insertion biasing member 172210 and the retraction biasing member 172216 are springs, preferably compression springs. The hub 172212 may be engageably connected to a proximal end of needle 172214, such that displacement or axial translation of the hub 172212 causes related motion of the needle 172214. Manifold guide ring 172220C is configured to be supported by lockout pins 17208 in an initial, locked stage of operation.

Travel limiter 172229, shown in FIG. 114, may be configured to include a living hinge 172229D which allows arms 172229C of travel limiter 172229 to transform from a “closed” position in which proximal faces 172229B restrict axial movement of manifold guide 172220 to an “open” position in which travel limiter 172229 allows additional axial movement of manifold guide 172220, thereby allowing needle retraction. Travel limiter 172229 is configured to be at least partially within the interior of housing 172202 in an initial, installed configuration. After transformation to its “open” position travel limiter 172229 may be positioned substantially outside of housing 172202 or may remain partially within housing 172202 but allow additional distal movement of manifold guide 172220. Alternatively, transformation from the “closed” position to the “open” position may be performed by translating travel limiter 172229 in a direction perpendicular to axis A such that proximal faces 172229B allow additional movement of manifold guide 172220.

As used herein, “needle” is intended to refer to a variety of needles including but not limited to conventional hollow needles, such as a rigid hollow steel needles, and solid core needles more commonly referred to as a “trocars.” The needle may be any size needle suitable for the type of drug and drug administration (e.g., subcutaneous, intramuscular, intradermal, etc.) intended. As with the needle 17214 of the first embodiment, the needle 172214 may include at least one side port 172214A for admitting fluid into the hollow interior thereof. While one such side port 172214A is illustrated, it will be appreciated that a plurality of side ports may be provided for admitting fluid into the hollow interior of the needle 172214. Upon assembly, the proximal end of needle 172214 is maintained in fixed contact with hub 172212; the proximal end of the needle may be filled with a plug (e.g., a plastic plug, a plug of bonding agent) or may be encapsulated within hub 172212. By plugging the proximal end of needle 172214 fluid is prevented from flowing out of the needle in this direction during drug delivery. The remainder of needle 172214 is permitted to pass through retraction biasing member 172216, an aperture 172218C of clip 172218 and manifold guide 172220. The needle 172214 may further pass through septa 172230, manifold body 172240B through manifold header 172242, sterile boot 172250, and base 172252 through base opening 172252A. Septa 172230 and manifold body 172240B may reside within lower chamber 172220B of manifold guide 172220 and within sterile boot 172250 until operation of the insertion mechanism. Similarly, septum 172230A resides substantially fixed and in sealed engagement within the upper portion of the manifold body 172240B and septum 172230B resides substantially fixed and in sealed engagement within the lower portion of the manifold body 172240B to maintain the sterility of the manifold header 172242. Upon insertion of needle 172214 into the target, port 172214A is located within manifold 172220 between the upper and lower septa. This allows fluid to pass into the needle 172214 for delivery into the target.

Sterile boot 172250 is a collapsible or compressible sterile membrane that is in fixed engagement at a proximal end with the manifold 172240 and at a distal end with the base 172252. In at least on embodiment, the sterile boot 172250 is maintained in fixed engagement at a distal end between base 172252 and insertion mechanism housing 172202, as shown in FIGS. 115A-C. Base 172252 includes a base opening 172252A through which the needle may pass through during operation of the insertion mechanism, as will be described further below. Sterility of the needle is maintained by its initial positioning within the sterile portions of the insertion mechanism. Specifically, as described above, needle 172214 is maintained in the sterile environment of the manifold header 172242 and sterile boot 172250. The base opening 172252A of base 172252 may be closed from non-sterile environments as well, such as by for example a sealing membrane 172254.

The operation of one embodiment of the insertion mechanism is described herein with reference to the above components, in view of FIGS. 115A-C. FIG. 115A shows a cross-sectional view of the insertion mechanism, according to at least one embodiment of the present disclosure, in a locked and ready to use stage. Lockout pin(s) 172208 are initially positioned within lockout windows 172202A of insertion mechanism housing 172202. In this initial position, manifold guide ring 172220C of manifold guide 172220, clip 172218, and hub 172212 are retained above lockout windows 172202A and locking pin(s) 172208. In this initial configuration, insertion biasing member 172210 and retraction biasing member 172216 are each retained in their compressed, energized states.

As shown in FIG. 1B, the lockout pin(s) 172208 (not visible) may be directly displaced by user depression of the activation mechanism 14. As the user disengages any safety mechanisms, such as an optional sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 17208 from their initial position within locking windows 172202A of insertion mechanism housing 172202. Displacement of the lockout pin(s) 172208 permits insertion biasing member 172210 to decompress and/or de-energize from its initial compressed, energized state.

As shown in FIG. 115B, hub ledges 172212A maintain retraction biasing member 172216 in a compressed, energized state between hub 172212 and manifold guide 172220 within chamber 172219B. The hub 172212 fixedly engages proximal end of needle 172214 at hub recess 172212B. Prior to operation, sealing member 172254 may be removed from bottom of base 172252 and base 172252 is placed in contact with the target injection site on the target. As lockout pin(s) 172208 are displaced by the activation mechanism, as described above, and insertion biasing member 172210 is permitted to expand axially in the distal direction (i.e., in the direction of the solid arrow in FIG. 115A), guide ring 172220C is forced by the decompression and/or de-energizing of the insertion biasing member 172210 to translate axially in the distal direction to insert the needle 172214 into a target. The axial translation of the manifold guide is directed, and maintained in rotational alignment by interaction between the guide protrusions 172204 of the insertion mechanism housing 172202 and corresponding pass-throughs 172220D of the manifold guide 172220. Release surfaces 172218A of clip 172218 engage hub 172212 and retain the retraction biasing member 172216 in a compressed, energized state while the manifold guide 172220 travels axially in the distal direction. FIG. 115B shows a cross-sectional view of an insertion mechanism according to at least one embodiment in an administration configuration, that is, with the needle 172214 and hub 172212 in an administration position. In this position, manifold guide 172220 is in contact with proximal surfaces 172229B of travel limiter 172229. As shown, sterile boot 172250 is permitted to collapse as the insertion biasing member 172210 expands and inserts the needle 172214 into the target. At this stage, needle 172214 is introduced into the target for drug delivery. As the fluid pathway connection is made to the drug container and the drive mechanism is activated, the fluid drug treatment is forced from the drug container through the fluid pathway connection and the sterile fluid conduit into the manifold header 172242 and through the needle 172214 for delivery into the target. Accordingly, activation of the insertion mechanism inserts the needle 172214 into the target, which may be a tissue, for example, placing the fluid pathway in communication with the target. As can be seen in FIG. 115B arms 172218D are flexed inward due to contact with guide protrusions 172204. Hence, release surfaces 172218A maintain contact with hub 172212 and prevent retraction biasing member 172216 from decompressing or de-energizing.

As shown in FIG. 115C, needle 172214 is retracted back (i.e., axially translated in the proximal direction) into the insertion mechanism housing 172202. This retraction may be triggered by user activation, automatic retraction at completion of dose delivery, failure or fault of the drive mechanism, or upon activation by one or more sensors. To effect retraction of needle 172214, travel limiter 172229 is displaced and/or transformed such that manifold guide ring 172220C is no longer supported by proximal faces 172229B. Hence, further decompression or de-energizing of insertion biasing member 172210 causes manifold guide 172220 to move in the distal direction (direction of solid arrow in FIG. 115A). In this position arms 172218D of clip 172218 are no longer restrained by guide protrusions 172204, hence, arms 172218D flex radially outward (i.e., in the direction of the hollow arrows shown in FIG. 115B) due to their outward bias. This causes release surfaces 172218A to disengage from hub 172212. Upon disengagement of the release surfaces 172218A from hub 172212, retraction biasing member 172216 is permitted to expand axially in the proximal direction (i.e., in the direction of hatched arrow in FIG. 115C) from its initial compressed, energized state. The clip 172218 is prevented from retracting or axial translation in the proximal direction by contact between the lockout surfaces 172218B and the distal ends of the guide protrusions 172204, as shown in FIG. 115C. This lockout also prevents axial translation in the proximal direction of the manifold guide 172220 and insertion mechanism components that are distal to (i.e., below) the manifold guide ring 172220C. In this configuration, needle 172214 is no longer exposed, therefore making pump 10 safe to handle.

Activating retraction of the needle may be accomplished through many mechanisms. For example, a retraction activation mechanism such as a button may be provided on the outside of housing 12 which, when depressed by the user, activates retraction of the needle from the target. For example, in one embodiment, depressing the retraction activation mechanism may cause clip retainer 17219 to rotate to position B, hence allowing retraction biasing member 17216 to expand and retract needle 17214. In another embodiment, depression of the retraction activation mechanism may cause displacement and/or transformation of travel limiter 172229 and allow retraction biasing member 172216 to decompress and retract the needle. Actuation of the retraction activation mechanism may be spring assisted such that the travel and/or force required to depress the retraction activation mechanism is reduced. Alternatively, or additionally, upon drive mechanism 100 reaching end-of-dose an electrical or mechanical actuator may cause activation of retraction. For example, upon end-of-dose, an electrical connection may be made such that a current is applied to a nitinol component. Upon application of the current the nitinol component's temperature rises. Because of the shape-memory characteristics of nitinol, this component may be configured, upon an increase in temperature, to transform from a first configuration to a second configuration. In this second configuration, the nitinol component may allow or cause the actuation of the retraction of the needle by, for example, rotating clip retainer 17219 or displacing or transforming travel limiter 172229.

Alternatively, or additionally, a sensor such as sensor 24 may, when drug pump 10 is removed from the target, cause or allow activation of the retraction of the needle. For example, when pump 10 is installed on the target the position of sensor 24 may prevent retraction of the needle. Upon removal from the target a change in configuration of sensor 24 may allow retraction. In another embodiment, a light sensor may be placed on drug pump 10 near to base opening 17252. When drug pump 10 is in place on the target, light would be substantially blocked from entering the light sensor. Upon removal of drug pump 10 from the target, light may be sensed by the light sensor and the light sensor may trigger an electromechanical actuator to allow or cause activation of retraction. In other embodiments, a pin-type press-fit interconnect is used to initiate retraction of the needle. The pin may be biased to at least partially protrude from housing 12 and be displaced upon placement of pump 10 on the target. When displaced, the pin may engage a female hole on a PCB which may be a part of power and control system 400. Upon removal of pump 10 from the target, the biased pin disengages the female PCB hole, thereby causing a signal to activate the retraction of the needle.

Further, the insertion mechanism may be configured such that existence or detection of an unsafe condition, such as displacement of the insertion mechanism with respect to housing 12 or platform 1720, causes actuation of the retraction of the needle. For example, upon removal of locking pins 17208 from the lockout windows, the needle insertion mechanism may be free to float in a distal direction relative to housing 12 and/or platform 1720. A biasing member may be used such that the needle insertion mechanism is biased to move in a distal direction with respect to housing 12 and/or platform 1720. However, when pump 10 is in place on a target, motion is restrained by the target. Upon removal of pump 10 from the target, the biasing member may decompress or de-energize and cause the needle insertion mechanism to move distally with respect to housing 12 and/or platform 1720. This distal displacement may cause or allow the activation of retraction. Alternatively, or additionally, adhesive may be located on the distal face of the needle insertion mechanism which resists removal from the target and causes the needle insertion mechanism to move distally with respect to the housing 12 or platform 1720. The safety to the user may be enhanced through the use of one or more of these mechanisms for needle retraction. For example, if drug pump 10 is inadvertently removed from the target after needle insertion, the automatic retraction of the needle by one of the means described above reduces the risk of a needle-stick injury.

FIG. 116 shows one embodiment of a retraction activation mechanism. Retraction activation biasing member 64 is connected at the one end to control arm 40 and at the other end to connection arm 78 of pivot 70. Target contact portion 72 of pivot 70 may extend through lower housing 12B and its motion may be restrained by contact with the target when pump 10 is installed on the target. Pin 76 of pivot 70 is configured to engage housing 12 or another component of the pump, thereby allowing rotation of pivot 70 about pin 76. Extension 74 of pivot 70 is configured to contact protrusion 17219H during operation. Depression of activation mechanism 14 by the user causes displacement of slide 40, which activates the drug pump to insert the needle into the target by transforming lockout pins 17208; depression of the activation mechanism 14 may also activate the drug pump to perform additional actions. Displacement of control arm 40 displaces the first end of retraction activation biasing member 64, displacement of the second end of retraction activation biasing member is resisted by pivot 70 due to contact between target contact portion 72 of pivot 70 with the target. Upon removal of drug pump 10 from the target, pivot 70 is permitted to rotate and is caused to rotate by the energy stored in retraction activation biasing member 64. As pivot 70 rotates, extension 74 contacts protrusion 17219H and imparts rotation to clip retainer 17219, thereby causing or allowing retraction of the needle from the target.

Retraction of the needle may further be initiated upon a failure and/or fault of drive mechanism 100. For example, the drive mechanism may include a tether which serves to meter or control the rate of delivery of the contents of drug container 50. The tension applied to, or sustained by, the tether may be monitored by one or more sensors. A reduction in the tension of the tether may be an indication that the tether is not properly metering or controlling the delivery of the medicament. The sensor may be a mechanical component or linkage which is in contact with a portion of the tether, the contact at least partially controlling the position and/or configuration of the sensor. In response to a reduction in tension in the tether, the sensor transforms from a first position to a second position. This transformation may, directly or indirectly, cause retraction of the needle. The retraction may be caused by a purely mechanical action or, alternatively, may involve an electrical signal received and/or generated by power and control system 400.

In other embodiments, the sensor may be a strain gauge, load cell, force sensor or other sensor which is configured to measure and/or monitor the strain, load, or tension present in the tether. In these embodiments, the sensor is at least partially affixed to the tether and generates an electrical signal based on the tension of the tether. The electrical signal may vary in magnitude in proportion to the magnitude of tension in the tether. Alternatively, the signal may be either interrupted or initiated when the tension in the tether falls below or exceeds a specified magnitude. The signal may be monitored by the power and control system which, based on the presence, absence, or magnitude of the signal, may cause or allow the retraction of the needle and/or cannula.

In still other embodiments, a mechanical failure of the tether may directly cause an electrical signal to be initiated or interrupted. For example, the tether may be constructed, at least partially, from a conductive material. The tether may be in electrical communication with the power and control system. The mechanical failure of the tether may interrupt a current path through the tether and cause a change in the flow of current in one or more circuits. This change may initiate or allow the retraction of the needle.

Additionally, or alternatively, the position and/or velocity of one or more features of the drive system may be monitored by a sensor such as: an optical sensor, such as an encoder; a potentiometer; or a transducer. If the position and/or velocity of the monitored feature exceeds or falls below a specified threshold, the power and control system may initiate and/or allow retraction of the needle.

A similar mechanism may be used to transform travel limiter 172229 from a configuration in which it restricts axial motion of manifold guide 172220 to a configuration in which it allows manifold guide 172220 to axially translate in the distal direction, thereby allowing for retraction of the needle from the target. For example, travel limiter 172229 may be caused to flex at living hinge feature 172229D, causing travel limiter 172229 to transform to its "open" position.

A method of operating an insertion mechanism according to the present disclosure includes: removing one or more lockout pins from corresponding one or more locking windows of an insertion mechanism housing, wherein removal of said lockout pins permits an insertion biasing member to expand from its initially energized state; driving, by expansion of the insertion biasing member, a clip retainer and manifold guide axially in the distal direction to force a needle at least partially out of the insertion mechanism and into a target; maintain the needle in an administration position, as it would be when inserted into the target for fluid delivery; rotating a clip retainer and a clip; permitting outwards flexion of a clip retained in a chamber of a clip retainer, wherein said clip initially retains a hub and a retraction biasing member in an energized state and wherein flexion disengages one or more release surfaces of the clip from contact with a hub thereby permitting expansion of the retraction biasing member axially in the proximal direction; and retracting the needle upon retraction of the hub through a fixed connection between the needle and the hub.

In another embodiment, a method of operating an insertion mechanism according to the present disclosure includes: removing one or more lockout pins from corresponding one or more locking windows of an insertion mechanism housing, wherein removal of said lockout pins permits an insertion biasing member to expand from its initially energized state; driving, by expansion of the insertion biasing member, a manifold guide axially in the distal direction to force a needle at least partially out of the insertion mechanism and into the target; maintain the needle in an administration position for fluid delivery; transforming or displacing a travel limiter, permitting additional distal displacement of the manifold guide; permitting outwards flexion of a clip retained in a chamber of the manifold guide, wherein said clip initially retains a hub and a retraction biasing member in an energized state and wherein flexion disengages one or more release surfaces of the clip from contact with a hub thereby permitting expansion of the retraction biasing member axially in the proximal direction; and retracting the needle upon retraction of the hub through a fixed connection between the needle and the hub.

Certain optional standard components or variations of the insertion mechanism or drug pump 10 are contemplated while remaining within the breadth and scope of the present disclosure. For example, upper or lower housings may optionally contain one or more transparent or translucent windows 18, as shown in FIGS. 1A-1C, to enable the user to view the operation of the drug pump 10 or verify that drug dose has completed. Additionally, the drug pump 10 may contain an adhesive patch 1726 and a patch liner 1728 on the bottom surface of the housing 12. The adhesive patch 1726 may be utilized to adhere the drug pump 10 to the target for delivery of the drug dose. As would be readily understood by one having ordinary skill in the art, the adhesive patch 1726 may have an adhesive surface for adhesion of the drug pump to the target. The adhesive surface of the adhesive patch 1726 may initially be covered by a non-adhesive patch liner 1728, which is removed from the adhesive patch 1726 prior to placement of the drug pump 10 in contact with the target. Adhesive patch 1726 may optionally include a protective shroud that prevents actuation of the optional sensor 24 and covers the base opening of the insertion mechanism. Removal of the patch liner 1728 may remove the protective shroud or the protective shroud may be removed separately. Removal of the patch liner 1728 may further remove the sealing membrane of the insertion mechanism, opening the insertion mechanism to the target for drug delivery.

Similarly, one or more of the components of the insertion mechanism and drug pump 10 may be modified while remaining functionally within the breadth and scope of the present disclosure. For example, as described above, while the housing of drug pump 10 is shown as two separate components upper housing 12A and lower housing 12B, these components may be a single unified component. Similarly, while guide protrusions 172204 are shown as a unified pre-formed component of insertion mechanism housing 172202, it may be a separate component fixedly attached to the interior surface of the insertion mechanism housing 17202. As discussed above, a glue, adhesive, or other known materials or methods may be utilized to affix one or more components of the insertion mechanism and/or drug pump to each other. Alternatively, one or more components of the insertion mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the insertion mechanisms and drug pumps disclosed herein provide an efficient and easily-operated system for automated drug delivery from a drug container. The novel embodiments described herein provide integrated safety features; enable direct user activation of the insertion mechanism; and are configured to maintain the sterility of the fluid pathway. As described above, the integrated safety features include optional sensors, redundant lock-outs, automated needle insertion and retraction upon user activation, and numerous user feedback options, including visual and auditory feedback options. The novel insertion mechanisms of the present disclosure may be directly activated by the user. For example, in at least one embodiment the lockout pin(s) which maintain the insertion mechanism in its locked, energized state are directly displaced from the corresponding lockout windows of the insertion mechanism housing by user depression of the activation mechanism. Alternatively, one or more additional components may be included, such as a spring mechanism, which displaces the lockout pin(s) upon direct displacement of the activation mechanism by the user without any intervening steps.

Furthermore, the novel configurations of the insertion mechanism and drug pumps of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present disclosure, the power and control system, the assembly platform, the control arm, the activation mechanism, the housing, and other components of the drug pump do not need to be sterilized. This greatly improves the manufacturability of the device and reduces associated assembly costs. Accordingly, the devices of the present disclosure do not require terminal sterilization upon completion of assembly. A further benefit of the present disclosure is that the components described herein are designed to be modular such that, for example, housing and other components of the pump drug may readily be configured to accept and operate insertion mechanism 17200, insertion mechanism 172000, or a number of other variations of the insertion mechanism described herein.

Assembly and/or manufacturing of the insertion mechanism, drug pump 10, or any of the individual components may utilize a number of known materials and methodologies in the art. For example, a number of known cleaning fluids such as isopropyl alcohol may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

The insertion mechanism may be assembled in a number of methodologies. In one method, a hub is initially connected to a proximal end of a needle. The hub and needle are inserted into an inner chamber of a clip retainer, wherein a retraction biasing member is maintained in an energized state between the clip retainer and the hub. The hub, needle, and retraction biasing member are held in this alignment by a clip, wherein the clip is fixedly and flexibly connected to the clip retainer at a clip interface. One or more septa are inserted into the manifold to create a manifold header. The manifold and septum are inserted into a lower chamber of the manifold guide such that the needle pierces through the septum. A sterile boot is connected to the manifold, wherein the needle resides within the sterile boot when the latter is in an expanded configuration.

An insertion spring is inserted into the insertion mechanism housing between the housing and one or more guide protrusions extending into the interior of the housing from the housing cap. The manifold guide and clip retainer, having the components attached thereto as described herein, is inserted into the insertion mechanism housing such that the guide protrusions extend through corresponding pass-throughs on a clip retainer flange and manifold guide ring aspect of the manifold guide. As the clip retainer and manifold guide is translated in the proximal direction, the insertion biasing member is caused to contact the manifold guide ring and become energized. As translation of the clip retainer and manifold guide and compression of the insertion biasing member reach a point above one or more lockout windows of the insertion mechanism housing, one or more corresponding lockout pin(s) may be inserted to retain the manifold guide in this position and the insertion biasing member in the compressed, energized state. A travel limiter may further be inserted into the housing such that the prongs of the travel limiter engage the aperture of the housing.

The distal end of the sterile boot may be positioned and held in fixed engagement with the distal end of the insertion mechanism housing by engagement of the housing with a base. In this position, the sterile boot is in an expanded configuration around the needle and creates an annular volume which may be sterile. A fluid conduit may be connected to the manifold at a manifold intake such that the fluid pathway, when open, travels directly from the fluid conduit, through the manifold intake, into the manifold header, and through the needle. A fluid pathway connection may be attached to the opposite end of the fluid conduit. The fluid pathway connection, and specifically a sterile sleeve of the fluid pathway connection, may be connected to a cap and pierceable seal of the drug container. The plunger seal and drive mechanism may be connected to the drug container at an end opposing the fluid pathway connection. A sealing membrane may be attached to the bottom of the base to close off the insertion mechanism from the environment. The components which constitute the pathway for fluid flow are now assembled. These components may be sterilized, by a number of known methods, and then mounted either fixedly or removably to an assembly platform or housing of the drug pump.

Manufacturing of a drug pump includes the step of attaching the base of the insertion mechanism to an assembly platform or housing of the drug pump. In at least one embodiment, the attachment is such that the base of the insertion mechanism is permitted to pass through the assembly platform and/or housing to come in direct contact with the target. The method of manufacturing further includes attachment of the fluid pathway connection, drug container, and drive mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the target during operation of the device.

A method of operating the drug pump includes the steps of: activating, by a user, the activation mechanism; displacing a control arm to actuate an insertion mechanism; and actuating a power and control system to activate a drive control mechanism to drive fluid drug flow through the drug pump. The method may further include the step of: engaging an optional sensor prior to activating the activation mechanism. The method similarly may include the step of: establishing a connection between a fluid pathway connection to a drug container. Furthermore, the method of operation may include translating a plunger seal within the drive control mechanism and drug container to force fluid drug flow through the drug container, the fluid pathway connection, a sterile fluid conduit, and the insertion mechanism for delivery of the fluid drug to the target. The method of operation of the insertion mechanism and the drug pump may be better appreciated with reference to FIGS. 108-110 and FIG. 115, as described above.

In at least one embodiment, the present disclosure provides an insertion mechanism for a drug pump, said insertion mechanism including: an insertion mechanism housing having an internal chamber; a manifold guide having an upper chamber and a lower chamber separated by a manifold guide ring; one or more insertion biasing members initially held in an energized state within the internal chamber of insertion mechanism housing between the housing cap and the manifold guide ring; a clip flexibly engaged with the upper chamber of the manifold guide; a retraction biasing member and a hub connected to a proximal end of a needle, wherein the retraction biasing member is held initially in an energized state between the hub and the manifold guide; and a manifold having one or more septa, wherein the annular space between the septa defines a manifold header.

In at least one embodiment, the insertion mechanism may include two or more insertion biasing members. The manifold has a manifold intake for connection to a fluid conduit. The insertion mechanism further includes a travel limiter, engaged with the housing, at least a portion of which is located within the housing internal chamber.

In another embodiment, the present disclosure provides an insertion mechanism for a drug pump, said insertion mechanism including: an insertion mechanism housing having an internal chamber; a housing cap engaged with the housing; a clip retainer including an internal chamber and a flange; a manifold guide having an internal chamber and a manifold guide ring; one or more insertion biasing members initially held in an energized state within the internal chamber of the insertion mechanism housing between the housing cap and the clip retainer flange; a clip flexibly engaged with the internal chamber of the clip retainer; a retraction biasing member and a hub connected to a proximal end of a needle, wherein the retraction biasing member is held initially in an energized state between the hub and the clip retainer; and a manifold having one or more septa, wherein the annular space between the septa defines a manifold header. In an alternative embodiment, the insertion mechanism may include two or more insertion biasing members. The manifold has a manifold intake for connection to a fluid conduit. The insertion mechanism further includes a travel limiter, engaged with the housing, at least a portion of which is located within the housing internal chamber.

The insertion mechanism may further include a base connected to a distal end of the insertion mechanism housing. A sterile boot may be fixedly connected between the manifold and the base connected to a distal end of the insertion mechanism housing. The term “sterile boot” is used to describe a boot within which certain internal components may reside, at one or more stages of operation, in a sterile condition. The boot need not be sterile through the entire operation of the mechanism or pump and, in fact, may not be initially sterile until assembly and sterilization of certain components has occurred. Additionally, the term “boot” is not intended to mean any specific shape or configuration, but is instead utilized to describe a component that can provide an interior space within which other components may reside at one or more stages of operation.

One or more guide protrusions may extend from a proximal end of the insertion mechanism housing or housing cap into the internal chamber. Alternatively, the one or more guide protrusions may be a separate component that is fixed to the insertion mechanism housing. The manifold guide ring and/or clip retainer flange has one or more pass-throughs which correspond with the guide protrusions, wherein the manifold guide and/or the clip retainer is slidably engaged with the housing by interaction between the pass-throughs and the guide protrusions. The interaction between the pass-throughs and the guide protrusions may also function to maintain the rotational alignment of the manifold guide and/or to promote proper assembly of the components.

The clip may have one or more arms, with each arm having a release surface and a lockout surface. In an initial locked configuration the release surfaces engage the hub to maintain the retraction biasing member in an energized state; and, in a retracted configuration the release surfaces disengage the hub to permit de-energizing of the retraction biasing member, thereby retracting the hub and the needle. The manifold and manifold guide and clip retainer are maintained in their final positions and prevented from axial translation in the proximal direction by interaction between the lockout surfaces of the clips and the distal ends of the guide protrusions, effectively locking out further motion of these components. In some embodiments, the clip is caused or allowed to transform from the locked configuration to the retracted configuration by transformation of the travel limiter from a first configuration to a second configuration. In the first configuration, the travel limiter restricts distal movement of the manifold guide and prevents the release surfaces of the clip from disengaging from the hub. In the second configuration, the travel limiter allows some additional distal movement of the manifold guide which allows the release surfaces of the clip to disengage the hub. In other embodiments, the clip retainer is rotated from a first position to a second configuration; this rotation is transmitted to the clip. In the first configuration, the release surfaces of the clip are prevented from disengaging the hub. In the second configuration, the release surfaces of the clip are not prevented from disengaging the hub.

In another embodiment, the present disclosure provides a drug delivery pump with integrated safety features including a housing and an assembly platform, upon which an activation mechanism, a drive mechanism, a fluid pathway connection, a power control system, and an insertion mechanism for a drug pump may be mounted, said insertion mechanism including: an insertion mechanism housing having an internal chamber; a manifold guide having an upper chamber and a lower chamber separated by a manifold guide ring; one or more insertion biasing members initially held in an energized state within the internal chamber of insertion mechanism housing between the housing cap and the manifold guide ring; a clip flexibly engaged with the upper chamber of the manifold guide; a retraction biasing member and a hub connected to a proximal end of a needle, wherein the retraction biasing member is held initially in an energized state between the hub and the manifold guide; a manifold having one or more septa, wherein the annular space between the septa defines a manifold header; a travel limiter engaged with insertion mechanism housing and a base for connection of the insertion mechanism to the assembly platform.

In another embodiment, the present disclosure provides a drug delivery pump with integrated safety features including a housing and an assembly platform, upon which an activation mechanism, a drive mechanism, a fluid pathway connection, a power control system, and an insertion mechanism for a drug pump may be mounted, said insertion mechanism including: an insertion mechanism housing having an internal chamber; a housing cap attached to the housing; a clip retainer having an internal chamber and a flange; a manifold guide having an internal chamber and a manifold guide ring; one or more insertion biasing members initially held in an energized state within the internal chamber of the insertion mechanism housing between the housing cap and the manifold guide ring; a clip flexibly engaged with the internal chamber of the clip retainer; a retraction biasing member and a hub connected to a proximal end of a needle, wherein the retraction biasing member is held initially in an energized state between the hub and the clip retainer; a manifold having one or more septa, wherein the annular space between the septa defines a manifold header; a travel limiter engaged with the insertion mechanism housing; and a base for connection of the insertion mechanism to the assembly platform.

The insertion mechanism of the drug pump may further include a base connected to a distal end of the insertion mechanism housing. The manifold may have a manifold intake for connection to a fluid conduit, wherein the fluid conduit is employable for fluid transfer between the fluid pathway connection and the insertion mechanism. A sterile boot may be fixedly connected between the manifold and the base connected to a distal end of the insertion mechanism housing. These components function to maintain the sterility of the fluid pathway and the needle, prior to insertion into the target.

In a further embodiment, the present disclosure provides a method of assembling the insertion mechanism including the steps of: connecting a hub to a proximal end of a needle; inserting the hub and needle into an inner upper chamber of a manifold guide, wherein a retraction biasing member is maintained in an energized state between the manifold guide and the hub, and maintained in the energized state by a clip fixedly and flexibly connected to the manifold guide at a clip interface. The method further includes: inserting one or more septa into the manifold to create a manifold header there-between, and subsequently inserting the manifold and septa into a lower chamber of the manifold guide such that the needle pierces through at least one septum and resides initially at least partially within the manifold header. Furthermore, the method includes: inserting an insertion biasing member into an insertion mechanism housing between the housing and one or more guide protrusions extending into the interior of the housing from a proximal end or from a housing cap; inserting the manifold guide into the insertion mechanism housing such that the guide protrusions extend through corresponding pass-throughs on a manifold guide ring aspect of the manifold guide, wherein as the manifold guide is translated in the proximal direction, the insertion biasing member is caused to contact the manifold guide ring and become energized.

In an alternative embodiment, the present disclosure provides a method of assembling the insertion mechanism includes the steps of: connecting a hub to a proximal end of a needle; inserting the hub and needle into an internal chamber of a clip retainer, wherein a retraction biasing member is maintained in an energized state between the clip retainer and the hub, and maintained in the energized state by a clip fixedly and flexibly connected to the clip retainer at a clip interface. The method further includes: inserting one or more septa into the manifold to create a manifold header there-between, and subsequently inserting the manifold and septa into an internal chamber of a manifold guide such that the needle pierces through at least one septum and resides initially at least partially within the manifold header. Furthermore, the method includes: inserting an insertion biasing member into an insertion mechanism housing between the housing and one or more guide protrusions extending into the interior of the housing from a proximal end or from a housing cap; inserting the clip retainer and manifold guide into the insertion mechanism housing such that the guide protrusions extend through corresponding pass-throughs on a flange of the clip retainer and manifold guide ring aspect of a manifold guide, wherein as the clip retainer and manifold guide are translated in the proximal direction, the insertion biasing member is caused to contact the clip retainer flange and become energized.

Upon translation of the manifold guide and/or clip retainer and compression of the insertion biasing member to a point above one or more lockout windows of the insertion mechanism housing, the method includes the step of: placing one or more corresponding lockout pin(s) into the lockout windows and in removable engagement with the manifold guide to retain the manifold guide in this position and the insertion biasing member in the energized state. Finally, a base may be attached to the distal end of the insertion mechanism housing to maintain the components in position. The method of assembly may further include the step of: attaching a sterile boot in fixed engagement at a proximal end to the manifold and in a fixed engagement at a distal end to the base. Similarly, the method may include: attaching a fluid conduit to the manifold at a manifold intake. The method of assembly may further include the step of: attaching a travel limiter to the housing such that at least a portion of the travel limiter is located internal to the housing.

In yet another embodiment, the present disclosure provides a method of operating the drug delivery pump. The method of operation includes: displacing an activation mechanism to disengage one or more lockout pins from corresponding lockout windows of an insertion mechanism housing, wherein such disengagement permits an insertion biasing member to expand in a distal direction substantially along a longitudinal axis of the insertion mechanism housing from its initial energized state, wherein such expansion drives insertion of a needle into the target; connecting a fluid pathway connection having a piercing member to a drug container having a pierceable seal; and activating a drive mechanism to force a fluid through the fluid pathway connection, the needle, and into the target. The method further includes: disengaging one or more release surfaces of a clip from engagement with a hub retained within a manifold guide or clip retainer within the insertion mechanism housing, wherein such disengagement permits a retraction biasing member to expand in a proximal direction substantially along a longitudinal axis of the insertion mechanism housing from its initial energized state, wherein such expansion drives retraction of the needle. In a preferred embodiment, the method of operation may include: first displacing one or more sensors to permit displacement of the activation mechanism. The method may include one or more additional steps to activate the retraction of the needle. These steps may be performed by the user such as, for example, displacing a second activation member or may be automatically performed by the drug pump upon completion of dose delivery, failure or fault of the drive mechanism, or removal of the drug pump from the target.

XVIII. Additional Embodiments of Fluid Pathway Connector

At least some of the drug delivery devices described in this application, including at least those described in connection with FIGS. 1-47, 74, 75, and 77-117, may be configured to incorporate the embodiments of the fluid pathway connector described below in connection with FIGS. 118-127D. The embodiments of the fluid pathway connected described below in connection with FIGS. 118-127D may be used to replace, in its entirety or partially, the above-described fluid pathway connector 300, fluid pathway connector 622, fluid pathway connector 722, fluid pathway connector 922, fluid pathway connector 1122, fluid pathway connector 2300, or any other fluid pathway connector described herein, where appropriate.

As discussed above, in the processes of filling drug containers and other drug delivery devices, it is sometimes necessary to connect two or more sterile components or subassemblies. For example, wearable injectors or drug pumps may include a drug container which may be filled with a fluid drug using standard aseptic pharmaceutical fill-finish processes. After filling of the drug container, it may be necessary to connect the drug container to one or more additional components or subassemblies such that a fluid communication may be established between the drug container and these components. Maintaining the fluid path in an aseptic condition is critical, preventing the introduction of harmful microbes to the drug and/or fluid pathway. The connection of two or more aseptic components or subassemblies is typically performed in an aseptic environment, thereby ensuring that no harmful foreign matter is introduced to the assembly. This, however, may lead to increased cost to manufacture the drug delivery devices. The fluid pathway connections of the present disclosure may be assembled to the drug container in a non-aseptic environment while maintaining the aseptic condition of the fluid path and drug fluid.

As shown in the embodiment of FIGS. 118-120, the drug container 1850 may consist of barrel 1858, cap 1852, and pierceable seal 1856. Base 1856A of pierceable seal 1856 may be in sealing engagement with the inside of barrel 1858. Cap 1852 may be fixedly engaged to the outside of barrel 1858 and may retain pierceable seal 1856 in position and restrict movement of pierceable seal 1856 with respect to barrel 1858. Cap 1852 may include one or more locking arms 1852A which extend from ring 1852B of cap 1852 substantially parallel to axis A-A and in a distal direction. The locking arms 1852A may include a radially extending protrusion 1852C at or near their distal ends. The drug container may further include toroidal seal 1857. In an initial configuration, shown in FIG. 118, the toroidal seal is retained between protrusions 1852B and proximal circumferential rib 1856B of pierceable seal 1856. Pierceable seal 1856 may further include distal circumferential rib 1856C which further retains toroidal seal 1857. By placing the toroidal seal in this position when the drug container is in an aseptic environment the portion of pierceable seal 1856 in contact with the inner face of toroidal seal 1857 (i.e., the area between the proximal circumferential rib and the distal circumferential rib) is maintained in an aseptic condition even if the drug container is moved to a septic environment.

The fluid pathway connection 18300 includes connection hub 18310, retainer 18320, piercing member 18330, and plug seal 18330. As shown in FIG. 120A, plug seal 18330 is initially disposed within bore 18310A of connection hub 18310. When the fluid pathway connection is assembled, the plug seal maintains the aseptic condition of at least a portion of the fluid pathway connection by maintaining a sealing engagement with bore 18310A. The retainer is disposed for sliding translation with respect to connection hub 18310 in a direction parallel to axis B-B (shown in FIG. 120D). Initially, translation of retainer 18320 may be restricted. The restriction may be by engagement of flex arms 18320B with recesses in connection hub 18310. Piercing member 18330 may be fixedly engaged with retainer 18320 such that translation of retainer 18320 is transferred to the piercing member. The piercing member may be bonded, press-fit, or engaged to the retainer using other appropriate means. The piercing member may initially be at least partially disposed within cavity 18310D and/or aperture 18310C of connection hub 18310. Both cavities 18310D and 18310C are maintained in an aseptic condition by plug seal 18340. Retainer 18320 may further include conduit connection 18320A to which the sterile fluid conduit 30 (see FIG. 1B) may be attached. This provides a sterile fluid path from the sterile fluid pathway connection to the insertion mechanism. Piercing member 18330 may be a hollow needle such that fluids may pass through the hollow interior of the piercing member and into the sterile fluid conduit.

FIGS. 120A-D show the steps of connecting the fluid pathway connection to the drug container. This connection may be performed in a non-aseptic environment. In FIG. 120A, the plug seal of the fluid pathway connection is substantially aligned with axis A-A (i.e., the plug seal 18340 is aligned with the distal end of the pierceable seal 56). FIG. 120B shows a cross-section view of the fluid pathway connection 18300 in contact with the drug container. Recesses 18310B of connection hub 18310 are aligned with locking arms 1852A, this alignment guides the installation of the fluid pathway connection and prevents rotation of the fluid pathway connection with respect to the drug container. As shown in FIG. 120C, as the connection hub is translated in the proximal direction along axis A-A the plug seal 18340 is prevented from translating with the connection hub due to contact with pierceable seal 1856. This causes the plug seal to be displaced from its position within bore 18310A. Additionally, contact of shoulder 18310E of connection hub 18310 with toroidal seal 1857 causes the toroidal seal to translate in the proximal direction along axis A-A. As the connection hub is translated along axis A-A only bore 18310A comes in contact with the portion of the pierceable seal which was previously covered by toroidal seal 1857. Further, as the connection hub comes into contact with the toroidal seal these components sealingly engage such that microbes and other foreign substances may not come in contact with the sterile portions of the pierceable seal and fluid pathway connection. In this way the aseptic condition of the pierceable seal 1856, aperture 18310C, cavity 18310D, and piercing member 18330 are maintained during installation of the fluid pathway connection.

As seen in FIG. 120D, further proximal translation of the connection hub brings the connection hub into contact with a portion of drug container 1850, thus preventing further distal translation of the connection hub. In the embodiment shown, the connection hub contacts a portion of cap 1852. When the connection hub reaches this position, the plug seal may be removed from the assembly and discarded. Snap arms 1852A may engage one or more aspects of the connection hub and thereby prevent the connection hub from being removed from the drug container.

After installation, the piercing member is aligned with the sterile portion of the pierceable seal which was originally engaged with the toroidal seal. The components may be assembled into the drug delivery device 10 (see FIGS. 1A-1C) and remain in this configuration until activation of the drug pump by the user. Upon activation, the retainer 18320 is translated in a direction parallel to axis B-B with respect to the connection hub, causing translation of piercing member 18330. Due to this translation, the piercing member comes in contact with and, subsequently, pierces the pierceable seal 1856. This opens a fluid pathway from the drug container and through the piercing member. The fluid pathway may further include sterile fluid conduit 30 (see FIG. 1B) which is engaged with conduit connection 18320A of retainer 18320. In this way a sterile fluid path is provided from the drug container to the insertion mechanism for delivery to the patient.

FIGS. 121A-121B show another embodiment of the present disclosure in which connection hub 181310 includes snap arms 181310F which may engage cap 181052 of drug container 181050. Toroidal seal 181057 is initially retained between proximal circumferential rib 181056B and distal circumferential rib 181056C of pierceable seal 181056 and is caused to translate in the proximal direction by contact with the connection hub. After mounting of the fluid pathway connection to the drug container, opening of the fluid pathway is substantially similar as that described above.

FIG. 122 shows a detail view of the plug seal disposed within the bore of the connection hub. This shows a possible method of retaining the plug seal in position using tabs 181310G. These tabs control the location of the plug seal in the inner bore.

FIGS. 123-125 show additional embodiments of the disclosure illustrating alternative configurations of the cap and pierceable seal.

In the embodiment shown in FIG. 126, bore 182310A is enclosed on its distal face by distal film 182350 and on its proximal face by proximal film 182352. The proximal and distal films may be constructed from any material with barrier properties sufficient to prevent the passage of foreign matter. For example, the films may be constructed from a foil material. The films may be bonded or otherwise securely affixed to the connection hub. In this way, bore 182310A is maintained in an aseptic condition.

As the fluid pathway connection is brought into contact with the drug container, a portion of the drug container pierces, tears, or otherwise removes a portion of proximal film 182352 from the connection hub. For example, as shown in FIG. 126, a portion of the cap 182052 contacts the proximal film during installation and disengages a portion thereof from the connection hub. The disengaged portion of proximal seal 182352 may be retained within void 182055 formed by cap 182052 and pierceable seal 182056, thereby preventing the septic portion of proximal film 182352 from contacting the aseptic portion of pierceable seal 182056.

Also shown in FIG. 126, seal 182057 may be configured to maintain the aseptic condition of only a portion of the circumference of pierceable seal 182056. This portion may be configured to be aligned with aperture 182310C and piercing member 182330 after installation of fluid pathway connection 182300. During installation, seal 182057 is displaced by the connection hub as described in reference to other embodiments. Seal 182057 may be retained in position with respect to the pierceable seal by engagement of the seal with slot 182052D of cap 182052, proximal circumferential rib 182056B, and distal circumferential rib 182056C. During displacement, the seal may translate within slot 182052D in the proximal direction.

FIGS. 127A-127D show another embodiment of a fluid pathway connection in which the fluid pathway connection includes first rotating disk 183360 and drug container 183050 includes second rotating disk 183051. First rotating disk 183360 may be configured for rotation with respect to connection hub 183310 about a central axis and further include first opening 183360A. As shown in FIG. 127A, the first rotating disk may also include post 183360B and receptacle 183360C. Second rotating disk 183051 may include complementary features to allow for alignment of the first opening 183360A with the second opening 183051A. Second rotating disk 183051 may be configured for rotation with respect to the drug container and have second opening 183051A. One or both of the openings may initially be covered by a film such that the film prevents foreign materials from entering the openings.

As seen in FIG. 127C, during installation the first and second rotating disks are brought into contact such that the first and second openings are aligned. The rotating disks may be joined through the use of an adhesive or, alternatively, may be held in contact by features such as the snap arms described previously in relation to other embodiments. Once connected, the disks may be rotated such that they align with chimney 183053 and third opening 183310F in connection hub 183310. Chimney 183053 may be biased for axial movement in the distal direction, such as by a spring or other biasing member capable of storing energy. As shown in FIG. 127D, upon alignment with the first and second opening, the chimney translates in the distal direction, passing through both the first and second opening. The chimney may have a pass-through which allows contents to flow from the drug container. In this way, a sterile fluid path is created between the drug container and the fluid pathway connection. The fluid pathway connection may further include a piercing member which is configured to, upon activation by a user, pass through the chimney and pierce a pierceable seal of the drug container. After the pierceable seal is pierced, drug fluid may pass through the piercing member and be delivered to the patient. The piercing member may be engaged with retainer 183320. The retainer may also be configured for connection of sterile fluid conduit 30 (see FIG. 1B) at conduit connection 183320A. The translation of the piercing member may be caused by translation of the retainer.

In at least one embodiment, the present disclosure provides a user-initiated fluid pathway connection. The fluid pathway connection includes: a connection hub, a piercing member, a piercing member retainer, and a drug container having a cap, a pierceable seal, and a barrel, wherein the piercing member is at least partially disposed in a sterile chamber defined by the connection hub. The fluid pathway connection is configured such that it may be connected to the drug container while maintaining the aseptic condition of a fluid pathway. The drug container may contain a drug fluid for delivery. The fluid pathway connection may further be in fluid communication with a conduit that provides a fluid pathway for delivery of the fluid drug to the patient. Upon initiation by the user, the fluid drug is delivered through the fluid pathway to the body of the user. The pierceable seal includes a seal barrier that may be penetrated, upon user initiation, by the piercing member.

In another embodiment, the present disclosure provides a drug delivery pump with integrated sterility maintenance features having a housing and an assembly platform, upon which an activation mechanism, a fluid pathway connection, a power and control system, and a drive mechanism having a drug container may be mounted, said fluid pathway connection including a connection hub, a piercing member, a piercing member retainer, and a drug container having a cap, a pierceable seal, and a barrel, wherein the piercing member is at least partially disposed in a sterile chamber defined by the connection hub. The fluid pathway connection is configured such that it may be connected to the drug container while maintaining the aseptic condition of a fluid pathway. The drug container may contain a drug fluid for delivery. The fluid pathway connection may further be in fluid communication with a conduit that provides a fluid pathway for delivery of the fluid drug to the patient. Upon initiation by the user, the fluid drug is delivered through the fluid pathway connection to the body of the user. The pierceable seal includes a seal barrier that may be penetrated, upon user initiation, by the piercing member.

XIX. Additional Embodiments Relating to Skin Attachment

At least some of the drug delivery devices described in this application, including at least those described in connection with FIGS. 1-127D, may be configured to incorporate the embodiments of the adhesive described below in connection with FIGS. 128A-129D.

The present embodiments disclose adhesives which have bond strengths which are sensitive to the presence of a stimulant. The adhesive may be used to adhere the drug delivery device to the skin of a patient. The introduction of a stimulus may cause the bond strength of the adhesive to decrease such that the device may be more easily removed from the patient's skin as well as possibly reducing the pain or discomfort to the patient due to the removal. The stimulus may be chosen from any of the group of stimuli that is capable of decreasing the strength of the bond including: light, such as a UV light, heat, and electricity. The stimulant source may be integrated into the medical device or, alternatively, may be independent from the medical device. Methods of use and assembly are also described.

As seen in FIGS. 128A-128C, the drug delivery device 19010 may include a body 19001, stimulant source 19002, first adhesive patch 19003, and second adhesive patch 19004. Body 19001 may encompass or enclose stimulant source 2 or, alternatively, stimulant source 19002 may be located on the outside of body 19001. The stimulant source has an inactive state and an active state. In the inactive state the stimulant source does not produce and/or emit a stimulus. In the active state, the stimulant source does produce and emit a stimulus. The bond strength of first adhesive 19003 may be such that it does not decrease in response to activation of stimulant source 19002. The first adhesive may retain the second adhesive in connection with the medical device. The bond strength of second adhesive 19004 may initially have a first bond strength in the absence of a stimulant and a second bond strength in the presence of a stimulant. The device 190010 may, optionally, include a removable adhesive cover which protects and isolates the adhesive during shipment and prior to application of the medical device to the patient.

Prior to initiation of delivery of the medicament, the patient or a medical practitioner may remove the adhesive cover, if equipped. The medical device may then be secured to the patient using the adhesive. The first bond strength of the second adhesive may be such that it securely attaches the device to the patient's skin, preventing unintentional removal. After delivery of the medicament or, at any other desired time, stimulant source 19002 may be activated. The activation may occur automatically at completion of medicament delivery or may occur in response to an input by the patient. For example, the device may include a stimulant activation mechanism such as a button, switch, or any other mechanism known to one skilled in the art. Activation of the stimulant source causes the bond strength of at least a portion of second adhesive patch 19004 to decrease to the second bond strength. In at least one embodiment, the bond strength of the outer perimeter of the second adhesive may be decreased to the second bond strength, thereby allowing the user to easily engage the edge of the adhesive and thereby remove or peel off the remainder of the adhesive from the patient's skin. In these embodiments, a stimulant source may be arranged around the outer profile of the device, the position of the stimulant source and the intensity of the stimulant controlling the portion of the second adhesive which is affected. In other embodiments, the bond strength of substantially all of the second adhesive is decreased, thereby allowing easy removal of the device from the patient's skin. The bond strength of the second adhesive does not need to be decreased uniformly in response to activation of the stimulant source. In other words, the bond strength of some portion of the second adhesive may be decreased to a greater extent than other portions. The cohesive properties of the adhesive may be completely eliminated or, alternatively, may retain some bonding strength. For example, the bond strength of the adhesive, in the presence of the activated stimulant may be sufficient to maintain its adhesion to the patient's skin until a removal operation is performed by the patient.

The stimulant may be a UV light source and be an integral aspect of the device as seen in FIGS. 128A-128C. The UV light source may be located on the bottom portion of the device such that it is in proximity to the adhesive patch. The UV light source may be in electronic communication with one or more other aspects of the device such that activation of the UV light source may be performed and/or controlled by a PCB or other type of electronic controller. Activation, by the electronic controller, may occur in response to completion of the delivery of a medicament to the patient. The activation may also be triggered by an input by the user, such as by depression of a button.

In other embodiments, shown in FIGS. 129A-129D, the stimulant source 190015 is an external stimulant source (i.e., not physically connected to the medical device). In these embodiments, the stimulant source may be supplied, with the drug delivery device 19020, to the user or may be supplied separately. The external stimulant source may be used multiple times and for multiple devices. To facilitate application of the stimulant to the adhesive, one or more aspects of the body of the device may be at least partially translucent, thereby allowing a stimulant such as a UV light to pass through. In at least one embodiment, the medical device may have a removable portion 190011. The removal of this portion of the medical device may expose a translucent portion 190012. Translucent portion 190012 may be a thin portion of the device thereby allowing the stimulant source to come into close proximity with the adhesive. A first adhesive 190013 may be bonded to translucent portion 190012. The bond strength of the first adhesive may not be affected by the presence of the stimulant. A second adhesive 190014 may be applied, the bond strength of which is altered by the presence of a stimulant as described previously. The external stimulus may be in the form of a handheld UV light source such that the user may direct the light source toward the adhesive.

In another aspect of the invention, the secondary adhesive may be re-useable. Removal of the stimulant may allow the adhesive to return to its first bond strength. After returning to the first bond strength the device may be re-applied to the patient's skin. This may be useful in applications of re-usable medical devices.

In applications in which the bond strength of the adhesive is affected by light, the adhesive may be configured such that it responds only to light of certain wavelengths. This may allow filters to be applied that prevent an inadvertent decrease in bond strength.

The bond strength of the adhesive may be immediately decreased in the presence of the stimulant. Alternatively, it may be necessary that the adhesive be exposed to the stimulus for a prolonged period of time in order to decrease the bond strength. The time may be as short as a few seconds to as long as a few minutes.

In other embodiments, a method of use is provided. The method of use may include the steps of: applying a medical device to a patient's skin using an adhesive; initiating operation of the medical device; activating a stimulant source to decrease the bond strength of at least a portion of the adhesive; and removal of the medical device from the patient. The stimulant source may be integral to the medical device or may be independent from the device. The method may optionally also include the step of removing an adhesive patch cover. The method may also include removal of one or more portions of the medical device from one or more other portions of the medical device.

In still other embodiments, a method of assembly is provided. The method of assembly may include the steps of: applying a first adhesive to a portion of the medical device; applying a second adhesive at least partially to the second adhesive. The method of assembly may further include assembling a stimulant source into the medical device.

XX. Additional Embodiments of Fluid Pathway Connector

At least some of the drug delivery devices described in this application, including at least those described in connection with FIGS. 1-56, 74-129, may be configured to incorporate the embodiments of the fluid pathway connector described below in connection with FIGS. 130-136B. The embodiments of the fluid pathway connected described below in connection with FIGS. 130-136B may be used to replace, in its entirety or partially, the above-described fluid pathway connector 300, fluid pathway connector 622, fluid pathway connector 722, fluid pathway connector 922, fluid pathway connector 1122, fluid pathway connector 2300, or any other fluid pathway connector described herein, where appropriate.

In general, the present embodiments relate to fluid restriction mechanisms that control the rate of drug delivery by providing resistance and/or increasing the length of the fluid delivery pathway from the drug container to the needle insertion mechanism, for drug delivery into the patient. Additionally, the fluid restriction mechanisms of the present disclosure may be readily replaceable, configurable, and/or stackable to provide a range of fluid pathways and to meet a myriad of drug delivery needs. For example, the manufacturer, drug-filler, assembler, or another member of the production process may select and insert the necessary fluid restriction mechanism to meet the desired drug delivery profile. This selection and insertion may be performed by initial placement or replacement of the fluid restriction mechanism. Additionally or alternatively, this may be performed by adjusting the fluid restriction mechanism, such as by rotation of a configurable fluid restriction mechanism having a plurality of fluid pathway channels or a single pathway with passages that may be opened or closed to modify the fluid pathway prior to assembly. Additionally or alternatively, the fluid delivery profile may be met by utilizing a multitude of fluid restriction mechanisms, at least in part, in a series configuration or in a parallel configuration. Each of these variations of the fluid restriction mechanism may be utilized to meet the desired fluid delivery profile from the drug delivery device.

Furthermore, the fluid restriction mechanisms of the present embodiments may include permeable membranes to permit venting of gaseous fluids from the fluid pathway. The pump type drug delivery systems which include such fluid pathway systems and fluid restriction mechanisms are capable of being primed to reduce or eliminate gaseous fluids from the fluid pathway system prior to introduction of a liquid fluid to a patient. When delivering fluid subcutaneously it is important to minimize or eliminate the amount of gaseous fluid that is delivered into the patient. Delivery of gaseous fluids, such as air or inert gases, is correlated to increased perception of pain for patients and may adversely affect absorption profiles of pharmaceutical treatments. As such, it is important to minimize or eliminate such gaseous fluids from the system prior to injection of the drug. The fluid restriction mechanisms are also easily configurable to permit the manufacture of one type of mechanism (e.g., plate, chip, etc.) while enabling customization of the fluid restriction mechanism prior to or during assembly to enable a range of fluid restriction parameters.

As described in more detail below, a single restriction mechanism may have a number of selectable fluid pathways or channels with different restriction parameters. Based on the desired fluid flow characteristics, the manufacturer or assembler can select the appropriate fluid pathway and assemble the components such that the desired fluid pathway is utilized. Similarly, the fluid pathways may be opened or closed by the assembler/manufacturer to enable longer or shorter fluid pathways, as may be desired to meet the particular flow characteristics. While these are important and desirable features of drug delivery devices, such features should not be cumbersome or complicated for the user. The present disclosure provides a system which enables the configurability of the fluid restriction mechanisms and also the reduction or elimination of gaseous fluids from the fluid pathway, but yet is easy to use for clinicians and patients.

When delivering fluid subcutaneously it is important to control or restrict the flow of fluid that is delivered into the patient. A drug delivery device, such as an infusion pump or a bolus injector, may be needed to deliver a particular amount of drug fluid within a period of time. The flow of drug fluid, however, may need to be restricted as it passes through the system from a drug container to the needle insertion mechanism and into the patient. Some drug delivery device systems may utilize one or more an active fluid restriction mechanisms, one or more passive fluid restriction mechanisms, or a combination of both. The present disclosure provides configurable fluid restriction mechanisms (e.g., plates, chips, etc.) for microfluidic pathways which can be readily integrated into a pump type delivery device within the fluid pathway between the drug container and the needle insertion mechanism.

The pump type delivery devices may be connected in fluid flow communication to a patient or user, for example, through any suitable hollow tubing. The hollow tubing may be connected to a hollow needle that is designed to pierce the skin of the patient and to deliver a fluidic medium therethrough. Alternatively, the hollow tubing may be connected directly to the patient as through a cannula, or the like. As a further option, a solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, microneedle array, or infusion set tubing. The flow of fluid may be initiated by a number of different drive mechanisms which push a plunger seal within a drug container, thereby forcing a drug fluid out of the drug container. In at least one embodiment, the drive mechanism may be a spring-based drive mechanism that utilizes one or more springs to drive or push the plunger seal. The activation of the drive mechanism and the pushing of the plunger seal may occur before or after a fluid connection is completed, or itself may first cause a fluid connection to be made before forcing fluid through the fluid connection. Once the fluid flow is initiated, the fluid restriction mechanisms of the present disclosure may be utilized to control the duration of fluid flow through the drug delivery device. The fluid restriction mechanism may be located between the drug container and the fluid conduit leading to the insertion mechanism, or at one or more locations within the fluid pathway from drug container to patient through the insertion mechanism.

In a first embodiment, the present disclosure provides a selectively replaceable fluid restriction mechanism for a drug delivery device. The fluid restriction mechanism includes an aperture residing adjacent to a fluid pathway connection and configured to permit flow of a drug fluid through the aperture when the fluid pathway connection is open; an entry point of a fluid channel configured such that the flow of drug fluid can travel through aperture to the entry point and through the fluid channel to an exit point; and an outlet aperture of a port through which the flow of drug fluid may travel after exiting the exit point, wherein a fluid conduit is connected to the fluid restriction mechanism at the outlet aperture. The selectively replaceable fluid restriction mechanism may further include a vent aperture to vent air or gas from a proximal side of the fluid restriction mechanism to a distal side of the fluid restriction mechanism; and a membrane to facilitate the passage of air or gas in one direction while preventing fluid passage therethrough. The membrane may be a permeable membrane.

In another embodiment, the present disclosure provides a configurable fluid restriction mechanism for a drug delivery device which includes an aperture residing adjacent to a fluid pathway connection and configured to permit flow of a drug fluid through the aperture when the fluid pathway connection is open; an entry point configured such that the flow of drug fluid can travel through aperture to the entry point; a plurality of fluid channels, selectable to align with the entry point and an exit point of the fluid restriction mechanism; and an outlet aperture of a port through which the flow of drug fluid may travel after exiting the exit point, wherein a fluid conduit is connected to the fluid restriction mechanism at the outlet aperture. The configurable fluid restriction mechanism may include a vent aperture to vent air or gas from a proximal side of the fluid restriction mechanism to a distal side of the fluid restriction mechanism; and a membrane to facilitate the passage of air or gas in one direction while preventing fluid passage therethrough. The plurality of fluid channels may vary in length to provide different durations of travel for the flow of drug fluid, and/or the plurality of fluid channels may vary in diameter to provide different fluid restrictions to the flow of drug fluid.

In at least one embodiment, a plurality of the configurable fluid restriction mechanisms may be connected in series in a stacked configuration, and wherein the aperture of the first fluid restriction mechanism resides adjacent to a fluid pathway connection and configured to permit flow of a drug fluid through the aperture when the fluid pathway connection is open, and the fluid conduit is connected to the outlet aperture of the last fluid restriction mechanism in the stacked configuration. In another embodiment, the one or more fluid channels may be selectively opened to permit the flow of drug fluid, and/or selectively closed to prevent the flow of drug fluid. In at least one embodiment, one or more fluid channels may be connected to each other to increase the duration of travel that the drug fluid must flow through. The fluid restriction mechanisms may be in the shape of a disc, a spheroid, a square, a sphere, a cube, a rectangle, or a pyramid.

In yet another embodiment, the present disclosure provides a drug delivery device with fluid delivery control which includes a housing, within which an activation mechanism, an insertion mechanism, a drug container having a plunger seal may be mounted, and one or more of the fluid restriction mechanisms described above, wherein the drug container is connected at one end to a drive mechanism and at another end to a fluid pathway connection, and the fluid restriction mechanism is connected at one end to the fluid pathway connection and at the other end to a fluid conduit, and the fluid conduit is connected at another end to the insertion mechanism; such that the fluid restriction mechanism is configured to restrict or control a flow of a drug fluid from the drug container to the insertion mechanism. The fluid restriction mechanism may be a component of the fluid pathway connection mounted to and integrated within the barrel of a drug container, or the fluid restriction mechanism may be a component adjacent to the fluid pathway connection and configured to restrict the flow of drug fluid from the barrel of a drug container through the drug delivery device once the fluid pathway connection is opened. Alternatively, the fluid restriction mechanism may be connected to the fluid pathway connection by a first fluid conduit, and the fluid restriction mechanism is connected to the insertion mechanism by a second fluid conduit, such that the flow of drug fluid is restricted between the drug container and the insertion mechanism by the fluid restriction mechanism.

Referring now to FIG. 130, illustrated is an embodiment of a fluid restriction mechanism 20500 implemented in the drug delivery device 10. As described above, the drug delivery device 10 may be utilized to administer delivery of a drug treatment into a body of a user. The drug delivery device 10 includes the pump housing 12. The pump housing 12 may include one or more housing subcomponents which are fixedly engageable to facilitate easier manufacturing, assembly, and operation of the drug delivery device 10. For example, the pump housing 12 may includes the upper housing 12A and the lower housing 12B. The drug delivery device 10 may further include the activation mechanism 14, the status indicator 16, and the window 18. The window 18 may be any translucent or transmissive surface through which the operation of the drug delivery device may be viewed. As shown in FIG. 130, drug delivery device 10 further includes the assembly platform 20, the sterile fluid conduit 30, the drive mechanism 100 having the drug container 50, the insertion mechanism 200, the fluid pathway connection 300, and the power and control system 400. The fluid restriction mechanism 20500 may be connected to the sterile fluid conduit 30, preferably, between the fluid pathway connection 300 and the insertion mechanism 200. One or more of the components of such drug delivery devices may be modular in that they may be, for example, pre-assembled as separate components and configured into position onto the assembly platform 20 of the drug delivery device 10 during manufacturing.

The fluid restriction mechanisms of the present disclosure may take a number of configurations while remaining within the scope of the presently claimed embodiments. The fluid restriction mechanisms provide a means for fluid delivery control, by restricting the flow of fluid travel and/or by increasing the length of the fluid pathway that the fluid must travel through between the drug container and the insertion mechanism before delivery into the patient. The fluid restriction mechanisms of the present disclosure are readily replaceable, configurable, and/or stackable to enable the drug delivery device to meet the desired drug delivery profile (e.g., delivery duration). The fluid restriction mechanism 20500 may be connected to the sterile fluid conduit 30, preferably, between the fluid pathway connection 300 and the insertion mechanism 200. For example, the fluid restriction mechanism 20500 may be connected at the beginning of the fluid conduit 30 (between the sterile fluid pathway connection 300 and the fluid conduit 30), at the end of the fluid conduit 30 (between the fluid conduit 30 and the insertion mechanism 200), or anywhere in between along the fluid conduit 30.

The fluid restriction mechanism 20500 resides within the housing of the drug delivery device, as shown in FIG. 130. FIG. 131A shows an isometric view of a fluid restriction mechanism, according to at least one embodiment of the present disclosure, attached to an integrated sterile fluid pathway connection and drug container. In such an embodiment, the fluid restriction mechanism may be a component of the integrated sterile fluid pathway connection and drug container. As shown in FIG. 131B, the fluid restriction mechanism may be attached to the sterile fluid pathway connection and drug container, such as by retention by cap 52 which may be a cap that is crimped to the barrel 58. In this configuration, the fluid restriction mechanism may include a piercing member 20510, such as a needle, that is capable of piercing a seal 56 of the sterile fluid pathway connection 300 to permit fluid flow from the drug chamber 21 of barrel 58 of the drug container 50. In this configuration, the seal 56 is caused to slide upon, and be pierced by the piercing member 510 upon hydraulic and/or pneumatic pressure of the fluid within the drug chamber 21 that is caused by a drive mechanism 100 acting upon plunger seal 60. Once the sterile fluid pathway connection 300 is opened, drug fluid may travel through piercing member 510, through the fluid channel(s) of the fluid restriction mechanism 20500, out through port 20512 through the fluid conduit 30 to the insertion mechanism 200 for drug delivery to the patient. FIG. 131C shows a side view of the fluid restriction mechanism shown in FIG. 131A. As will be detailed further herein, the fluid restriction mechanism 20500 may also include a membrane 20309, such as a partially permeable membrane, that is capable of venting air or other gas from the sterile cavity between the fluid restriction mechanism 20500 and the seal 56. In such a configuration, the fluid restriction mechanism 20500 does not need to move or translate once assembled to barrel 58 of the drug container 50 as the sterile fluid pathway connection 300 occurs integrated within the drug container 50. This configuration of the fluid restriction mechanism may be preferred for use with the integrated fluid pathway connection and drug container described in International Patent Application No. PCT/US2013/030478, which is hereby incorporated by reference in its entirety.

FIG. 132A shows an isometric view of a fluid restriction mechanism, according to another embodiment of the present disclosure. In this configuration, the fluid restriction mechanism 201500 is attached to a sterile fluid pathway connection which may or may not be integrated within the drug container. In this configuration, the seal 56 may be retained in position at the distal end of the barrel 58 by cap 52, and the sterile fluid pathway connection 300 may be external (i.e., not integrated) to the barrel 58 of the drug container 50. This configuration of the fluid restriction mechanism may be preferred for use with the fluid pathway connection and drug container described in International Patent Application No. PCT/US2012/054861, which is hereby incorporated by reference in its entirety. The fluid restriction mechanism 201500 of this embodiment may be attached to the distal end of the sterile fluid pathway connection 300 which is capable of acting upon and piercing the seal 56 retained within barrel 58 of the drug container 50. In that embodiment, the piercing member 201510 would instead be a conduit or port connected to the distal surface of the fluid pathway connection. Alternatively, a piercing member 201510 may be utilized in this embodiment to function as part of the integrated fluid pathway connection and drug container, and to pierce the seal 56 to permit drug flow from the drug container 50. FIG. 132B shows an exploded isometric view of the fluid restriction mechanism, and sterile fluid pathway connection and drug container, shown in FIG. 132A. FIG. 132C shows a side view of the fluid restriction mechanism shown in FIG. 132A.

FIG. 133A shows an exploded isometric view of the fluid restriction mechanism shown in FIGS. 131A-131C. Though the description below provides details with reference to the embodiments shown in FIGS. 131A-131C, the description with reference to the function of the fluid restriction mechanism may also provide detail to the embodiments shown in FIGS. 132A-132C. FIG. 4A shows the fluid restriction mechanism 20500 as two separate components. FIG. 133B shows another angle of the exploded isometric view of the fluid restriction mechanism shown in FIG. 133A. As would be understood by one having ordinary skill in the relevant art, this is primarily for ease of manufacture and the mechanism 20500 may be a single unified component if manufactured, for example, by injection molding or other suitable means. In this two-part assembly the fluid channel(s) may be imparted, such as by carving or other suitable means of manufacture, onto a first component 20500B of the fluid restriction mechanism and then closed by attachment of a second component 20500A. The two components may be affixed and held together by snap arms, adhesives, etc., or other mechanisms which are readily known in the industry to provide a tight seal to the fluid channel(s) of the fluid restriction mechanism. The second component (e.g., cover plate) 20500A may be fused, molded, or otherwise connected to the first component (e.g., restriction plate) 20500B. The fluid pathway of each of the fluid channels may be adjusted for pathway thickness, length, curvature, and any number of tortuous path parameters, for example, to produce a fluid restriction of any desired range. The pathway that a drug fluid may travel through the fluid restriction mechanism 20500 is shown with reference to FIG. 133C, which provides a cross-sectional view of the fluid restriction mechanism shown in FIGS. 133A-133B. Drug fluid may enter the fluid restriction mechanism 20500 through aperture 20520A of a piercing member 510. The drug fluid then enters the fluid channel(s) at entry point 20520B. The drug fluid is retained in the fluid channel(s) 20520C because of the tight seal provided by the mating of the second component 20500A to the first component 20500B.

In the embodiment shown, the fluid channel(s) are in a spiral shape to elongate the length of travel that the fluid must pass (i.e., extending the time or duration of drug delivery). The width of the channel(s) may also be modified and utilized to control the flow parameters through the fluid restriction mechanism. The drug fluid then travels through the fluid channel(s) 20520C to exit point 20520D, at which point the drug fluid is caused to travel through outlet aperture 20514 of port 20512 to the fluid conduit 30 (visible in FIGS. 131A-131C). The fluid channel(s) may be shortened or lengthened to provide the desired duration of fluid delivery time (i.e., the drug fluid may be caused to travel a longer path or a shorter path through the fluid restriction mechanism). Additionally or alternatively, the fluid channel(s) may restrict the flow of drug fluid by functioning as an orifice. As would be readily understood by an ordinarily skilled artisan in the relevant arts, fluid flow in a pipe or conduit is always accompanied by friction of fluid particles rubbing against one another, and consequently, by loss of energy available for work. In other words, there must be a pressure drop in the direction of flow. Accordingly, the fluid channel(s) of the fluid restriction mechanism may function as an orifice to meter rate of flow, by restricting flow and/or to reduce pressure. For liquid flow, several orifices are sometimes used to reduce pressure in steps so as to avoid cavitation. Concurrently, a vent aperture 20530A, 20530B may be utilized to vent the air or gas from the proximal side of the fluid restriction mechanism 20500 to the distal side of the fluid restriction mechanism 20500. A membrane 20309, such as a partially permeable membrane, may be utilized for example to facilitate the passage of gas (e.g., air) in one direction while preventing fluid passage therethrough.

FIGS. 134A-134B show a configurable fluid restriction mechanism, according to another embodiment of the present disclosure, in the exploded and front views respectively. In this embodiment, the fluid restriction mechanism 20500 contains more than one fluid channel 20520C, 20521C, 20522C, and 20523C. Accordingly, the same fluid restriction mechanism 20500 may be utilized in a number of configurations to provide the desired fluid flow parameters. If shorter drug delivery duration is desired, channel 20522C may be selected and aligned with entry point 20520B and exit point 20520D. If more restrictive fluid flow is desired, channel 20523C may be selected and aligned with entry point 20520B and exit point 20520D. Alternatively, channels 20521C or 20520C may be selected and aligned with entry point 20520B and exit point 20520D to reach the desired drug delivery parameters. This is facilitated, for example during assembly of the device, by identifying the desired drug delivery parameters and the appropriate fluid channel, and rotating and mounting the fluid chip 20550A into the corresponding recess 20550B such that the selected fluid channel aligns with entry point 20520B and exit point 20520D. This is shown in FIG. 134B.

Any number of distinct channels may be provided and utilized in this embodiment of a configurable fluid restriction mechanism. Additionally, the desired channels may be opened or closed by removing or adding, respectively, barriers between the channels. For example, if an even longer fluid channel is desired, the barriers between channels 20521C and 20520C may be modified such that the fluid flows initially into channel 20520C through entry point 20520B, then through channel 20521C, then back through the remainder of channel 20520C to exit point 20520D. In a further embodiment, the fluid restriction plate may have a number of sequential or parallel pathways which are configurable to deliver the desired fluid restriction parameters. For example, the fluid restriction plate may have a number of different pathways of different lengths and constraints, and the specifically desired fluid pathway may be selected during assembly to produce the desired fluid restriction for the drug delivery device system. One or more of these pathways may be "opened" or "closed" prior to assembly to enable a range of configurable fluid pathways. While plates are discussed and shown herein, the fluid restrictors may take on a number of different shapes and configurations including, but not limited to, spheres, discs, pucks, semi-circles, rectangles, cubes, pyramids, and the like. This configurability provides even more variation to the number of channels or fluid path configurations capable of being employed by the present disclosure. More complex shapes may be utilized which include different fluid pathway channels, and these are only restricted by economically-feasible and known manufacturing methods. For example, more complex shapes and fluid channel configurations may be possible via 3D-printing, or other complex manufacturing methods. Concurrently, a vent aperture 20530A, 20530B may be utilized to vent the air or gas from the proximal side of the fluid restriction mechanism 20500 to the distal side of the fluid restriction mechanism 20500. A membrane 20309, such as a partially permeable membrane, may be utilized for example to facilitate the passage of gas (e.g., air) in one direction while preventing fluid passage therethrough.

FIG. 135A shows an isometric view of a stackable fluid restriction mechanism, according to another embodiment of the present disclosure. FIG. 135B shows an exploded isometric view of the stackable fluid restriction mechanism. The stackable fluid restriction mechanism may utilize any of the fluid restriction arrangement described above with reference to FIG. 133A and FIG. 134A, in the configurations shown in FIGS. 131A-131C, FIGS. 132A-132C, or the other configurations described herein. Accordingly, one or more fluid restriction mechanisms may be utilized in a stacked configuration to provide an additional distance that the drug fluid must travel to prolong the duration of drug delivery. In such a stacked configuration, a spacer plate 20503B may be utilized between two restriction plates 20503A and 20500B, in order to align the fluid entry points and exit points with the corresponding or abutting plates. Any number of these plates may be utilized to reach the desired drug delivery parameters.

The fluid restriction mechanisms of the present disclosure are shown primarily in a disc-shaped configuration, though the shape is not a necessary limitation on the present disclosure and any number of known shapes may be utilized. For example, FIG. 136A shows an isometric view of a rectangular fluid restriction mechanism, according to a further embodiment of the present disclosure. FIG. 136B shows the isometric view of the fluid restriction mechanism 202500 shown in FIG. 136A, with the top component of the fluid restriction mechanism removed. As shown, the fluid restriction mechanism 202500 may take any number of shapes or dimensions, provided that there is at least one fluid channel therein having at least one entry point and at least one exit point through which the drug fluid may travel. Additionally, the fluid restriction mechanism 202500 may be connected to the sterile fluid conduit 30, preferably, between the fluid pathway connection 300 and the insertion mechanism 200. For example, the fluid restriction mechanism 202500 may be connected at the beginning of the fluid conduit 30 (between the sterile fluid pathway connection 300 and the fluid conduit 30), at the end of the fluid conduit 30 (between the fluid conduit 30 and the insertion mechanism 200), or anywhere in between along the fluid conduit 30 (as shown in FIG. 136A-136B).

Assembly and/or manufacturing of the above-described embodiments of the fluid restriction mechanism, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

A fluid pathway connection, and specifically a sterile sleeve of the fluid pathway connection, may be connected to the cap and/or pierceable seal of the drug container. The fluid restriction mechanism may be connected to the other end of the fluid pathway connection. A fluid conduit may be connected to the fluid restriction mechanism at one end and the insertion mechanism at the other end, such that the fluid pathway, when opened, connected, or otherwise enabled travels directly from the drug container, fluid pathway connection, fluid restriction mechanism, fluid conduit, insertion mechanism, and through the cannula for drug delivery into the body of a user. As described above, the fluid restriction mechanism may alternatively be located between the sterile pathway connection and the insertion mechanism such that a first fluid conduit is connected directly to the sterile pathway connection and to the fluid restriction mechanism, and then a second fluid conduit is connected to the fluid restriction mechanism and to the insertion mechanism. Regardless of the configuration, or order of components, the fluid pathway, when opened, connected, or otherwise enabled travels directly from the drug container, fluid pathway connection, fluid restriction mechanism, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 130.)

XXI. Additional Embodiments of Insertion Mechanism

At least some of the drug delivery devices described in this application, including at least those described in connection with FIGS. 1-56, 74-136B, may be configured to incorporate the embodiments of the insertion mechanism described below in connection with FIGS. 137A-139C. The embodiments of the insertion mechanism described below in connection with FIGS. 137A-139C may be used to replace, in its entirety or partially, the above-described insertion mechanism 200, the insertion mechanism 2000, the insertion mechanism 17200, the insertion mechanism 172200, or any other insertion mechanism described herein, where appropriate.

When delivering drug fluid to a user, such as by subcutaneous or intramuscular injection, it is important to minimize or eliminate the amount of gaseous fluid that is delivered into the user. Delivery of gaseous fluids, such as air or inert gases, is correlated to increased perception of pain for patients and may adversely affect absorption profiles of pharmaceutical treatments. As such, it is important to minimize or eliminate such gaseous fluids from the system prior to injection of the drug. While this is an important and desirable feature of drug delivery devices, such features should not be cumbersome or complicated for the user. The present embodiments provide a system which enables the reduction or elimination of gaseous fluids from the fluid pathway, but yet is easy to use for clinicians and patients.

More particularly, the present embodiments provide insertion mechanisms having vented fluid pathways, and pump-type drug delivery systems which includes such vented fluid pathways, which are capable of being primed to reduce or eliminate gaseous fluids from the fluid pathway system prior to introduction of a liquid fluid to a user. The present embodiments relate to vented fluid pathway systems having a membrane, such as a permeable or semi-permeable membrane, and drug delivery pumps which utilize such vented fluid pathway systems for the parenteral delivery of drug fluids. Such novel components and devices provide a mechanism to prime (e.g., the evacuation or removal of air or other gaseous fluid) the fluid pathway prior to injection and dosing of the drug treatment. The novel systems and devices of the present disclosure can be employed in a number of different configurations, and can be utilized with both pre-filled cartridges and fill-at-time-of-use primary drug containers.

In at least one embodiment, the present disclosure provides an insertion mechanism having a vented fluid pathway which includes: one or more insertion biasing members, a hub, a needle, a refraction biasing member, and a manifold having a septum, a cannula, a manifold intake, and a membrane, wherein the annular space within the manifold between the septum, the cannula, the manifold intake, and the membrane defines a manifold header, wherein the manifold is configured to vent a gaseous fluid through the membrane and fill with a liquid fluid for delivery to the user through the cannula. The manifold intake is capable of connection with a fluid conduit. The insertion mechanism may be configured to be internally mounted within a drug pump or externally tethered to a drug pump by a conduit. In at least one embodiment, the vented or ventable insertion mechanism comprises two insertion biasing members. The septum closes the upper portion of the manifold while allowing the needle to pass through it. Another opening from the manifold is at least temporarily blocked by the needle as it resides within the cannula and/or another occlusion element such as a ferrule or plug, prior to operation of the insertion mechanism. The manifold intake receives fluid flow from the fluid conduit. The only remaining opening from manifold is blocked by membrane until operation of the insertion mechanism.

The membrane may be a number of filtering membranes which are capable of permitting passage of gaseous fluids but prohibiting passage of liquid fluids. For example, the membrane may be a permeable membrane or a semi-permeable membrane. Additionally, the membrane may be or function as a sterile barrier. In at least one embodiment, the membrane is a permeable membrane selected from the group consisting of polyethylene terephthalate (PET), polytetrafluoroethylene (PTFE), one or more styrenes, and polyethylene fibers, and the combinations thereof. The membrane may be a separate component or be an integrated portion, such as part of the wall, of the manifold.

The insertion mechanism having a vented fluid pathway may further include a sensor. The sensor may be any number of sensors known to an ordinarily skilled artisan, such as those selected from the group consisting of pressure sensors, fluid sensors, optical sensors, mechanical sensors, electrical sensors, and electro-mechanical sensors, and the combinations thereof.

In another embodiment, the present disclosure provides a drug delivery pump which includes a housing and an assembly platform, upon which an activation mechanism, a drive mechanism, a fluid pathway connection, a power and control system, and an insertion mechanism having a vented fluid pathway may be mounted. The insertion mechanism having vented fluid pathway may be as described above. In a preferred embodiment, the drug pump utilizes a vented or ventable insertion mechanism having a vented fluid pathway which includes: one or more insertion biasing members, a hub, a needle, a refraction biasing member, and a manifold having a septum, a cannula, a manifold intake, and a membrane, wherein the annular space within the manifold between the septum, the cannula, the manifold intake, and the membrane defines a manifold header, wherein the manifold is configured to vent a gaseous fluid through the membrane and fill with a liquid fluid for delivery to the user through the cannula. The manifold intake is capable of connection with a fluid conduit. The insertion mechanism may be configured to be internally mounted within a drug pump or externally tethered to a drug pump by a conduit. In at least one embodiment, the vented or ventable insertion mechanism comprises two insertion biasing members.

In yet another embodiment of the present disclosure, a method of operating the insertion mechanism having a vented fluid pathway includes the steps of: (i.) initially maintaining a needle in a first position wherein fluid passage from a manifold header of a manifold through the cannula is blocked; (ii.) activating the flow of liquid drug fluid from a drug container through a fluid conduit to the manifold header of the manifold; (iii.) venting a gaseous fluid through a membrane within the manifold while prohibiting passage of the liquid drug fluid through the membrane; (iv.) activating an insertion biasing member to translate the needle and the cannula from the first position to a second position within a body of a user; and (v.) activating a retraction biasing member to translate the needle from the second position to a third position, wherein the third position permits passage of the liquid drug fluid from the manifold header of the manifold through the cannula and into the body of the user. In at least one embodiment, the step of activating an insertion biasing member to translate the needle and the cannula from the first position to a second position occurs after the step of venting a gaseous fluid through a membrane within the manifold. In another embodiment, the step of activating an insertion biasing member to translate the needle and the cannula from the first position to a second position may occur before the step of venting a gaseous fluid through a membrane within the manifold such that venting through the membrane is permitted only once the needle is in the second position. In such an embodiment, the step of activating an insertion biasing member to translate the needle and the cannula from the first position to a second position may cause the removal of a covering element from the membrane outside of the manifold to permit venting of any gaseous fluid from the fluid pathway. The covering element may be, for example, a cover, sheath, or sleeve. In either embodiment, however, the passage of the liquid drug fluid is permitted to occur only after the venting step and upon translation of the needle from the second position to a third position, wherein the third position permits passage of the liquid drug fluid from the manifold header of the manifold through the cannula and into the body of the user. In yet another embodiment, the method further includes, prior to the step of activating a retraction biasing member to translate the needle from the second position to a third position, the step of: measuring by a sensor the substantial completion of venting the gaseous fluid through the membrane.

Turning to the figures, the pump-type drug delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a single spring insertion mechanism (as shown in FIG. 7A) or a dual spring insertion mechanism (as shown in FIG. 7B) may be employed to provide sufficient force to cause the needle and cannula to pierce the skin of the patient. The same spring, an additional spring, or another similar mechanism may be utilized to retract the needle from the patient. In at least one embodiment, the insertion mechanism may generally be as described in International Patent Application No. PCT/US2012/53174, which is hereby incorporated by reference herein in its entirety. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure.

In a first embodiment, the present disclosure provides a fluid pathway system that allows a tube, conduit, or other fluid channel to be evacuated of air (or another gaseous fluid) prior to operation. In one such embodiment, the ventable fluid pathway system is integrated into an insertion mechanism 200. The insertion mechanism includes an insertion mechanism housing 202 having one or more lockout windows 202A, a base 252, and a sterile boot 250, as shown in FIG. 8A. Base 252 may be connected to assembly platform 20 to integrate the insertion mechanism into the drug delivery pump 10 (as shown in FIG. 1B). The connection of the base 252 to the assembly platform 20 may be, for example, such that the bottom of the base is permitted to pass-through a hole in the assembly platform to permit direct contact of the base to the body of the user. In such configurations, the bottom of the base 252 may include a sealing membrane 254 that, at least in one embodiment, is removable prior to use of the drug delivery pump 10. Alternatively, the sealing membrane 254 may remain attached to the bottom of the base 252 such that the needle 214 pierces the sealing membrane 254 during operation of the drug delivery pump 10. As shown in FIGS. 8A and 8B, the insertion mechanism 200 may further include an insertion biasing member 210, a hub 212, a needle 214, a retraction biasing member 216, a clip 218, a manifold guide 220, a septum 230, a cannula 234, and a manifold 240. The manifold 240 may connect to fluid conduit 30 to permit fluid flow through the manifold 240, cannula 234, and into the body of the user during drug delivery, as described below in more detail.

The manifold guide 220 may include an upper chamber 222 and a lower chamber 226 separated by a manifold guide ring 228. The upper chamber 222 may have an inner upper chamber 222A, within which the retraction biasing member 216, the clip 218, and the hub 212 may reside during an initial locked stage of operation, and an outer upper chamber 222B, which interfaces with the insertion biasing member 210. In at least one embodiment, the insertion biasing member 210 and the refraction biasing member 216 are springs, preferably compression springs. The hub 212 may be engageably connected to a proximal end of needle 214, such that displacement or axial translation of the hub 212 causes related motion of the needle 214. FIGS. 137A and 137B show isometric views of the fluid conduit 30 connected to the manifold 240 at the manifold intake 240A. FIGS. 137A and 137B show an embodiment of the present disclosure in which the membrane 21233 is located in a portion of the manifold 240 substantially opposite the manifold intake 240A; however, the membrane could be located in any number of positions within the manifold 240. Septum 230 closes the top portion of the manifold 240 from the environment and/or the inside of the pump housing, while permitting a pass-through for the needle or trocar.

As used herein, "needle" is intended to refer to a variety of needles including but not limited to conventional hollow needles, such as a rigid hollow steel needles, and solid core needles more commonly referred to as a "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. Upon assembly, the proximal end of needle 214 is maintained in fixed contact with hub 212, while the remainder of needle 214 is permitted to pass-through retraction biasing member 216, an aperture of clip 218, and manifold guide 220. The needle 214 may further pass-through septum 230, cannula 234, manifold 240 through manifold header 242, sterile boot 250, and base 252 through base opening 252A. Septum 230, cannula 234, and manifold 240 may reside within lower chamber 226 of manifold guide 220 and within sterile boot 250 until operation of the insertion mechanism. In this position, the cannula 234 may reside over a distal portion of the needle 214 and held in place within the manifold header 242 of manifold 240 by a ferrule 232. Ferrule 232 ensures that cannula 234 remains substantially fixed and in sealed engagement within the manifold 240 to, for example, maintain the sterility of the manifold header 242 until operation of the device. As described above, the ferrule 232 may also function as a restriction or occlusion element to restrict, at least partially, the flow of liquid fluid from the manifold 240 through the cannula 234. Similarly, septum 230 resides substantially fixed and in sealed engagement within the upper portion of the manifold 240 to maintain the sterility of the manifold header 242. These aspects and components may be more clearly visible in the cross-sectional view shown in FIG. 138A.

As would be appreciated by one having ordinary skill in the art, the restriction of fluid flow from the manifold header to the user through the cannula may be adjusted to reach the desired fluid flow characteristics. In at least one embodiment, the fluid flow is substantially entirely prevented until it is desirable and permitted by the removal of the restriction.

In other embodiments, however, the restriction (e.g., the needle, the plug, or other occlusion element that prevents or reduces fluid flow) does not entirely prevent fluid flow but instead may be used to reduce or meter the fluid flow through the cannula. This may be desirable, for example, when the fluid flow is initially low volume and then increased at a later time as operation of the device progresses. Similarly, one or more restrictions or occlusion elements may be utilized separately or concurrently. For example, as described further herein, the ferrule may be utilized to restrict fluid flow from the manifold through the cannula to the user.

Similar to the insertion mechanism 200 described in connection with FIGS. 7A and 8A-8B, the insertion mechanism 21200 of 138A-138F may have a vented fluid pathway and may utilize a single insertion biasing member 210. In an alternative embodiment of the insertion mechanism 2121200 having a vented fluid pathway, as shown in FIG. 7B, the insertion mechanism 21200 may include two insertion biasing members 210 A, B. Insertion mechanism 21200 further includes insertion mechanism housing 202 (shown in transparent view), manifold guide 220, sterile boot 250, base 252, and other components similar to those described above with reference to insertion mechanism 21200. In the two insertion biasing members embodiment of the insertion mechanism shown in FIG. 7B, manifold guide ring includes two circular platforms upon which insertion biasing member 2210 A, B may bear. Insertion mechanism 21200 may function identically to insertion mechanism 21200, but may provide additional insertion force and/or facilitate different packaging configurations through the use of multiple insertion biasing members 210 A, B. The components and functions of the insertion mechanisms will be described further herein with the understanding that similar or identical components may be utilized for insertion mechanism 21200, insertion mechanism 22200, and all reasonably understood variations thereof. Regardless of the single or multiple insertion biasing member configuration, the insertion mechanisms of the present disclosure incorporate a vented fluid pathway capable of permitting priming (e.g., evacuation or expulsion of the gaseous fluid) of the drug container, the fluid conduit, and manifold prior to delivery of the drug fluid to the patient. This is enabled, at least in part, by the location of the membrane 21233 in the manifold 240 and the function of the insertion mechanism 21200 during the insertion and refraction stages of operation.

The operation of the insertion mechanism having a vented fluid pathway is described herein with reference to the above components, in view of FIGS. 138A-138F. FIG. 138A shows a cross-sectional view of the insertion mechanism 21200 having a vented fluid pathway, according to at least one embodiment of the present disclosure, in a locked and ready to use stage. In this initial configuration, insertion biasing member 210 and retraction biasing member 216 are each retained in their compressed, energized states. As shown, the needle 214 may pass through an aperture of clip 218 and manifold guide 220 into septum 230 and manifold 240. Septum 230 resides within manifold 240. Manifold 240 further includes a manifold intake 240A at which the fluid conduit 30 may be connected. This connection is such that the sterility is maintained from the drug container 50 of the drive mechanism 100, through the fluid pathway connection 300 and the fluid conduit 30, into sterile manifold header 242 of manifold 240 and sterile boot 250 to maintain the sterility of the needle 214, cannula 234, and the fluid pathway until insertion into the user for drug delivery. The fluid conduit 30 connects the fluid path from the drug container 50 (visible in FIG. 1B) to the insertion mechanism 21200 at manifold intake 240A and into manifold header 242. As described earlier, septum 230 closes the upper portion of the manifold 240 while allowing the needle 214 to pass through it. Another opening from the manifold 240 is at least temporarily blocked by the needle 214 as it resides within the cannula 234, and/or by another occlusion element such as the ferrule 232, prior to operation of the insertion mechanism 21200. The only remaining opening from manifold 240 is blocked by membrane 21233. As would be readily understood by an ordinarily skilled artisan, membrane 21233 may be any number of permeable or semi-permeable membranes which are capable of permitting passage of gaseous fluids while prohibiting passage through the membrane 21233 of liquid fluids. In at least one embodiment of the present disclosure, this is accomplished by utilizing a permeable membrane, such as a hydrophobic permeable membrane, that is permeable to a gaseous fluid but not a liquid fluid, such as the liquid drug treatment. In at least one embodiment of the present disclosure, it may be beneficial to utilize a permeable membrane that is also a sterile barrier. For example, the membrane 21233 may be a polymeric filter made of polyethylene terephthalate (PET) or polytetrafluoroethylene (PTFE), a number of types of styrene, and/or a high-density polyethylene fiber (such as that sold under the trade name TYVEK by DuPont), among many other types of suitable medical-grade gas filtering membranes. Accordingly, because the desired fluid pathway from the manifold 240 to the user through the cannula 234 is blocked by the needle 214, the only available pathway for any gaseous fluid is through the membrane 21233.

As shown in FIG. 138B, as the drug pump is activated and liquid drug fluid (shown as a hatched area) is permitted to pass through the fluid conduit 30, any gaseous fluid in the fluid pathway is caused to enter into the manifold header 242 of the manifold 240. As the pressure of the liquid drug fluid continues to build in the fluid conduit 30, it pushes the gaseous fluid out of the manifold header 242 through the membrane 21233 (shown as solid arrows). As stated above, this is possible because the fluid pathway to the user through the cannula 234 remains blocked by the needle 214. FIG. 138C shows a cross-sectional view of an insertion mechanism having a vented fluid pathway as liquid drug fluid fills the manifold and gaseous fluid is substantially fully pushed through the permeable membrane (as shown by the hatched area nearly reaching the membrane 21233 and filling the entire manifold header 242). Through the stages of operation of the insertion mechanism having a vented fluid pathway shown in FIGS. 138A-138C, the needle 214 remains at substantially a first position, e.g., a blocking position, within the insertion mechanism 21200. In this first position, the needle 214 blocks the fluid pathway through the cannula 234 to the user. As the drug container, fluid conduit 30, and manifold header 242 are vented of gaseous fluid, such as air or inert gas, the needle insertion mechanism may be unlocked and activated to move the needle 214 to a second position, e.g., an inserted position. FIG. 138D shows a cross-sectional view of an insertion mechanism having a vented fluid pathway, according to a first embodiment of the present disclosure, in an unlocked and inserted stage with the needle 214 in the second position. In this second position, the needle 214 and cannula 234 are inserted (in the direction of the solid arrow in FIG. 138D) into the body of the user.

The timing of the activation of the insertion mechanism 21200 to move the needle 214 from the first position to the second position may be coordinated by a timing mechanism controlled by, for example, the power and control system or by a mechanical delay directly from user activation of the drug pump. Additionally or alternatively, a number of sensors may be utilized to identify when the gaseous fluid has been substantially entirely expelled from the fluid pathway and the fluid pathway is primed for delivery of liquid drug fluid to the user. For example, pressure sensors may be utilized to monitor back-pressure (e.g., pressure build-up) in the fluid pathway resulting from the liquid fluid substantially filling the manifold header 242 and expulsion of any gaseous fluid from the drug container, fluid conduit 30, and manifold 240. Similarly, the rate of fluid flow may be actively controlled or passively controlled. For example, in at least one embodiment of the present disclosure, tubing or other fluid conduits with a controlled diameter or geometry, orifice, or other limiting mechanism may be utilized to control the rate of flow. Such mechanisms may provide means for passive control of the rate of delivery. The orifice or tubing can be used to passively modulate flow when coupled with an induced pressure in the primary drug container, i.e., the pressure exerted by the pump mechanism on the liquid fluid as it is forced out of the primary drug container. In some embodiments, the device may be configured to actively control the flow of delivery by an electrical means, a mechanical means, or a combination of both. For example, one or more solenoids may be utilized to actively control the flow of delivery by closing and/or opening the fluid pathway.

Additionally or alternatively, one or more timing mechanisms may be utilized which are directly coupled to the drive mechanism which subsequently brake or meter the delivery rate or total time to deliver a volume of liquid fluid from the primary drug container. It is to be understood that the mechanisms, methods, and devices of the present disclosure may be used control the total time of drug delivery, the static rate of delivery during the entire time of delivery, a dynamic rate of delivery during any interval period of the entire time of delivery, or any combination of the above. For example, the device may be configured to provide drug delivery which, start to finish, completes in a specified amount of time, for example 5 minutes. This could be configured to be irrespective of the rate of delivery, such that: (a) the rate of delivery may be initially high and then later low; (b) a constant rate during the entire time of delivery; or (c) constant rates that vary at different intervals within the entire time of delivery; (d) or any combination of these delivery methodologies. The insertion of the blocking needle and activation of the liquid fluid (e.g., drug treatment) flow may similarly be controlled to ensure there is enough time for the system to vent (i.e., prime the fluid pathway) prior to introduction of the liquid fluid to the user. After substantially all of the gaseous fluid has been expelled from the drug container, fluid conduit, and manifold, and the insertion mechanism has moved the needle from the first position to the second position, the fluid pathway is ready to permit delivery of the drug fluid to the user.

FIG. 138D shows a cross-sectional view of an insertion mechanism in the second, e.g., needle inserted, position. As shown, sterile boot 250 is permitted to collapse as the insertion biasing member 210 expands and inserts the needle 214 and cannula 234 into the body of the user. At this stage, needle 214 is introduced into the body of the user to place the cannula 234 into position for drug delivery. As shown in FIG. 138E, upon needle 214 and cannula 234 insertion by operation of the insertion biasing member 210 as described above, the needle 214 is retracted back (i.e., axially translated in the proximal direction) into the housing of the insertion mechanism 21200. Manifold guide 220 and clip 218 (shown in FIGS. 8A and 8B), and guide protrusions 204, are dimensioned such that, as the manifold 240 substantially bottoms-out on base 252, i.e., reaches its full axial translation in the distal direction, the clip 218 escapes the guide protrusions 204 and is permitted to flex outwards to disengage from hub 212. Upon such disengagement, retraction biasing member 216 is permitted to expand axially in the proximal direction (i.e., in the direction of solid arrow in FIG. 138E) from its initial compressed, energized state. A suitable lockout mechanism prevents axial translation in the proximal direction of the manifold guide 220 and insertion mechanism components that are distal to (i.e., below) the manifold guide ring 228. Expansion of the retraction biasing member 216 translates hub 212, and needle 214 to which it is connected, axially in the proximal direction from the second position to a third position, i.e., a needle retracted position. Ferrule 232 retains cannula 234 inserted within the body of the user through base opening 252A. Upon retraction of the needle 214 from cannula 234, the fluid pathway from manifold header 242 to the body of the user through the cannula 234 is opened and fluid may begin to pass-through the cannula 234, as shown in FIG. 138E. As the fluid pathway connection to the user is completed, the fluid drug treatment is forced from the drug container through the fluid pathway connection and the sterile fluid conduit into the manifold header 242 and through the cannula 234 for delivery into the body of the user. Accordingly, activation of the insertion mechanism inserts the needle 214 and cannula 234 into the body of the user from a first position to a second position, and sequentially retracts the needle 214 from the second position to a third position, i.e., the retracted position, while maintaining the cannula 234 in fluid communication with the body of the user. FIG. 138F shows a cross-sectional view of an insertion mechanism having a vented fluid pathway in the third retracted position for drug delivery. As shown, the needle 214 does not need to be fully retracted from septum 230, though this may be desirable and permissible in other embodiments of the present disclosure, so long as the fluid pathway through the cannula 234 to the body of the user is opened. At the end of the drug dose delivery, the cannula 234 may be removed from the body of the user by removal of the drug pump from contact with the user.

In another embodiment of the present disclosure, the fluid pathway may be blocked by a plug, stopper, cork, or other removable occlusion element. For example, during the venting stage a removable plug or stopper may be utilized to block the portion of the fluid pathway that is in connection with the user. The plug, stopper, or other similar occlusion element is retracted or removed from the pathway after venting has substantially completed, enabling the liquid fluid to be delivered into the user. This may be desirable in configurations which use, for example, a rigid needle in fluid connection with the patient. For example, in at least one embodiment of the present disclosure, a rigid hollow needle may be utilized in place of the solid core trocar needle described above. In such an embodiment, the needle and, optionally, a cannula are inserted from a first position to a second position into the user. The needle and optional cannula are then retained within the body of the user. Instead of retracting the needle, the needle remains in the second position and a plug, stopper, or other similar occlusion element is removed or retracted from the needle to a third position, after the venting stage, to open the fluid pathway for drug delivery to the user.

A method of operating an insertion mechanism having a vented fluid pathway according to the present disclosure includes: initially maintaining a needle in a first position within a cannula and thereby blocking fluid passage from a manifold header of a manifold through the cannula; activating the flow of liquid drug fluid from a drug container through a fluid conduit to the manifold header of the manifold; venting a gaseous fluid through a membrane within the manifold while prohibiting passage of the liquid drug fluid through the membrane; activating an insertion biasing member to translate the needle and the cannula from the first position to a second position within a body of a user; and activating a retraction biasing member to translate the needle from the second position to a third position, wherein the third position permits passage of the liquid drug fluid from the manifold header of the manifold through the cannula and into the body of the user. In at least one embodiment of the present disclosure, the step of activating an insertion biasing member to translate the needle and the cannula from the first position to a second position occurs after the step of venting a gaseous fluid through a membrane within the manifold. In an alternative embodiment, however, the step of activating an insertion biasing member to translate the needle and the cannula from the first position to a second position may occur before the step of venting a gaseous fluid through a membrane within the manifold such that venting through the membrane is permitted only once the needle is in the second position. Such an embodiment of a needle insertion mechanism 22200 is shown in FIGS. 139A-139C. In this embodiment, the fluid pressure in the fluid conduit may build and force any gaseous fluid in the fluid pathway into the manifold for venting through the membrane, as shown in FIG. 139A. Once the fluid pathway has been suitably pressurized in this way, the insertion biasing member may be triggered to translate the needle and the cannula from the first position to a second position, thereby opening, uncovering, or otherwise unblocking the membrane to evacuate the gaseous fluid from the manifold. This is visible in FIG. 139B. A blocking or covering element 22263 such as a sleeve, cover, sheath, or other similar component may be utilized outside of the manifold adjacent the membrane to initially cover or block the membrane in the first position and to uncover or unblock the membrane in the second position to permit venting, as shown in FIG. 139C. In either embodiment, however, passage of the liquid drug fluid is permitted to occur only after the venting step and upon translation of the needle from the second position to a third position, wherein the third position permits passage of the liquid drug fluid from the manifold the manifold header of the manifold through the cannula and into the body of the user. The method may further include, prior to the step of activating a retraction biasing member to translate the needle from the second position to a third position, the step of: measuring by a sensor the substantial completion of venting the gaseous fluid through the membrane.

Certain optional standard components or variations of insertion mechanism 21200 or drug delivery device 10 are contemplated while remaining within the breadth and scope of the present disclosure. For example, upper or lower housings may optionally contain one or more transparent or translucent windows 18, as shown in FIGS. 1A-1C, to enable the user to view the operation of the drug delivery device 10 or verify that drug dose has completed. Additionally, the drug delivery device 10 may contain an adhesive patch 26 and a patch liner 28 on the bottom surface of the housing 12. The adhesive patch 26 may be utilized to adhere the drug delivery device 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug delivery device 10 in contact with the body of the user. Adhesive patch 26 may optionally include a protective shroud that prevents actuation of the optional on-body sensor 24 and covers base opening 252A. Removal of the patch liner 28 may remove the protective shroud or the protective shroud may be removed separately. Removal of the patch liner 28 may further remove the sealing membrane 254 of the insertion mechanism 21200, opening the insertion mechanism to the body of the user for drug delivery.

Similarly, certain components of the present disclosure may be unified components or separate components while remaining within the breadth and scope of the described embodiments. For example, the membrane is shown as a component of the manifold of the insertion mechanism. The membrane may be a separate component or may comprise a wall of the manifold, as would readily be appreciated by one having ordinary skill in the art. In an alternative embodiment, the membrane may be located at the distal end of the fluid conduit or be a distal portion of the fluid conduit itself. The vent location enabled by the membrane determines the degree to which the system may be primed, however. To reduce dead volume within the fluid pathway and reduce the gaseous fluid that may be delivered to the user, it may be desirable to have the membrane as close as possible to the end of the fluid pathway. Accordingly, the membrane is preferably an integrated aspect of the manifold of the needle insertion mechanism. Such standard components and functional variations would be appreciated by one having ordinary skill in the art and are, accordingly, within the breadth and scope of the present disclosure.)

XXII. Additional Embodiments of Fluid Pathway Connector

At least some of the drug delivery devices described in this application, including at least those described in connection with FIGS. 1-139C, may be configured to incorporate the embodiments of the fluid pathway connector described below in connection with FIGS. 140A-155. The embodiments of the fluid pathway connector described below in connection with FIGS. 140A-155 may be used to replace, in its entirety or partially, the above-described fluid pathway connector 300, fluid pathway connector 622, fluid pathway connector 722, fluid pathway connector 922, fluid pathway connector 1122, fluid pathway connector 2300, or any other fluid pathway connector described herein, where appropriate.

In general, the present embodiments provide for container connections that maintain the sterility of a fluid pathway and are integrated into a fluid container; drug delivery devices that incorporate such sterile fluid pathway connectors to fluid containers; methods of operating such devices; and methods of assembling such devices. The fluid pathway connectors of the present embodiments provide integrated safety features that ensure the sterility of the fluid pathway before, during, and after fluid delivery. In one aspect, the fluid pathway remains disconnected from the fluid container until the device has been initiated by the operator. In another aspect, the fluid pathway maintains the sterility of a piercing member prior to connection with the fluid container within a sterile cavity prior to activation by the operator. Upon activation by the operator, at least a portion of a pierceable seal is translated, such as by pneumatic and/or hydraulic pressure or force within the fluid, towards a substantially fixed piercing member such that the pierceable seal is pierced and the fluid pathway is connected or opened to enable fluid flow through the fluid pathway for fluid delivery from the device.

A drug delivery device, such as an infusion pump or a bolus injector, may be needed to deliver a particular amount of fluid within a period of time. For example, when delivering a drug fluid subcutaneously it is important to control the flow of fluid that is delivered into the patient and to maintain the sterility of the fluid container and fluid pathway prior to activation or operation of the fluid delivery device. It may be desired that the fluid pathway connector remains disconnected, for container integrity, sterility, and other purposes, until the user has activated the device and initiated fluid flow from a container. Some drug delivery devices may utilize one or more active fluid pathway control mechanisms to prevent premature fluid pathway connector or drug delivery. Other drug delivery devices are configured such that fluid pathway connector is made upon manufacture, and fluid delivery is blocked until desired by the user. Such designs do not provide the beneficial advantages associated with maintaining container integrity and sterility of the internal components of the drug delivery device. The present embodiments provide an integrated fluid pathway connector mechanism for sterile drug delivery devices. These novel embodiments provide both a connection mechanism to open or connect a sterile fluid pathway between a fluid container and a fluid conduit, without adding unnecessary steps for the user. This is enabled by activation of the drive mechanism and translation of the plunger seal, resulting in pneumatic and/or hydraulic pressure within the fluid that forces translation of at least a portion of a pierceable seal, causing it to impact upon a substantially stationary piercing member, thus opening a sterile fluid pathway between the fluid container and the fluid conduit.

Accordingly, the embodiments of the present disclosure provide a sterile fluid pathway connector that is integrated into a fluid container and opened, connected, activated, or otherwise enabled by the operation of the device and drive mechanism. The activation of the drive mechanism and the force transferred from the drive mechanism to the plunger seal is, itself, used to open a sterile fluid pathway between the fluid container and the fluid conduit. Accordingly, container integrity and sterility of the fluid container may be maintained prior to and during operation of the device. This novel configuration also automates the sterile fluid pathway connector step, greatly reducing the complexity of the device and operational steps needed to be performed by the device or the user. The novel embodiments of the present disclosure also permit flexibility in device component configurations, and reduce the layout or overall footprint of the device because no separate sterile fluid pathway connector mechanism is needed on the cap-side of the fluid container. The present embodiment may also be implemented fully or utilized in standard production of sterile fluids, including drug fill-finish processes, including applications that require the pulling of a vacuum. Additionally, the present embodiments may also integrate a number of different status indication mechanisms into the device, including utilizing the piercing member or the plunger seal as parts of an indication mechanism that relates status of fluid transfer from the sterile fluid container to the connector. For example, when the fluid container is a drug container, such components and devices provide an end-of-dose indication coupled to the actual travel and drug delivery status of the plunger seal.

At least one embodiment provides for a sterile fluid pathway connector that includes a piercing member, a connector hub, and a pierceable seal. More specifically, at least one embodiment provides for sterile fluid connector comprising a first portion configured to connect a sterile fluid pathway and a second portion comprising a housing configured to mount a sterile fluid container; a connector hub; a pierceable seal disposed at least partially between the connector hub and the sterile fluid container and forming a sterile fluid chamber between the connector hub and the pierceable seal; and a piercing member disposed within the connector hub capable of providing a sterile fluid communication between the sterile fluid chamber and the sterile fluid pathway; wherein at least a portion of the pierceable seal is configured to transform from a non-activated state in which the pierceable seal is intact, to an activated state in which the pierceable seal is disrupted by the piercing member to create a sterile fluid communication between the sterile fluid container and the sterile fluid pathway. The housing may be further configured to recess a portion of the connector within the sterile fluid container. The connector hub may further comprise at least one port or vent. The sterile fluid pathway may also include at least one sensor configured to indicate the status of fluid transfer from the sterile fluid container to the connector. Additionally, the sterile fluid pathway connector may include one or more flow restrictors. In at least one embodiment, the connector hub may at least partially function as a fluid conduit or flow restrictor. In at least one embodiment, the fluid pathway connector further includes a filter. A number of known filters may be utilized within the embodiments of the present disclosure, which would readily be appreciated by an ordinarily skilled artisan. For example, the filter may comprise a permeable membrane, semi-permeable membrane or porous membrane, which encloses the sterile cavity from the outside environment.

The piercing member is initially retained in a substantially fixed position within a sterile cavity between the connector hub and the pierceable seal. Upon activation by the operator (e.g., a patient), at least a portion of the pierceable seal is caused to move to a second position in which the pierceable seal is penetrated by the piercing member. Force, such as pneumatic and/or hydraulic force, applied on the pierceable seal on the side opposing the sterile cavity, causes translation of at least a portion of the pierceable seal towards the piercing member. The translation of the pierceable seal causes it to impact upon the substantially stationary or fixed piercing member to open a fluid pathway through the pierceable seal. Accordingly, at least a portion of the pierceable seal is configured to move from the first position to the second position by force applied by a fluid on the pierceable seal. Penetration by the piercing member of the pierceable seal upon movement of a portion of the pierceable seal from the first position to the second position opens a fluid pathway through the pierceable seal and the piercing member to a fluid conduit.

In at least one embodiment, the pierceable seal comprises a seal barrier that can be penetrated by the piercing member. The piercing member may initially be in contact with, or adjacent to, the seal barrier.

The fluid pathway connector may further include a piercing member guide, wherein the piercing member guide is capable of engaging with or translating upon the connector hub. The piercing member guide may function to ensure that the pierceable seal, or at least a portion thereof such as a seal barrier, properly contacts the piercing member and translates thereupon to become pierced and open the fluid pathway through the pierceable seal and piercing member to a fluid conduit.

The piercing member may be configured to pass into the connector hub and connect to a fluid conduit. In another embodiment, the connector hub may connect the piercing member to the fluid conduit, and the fluid conduit may be at least partially a part of the connector hub. In at least one embodiment, the fluid conduit passes into the connector hub at a port in the connector hub.

In at least one embodiment, the sterile fluid connector includes at least one sensor configured to indicate the status of fluid transfer from the sterile fluid container to the connector. For example, the sterile fluid pathway connector may further include one or more interconnects and, optionally, one or more corresponding contacts, to transmit a signal to the user. For example, the interconnect(s) may be within or at least partially proximal to a plunger seal translatable within a fluid container such that the piercing member is capable of penetrating the plunger seal and acting as a contact(s) for the interconnect(s) to transmit a signal to the user. Additionally or alternatively, the interconnect(s) or the contact(s) is within or at least partially proximal to a plunger seal translatable within a drug container and the other is within or at least partially distal to the pierceable seal to transmit a signal to the user when the plunger seal and the pierceable seal are substantially in contact. Additionally or alternatively, the interconnect(s) and contact(s) are within the sterile cavity between the connector hub and pierceable seal such that release of pneumatic and/or hydraulic pressure at the end of fluid transfer releases interconnection to transmit or cease transmission of a signal to the user. A number of known interconnects and contacts may be utilized within the embodiments of the present disclosure, which would readily be appreciated by an ordinarily skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes.

Another embodiment provides for an integrated fluid pathway connector and drug container having a piercing member, a connector hub, and a pierceable seal integrated at least partially within a drug container having a barrel and a plunger seal. The pierceable seal is translatable upon a substantially stationary piercing member, and the pierceable seal is configured to move from a first position, where the piercing member is positioned within a sterile cavity between the connector hub and the pierceable seal, to a second position, where the pierceable seal has been penetrated by the piercing member. The fluid container contains a fluid chamber between the pierceable seal and the plunger seal to initially retain a fluid, and the pierceable seal is configured to move from the first position to the second position by a force applied by the fluid on the pierceable seal. In at least one embodiment, the pierceable seal has a seal barrier that can be penetrated by the piercing member, and the piercing member is initially in contact with, or adjacent to, the seal barrier.

The integrated fluid pathway connector may further include a piercing member guide piece attached to the connector hub or piercing member, wherein the piercing member guide slidably engages the connector hub or piercing member to permit translation of the pierceable seal, or a portion thereof, in the direction of fluid exit from the connector. Translation of the pierceable seal in the direction of the fluid container may be prevented by retention of a portion of the pierceable seal by, for example, a housing, such as a crimped cap, mounted to the fluid container barrel that retains the connector hub, piercing member, and pierceable seal in position during operation. Such a configuration may be used to permit the fluid chamber of the fluid container to be evacuated, such as by vacuum, prior to filling with a fluid without compromising the function of the sterile fluid pathway connector.

In at least one embodiment, the connector hub has a header with a conduit port, a chamber, and a vacuum port with a channel that leads into the chamber such that the sterile cavity may be evacuated through the channel. The conduit port may have a membrane or seal that permits fluid flow out of the chamber, and may be capable of being plugged. Similarly, the vacuum port may be capable of being plugged, such as by a polymeric plug. Such configurations allow, for example, the sterile cavity to be evacuated to maintain both sterility and pressure equilibrium between the sterile cavity and the opposing side of the pierceable seal, or otherwise assist in maintaining the relative positions of the components prior to or during operation of the device by the user.

In at least one embodiment, the pierceable seal, or at least a portion thereof, is translatable upon the piercing member and the pierceable seal is further configured to move from the second position, where the pierceable seal has been penetrated by the piercing member, to a third position wherein at least one sensor indicates the status of fluid transfer from the sterile fluid container to the connector. For example, in a third position, one or more interconnects and one or more corresponding contacts are permitted to transmit a signal to the user. In one such embodiment, the interconnect(s) or the contact(s) is upon an aspect of a drive mechanism and the other is within or at least partially proximal to the plunger seal to transmit a signal to the user when the plunger seal and the pierceable seal are substantially in contact. Alternatively, the interconnect(s) or the contact(s) is within or at least partially distal to the pierceable seal and the other is proximal to the connector hub to transmit a signal to the user when the plunger seal and the pierceable seal are substantially in contact. Additionally or alternatively, the interconnect(s) and contact(s) are within the sterile cavity between the connector hub and pierceable seal such that release of pneumatic and/or hydraulic pressure at end of dose releases interconnection to transmit or cease transmission of a signal to the user. A number of known interconnects and contacts may be used with the present embodiments, which would readily be appreciated by a skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes.

Yet another embodiment provides a drug delivery device with integrated sterility maintenance features comprising a housing within which an activation mechanism, an insertion mechanism, and a fluid container having a plunger seal may be mounted. The fluid container is connected at one end to a drive mechanism and at another end to a fluid pathway connector. The fluid pathway connector includes a piercing member, a connector hub, and a pierceable seal, wherein the piercing member is retained within a sterile cavity between the connector hub and the pierceable seal, and wherein the pierceable seal is configured to move from a first position to a second position in which the pierceable seal has been penetrated by the piercing member. The fluid container contains a fluid chamber between the pierceable seal and the plunger seal to initially retain a fluid, and wherein the pierceable fluid seal is configured to move from the first position to the second position by a force applied by the fluid on the pierceable seal. In at least one embodiment, the pierceable seal has a seal barrier that can be penetrated by the piercing member, and the piercing member is initially in contact with, or adjacent to, the seal barrier.

The drug delivery device may further include a piercing member guide engaged with the connector hub or piercing member, wherein the piercing member guide slidably engages the connector hub or piercing member to permit translation of the pierceable seal, or a portion thereof, in the distal direction (i.e., towards the fluid conduit from where fluid exits the connector). Translation of the pierceable seal in the proximal direction may be prevented by retention of the pierceable seal, or a portion thereof, by, for example, a housing such as a crimped cap mounted to the barrel, which housing retains the connector hub, piercing member, and pierceable seal in position during operation. Such a configuration may be used to permit the drug chamber of the drug container to be evacuated, such as by vacuum, prior to filling with a fluid without compromising the function of the sterile fluid pathway connector. In at least one embodiment, the connector hub has a header with a conduit port, a chamber, and a vacuum port with a channel that leads into the chamber such that the sterile cavity may be evacuated through the channel. The conduit port may have a filter, membrane or seal to permit or restrict fluid flow out of the chamber. Similarly, the vacuum port may be capable of being plugged, such as by a polymeric plug. Such configurations may allow, for example, the sterile cavity to be evacuated to maintain sterility, the maintenance of pressure equilibrium between the sterile cavity and the opposing side of the pierceable seal, or assist in maintaining the relative positions of the components prior to or during operation of the device by a user.

In at least one embodiment, the pierceable seal is translatable upon the piercing member or an aspect of the connector hub and is further configured to move from the second position, where the pierceable seal has been penetrated by the piercing member, to a third position where one or more interconnects and one or more corresponding contacts are permitted to transmit a signal to the user. The interconnect(s) and the corresponding contact(s) are configured such that, for example: (a) the interconnect(s) or the contact(s) is positioned upon an aspect of the drive mechanism and the other is positioned within or at least partially proximal to the plunger seal, to transmit a signal to the user when the plunger seal and the pierceable seal are substantially in contact; (b) the interconnect(s) or the contact(s) is positioned within or at least partially distal to the pierceable seal and the other is positioned proximal to the connector hub, to transmit a signal to the user when the plunger seal and the pierceable seal are substantially in contact; (c) the interconnect(s) and the contact(s) are situated within the sterile cavity between the connector hub and the pierceable seal, such after the seal is pierced, continued pressure within the drug chamber causes interconnection which transmits a signal to the user, which signal is terminated once pressure inside the drug chamber drops and interconnection is lost, i.e., at end of dose. A number of known interconnects and contacts may be utilized within the embodiments of the present disclosure, which would readily be appreciated by an ordinarily skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes.

Additionally, the fluid pathway connectors may include one or more flow restrictors. In at least one embodiment, the connector hub may at least partially function as a fluid conduit or flow restrictor. In at least one embodiment, the fluid pathway connector further includes a filter. A number of known filters can be utilized within the embodiments of the present disclosure, which would readily be appreciated by an ordinarily skilled artisan. For example the filter may be a permeable membrane, semi-permeable membrane, or porous membrane, which encloses the sterile cavity from the outside environment.

The novel devices of the present embodiments provide container fluid pathway connectors that maintain the sterility of the fluid pathway and that are integrated into the fluid container, and drug delivery devices that incorporate such integrated sterile fluid pathway connectors to fluid containers. Because the fluid path is disconnected until fluid delivery is desired by the operator, the sterility of the fluid pathway connector, the fluid container, the fluid, and the interior of the device as a whole is maintained. Furthermore, the novel configurations of the fluid pathway connectors and drug delivery devices of the present disclosure maintain the sterility of the fluid path through operation of the device. Because the path that the fluid travels within the device is entirely maintained in a sterile condition, only these components need be sterilized during the manufacturing process. Such components include the fluid container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present embodiments do not require terminal sterilization upon completion of assembly. A further benefit of the present embodiments is that the components described herein are designed to be modular such that, for example, the fluid pathway connector and other components of the device may be integrated into a housing and readily interface to function as a drug delivery device.

A further embodiment provides a method of assembly of an integrated sterile fluid pathway connector and fluid container. The sterile fluid pathway connector may first be assembled and then attached, mounted, connected, or otherwise integrated into fluid container such that at least a portion of the pierceable seal is contained within the drug container. The fluid container can then be filled with a fluid for delivery to the user and plugged with a plunger seal at an end opposite the pierceable seal. The barrel can be filled with a fluid through the open proximal end prior to insertion of the plunger seal from the proximal end of the barrel. A drive mechanism can then be attached to the proximal end of the fluid container such that a component of the drive mechanism is capable of contacting the plunger seal. An insertion mechanism can be assembled and attached to the other end of the fluid conduit. This entire sub-assembly, including drive mechanism, drug container, fluid pathway connector, fluid conduit, and insertion mechanism can be sterilized, as described above, before assembly into a drug delivery device. Certain components of this sub-assembly may be mounted to an assembly platform within the housing or directly to the interior of the housing, and other components may be mounted to a guide, channel, or other component or aspect for activation by the user. A method of manufacturing a drug delivery device includes the step of attaching both the fluid pathway connector and fluid container, either separately or as a combined component, to an assembly platform or housing of the drug delivery device. The method of manufacturing further includes attachment of the drive mechanism, fluid container, and insertion mechanism to the assembly platform or housing. The additional components of the drug delivery device, as described herein, including the power and control system, the activation mechanism, and the control arm may be attached, preformed, or pre-assembled to the assembly platform or housing. In the instance in which the fluid is a drug, and the drug delivery device is an ambulatory infusion device, an adhesive patch and patch liner may be attached to the housing surface of the drug delivery device that contacts the user during operation of the device.

A method of operating the drug delivery device includes one or more of the following steps: activating, by a user, the activation mechanism; displacing a control arm to actuate an insertion mechanism; activating a drive control mechanism to push the plunger seal, connect the sterile fluid pathway connector, and drive fluid flow through the drug delivery device; wherein the pushing of the plunger seal translates the fluid and thus causes a pierceable seal to deform in the direction of the fluid conduit and be pierced by a piercing member, to thereby open a fluid path from the fluid container to the fluid conduit. The drive control mechanism may be activated by actuating a power and control system. The method may further include the step of: engaging an optional on-body sensor prior to activating the activation mechanism. Furthermore, the method of operation may include translating a plunger seal within the drive control mechanism and fluid container to force fluid flow through the fluid container, the fluid pathway connector, the fluid conduit, and the insertion mechanism for delivery of the fluid to the desired target, e.g., to the body of a patient.

The novel devices of the present embodiments provide container connections which maintain the sterility of the fluid pathway and which are integrated into the fluid container, and drug delivery devices which incorporate such integrated sterile fluid pathway connectors to fluid containers. For example, such devices are safe and easy to use, and are aesthetically and ergonomically appealing for self-administering patients.

In at least one embodiment, the presently disclosed sterile fluid pathway connector includes a piercing member, a connector hub, and a pierceable seal; wherein at least a portion of the pierceable seal is configured to move from a first position in which the piercing member is retained within a sterile cavity between the pierceable seal and the connector hub, to a second position in which the pierceable seal has been penetrated by the piercing member. A filter may be utilized to enclose the sterile cavity from the outside environment. Such fluid pathway connectors may be integrated into a fluid container having a barrel and a plunger seal. The components of the fluid pathway connector may further be capable of transmitting a signal to the user upon completion of fluid delivery, for example, upon contact between the plunger seal and the pierceable seal. A fluid delivery pump includes such integrated fluid pathway connectors and fluid containers.

The novel embodiments presented herein provide integrated sterile fluid pathway connectors and fluid containers, and drug delivery devices that utilize such connections, configured to maintain the sterility of the fluid pathway before, during, and after operation of the device, and that enable active safety controls for the device. Integration of the fluid pathway connector into a portion of the fluid container helps ensure container integrity and sterility of the fluid pathway. Additionally, by integrating the sterile fluid pathway connector into a portion of the fluid container, the connection for fluid transfer can be controlled by the user (i.e., is user-activated) and enabled by the function of the drive mechanism. Accordingly, user-activation steps and the internal operation of the drug delivery device can be greatly simplified by the novel integrated sterile fluid pathway connectors of the present embodiments.

The novel embodiments provide container connections that maintain the sterility of the fluid pathway and are integrated into the fluid container, and drug delivery devices that incorporate such integrated sterile fluid pathway connectors to fluid containers. The present embodiments also further integrate the sterile pathway connector into the fluid container, to reduce the necessary components or to provide easier and more efficient operation of the connection and drug delivery devices. The connector, the sterile fluid pathway assembly, and the infusion pump disclosed here are not limited to medical applications, but may include any application, including industrial uses, where sterile or uncontaminated fluid delivery may be desired. When the fluid is a drug, the present embodiments provide for devices that are safe and easy to use, and are aesthetically and ergonomically appealing for self-administering patients. The embodiment described herein incorporate features which make activation, operation, and lock-out of the device simple for even untrained users. One or more of the components of the present embodiments may be modular in that they can be, for example, pre-assembled as separate components and configured into position within the housing of the drug delivery device during manufacturing.

FIG. 140A and FIG. 140B show an initial configuration of an embodiment of a sterile fluid pathway connector 23030 integrated with fluid container 23050 having fluid chamber 23021 and plunger seal 23060. In some embodiments, the fluid pathway connector 23030 and the fluid container 23050 may be substituted, partially or entirely, for the fluid pathway connector 30 and the fluid container 50 illustrated in FIG. 1B of the present application. Fluid pathway connector 23030 may be mounted, connected or otherwise attached, permanently or removably, to fluid container 23050 at an end opposite plunger seal 23060. As shown in the embodiment of FIG. 140A and FIG. 140B, fluid container 23050 has mutable fluid chamber 23021 within barrel 23058, defined by the position of pierceable seal 23056 and plunger seal 23060. The seals described herein can be made of a number of materials, but are typically made of one or more elastomers or rubbers. Fluid chamber 23021 may contain a fluid for delivery through the integrated sterile fluid pathway connector 23030. In the embodiment of FIG. 140A and FIG. 140B, the fluid pathway connector 23030 includes sterile fluid conduit 23035, piercing member 23033, connector hub 23031, and pierceable seal 23056. Fluid pathway connection 23030 includes piercing member guide 37 engaged with connector hub 23031, upon which pierceable seal 23056 may interface with piercing member 23033 of connector hub

23031 during operation. A permeable, semi-permeable, or porous membrane, such as filter 23039, may be used to allow venting of air from within the fluid pathway connector 23030 during operation of the device, such as through port or vent 23031B in connector hub 23031. Filter 23039 may be attached, mounted, bonded, over-molded, co-molded, pre-formed, or otherwise connected to enclose sterile cavity 23032 between the exterior of connector hub 23031 and pierceable seal 23056. The term "enclose" or "enclosure" is used herein to define at least a semi-permeable or porous confined area that is capable of being sterilized, evacuated by vacuum, and vented, but is not penetrable by microorganisms, contaminants, or other undesirable environmental factors. For example, filter 23039 can be over-molded at least partially within connector hub 23031 to separate the sterile cavity 23032 from the outside environment. In some embodiments, the filter is a membrane, e.g., a semi-permeable membrane, which allows the venting of air during the actuation of pierceable seal 23056, fluid pathway connection 23030, and the pump device. Filter 23039 may be sterilized by methods well-known to one having skill in the art, thus the filter can maintain a sterile barrier to prevent exposure of the piercing member 23033 to microorganisms, contaminants, or other undesirable environmental factors.

As shown in FIG. 140B, piercing member 23033 is retained within the integrated sterile fluid pathway connection 23030, at or near seal barrier 23056C of pierceable seal 23056. Piercing member 23033 may be an aspect of fluid conduit 23035 or may be a separate component from fluid conduit 23035, as would readily be appreciated by one having skill in the art. Additionally, fluid pathway connector 23030 may optionally include one or more gaskets, O-rings, or other sealing members, compressed to seal between barrel 23058, particularly at lip 23058A, connector hub 23031, and housing 23052. In at least one embodiment, sealing aspect 23056A of the pierceable seal 23056 may be configured as a seal between barrel lip 23058A, connector hub 23031, and housing 23052. Housing 23052 may be a separate component, such as a crimp cap, or may be an aspect of connector hub 23031 capable of mounting to barrel 23058. The housing or cap could also have screw threads configured to complement screw threads in a fluid container, or use other impermanent means for connecting the fluid container to the sterile fluid pathway connector. As shown in FIG. 140A and FIG. 140B, the sterile fluid pathway connector 23030 may be attached to (i.e., integrated with) fluid container 23050; which in turn can be mounted, by a number of known methods, either fixedly or removably to an assembly platform or housing of a fluid pump, such as the drug delivery device 10 as shown in FIGS. 1A-1C. The assembly platform may be a separate component from the housing, or may be a unified component of the housing such as a pre-formed mounting aspect on the interior surfaces of the housing. In such configurations, the sterility of the fluid pathway is maintained, the pathway for fluid flow is not connected until desired by the user, and user-initiated activation causes the connection of the fluid chamber and the fluid pathway connection. The fluid pathway connection may, optionally, further include one or more separate flow restrictors or one or more of piercing member 23033 and fluid conduit 23035 may additionally function as flow restrictors.

The integrated fluid connection of the present embodiments is further illustrated with reference to a drive mechanism, as shown in FIG. 141A and FIG. 141B. The embodiment comprises fluid conduit 23035, engaged with piercing member 23033 at engagement 23038, connector hub 23031 that includes vent 23031B, filter 23039 which is housed against connector hub 23031, and pierceable seal 23056, which sealing portion 23056A abuts connector hub 23031 and the end of barrel 23058, all of which are housed in cap 23052. Barrel 23058 comprises mutable fluid chamber 23021, and houses plunger seal 23060 which is slidably disposed therein and in contact with a drive mechanism (e.g., the drive mechanism 50 illustrated in FIG. 1B), which includes biasing member 23099. FIG. 141A is an exploded side view of components of an integrated sterile fluid pathway connector and fluid container according to at least one embodiment. FIG. 141B shows a sectional exploded view of the same embodiment. Sterile fluid pathway connector 23030 may be integrated at least partially within fluid container 23050 at an end opposite of plunger seal 23060. An exemplary drive mechanism 23090 is shown in these figures to clarify the orientation of these components. The components of the novel sterile fluid pathway connection 23030 may be pre-assembled (see, e.g., FIG. 143A) and subsequently attached, mounted, connected or otherwise mated, permanently or removably, with a fluid container such as fluid container 23050.

A number of drive mechanisms may be utilized to force fluid from a fluid container for delivery. In one such embodiment, the drive mechanism 23090 may be substantially similar to that described in WO 2013/023033467 (PCT/US2012/023052303241). The components of the drive mechanism upon activation, may be used to drive axial translation in the distal direction (i.e., toward housing 23052 of FIG. 140) of the plunger seal of the fluid container. Optionally, the drive mechanism may include one or more compliance features that enable additional axial translation of the plunger seal to ensure, for example, that substantially the entire drug dose has been delivered to the user and that the feedback contact mechanisms have connected or interconnected. Furthermore, the drive mechanism may include one or more safety mechanisms, such as premature activation prevention mechanisms, to enhance the safety and usability of the mechanism and the device.

In a particular embodiment, drive mechanism 23090 employs one or more compression springs 23099 as biasing member(s), as shown in FIG. 141B. Upon activation of the fluid pump by the user, the power and control system is actuated to directly or indirectly release the compression spring(s) from an energized state. Upon release, the compression spring(s) may bear against and act upon the plunger seal 23060 to force the fluid out of the mutable fluid chamber 23021 of drug container 23050 as further described with reference to FIG. 142A-142C.

FIG. 142A to FIG. 142C illustrate the features of an embodiment before use, upon piercing of the pierceable seal, and upon completion of fluid delivery. More specifically, in the configuration shown in FIG. 142A, piercing member 23033 is maintained within sterile cavity 23032 with a first end (a proximal end) adjacent to, or contacting, pierceable seal 23056 of fluid pathway connector 23030. The sterility of cavity 23032 and piercing member 23033 is maintained, for example, by filter 23039 disposed between sterile cavity 23032 and the outside environment. In at least one embodiment, as shown in FIG. 142, filter 23039 is connected to, engaged with, or part of connector hub 23031, and encloses sterile cavity 23032 from the outside environment. Sterile cavity 23032 can be vented via vent or port 23031B within hub connection 23031. Accordingly, fluid pathway connector 23030, in at least one embodiment, is mounted to and integrated with fluid container 23050, for example by housing (cap) 23052 engaged with lip 23058A of barrel 23058. The piercing member may be a number of cannulas or conduits, such as rigid needles, and may be comprised of a number of materials, such as steel. In at least one embodiment, piercing member 23033 is a rigid steel needle. Pierceable seal 23056 may have sealing aspect 23056A that permits pierceable seal 23056 to be mounted directly to or otherwise be held in position between barrel 23058, connector hub 23031, and cap 23052. Connector hub 23031 includes an internal seal mount 23034 that further stabilizes the position of more stationary aspects of pierceable membrane 23056. At least a portion of pierceable seal 23056, such as seal barrier 23056C, is translatable upon connector hub 23031, as described herein, to rupture against piercing member 23033 and enable the fluid pathway connection to sterile fluid conduit 23035. Advantageously, such an arrangement permits pierceable seal 23056 to translate towards cap 23052 but not towards the plunger seal 23060. This is a desirable feature that permits the mutable fluid chamber 23021 of the fluid container 23050 to be evacuated, such as by vacuum, prior to filling with a fluid without compromising the function of sterile fluid pathway connector 23030.

In an initial position the proximal end of piercing member 23033 may reside adjacent to, or in contact with, seal barrier 23056C of pierceable seal 23056 to, for example, minimize the distance of translation of the seal barrier 23056C to become pierced and open fluid container 23050 to fluid pathway connector 23030. In a particular embodiment, proximal end of the piercing member 23033 may reside at least partially within seal barrier 23056C of pierceable seal 23056, yet not fully passing there-through, until activation of the device by a user.

As shown in FIG. 142B, once the pump device is activated and the drive mechanism pushes plunger seal 23060, plunger seal 23060 asserts a force on fluid chamber 23021, and pneumatic and/or hydraulic pressure builds by compression of the fluid in chamber 23021. As pneumatic and/or hydraulic pressure builds within fluid chamber 23021, the force is relayed to pierceable seal 23056, causing barrier seal 23056C to transform. This transformation may include a shift, inversion, translation, flexion, deformation, pop, snap, or any other functionally equivalent change, such that a portion of pierceable seal 23056, such as seal barrier 23056C, impinges against the substantially fixed position of piercing member 23033 and causes piercing member 23033 to pierce pierceable seal 23056 at seal barrier 23056C, as shown in FIG. 142B, thereby opening or otherwise connecting the fluid pathway between mutable fluid chamber 23021, piercing member 23033, and fluid conduit 23035.

Accordingly, integrated sterile fluid pathway connector 23030 is connected (i.e., the fluid pathway is opened) by the pneumatic and/or hydraulic force of the fluid within the fluid chamber 23021 created by activation of the drive mechanism. Once integrated sterile fluid pathway connection 23030 is connected or opened, fluid is permitted to flow from the fluid container 23050, through integrated sterile fluid pathway connection 23030 and sterile fluid conduit 23035. In aspects in which the fluid pump is an ambulatory drug infusion pump, fluid drug then flows through the insertion mechanism and into the body of the user for drug delivery. In at least one embodiment, a number of flow restrictors may be optionally utilized to modify the flow of fluid within the fluid pathway connection. In at least one embodiment, the fluid flows through only a manifold and a cannula or needle of the insertion mechanism, thereby maintaining the sterility of the fluid pathway before and during fluid delivery.

Additionally or alternatively, plunger seal 23060 or the pierceable seal 23056 may have some compressibility permitting a compliance push of fluid from drug container 23050. Additionally, the drive mechanism, plunger seal 23060, connector hub 23031, pierceable seal 23056, or a combination thereof, may include one or more sensors or status indication mechanisms, such as interconnects and contacts, to measure and communicate the status of drug delivery drive before, during, and after operation of the device to deliver fluid.

FIG. 142C shows the components of fluid container 23050 and sterile fluid pathway connector 23030 after substantially all of the fluid has been pushed out of the fluid container 23050. In particular, plunger seal 23060 is in the most-distal position in barrel 23058. In the embodiment of FIG. 142C, the connector hub-side (e.g., distal end) of plunger seal 23060 is configured with an optional protrusion and cavity aspect 23069, which structure minimizes residual volume left in fluid chamber 23021, now collapsed. Alternatively, plunger seal may be a flat-faced plunger seal (e.g., plunger seal 23160 in FIG. 144A and FIG. 145), or may have any number of other configurations as would be readily appreciated by one having skill in the art. In the embodiment shown in FIG. 142, plunger seal 23060 further comprises interconnect/contact 23061; and connector hub 23031 further comprises interconnect/contact 62. At end-of-delivery, interconnect/contact 61 of plunger seal 23060 and interconnect/contact 62 of connector hub 23031 interconnect and transduce a signal that may be perceived by a user. As described herein, numerous sensors and signal transducing means can be incorporated or adapted for use in the present embodiments.

Because of the novel design of the fluid pathway connector of the present embodiments and their integration at least partially within fluid containers, sterility of the fluid pathway is maintained throughout transport, storage, and operation of the device; user-activation of the device is simplified; and the fluid pathway is only connected when desired by the user. The sterility of the fluid pathway connection is initially maintained by performing the connection within a sterile cavity 23032 between connector hub 23031, pierceable seal 23056, and piercing member guide 23037. In at least one embodiment, the sterility of cavity 23032 is maintained by filter 23039 that abuts, is engaged with or part of, connector hub 23031. Filter 23039 may be, for example, a semi-permeable membrane that allows the venting of air through vent 23031B of connector hub 23031 during the actuation and translation of pierceable seal 23056. Filter 23039 may be sterilized by typical sterilization methods, which would readily be appreciated by one having skill in the art, and may be used to maintain a sterile barrier that prevents exposing piercing member 23033 to microorganisms, contaminants, or other undesirable environmental factors. For example, upon substantially simultaneous activation of the insertion mechanism, the fluid pathway between mutable fluid chamber 23021 and insertion mechanism is complete to permit drug delivery into the body of the user. Because fluid pathway connector 23030 is not in fluid connection or communication with fluid chamber 23021 until activation of the fluid pump and drive mechanism, fluid flow from the fluid container 23050 is prevented until desired by the user. This provides an important safety feature to the user and also maintains the container integrity of the fluid container and sterility of the fluid pathway.

The drive mechanism that translates the plunger seal 23060 may contain one or more drive biasing members (e.g., as shown in FIG. 141B). The components of the drive mechanism function to force a fluid from the mutable fluid chamber 23021 through pierceable seal 23056 and through the piercing member 23033 or sterile fluid conduit 23035, for delivery through fluid pathway connector 23030. Further regarding the drive mechanism, a number of drive mechanisms may be utilized to force fluid from a drug container for delivery into the body of a user. In one such embodiment, the drive mechanism 23090 may be substantially similar to that described in WO 2013/023033467 (PCT/US2012/023052303241), which is hereby incorporated by reference in its entirety. The components of the drive mechanism, upon activation, drive axial translation in the distal direction of the plunger seal of the drug container. Optionally, drive mechanism may include one or more compliance features which enable additional axial translation of the plunger seal to, for example, ensure that substantially the entire fluid dose has been delivered to the user and make sure that the feedback contact mechanisms have connected. Furthermore, the drive mechanism may include one or more safety mechanisms, such as premature activation prevention mechanisms, to enhance the safety and usability of the mechanism and the device.

At least one embodiment provides for a modular fluid pathway connection. FIG. 143A and FIG. 143B detail an embodiment of a modular fluid pathway connector that comprises connector hub 23031, which abuts filter 23039 and pierceable seal 23056 at sealing member 23056A. Connector hub 23031, filter 23039 and pierceable seal 23056 are housed within cap 23052, as shown in FIG. 143A. Connector hub 23031 further comprises header 23031C, which forms a junction for fluid conduit 23035 and piercing member 23033. As shown in FIG. 143A and FIG. 143B, fluid conduit 23035 may be connected directly to piercing member 23033. Alternatively, as shown in FIG. 144A fluid conduit 223035 may be connected via conduit port 223038. Nevertheless, a modular fluid pathway connection can be adapted for use with a number of alternative barrel and drive configurations, and used within a variety of ambulatory infusion devices. The components of the novel sterile fluid pathway connector 23030 may be pre-assembled, to appear as exemplified in FIG. 143A, and subsequently attached, mounted, connected, or otherwise mated with a fluid container such as fluid container 23050. Alternatively, the components of sterile fluid pathway connector 23030 may be assembled directly into drug container 23050. As would be readily appreciated by one skilled in the art, a number of glues or adhesives, or other connection methods such as snap-fit, interference fit, screw fit, fusion joining, welding, ultrasonic welding, laser welding, and mechanical fastening, and the like, can be used to engage one or more of the components described herein in permanent or impermanent connection as desired for a particular use. For example, glue can be used between distal end of barrel 23058, sealing member 23056A, or connector hub 23031A. Additionally or alternatively, the components of the sterile fluid pathway connector 23030 may be mounted to barrel 23058 and held in place crimping cap 23052 to distal aspect of barrel 23058, such as to a flanged aspect or lip of barrel 23058A.

In at least one embodiment, as shown in FIG. 144A to FIG. 144C, piercing member guide 230237 may be utilized to guide pierceable seal 23056 and to slidably engage the connector hub 230231. Additionally or alternatively, piercing member guide 230237 may be utilized to ensure that piercing member 230233 remains substantially centered on the axis so as to pierce pierceable seal 23056 at the desired portion of seal barrier 23056C. The embodiment of FIG. 144A shows fluid container comprising barrel 23058 and forming mutable fluid chamber 23021 between plunger seal 230260 and pierceable seal 56. As shown in FIG. 144A, plunger seal 230260 is a flat plunger seal, but a variety of plunger seal shapes can be adapted for use with the fluid connection and infusion pumps of the present embodiments. The embodiment of FIG. 144A further comprises filter 23039, which abuts connector hub 230231 and is used to maintain sterility of sterile chamber 23032 between connector hub 230231 and pierceable seal 23056. Connector hub 230231 also includes seal mount 230234 that abuts pierceable seal 23056; and flange 230231A that abuts seal member 23056A of seal 23056, and that, in turn, abuts the distal lip 23058A of barrel 23058. The meeting surfaces of connector hub 230231A, sealing member 23056A and barrel lip 23058A are positioned in place and secured within the rims of cap 23052. Connector hub 230231 also houses piercing member 230233, which connects to fluid conduit 230235. Connector hub 230231 also has vacuum port 230231B, a filtered channel that leads into sterile chamber 23032. Connector hub 230231 is also configured with conduit port 230231D, which provides exit from sterile fluid connector 230230 to the rest of the infusion device (e.g., injection means), such as via sterile fluid conduit 23035 (not shown). Conduit port 230231D and vacuum port 230231B may contain a membrane or seals, such as one-way seals, which permit fluid flow out of chamber 23032 through the respective ports but do not permit fluid flow into the chamber 23032 through these ports. Additionally, or alternatively, conduit port 230231D and vacuum port 230231B may be plugged at certain points of assembly or operation. For example, vacuum port 230231B may be used to evacuate sterile cavity 23032 during manufacturing, assembly, or at any point prior to operation of the device; and then vacuum port 230231B can be plugged after the evacuation has been completed.

Further regarding piercing member guide 230237, this component may be slidably attached to connector hub 230231. A number of means known in the art may be used to facilitate this slidable attachment such as, for example, engagement between a connector prong 230237D and leg 230237A of piercing member guide 230237 with complementary cavity 230236 in connector hub 230231. These components are more clearly visible in FIG. 144A and FIG. 144B. FIG. 144B shows the orientation of piercing member 230233 within piercing member guide 230237, which emerges from piercing member guide 230237 at header 230237C; and FIG. 144C shows the orientation of piercing member 23033 and piercing member guide 230237 within connector hub 230231. Such an arrangement permits the pierceable seal 23056 and piercing member guide 230237 to translate towards housing 23052 together, at least for a portion of the translation of seal barrier 23056C. Additionally, pierceable seal 23056 may be removably attached to piercing member guide 230237 by a number of means known in the art such as, for example, removable snap-fit engagement or it may be configured to enable contact between the components to guide the translation of the seal barrier 23056C upon the piercing member 230233. When a piercing member guide is used, such as piercing member guide 230237 in FIG. 144A, the piercing member guide may translate with pierceable seal 23056, for at least a portion of the translation, to ensure that the seal barrier 23056C contacts and is pierced by the piercing member 230233. Once the fluid pathway is opened or connected, translation of plunger seal 230160 in the distal direction by the drive mechanism causes fluid within drug chamber 23021 to be forced through the sterile fluid connector. In some embodiments, a needle insertion mechanism, as described herein, may be connected at the other end of the fluid conduit 23035 to insert a needle into the body of the user to facilitate fluid transfer to the user.

The embodiment shown in FIG. 144A also comprises plunger seal 260, which may be used as a part of the status indication mechanism along with piercing member guide 237. More specifically, in this embodiment plunger seal 260 includes interconnect/contact 261 and the corresponding interconnect/contact 262 is located on piercing member guide 237. When plunger seal 260 and piercing member guide 237 reach proximity at end-of-delivery (e.g., as in FIG. 144C), interconnect/contact 261 and interconnect/contact 261 interconnect and transduce a perceptible signal to the user.

The novel embodiments presented herein provide integrated sterile fluid pathway connections and fluid containers, and fluid pumps that utilize such connections, that are configured to maintain the sterility of the fluid pathway before, during, and after operation of the device, and that enable active safety controls for the device. Integration of the fluid pathway connector into a portion of the fluid container helps ensure container integrity and sterility of the fluid pathway. Additionally, by integrating the sterile fluid pathway connector into a portion of the fluid container, the connection for fluid transfer can be controlled by the user (i.e., user-activated) and enabled by the function of the drive mechanism. Accordingly, user-activation steps and the internal operation of the fluid pump can be greatly simplified by the novel integrated sterile fluid pathway connections of the present embodiments.

In another embodiment, the fluid container comprises at least two mutable internal compartments, wherein each compartment-compartment interface comprises a distinct pierceable seal capable of being disrupted by the piercing member of the sterile fluid pathway connector to create a sterile fluid communication between the sterile fluid pathway and that compartment of the sterile fluid container. As shown in FIG. 145, container 23050 may utilize one or more seals in addition to plunger seal 230160 and pierceable seal 230156. This may be applicable, for example, when multiple fluid substances are desired to be delivered by the container and the infusion pump device. FIG. 145 shows one such embodiment that utilizes two additional seals, 230163 and 230165, to create compartments or chambers 230121A, 230121B and 230121C, within which one or more fluid substances may be stored for delivery. The embodiment of FIG. 145, pierceable seal 230156 includes seal barrier 230156C and base 230156A, which base 230156A abuts barrel lip 23058A on its distal side and connector hub 230131A on its proximal side, which abutments are held within housing 23052. Connector hub 230151 further includes vacuum port 230131B, with a channel that leads into sterile chamber 23032. Connector hub 230131 is also configured with conduit port 230131D, which provides exit from sterile fluid connector 230130 to the rest of the infusion device (e.g., an injection mechanism). Conduit port 230131D and vacuum port 230131B may each contain a membrane, filter or seals, such as one-way seals, which permit fluid flow out of chamber 23032 through the respective ports but do not permit fluid flow into the chamber 23032 through said ports. Additionally, or alternatively, conduit port 230131D and vacuum port 230131B may be plugged at certain points of assembly or operation. For example, vacuum port 230131B may be used to evacuate sterile cavity 32 during manufacturing, assembly, or at any point prior to operation of the device; and then vacuum port 230131B can be plugged after the evacuation has been completed.

Upon activation of the fluid pump, pressure at interface 230168 of plunger seal 230160 causes distal translation of plunger seal 230160 towards housing 23052. The pneumatic and/or hydraulic pressure within the fluid substance(s) held in drug chambers 230121A, 230121B and 230121C relays the force to, and causes distal translation of, chamber seal 230163, chamber seal 230165, and pierceable seal 230156, causing seal barrier 230156C to translate towards housing 23052 and become pierced by piercing member 230133. This causes the sterile fluid pathway connection to be made or opened, as described herein. Upon further translation of plunger seal 160, the fluid substance held in mutable drug chamber 230121A is dispensed through conduit 230135. Upon further translation of the fluids and seals, seal 230165 may be then be pierced by piercing member 230133, thereby permitting the fluid substance in mutable fluid chamber 230121B to be dispensed from the fluid pathway connector. If further compartments or chambers are desired, more seals and chambers (such as seal 230163 and mutable chamber 230121C) may be configured, and subsequently engaged in the same manner until plunger seal 230160 has been fully translated towards housing 23052. This configuration may offer advantages over single-compartment fluid containers. For example, a diluent may be stored in mutable fluid chamber 230121A and a therapeutic drug may be stored in mutable fluid chamber 230121B, such that the sterile fluid pathway is first purged by the diluent prior to delivery of the drug therapy to the patient. When drug combinations are desired for delivery, multiple therapeutic agents may be stored and delivered using the configuration provided by this embodiment. Any number of seals and drug chambers may be utilized in such a configuration provided that the piercing member 230133, the drive mechanism, and other components of the embodiments are configured appropriately for such delivery.

The novel integrated sterile fluid pathway connectors of the present invention may additionally incorporate status indication into the fluid delivery mechanisms. Such status indication features may be incorporated into the drive mechanism 23090, as described in WO 2013033467. Additionally or alternatively, status indication features may be incorporated into the components of the sterile fluid pathway connectors. In one embodiment, one or more interconnects are contained within, or proximal of, the plunger seal. At the end of fluid delivery, the piercing member may be utilized to contact the, or as a contact for, interconnect to open, close, or otherwise create a signal to the power and control system to provide feedback to the user. In another embodiment, one of either interconnects/contacts are contained within, or proximal of the plunger seal, while the other is contained within or distal of the pierceable seal, such as in or on a seal mount or guide piece. At the end of fluid delivery, interconnects and corresponding contacts are close enough to permit a signal to be sent to the power and control system to provide feedback to the user.

In another embodiment, the surface of the connector hub sequestered in sterile chamber 23032 may incorporate, or itself be utilized as, a contact or interconnect for the status indication mechanism. For example, an end-of-delivery signal can be provided using a leaf/flex arm or spring style switch mechanism contained within sterile compartment 23032, engaged with the surface of the connector hub and connected through the hub to the appropriate electronics. In this arrangement, in the unpressurized state (before device activation), the switch rests in the open position, and there is no contact/interconnect or signal transduced. When the device is activated, i.e., when the drive engages the plunger seal within the drug container, pneumatic and/or hydraulic pressure causes the pierceable seal to translate into the piecing member, thus disrupting the pierceable seal and allowing fluid to flow through the sterile fluid connector. Pneumatic and/or hydraulic pressure further causes the septum of the pierceable seal to press against the switch mechanism until it interconnects with its complementary contacts, which closes the circuit and allows a signal to transduce to the user, indicating that drug delivery has started. At end-of-delivery, the pneumatic and/or hydraulic pressure within the sterile chamber is released and the switch re-opens, breaking the circuit and providing an end-of-delivery signal to the user.

Figure 146A:
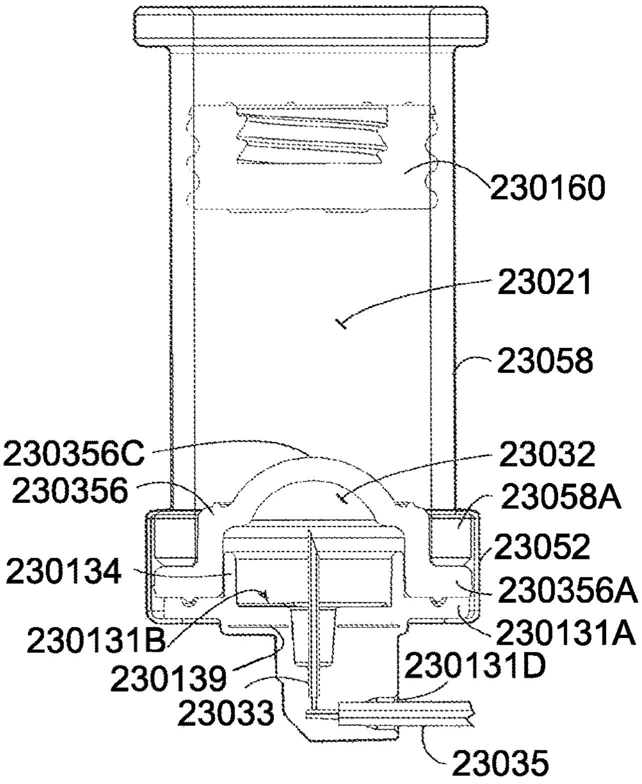
Figure 146B:
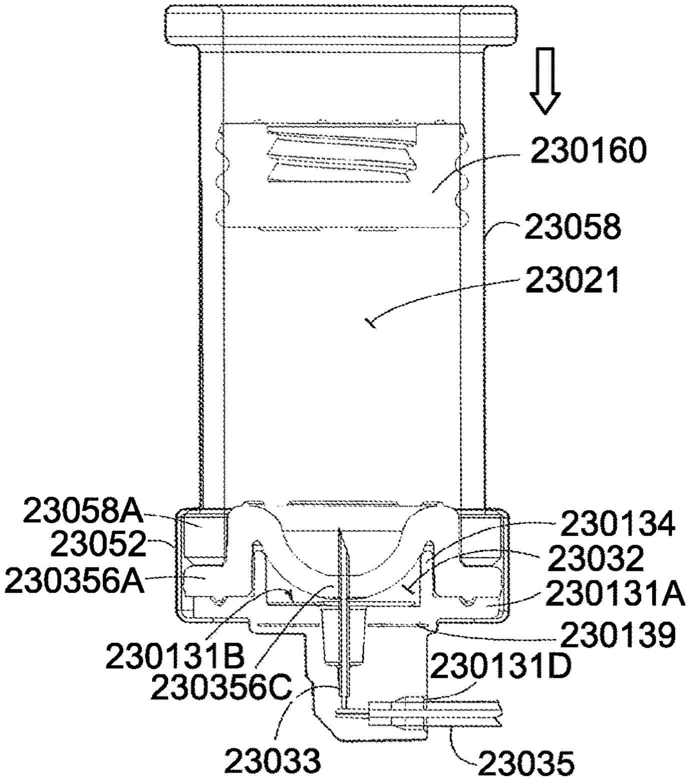
Figure 146C:
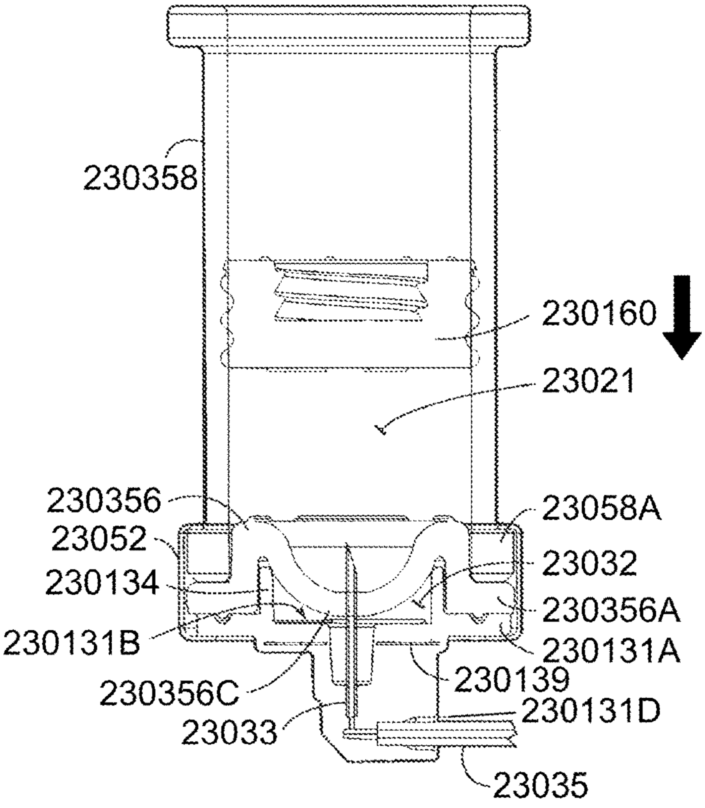
Figure 146D:
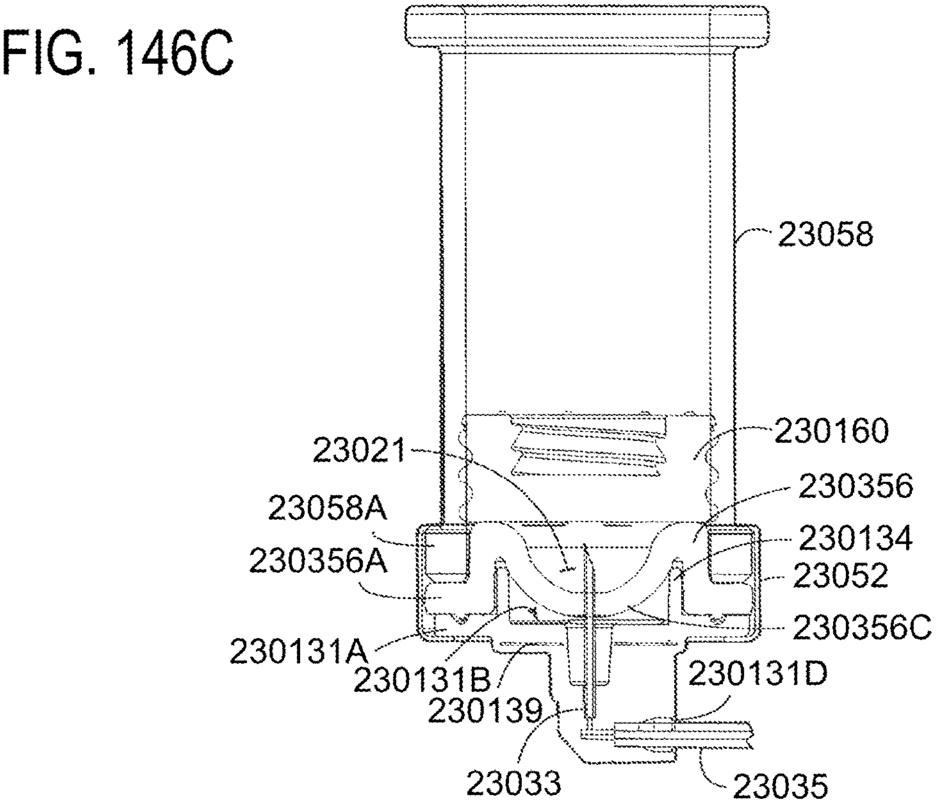
Figure 146E:
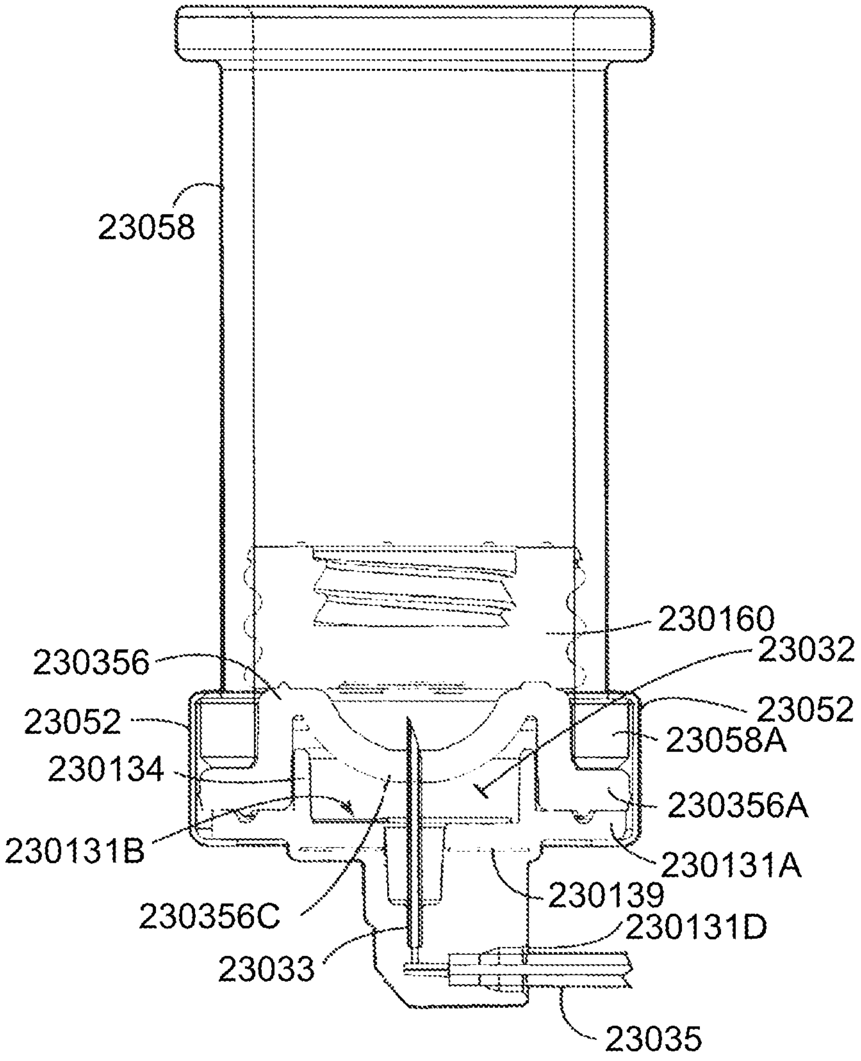

Such a configuration, in which the surface of the connector hub sequestered in the sterile chamber of the sterile fluid pathway connector may incorporate, or itself be utilized as, a contact or interconnect for the status indication mechanism, may be facilitated by a configuration of the pierceable seal. For example, as shown in FIG. 146A to FIG. 146E, fluid chamber 23058 comprises plunger seal 230160, configured to engage a drive mechanism that forces plunger seal 230160 towards sterile fluid connector 230130. In the initial position (i.e., before the drive is engaged), pierceable seal 230356 maintains sterile chamber 23032 within the space defined by pierceable seal 230356 and connector hub 230131, particularly as partially maintained by seal mount 230134, as shown in FIG. 146A. Connector hub 230131 further includes piercing member 23033, and vacuum port or vent 131B in which sterility of chamber 23032 is maintained by filter 23039. Connector hub base 230131A, sealing member 230356A of pierceable member 230356, and barrel lip 23058A are all secured in housing 23052, which housing can be a cap such as a crimp cap. Connector hub 230131 also includes exit port 230131D, which provides an exit passage for fluid conduit 23035 from the sterile fluid pathway connector. Once a pump drive is activated and plunger seal 230160 is forced toward piercing member 23033, pneumatic and/or hydraulic pressure within mutable fluid chamber 23021 forces seal barrier 230356C of pierceable seal 230356 into piercing member 23033, which pierces seal barrier 230356C and opens the sterile fluid pathway. Continued pneumatic and/or hydraulic pressure within mutable chamber 23021 forces at least a portion of pierceable seal 230356 to contact at least a portion of connector hub 230131 within sterile chamber 23032, as shown in FIG. 146B. This continued pneumatic and/or hydraulic pressure, as long as the drive is activated and fluid remains in mutable chamber 23021, maintains the contact between seal 230356 and connector hub 230131, as shown in FIGS. 146C and 146D. When fluid has been pumped out of mutable fluid chamber 23021, such that this chamber essentially no longer exists, pneumatic and/or hydraulic pressure against seal 230356 is released, and seal 230356 returns to a non-pressurized state within chamber 23032, in which there is no longer contact between seal 230356 and hub 230131, as shown in FIG. 146E.

Figure 147A:
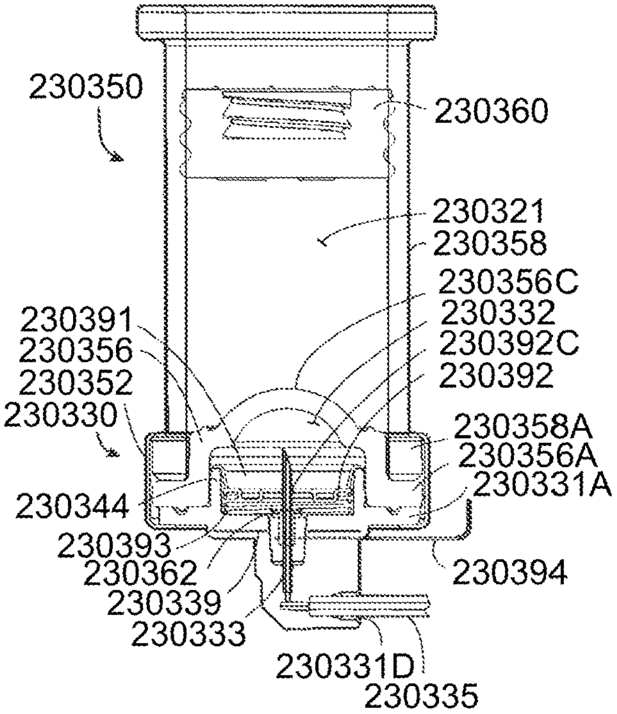
Figure 147B:
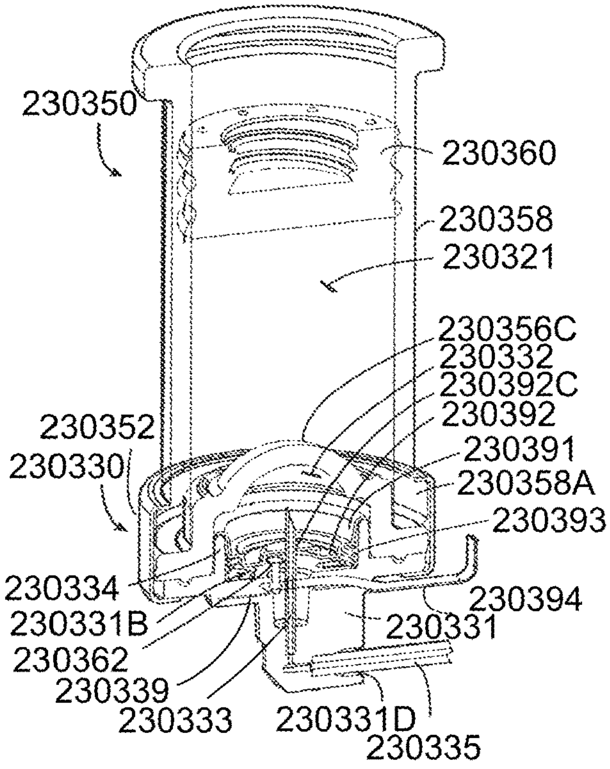

This aspect of the embodiments is advantageous for a number of devices and configurations useful to provide the sterile fluid pathway connector with at least one sensor configured to indicate the status of fluid transfer from the sterile fluid container to the connector. An example of such a sensor is a "switch" mechanism contained within the sterile chamber in the sterile fluid connector. For example, in the embodiment shown in FIG. 147A to FIG. 147H, fluid container 230350 includes barrel 230358, which houses fluid chamber 230321 and plunger seal 230360, configured to engage a drive mechanism that forces plunger seal 230360 and fluid in mutable fluid chamber 230321 toward sterile fluid connector 230330. Pierceable seal 230356 maintains sterile chamber 230332 within the space defined by pierceable seal 230356 and connector hub 230331, as shown in FIG. 147A and FIG. 147B, in which the fluid pathway is "closed." Connector 230330 further includes connector hub 230331, which further vacuum port 230331B, in which sterility of chamber 230332 is maintained by filter 230339; exit port 230331D, which provides an exit passage for fluid conduit 230335 from sterile fluid pathway connector 230330; and engages piercing member 333. Connector hub base 230331A, pierceable seal 230356 sealing member 230356A, and barrel lip 230358A are secured in housing 230352. Connector hub 230331 further houses, in sterile chamber 230332, stamped ring 230391 fitted on seal mount 230334 of connector hub 230331; contact 230392; spring 230393; and interconnects 230362 which are in communication with flexible power strip 230394 (flex). As shown in FIG. 147A and FIG. 147B, in the initial state before activation of the drive, spring 230393 rests in a non-compressed state, and contact 230392 is held between spring 230393 and stamped ring 230391 in a position in which there is no contact between interconnects 230362 and contact 230392. Contact 230392 is further stabilized within sterile chamber 230332 by the position of piercing member 230333 that passes through contact 230392 through passage 230392C.

Figure 147C:
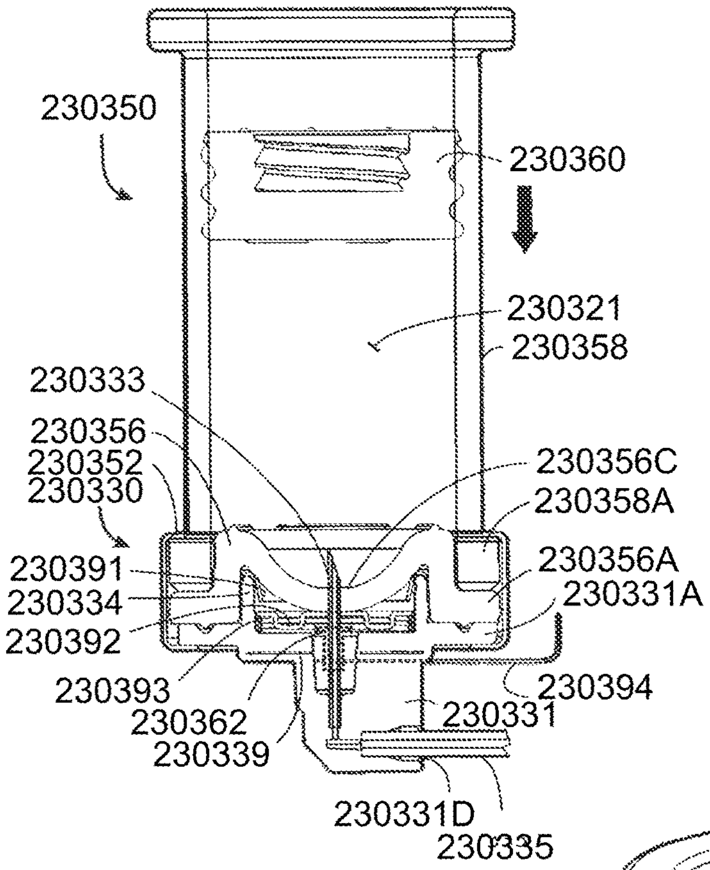
Figure 147D:
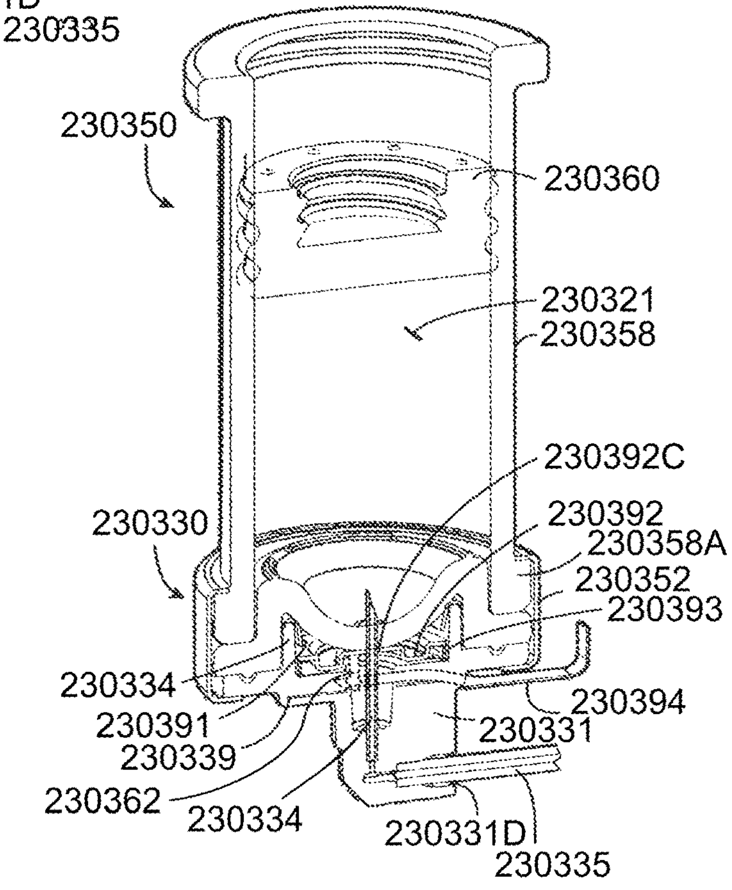
Figure 147E:
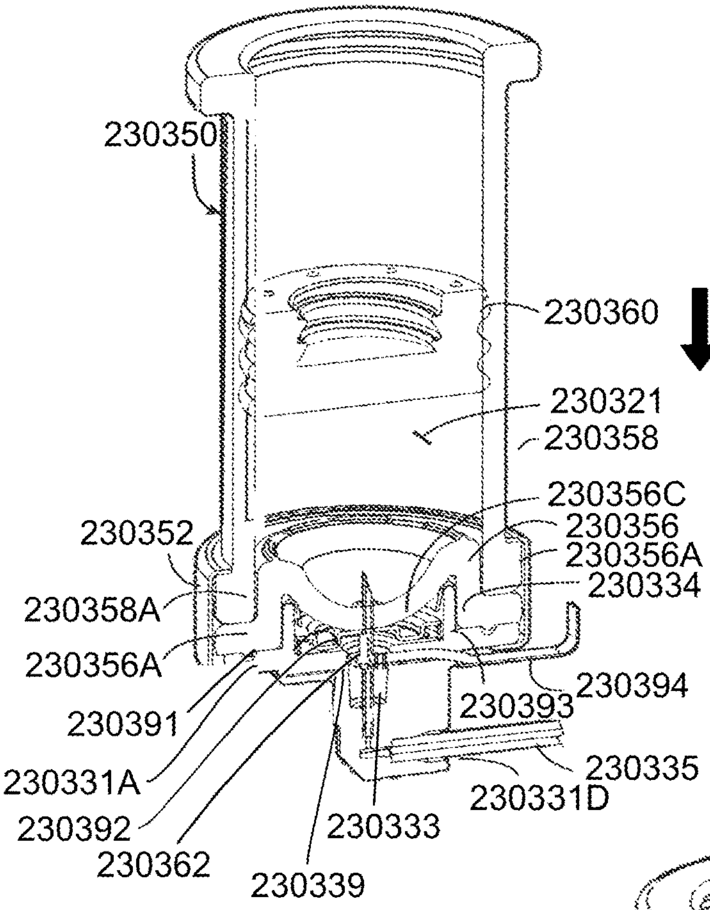
Figure 147F:
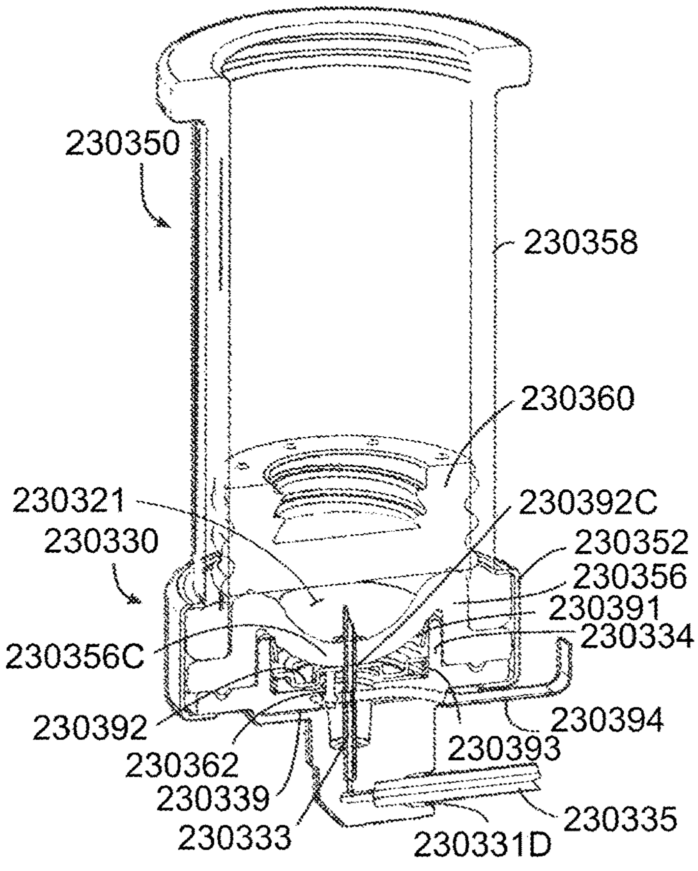
Figure 147G:
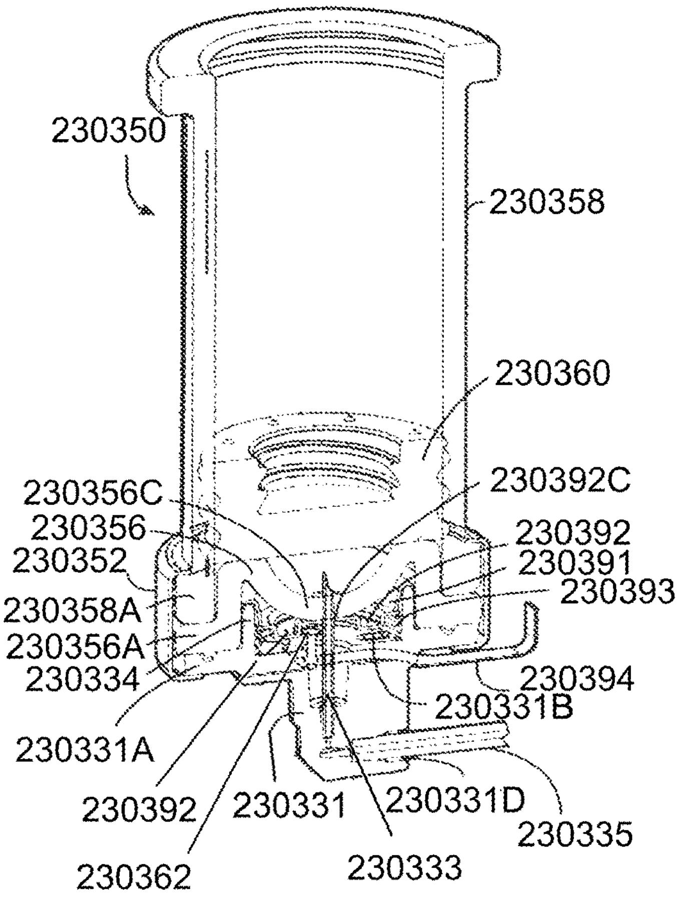
Figure 147H:
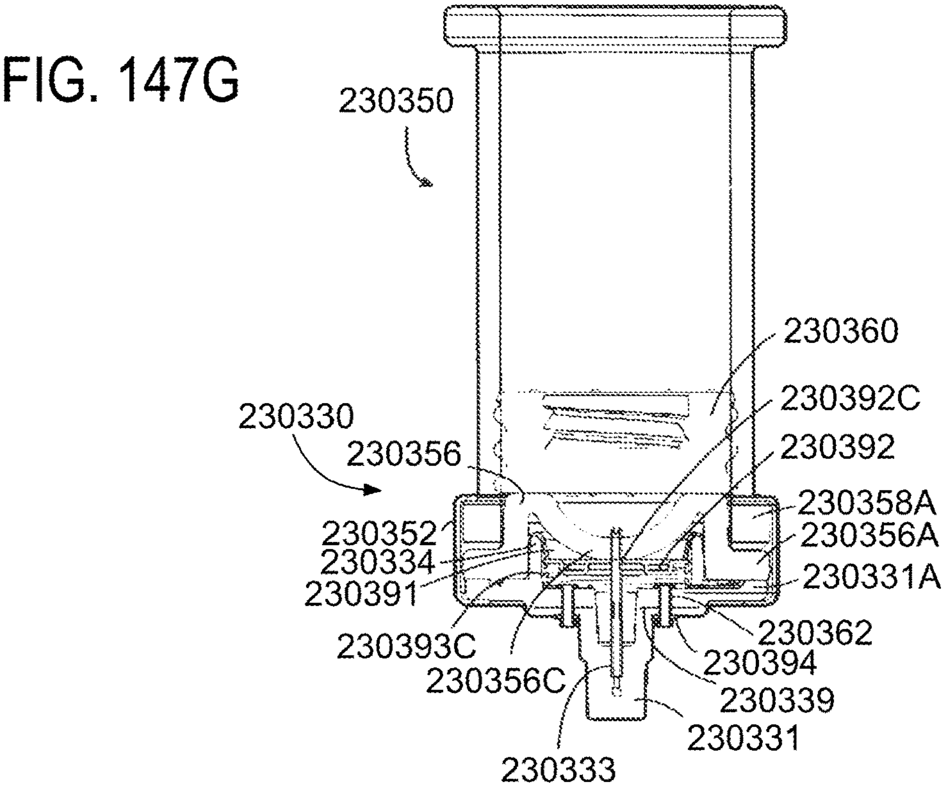

As shown in FIG. 147C and FIG. 147D, once the drive mechanism is activated and plunger seal 230360 is forced toward piercing member 230333, as indicated by the arrow, pneumatic and/or hydraulic pressure within mutable fluid chamber 230321 forces seal barrier 230356C of pierceable seal 230356 into piercing member 230333, thereby piercing seal barrier 230356C and opening the sterile fluid pathway such that fluid can pass to sterile fluid conduit 230335. This pneumatic and/or hydraulic pressure within mutable chamber 230321 also forces at least a portion of barrier seal 230356C against at least a portion of contact 230392, such that spring 230393 is compressed until contact 230392 meets with interconnects 230362 within sterile chamber 230332, forming an interconnection. A signal can then be transduced via contact 230392, interconnect 230362, and flex 230394. Continued pneumatic and/or hydraulic pressure (see arrow), as long as the drive is activated and fluid remains in mutable chamber 230321, compresses spring 230393 and maintains the contact between seal 230356, contact 230392 and interconnect 230362, such that interconnection continues, as shown in FIG. 147E to FIG. 147F. When fluid has been pumped out of mutable fluid chamber 230321, such that this chamber essentially no longer exists and flow through the sterile fluid connector 230330 has ceased, as shown in FIG. 147G and FIG. 147H (the latter is a different sectional view of the sterile fluid pathway connector showing the position of interconnects 230362 within connector hub 230331), pneumatic and/or hydraulic pressure against seal 230356 is released, and spring 230393 returns to the non-compressed state, pushing contact 230362 back toward stamped ring 230391 and breaking interconnection between contact 230392 and interconnect 230362. Once this interconnection is broken, signal can no longer be transduced via flex 230394.

Figure 148A:
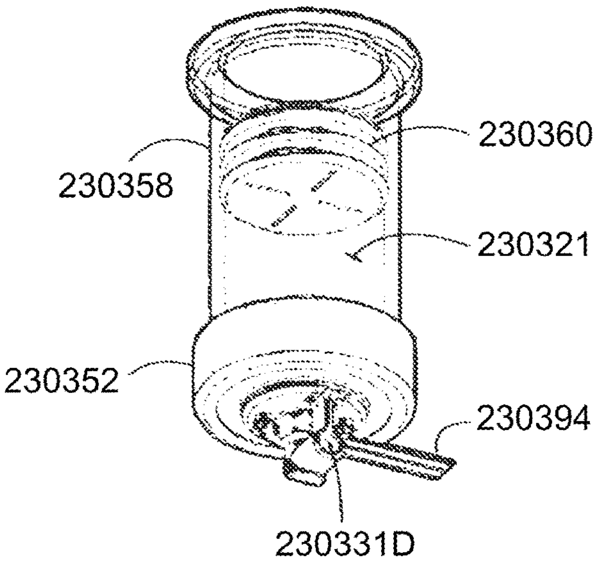
Figure 148B:
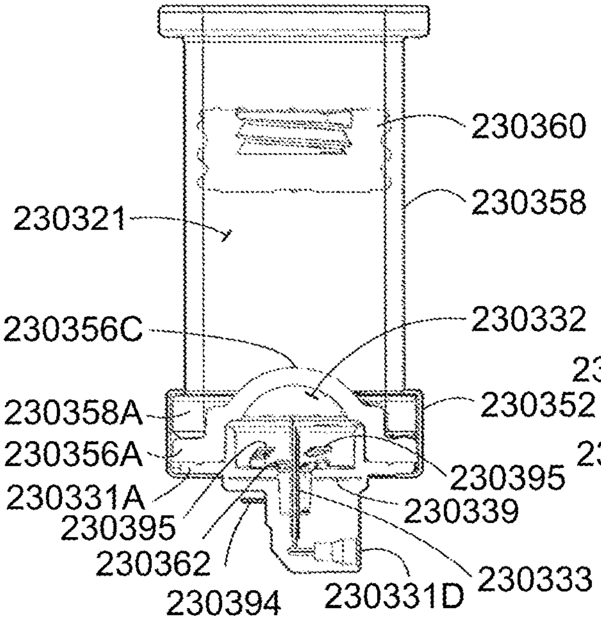
Figure 148C:
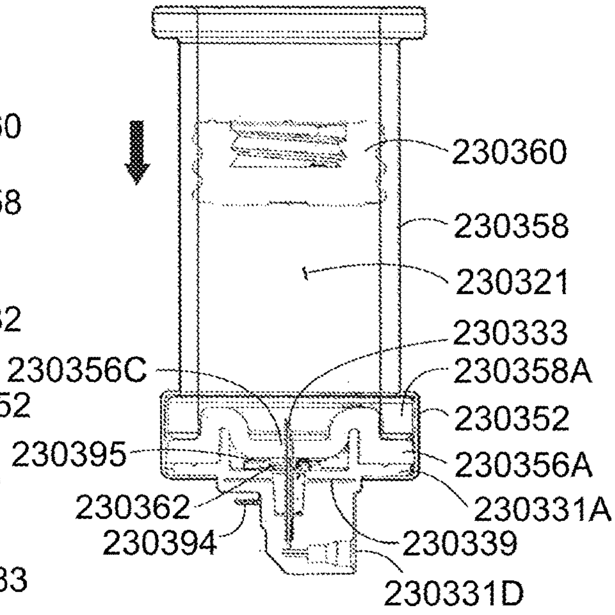
Figure 148D:
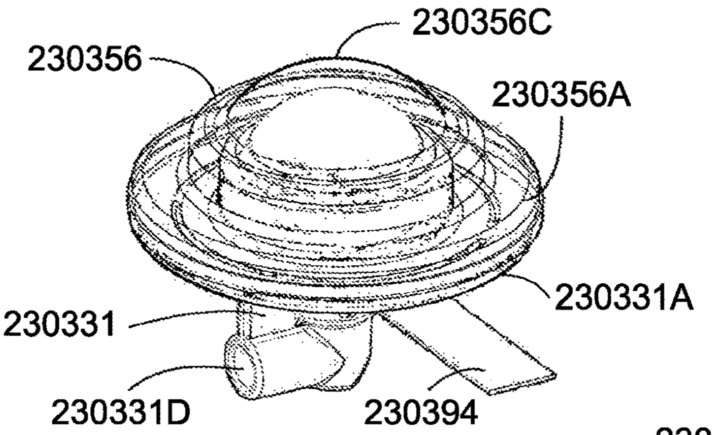
Figure 148E:
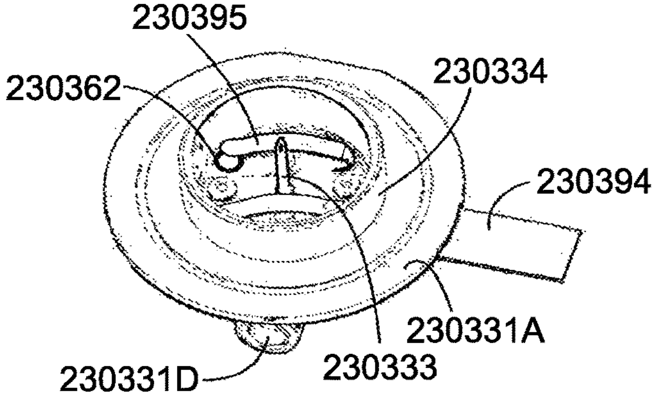
Figure 148F:
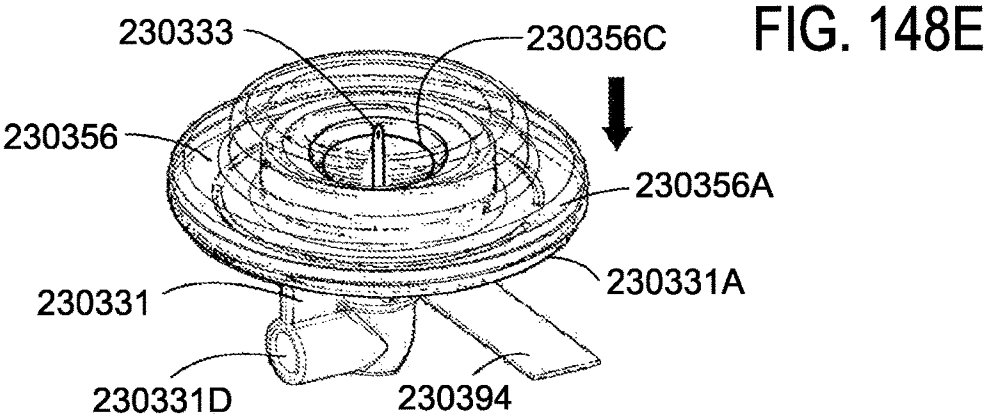
Figure 148G:
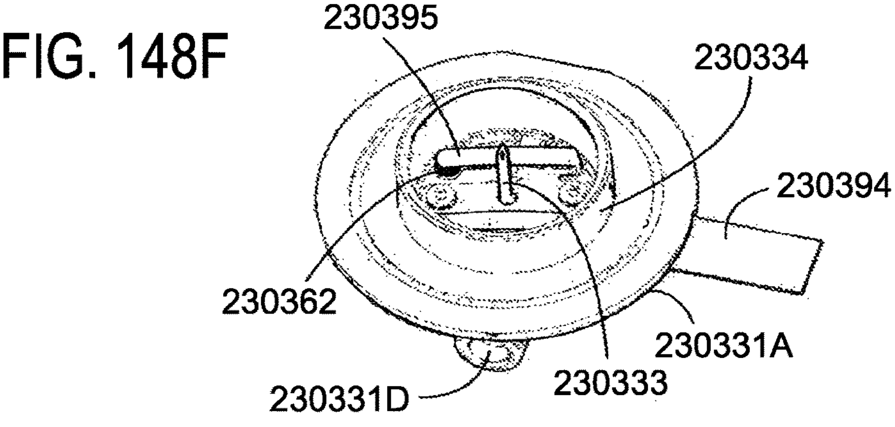

Other switch mechanisms can be designed that use the position of the membrane in pressured and unpressurized states to facilitate transduction of a signal to indicate the status of fluid transfer from the sterile fluid container to the connector. For example, as shown in FIG. 148A to FIG. 148G, connector hub 230331 can house components of a switch comprising a leaf/flex arm contacts 395. FIG. 148B, FIG. 148D and FIG. 148E show the sterile fluid pathway connector in the pre-use position, in which pierceable seal 230356 is unpierced and intact. In this position, contacts 230395 are not touching (or in close enough proximity with) interconnects 230362, and no signal can be transduced. FIG. 148C, FIG. 148F and FIG. 148G show the sterile fluid pathway connector in the activated, pressurized position, in which pneumatic and/or hydraulic pressure from the fluid chamber has deformed barrier seal 230356C against piercing member 230333, piercing pierceable seal 230356 and opening the fluid pathway. In this position, barrier seal 230356C has further been forced against contacts 230395, such that contacts 230395 meet (or become in close enough proximity) with interconnects 230362, such that interconnection forms a signal that can be transduced via flex 230394. FIGS. 148D and 10F are perspectives (in which the barrel and housing are not shown), that illustrate the positions of pierceable seal 230356, connector hub 230331, and piercing member 230333 in pre-use and pressurized positions, respectively. FIGS. 148E and 148G are perspectives in which the barrel, housing and pierceable seal are not shown, to illustrate the positions of contacts 230395 and interconnects 230362 in pre-use (no interconnection) and pressurized (interconnected) positions, respectively.

Figure 149A:
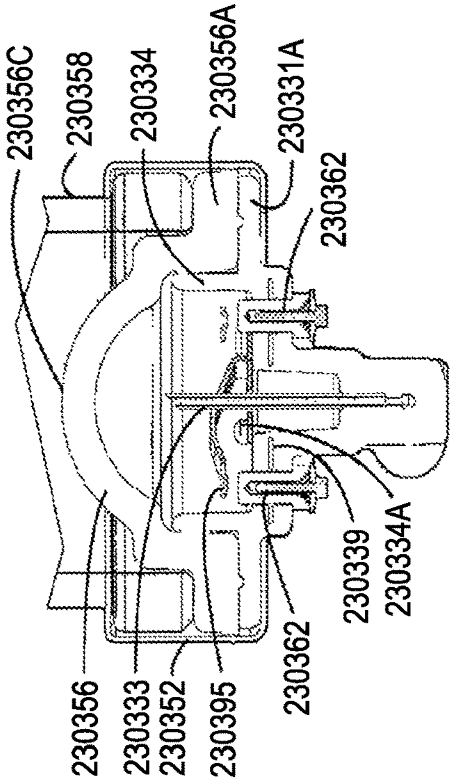
Figure 149B:
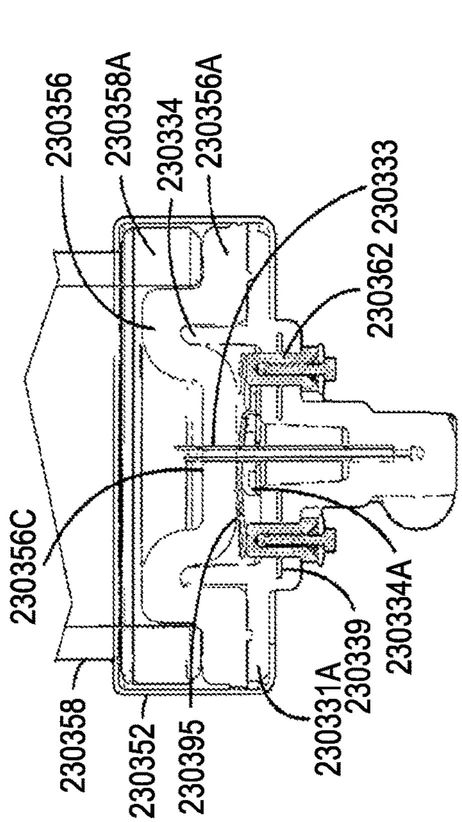
Figure 149C:
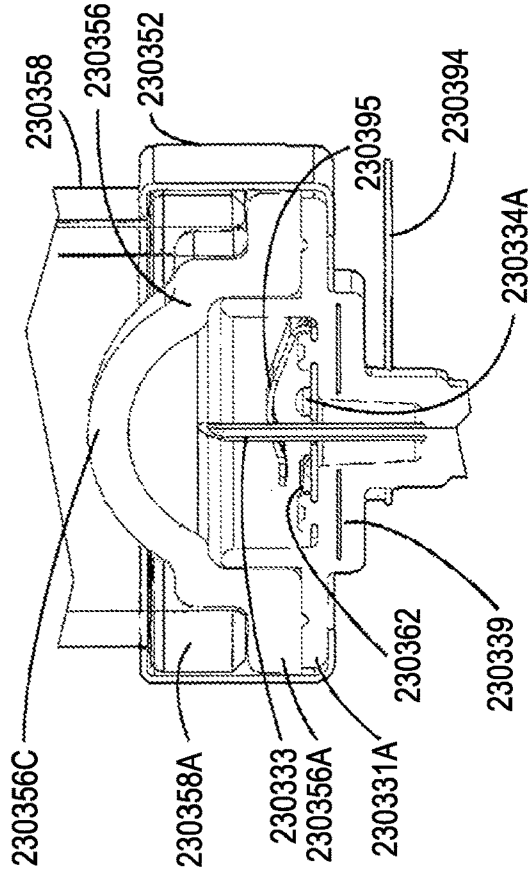
Figure 149D:
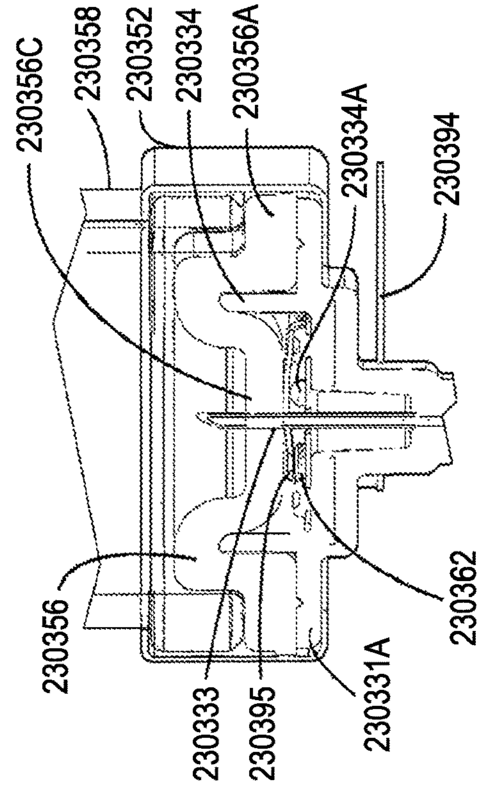

FIG. 149A to FIG. 149D further illustrate an embodiment in which leaf/arm contacts 230395 do not form interconnection with interconnects 362 until and unless, as shown in FIG. 149B and FIG. 149D, pneumatic and/or hydraulic pressure force seal barrier 230356C onto connects 230395, which force then transferred to place contacts 230395 in contact with interconnects 230362, which then allows signal flow via flex 230394. Additionally, as shown in the embodiment of FIG. 149A to FIG. 149D, connector hub 230331 further includes internal post 230334A, a structure that limits position of contacts 230395 and membrane 230356 to avoid an over-center position that might interfere with fluid passage through the sterile fluid pathway connector.

Figure 150A:
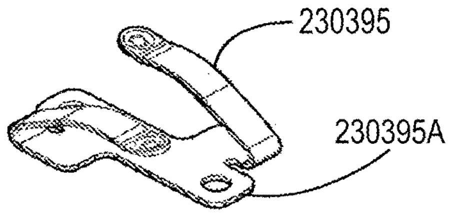
Figure 150B:
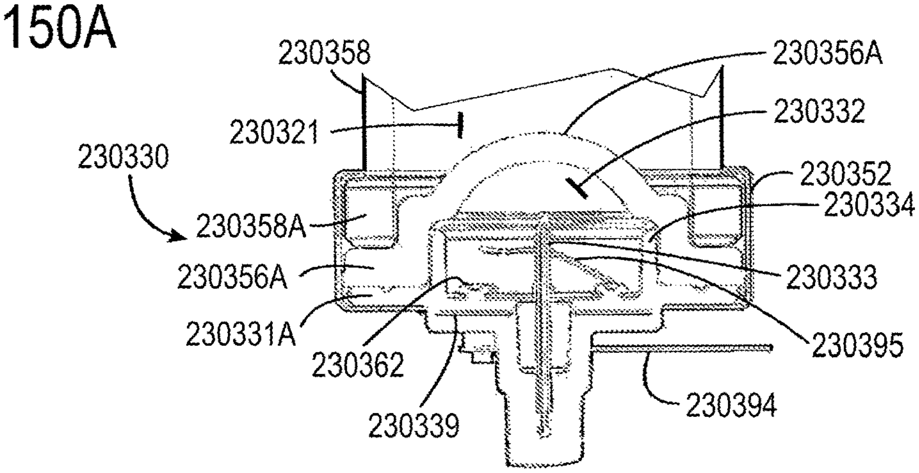
Figure 150C:
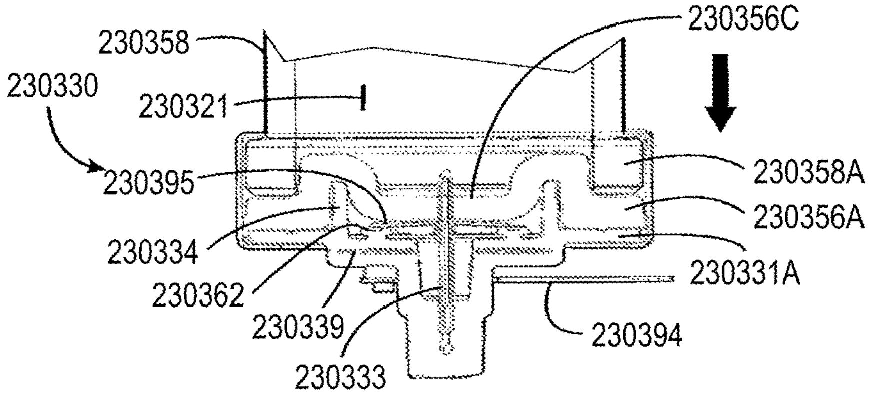
Figure 150D:
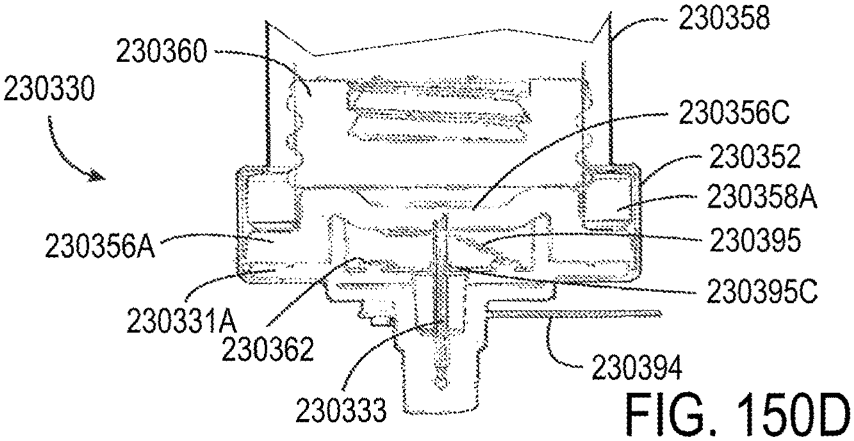

FIG. 12A to FIG. 12D further illustrate an embodiment of a sterile fluid connector capable of transmitting a signal indicating the status of fluid transfer from the sterile fluid container to the connector. FIG. 150B illustrates the position of components of a sterile fluid connector 230330 in an unpressurized state, while FIG. 150C illustrates the pressurized state and FIG. 150D illustrates an end-of-delivery state. Interconnect(s) 230362 and contact(s) 230395 are situated within sterile chamber 230332 between connector hub 230331 and pierceable seal 230356, such that after pierceable seal 230356 is pierced, continued pressure within drug chamber 230321 causes interconnection between one or more interconnect(s) 230362 and one or more contact(s) 230395, which transmits a signal to the user, and which signal is terminated once pressure inside the drug chamber 321 drops and interconnection is lost, i.e., at end-of-delivery. A number of known interconnects and contacts may be used with the present embodiments, which would readily be appreciated by a skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes. FIG. 151A to FIG. 151C illustrate another embodiment of a sterile fluid connector capable of transmitting a signal indicating the status of fluid transfer from the sterile fluid container to the connector.

Yet another switch mechanism is shown in FIG. 152A and FIG. 152B, which show sectional and sectional isometric views of a sterile fluid pathway connector (barrel not shown). In this embodiment, sterile chamber 230332, defined in part by the position of pierceable seal 230356 seal mount 230334 and hub connection 230331. Connector hub also holds piercing member 230333 and interconnects 230362 within the sterile chamber 230332. The switch mechanism includes interconnects 230362, first compression spring 230393, contact 230392, and second compression spring 230396. In this embodiment, shown in the un-activated, depressurized state, both compression springs 230393 and 396 compress in order for contact 230392 to form an interconnection with interconnects 230362. Before and upon release of pneumatic and/or hydraulic pressure against seal barrier 230356, compression springs 230393 and 230396 decompress and interconnection is broken.

Another embodiment of a switch mechanism is shown in FIG. 153A and FIG. 153B. In this embodiment, pierceable seal 230456 comprises a conductive material or coating. Connector hub 230431 includes rib 434A, a structure that ensures that continuity between conductive pierceable seal 230456 and contacts 230462 is broken when system pressure drops at the end of fluid delivery. More specifically, as shown in FIG. 151B, in the pressurized system in which pneumatic and/or hydraulic pressure has caused conductive pierceable membrane 230456 to have been ruptured by piercing member 230433, conductive pierceable membrane 230456 must deform further proximal to rib 230434 in order to meet interconnects 230462. Once pneumatic and/or hydraulic pressure ceases, i.e., at the end of fluid delivery, conductive pierceable membrane 230456 is naturally released from interconnection by proximal to rib 230434

Yet another embodiment of a switch mechanism is shown in FIG. 154. In this embodiment, connector hub 230531 comprises conductive elastomer 230597 held in sterile chamber 230532 between connector hub 230531 and pierceable membrane 230556. In this embodiment, at least a portion of conductive elastomer 230597 is affixed to or otherwise engaged with seal mount 230534, and is configured with a centrally located aperture to allow barrier seal 230556C to be forced into contact with piercing member 230533 upon activation of the pump and creation of pneumatic and/or hydraulic pressure against pierceable membrane 230556. Conductive elastomer 230597 is “springy” in nature and can deform (i.e., stretch) in response to distal force from pierceable seal 230556, thereby deformed into meeting interconnects 230362 under pressure from pierceable seal 230356. The elastomeric nature of conductive elastomer 230597 allows it to return to the pre-deformed state, in which there is no interconnection, in an unpressurized environment. Therefore, once pneumatic and/or hydraulic pressure ceases, i.e., at end-of-delivery, conductive elastomer film 230597 is passively released from contact with interconnections 230562, and signal is interrupted.

In another embodiment, shown in FIG. 155, the sterile fluid pathway connector includes a sensor mechanism comprising dome switch 230666, which dome is made or of includes conductive material such that dome switch 230666 can act as a contact to create a signal when dome switch 230666 meets with, or moves sufficiently close to, interconnects 230662 to complete the circuit. Dome switch 230666 is configured with at least one outer portion 230666A that resists deformation and engages with or bears against the inner wall of connector hub seal mount 230634. Alternatively, the outer deformation-resistant portion of the dome switch can be a radial ring, or any structure that will stabilize the position of the dome within the sterile fluid pathway connector. The conductive portion of the dome switch may comprise shape-memory alloy that "remembers" its dome shape, but can be deformed into a more flattened shape under pressure, then return to the dome shape once pressure is relieved. In the embodiment of FIG. 155, dome switch 230666 further comprises aperture 230666C through which piercing member 230633 can pass as dome switch 230666 is pressed in the direction of interconnects 230662. More specifically, when the pump device is actuated and pneumatic and/or hydraulic pressure builds against the pierceable membrane (not shown), the pierceable membrane is forced onto piercing member 230633 and ruptured to open the fluid pathway. Dome switch 230666 is similarly deformed by the pneumatic and/or hydraulic pressure or by the distal pressure of the deformed portion of the pierceable seal bearing against it, and dome switch 666 flattens towards interconnects 230662 to allow a signal to be transduced. Once the pneumatic and/or hydraulic pressure stops, i.e., at end-of-delivery, the dome switch returns to its pre-deformed dome shape and interconnection ceases. As shown in FIG. 155, dome switch 230666 is configured for placement under the pierceable seal (not shown), within the sterile cavity of the fluid pathway connector. The dome switch could, however, be configured to "ride" on top of the pierceable seal, and upon pressurization would be pushed in close enough proximity with interconnects 230662 to generate a signal. Alternatively, the dome switch could be made of evenly deformable/resistant shape-memory material with the conductive portion of the dome switch configured in the outer portions or rim of the dome, and be placed "upside down" (as a bowl shape) in the sterile chamber of the fluid pathway connector. In this configuration, the pneumatic and/or hydraulic pressure against the pierced pierceable membrane would sufficiently flatten the dome until the outer conductive part of the dome made sufficient contact with interconnects positioned in the connector hub to allow a signal. Upon cessation of pressure, i.e., at end-of-delivery, the dome would pop back to its remembered dome shape, and thereby remove the connective contacts from interconnection.

As should be clear from the preceding discussions, a number of known interconnects and contacts, or similar components, are known in the art and may be utilized within the novel embodiments disclosed herein. As would readily be appreciated by one having skill in the art, a vast range of magnets, sensors, coils, and the like may be utilized to connect, transmit, or relay a signal for user feedback. Generally, any RLC circuit systems having a resistor, an inductor, and a capacitor, connected in series or in parallel, may be utilized for this purpose. For example, Hall effect sensors; giant magneto resistance (GMR) or magnetic field sensors; optical sensors; capacitive or capacitance change sensors; ultrasonic sensors; or linear travel, LVDT, linear resistive, or radiometric linear resistive sensors may be utilized as interconnects and corresponding contacts used to permit a signal to be sent to the power and control system to provide feedback to the user. The location of the contacts and interconnects may be interchanged or in a number of other configurations which permit completion of an electrical circuit or otherwise permit a transmission between the components. By use of one or more status switch interconnects and one or more corresponding electrical contacts, the status of the drive mechanism before, during, and after operation can be relayed to the power and control system to provide feedback to the user. Such feedback may be tactile, visual or auditory, and may be redundant such that more than one signals or types of feedback are provided to the user during use of the device.

Additionally, the embodiments of the present invention provide end-of-delivery compliance to ensure that substantially the entire fluid volume has been delivered and that the status indication features have been properly contacted to provide accurate feedback to the user. Through these mechanisms, confirmation of fluid delivery can accurately be provided to the user or administrator. Accordingly, the novel devices of the present invention alleviate one or more of the problems associated with prior art devices. Optionally, the drive mechanism may include one or more compliance features that enable additional axial translation of the plunger seal to, for example, ensure that substantially the entire fluid volume has been delivered and make sure that the feedback contact mechanisms have connected. For example, in one embodiment of the present invention, the drive mechanism may be configured to drive further axial translation of at least a portion of the plunger seal for a compliance push of the plunger seal, or of fluid, from the fluid container. Additionally or alternatively, the plunger seal, itself, may have some compressibility permitting a compliance push. For example, when a pop-out plunger seal is employed, i.e., a plunger seal that is deformable from an initial state, the plunger seal may be caused to deform or "pop-out" to provide a compliance push. Similarly, the plunger seal may be porous, compressible, deformable, or the like to itself be capable of providing a compliance push.

As described above, the location of the contacts and interconnects may be interchanged or in a number of other configurations that permit completion of an electrical circuit or otherwise permit a transmission between the components. In one embodiment, the plunger seal may incorporate, or itself be utilized as, a contact or interconnect for the status indication mechanism (e.g., 61 in FIG. 142C). In one embodiment, the seal mount may incorporate, or itself be utilized as, a contact or interconnect for the status indication mechanism (e.g., 62 in FIG. 142C). In one embodiment, a guide piece may incorporate, or itself be utilized as, a contact or interconnect for the status indication mechanism (e.g., 232 in FIG. 144A). In another embodiment, the proximal surface of the connector hub sequestered in sterile chamber 32 may incorporate, or itself be utilized as, a contact or interconnect for the status indication mechanism (e.g., FIG. 147 to FIG. 155).

Other components of the sterile fluid pathway connection may similarly be utilized for multiple functions. Alternatively, other optional components may be utilized within the novel embodiments of the present invention. For example, one or more optional flow restrictors may be utilized within the configurations of the fluid pathway connection described herein. In at least one embodiment, a flow restrictor may be utilized at the connection between the piercing member and the fluid conduit. The fluid pump is capable of delivering a range of fluid with different viscosities and volumes. The fluid pump is capable of delivering a fluid at a controlled flow rate (speed) or of a specified volume. In one embodiment, the fluid delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the fluid container to dispense the fluid therein, or combinations thereof. In at least one embodiment of the present invention, the connector hub itself may be utilized as part of the fluid path and may, optionally, function as a flow restrictor.

It will be appreciated from the above description that the fluid pathway connections and fluid pumps disclosed herein provide an efficient and easily-operated system for automated fluid delivery from a fluid container. The novel devices of the present invention provide container connections which maintain the sterility of the fluid pathway and which are integrated into the fluid container, and fluid delivery pumps that incorporate such integrated sterile fluid pathway connections to fluid containers. Such devices are safe and easy to use, and are aesthetically and ergonomically appealing for self-administering patients. The devices described herein incorporate features which make activation, operation, and lock-out of the device simple for even untrained users. Because the fluid path is disconnected until fluid delivery is desired by the operator, the sterility of the fluid pathway connection, the fluid container, the fluid, and the device as a whole is maintained. These aspects of the present embodiments provide highly desirable storage, transportation, and safety advantages to the operator. Furthermore, the novel configurations of the fluid pathway connections and drug pumps of the present invention maintain the sterility of the fluid path through operation of the device. Because the path that the fluid travels within the device is entirely maintained in a sterile condition, only these components need be sterilized during the manufacturing process. Such components include the fluid container of the drive mechanism, the fluid pathway connection, the sterile fluid conduit, and, when the fluid is a drug, the insertion mechanism. In at least one embodiment of the present invention, the power and control system, the assembly platform, the control arm, the activation mechanism, the housing, and other components of the fluid pump do not need to be sterilized. This greatly improves the manufacturability of the device and reduces associated assembly costs. Accordingly, the devices of the present invention do not require terminal sterilization upon completion of assembly. A further benefit of the present embodiments is that the components described herein are designed to be modular such that, for example, the fluid pathway connection and other components of the device may be integrated into a housing and readily interface to function as a fluid pump.

Assembly or manufacturing of fluid pathway connection 23030 or any of the individual components may utilize a number of known materials and methodologies in the art. For example, a number of known cleaning fluids such as isopropyl alcohol and hexane may be used to clean the components or the devices. A number of known adhesives may similarly be employed in the manufacturing process. Additionally, known siliconization or lubrication fluids and processes may be employed during the manufacture of the novel components and devices. Furthermore, known sterilization processes may be employed at one or more of the manufacturing or assembly stages to ensure the sterility of the final product.

The fluid pathway connection may be assembled in a number of methodologies. In one method of assembly, the sterile fluid pathway connection may be assembled, e.g., as shown in FIG. 143A and FIG. 143B, and then attached, mounted, connected, or otherwise integrated into fluid container 23050 such that at least a portion of the pierceable seal 23056 is contained within the fluid container 23050. The fluid container 23050 may then be filled with a fluid and plugged with a plunger seal 23060 at an end opposite the pierceable seal 23056. The barrel 23058 may be filled with a fluid through the open proximal end prior to insertion of the plunger seal 23060 from the proximal end of the barrel 23058. The drive mechanism 23090 may then be attached to the proximal end of the fluid container 23050 such that a component of the drive mechanism 23090 is capable of contacting the plunger seal 23060. The insertion mechanism 23070 may be assembled and attached to the other end of the fluid conduit 23035. This entire sub-assembly, including drive mechanism 23090, fluid container 23050, fluid pathway connection 23030, fluid conduit 23035, and insertion mechanism 23070, may be sterilized by known techniques before assembly into the drug delivery device 230100. Certain components of this sub-assembly may be mounted to an assembly platform within the housing 12A, 12B or directly to the interior of the housing 12A, 12B, while other components may be mounted to a guide, channel, or other component or aspect for activation by the user.

Manufacturing of a fluid pump includes the step of attaching both the fluid pathway connection and fluid container, either separately or as a combined component, to an assembly platform or housing of the drug pump. The method of manufacturing further includes attachment of the drive mechanism, fluid container, and insertion mechanism to the assembly platform or housing. The additional components of the fluid pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the fluid pump includes one or more of the following steps: activating, by a user, the activation mechanism; displacing a control arm to actuate an insertion mechanism; activating a drive control mechanism to push the plunger seal, connect the sterile fluid pathway connection, and drive fluid flow through the fluid pump, wherein translating the fluid pathway connection causes a pierceable seal to be pierced by a piercing member thereby opening a fluid path from the fluid container to the fluid pathway connection. The drive control mechanism may be activated by actuating a power and control system. The method may further include the step of: engaging an optional on-body sensor prior to activating the activation mechanism. Furthermore, the method of operation may include translating a plunger seal within the drive control mechanism and fluid container to force fluid drug flow through the fluid container, the fluid pathway connection, a sterile fluid conduit, and, optionally the insertion mechanism for delivery of the fluid to the body of a user.

XXIII. Additional Embodiments of Drive Mechanism

At least some of the drug delivery devices described in this application, including at least those described in connection with FIGS. 1-56 and 74-157B, may be configured to incorporate the embodiments of the drive mechanism described below in connection with FIGS. 156-157B. The embodiments of the drive mechanism described below in connection with FIGS. 156-157B may be used to replace, in its entirety or partially, the above-described drive mechanisms 100, 500, 1000, 2100, 10100, or any other drive mechanism described herein, where appropriate.

In general, the present embodiments provide drive mechanisms with integrated status indication, drug delivery devices which incorporate such drive mechanisms, the methods of operating such devices, and the methods of assembling such devices. The drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user. Additionally, the embodiments of the present disclosure provide end-of-dose compliance to ensure that substantially the entire drug dose has been delivered to the user and that the status indication features have been properly contacted to provide accurate feedback to the user. Through these mechanisms, confirmation of drug dose delivery can accurately be provided to the user or administrator.

In at least one embodiment, the present disclosure provides a drive mechanism having integrated status indication which includes: a drive housing, a status switch interconnect, a drive biasing member, a piston, and a drug container having a cap, a pierceable seal, a barrel, and a plunger seal. The drive biasing member may be configured to bear upon an interface surface of the piston. The drug container may preferably contain a drug fluid for delivery to the user. The drive mechanism may further include a connection mount attached to the pierceable seal. A cover sleeve may be utilized between the drive biasing member and the interface surface of the piston to, for example, provide more even distribution of force from the biasing member to the piston. A contact sleeve may be slidably mounted to the drive housing through an axial aperture of the drive housing, such that sleeve hooks at a distal end of the contact sleeve are caused to contact the piston between interface surface and a contact protrusion near the proximal end of the piston. The piston may also include a locking groove, between contact protrusion and the proximal end of the piston. The contact sleeve may have a radially extending ring at its proximal end, upon which reside one or more flex prongs.

The drive mechanism may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power control system. In at least one embodiment, as described further herein, the contact surfaces may be electrical contact surfaces which are initially disconnected and caused to come into engagement whereby, upon such engagement, contact surfaces are capable of continuing an energy pathway or otherwise relaying a signal to the power and control system. In another embodiment of the present disclosure, the contact surfaces are mechanical contact surfaces which are initially in contact and caused to disengage whereby, upon such disengagement, such disengagement is communicated to the power and control system. Such signals may be transferred across one or more interconnects to the power and control system or by mechanical action to the power and control system. Such components may be utilized within the drive mechanism to measure and relay information related to the status of operation of the drive mechanism, which may be converted by the power and control system into tactile, auditory, and/or visual feedback to the user. Regardless of the electrical or mechanical nature of the contact surfaces, the motion of the components which permits transmission of a signal to the power control system is enabled by a biasing member axially translating a contact sleeve in the distal direction during operation of the device.

The drive mechanism may include a piston extension slidably mounted at a distal end and within an axial pass-through of piston; a piston extension biasing member, which is mounted within the axial pass-through of piston and initially compressed between piston extension and piston; and, optionally, a piston biasing member support between piston extension biasing member and piston extension. The piston extension is retained within piston by interaction between one or more extension arms of the piston extension and one or more corresponding connection slots of piston. The piston extension may be utilized to perform a compliance push of drug fluid from the drug container. Additionally or alternatively, the drive mechanism may utilize a compressible plunger seal, wherein such compression capacity or distance permits a compliance push of drug fluid from the drug container. Other compliance features are described further herein.

In another embodiment of the present disclosure, a drive mechanism having integrated incremental status indication includes a drive housing, a drive biasing member, a piston, an incremental status stem having a stem interconnect mounted, affixed, printed, or otherwise attached thereon, and a drug container having a cap, a pierceable seal, a barrel, and a plunger seal, wherein the incremental status stem resides within axial pass-throughs of the drive housing and the piston. The incremental status stem may have one or more interconnects which contact one or more contacts on the piston to provide incremental status feedback to the user. The incremental status embodiment may similarly utilize the electrical, mechanical, or electro-mechanical interconnects and contacts, and/or one or more of the compliance features, described above.

In a further embodiment, the present disclosure provides a drug delivery device with integrated status indication. The drug delivery device includes a housing and an assembly platform, upon which an activation mechanism, an insertion mechanism, a fluid pathway connection, a power and control system, and a drive mechanism having a drug container may be mounted. The drive biasing member may be configured to bear upon an interface surface of the piston. The drug container may preferably contain a drug fluid for delivery to the user. The drive mechanism may further include a connection mount attached to the pierceable seal. A cover sleeve may be utilized between the drive biasing member and the interface surface of the piston to, for example, provide more even distribution of force from the biasing member to the piston. A contact sleeve may be slidably mounted to the drive housing through an axial aperture of the drive housing, such that sleeve hooks at a distal end of the contact sleeve are caused to contact the piston between interface surface and a contact protrusion near the proximal end of the piston. The piston may also include a locking groove, between contact protrusion and the proximal end of the piston. The contact sleeve may have a radially extending ring at its proximal end, upon which reside one or more flex prongs. The drive mechanism may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power control system. In at least one embodiment, as described further herein, the contact surfaces may be electrical contact surfaces which are initially disconnected and caused to come into engagement whereby, upon such engagement, contact surfaces are capable of continuing an energy pathway or otherwise relaying a signal to the power and control system. In another embodiment of the present disclosure, the contact surfaces are mechanical contact surfaces which are initially in contact and caused to disengage whereby, upon such disengagement, such disengagement is communicated to the power and control system. Regardless of the electrical or mechanical nature of the contact surfaces, the motion of the components which permits transmission of a signal to the power control system is enabled by a biasing member axially translating a contact sleeve in the distal direction during operation of the device.

In yet another embodiment, the present disclosure provides a drug delivery device with incremental status indication. The drug delivery device includes a housing and an assembly platform, upon which an activation mechanism, an insertion mechanism, a fluid pathway connection, a power and control system, and a drive mechanism having a drug container may be mounted, and further includes an incremental status stem having a stem interconnect mounted, affixed, printed, or otherwise attached thereon, wherein the incremental status stem resides within axial pass-throughs of the drive housing and the piston, and wherein the incremental status stem has one or more interconnects which contact one or more contacts on the piston to complete an transmission to the power and control system to provide incremental feedback to the user. The drug delivery device with incremental status indication may similarly utilize the electrical, mechanical, or electro-mechanical interconnects and contacts, and/or one or more of the compliance features, described above.

The present disclosure further provides a method of assembly. The drug container may first be assembled and filled with a drug fluid. The drug container includes a cap, a pierceable seal, a barrel, and a plunger seal. The pierceable may be fixedly engaged between the cap and the barrel, at a distal end of the barrel. The barrel may be filled with a drug fluid through the open proximal end prior to insertion of the plunger seal from the proximal end of the barrel 58. An optional connection mount may be mounted to a distal end of the pierceable seal. The connection mount to guide the insertion of the piercing member of the fluid pathway connection into the barrel of the drug container. The drug container may then be mounted to a distal end of drive housing.

Prior to mounting the drug container to the housing, a switch status interconnect may be mounted to a proximal end of drive housing. A contact sleeve, having one or more sleeve hooks at a distal end and a ring at a proximal end having an electrical contact thereon, may be mounted to the drive housing through an axial pass-through from the proximal end of the drive housing. A drive biasing member may be inserted into a distal end of the drive housing. Optionally, a cover sleeve may be inserted into a distal end of the drive housing to substantially cover biasing member. A piston may be inserted into the distal end of the drive housing and through an axial pass-through of contact sleeve, such that a contact protrusion of piston is proximal to the sleeve hooks of contact sleeve. The piston and drive biasing member, and optional cover sleeve, may be compressed into the drive housing. Such assembly positions the drive biasing member in an initial compressed, energized state and preferably places a piston interface surface in contact with the proximal surface of the plunger seal within the proximal end of barrel. When a piston extension is employed, the piston extension and piston extension biasing member, and optional piston biasing member support, may be compressed into an axial pass-through of piston prior to compression of the components. Prior to, or after, installing these components into the drive mechanism housing, the primary container may be attached.

When one or more interconnects or contacts are utilized for status indication, such components may be mounted, connected, printed, or otherwise attached to their corresponding components prior to assembly of such components into the drive mechanism. When a separate incremental status stem and a corresponding stem interconnect are utilized for such incremental status indication, the stem interconnect may be mounted, affixed, printed, or otherwise attached to incremental status stem prior to assembly of the incremental status stem to the proximal end of the contact sleeve and/or the proximal end of the drive housing in a manner such that the incremental status stem resides within an axial pass-through of contact sleeve and drive housing. The incremental status stem is further mounted to reside within an axial pass-through of piston.

The disclosure describes, in one aspect, a drug delivery device drive mechanism for use in cooperation with a drug container including a plunger seal. The drive mechanism has an axis and includes a drive housing, a piston adapted to impart movement to the plunger seal within the drug container, a plurality of biasing members disposed in parallel, and a retainer. The piston is disposed for movement from a retracted first position along the axis to an extended second position. The biasing members are adapted to move from an energized first position to a deenergized second position as a result of the release of energy. The biasing members are disposed to cause movement of the piston from the retracted first position to the extended second position as the biasing members move from the energized first position to the deenergized second position. The retainer is disposed to maintain the biasing members in the energized first position when the retainer is in a retaining first position, and to release the biasing members from the first energized position when the retainer moves to a releasing second position.

In at least one embodiment, the plurality of biasing members includes at least one of a tension spring or a compression spring. In at least one embodiment, the plurality of biasing members includes a pair of springs, in at least one embodiment of which the springs are compression springs. In at least embodiment, the compression springs are concentrically disposed, and disposed about at least a portion of the piston. In at least one embodiment, the retainer engages at least a portion of the piston to retain the piston in its retracted position when the retainer is in its retaining first position. At least one embodiment further includes a sleeve assembly disposed about at least one of the plurality of biasing members. In at least one embodiment, the sleeve assembly includes a plurality of telescoping sleeves, and the sleeve assembly is disposed to move to axially with the piston. At least one embodiment further includes at least one window and at least a portion of the sleeve assembly is visible through the window with at least a portion of the sleeve assembly being visible through said window until the piston is in the extended second position. At least one embodiment further includes an end-of-dose indicator disposed substantially adjacent the window, the end-of-dose indicator being adapted to identify at least one of when the sleeve assembly is disposed subjacent the window and when the sleeve assembly is not disposed subjacent the window, the relative motion of the sleeve assembly with reference to the window or another reference component, the stoppage of such motion, and the rate or change of rate of motion. In at least one embodiment, the end-of-dose indicator includes a sensor disposed to sense at least one of when the sleeve assembly is disposed subjacent the window and when the sleeve assembly is not disposed subjacent the window. In at least one embodiment, the sensor is a mechanical sensor, an electrical sensor, an ultrasonic sensor, a capacitive sensor, a magnetic sensor, or an optical sensor. In at least one embodiment, the sensor is a mechanical sensor disposed to bear against the sleeve assembly when the sleeve assembly is disposed subjacent the window.

In another aspect of the disclosure, there is provided a drug delivery device drive mechanism for use in cooperation with a drug container including a plunger seal; the drive mechanism has an axis and includes a drive housing, a piston adapted to impart movement to the plunger seal within the drug container, at least one biasing member, a retainer, a sleeve assembly, and an end-of-dose indicator. The piston is disposed for movement from at least a retracted first position to an extended second position along said axis. The at least one biasing member is disposed and adapted to move from an energized first position to a deenergized second position as a result of the release of energy. The biasing member is disposed to cause movement of the piston from the retracted first position to the extended second position as the biasing member moves from the energized first position to the deenergized second position. The retainer disposed to maintain the biasing member in the energized first position when the retainer is in a retaining first position, and to release the biasing member from the first energized position when the retainer moves to a releasing second position. The sleeve assembly is adapted to move along the axis with the piston. The sleeve assembly is disposed at least partially within the drive housing, and at least a portion of the sleeve assembly being visible through a window in the housing when the piston is one of the retracted first position or the extended second position. The sleeve assembly is not visible through said window when the piston is in the other of the retracted first position or the extended second position. The end-of-dose indicator is disposed substantially adjacent the window. The end-of-dose indicator is adapted to identify at least one of when the sleeve assembly is disposed subjacent the window and when the sleeve assembly is not disposed subjacent the window.

In at least one embodiment, the sleeve assembly is disposed about the at least one biasing member and includes a plurality of telescoping sleeves. In an embodiment, the sleeve assembly is disposed about the biasing member(s). In at least one embodiment, the at least one biasing member includes a plurality of biasing members. A particular embodiment includes at least two compression springs disposed in parallel. In at least on embodiment, the end-of-dose indicator includes a sensor disposed to sense at least one of when the sleeve assembly is disposed subjacent the window and when the sleeve assembly is not disposed subjacent the window. In at least one embodiment, the sensor is at least one of a mechanical sensor, a mechanical sensor, an electrical sensor, an ultrasonic sensor, a capacitive sensor, a magnetic sensor, or an optical sensor. In a particular embodiment, the sensor is a mechanical sensor disposed to bear against the sleeve assembly when the sleeve assembly is disposed subjacent the window. In some embodiments, at least a portion of a distal end of the piston is adapted to be disposed within the drug container when the piston is disposed in the retracted first position and the drug delivery device drive mechanism is disposed for use in cooperation with the drug container.

At least some embodiments of the present disclosure provide the necessary drive force to push a plunger seal and a drug fluid within a drug container, while reducing or minimizing the drive mechanism and overall device footprint. Accordingly, the present disclosure may provide a drive mechanism which may be utilized within a more compact drug delivery device. Some embodiments of the present disclosure may similarly be utilized to provide additional force, as may be needed for highly viscous drug fluids or for larger volume drug containers.

According to another aspect of the disclosure, there is provided a drug delivery device drive mechanism for use in cooperation with a drug container that includes a plunger seal and a power and control system. The drive mechanism includes a drive housing, a piston, at least one biasing member, a retainer, sleeve assembly, and an end-of-dose indicator. The drive housing includes an axis, the housing further includes at least one window. The piston is disposed for movement from at least a retracted first position to an extended second position along the axis. The piston is also adapted to impart movement to the plunger seal within the drug container. The at least one biasing member is disposed and adapted to move from an energized first position to a deenergized second position as a result of the release of energy. The biasing member is also disposed to cause movement of the piston from the retracted first position to the extended second position as the biasing member moves from the energized first position to the deenergized second position. The retainer is moveable between a retaining first position and a releasing second position. The retainer is disposed to maintain the biasing member in the energized first position when the retainer is in the retaining first position, and to release the biasing member from the first energized position when the retainer moves to the releasing second position. The sleeve assembly is disposed at least partially within the drive housing. At least a portion of the sleeve assembly is adapted to move along the axis with the piston. At least a portion of the sleeve assembly is visible through the window when the piston is one of the retracted first position or the extended second position, and the sleeve assembly is not visible through the window when the piston is in the other of the retracted first position or the extended second position. The end-of-dose indicator includes at least one switch interconnect, at least a portion of which is disposed substantially adjacent the window and adapted to identify at least one of when the sleeve assembly is disposed subjacent the window and when the sleeve assembly is not disposed subjacent the window. The switch interconnect includes a mechanical trigger adapted to engage the sleeve assembly through the window. The switch interconnect is further adapted to selectively engage the power and control system as a result of the engagement or disengagement end of the trigger.

The novel embodiments of the present disclosure provide drive mechanisms with integrated status indication, which are capable of provide incremental status of the drug delivery before, during, and after operation of the device, and provides means for ensuring drug dose compliance, i.e., ensuring substantially the entire drug dose has been delivered to the user. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present disclosure may include one or more additional components which may be considered standard components in the industry of medical devices. The components, and the embodiments containing such components, are within the contemplation of the present disclosure and are to be understood as falling within the breadth and scope of the present disclosure.

FIGS. 156 and 157A-157B illustrate an embodiment of the drive mechanism 3100 which includes an end-of-dose indicator 3133. The end-of-dose indicator 3133 includes a switch interconnect 3132 and a contact sleeve assembly 3120 adapted for movement with the piston. As described above with reference to the embodiments shown in FIGS. 20A-24B, the piston has an interface surface that is capable of contacting or otherwise bearing upon plunger seal to force drug fluid out of barrel through the fluid pathway connection for delivery to a patient. In order to provide access of the end-of-dose indicator 3133 to the interior of the drive housing 3130, the drive housing 3130 includes an access window 3131. In at least one embodiment, the drive housing 3130 includes more than one access window 3131 to permit pass-through of more than one switch interconnect, sensor and/or trigger to, for example, interface with the sleeve assembly 3120. In order to better illustrate the relationship of the end-of-dose indicator 3133 and the sleeve assembly 3120 during movement of the sleeve assembly 3120, FIGS. 157A and 157B show the housing 3130, sleeve 3126, biasing members 3106, 3122, and end-of-dose indicator 3133 in cross-section taken along line 15-15 in FIG. 156, before and after actuation, respectively. The PCB board 3138 is included in this view of the drive mechanism 3100 to show the interaction between the end-of-dose indicator 3133 and the PCB board 3138.

The end-of-dose indicator 3133 illustrated includes a sensor 3134 that includes a mechanical, pivotably mounted trigger 3135, in essence, an on/off mechanical switch. In at least one embodiment, the end-of-dose indicator 3133 has more than one trigger 3135 mounted through more than one corresponding window 3131 of the drive mechanism 3100, for functional redundancy and/or operational robustness. Each of the triggers 3135 is disposed in a first position in contact with the sleeve assembly 3120, particularly the sleeve 3126 thereof, when the piston 3110 is in a retracted first position, illustrated in FIG. 157A. As the piston 3110 moves outward from the drive housing 3130, the triggers 3135 slide along the telescoping sleeve assembly 3120 until such time as the proximal end of the second sleeve 3126 passes the windows 3131, that is, the triggers 3135. As the second sleeve 3126 passes at least one of the triggers 3135, the trigger 3135 moves to a second position, illustrated in FIG. 157B. The movement of the trigger 3135 to the second position results in the transmission of a signal indicating the end of dose to the power and control system. In this configuration, movement of at least one trigger 3135 will cause the transmission of the signal to occur.

Those of skill in the art will appreciate that in some configurations, there is the possibility that the disposal of the spring 3122 subjacent the window 3131 following axial movement of the sleeve 3126 may inhibit actuation of the sensor 3134 of the switch interconnect 3132, for example, by inhibiting movement of the trigger 3135 to an actuated position. Although the sensor 3134, or trigger 3135, may be prevented from actuation only temporarily, such delay may result in a corresponding delay in the indication of the end of the dose. Accordingly, the inclusion of two or more sensors 3134 or triggers 3135 may provide a desirable redundancy. Moreover, the windows 3131 and sensors 3134 may be positioned to maximize the opportunity for actuation of at least one of the triggers 3135 concurrently with the end of the dose delivery. Because more than one trigger 3135 is utilized in this configuration, the end-of-dose indicator 3133 provides functional redundancy to ensure that an accurate signal is transmitted to the power and control system.

For the purposes of this disclosure and the appended claims, the transmission of a signal means the provision of an indication that the end of dose has occurred. That transmission may be associated with a mechanical movement, for example, the engagement or disengagement, or an electrical signal, for example, the provision of an electrical signal or connection, or the discontinuation of an electrical signal or connection, or a combination of such transmissions.

In at least one embodiment of the configuration shown in FIGS. 156-157B, the switch interconnects 3132 directly engage with a PCB board 3138 to permit transmission of a signal to the power control system. The switch interconnects 3132 may further be configured to initially be connected (e.g., a closed or complete circuit) or disconnected (e.g., an open or broken circuit) from a PCB board 3138, though the embodiment shown in FIGS. 157A-157B shows the switch interconnects 3132 initially connected to the PCB board 3138, that is, prior to the end of dose. As the second sleeve 3126 passes at least one of the triggers 3135, as shown in the transition from FIG. 157A to FIG. 157B, the trigger 3135 moves to a second position, namely, a distance shown as 'D1' in FIG. 157B. The movement of the trigger 3135 to the second position results, in at least one embodiment, in a disconnection of the switch interconnect 3132 from the PCB board 3138 and the resulting transmission of a signal indicating the end of dose to the power and control system. While the illustrated design shows the switch interconnect 3132 directly engaged with the PCB board 3138, it will be appreciated that the switch interconnect 3132 could alternatively or additionally engage one or more intermediate conductive or nonconductive structures.

The end-of-dose indicator 3133, triggers 3135, and PCB board 3138 may alternatively be configured, as would be readily appreciated by an ordinarily skilled artisan, to cause a connection there-between upon the movement of the trigger 3135 to the second position. By way of example only, a trigger may be toggled such that the switch interconnect is not in communication with the PCB board prior to the end of dose, movement of the trigger at the end of dose yielding a connection directly with or conveyed to the PCB board. Additionally, as described below, the connection and disconnection (or vice versa) between the switch interconnects 3132 and the PCB board may be utilized to provide incremental status indication.

The end-of-dose indicator 3133 may be of any appropriate design and formed of any appropriate material or materials and by any appropriate fabrication method. The illustrated switch interconnect 3132 may be formed in whole or in part of a conductive material, for example. In an arrangement wherein an electrical connection occurs when the trigger 3135 is in the position illustrated in FIG. 157A and electrical connection is discontinued when the trigger 3135 is in the position illustrated in FIG. 157B, for example, at least a portion of the switch interconnect 3132 disposed to engage with the PCB board 3138 may be formed of or coated with a conductive material. Conversely, in an arrangement wherein no electrical connection occurs when the trigger 3135 is in the position illustrated in FIG. 157A and electrical connection occurs when the trigger 3135 is in the position illustrated in FIG. 157B, for example, at least a portion of the switch interconnect 3132 disposed to engage with the PCB board 3138 may be formed of or coated with an insulative material.

Although illustrated as an electromechanical arrangement that reads the position of a telescoping sleeve, any appropriate arrangement may be provided to read the relative position of any appropriate component, the end-of-dose indicator providing a signal to the power and control system to indicate that all of the drug has been administered. Additionally, the switch interconnects and corresponding contacts and/or reference component may be utilized to provide incremental status indication in addition to an end-of-dose indication. For example, in the switch interconnect arrangement described above with reference to FIGS. 20A-24B or FIGS. 156-157B, the switch interconnect 2132, 3132 may be an electromechanical sensor configured to recognize a number of bumps, ridges, or grooves, in the corresponding sleeve 2126, 3126 or any other reference component, the contact with which permits the switch interconnect to signal an incremental status indication (e.g., delivery initiation, amount of volumes delivered, duration of plunger travel, etc.) and a final end-of-dose indication. As described herein, similar incremental status indication may be provided in this configuration by utilizing a different type of sensor arrangement. For example, the switch interconnect 2132, 3132 may be an optical sensor configured to recognize a number of markings on the corresponding sleeve 2126, 3126 or any other reference component. As the optical sensor recognizes the number of markings, it permits the switch interconnect to signal an incremental status indication (e.g., delivery initiation, amount of volumes delivered, duration of plunger travel, etc.) and a final end-of-dose indication. Any appropriate arrangement may be provided to read the relative position of a number of markings, ridges, grooves, or respective indicators on any appropriate reference component, and recognition of such indicators by the switch interconnect permits it to provide a signal to the power and control system to indicate the incremental status of drug delivery, including the final status that all of the drug has been administered. As would be appreciated by an ordinarily skilled artisan in the relevant arts, the indicators may not necessarily be defined aspects on a reference component, and the switch interconnects may be configured to recognize the actual travel of the reference component itself. The switch interconnects may thus be configured to recognize the rate of change, the distance of travel, or other related measurements in the actual travel of the reference components and enable a signal to the power and control system to provide the user with such information or feedback.

It will be appreciated by those of skill in the art that the embodiments of the present disclosure provide the necessary drive force to push a plunger seal and a drug fluid within a drug container, while reducing or minimizing the drive mechanism and overall device footprint. Accordingly, the present disclosure provides a drive mechanism which may be utilized within a more compact drug delivery device. The embodiments of the present disclosure may similarly be utilized to provide additional force, as may be needed for highly viscous drug fluids or for larger volume drug containers.

The embodiments shown and detailed herein disclose only a few possible variations of the present disclosure; other similar variations are contemplated and incorporated within the breadth of this disclosure.

The drive mechanism may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power control system 2400.

A fluid pathway connection, and specifically a sterile sleeve of the fluid pathway connection, may be connected to the cap and/or pierceable seal of the drug container. A fluid conduit may be connected to the other end of the fluid pathway connection which itself is connected to the insertion mechanism such that the fluid pathway, when opened, connected, or otherwise enabled travels directly from the drug container, fluid pathway connection, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device 10, as shown in FIG. 1B.

Certain optional standard components or variations of drive mechanism 100 or drug delivery device 10 are contemplated while remaining within the breadth and scope of the present disclosure. For example, upper or lower housings may optionally contain one or more transparent or translucent windows 18, as shown in FIG. 1A, to enable the user to view the operation of the drug delivery device 10 or verify that drug dose has completed. Additionally, the drug delivery device 10 may contain an adhesive patch 26 and a patch liner 28 on the bottom surface of the housing 12. The adhesive patch 26 may be utilized to adhere the drug delivery device 10 to the body of the user for delivery of the drug dose. As would be readily understood by one having ordinary skill in the art, the adhesive patch 26 may have an adhesive surface for adhesion of the drug delivery device to the body of the user. The adhesive surface of the adhesive patch 26 may initially be covered by a non-adhesive patch liner 28, which is removed from the adhesive patch 26 prior to placement of the drug delivery device 10 in contact with the body of the user. Removal of the patch liner 28 may further remove the sealing membrane 254 of the insertion mechanism 200, opening the insertion mechanism to the body of the user for drug delivery (as shown in FIG. 1C).

Similarly, one or more of the components of drive mechanism 100 and drug delivery device 10 may be modified while remaining functionally within the breadth and scope of the present disclosure. For example, as described above, while the housing of drug delivery device 10 is shown as two separate components upper housing 12A and lower housing 12B, these components may be a single unified component. Similarly, while electrical contact 134 is shown as a separate component from contact sleeve 140, it may be a unified component printed onto the ring surface of the contact sleeve 140. As discussed above, a glue, adhesive, or other known materials or methods may be utilized to affix one or more components of the drive mechanism and/or drug delivery device to each other. Alternatively, one or more components of the drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the drive mechanisms and drug delivery devices disclosed herein provide an efficient and easily-operated system for automated drug delivery from a drug container. The novel embodiments described herein provide integrated status indication to provide feedback to the user. The novel drive mechanisms of the present disclosure may be directly or indirectly activated by the user. For example, in at least one embodiment the lockout pin(s) which maintain the drive mechanism in its locked, energized state are directly displaced from the corresponding lockout grooves of the piston 110 by user depression of the activation mechanism. Furthermore, the novel configurations of the drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly. A further benefit of the present disclosure is that the components described herein are designed to be modular such that, for example, housing and other components of the drug delivery device may readily be configured to accept and operate drive mechanism 100, drive mechanism 500, or a number of other variations of the drive mechanism described herein.

Manufacturing of a drug delivery device includes the step of attaching both the drive mechanism and drug container, either separately or as a combined component, to an assembly platform or housing of the drug delivery device. The method of manufacturing further includes attachment of the fluid pathway connection, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a drive control mechanism to drive fluid drug flow through the drug delivery device. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the drive control mechanism and drug container to force fluid drug flow through the drug container, the fluid pathway connection, a sterile fluid conduit, and the insertion mechanism for delivery of the fluid drug to the body of a user. The method of operation of the insertion mechanism and the drug delivery device may be better appreciated with reference to FIGS. 14A-14E, as described above.)

XXIV. Drug Information

The above description describes various systems and methods for use with various drug delivery devices. It should be clear that the systems, drug delivery devices or methods can further comprise use of a medicament listed below with the caveat that the following list should neither be considered to be all inclusive nor limiting. The medicament will be contained in a reservoir (e.g., container 50, container 618, container 718, container 818, container 918, container 1118, container 2050, container 6050, container 8050). In some instances, the reservoir is a primary container that is either filled or pre-filled for treatment with the medicament. The primary container can be a cartridge or a pre-filled syringe. Additionally, in some instances, the reservoir may be a primary container that is pre-loaded.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12;

AblA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 14687;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and 0A-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/Ilia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No. 2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2013/048714, International Patent Application No. PCT/US2015/040211, International Patent Application No. PCT/US2015/056972, International Patent Application Publication No. WO/2008/

057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

XXV. Additional Aspects

The drug delivery devices, assemblies, mechanisms, components, features, functionalities, methods of manufacture, and methods of use described above may incorporate various aspects of the drug delivery devices, assemblies, mechanisms, components, features, functionalities, methods of manufacture, and methods of use described in the following documents, each of which is incorporated in its entirety for all purposes: U.S. Pat. No. 8,939,935; U.S. Patent Application Publication No. 2013/0060233; U.S. Patent Application Publication No. 2013/0066274; U.S. Patent Application Publication No. 2013/0237916; U.S. Patent Application Publication No. 2014/0200510; U.S. Patent Application Publication No. 2014/0288511A1; U.S. Patent Application Publication No. 2015/0290390; U.S. Patent Application Publication No. 2015/0374919A1; U.S. Patent Application Publication No. 2015/0209505; U.S. Patent Application Publication No. 2015/0297827; U.S. Patent Application Publication No. 2015/0359965; U.S. Patent Application Publication No. 2015/0190588; U.S. Patent Application Publication No. 2015/0217045; U.S. Patent Application Publication No. 2015/0057613; U.S. Patent Application Publication No. 2014/0296787; U.S. Provisional Patent Application No. 62/094,395 entitled "DRUG DELIVERY DEVICE WITH PROXIMITY SENSOR"; U.S. Provisional Patent Application No. 62/114,200 entitled "ROTATIONALLY BIASED INSERTION MECHANISM FOR A DRUG DELIVERY PUMP"; U.S. Provisional Patent Application No. 62/117,420 entitled "DRUG DELIVERY DEVICE WITH VACUUM ASSISTED SECUREMENT AND/OR FEEDBACK"; U.S. Provisional Patent Application No. 62/127,021 entitled "DEVICE AND METHOD FOR MAKING ASEPTIC CONNECTIONS"; U.S. Provisional Patent Application No. 62/130,318 entitled "MULTI-FUNCTION DRIVE MECHANISMS FOR CONTROLLED DRUG DELIVERY PUMPS"; U.S. Provisional Patent Application No. 62/266,788 entitled "DRUG DELIVERY STORAGE DEVICE AND SYSTEM"; U.S. Provisional Patent Application No. 62/293,556 filed on Feb. 10, 2016 entitled "DRUG DELIVERY DEVICE"; U.S. Provisional Patent Application No. 62/133,690 entitled "ROTATIONALLY BIASED INSERTION MECHANISM FORA DRUG DELIVERY PUMP"; U.S. Provisional Patent Application No. 62/201,456 entitled "MULTI-FUNCTION DRIVE MECHANISMS FOR CONTROLLED DRUG DELIVERY PUMPS"; U.S. Provisional Patent Application No. 62/147,435 entitled "MULTI-FUNCTION DRIVE MECHANISMS FOR CONTROLLED DRUG DELIVERY PUMPS"; U.S. Provisional Patent Application No. 62/134,226 entitled "MULTI-FUNCTION DRIVE MECHANISMS FOR CONTROLLED DRUG DELIVERY PUMPS"; U.S. Provisional Patent Application No. 62/147,403 entitled "ROTATIONALLY BIASED INSERTION MECHANISM FORA DRUG DELIVERY PUMP"; U.S. Provisional Patent Application No. 62/220,754 entitled "CONTROLLED DELIVERY DRIVE MECHANISMS FOR DRUG DELIVERY PUMPS"; U.S. Provisional Patent Application No. 62/290,064 entitled "ASEPTIC CONNECTIONS FOR DRUG DELIVERY DEVICES"; U.S. Provisional Patent Application No. 62/201,468 entitled "DRUG DELIVERY PUMPS HAVING MULTIPLE CHAMBERS"; U.S. Provisional Patent Application No. 62/262,666 entitled "SYSTEMS FOR THE CONTROL OF DRUG DELIVERY PUMPS BASED ON INPUT DATA"; U.S. Provisional Patent Application No. 62/241,906 entitled "FILL-FINISH CARRIERS FOR DRUG CONTAINERS"; U.S. Provisional Patent Application No. 62/262,683 entitled "SYSTEMS AND METHODS FOR CONTROLLED DRUG DELIVERY PUMPS"; U.S. Provisional Patent Application No. 62/204,866 entitled "AUTOMATIC DRUG INJECTORS AND ASSOCIATED DEVICES INCORPORATING DATA RECORDING, TRANSMISSION, AND RECEIVING"; U.S. Provisional Patent Application No. 62/239,116 entitled "AUTOMATIC INJECTORS FOR INJECTABLE CARTRIDGES INCORPORATING SIMPLIFIED LOADING OF CARTRIDGES"; U.S. Provisional Patent Application No. 62/206,503 entitled "ARCUATE DRIVE MECHANISMS FOR AUTOMATIC INJECTORS"; U.S. Provisional Patent Application No. 62/278,028 entitled "MEDICAL DEVICE INCORPORATING ADHESIVE WITH STIMULANT SENSITIVE BONDING STRENGTH"; International Patent Application Publication No. WO/2015/061386; International Patent Application Publication No. WO/2015/061389; International Patent Application Publication No. WO/2015/187793; International Patent Application Publication No. WO/2015/187797; International Patent Application Publication No. WO/2015/187799; International Patent Application Publication No. WO/2015/187802; International Patent Application Publication No. WO/2015/187805; International Patent Application Publication No. WO/2016/003813; International Patent Application No. PCT/US2016/017534 entitled "ROTATIONALLY BIASED INSERTION MECHANISM FORA DRUG DELIVERY PUMP"; International Patent Application No. PCT/US2016/017534 entitled "ROTATIONALLY BIASED INSERTION MECHANISM FORA DRUG DELIVERY PUMP"; International Patent Application No. PCT/US2015/052311 entitled "CONCENTRIC BARREL DRUG CONTAINERS AND DRUG DELIVERY PUMPS THAT ALLOW MIXING AND DELIVERY"; International Patent Application No. PCT/US2015/052367 entitled "SEQUENTIAL CHAMBER DRUG DELIVERY PUMPS FOR DRUG MIXING AND DELIVERY"; International Patent Application No. PCT/US2015/047487 entitled "SKIN SENSORS FOR DRUG DELIVERY DEVICES"; International Patent Application No. PCT/US2015/052815 entitled "RIGID NEEDLE INSERTION MECHANISM FORA DRUG DELIVERY PUMP"; International Patent Application No. PCT/US2015/047503 entitled "SENSOR SYSTEMS FOR DRUG DELIVERY DEVICES"; International Patent Application No. PCT/US2016/021585 entitled "DRIVE MECHANISMS FOR DRUG DELIVERY PUMPS"; International Patent Application No. PCT/US2016/020486 entitled "DEVICE AND METHOD FOR MAKING ASEPTIC CONNECTIONS"; International Patent Application No. PCT/US15/29485 entitled "AUTOINJECTOR WITH SHOCK REDUCING ELEMENTS". Furthermore, the drug delivery devices, assemblies, mechanisms, components, features, functionalities, methods of manufacture, and methods of use described in any of the above-listed-incorporated-by-reference disclosures may include a container filled partially or entirely with one or more of the drugs described above, including, for example, a PCSK9 specific antibody, a G-CSF, a sclerostin antibody, or a CGRP antibody.

Throughout the specification, the aim has been to describe the preferred embodiments of the disclosure without limiting the disclosure to any one embodiment or specific collection of features. Various changes and modifications may be made to the embodiments described and illustrated without departing from the present disclosure. The disclosure of each patent and scientific document, computer program and algorithm referred to in this specification is incorporated by reference in its entirety.

What is claimed is:

1. A wearable drug delivery device comprising:

a housing;

a container disposed at least partially within the housing;

a first seal at least partially covering an opening formed in a wall of the container;

a plunger seal moveably disposed within the container;

a drug disposed within the container, the drug comprising at least one of a granulocyte colony-stimulating factor (G-CSF) or a Proprotein Convertase Subtilisin/Kexin Type 9 (PCSK9) specific antibody;

a drive mechanism configured to move the plunger seal through the container to expel the drug from the container;

a needle having at least: a first position wherein a point of the needle is not disposed through a surface of the first seal, and a second position wherein the point of the needle is disposed through the surface of the first seal into the container;

an insertion mechanism disposed at least partially within the housing, wherein the insertion mechanism comprises:

a rotational biasing member configured to rotate the insertion mechanism housing, a delivery member connected or configured to be connected in fluid communication with the container, the delivery member being moveable between a first position wherein an insertion portion of the delivery member is positioned within the housing and a second position wherein the insertion portion of the delivery member is positioned exterior to the housing for insertion into a patient, a hub operably coupled with the delivery member, and wherein the insertion mechanism housing is operably coupled with the hub such that initial rotation of the insertion mechanism housing causes the delivery member to move axially from the first position to the second position;

an ultraviolet (UV) light source; and wherein at least a portion of the wearable drug delivery device is configured to facilitate UV sterilization of at least a portion of the surface of the first seal.

2. The wearable drug delivery device of claim 1, wherein the UV light source is disposed at least partially within the housing.

3. The wearable drug delivery device of claim 1, wherein the insertion mechanism housing comprises a cylindrical portion and at least a portion of the delivery member is positioned within the cylindrical portion when the delivery member is in the first position.

4. The wearable drug delivery device of claim 1, wherein the insertion mechanism housing comprises a first guide surface and the hub comprises an outwardly extending follower configured to slidably engage the first guide surface during rotation of the insertion mechanism housing.

5. The wearable drug delivery device of claim 4, wherein at least a portion of the first guide surface extends in an axial direction and a circumferential direction.

6. The wearable drug delivery device of claim 4, comprising a second guide surface fixed rotationally with respect to the housing, wherein the outwardly extending follower is configured to slidably engage the second guide surface to facilitate axial movement of the hub during rotation of the insertion mechanism housing.

7. The wearable drug delivery device of claim 1, wherein the insertion mechanism housing is rotatable about a rotational axis and the rotational axis is parallel to a longitudinal axis of the delivery member.

8. The wearable drug delivery device of claim 7, wherein the rotational axis of the insertion mechanism housing is coaxial with the longitudinal axis of the delivery member.

9. The wearable drug delivery device of claim 1, comprising a first abutment member having a first position wherein the first abutment member engages the insertion mechanism housing to prevent the rotational biasing member from rotating the insertion mechanism housing and second position wherein the first abutment member is disengaged from the insertion mechanism housing to allow the rotational biasing member to rotate the insertion mechanism housing.

10. The wearable drug delivery device of claim 9, wherein the insertion mechanism housing includes a cylindrical portion and a second abutment member extending outwardly from the cylindrical portion, the second abutment member engaging the first abutment member when the first abutment member is in the first position.

11. The wearable drug delivery device of claim 1, wherein the drive mechanism is configured to expel the drug from the container and into the patient via the delivery member.

12. The wearable drug delivery device of claim 1, comprising at least one fluid conduit positioned at least partially in the housing and configured to fluidly connect the delivery member and the container, the at least one fluid conduit being coupled to the hub such that at least a portion of the fluid conduit and the hub translate jointly during insertion of the delivery member into the patient.

13. The wearable drug delivery device of claim 1, wherein the rotational biasing member comprises a torsion spring.

14. The wearable drug delivery device of claim 1, wherein the delivery member comprises a second needle.

15. The wearable drug delivery device of claim 14, wherein the second needle has a hollow interior.

16. The wearable drug delivery device of claim 1, wherein at least a portion of the rotational biasing member surrounds the insertion mechanism housing.

17. The wearable drug delivery device of claim 16, wherein the insertion mechanism lacks a cover surrounding the rotational biasing member.

18. The wearable drug delivery device of claim 1, comprising an adhesive applied to a wall of the housing for removably attaching the housing to skin of a patient.

19. The wearable drug delivery device of claim 18, comprising an opening formed in the wall of the housing, wherein the insertion portion of the delivery member extends through the opening in the second position.

* * * * *